United States Patent
Bolton et al.

(10) Patent No.: US 12,186,645 B2
(45) Date of Patent: Jan. 7, 2025

(54) USER INTERFACES FOR PHYSICAL ACTIVITY INFORMATION

(71) Applicant: Apple Inc., Cupertino, CA (US)

(72) Inventors: Craig D. Bolton, Manhattan Beach, CA (US); Julie A. Arney, Los Gatos, CA (US); Edward Chao, Palo Alto, CA (US); Lynne Devine, San Francisco, CA (US); Victoria E. Hinn, Brooklyn, NY (US); Daniel S. Keen, San Jose, CA (US); Julia K. Nichols, Alameda, CA (US); James P. Ochs, San Francisco, CA (US); Jennifer D. Patton, Cupertino, CA (US)

(73) Assignee: Apple Inc., Cupertino, CA (US)

( * ) Notice: Subject to any disclaimer, the term of this patent is extended or adjusted under 35 U.S.C. 154(b) by 0 days.

(21) Appl. No.: 18/405,969

(22) Filed: Jan. 5, 2024

(65) Prior Publication Data

US 2024/0139608 A1     May 2, 2024

Related U.S. Application Data

(63) Continuation of application No. 17/952,239, filed on Sep. 24, 2022, now Pat. No. 11,896,871.

(60) Provisional application No. 63/349,119, filed on Jun. 5, 2022.

(51) Int. Cl.
| | |
|---|---|
| A63B 24/00 | (2006.01) |
| A63B 71/06 | (2006.01) |
| G06F 3/0482 | (2013.01) |
| G06F 3/0486 | (2013.01) |
| G16H 20/30 | (2018.01) |

(52) U.S. Cl.
CPC ...... *A63B 71/0622* (2013.01); *A63B 24/0062* (2013.01); *A63B 24/0075* (2013.01); *A63B 71/0619* (2013.01); *G06F 3/0482* (2013.01); *G06F 3/0486* (2013.01); *G16H 20/30* (2018.01); *A63B 2024/0068* (2013.01); *A63B 2024/0078* (2013.01); *A63B 2071/0675* (2013.01); *A63B 2220/14* (2013.01)

(58) Field of Classification Search
CPC ........ A63B 2024/0068; A63B 2220/14; A63B 24/0062; G06F 3/0482
See application file for complete search history.

(56) References Cited

U.S. PATENT DOCUMENTS

| | | | |
|---|---|---|---|
| 4,205,628 | A | 6/1980 | Null |
| 4,842,266 | A | 6/1989 | Sweeney et al. |
| 5,349,962 | A | 9/1994 | Lockard et al. |
| 5,423,863 | A | 6/1995 | Felblinger et al. |

(Continued)

FOREIGN PATENT DOCUMENTS

| | | |
|---|---|---|
| AU | 2011302438 A1 | 5/2013 |
| CA | 2815518 A1 | 5/2012 |

(Continued)

OTHER PUBLICATIONS

Brief Communication Regarding Oral Proceedings received for European Patent Application No. 21165295.3, mailed on Feb. 27, 2024, 1 page.

(Continued)

*Primary Examiner* — Charles J Han
(74) *Attorney, Agent, or Firm* — DLA Piper LLP (US)

(57) ABSTRACT

The present disclosure generally relates to user interfaces for managing, modifying, and/or outputting workout content.

60 Claims, 61 Drawing Sheets

(56) References Cited

U.S. PATENT DOCUMENTS

| | | |
|---|---|---|
| 5,458,548 A | 10/1995 | Crossing et al. |
| 5,474,077 A | 12/1995 | Suga |
| 5,642,731 A | 7/1997 | Kehr |
| 5,685,723 A | 11/1997 | Ladin et al. |
| 5,730,141 A | 3/1998 | Fain et al. |
| 5,788,655 A | 8/1998 | Yoshimura et al. |
| 5,845,235 A | 12/1998 | Luukkanen et al. |
| 5,944,633 A | 8/1999 | Wittrock |
| 6,013,008 A | 1/2000 | Fukushima |
| 6,061,592 A | 5/2000 | Nigam |
| 6,095,949 A | 8/2000 | Arai |
| 6,095,984 A | 8/2000 | Amano et al. |
| 6,097,371 A | 8/2000 | Siddiqui et al. |
| 6,097,385 A | 8/2000 | Robinson |
| 6,199,012 B1 | 3/2001 | Hasegawa |
| 6,244,988 B1 | 6/2001 | Delman |
| 6,302,789 B2 | 10/2001 | Harada et al. |
| 6,416,471 B1 | 7/2002 | Kumar et al. |
| 6,603,477 B1 | 8/2003 | Tittle |
| 6,639,584 B1 | 10/2003 | Li |
| 6,705,972 B1 | 3/2004 | Takano et al. |
| 6,837,827 B1 | 1/2005 | Lee |
| 6,866,613 B1 | 3/2005 | Brown et al. |
| 7,020,514 B1 | 3/2006 | Wiesel |
| 7,128,693 B2 | 10/2006 | Brown et al. |
| 7,251,454 B2 | 7/2007 | White |
| 7,302,272 B2 | 11/2007 | Ackley |
| 7,534,206 B1 | 5/2009 | Lovitt et al. |
| 7,662,065 B1 | 2/2010 | Kahn |
| 7,695,406 B2 | 4/2010 | Waters |
| 7,739,148 B2 | 6/2010 | Suzuki et al. |
| 7,853,428 B2 | 12/2010 | Usui et al. |
| 7,870,013 B1 | 1/2011 | Allemann et al. |
| 8,060,229 B2 | 11/2011 | Gupta et al. |
| 8,105,208 B2 | 1/2012 | Oleson et al. |
| 8,200,323 B2 | 6/2012 | Dibenedetto et al. |
| 8,321,006 B1 | 11/2012 | Snyder et al. |
| 8,341,557 B2 | 12/2012 | Pisula et al. |
| 8,475,339 B2 | 7/2013 | Hwang et al. |
| 8,496,563 B2 | 7/2013 | Komatsu et al. |
| 8,676,170 B2 | 3/2014 | Porrati et al. |
| 8,734,296 B1 | 5/2014 | Brumback et al. |
| 8,768,648 B2 | 7/2014 | Panther et al. |
| 8,784,115 B1 | 7/2014 | Chuang |
| 8,784,271 B2 | 7/2014 | Brumback et al. |
| 8,825,445 B2 | 9/2014 | Hoffman et al. |
| 8,934,963 B1 | 1/2015 | Farazi |
| 8,947,239 B1 | 2/2015 | Park |
| 8,990,006 B1 | 3/2015 | Wallace et al. |
| 9,011,292 B2 | 4/2015 | Weast et al. |
| 9,020,538 B1 | 4/2015 | White et al. |
| 9,063,164 B1 | 6/2015 | Yuen et al. |
| 9,087,234 B2 | 7/2015 | Hoffman et al. |
| 9,148,483 B1 | 9/2015 | Molettiere et al. |
| 9,164,663 B1 | 10/2015 | Berard |
| 9,224,291 B2 | 12/2015 | Moll-Carrillo et al. |
| 9,230,076 B2 | 1/2016 | King et al. |
| 9,449,365 B2 | 9/2016 | Roberts |
| 9,532,734 B2 | 1/2017 | Hoffman et al. |
| 9,557,881 B1 | 1/2017 | Jain et al. |
| 9,582,165 B2 | 2/2017 | Wilson et al. |
| 9,589,445 B2 | 3/2017 | White et al. |
| 9,712,629 B2 | 7/2017 | Molettiere et al. |
| 9,723,381 B2 | 8/2017 | Swanson |
| 9,734,477 B2 | 8/2017 | Weast et al. |
| 9,798,443 B1 | 10/2017 | Gray |
| 9,800,525 B1 | 10/2017 | Lerner et al. |
| 9,813,642 B1 | 11/2017 | Chen et al. |
| 9,817,481 B2 | 11/2017 | Pantelopoulos et al. |
| 9,854,653 B1 | 12/2017 | Ackmann et al. |
| 9,880,805 B1 | 1/2018 | Guralnick |
| 9,910,571 B2 | 3/2018 | Chen et al. |
| 9,918,664 B2 | 3/2018 | Blahnik et al. |
| 9,931,539 B1 | 4/2018 | De Pablos et al. |
| 9,940,682 B2 | 4/2018 | Hoffman et al. |
| 10,056,006 B1 | 8/2018 | Hsu-Hoffman et al. |
| 10,105,573 B2 | 10/2018 | Park et al. |
| 10,220,258 B2 | 3/2019 | Gu et al. |
| 10,226,195 B2 | 3/2019 | Briante et al. |
| 10,272,294 B2 | 4/2019 | Williams et al. |
| 10,300,334 B1 | 5/2019 | Chuang |
| 10,304,347 B2 | 5/2019 | Wilson et al. |
| 10,339,830 B2 | 7/2019 | Han et al. |
| 10,398,381 B1 | 9/2019 | Heneghan et al. |
| 10,489,508 B2 | 11/2019 | Zhai et al. |
| 10,500,441 B2 | 12/2019 | Lagree |
| 10,639,521 B2 | 5/2020 | Foley et al. |
| 10,736,543 B2 | 8/2020 | Chen et al. |
| 10,777,314 B1 | 9/2020 | Williams et al. |
| 10,898,132 B2 | 1/2021 | White et al. |
| 10,978,195 B2 | 4/2021 | Blahnik et al. |
| 11,103,161 B2 | 8/2021 | Williams et al. |
| 11,107,567 B2 | 8/2021 | Blahnik et al. |
| 11,107,569 B1 | 8/2021 | Devoto |
| 11,152,100 B2 | 10/2021 | Crowley et al. |
| 11,202,598 B2 | 12/2021 | Soli et al. |
| 11,209,957 B2 | 12/2021 | Dryer et al. |
| 11,216,119 B2 | 1/2022 | De Vries et al. |
| 11,317,833 B2 | 5/2022 | Williams et al. |
| 11,446,548 B2 | 9/2022 | Devine et al. |
| 11,452,915 B2 | 9/2022 | Devine et al. |
| 11,458,363 B2 | 10/2022 | Powers et al. |
| 11,529,074 B2 | 12/2022 | Vaterlaus |
| 11,801,423 B2 | 10/2023 | Bissonnette et al. |
| 2001/0049470 A1 | 12/2001 | Mault et al. |
| 2002/0045960 A1 | 4/2002 | Phillips et al. |
| 2002/0086774 A1 | 7/2002 | Warner |
| 2002/0118121 A1 | 8/2002 | Lehrman et al. |
| 2003/0023178 A1 | 1/2003 | Bischoff et al. |
| 2003/0064860 A1 | 4/2003 | Yamashita et al. |
| 2003/0134714 A1 | 7/2003 | Oishi et al. |
| 2003/0179229 A1 | 9/2003 | Van et al. |
| 2003/0181291 A1 | 9/2003 | Ogawa |
| 2003/0182628 A1 | 9/2003 | Lira |
| 2003/0216971 A1 | 11/2003 | Sick et al. |
| 2003/0226695 A1 | 12/2003 | Mault |
| 2004/0014567 A1 | 1/2004 | Mendel |
| 2004/0077462 A1 | 4/2004 | Brown et al. |
| 2004/0128286 A1 | 7/2004 | Yasushi et al. |
| 2004/0236189 A1 | 11/2004 | Hawthorne et al. |
| 2005/0015803 A1 | 1/2005 | Macrae et al. |
| 2005/0075214 A1 | 4/2005 | Brown et al. |
| 2005/0079905 A1 | 4/2005 | Martens |
| 2005/0113650 A1 | 5/2005 | Pacione et al. |
| 2005/0124324 A1 | 6/2005 | Thomas et al. |
| 2005/0130802 A1 | 6/2005 | Kinnunen et al. |
| 2005/0139852 A1 | 6/2005 | Chen et al. |
| 2005/0165627 A1 | 7/2005 | Fotsch et al. |
| 2005/0171410 A1 | 8/2005 | Hjelt et al. |
| 2005/0172311 A1 | 8/2005 | Hjelt et al. |
| 2005/0190059 A1 | 9/2005 | Wehrenberg |
| 2005/0197063 A1 | 9/2005 | White et al. |
| 2005/0215848 A1 | 9/2005 | Lorenzato et al. |
| 2005/0216867 A1 | 9/2005 | Marvit et al. |
| 2005/0228735 A1 | 10/2005 | Duquette |
| 2005/0272564 A1 | 12/2005 | Pyles et al. |
| 2006/0017692 A1 | 1/2006 | Wehrenberg et al. |
| 2006/0020174 A1 | 1/2006 | Matsumura et al. |
| 2006/0047208 A1 | 3/2006 | Yoon |
| 2006/0048076 A1 | 3/2006 | Vronay et al. |
| 2006/0052727 A1 | 3/2006 | Palestrant |
| 2006/0098109 A1 | 5/2006 | Ooki |
| 2006/0106741 A1 | 5/2006 | Janarthanan |
| 2006/0117014 A1 | 6/2006 | Qi |
| 2006/0160090 A1 | 7/2006 | Macina et al. |
| 2006/0184800 A1 | 8/2006 | Rosenberg |
| 2006/0240959 A1 | 10/2006 | Huang |
| 2006/0250524 A1 | 11/2006 | Roche |
| 2007/0016091 A1 | 1/2007 | Butt et al. |
| 2007/0021269 A1 | 1/2007 | Shum |
| 2007/0032733 A1 | 2/2007 | Burton |
| 2007/0033069 A1 | 2/2007 | Rao et al. |
| 2007/0056727 A1 | 3/2007 | Newman |
| 2007/0071256 A1 | 3/2007 | Ito |

(56) References Cited

U.S. PATENT DOCUMENTS

| | | |
|---|---|---|
| 2007/0113726 A1 | 5/2007 | Oliver et al. |
| 2007/0136093 A1 | 6/2007 | Rankin et al. |
| 2007/0143433 A1 | 6/2007 | Daigle |
| 2007/0169614 A1 | 7/2007 | Sasaki et al. |
| 2007/0249949 A1 | 10/2007 | Hadley |
| 2007/0271065 A1 | 11/2007 | Gupta et al. |
| 2008/0020803 A1 | 1/2008 | Rios et al. |
| 2008/0027673 A1 | 1/2008 | Trumm |
| 2008/0051919 A1 | 2/2008 | Sakal et al. |
| 2008/0052945 A1 | 3/2008 | Matas et al. |
| 2008/0058626 A1 | 3/2008 | Miyata et al. |
| 2008/0076637 A1 | 3/2008 | Gilley et al. |
| 2008/0077026 A1 | 3/2008 | Banet et al. |
| 2008/0082145 A1 | 4/2008 | Skwarek et al. |
| 2008/0086318 A1 | 4/2008 | Gilley et al. |
| 2008/0096726 A1 | 4/2008 | Riley et al. |
| 2008/0141135 A1 | 6/2008 | Mason et al. |
| 2008/0150731 A1 | 6/2008 | Laukkanen et al. |
| 2008/0161161 A1 | 7/2008 | Pipinich et al. |
| 2008/0161707 A1 | 7/2008 | Farringdon et al. |
| 2008/0195600 A1 | 8/2008 | Deakter |
| 2008/0200312 A1 | 8/2008 | Tagliabue |
| 2008/0229226 A1 | 9/2008 | Rowbottom et al. |
| 2008/0254767 A1 | 10/2008 | Jin |
| 2008/0262946 A1 | 10/2008 | Wren |
| 2008/0278333 A1 | 11/2008 | Fennell et al. |
| 2008/0300110 A1 | 12/2008 | Smith et al. |
| 2009/0007017 A1 | 1/2009 | Anzures et al. |
| 2009/0012821 A1 | 1/2009 | Besson et al. |
| 2009/0012988 A1 | 1/2009 | Brown |
| 2009/0047645 A1 | 2/2009 | Dibenedetto et al. |
| 2009/0075782 A1 | 3/2009 | Joubert et al. |
| 2009/0106685 A1 | 4/2009 | Care et al. |
| 2009/0118100 A1 | 5/2009 | Oliver et al. |
| 2009/0144639 A1 | 6/2009 | Nims et al. |
| 2009/0149299 A1 | 6/2009 | Tchao et al. |
| 2009/0158167 A1 | 6/2009 | Wang et al. |
| 2009/0164567 A1 | 6/2009 | Hara |
| 2009/0170532 A1 | 7/2009 | Lee et al. |
| 2009/0192823 A1 | 7/2009 | Hawkins et al. |
| 2009/0210078 A1 | 8/2009 | Crowley |
| 2009/0216556 A1 | 8/2009 | Martin et al. |
| 2009/0222056 A1 | 9/2009 | Lindh et al. |
| 2009/0222761 A1 | 9/2009 | Hayashi |
| 2009/0233771 A1 | 9/2009 | Quatrochi et al. |
| 2009/0249076 A1 | 10/2009 | Reed et al. |
| 2009/0259134 A1 | 10/2009 | Levine |
| 2009/0262088 A1 | 10/2009 | Moll-Carrillo et al. |
| 2009/0268949 A1 | 10/2009 | Ueshima et al. |
| 2009/0287103 A1 | 11/2009 | Pillai |
| 2009/0291805 A1 | 11/2009 | Blum et al. |
| 2009/0292561 A1 | 11/2009 | Itoh |
| 2009/0319243 A1 | 12/2009 | Suarez-Rivera et al. |
| 2010/0030094 A1 | 2/2010 | Lundback |
| 2010/0031202 A1 | 2/2010 | Morris et al. |
| 2010/0042949 A1 | 2/2010 | Chen |
| 2010/0048358 A1 | 2/2010 | Tchao et al. |
| 2010/0060586 A1 | 3/2010 | Pisula et al. |
| 2010/0062818 A1 | 3/2010 | Haughay et al. |
| 2010/0062905 A1 | 3/2010 | Rottler et al. |
| 2010/0064255 A1 | 3/2010 | Rottler et al. |
| 2010/0076331 A1 | 3/2010 | Chan et al. |
| 2010/0079291 A1 | 4/2010 | Kroll et al. |
| 2010/0103101 A1 | 4/2010 | Song et al. |
| 2010/0121700 A1 | 5/2010 | Wigder et al. |
| 2010/0130890 A1 | 5/2010 | Matsumura et al. |
| 2010/0137106 A1 | 6/2010 | Oshima et al. |
| 2010/0145209 A1 | 6/2010 | Lee et al. |
| 2010/0152600 A1 | 6/2010 | Droitcour et al. |
| 2010/0179832 A1 | 7/2010 | Van et al. |
| 2010/0179833 A1 | 7/2010 | Roizen et al. |
| 2010/0184564 A1 | 7/2010 | Molyneux et al. |
| 2010/0194692 A1 | 8/2010 | Orr et al. |
| 2010/0197463 A1 | 8/2010 | Haughay et al. |
| 2010/0198453 A1 | 8/2010 | Dorogusker et al. |
| 2010/0222859 A1 | 9/2010 | Govari et al. |
| 2010/0231612 A1 | 9/2010 | Chaudhri et al. |
| 2010/0264097 A1 | 10/2010 | Sun et al. |
| 2010/0269055 A1 | 10/2010 | Daikeler et al. |
| 2010/0269157 A1 | 10/2010 | Experton |
| 2010/0273610 A1 | 10/2010 | Johnson |
| 2010/0281374 A1 | 11/2010 | Schulz et al. |
| 2010/0292599 A1 | 11/2010 | Oleson et al. |
| 2010/0292600 A1 | 11/2010 | Dibenedetto et al. |
| 2010/0298899 A1 | 11/2010 | Donnelly et al. |
| 2010/0305965 A1 | 12/2010 | Benjamin et al. |
| 2010/0309149 A1 | 12/2010 | Blumenberg et al. |
| 2010/0331145 A1 | 12/2010 | Lakovic et al. |
| 2011/0003665 A1 | 1/2011 | Burton et al. |
| 2011/0016120 A1 | 1/2011 | Haughay et al. |
| 2011/0032105 A1 | 2/2011 | Hoffman et al. |
| 2011/0052005 A1 | 3/2011 | Selner |
| 2011/0066051 A1 | 3/2011 | Moon et al. |
| 2011/0071869 A1 | 3/2011 | Obrien et al. |
| 2011/0074699 A1 | 3/2011 | Marr et al. |
| 2011/0087076 A1 | 4/2011 | Brynelsen et al. |
| 2011/0098928 A1 | 4/2011 | Hoffman et al. |
| 2011/0106553 A1 | 5/2011 | Tanaka et al. |
| 2011/0112418 A1 | 5/2011 | Feild et al. |
| 2011/0113430 A1 | 5/2011 | Fuse |
| 2011/0125041 A1 | 5/2011 | Fischell et al. |
| 2011/0137678 A1 | 6/2011 | Williams |
| 2011/0137836 A1 | 6/2011 | Kuriyama et al. |
| 2011/0159469 A1 | 6/2011 | Hwang et al. |
| 2011/0167369 A1 | 7/2011 | Van |
| 2011/0201911 A1 | 8/2011 | Johnson et al. |
| 2011/0213276 A1 | 9/2011 | Sarussi et al. |
| 2011/0227872 A1 | 9/2011 | Huska et al. |
| 2011/0230169 A1 | 9/2011 | Ohki |
| 2011/0230986 A1 | 9/2011 | Lafortune et al. |
| 2011/0246509 A1 | 10/2011 | Migita et al. |
| 2011/0257638 A1 | 10/2011 | Boukhny et al. |
| 2011/0261079 A1 | 10/2011 | Ingrassia et al. |
| 2011/0275940 A1 | 11/2011 | Nims et al. |
| 2011/0281249 A1 | 11/2011 | Gammell et al. |
| 2011/0306389 A1 | 12/2011 | Nagayama |
| 2011/0307821 A1 | 12/2011 | Martens |
| 2012/0015778 A1 | 1/2012 | Lee et al. |
| 2012/0015779 A1 | 1/2012 | Powch et al. |
| 2012/0022884 A1 | 1/2012 | Chillemi |
| 2012/0030623 A1 | 2/2012 | Hoellwarth |
| 2012/0034897 A1 | 2/2012 | Kreitzer et al. |
| 2012/0041767 A1 | 2/2012 | Hoffman et al. |
| 2012/0042039 A1 | 2/2012 | Mark |
| 2012/0046784 A1 | 2/2012 | Malina et al. |
| 2012/0059664 A1 | 3/2012 | Georgiev et al. |
| 2012/0060118 A1 | 3/2012 | Gupta et al. |
| 2012/0071770 A1 | 3/2012 | Grey et al. |
| 2012/0092379 A1 | 4/2012 | Tsuji et al. |
| 2012/0092383 A1 | 4/2012 | Hysek et al. |
| 2012/0105225 A1 | 5/2012 | Valtonen |
| 2012/0116550 A1 | 5/2012 | Hoffman et al. |
| 2012/0116684 A1 | 5/2012 | Ingrassia et al. |
| 2012/0119911 A1 | 5/2012 | Jeon et al. |
| 2012/0143094 A1 | 6/2012 | Jallon |
| 2012/0143095 A1 | 6/2012 | Nakamura |
| 2012/0150759 A1 | 6/2012 | Tarjan |
| 2012/0159380 A1 | 6/2012 | Kocienda et al. |
| 2012/0169882 A1 | 7/2012 | Millar et al. |
| 2012/0171649 A1 | 7/2012 | Wander et al. |
| 2012/0179278 A1 | 7/2012 | Riley et al. |
| 2012/0179319 A1 | 7/2012 | Gilman et al. |
| 2012/0215328 A1 | 8/2012 | Schmelzer |
| 2012/0232414 A1 | 9/2012 | Mollicone et al. |
| 2012/0251079 A1 | 10/2012 | Meschter et al. |
| 2012/0253485 A1 | 10/2012 | Weast et al. |
| 2012/0253488 A1 | 10/2012 | Shaw et al. |
| 2012/0254263 A1 | 10/2012 | Hiestermann et al. |
| 2012/0274508 A1 | 11/2012 | Brown et al. |
| 2012/0283855 A1 | 11/2012 | Hoffman et al. |
| 2012/0290109 A1 | 11/2012 | Engelberg et al. |
| 2012/0302840 A1 | 11/2012 | Kubo |
| 2012/0302843 A1 | 11/2012 | Otsubo et al. |
| 2012/0310389 A1 | 12/2012 | Martin |

(56) References Cited

U.S. PATENT DOCUMENTS

| | | |
|---|---|---|
| 2012/0313776 A1 | 12/2012 | Utter, II |
| 2012/0317167 A1 | 12/2012 | Rahman et al. |
| 2012/0317430 A1 | 12/2012 | Rahman et al. |
| 2012/0323129 A1 | 12/2012 | Fujita et al. |
| 2012/0326873 A1 | 12/2012 | Utter, II |
| 2013/0053990 A1 | 2/2013 | Ackland |
| 2013/0054150 A1 | 2/2013 | Sacks et al. |
| 2013/0054720 A1 | 2/2013 | Kang et al. |
| 2013/0067050 A1 | 3/2013 | Kotteri et al. |
| 2013/0081083 A1 | 3/2013 | Yu et al. |
| 2013/0093715 A1 | 4/2013 | Marsden et al. |
| 2013/0106603 A1 | 5/2013 | Weast et al. |
| 2013/0106684 A1 | 5/2013 | Weast et al. |
| 2013/0110264 A1 | 5/2013 | Weast et al. |
| 2013/0115583 A1 | 5/2013 | Gordon et al. |
| 2013/0132028 A1 | 5/2013 | Crankson et al. |
| 2013/0137073 A1 | 5/2013 | Nacey et al. |
| 2013/0138734 A1 | 5/2013 | Crivello et al. |
| 2013/0141233 A1 | 6/2013 | Jacobs et al. |
| 2013/0142495 A1 | 6/2013 | Terai |
| 2013/0151285 A1 | 6/2013 | Mclaren et al. |
| 2013/0158367 A1 | 6/2013 | Pacione et al. |
| 2013/0184613 A1 | 7/2013 | Homsi et al. |
| 2013/0185097 A1 | 7/2013 | Saria et al. |
| 2013/0187923 A1 | 7/2013 | Yoshimoto et al. |
| 2013/0188322 A1 | 7/2013 | Lowe et al. |
| 2013/0191034 A1 | 7/2013 | Weast et al. |
| 2013/0197679 A1 | 8/2013 | Balakrishnan et al. |
| 2013/0198672 A1 | 8/2013 | Yoon et al. |
| 2013/0203475 A1 | 8/2013 | Shin et al. |
| 2013/0209972 A1 | 8/2013 | Carter et al. |
| 2013/0215119 A1 | 8/2013 | Vanhoecke |
| 2013/0217253 A1 | 8/2013 | Golko et al. |
| 2013/0217979 A1 | 8/2013 | Blackadar et al. |
| 2013/0223707 A1 | 8/2013 | Stephenson |
| 2013/0231575 A1 | 9/2013 | Erkkila et al. |
| 2013/0231711 A1 | 9/2013 | Kaib |
| 2013/0233097 A1 | 9/2013 | Hayner et al. |
| 2013/0238287 A1 | 9/2013 | Hoffman et al. |
| 2013/0245966 A1 | 9/2013 | Burroughs et al. |
| 2013/0262155 A1 | 10/2013 | Hinkamp |
| 2013/0263719 A1 | 10/2013 | Watterson et al. |
| 2013/0274904 A1 | 10/2013 | Coza et al. |
| 2013/0324210 A1 | 12/2013 | Doig et al. |
| 2013/0325358 A1 | 12/2013 | Oshima et al. |
| 2013/0325394 A1 | 12/2013 | Yuen et al. |
| 2013/0325396 A1 | 12/2013 | Yuen et al. |
| 2013/0325758 A1 | 12/2013 | Alphin et al. |
| 2013/0330694 A1 | 12/2013 | Watterson |
| 2013/0332286 A1 | 12/2013 | Medelius et al. |
| 2013/0345978 A1 | 12/2013 | Lush et al. |
| 2014/0035761 A1 | 2/2014 | Burton et al. |
| 2014/0037107 A1 | 2/2014 | Marino et al. |
| 2014/0038781 A1 | 2/2014 | Foley et al. |
| 2014/0039840 A1 | 2/2014 | Yuen et al. |
| 2014/0067096 A1 | 3/2014 | Aibara |
| 2014/0081666 A1 | 3/2014 | Teller et al. |
| 2014/0089836 A1 | 3/2014 | Damani et al. |
| 2014/0107524 A1 | 4/2014 | Brull et al. |
| 2014/0108998 A1 | 4/2014 | Chaudhri et al. |
| 2014/0135955 A1 | 5/2014 | Burroughs |
| 2014/0139637 A1 | 5/2014 | Mistry et al. |
| 2014/0143678 A1 | 5/2014 | Mistry et al. |
| 2014/0156292 A1 | 6/2014 | Kozicki et al. |
| 2014/0172460 A1 | 6/2014 | Kohli |
| 2014/0176346 A1 | 6/2014 | Brumback et al. |
| 2014/0176475 A1 | 6/2014 | Myers et al. |
| 2014/0180786 A1 | 6/2014 | Sullivan |
| 2014/0189584 A1 | 7/2014 | Weng et al. |
| 2014/0197946 A1 | 7/2014 | Park et al. |
| 2014/0200691 A1 | 7/2014 | Lee et al. |
| 2014/0213415 A1 | 7/2014 | Parker et al. |
| 2014/0218369 A1 | 8/2014 | Yuen et al. |
| 2014/0221790 A1 | 8/2014 | Pacione et al. |
| 2014/0228647 A1 | 8/2014 | Sakamoto et al. |
| 2014/0239065 A1 | 8/2014 | Zhou et al. |
| 2014/0240122 A1 | 8/2014 | Roberts et al. |
| 2014/0240349 A1 | 8/2014 | Tuukkanen |
| 2014/0244009 A1 | 8/2014 | Mestas |
| 2014/0245161 A1 | 8/2014 | Yuen et al. |
| 2014/0257537 A1 | 9/2014 | Stroupe et al. |
| 2014/0266731 A1 | 9/2014 | Malhotra |
| 2014/0274413 A1 | 9/2014 | Chelst |
| 2014/0275852 A1 | 9/2014 | Hong et al. |
| 2014/0275854 A1 | 9/2014 | Venkatraman et al. |
| 2014/0277628 A1 | 9/2014 | Nieminen et al. |
| 2014/0278229 A1 | 9/2014 | Hong et al. |
| 2014/0280498 A1 | 9/2014 | Frankel et al. |
| 2014/0282153 A1 | 9/2014 | Christiansen et al. |
| 2014/0288680 A1 | 9/2014 | Hoffman et al. |
| 2014/0310598 A1 | 10/2014 | Sprague et al. |
| 2014/0310643 A1 | 10/2014 | Karmanenko et al. |
| 2014/0331314 A1 | 11/2014 | Fujioka |
| 2014/0336796 A1 | 11/2014 | Agnew |
| 2014/0337041 A1 | 11/2014 | Madden et al. |
| 2014/0337450 A1 | 11/2014 | Choudhary et al. |
| 2014/0337451 A1 | 11/2014 | Choudhary et al. |
| 2014/0344693 A1 | 11/2014 | Reese et al. |
| 2014/0344723 A1 | 11/2014 | Malik et al. |
| 2014/0344951 A1 | 11/2014 | Brewer |
| 2014/0358473 A1 | 12/2014 | Goel et al. |
| 2014/0358584 A1 | 12/2014 | Worden et al. |
| 2014/0365913 A1 | 12/2014 | Santamaria et al. |
| 2014/0371887 A1 | 12/2014 | Hoffman et al. |
| 2015/0004578 A1 | 1/2015 | Gilley et al. |
| 2015/0011204 A1 | 1/2015 | Seo et al. |
| 2015/0018632 A1 | 1/2015 | Khair |
| 2015/0033149 A1 | 1/2015 | Kuchoor |
| 2015/0046814 A1 | 2/2015 | Haughay et al. |
| 2015/0057942 A1 | 2/2015 | Self et al. |
| 2015/0057943 A1 | 2/2015 | Self et al. |
| 2015/0057945 A1 | 2/2015 | White et al. |
| 2015/0058093 A1 | 2/2015 | Jakobs |
| 2015/0058263 A1 | 2/2015 | Landers |
| 2015/0065095 A1 | 3/2015 | Seo et al. |
| 2015/0065302 A1 | 3/2015 | Ou et al. |
| 2015/0066172 A1 | 3/2015 | Chiang |
| 2015/0067513 A1 | 3/2015 | Zambetti et al. |
| 2015/0067811 A1 | 3/2015 | Agnew et al. |
| 2015/0074571 A1 | 3/2015 | Marti et al. |
| 2015/0081059 A1 | 3/2015 | Hwang et al. |
| 2015/0081060 A1 | 3/2015 | Hwang et al. |
| 2015/0081529 A1 | 3/2015 | Lee et al. |
| 2015/0082167 A1 | 3/2015 | Yeh et al. |
| 2015/0083970 A1 | 3/2015 | Koh et al. |
| 2015/0098309 A1 | 4/2015 | Adams et al. |
| 2015/0100245 A1 | 4/2015 | Huang et al. |
| 2015/0106025 A1 | 4/2015 | Keller et al. |
| 2015/0112700 A1 | 4/2015 | Sublett et al. |
| 2015/0112990 A1 | 4/2015 | Van Os et al. |
| 2015/0113553 A1 | 4/2015 | Pan |
| 2015/0118657 A1 | 4/2015 | Shrake et al. |
| 2015/0124067 A1 | 5/2015 | Bala et al. |
| 2015/0130830 A1 | 5/2015 | Nagasaki et al. |
| 2015/0133748 A1 | 5/2015 | Edmonds et al. |
| 2015/0142689 A1 | 5/2015 | Squires |
| 2015/0153943 A1 | 6/2015 | Wang |
| 2015/0164349 A1 | 6/2015 | Gopalakrishnan et al. |
| 2015/0180746 A1 | 6/2015 | Day et al. |
| 2015/0181314 A1 | 6/2015 | Swanson |
| 2015/0182843 A1 | 7/2015 | Esposito et al. |
| 2015/0185967 A1 | 7/2015 | Ly et al. |
| 2015/0193805 A1 | 7/2015 | Filipiak |
| 2015/0196804 A1 | 7/2015 | Koduri et al. |
| 2015/0196805 A1 | 7/2015 | Koduri et al. |
| 2015/0199494 A1 | 7/2015 | Koduri et al. |
| 2015/0205492 A1 | 7/2015 | Nobil |
| 2015/0205930 A1 | 7/2015 | Shaanan et al. |
| 2015/0217163 A1 | 8/2015 | Amis et al. |
| 2015/0220523 A1 | 8/2015 | Lagree |
| 2015/0220883 A1 | 8/2015 | Bfar et al. |
| 2015/0248535 A1 | 9/2015 | Cho |
| 2015/0251053 A1 | 9/2015 | Hoffman et al. |
| 2015/0262497 A1 | 9/2015 | Landau et al. |

(56) References Cited

U.S. PATENT DOCUMENTS

| | | |
|---|---|---|
| 2015/0269848 A1 | 9/2015 | Yuen et al. |
| 2015/0293592 A1 | 10/2015 | Cheong et al. |
| 2015/0294440 A1 | 10/2015 | Roberts |
| 2015/0297134 A1 | 10/2015 | Albert et al. |
| 2015/0301691 A1 | 10/2015 | Qin |
| 2015/0324751 A1 | 11/2015 | Orenstein et al. |
| 2015/0331589 A1 | 11/2015 | Kawakita |
| 2015/0343709 A1 | 12/2015 | Gerstle et al. |
| 2015/0347711 A1 | 12/2015 | Soli et al. |
| 2015/0350861 A1 | 12/2015 | Soli et al. |
| 2015/0351655 A1 | 12/2015 | Coleman |
| 2015/0364057 A1 | 12/2015 | Catani et al. |
| 2015/0374267 A1 | 12/2015 | Laughlin |
| 2015/0374310 A1 | 12/2015 | Lee |
| 2016/0000379 A1 | 1/2016 | Pougatchev et al. |
| 2016/0004432 A1 | 1/2016 | Bernstein et al. |
| 2016/0015275 A1 | 1/2016 | Samadani et al. |
| 2016/0019360 A1 | 1/2016 | Pahwa et al. |
| 2016/0027282 A1 | 1/2016 | Lee |
| 2016/0034133 A1 | 2/2016 | Wilson et al. |
| 2016/0034148 A1 | 2/2016 | Wilson et al. |
| 2016/0048298 A1 | 2/2016 | Choi et al. |
| 2016/0058331 A1 | 3/2016 | Keen et al. |
| 2016/0058336 A1 | 3/2016 | Blahnik et al. |
| 2016/0058337 A1 | 3/2016 | Blahnik et al. |
| 2016/0062464 A1 | 3/2016 | Moussette et al. |
| 2016/0062582 A1 | 3/2016 | Wilson et al. |
| 2016/0062589 A1 | 3/2016 | Wan et al. |
| 2016/0063748 A1 | 3/2016 | Kim et al. |
| 2016/0065505 A1 | 3/2016 | Iskander |
| 2016/0070275 A1 | 3/2016 | Anderson et al. |
| 2016/0072896 A1 | 3/2016 | Petersen et al. |
| 2016/0085937 A1 | 3/2016 | Dettinger et al. |
| 2016/0098160 A1 | 4/2016 | Groset |
| 2016/0107031 A1 | 4/2016 | Palatsi et al. |
| 2016/0135731 A1 | 5/2016 | Drennan |
| 2016/0140828 A1 | 5/2016 | Deforest |
| 2016/0156584 A1 | 6/2016 | Hum et al. |
| 2016/0193500 A1 | 7/2016 | Webster et al. |
| 2016/0196635 A1 | 7/2016 | Cho et al. |
| 2016/0196759 A1 | 7/2016 | Kim et al. |
| 2016/0203691 A1 | 7/2016 | Arnold et al. |
| 2016/0210099 A1 | 7/2016 | Hampapuram et al. |
| 2016/0210568 A1 | 7/2016 | Krupa et al. |
| 2016/0220225 A1 | 8/2016 | Wang et al. |
| 2016/0235374 A1 | 8/2016 | Miller et al. |
| 2016/0246880 A1 | 8/2016 | Battiah et al. |
| 2016/0249864 A1 | 9/2016 | Kang et al. |
| 2016/0250517 A1 | 9/2016 | Tilvis et al. |
| 2016/0256082 A1 | 9/2016 | Ely et al. |
| 2016/0256741 A1 | 9/2016 | Holma et al. |
| 2016/0263435 A1 | 9/2016 | Venkatraman et al. |
| 2016/0278659 A1 | 9/2016 | Kaib et al. |
| 2016/0278667 A1 | 9/2016 | Villard et al. |
| 2016/0279475 A1 | 9/2016 | Aragones et al. |
| 2016/0296798 A1 | 10/2016 | Balakrishnan et al. |
| 2016/0301794 A1 | 10/2016 | Schlakman et al. |
| 2016/0302680 A1 | 10/2016 | Narusawa et al. |
| 2016/0302717 A1 | 10/2016 | Tawa et al. |
| 2016/0321932 A1 | 11/2016 | Mitchell et al. |
| 2016/0324457 A1 | 11/2016 | Dagum |
| 2016/0328736 A1 | 11/2016 | Wang et al. |
| 2016/0332025 A1 | 11/2016 | Repka |
| 2016/0346607 A1 | 12/2016 | Rapfogel |
| 2016/0371464 A1 | 12/2016 | Bricker |
| 2016/0373631 A1 | 12/2016 | Titi et al. |
| 2016/0375306 A1 | 12/2016 | Gu et al. |
| 2016/0379511 A1 | 12/2016 | Dawson et al. |
| 2017/0001073 A1 | 1/2017 | Krueger et al. |
| 2017/0007882 A1 | 1/2017 | Werner |
| 2017/0011210 A1 | 1/2017 | Cheong et al. |
| 2017/0014037 A1 | 1/2017 | Coppola et al. |
| 2017/0021184 A1 | 1/2017 | Pavel et al. |
| 2017/0024399 A1 | 1/2017 | Boyle et al. |
| 2017/0024539 A1 | 1/2017 | Webb et al. |
| 2017/0032168 A1 | 2/2017 | Kim |
| 2017/0045866 A1 | 2/2017 | Hou et al. |
| 2017/0046108 A1 | 2/2017 | Kang et al. |
| 2017/0053542 A1 | 2/2017 | Wilson et al. |
| 2017/0056722 A1 | 3/2017 | Singh et al. |
| 2017/0065224 A1 | 3/2017 | Rahko et al. |
| 2017/0087412 A1 | 3/2017 | Blahnik |
| 2017/0087469 A1 | 3/2017 | Hardee et al. |
| 2017/0095695 A1 | 4/2017 | Mangusson et al. |
| 2017/0124276 A1 | 5/2017 | Tee |
| 2017/0140143 A1 | 5/2017 | Ahmad et al. |
| 2017/0143262 A1 | 5/2017 | Kurunmäki et al. |
| 2017/0153606 A1 | 6/2017 | Pitis et al. |
| 2017/0153804 A1 | 6/2017 | Kim et al. |
| 2017/0161014 A1 | 6/2017 | Kikugawa et al. |
| 2017/0161462 A1 | 6/2017 | Parker et al. |
| 2017/0177086 A1 | 6/2017 | Yuen et al. |
| 2017/0209766 A1 | 7/2017 | Riley et al. |
| 2017/0237694 A1 | 8/2017 | Choudhary et al. |
| 2017/0239524 A1 | 8/2017 | Lee et al. |
| 2017/0239525 A1 | 8/2017 | Kim et al. |
| 2017/0243508 A1 | 8/2017 | Cheng et al. |
| 2017/0249417 A1 | 8/2017 | Gosieski et al. |
| 2017/0255169 A1 | 9/2017 | Lee et al. |
| 2017/0266494 A1 | 9/2017 | Crankson et al. |
| 2017/0266531 A1 | 9/2017 | Elford et al. |
| 2017/0269792 A1 | 9/2017 | Xu et al. |
| 2017/0274149 A1 | 9/2017 | Aeschlimann |
| 2017/0274267 A1 | 9/2017 | Blahnik |
| 2017/0281026 A1 | 10/2017 | Nick et al. |
| 2017/0281057 A1 | 10/2017 | Blahnik et al. |
| 2017/0294174 A1 | 10/2017 | Albadawi et al. |
| 2017/0300186 A1 | 10/2017 | Kuhar et al. |
| 2017/0301039 A1 | 10/2017 | Dyer et al. |
| 2017/0319941 A1 | 11/2017 | Smith et al. |
| 2017/0329933 A1 | 11/2017 | Brust et al. |
| 2017/0330297 A1 | 11/2017 | Cronin et al. |
| 2017/0333752 A1 | 11/2017 | Korkala et al. |
| 2017/0337033 A1 | 11/2017 | Duyan et al. |
| 2017/0348562 A1 | 12/2017 | Jung et al. |
| 2017/0354845 A1 | 12/2017 | Williams et al. |
| 2017/0357520 A1 | 12/2017 | De Vries et al. |
| 2017/0359623 A1 | 12/2017 | Folse et al. |
| 2018/0000426 A1 | 1/2018 | Li |
| 2018/0001184 A1 | 1/2018 | Tran et al. |
| 2018/0032234 A1 | 2/2018 | Michalske |
| 2018/0036591 A1 | 2/2018 | King et al. |
| 2018/0053200 A1 | 2/2018 | Cronin et al. |
| 2018/0056132 A1 | 3/2018 | Foley et al. |
| 2018/0065025 A1 | 3/2018 | Toda et al. |
| 2018/0074462 A1 | 3/2018 | Helder et al. |
| 2018/0074464 A1 | 3/2018 | Essery et al. |
| 2018/0078182 A1 | 3/2018 | Chen et al. |
| 2018/0085058 A1 | 3/2018 | Chakravarthi et al. |
| 2018/0126248 A1 | 5/2018 | Dion et al. |
| 2018/0133537 A1 | 5/2018 | Montantes |
| 2018/0137937 A1 | 5/2018 | Gass et al. |
| 2018/0140211 A1 | 5/2018 | Nakazawa et al. |
| 2018/0140903 A1 | 5/2018 | Poure et al. |
| 2018/0140927 A1 | 5/2018 | Kito et al. |
| 2018/0150709 A1 | 5/2018 | Ha |
| 2018/0177437 A1 | 6/2018 | Yoshioka |
| 2018/0182491 A1 | 6/2018 | Belliveau et al. |
| 2018/0189077 A1 | 7/2018 | Gupta et al. |
| 2018/0206766 A1 | 7/2018 | Blahnik et al. |
| 2018/0247706 A1 | 8/2018 | Riley et al. |
| 2018/0272190 A1 | 9/2018 | Miura et al. |
| 2018/0294053 A1 | 10/2018 | Runyon et al. |
| 2018/0300037 A1 | 10/2018 | Takeda et al. |
| 2018/0316964 A1 | 11/2018 | Dillon et al. |
| 2018/0318647 A1 | 11/2018 | Foley et al. |
| 2018/0329584 A1 | 11/2018 | Williams et al. |
| 2018/0339195 A1 | 11/2018 | Bernotas |
| 2018/0345078 A1 | 12/2018 | Blahnik et al. |
| 2018/0367484 A1 | 12/2018 | Rodriguez et al. |
| 2019/0008467 A1 | 1/2019 | Averina et al. |
| 2019/0025995 A1 | 1/2019 | Williams |
| 2019/0026011 A1 | 1/2019 | Wang et al. |
| 2019/0034049 A1 | 1/2019 | Williams et al. |

(56) References Cited

U.S. PATENT DOCUMENTS

| | | |
|---|---|---|
| 2019/0034050 A1 | 1/2019 | Williams et al. |
| 2019/0089701 A1 | 3/2019 | Mercury et al. |
| 2019/0102049 A1 | 4/2019 | Anzures et al. |
| 2019/0104951 A1 | 4/2019 | Valys et al. |
| 2019/0126099 A1 | 5/2019 | Hoang |
| 2019/0143194 A1 | 5/2019 | Evancha et al. |
| 2019/0184234 A1 | 6/2019 | Packles et al. |
| 2019/0209777 A1 | 7/2019 | O'Connell et al. |
| 2019/0232110 A1 | 8/2019 | Williams et al. |
| 2019/0232111 A1 | 8/2019 | Williams et al. |
| 2019/0240536 A1 | 8/2019 | Dibenedetto et al. |
| 2019/0274565 A1 | 9/2019 | Soli et al. |
| 2019/0279520 A1 | 9/2019 | Wilson et al. |
| 2019/0336044 A1 | 11/2019 | Williams et al. |
| 2019/0336045 A1 | 11/2019 | Williams et al. |
| 2019/0336827 A1 | 11/2019 | Intonato et al. |
| 2019/0339849 A1 | 11/2019 | Williams et al. |
| 2019/0339860 A1 | 11/2019 | Chen et al. |
| 2019/0342616 A1 | 11/2019 | Domm et al. |
| 2019/0364120 A1 | 11/2019 | Bandela et al. |
| 2019/0387982 A1 | 12/2019 | Buller |
| 2020/0014967 A1 | 1/2020 | Putnam |
| 2020/0026398 A1 | 1/2020 | Kim |
| 2020/0054931 A1 | 2/2020 | Martin et al. |
| 2020/0098278 A1 | 3/2020 | Doti et al. |
| 2020/0101365 A1 | 4/2020 | Wilson et al. |
| 2020/0110814 A1 | 4/2020 | Abuelsaad et al. |
| 2020/0149921 A1 | 5/2020 | Hoffman et al. |
| 2020/0160961 A1 | 5/2020 | Wadhawan et al. |
| 2020/0261011 A1 | 8/2020 | Seppänen et al. |
| 2020/0261763 A1 | 8/2020 | Park et al. |
| 2020/0289919 A1 | 9/2020 | Gruben |
| 2020/0297249 A1 | 9/2020 | Williams et al. |
| 2020/0356242 A1 | 11/2020 | Wilson et al. |
| 2020/0357522 A1 | 11/2020 | Pahwa et al. |
| 2020/0381100 A1 | 12/2020 | Williams et al. |
| 2020/0382613 A1 | 12/2020 | Sundstrom et al. |
| 2021/0001226 A1 | 1/2021 | Suzuki et al. |
| 2021/0007632 A1 | 1/2021 | Blahnik et al. |
| 2021/0007633 A1 | 1/2021 | Blahnik et al. |
| 2021/0008413 A1 | 1/2021 | Asikainen et al. |
| 2021/0042132 A1 | 2/2021 | Park et al. |
| 2021/0093919 A1 | 4/2021 | Lyke et al. |
| 2021/0106873 A1 | 4/2021 | Lee |
| 2021/0110908 A1 | 4/2021 | Blahnik et al. |
| 2021/0113116 A1 | 4/2021 | Chen et al. |
| 2021/0113137 A1 | 4/2021 | Soli et al. |
| 2021/0145321 A1 | 5/2021 | Chen et al. |
| 2021/0191584 A1 | 6/2021 | Williams et al. |
| 2021/0193293 A1 | 6/2021 | Blahnik et al. |
| 2021/0236903 A1 | 8/2021 | Briel |
| 2021/0252337 A1 | 8/2021 | Devine et al. |
| 2021/0252341 A1 | 8/2021 | Devine et al. |
| 2021/0252369 A1 | 8/2021 | Devine et al. |
| 2021/0255747 A1 | 8/2021 | Devine et al. |
| 2021/0255758 A1 | 8/2021 | Devine et al. |
| 2021/0255826 A1 | 8/2021 | Devine et al. |
| 2021/0294438 A1 | 9/2021 | Yang et al. |
| 2021/0316185 A1 | 10/2021 | Mckenna et al. |
| 2021/0350900 A1 | 11/2021 | Blahnik et al. |
| 2021/0352118 A1 | 11/2021 | Ahn et al. |
| 2021/0379447 A1 | 12/2021 | Lee |
| 2021/0394020 A1 | 12/2021 | Killen et al. |
| 2022/0047918 A1 | 2/2022 | Williams et al. |
| 2022/0062707 A1 | 3/2022 | Bedekar et al. |
| 2022/0066902 A1 | 3/2022 | Narra et al. |
| 2022/0121299 A1 | 4/2022 | De Vries et al. |
| 2022/0157184 A1 | 5/2022 | Wilson et al. |
| 2022/0160258 A1 | 5/2022 | Williams et al. |
| 2022/0262485 A1 | 8/2022 | Meschter et al. |
| 2022/0262509 A1 | 8/2022 | Pahwa et al. |
| 2022/0328161 A1 | 10/2022 | Gilravi et al. |
| 2022/0336077 A1 | 10/2022 | Chen et al. |
| 2022/0386901 A1 | 12/2022 | Chen et al. |
| 2023/0012755 A1 | 1/2023 | D'auria et al. |
| 2023/0013809 A1 | 1/2023 | D'auria et al. |
| 2023/0013932 A1 | 1/2023 | Blahnik et al. |
| 2023/0014053 A1 | 1/2023 | Devine et al. |
| 2023/0014290 A1 | 1/2023 | Davydov et al. |
| 2023/0017793 A1 | 1/2023 | Williams et al. |
| 2023/0019337 A1 | 1/2023 | D'auria et al. |
| 2023/0024084 A1 | 1/2023 | D'auria et al. |
| 2023/0025724 A1 | 1/2023 | Gilravi et al. |
| 2023/0027358 A1 | 1/2023 | Williams et al. |
| 2023/0066552 A1 | 3/2023 | Van Os et al. |
| 2023/0107803 A1 | 4/2023 | Dugan |
| 2023/0119253 A1 | 4/2023 | Sundstrom et al. |
| 2023/0136700 A1 | 5/2023 | Williams et al. |
| 2023/0191198 A1 | 6/2023 | Lee et al. |
| 2023/0260416 A1 | 8/2023 | Wilson et al. |
| 2023/0390606 A1 | 12/2023 | Bolton et al. |
| 2023/0390626 A1 | 12/2023 | Bolton et al. |
| 2023/0390627 A1 | 12/2023 | Bolton et al. |
| 2023/0393723 A1 | 12/2023 | Arney et al. |
| 2024/0077309 A1 | 3/2024 | Felton et al. |
| 2024/0081751 A1 | 3/2024 | Murphy et al. |
| 2024/0256115 A1 | 8/2024 | Arney et al. |
| 2024/0257940 A1 | 8/2024 | Williams et al. |

FOREIGN PATENT DOCUMENTS

| | | |
|---|---|---|
| CA | 2826239 C | 1/2017 |
| CN | 1337638 A | 2/2002 |
| CN | 1397904 A | 2/2003 |
| CN | 1523500 A | 8/2004 |
| CN | 1585943 A | 2/2005 |
| CN | 1628609 A | 6/2005 |
| CN | 1767789 A | 5/2006 |
| CN | 1824358 A | 8/2006 |
| CN | 101150810 A | 3/2008 |
| CN | 101219046 A | 7/2008 |
| CN | 101444419 A | 6/2009 |
| CN | 101541387 A | 9/2009 |
| CN | 101651870 A | 2/2010 |
| CN | 101658423 A | 3/2010 |
| CN | 101668482 A | 3/2010 |
| CN | 101836894 A | 9/2010 |
| CN | 101890217 A | 11/2010 |
| CN | 101894206 A | 11/2010 |
| CN | 101910992 A | 12/2010 |
| CN | 101978374 A | 2/2011 |
| CN | 102339201 A | 2/2012 |
| CN | 102438521 A | 5/2012 |
| CN | 102448555 | 5/2012 |
| CN | 102449560 A | 5/2012 |
| CN | 102449561 A | 5/2012 |
| CN | 102449566 A | 5/2012 |
| CN | 102549590 A | 7/2012 |
| CN | 102804238 A | 11/2012 |
| CN | 102814037 A | 12/2012 |
| CN | 102834079 A | 12/2012 |
| CN | 102989159 A | 3/2013 |
| CN | 103003668 A | 3/2013 |
| CN | 103154954 A | 6/2013 |
| CN | 103182175 A | 7/2013 |
| CN | 103210355 A | 7/2013 |
| CN | 103212197 A | 7/2013 |
| CN | 103270540 A | 8/2013 |
| CN | 103294124 A | 9/2013 |
| CN | 103370924 A | 10/2013 |
| CN | 103403627 A | 11/2013 |
| CN | 203276086 U | 11/2013 |
| CN | 103646570 A | 3/2014 |
| CN | 103682785 A | 3/2014 |
| CN | 103701504 A | 4/2014 |
| CN | 104288983 A | 1/2015 |
| CN | 104501043 A | 4/2015 |
| CN | 104508426 A | 4/2015 |
| CN | 104815428 A | 8/2015 |
| CN | 104857692 A | 8/2015 |
| CN | 105187282 A | 12/2015 |
| CN | 105260078 A | 1/2016 |
| CN | 105320454 A | 2/2016 |
| CN | 105392064 A | 3/2016 |

(56) References Cited

FOREIGN PATENT DOCUMENTS

| | | |
|---|---|---|
| CN | 105681328 A | 6/2016 |
| CN | 105808959 A | 7/2016 |
| CN | 106310638 A | 1/2017 |
| CN | 106510719 A | 3/2017 |
| CN | 106537397 A | 3/2017 |
| CN | 106709235 A | 5/2017 |
| CN | 106878550 A | 6/2017 |
| CN | 107469327 A | 12/2017 |
| CN | 107580776 A | 1/2018 |
| CN | 107749310 A | 3/2018 |
| CN | 107921317 A | 4/2018 |
| CN | 108200464 A | 6/2018 |
| CN | 108211310 A | 6/2018 |
| EP | 0943290 A1 | 9/1999 |
| EP | 1559372 A1 | 8/2005 |
| EP | 1935339 A1 | 6/2008 |
| EP | 2025368 A2 | 2/2009 |
| EP | 1964022 B1 | 3/2010 |
| EP | 2309475 A1 | 4/2011 |
| EP | 2407219 A2 | 1/2012 |
| EP | 2529663 A1 | 12/2012 |
| EP | 2631830 A2 | 8/2013 |
| EP | 2728680 A1 | 5/2014 |
| EP | 2733578 A2 | 5/2014 |
| EP | 2993602 A1 | 3/2016 |
| EP | 3117767 A1 | 1/2017 |
| EP | 3122038 A1 | 1/2017 |
| EP | 3130997 A1 | 2/2017 |
| JP | 5-288869 A | 11/1993 |
| JP | 6-187118 A | 7/1994 |
| JP | 8-126632 A | 5/1996 |
| JP | 11-84030 A | 3/1999 |
| JP | 2001-76078 A | 3/2001 |
| JP | 2001-216336 A | 8/2001 |
| JP | 2002-190007 A | 7/2002 |
| JP | 2002-346013 A | 12/2002 |
| JP | 2003-102868 A | 4/2003 |
| JP | 2003-157323 A | 5/2003 |
| JP | 2003-248721 A | 9/2003 |
| JP | 2003-319912 A | 11/2003 |
| JP | 2003-337863 A | 11/2003 |
| JP | 2004-102609 A | 4/2004 |
| JP | 2004-113466 A | 4/2004 |
| JP | 2004-174006 A | 6/2004 |
| JP | 2005-79814 A | 3/2005 |
| JP | 3635663 B2 | 4/2005 |
| JP | 2006-155104 A | 6/2006 |
| JP | 2006-180899 A | 7/2006 |
| JP | 2006-230679 A | 9/2006 |
| JP | 2006-338233 A | 12/2006 |
| JP | 2007-260288 A | 10/2007 |
| JP | 2007-330513 A | 12/2007 |
| JP | 2008-104758 A | 5/2008 |
| JP | 2008-183339 A | 8/2008 |
| JP | 2009-50471 A | 3/2009 |
| JP | 2009-78134 A | 4/2009 |
| JP | 2009-88989 A | 4/2009 |
| JP | 2009-112731 A | 5/2009 |
| JP | 2009-211241 A | 9/2009 |
| JP | 2009-282670 A | 12/2009 |
| JP | 2010-12335 A | 1/2010 |
| JP | 2010-517725 A | 5/2010 |
| JP | 2010-122901 A | 6/2010 |
| JP | 2010-162297 A | 7/2010 |
| JP | 2010-181280 A | 8/2010 |
| JP | 2010-182287 A | 8/2010 |
| JP | 2010-186249 A | 8/2010 |
| JP | 2010-206668 A | 9/2010 |
| JP | 2011-514192 A | 5/2011 |
| JP | 2011-125633 A | 6/2011 |
| JP | 2011-183101 A | 9/2011 |
| JP | 2011-192126 A | 9/2011 |
| JP | 2011-198184 A | 10/2011 |
| JP | 2011-206323 A | 10/2011 |
| JP | 2011-210119 A | 10/2011 |
| JP | 2011-229141 A | 11/2011 |
| JP | 2011-259253 A | 12/2011 |
| JP | 2012-20134 A | 2/2012 |
| JP | 2012-35071 A | 2/2012 |
| JP | 2012-59264 A | 3/2012 |
| JP | 2012-86088 A | 5/2012 |
| JP | 2012-524640 A | 10/2012 |
| JP | 2012-230503 A | 11/2012 |
| JP | 2012-232114 A | 11/2012 |
| JP | 2013-103020 A | 5/2013 |
| JP | 2013-117690 A | 6/2013 |
| JP | 2013-146557 A | 8/2013 |
| JP | 2013-530776 A | 8/2013 |
| JP | 2013-543156 A | 11/2013 |
| JP | 5346115 B1 | 11/2013 |
| JP | 2013-544140 A | 12/2013 |
| JP | 2014-500740 A | 1/2014 |
| JP | 2014-45782 A | 3/2014 |
| JP | 2014-45783 A | 3/2014 |
| JP | 2014-104139 A | 6/2014 |
| JP | 2014-143473 A | 8/2014 |
| JP | 2014-168685 A | 9/2014 |
| JP | 2014-171831 A | 9/2014 |
| JP | 2014-230630 A | 12/2014 |
| JP | 2015-58218 A | 3/2015 |
| JP | 2015-507811 A | 3/2015 |
| JP | 2015-509019 A | 3/2015 |
| JP | 2015-509755 A | 4/2015 |
| JP | 2015-134111 A | 7/2015 |
| JP | 2016-17331 A | 2/2016 |
| JP | 2016-502875 A | 2/2016 |
| JP | 2016-52512 A | 4/2016 |
| JP | 2016-517329 A | 6/2016 |
| JP | 2016-158867 A | 9/2016 |
| JP | 2016-528016 A | 9/2016 |
| JP | 2016-177151 A | 10/2016 |
| JP | 2016-185288 A | 10/2016 |
| JP | 2016-202751 A | 12/2016 |
| JP | 2017-503264 A | 1/2017 |
| JP | 2017-83978 A | 5/2017 |
| JP | 2017-134689 A | 8/2017 |
| JP | 2017-156267 A | 9/2017 |
| JP | 2017-531235 A | 10/2017 |
| JP | 2017-211994 A | 11/2017 |
| JP | 2017-532069 A | 11/2017 |
| JP | 2018-102908 A | 7/2018 |
| JP | 2018-202174 A | 12/2018 |
| JP | 2019-003670 A | 1/2019 |
| KR | 10-2006-0117570 A | 11/2006 |
| KR | 10-2011-0017076 A | 2/2011 |
| KR | 10-2011-0121394 A | 11/2011 |
| KR | 10-2012-0023657 A | 3/2012 |
| KR | 10-2012-0076559 A | 7/2012 |
| KR | 10-2020-098854 A | 9/2012 |
| KR | 10-2012-0132732 A | 12/2012 |
| KR | 10-2013-0043698 A | 5/2013 |
| KR | 10-2013-0097235 A | 9/2013 |
| KR | 10-2013-0111569 A | 10/2013 |
| KR | 10-2013-0111570 A | 10/2013 |
| KR | 10-2013-0135282 A | 12/2013 |
| KR | 10-2015-0026635 A | 3/2015 |
| KR | 10-2015-0062761 A | 6/2015 |
| KR | 10-2016-0027943 A | 3/2016 |
| KR | 10-2016-0084705 A | 7/2016 |
| KR | 10-2016-0105129 A | 9/2016 |
| KR | 10-2016-0142418 A | 12/2016 |
| KR | 10-2017-0003608 A | 1/2017 |
| KR | 10-2017-0020085 A | 2/2017 |
| KR | 10-2017-0029014 A | 3/2017 |
| KR | 10-2017-0032471 A | 3/2017 |
| KR | 10-2018-0026066 A | 3/2018 |
| KR | 10-2019-0022883 A | 3/2019 |
| KR | 10-2019-0141702 A | 12/2019 |
| KR | 10-2228511 B1 | 3/2021 |
| WO | 97/38626 A1 | 10/1997 |
| WO | 99/41682 A2 | 8/1999 |
| WO | 02/27530 A2 | 4/2002 |
| WO | 2005/029242 A2 | 3/2005 |
| WO | 2005/070289 A1 | 8/2005 |

(56) References Cited

FOREIGN PATENT DOCUMENTS

| | | |
|---|---|---|
| WO | 2006/103965 A1 | 10/2006 |
| WO | 2007/081629 A2 | 7/2007 |
| WO | 2009/129402 A1 | 10/2009 |
| WO | 2009/152608 A1 | 12/2009 |
| WO | 2010/126821 A1 | 11/2010 |
| WO | 2010/126825 A1 | 11/2010 |
| WO | 2010/129221 A1 | 11/2010 |
| WO | 2011/072111 A2 | 6/2011 |
| WO | 2011/108335 A1 | 9/2011 |
| WO | 2012/021507 A2 | 2/2012 |
| WO | 2012/036891 A2 | 3/2012 |
| WO | 2012/061438 A2 | 5/2012 |
| WO | 2012/061440 A2 | 5/2012 |
| WO | 2012/078079 A2 | 6/2012 |
| WO | 2012/086910 A1 | 6/2012 |
| WO | 2012/095712 A1 | 7/2012 |
| WO | 2013/052789 A1 | 4/2013 |
| WO | 2013/109762 A1 | 7/2013 |
| WO | 2013/109776 A1 | 7/2013 |
| WO | 2013/109777 A1 | 7/2013 |
| WO | 2013/109916 A1 | 7/2013 |
| WO | 2013/157307 A1 | 10/2013 |
| WO | 2013/169870 A1 | 11/2013 |
| WO | 2013/173838 A2 | 11/2013 |
| WO | 2014/059259 A1 | 4/2014 |
| WO | 2014/105276 A1 | 7/2014 |
| WO | 2014/200730 A1 | 12/2014 |
| WO | 2014/207294 A1 | 12/2014 |
| WO | 2015/027178 A1 | 2/2015 |
| WO | 2015027133 A1 | 2/2015 |
| WO | 2015/179592 A1 | 11/2015 |
| WO | 2015/183828 A1 | 12/2015 |
| WO | 2015/198488 A1 | 12/2015 |
| WO | 2016/022203 A1 | 2/2016 |
| WO | 2016/025036 A1 | 2/2016 |
| WO | 2016/036472 A1 | 3/2016 |
| WO | 2016/036582 A2 | 3/2016 |
| WO | 2016/036582 A3 | 6/2016 |
| WO | 2017/014403 A1 | 1/2017 |
| WO | 2017/030646 A1 | 2/2017 |
| WO | 2017/037242 A1 | 3/2017 |
| WO | 2018/048510 A1 | 3/2018 |
| WO | 2018/213066 A1 | 11/2018 |
| WO | 2018/222313 A1 | 12/2018 |
| WO | 2018/236291 A1 | 12/2018 |
| WO | 2019/017508 A1 | 1/2019 |
| WO | 2019/024383 A1 | 2/2019 |
| WO | 2019/024603 A1 | 2/2019 |
| WO | 2019/183422 A1 | 9/2019 |
| WO | 2019/190001 A1 | 10/2019 |
| WO | 2019/217249 A2 | 11/2019 |
| WO | 2019/231982 A1 | 12/2019 |

OTHER PUBLICATIONS

Extended European Search Report received for European Patent Application No. 23192409.3, mailed on Feb. 20, 2024, 13 pages.
Non-Final Office Action received for U.S. Appl. No. 17/952,133, mailed on Feb. 28, 2024, 22 pages.
Notice of Acceptance received for Australian Patent Application No. 2023237090, mailed on Feb. 23, 2024, 3 pages.
Notice of Allowance received for U.S. Appl. No. 17/892,534, mailed on Feb. 21, 2024, 7 pages.
Corrected Notice of Allowance received for U.S. Appl. No. 17/952,181, mailed on Aug. 13, 2024, 2 pages.
Extended European Search Report received for European Patent Application No. 24179066.6, mailed on Aug. 8, 2024, 10 pages.
Notice of Acceptance received for Australian Patent Application No. 2023210876, mailed on Aug. 20, 2024, 3 pages.
Notice of Allowance received for Japanese Patent Application No. 2023-065859, mailed on Aug. 16, 2024, 4 pages (1 page of English Translation and 3 pages of Official Copy).
Notice of Allowance received for Chinese Patent Application No. 202310828052.7, mailed on Jul. 29, 2024, 4 pages (1 page of English Translation and 3 pages of Official Copy).
Notice of Allowance received for Korean Patent Application No. 10-2022-7026884, mailed on Jul. 30, 2024, 8 pages (2 pages of English Translation and 6 pages of Official Copy).
Notice of Allowance received for Korean Patent Application No. 10-2023-7025320, mailed on Jul. 31, 2024, 7 pages (2 pages of English Translation and 5 pages of Official Copy).
Notice of Allowance received for U.S. Appl. No. 17/952,181, mailed on Jul. 26, 2024, 5 pages.
Office Action received for Chinese Patent Application No. 202210312775.7, mailed on Jun. 19, 2024, 13 pages (6 pages of English Translation and 7 pages of Official Copy).
Office Action received for Chinese Patent Application No. 202211193170.7, mailed on Jul. 12, 2024, 22 pages (12 pages of English Translation and 10 pages of Official Copy).
Office Action received for Chinese Patent Application No. 202310774963.6, mailed on Jul. 17, 2024, 21 pages (13 pages of English Translation and 8 pages of Official Copy).
Office Action received for Japanese Patent Application No. 2023-158326, mailed on Jul. 25, 2024, 6 pages (3 pages of English Translation and 3 pages of Official Copy).
Adeniyi Samuel, "How to connect a second PS4 controller to a PlayStation 4 console", Online available on:- https://www.youtube.com/watch?v=mOZX SINISE, May 28, 2017, 2 pages.
Advisory Action received for U.S. Appl. No. 16/144,864, mailed on Jul. 29, 2019, 6 pages.
Advisory Action received for U.S. Appl. No. 14/732,773, mailed on Aug. 23, 2019, 6 pages.
Advisory Action received for U.S. Appl. No. 14/732,773, mailed on Nov. 9, 2018, 6 pages.
Advisory Action received for U.S. Appl. No. 14/839,922, mailed on Mar. 24, 2017, 4 pages.
Advisory Action received for U.S. Appl. No. 16/144,849, mailed on Aug. 12, 2019, 5 pages.
Advisory Action received for U.S. Appl. No. 16/144,864, mailed on Jul. 8, 2020, 6 pages.
Advisory Action received for U.S. Appl. No. 16/377,892, mailed on Apr. 9, 2021, 4 pages.
Advisory Action received for U.S. Appl. No. 16/378,136, mailed on Apr. 12, 2021, 4 pages.
Advisory Action received for U.S. Appl. No. 17/381,570, mailed on May 23, 2023, 5 pages.
Allen Ray, "Join the Nike Training Club and let your iPhone be your fitness instructor", Apr. 19, 2011, 26 pages.
Allison Conor, "Working out with Fiit's wearable-powered boutique fitness classes", Online available at:- <https://www.wareable.com/wearable-tech/fiit-fitness-classes-review-3849>, May 14, 2018, 8 pages.
Androidandyuk, "Endomondo Android App Review", Available online at: https://www.youtube.com/watch?v=Wyjyrza-P1E, Jan. 9, 2013, 17 pages.
Apple, "iPhone User's Guide", Available at <http://mesnotices.20minutes.fr/manuel-notice-mode-emploi/APPLE/IPHONE%2D%5FE#>, Retrieved on Mar. 27, 2008, Jun. 2007, 137 pages.
Applicant Initiated Interview Summary received for U.S. Appl. No. 16/994,352, mailed on Nov. 2, 2021, 4 pages.
Applicant Initiated Interview Summary received for U.S. Appl. No. 15/608,848, mailed on Apr. 13, 2021, 4 pages.
Applicant Initiated Interview Summary received for U.S. Appl. No. 15/608,848, mailed on May 12, 2020, 5 pages.
Applicant Initiated Interview Summary received for U.S. Appl. No. 15/608,848, mailed on Oct. 26, 2020, 3 pages.
Applicant Initiated Interview Summary received for U.S. Appl. No. 15/627,069, mailed on Nov. 4, 2019, 6 pages.
Applicant Initiated Interview Summary received for U.S. Appl. No. 16/144,735, mailed on Jun. 18, 2020, 3 pages.
Applicant Initiated Interview Summary received for U.S. Appl. No. 16/144,753, mailed on Jun. 18, 2020, 3 pages.
Applicant Initiated Interview Summary received for U.S. Appl. No. 16/144,849, mailed on Jan. 21, 2020, 6 pages.

(56) References Cited

OTHER PUBLICATIONS

Applicant Initiated Interview Summary received for U.S. Appl. No. 16/144,864, mailed on Apr. 29, 2020, 4 pages.
Applicant Initiated Interview Summary received for U.S. Appl. No. 16/894,309, mailed on Jan. 26, 2021, 3 pages.
Applicant Initiated Interview Summary received for U.S. Appl. No. 17/030,318, mailed on Jul. 30, 2021, 4 pages.
Applicant Initiated Interview Summary received for U.S. Appl. No. 17/030,321, mailed on Jul. 30, 2021, 2 pages.
Applicant Initiated Interview Summary received for U.S. Appl. No. 17/381,570, mailed on Apr. 26, 2022, 5 pages.
Applicant-Initiated Interview Summary received for U.S. Appl. No. 15/600,243, mailed on Nov. 1, 2019, 6 pages.
Applicant Initiated Interview Summary received for U.S. Appl. No. 15/608,848, mailed on Nov. 1, 2019, 3 pages.
Applicant Initiated Interview Summary received for U.S. Appl. No. 15/627,069, mailed on Jan. 22, 2021, 4 pages.
Applicant-Initiated Interview Summary received for U.S. Appl. No. 15/627,069, mailed on Jul. 20, 2020, 5 pages.
Applicant-Initiated Interview Summary received for U.S. Appl. No. 15/705,849, mailed on Feb. 14, 2020, 3 pages.
Applicant Initiated Interview Summary received for U.S. Appl. No. 15/705,849, mailed on Jun. 29, 2020, 3 pages.
Applicant-Initiated Interview Summary received for U.S. Appl. No. 15/925,652, mailed on Nov. 3, 2020, 4 pages.
Applicant-Initiated Interview Summary received for U.S. Appl. No. 16/138,809, mailed on Dec. 16, 2020, 7 pages.
Applicant-Initiated Interview Summary received for U.S. Appl. No. 16/138,809, mailed on Jun. 9, 2020, 4 pages.
Applicant-Initiated Interview Summary received for U.S. Appl. No. 16/144,753, mailed on Nov. 4, 2020, 3 pages.
Applicant-Initiated Interview Summary received for U.S. Appl. No. 16/144,862, mailed on Jun. 22, 2020, 3 pages.
Applicant-Initiated Interview Summary received for U.S. Appl. No. 16/377,892, mailed on Mar. 26, 2021, 2 pages.
Applicant-Initiated Interview Summary received for U.S. Appl. No. 16/377,892, mailed on Oct. 13, 2020, 5 pages.
Applicant-Initiated Interview Summary received for U.S. Appl. No. 16/378,136, mailed on Mar. 26, 2021, 2 pages.
Applicant-Initiated Interview Summary received for U.S. Appl. No. 16/378,136, mailed on Oct. 13, 2020, 4 pages.
Applicant-Initiated Interview Summary received for U.S. Appl. No. 16/418,786, mailed on Mar. 30, 2021, 4 pages.
Applicant-Initiated Interview Summary received for U.S. Appl. No. 16/418,786, mailed on May 9, 2022, 2 pages.
Applicant-Initiated Interview Summary received for U.S. Appl. No. 16/418,786, mailed on Sep. 23, 2022, 2 pages.
Applicant-Initiated Interview Summary received for U.S. Appl. No. 16/820,383, mailed on Aug. 12, 2022, 2 pages.
Applicant-Initiated Interview Summary received for U.S. Appl. No. 16/820,383, mailed on Mar. 11, 2021, 2 pages.
Applicant-Initiated Interview Summary received for U.S. Appl. No. 16/820,383, mailed on May 10, 2022, 2 pages.
Applicant-Initiated Interview Summary received for U.S. Appl. No. 16/888,629, mailed on Aug. 4, 2021, 5 pages.
Applicant-Initiated Interview Summary received for U.S. Appl. No. 16/894,309, mailed on Jun. 25, 2021, 4 pages.
Applicant-Initiated Interview Summary received for U.S. Appl. No. 16/987,275, mailed on Feb. 3, 2022, 4 pages.
Applicant-Initiated Interview Summary received for U.S. Appl. No. 17/030,337, mailed on Jul. 27, 2022, 2 pages.
Applicant-Initiated Interview Summary received for U.S. Appl. No. 17/031,543, mailed on Apr. 21, 2022, 2 pages.
Applicant-Initiated Interview Summary received for U.S. Appl. No. 17/031,854, mailed on Apr. 6, 2023, 5 pages.
Applicant-Initiated Interview Summary received for U.S. Appl. No. 17/031,854, mailed on Feb. 25, 2022, 5 pages.
Applicant-Initiated Interview Summary received for U.S. Appl. No. 17/031,854, mailed on Jan. 24, 2023, 6 pages.
Applicant-Initiated Interview Summary received for U.S. Appl. No. 17/031,854, mailed on Jul. 27, 2022, 5 pages.
Applicant-Initiated Interview Summary received for U.S. Appl. No. 17/031,859, mailed on Aug. 1, 2023, 4 pages.
Applicant-Initiated Interview Summary received for U.S. Appl. No. 17/031,859, mailed on Dec. 27, 2022, 5 pages.
Applicant-Initiated Interview Summary received for U.S. Appl. No. 17/031,859, mailed on Feb. 25, 2022, 4 pages.
Applicant-Initiated Interview Summary received for U.S. Appl. No. 17/031,859, mailed on Feb. 26, 2021, 4 pages.
Applicant-Initiated Interview Summary received for U.S. Appl. No. 17/031,859, mailed on Jul. 28, 2022, 3 pages.
Applicant-Initiated Interview Summary received for U.S. Appl. No. 17/031,859, mailed on Jun. 30, 2021, 4 pages.
Applicant-Initiated Interview Summary received for U.S. Appl. No. 17/031,859, mailed on Mar. 3, 2023, 5 pages.
Applicant-Initiated Interview Summary received for U.S. Appl. No. 17/031,874, mailed on Feb. 25, 2022, 4 pages.
Applicant-Initiated Interview Summary received for U.S. Appl. No. 17/031,874, mailed on Feb. 26, 2021, 4 pages.
Applicant-Initiated Interview Summary received for U.S. Appl. No. 17/031,874, mailed on Jan. 24, 2023, 5 pages.
Applicant-Initiated Interview Summary received for U.S. Appl. No. 17/031,874, mailed on Jul. 27, 2022, 5 pages.
Applicant-Initiated Interview Summary received for U.S. Appl. No. 17/031,874, mailed on Jun. 30, 2021, 4 pages.
Applicant-Initiated Interview Summary received for U.S. Appl. No. 17/041,438, mailed on Jun. 23, 2023, 4 pages.
Applicant-Initiated Interview Summary received for U.S. Appl. No. 17/157,728, mailed on Feb. 3, 2022, 5 pages.
Applicant-Initiated Interview Summary received for U.S. Appl. No. 17/192,161, mailed on Dec. 24, 2021, 4 pages.
Applicant-Initiated Interview Summary received for U.S. Appl. No. 17/192,161, mailed on Jun. 29, 2021, 4 pages.
Applicant-Initiated Interview Summary received for U.S. Appl. No. 17/192,161, mailed on Sep. 29, 2021, 3 pages.
Applicant-Initiated Interview Summary received for U.S. Appl. No. 17/381,570, mailed on Aug. 24, 2022, 5 pages.
Applicant-Initiated Interview Summary received for U.S. Appl. No. 17/381,570, mailed on Nov. 28, 2022, 5 pages.
Applicant-Initiated Interview Summary received for U.S. Appl. No. 17/516,537, mailed on Jul. 5, 2022, 4 pages.
Applicant-Initiated Interview Summary received for U.S. Appl. No. 17/516,537, mailed on Nov. 22, 2022, 2 pages.
Applicant-Initiated Interview Summary received for U.S. Appl. No. 17/591,184, mailed on Feb. 27, 2023, 2 pages.
Applicant-Initiated Interview Summary received for U.S. Appl. No. 17/591,184, mailed on Jun. 28, 2023, 2 pages.
Applicant-Initiated Interview Summary received for U.S. Appl. No. 17/591,184, mailed on Sep. 23, 2022, 2 pages.
Applicant-Initiated Interview Summary received for U.S. Appl. No. 17/666,301, mailed on Mar. 28, 2023, 4 pages.
Applicant-Initiated Interview Summary received for U.S. Appl. No. 17/735,395, mailed on Apr. 28, 2023, 2 pages.
Applicant-Initiated Interview Summary received for U.S. Appl. No. 17/735,395, mailed on Aug. 1, 2023, 2 pages.
Applicant-Initiated Interview Summary received for U.S. Appl. No. 17/744,500, mailed on May 30, 2023, 4 pages.
Applicant-Initiated Interview Summary received for U.S. Appl. No. 17/892,534, mailed on Aug. 3, 2023, 3 pages.
Applicant-Initiated Interview Summary received for U.S. Appl. No. 17/892,534, mailed on Feb. 6, 2023, 2 pages.
Applicant-Initiated Interview Summary received for U.S. Appl. No. 17/892,534, mailed on Feb. 10, 2023, 2 pages.
Applicant-Initiated Interview Summary received for U.S. Appl. No. 17/951,613, mailed on Sep. 8, 2023, 5 pages.
Applicant-Initiated Interview Summary received for U.S. Appl. No. 17/951,875, mailed on Feb. 28, 2023, 2 pages.
Applicant-Initiated Interview Summary received for U.S. Appl. No. 17/951,875, mailed on Jul. 27, 2023, 2 pages.
Applicant-Initiated Interview Summary received for U.S. Appl. No. 17/951,945, mailed on Apr. 28, 2023, 2 pages.

(56) References Cited

OTHER PUBLICATIONS

Applicant-Initiated Interview Summary received for U.S. Appl. No. 17/951,945, mailed on Aug. 1, 2023, 2 pages.
Applicant-Initiated Interview Summary received for U.S. Appl. No. 17/951,976, mailed on Aug. 23, 2023, 2 pages.
Applicant-Initiated Interview Summary received for U.S. Appl. No. 17/952,027, mailed on May 30, 2023, 4 pages.
Applicant-Initiated Interview Summary received for U.S. Appl. No. 17/952,027, mailed on Sep. 11, 2023, 3 pages.
Applicant-Initiated Interview Summary received for U.S. Appl. No. 17/952,133, mailed on Jul. 3, 2023, 4 pages.
Applicant-Initiated Interview Summary received for U.S. Appl. No. 17/952,233, mailed on May 24, 2023, 5 pages.
Applicant-Initiated Interview Summary received for U.S. Appl. No. 17/952,233, mailed on Sep. 7, 2023, 4 pages.
Applicant-Initiated Interview Summary received for U.S. Appl. No. 17/952,239, mailed on May 31, 2023, 2 pages.
Applicant-Initiated Interview Summary received for U.S. Appl. No. 17/381,570, mailed on Apr. 6, 2023, 4 pages.
Bagala et al., "Evaluation of Accelerometer-Based Fall Detection Algorithms on Real-World Falls", PloS ONE, vol. 7, No. 5, May 16, 2012, 9 pages.
Board Decision received for Chinese Patent Application No. 201380081349.6, mailed on Nov. 23, 2020, 2 pages.
Brief Communication Regarding Oral Proceedings received for European Patent Application No. 18727543.3, mailed on Mar. 23, 2023, 1 page.
Brief Communication Regarding Oral Proceedings received for European Patent Application No. 20182116.2, mailed on Apr. 13, 2022, 3 pages.
Brief Communication Regarding Oral Proceedings received for European Patent Application No. 20203526.7, mailed on Dec. 23, 2022, 4 pages.
Brief Communication Regarding Oral Proceedings received for European Patent Application No. 20203526.7, mailed on Jan. 18, 2023, 1 page.
Brief Communication Regarding Oral Proceedings received for European Patent Application No. 20721342.2, mailed on Oct. 18, 2022, 1 page.
CBS This Morning, "This smart mirror puts a personal trainer in your reflection", Available on: https://www.youtube.com/watch?v=nSmTTZcpVGg, Oct. 13, 2018, 4 pages.
Certificate of Examination received for Australian Patent Application No. 2018101855, mailed on Aug. 6, 2019, 2 pages.
Certification of Examination received for Australian Patent Application No. 2018100158, mailed on Oct. 23, 2018, 2 pages.
ChengCheng et al., "Platform of Development of Motion Control Systems Experimental Software", Experimental Technology and Management, vol. 30, No. 1, Jan. 2013, 3 pages.
Cho H.S. , "Satisfactory Innovative Smart-watch (fitbit force) . . . review after seven days of use, such as the amount of sleep and movement (improving sleep is the object of X-Blue", Online Available at: <https://x-blueuv.blogspot.com/2013/12/fitbit-force.html>, Dec. 3, 2013, 8 pages.
CNET, "Google Fit's automatic activity tracking is getting smarter on Android Wear", Available online at: https://www.youtube.com/watch?v=lttzlCid_d8, May 18, 2016, 1 page.
Codrington Simon, "Intuitive Scrolling Interfaces with CSS Scroll Snap Points", Online Available at: https://www.sitepoint.com/intuitive-scolling-interfaces-with-css-scroll-snap-points/, Dec. 8, 2015, 14 pages.
Communication of the Board of Appeal received for European Patent Application No. 13811085.3, mailed on Jul. 28, 2022, 13 pages.
Communication of the Board of Appeal received for European Patent Application No. 15771747.1, mailed on Aug. 25, 2021, 9 pages.
Corrected Notice of Allowance received for U.S. Appl. No. 14/732,773, mailed on Feb. 10, 2020, 3 pages.
Corrected Notice of Allowance received for U.S. Appl. No. 14/732,773, mailed on Mar. 24, 2020, 3 pages.
Corrected Notice of Allowance received for U.S. Appl. No. 15/183,663, mailed on Feb. 25, 2019, 3 pages.
Corrected Notice of Allowance received for U.S. Appl. No. 15/183,663, mailed on Mar. 27, 2019, 2 pages.
Corrected Notice of Allowance received for U.S. Appl. No. 15/600,243, mailed on Feb. 5, 2020, 3 pages.
Corrected Notice of Allowance received for U.S. Appl. No. 15/600,243, mailed on Mar. 13, 2020, 3 pages.
Corrected Notice of Allowance received for U.S. Appl. No. 15/600,243, mailed on Mar. 31, 2020, 5 pages.
Corrected Notice of Allowance received for U.S. Appl. No. 16/377,892, mailed on Aug. 11, 2021, 3 pages.
Corrected Notice of Allowance received for U.S. Appl. No. 16/378,136, mailed on Aug. 11, 2021, 2 pages.
Corrected Notice of Allowance received for U.S. Appl. No. 16/378,136, mailed on Jun. 11, 2021, 2 pages.
Corrected Notice of Allowance received for U.S. Appl. No. 16/418,786, mailed on Jan. 5, 2022, 3 pages.
Corrected Notice of Allowance received for U.S. Appl. No. 14/418,786, mailed on Jun. 23, 2022, 2 pages.
Corrected Notice of Allowance received for U.S. Appl. No. 16/82,383, mailed on Apr. 28, 2023, 2 pages.
Corrected Notice of Allowance received for U.S. Appl. No. 16/820,383, mailed on Aug. 13, 2021, 2 pages.
Corrected Notice of Allowance received for U.S. Appl. No. 16/820,383, mailed on Aug. 19, 2021, 2 pages.
Corrected Notice of Allowance received for U.S. Appl. No. 16/820,383, mailed on Oct. 5, 2021, 2 pages.
Corrected Notice of Allowance received for U.S. Appl. No. 16/888,629, mailed on Jan. 21, 2022, 2 pages.
Corrected Notice of Allowance received for U.S. Appl. No. 16/987,275, mailed on Jun. 8, 2022, 3 pages.
Corrected Notice of Allowance received for U.S. Appl. No. 17/030,318, mailed on Jan. 24, 2022, 2 pages.
Corrected Notice of Allowance received for U.S. Appl. No. 17/030,318, mailed on Jun. 1, 2023, 3 pages.
Corrected Notice of Allowance received for U.S. Appl. No. 17/030,321, mailed on Aug. 15, 2022, 3 pages.
Corrected Notice of Allowance received for U.S. Appl. No. 17/030,337, mailed on Aug. 31, 2022, 2 pages.
Corrected Notice of Allowance received for U.S. Appl. No. 17/030,337, mailed on Feb. 10, 2023, 2 pages.
Corrected Notice of Allowance received for U.S. Appl. No. 17/030,337, mailed on Feb. 17, 2023, 2 pages.
Corrected Notice of Allowance received for U.S. Appl. No. 17/030,337, mailed on Nov. 3, 2022, 2 pages.
Corrected Notice of Allowance received for U.S. Appl. No. 17/030,337, mailed on Nov. 15, 2022, 2 pages.
Corrected Notice of Allowance received for U.S. Appl. No. 17/030,337, mailed on Oct. 18, 2022, 2 pages.
Corrected Notice of Allowance received for U.S. Appl. No. 17/030,337, mailed on Sep. 21, 2022, 2 pages.
Corrected Notice of Allowance received for U.S. Appl. No. 17/031,543, mailed on Aug. 22, 2022, 2 pages.
Corrected Notice of Allowance received for U.S. Appl. No. 17/031,543, mailed on Jul. 18, 2022, 2 pages.
Corrected Notice of Allowance received for U.S. Appl. No. 17/031,543, mailed on Jun. 8, 2022, 3 pages.
Corrected Notice of Allowance received for U.S. Appl. No. 17/041,438, mailed on Sep. 27, 2023, 3 pages.
Corrected Notice of Allowance received for U.S. Appl. No. 17/157,728, mailed on Apr. 4, 2022, 3 pages.
Corrected Notice of Allowance received for U.S. Appl. No. 17/157,728, mailed on Apr. 14, 2022, 6 pages.
Corrected Notice of Allowance received for U.S. Appl. No. 17/192,161, mailed on Apr. 22, 2022, 2 pages.
Corrected Notice of Allowance received for U.S. Appl. No. 17/192,161, mailed on Mar. 23, 2022, 2 pages.
Corrected Notice of Allowance received for U.S. Appl. No. 17/197,628, mailed on Apr. 27, 2022, 3 pages.

(56) References Cited

OTHER PUBLICATIONS

Corrected Notice of Allowance received for U.S. Appl. No. 17/197,628, mailed on Jul. 29, 2022, 2 pages.
Corrected Notice of Allowance received for U.S. Appl. No. 17/952,239, mailed on Jul. 12, 2023, 2 pages.
Corrected Notice of Allowance received for U.S. Appl. No. 17/952,239, mailed on Nov. 15, 2023, 2 pages.
Decision of Appeal received for European Patent Appiication No. 15771747.1, mailed on Dec. 14, 2021, 21 pages.
Cyclespeed Tours, "The Most Useful Data Fields to Display on Your Garmin", Online Available at: https://www.youtube.com/watch?v=AN0Eo50yxdg, Nov. 16, 2016, 3 pages.
Dc Rainmaker. "Garmin Fenix3 New Auto Climb Functionality", Available online at: https://www.youtube.com/watch?v=iuavOSNpVRc, Feb. 19, 2015, 1 page.
Decision on Appeal received for Korean Patent Application No. 10-2019-7025538, mailed on Feb. 24, 2021, 20 pages.
Decision to Grant received for Danish Patent Application No. PA201670656, mailed on Jun. 21, 2021, 2 pages.
Decision to Grant received far Danish Patent Application No. PA201870379, mailed on Jul. 5, 2019, 2 pages.
Decision to Grant received for Danish Patent Application No. PA202070614, mailed on Nov. 10, 2022, 2 pages.
Decision in Grant received for Danish Patent Appiication No. PA202070615, mailed on Jul. 29, 2022, 2 pages.
Decision to Grant received far Danish Patent Application No. PA202070815, mailed on Dec. 23, 2022, 1 page.
Decision to Grant received for European Patent Application No. 18727543.3, mailed on Aug. 18, 2023, 2 pages.
Decision to Grant received for European Patent Application No. 19721883.7; mailed on Aug. 31, 2023, 4 pages.
Decision to Grant received for European Patent Application No. 20182116.2, mailed on Mar. 23, 2023, 3 pages.
Decision to Grant received for European Patent Application No. 20203526.7, mailed on Jun. 22, 2023, 4 pages.
Decision to Grant received for German Patent Application No. 112015002326.7, mailed on Jun. 15, 2021, 10 pages.
Decision in Grant received for German Patent Application No. 112015007285.3, mailed on Jul. 25, 2023, 11 pages.
Decision to Refuse received for European Patent Application No. 13811085.3, mailed on Sep. 11, 2018, 21 pages.
Decision to Refuse received for European Patent Application No. 15771747.1, mailed on Aug. 10, 2018, 22 pages.
Decision to Refuse received for European Patent Application No. 17810749.6, mailed on Jan. 29, 2021, 24 pages.
Decision to Refuse received for European Patent Application No. 18154145.9, mailed on Feb. 17, 2021, 20 pages.
Decision to Refuse received for European Patent Application No. 20721342.2, mailed on Nov. 10, 2022, 14 pages.
Dicristina John, "Fitness Monitoring Equipment Goes Wireless", Frontier Technology, China Academic journal Electronic Publishing House, Online Available at: http://www.cnki.net, Dec. 2012, pp. 44-45.
DWProgressBar v2: Stepping and Events, davidwaish.name/dwprogressbar-2-stepping-events-mootools-progress-bar, retrieved from the Wayback Machine, Aug. 31, 2008, 4 pages.
European Search Report received for European Patent Application No. 20182116.2, mailed on Oct. 21, 2020, 4 pages.
European Search Report received far European Patent Application No. 21165295.3, mailed on Jun. 18, 2021, 4 pages.
European Search Report received for European Patent Application No. 21168916.1, mailed on Jul. 14, 2021, 5 pages.
Evergreen et al., "Bar Chart", Better Evaluation, Available Online at: https://www.betterevaluation.org/en/evaluation-options/BarChart, Oct. 31, 2014, 8 pages.
Examiner-Initiated Interview received far U.S. Appl. No. 17/896,791, mailed on Sep. 1, 2023, 2 pages.
Extended European Search Report received for European Patent Application No. 16837432.0, mailed on Mar. 11, 2019, 10 pages.
Extended European Search Report received for European Patent Application No. 18154145.9, mailed on Mar. 2, 2018, 8 pages.
Extended European Search Report received for European Patent Application No. 20203526.7, mailed on Jan. 29, 2021, 13 pages.
Extended European Search Report received for European Patent Application No. 22194355.8, mailed on Dec. 23, 2022, 10 pages.
Extended European Search Report received for European Patent Application No. 23150297.2, mailed on Mar. 28, 2023, 8 pages.
Extended European Search Report received for European Patent Application No. 23153898.4, mailed on May 4, 2023, 11 pages.
Extended European Search Report received for European Patent Application No. 23153899.2, mailed on May 4, 2023, 10 pages.
Extended European Search Report received for European Patent Application No. 23153900.8, mailed on May 4, 2023, 10 pages.
Final Office Action received for U.S. Appl. No. 12/205,847, mailed on Apr. 25, 2012, 42 pages.
Final Office Action received for U.S. Appl. No. 16/994,352, mailed on Dec. 6, 2021, 14 pages.
Final Office Action received for U.S. Appl. No. 14/732,773, mailed on Jul. 13, 2018, 48 pages.
Final Office Action received for U.S. Appl. No. 14/732,773, mailed on Jun. 21, 2019, 32 pages.
Final Office Action received for U.S. Appl. No. 14/839,922, mailed on Dec. 14, 2016, 22 pages.
Final Office Action received for U.S. Appl. No. 15/608,848, mailed on Aug. 21, 2020, 15 pages.
Final Office Action received for U.S. Appl. No. 15/608,848, mailed on Jun. 26, 2019, 27 pages.
Final Office Action received for U.S. Appl. No. 15/627,069, mailed on Mar. 2, 2020, 22 pages.
Final Office Action received for U.S. Appl. No. 15/627,069, mailed on Oct. 20, 2020, 25 pages.
Final Office Action received for U.S. Appl. No. 15/705,849, mailed on May 1, 2020, 17 pages.
Final Office Action received for U.S. Appl. No. 15/925,652, mailed on Aug. 1, 2019, 30 Pages.
Final Office Action received for U.S. Appl. No. 16/138,809, mailed on Aug. 27, 2020, 24 pages.
Final Office Action received for U.S. Appl. No. 16/144,735, mailed on May 4, 2020, 12 pages.
Final Office Action received for U.S. Appl. No. 16/144,753, mailed on Sep. 22, 2020, 9 pages.
Final Office Action received for U.S. Appl. No. 16/144,849, mailed on Jun. 7, 2019, 29 pages.
Final Office Action received for U.S. Appl. No. 16/144,864, mailed on May 17, 2019, 24 pages.
Final Office Action received for U.S. Appl. No. 16/144,864, mailed on May 28, 2020, 29 pages.
Final Office Action received for U.S. Appl. No. 16/377,892, mailed on Jan. 28, 2021, 11 pages.
Final Office Action received for U.S. Appl. No. 16/378,136, mailed on Jan. 28, 2021, 9 pages.
Final Office Action received for U.S. Appl. No. 16/418,786, mailed on Jan. 13, 2021, 14 pages.
Final Office Action received for U.S. Appl. No. 16/820,383, mailed on Jun. 22, 2022, 21 pages.
Final Office Action received for U.S. Appl. No. 16/894,309, mailed on Feb. 24, 2021, 30 pages.
Final Office Action received for U.S. Appl. No. 17/030,318, mailed on Nov. 28, 2022, 13 pages.
Final Office Action received for U.S. Appl. No. 17/030,318, mailed on Sep. 30, 2021, 28 pages.
Final Office Action received for U.S. Appl. No. 17/030,321, mailed on Apr. 2, 2021, 28 pages.
Final Office Action received for U.S. Appl. No. 17/031,854, mailed on Feb. 23, 2023, 19 pages.
Final Office Action received for U.S. Appl. No. 17/031,854, mailed on Jun. 10, 2022, 15 pages.
Final Office Action received for U.S. Appl. No. 17/031,859, mailed on Apr. 16, 2021, 14 pages.
Final Office Action received for U.S. Appl. No. 17/031,859, mailed on Feb. 8, 2023, 15 pages.

(56) References Cited

OTHER PUBLICATIONS

Final Office Action received for U.S. Appl. No. 17/031,859, mailed on Jun. 10, 2022, 13 pages.
Final Office Action received for U.S. Appl. No. 17/031,874, mailed on Apr. 16, 2021, 17 pages.
Final Office Action received for U.S. Appl. No. 17/031,874, mailed on Jun. 2, 2022, 19 pages.
Final Office Action received for U.S. Appl. No. 17/031,874, mailed on Mar. 17, 2023, 24 pages.
Final Office Action received for U.S. Appl. No. 17/192,161, mailed on Aug. 16, 2021, 22 pages.
Final Office Action received for U.S. Appl. No. 17/192,161, mailed on Oct. 18, 2021, 22 pages.
Final Office Action received for U.S. Appl. No. 17/381,570, mailed on Feb. 10, 2023, 22 pages.
Final Office Action received for U.S. Appl. No. 17/516,570, mailed on Jul. 20, 2022, 22 pages.
Final Office Action received for U.S. Appl. No. 17/516,537, mailed on Oct. 11, 2022, 9 pages.
Final Office Action received for U.S. Appl. No. 17/591,184, mailed on Dec. 23, 2022, 10 pages.
Final Office Action received for U.S. Appl. No. 17/591,184, mailed on Sep. 22, 2023, 19 pages.
Final Office Action received for U.S. Appl. No. 17/735,395, mailed on May 17, 2023, 31 pages.
Final Office Action received for U.S. Appl. No. 17/744,500, mailed on Sep. 19, 2023, 35 pages.
Final Office Action received for U.S. Appl. No. 17/951,875, mailed on May 30, 2023, 12 pages.
Final Office Action received for U.S. Appl. No. 17/951,945, mailed on May 18, 2023, 18 pages.
Final Office Action received for U.S. Appl. No. 17/952,027, mailed on Aug. 21, 2023, 47 pages.
Final Office Action received for U.S. Appl. No. 17/952,133, mailed on Sep. 26, 2023, 20 pages.
Final Office Action received for U.S. Appl. No. 17/952,233, mailed on Jun. 26, 2023, 18 pages.
Fitbit App, Available online at: <http://web.archive.org/web/20180114083150/https://www.fitbit.com/au/app>, Jan. 14, 2018, 8 pages.
Garmin Edge 520, Owner's Manual, Online available at: https://www8.garmin.com/manuals/webhelp/edge520/EN-US/Edge_520_OM_EN-US.pdf, 2015, 24 pages.
Garmin, "EDGE 520 Plus Owner's Manual", Online Available at: https://www8.garmin.com/manuals/webhelp/edge520plus/EN-US/Edge_520_Plus_OM_EN-US.pdf, 2018, 30 pages.
Garmin, "Fenix 5x Owner's Manual", Oniine Available at :- https://web.archive.org/web/20180127170640/https://static.garmin.com/pumac/fenix5x_OM_EN.pdf, Jan. 27, 2018, 42 pages.
GPSCity, "Garmin Connect 2.0 Overview with GPS City", Available online at: https://www.youtube.com/watch?v=EJ6U10y_8y0, Feb. 28, 2014, 8 pages.
GPSCity, "Garmin Connect Mobile App EOS Overview with GPS City", Available on: https://www.youtube.com/watch?v=rD-KPOJpmOA. 2014, 9 pages.
Graphs and Charts. Online available at: <https://www.teachervision.com/lesson-planning/graph-chart-teacher-resources, retrieved on Dec. 12, 2018, 4 pages.
Gym Book—Strength Training Planner, Logger and Analyzer, GymBookApp, Available Online at : https://web.archive.org/web/20160401104508/https://gymbookapp.com/, Apr. 1, 2016, 10 pages.
Intention to Grant received for Danish Patent Application No. PA201570668, mailed on Mar. 27, 2017, 2 pages.
Hamilton Jim, "Peloton Tips", Online available on:- <https://www.youtube.com/watch?app=desktop&v=OneXtB0kaD4>, Oct. 22, 2015, 3 pages.
Heinrich Peter, "More Player Engagement Potential: GameCircle Now Rewards Players Experience across Games", Available online at: https://www.developer.amazon.com/es-mx/blogs/home/tag/badges, Apr. 11, 2014, 9 pages.

Intention to Grant received for Danish Patent Application No. PA201670656, mailed on Jan. 18, 2021, 2 pages.
Intention to Grant received for Danish Patent Application No. PA201870379, mailed on May 2, 2019, 2 pages.
Intention to Grant received for Danish Patent Application No. PA202070615, mailed on Jan. 27, 2022, 2 pages.
Intention to Grant received for Danish Patent Application No. PA202070815, mailed on Sep. 13, 2022, 2 pages.
Intention to Grant received for European Patent Application No. 16837432.0, mailed on Apr. 14, 2023, 8 pages.
Intention to Grant received for European Patent Application No. 16837432.0, mailed on Sep. 7, 2023, 9 pages.
Intention to Grant received for European Patent Application No. 18727543.3, mailed on Apr. 12, 2023, 9 pages.
Intention to Grant received for European Patent Application No. 19721883.7, mailed on May 11, 2023, 9 pages.
Intention to Grant received for European Patent Application No. 20182116.2, mailed on Jun. 2, 2022, 8 pages.
Intention to Grant received for European Patent Application No. 20182116.2, mailed on Nov. 11, 2022, 9 pages.
Intention to Grant received for European Patent Application No. 20203526.7, mailed on Feb. 10, 2023, 9 pages.
International Preliminary Report on Patentability received for PCT Application No. PCT/US2016/037686, mailed on Mar. 1, 2018, 12 pages.
International Preliminary Report on Patentability received for PCT Patent Application No. PCT/US2020/035199, mailed on Dec. 16, 2021, 14 pages.
International Preliminary Report on Patentability received for PCT Patent Application No. PCT/US2013/073195, mailed on Jun. 16, 2016, 10 pages.
International Preliminary Report on Patentability received for PCT Patent Application No. PCT/US2015/047282, mailed on Mar. 16, 2017, 26 pages.
International Preliminary Report on Patentability received for PCT Patent Application No. PCT/US2017/035554, mailed on Dec. 20, 2018, 39 pages.
International Preliminary Report on Patentability received for PCT Patent Application No. PCT/US2018/031662, mailed on Nov. 28, 2019, 12 pages.
International Preliminary Report on Patentability received for PCT Patent Application No. PCT/US2019/024570, mailed on Nov. 19, 2020, 10 pages.
International Preliminary Report on Patentability received for PCT Patent Application No. PCT/US2020/025997, mailed on Nov. 18, 2021, 10 pages.
International Preliminary Report on Patentability received for PCT Patent Application No. PCT/US2021/017736, mailed on Aug. 25, 2022, 19 pages.
International Search Report and Written Opinion received for PCT Patent Application No. PCT/US2015/047282, mailed on May 9, 2016, 33 pages.
International Search Report and Written Opinion received for PCT Patent Application No. PCT/US2016/037686, mailed on Sep. 9, 2016, 19 pages.
International Search Report and Written Opinion received for PCT Patent Application No. PCT/US2017/035554, mailed on Sep. 22, 2017, 42 pages.
International Search Report and Written Opinion received for PCT Patent Application No. PCT/US2018/031662, mailed on Sep. 27, 2018, 17 pages.
International Search Report and Written Opinion received for PCT Patent Application No. PCT/US2019/024570, mailed on Aug. 8, 2019, 18 pages.
International Search Report and Written Opinion received for PCT Patent Application No. PCT/US2020/25997, mailed on Jul. 1, 2020, 16 pages.
International Search Report and Written Opinion received for PCT Patent Application No. PCT/US2020/025997, mailed on Jul. 14, 2020, 15 pages.
International Search Report and Written Opinion received for PCT Patent Application No. PCT/US2020/35199, mailed on Oct. 30, 2020, 20 pages.

(56) References Cited

OTHER PUBLICATIONS

International Search Report and Written Opinion received for PCT Patent Application No. PCT/US2021/017736, mailed on Sep. 2, 2021, 25 pages.
International Search Report and Written Opinion received for PCT Patent Application No. PCT/US2022/029297, mailed on Aug. 11, 2022, 13 pages.
International Search Report and Written Opinion received for PCT Patent Application No. PCT/US2023/024104, mailed on Oct. 18, 2023, 18 pages.
International Search Report received for PCT Patent Application No. PCT/US2013/073195, mailed on Jun. 23, 2014, 3 pages.
International Written Opinion received for PCT Patent Application No. PCT/US2013/073195, mailed on Jun. 23, 2014, 8 pages.
Invitation to Pay Addition Fees and Partial International Search Repart received for PCT Patent Application No. PCT/US2018/031662, mailed on Jul. 16, 2018, 13 pages.
Invitation to Pay Additional Fee received for PCT Patent Application No. PCT/US2015/047282, mailed on Dec. 22, 2015, 7 pages.
Invitation to Pay Additional Fees received for PCT Patent Application No. PCT/US2017/035554, mailed on Jul. 20, 2017, 2 pages.
Invitation to Pay Additional Fees received for PCT Patent Application No. PCT/US2020/035199, mailed on Sep. 8, 2020, 12 pages.
Invitation to Pay Additional Fees received for PCT Patent Application No. PCT/US2021/017736, mailed on Jun. 15, 2021, 14 pages.
Invitation to Pay Search Fees received for European Patent Application No. 21714460.9, mailed on Aug. 8, 2023, 3 pages.
JENBSJOURNEY, "Wondering About a Fitbit?", Available at: https://jenbsjourney.blogspot.kr/2013/08/wondering-about-fitbit.html, Aug. 8, 2013, 12 pages.
Li-Yu et al., "Influence of exercise prescription on body composition of college students", Clinical Rehabilitation in China, vol. 9 Issue 24, Jun. 28, 2005, pp. 147-149.
Minutes of Oral Proceedings received for European Patent Application No. 13811085.3, mailed on Sep. 11, 2018, 3 pages.
Minutes of Oral Proceedings received for European Patent Application No. 15771747.1, mailed on Aug. 10, 2018, 11 pages.
Minutes of Oral Proceedings received for European Patent Application No. 20721342.2, mailed on Nov. 8, 2022, 5 pages.
Minutes of Oral Proceedings received for European Patent Application No. 15771747.1, mailed on Dec. 1, 2021, 4 pages.
Minutes of Oral Proceedings received for European Patent Application No. 17810749.6, mailed on Jan. 26, 2021, 8 pages.
Minutes of Oral Proceedings received for European Patent Application No. 18154145.9, mailed on Feb. 12, 2021, 8 pages.
Minutes of Oral Proceedings received for European Patent Application No. 20182116.2, mailed on May 24, 2022, 7 pages.
Mugs, Online Available at: https://web.archive.org/web/20151029034349/http://le-mugs.com/, Oct. 29, 2015, 14 pages.
Multi-Set Bar Chart, The Data Visualization Catalogue, Available Online at: https://datavizcatalogue/com/methods/multiset_barchart.html, Feb. 8, 2014, 3 pages.
My CalStep, http://www.surprisesoftware.com/mycalstep/, retrieved from the Wayback Machine, May 9, 2007, 2 pages.
Nakasuji Yoshito, "Apple Watch", First Edition 1st Printing, Japan, Incorporated Company Technical Hyoronsha, Jun. 15, 2015, 4 pages.
Non-Final Office Action received for U.S. Appl. No. 12/205,847, mailed on Oct. 3, 2011, 59 pages.
Non-Final Office Action received for U.S. Appl. No. 14/839,916, mailed on Feb. 4, 2016, 19 pages.
Non-Final Office Action received for U.S. Appl. No. 14/839,922, mailed on Feb. 25, 2016, 20 pages.
Non-Final Office Action received for U.S. Appl. No. 16/144,864, mailed on Dec. 18, 2018, 19 pages.
Non-Final Office Action received for U.S. Appl. No. 16/994,352, mailed on Jul. 30, 2021, 11 pages.
Non-Final Office Action received for U.S. Appl. No. 14/732,773, mailed on Feb. 8, 2019, 32 pages.
Non-Final Office Action received for U.S. Appl. No. 14/732,773, mailed on Jan. 19, 2018, 45 pages.
Non-Final Office Action received for U.S. Appl. No. 14/839,916, mailed on May 1, 2017, 18 pages.
Non-Final Office Action received for U.S. Appl. No. 14/839,922, mailed on Aug. 17, 2016, 25 pages.
Non-Final Office Action received for U.S. Appl. No. 15/183,663, mailed on Jul. 9, 2018, 13 pages.
Non-Final Office Action received for U.S. Appl. No. 15/600,243, mailed on Jun. 27, 2019, 17 pages.
Non-Final Office Action received for U.S. Appl. No. 15/608,848, mailed on Feb. 6, 2020, 12 pages.
Non-Final Office Action received for U.S. Appl. No. 15/608,848, mailed on Feb. 12, 2021, 14 pages.
Non-Final Office Action received for U.S. Appl. No. 15/608,848, mailed on Nov. 2, 2018, 21 pages.
Non-Final Office Action received for U.S. Appl. No. 15/627,069, mailed on Jun. 21, 2019, 22 pages.
Non-Final Office Action received for U.S. Appl. No. 15/627,069, mailed on May 26, 2020, 25 pages.
Non-Final Office Action received for U.S. Appl. No. 15/705,849, mailed on Nov. 12, 2019, 15 pages.
Non-Final Office Action received for U.S. Appl. No. 15/925,652, mailed on Apr. 5, 2019, 28 pages.
Non-Final Office Action received for U.S. Appl. No. 15/925,652, mailed on Aug. 7, 2020, 39 pages.
Non-Final Office Action received for U.S. Appl. No. 16/138,809, mailed on Feb. 28, 2020, 22 pages.
Non-Final Office Action received for U.S. Appl. No. 16/144,735, mailed on Feb. 19, 2020, 10 pages.
Non-Final Office Action received for U.S. Appl. No. 16/144,753, mailed on Mar. 5, 2020, 9 pages.
Non-Final Office Action received for U.S. Appl. No. 16/144,849, mailed on Dec. 31, 2018, 28 pages.
Non-Final Office Action received for U.S. Appl. No. 16/144,849, mailed on Sep. 17, 2019, 9 pages.
Non-Final Office Action received for U.S. Appl. No. 16/144,864, mailed on Jan. 31, 2020, 29 pages.
Non-Final Office Action received for U.S. Appl. No. 16/377,892, mailed on May 21, 2020, 9 pages.
Non-Final Office Action received for U.S. Appl. No. 16/378,136, mailed on Jun. 2, 2020, 8 pages.
Non-Final Office Action received for U.S. Appl. No. 16/418,786, mailed on Apr. 24, 2020, 16 pages.
Non-Final Office Action received for U.S. Appl. No. 16/418,786, mailed on Aug. 1, 2022, 18 pages.
Non-Final Office Action received for U.S. Appl. No. 16/418,786, mailed on Mar. 28, 2022, 14 pages.
Non-Final Office Action received for U.S. Appl. No. 16/418,786, mailed on Oct. 4, 2021, 10 pages.
Non-Final Office Action received for U.S. Appl. No. 16/820,383, mailed on Dec. 14, 2020, 11 pages.
Non-Final Office Action received for U.S. Appl. No. 16/820,383, mailed on Jan. 10, 2022, 18 pages.
Non-Final Office Action received for U.S. Appl. No. 16/888,629, mailed on Mar. 31, 2021, 14 pages.
Non-Final Office Action received for U.S. Appl. No. 16/894,309, mailed on Oct. 15, 2020, 24 pages.
Non-Final Office Action received for U.S. Appl. No. 16/987,275, mailed on Nov. 23, 2021, 17 pages.
Non-Final Office Action received for U.S. Appl. No. 17/030,318, mailed on Apr. 2, 2021, 28 pages.
Non-Final Office Action received for U.S. Appl. No. 17/030,318, mailed on Dec. 3, 2020, 22 pages.
Non-Final Office Action received for U.S. Appl. No. 17/030,318, mailed on Jun. 14, 2022, 9 pages.
Non-Final Office Action received for U.S. Appl. No. 17/030,321, mailed on Dec. 15, 2020, 25 pages.
Non-Final Office Action received for U.S. Appl. No. 17/030,321, mailed on Oct. 18, 2021, 28 pages.
Non-Final Office Action received for U.S. Appl. No. 17/030,337, mailed on Jun. 14, 2022, 13 pages.

(56) References Cited

OTHER PUBLICATIONS

Non-Final Office Action received for U.S. Appl. No. 17/030,340, mailed on Jun. 14, 2022, 15 pages.
Non-Final Office Action received for U.S. Appl. No. 17/031,543, mailed on Apr. 1, 2022, 9 pages.
Non-Final Office Action received for U.S. Appl. No. 17/031,854, mailed on Dec. 27, 2021, 13 pages.
Non-Final Office Action received for U.S. Appl. No. 17/031,854, mailed on Sep. 26, 2022, 17 pages.
Non-Final Office Action received for U.S. Appl. No. 17/031,859, mailed on Dec. 15, 2020, 13 pages.
Non-Final Office Action received for U.S. Appl. No. 17/031,859, mailed on Dec. 24, 2021, 16 pages.
Non-Final Office Action received for U.S. Appl. No. 17/031,859, mailed on Jul. 10, 2023, 15 pages.
Non-Final Office Action received for U.S. Appl. No. 17/031,859, mailed on Sep. 12, 2022, 17 pages.
Non-Final Office Action received for U.S. Appl. No. 17/031,874, mailed on Dec. 28, 2020, 14 pages.
Non-Final Office Action received for U.S. Appl. No. 17/031,874, mailed on Jan. 24, 2022, 18 pages.
Non-Final Office Action received for U.S. Appl. No. 17/031,874, mailed on Oct. 4, 2022, 20 pages.
Non-Final Office Action received for U.S. Appl. No. 17/041,438, mailed on May 25, 2023, 47 pages.
Non-Final Office Action received for U.S. Appl. No. 17/157,728, mailed on Nov. 26, 2021, 18 pages.
Non-Final Office Action received for U.S. Appl. No. 17/192,161, mailed on May 13, 2021, 28 pages.
Non-Final Office Action received for U.S. Appl. No. 17/381,570, mailed on Apr. 1, 2022, 29 pages.
Non-Final Office Action received for U.S. Appl. No. 17/381,570, mailed on Sep. 28, 2022, 20 pages.
Non-Final Office Action received for U.S. Appl. No. 17/516,537, mailed on May 5, 2022, 8 pages.
Non-Final Office Action received for U.S. Appl. No. 17/556,521, mailed on May 15, 2023, 12 pages.
Non-Final Office Action received for U.S. Appl. No. 17/591,184, mailed on Apr. 21, 2023, 15 pages.
Non-Final Office Action received for U.S. Appl. No. 17/591,184, mailed on Aug. 4, 2022, 18 pages.
Non-Final Office Action received for U.S. Appl. No. 17/666,301, mailed on Feb. 16, 2023, 24 pages.
Non-Final Office Action received for U.S. Appl. No. 17/735,395, mailed on Feb. 10, 2023, 28 pages.
Non-Final Office Action received for U.S. Appl. No. 17/735,395, mailed on Sep. 20, 2023, 29 pages.
Non-Final Office Action received for U.S. Appl. No. 17/744,500, mailed on Apr. 19, 2023, 30 pages.
Non-Final Office Action received for U.S. Appl. No. 17/892,534, mailed on Dec. 19, 2022, 20 pages.
Non-Final Office Action received for U.S. Appl. No. 17/892,534, mailed on May 10, 2023, 17 pages.
Non-Final Office Action received for U.S. Appl. No. 17/896,791, mailed on Aug. 30, 2023, 11 pages.
Non-Final Office Action received for U.S. Appl. No. 17/951,613, mailed on Aug. 2, 2012, 42 pages.
Non-Final Office Action received for U.S. Appl. No. 17/951,624, mailed on Sep. 19, 2023, 41 pages.
Non-Final Office Action received for U.S. Appl. No. 17/951,875, mailed on Jan. 23, 2023, 12 pages.
Non-Final Office Action received for U.S. Appl. No. 17/951,945, mailed on Mar. 24, 2023, 14 pages.
Non-Final Office Action received for U.S. Appl. No. 17/951,945, mailed on Sep. 20, 2023, 19 pages.
Non-Final Office Action received for U.S. Appl. No. 17/951,976, mailed on Aug. 3, 2023, 16 pages.
Non-Final Office Action received for U.S. Appl. No. 17/952,027, mailed on Apr. 28, 2023, 46 pages.
Non-Final Office Action received for U.S. Appl. No. 17/952,133, mailed on Jun. 2, 2023, 28 pages.
Non-Final Office Action received for U.S. Appl. No. 17/952,181, mailed on Aug. 7, 2023, 18 pages.
Non-Final Office Action received for U.S. Appl. No. 17/952,233, mailed on Apr. 28, 2023, 21 pages.
Non-Final Office Action received for U.S. Appl. No. 17/952,239, mailed on Apr. 4, 2023, 45 pages.
Notice of Acceptance received for Australian Patent Application No. 2015312215, mailed on Oct. 9, 2017, 3 pages.
Notice of Acceptance received for Australian Patent Application No. 2017277971, mailed on Feb. 17, 2021, 3 pages.
Notice of Acceptance received for Australian Patent Application No. 2018268972, mailed on Dec. 18, 2020, 3 pages.
Notice of Acceptance received for Australian Patent Application No. 2019201583, mailed on Jul. 15, 2019, 3 pages.
Notice of Acceptance received for Australian Patent Application No. 2019222943, mailed on May 5, 2020, 3 pages.
Notice of Acceptance received for Australian Patent Application No. 2019250251, mailed on Feb. 18, 2021, 3 pages.
Notice of Acceptance received for Australian Patent Application No. 2020204153, mailed on Jul. 6, 2020, 3 pages.
Notice of Acceptance received for Australian Patent Application No. 2020239743, mailed on Jan. 13, 2022, 3 pages.
Notice of Acceptance received for Australian Patent Application No. 2020239752, mailed on Jan. 31, 2022, 3 pages.
Notice of Acceptance received for Australian Patent Application No. 2020256383, mailed on Aug. 3, 2021, 3 pages.
Notice of Acceptance received for Australian Patent Application No. 2020288139, mailed on Feb. 2, 2023, 3 pages.
Notice of Acceptance received for Australian Patent Application No. 2021200787, mailed on Mar. 19, 2021, 3 pages.
Notice of Acceptance received for Australian Patent Application No. 2021201130, mailed on Mar. 28, 2022, 3 pages.
Notice of Acceptance received for Australian Patent Application No. 2021203636, mailed on Apr. 14, 2022, 3 pages.
Notice of Acceptance received for Australian Patent Application No. 2021204422, mailed on Aug. 15, 2022, 3 pages.
Notice of Acceptance received for Australian Patent Application No. 2021266294, mailed on Mar. 3, 2023, 3 pages.
Notice of Acceptance received for Australian Patent Application No. 2022201761, mailed on Jun. 15, 2023, 3 pages.
Notice of Acceptance received for Australian Patent Application No. 2022202977, mailed on Sep. 26, 2023, 3 pages.
Notice of Acceptance received for Australian Patent Application No. 2022209277, mailed on Apr. 28, 2023, 3 pages.
Notice of Acceptance received for Australian Patent Application No. 2022235614, mailed on Jul. 6, 2023, 3 pages.
Notice of Allowance received for U.S. Appl. No. 12/205,847, mailed on Aug. 20, 2012, 13 pages.
Notice of Allowance received for Australian Patent Application No. 2020239748, mailed on Mar. 7, 2022, 3 pages.
Notice of Allowance received for Chinese Patent Application No. 201380081349.6, mailed on Dec. 17, 2021, 2 pages.
Notice of Allowance received for Chinese Patent Application No. 201580037927.5, mailed on Oct. 17, 2019, 3 pages.
Notice of Allowance received for Chinese Patent Application No. 201680047983.1, mailed on Apr. 28, 2021, 3 pages.
Notice of Allowance received for Chinese Patent Application No. 201710439448.7, mailed on Jan. 26, 2021, 2 pages.
Notice of Allowance received for Chinese Patent Application No. 201780034203.4, mailed on Jan. 17, 2012, 2 pages.
Notice of Allowance received for Chinese Patent Application No. 201810105846.X, mailed on Feb. 18, 2020, 2 pages.
Notice of Allowance received for Chinese Patent Application No. 201811303556.2, mailed on Jul. 28, 2023, 2 pages.
Notice of Allowance received for Chinese Patent Application No. 201911396643.1, mailed on Jun. 15, 2023, 8 pages.
Notice of Allowance received for Chinese Patent Application No. 201911396744.9, mailed on Aug. 3, 2023, 5 pages.
Notice of Allowance received for Chinese Patent Application No. 201911396819.3, mailed on Aug. 3, 2023, 5 pages.

(56) References Cited

OTHER PUBLICATIONS

Notice of Allowance received for Chinese Patent Application No. 201911396876.1, mailed on Sep. 6, 2023, 5 pages.
Notice of Allowance received for Chinese Patent Application No. 201911401161.0, mailed on Apr. 24, 2023, 11 pages.
Notice of Allowance received for Chinese Patent Application No. 202010606407.4, mailed on Jan. 24, 2022, 2 pages.
Notice of Allowance received for Chinese Patent Application No. 202210238202.4, mailed on Jan. 13, 2023, 7 pages.
Notice of Allowance received for Danish Patent Application No. PA201570666, mailed on Sep. 15, 2016, 1 page.
Notice of Allowance received for Danish Patent Application No. PA201570668, mailed on Oct. 30, 2017, 2 pages.
Notice of Allowance received for Japanese Patent Application No. 2016-535045, mailed on Mar. 2, 2018, 4 pages.
Notice of Allowance received for Japanese Patent Application No. 2016-557650, mailed on Apr. 9, 2019, 4 pages.
Notice of Allowance received for Japanese Patent Application No. 2018-014096, mailed on Jan. 5, 2021, 3 pages.
Notice of Allowance received for Japanese Patent Application No. 2018-068846, mailed on Dec. 9, 2019, 4 pages.
Notice of Allowance received for Japanese Patent Application No. 2018-184532, mailed on Jan. 17, 2022, 4 pages.
Notice of Allowance received for Japanese Patent Application No. 2019-044107, mailed on Jul. 11, 2022, 31 pages.
Notice of Allowance received for Japanese Patent Application No. 2019-162293. mailed on Apr. 9, 2021, 4 pages.
Notice of Allowance received for Japanese Patent Application No. 2019-563407, mailed on Aug. 20, 2021, 4 pages.
Notice of Allowance received for Japanese Patent Application No. 2020-000492, mailed on Jul. 16, 2021, 4 pages.
Notice of Allowance received for Japanese Patent Application No. 2020-104679. mailed on Jan. 4, 2021, 4 pages.
Notice of Allowance received for Japanese Patent Application No. 2020-115940, mailed on Oct. 22, 2021, 4 pages.
Notice of Allowance received for Japanese Patent Application No. 2020-160052, mailed on Jun. 3, 2022, 4 pages.
Notice of Allowance received for Japanese Patent Application No. 2020-160053, mailed on Jan. 16, 2023, 4 pages.
Notice of Allowance received for Japanese Patent Application No. 2020-160054, mailed on Apr. 4, 2022, 4 pages.
Notice of Allowance received for Japanese Patent Application No. 2021-131726, mailed on Mar. 17, 2023, 4 pages.
Notice of Allowance received for Japanese Patent Application No. 2021-153558, mailed on Jun. 9, 2023, 4 pages.
Notice of Allowance received for Japanese Patent Application No. 2021-188824, mailed on Feb. 13, 2023, 4 pages.
Notice of Allowance received for Japanese Patent Application No. 2021-571468, mailed on May 19, 2023, 4 pages.
Notice of Allowance received for Japanese Patent Application No. 2022-022159, mailed on Aug. 10, 2023, 4 pages.
Notice of Allowance received for Japanese Patent Application No. 2022-076722, mailed on Jul. 28, 2023. 4 pages.
Notice of Allowance received for Japanese Patent Application No. 2022-107902, mailed on Aug. 26, 2022, 4 pages.
Notice of Allowance received for Japanese Patent Application No. 2022-107903, mailed on Sep. 1, 2023, 4 pages.
Notice of Allowance received for Korean Patent Application No. 10-2016-7014577, mailed on May 30, 2019, 5 pages.
Notice of Allowance received for Korean Patent Application No. 10-2016-7033638, mailed on May 31, 2017, 5 pages.
Notice of Allowance received for Korean Patent Application No. 10-2019-7025538, mailed on Mar. 10, 2021, 5 pages.
Notice of Allowance received for Korean Patent Application No. 10-2019-7025781, mailed on Jun. 29, 2021, 5 pages.
Notice of Allowance received for Korean Patent Application No. 10-2019-7033834, mailed on Jul. 3, 2021, 4 pages.
Notice of Allowance received for Korean Patent Application No. 10-2020-0123815, mailed on Aug. 26, 2022, 7 pages.
Notice of Allowance received for Korean Patent Application No. 10-2020-0123821, mailed on Mar. 28, 2023, 8 pages.
Notice of Allowance received for Korean Patent Application No. 10-2020-0123840, mailed on May 26, 2023, 9 pages.
Notice of Allowance received for Korean Patent Application No. 10-2020-7026035, mailed on Aug. 23, 2021, 4 pages.
Notice of Allowance received for Korean Patent Application No. 10-2021-7026284, mailed on Jul. 28, 2022, 6 pages.
Notice of Allowance received for Korean Patent Application No. 10-2021-7031939, mailed on Apr. 5, 2022, 4 pages.
Notice of Allowance received for Korean Patent Application No. 10-2021-7038005, mailed on Dec. 14, 2021, 4 pages.
Notice of Allowance received for Korean Patent Application No. 10-2022-0061486, mailed on Nov. 22, 2022, 7 pages.
Notice of Allowance received for Korean Patent Application No. 10-2022-7008569, mailed on May 19, 2022, 5 pages.
Notice of Allowance received for Korean Patent Application No. 10-2022-7017918, mailed on Jun. 13, 2022, 6 pages.
Notice of Allowance received for Korean Patent Application No. 10-2022-7031866, mailed on May 1, 2023, 7 pages.
Notice of Allowance received for Korean Patent Application No. 10-2023-0023706, mailed on Mar. 27, 2023, 8 pages.
Notice of Allowance received for Taiwanese Patent Application No. 104128685, mailed on May 3, 2017, 3 pages.
Notice of Allowance received for U.S. Appl. No. 14/732,773, mailed on Dec. 18, 2019, 21 pages.
Notice of Allowance received for U.S. Appl. No. 14/839,916, mailed on Aug. 31, 2016, 11 pages.
Notice of Allowance received for U.S. Appl. No. 14/839,916, mailed on Jan. 10, 2018, 19 pages.
Notice of Allowance received for U.S. Appl. No. 14/839,922, mailed on Jan. 26, 2018, 2 pages.
Notice of Allowance received for U.S. Appl. No. 14/839,922, mailed on Jul. 6, 2017, 8 pages.
Notice of Allowance received for U.S. Appl. No. 14/839,922, mailed on Nov. 2, 2017, 8 pages.
Notice of Allowance received for U.S. Appl. No. 15/183,663, mailed on Jan. 17, 2019, 6 pages.
Notice of Allowance received for U.S. Appl. No. 15/600,243, mailed on Dec. 12, 2019, 7 pages.
Notice of Allowance received for U.S. Appl. No. 15/608,848, mailed on Dec. 25, 2021, 9 pages.
Notice of Allowance received for U.S. Appl. No. 15/608,848, mailed on Oct. 29, 2021, 7 pages.
Notice of Allowance received for U.S. Appl. No. 15/616,480, mailed on Jan. 3, 2019, 8 pages.
Notice of Allowance received for U.S. Appl. No. 15/627,069, mailed on Jun. 17, 2021, 14 pages.
Notice of Allowance received for U.S. Appl. No. 15/705,849, mailed on Jul. 28, 2020, 10 pages.
Notice of Allowance received for U.S. Appl. No. 15/705,849, mailed on Oct. 16, 2020, 14 pages.
Notice of Allowance received for U.S. Appl. No. 15/925,652, mailed on Mar. 9, 2021, 9 pages.
Notice of Allowance received for U.S. Appl. No. 15/925,652, mailed on Nov. 20, 2020, 9 pages.
Notice of Allowance received for U.S. Appl. No. 16/138,809, mailed on Apr. 16, 2021, 11 pages.
Notice of Allowance received for U.S. Appl. No. 16/138,809, mailed on Jul. 20, 2021, 6 pages.
Notice of Allowance received for U.S. Appl. No. 14/144,671, mailed on Feb. 10, 2020, 17 pages.
Notice of Allowance received for U.S. Appl. No. 16/144,735, mailed on Jul. 21, 2020, 13 pages.
Notice of Allowance received for U.S. Appl. No. 16/144,735, mailed on Oct. 28, 2020, 13 pages.
Notice of Allowance received for U.S. Appl. No. 16/144,753, mailed on Dec. 4, 2020, 22 pages.
Notice of Allowance received for U.S. Appl. No. 16/144,753, mailed on Feb. 10, 2021, 8 pages.
Notice of Allowance received for U.S. Appl. No. 16/144,849, mailed on Apr. 17, 2020, 2 pages.

(56) References Cited

OTHER PUBLICATIONS

Notice of Allowance received for U.S. Appl. No. 16/144,849, mailed on Mar. 6, 2020, 9 pages.
Notice of Allowance received for U.S. Appl. No. 16/144,864, mailed on Feb. 9, 2021, 13 pages.
Notice of Allowance received for U.S. Appl. No. 16/144,864, mailed on Jul. 28, 2020, 27 pages.
Notice of Allowance received for U.S. Appl. No. 16/144,864, mailed on Mar. 12, 2021, 2 pages.
Notice of Allowance received for U.S. Appl. No. 16/144,864, mailed on Mar. 30, 2021, 2 pages.
Notice of Allowance received for U.S. Appl. No. 16/144,864, mailed on Sep. 10, 2020, 3 pages.
Notice of Allowance received for U.S. Appl. No. 16/144,864, mailed on Sep. 16, 2020, 2 pages.
Notice of Allowance received for U.S. Appl. No. 16/144,864, mailed on Sep. 29, 2020, 2 pages.
Notice of Allowance received for U.S. Appl. No. 16/377,892, mailed on May 24, 2021, 9 pages.
Notice of Allowance received for U.S. Appl. No. 16/377,892, mailed on Sep. 9, 2021, 9 pages.
Notice of Allowance received for U.S. Appl. No. 16/378,136, mailed on Jun. 3, 2021, 7 pages.
Notice of Allowance received for U.S. Appl. No. 16/378,136, mailed on Sep. 22, 2021, 7 pages.
Notice of Allowance received for U.S. Appl. No. 16/418,786, mailed on Dec. 9, 2021, 9 pages.
Notice of Allowance received for U.S. Appl. No. 16/418,786, mailed on Jun. 14, 2022, 9 pages.
Notice of Allowance received for U.S. Appl. No. 16/418,786, mailed on Nov. 22, 2022, 6 pages.
Notice of Allowance received for U.S. Appl. No. 16/556,023, mailed on Jan. 13, 2021, 8 pages.
Notice of Allowance received for U.S. Appl. No. 16/556,023, mailed on Oct. 15, 2020, 8 pages.
Notice of Allowance received for U.S. Appl. No. 16/588,950, mailed on Feb. 10, 2020, 9 pages.
Notice of Allowance received for U.S. Appl. No. 16/588,950, mailed on May 5, 2020, 9 pages.
Notice of Allowance received for U.S. Appl. No. 16/820,383, mailed on Aug. 2, 2023, 14 pages.
Notice of Allowance received for U.S. Appl. No. 16/820,383, mailed on Jul. 21, 2021, 11 pages.
Notice of Allowance received for U.S. Appl. No. 16/820,383, mailed on Mar. 8, 2023, 13 pages.
Notice of Allowance received for U.S. Appl. No. 16/820,383, mailed on Mar. 31, 2021, 11 pages.
Notice of Allowance received for U.S. Appl. No. 16/820,383, mailed on Nov. 22, 2022, 16 pages.
Notice of Allowance received for U.S. Appl. No. 16/888,629, mailed on Nov. 9, 2021, 11 pages.
Notice of Allowance received for U.S. Appl. No. 16/894,309, mailed on Feb. 25, 2022, 9 pages.
Notice of Allowance received for U.S. Appl. No. 16/894,309, mailed on Nov. 5, 2021, 12 pages.
Notice of Allowance received for U.S. Appl. No. 16/987,275, mailed on Jul. 27, 2022, 6 pages.
Notice of Allowance received for U.S. Appl. No. 16/987,275, mailed on May 16, 2022, 7 pages.
Notice of Allowance received for U.S. Appl. No. 16/994,352, mailed on Jun. 3, 2022, 9 pages.
Notice of Allowance received for U.S. Appl. No. 16/994,352, mailed on Mar. 2, 2022, 14 pages.
Notice of Allowance received for U.S. Appl. No. 17/030,318, mailed on Jan. 5, 2022, 8 pages.
Notice of Allowance received for U.S. Appl. No. 17/030,318, mailed on Jan. 25, 2023, 10 pages.
Notice of Allowance received for U.S. Appl. No. 17/030,318, mailed on May 16, 2023, 5 pages.
Notice of Allowance received for U.S. Appl. No. 17/030,321, mailed on Apr. 1, 2022, 8 pages.
Notice of Allowance received for U.S. Appl. No. 17/030,337, mailed on Aug. 22, 2022, 10 pages.
Notice of Allowance received for U.S. Appl. No. 17/030,337, mailed on Dec. 23, 2022, 9 pages.
Notice of Allowance received for U.S. Appl. No. 17/030,340, mailed on Sep. 28, 2022, 7 pages.
Notice of Allowance received for U.S. Appl. No. 17/030,343, mailed on Dec. 15, 2022, 9 pages.
Notice of Allowance received for U.S. Appl. No. 17/030,343, mailed on Sep. 16, 2022, 11 pages.
Notice of Allowance received for U.S. Appl. No. 17/031,543, mailed on May 11, 2022, 6 pages.
Notice of Allowance received for U.S. Appl. No. 17/041,438, mailed on Sep. 20, 2023, 11 pages.
Notice of Allowance received for U.S. Appl. No. 17/157,728, mailed on Feb. 24, 2022, 7 pages.
Notice of Allowance received for U.S. Appl. No. 17/192,161, mailed on Feb. 16, 2022, 8 pages.
Notice of Allowance received for U.S. Appl. No. 17/192,161, mailed on May 27, 2022, 8 pages.
Notice of Allowance received for U.S. Appl. No. 17/197,628, mailed on Jun. 24, 2022, 8 pages.
Notice of Allowance received for U.S. Appl. No. 17/197,628, mailed on Mar. 23, 2022, 35 pages.
Notice of Allowance received for U.S. Appl. No. 17/381,570, mailed on Jul. 26, 2023, 14 pages.
Notice of Allowance received for U.S. Appl. No. 17/516,537, mailed on Apr. 17, 2023, 8 pages.
Notice of Allowance received for U.S. Appl. No. 17/516,537, mailed on Dec. 27, 2022, 7 pages.
Notice of Allowance received for U.S. Appl. No. 17/591,184, mailed on Feb. 22, 2023, 5 pages.
Notice of Allowance received for U.S. Appl. No. 17/666,301, mailed on May 4, 2023, 10 pages.
Notice of Allowance received for U.S. Appl. No. 17/852,020, mailed on Jul. 12, 2023, 9 pages.
Notice of Allowance received for U.S. Appl. No. 17/951,875, mailed on Jul. 26, 2023, 7 pages.
Notice of Allowance received for U.S. Appl. No. 17/952,027, mailed on Oct. 4, 2023, 13 pages.
Notice of Allowance received for U.S. Appl. No. 17/952,181, mailed on Sep. 27, 2023, 9 pages.
Notice of Allowance received for U.S. Appl. No. 17/952,185, mailed on Aug. 30, 2023, 12 pages.
Notice of Allowance received for U.S. Appl. No. 17/952,239, mailed on Jun. 23, 2023, 5 pages.
Notice of Allowance received for U.S. Appl. No. 17/952,239, mailed on Oct. 20, 2023, 5 pages.
Office Action received for Australian Patent Application No. 2015312215, mailed on Oct. 13, 2016, 3 pages.
Office Action received for Australian Patent Application No. 2017100667, mailed on Aug. 3, 2017, 9 pages.
Office Action received for Australian Patent Application No. 2017277971, mailed on Aug. 12, 2020, 3 pages.
Office Action received for Australian Patent Application No. 2017277971, mailed on Jun. 3, 2020, 3 pages.
Office Action received for Australian Patent Application No. 2018100158, mailed on Apr. 23, 2018, 5 pages.
Office Action received for Australian Patent Application No. 2018101855, mailed on Feb. 22, 2019, 4 pages.
Office Action received for Australian Patent Application No. 2018200428, mailed on Mar. 7, 2018, 4 pages.
Office Action received for Australian Patent Application No. 2018200428, mailed on Nov. 15, 2018, 4 pages.
Office Action received for Australian Patent Application No. 2018268972, mailed on Jul. 9, 2020, 4 pages.
Office Action received for Australian Patent Application No. 2019100495, mailed on Mar. 6, 2020, 3 pages.
Office Action received for Australian Patent Application No. 2019100495, mailed on Mar. 16, 2020, 3 pages.

(56) References Cited

OTHER PUBLICATIONS

Office Action received for Australian Patent Application No. 2019100495, mailed on Sep. 17, 2019, 7 pages.
Office Action received for Australian Patent Application No. 2019222943, mailed on Oct. 3, 2019, 3 pages.
Office Action received for Australian Patent Application No. 2019250251, mailed on Aug. 6, 2020, 3 pages.
Office Action received for Australian Patent Application No. 2020239743, mailed on Mar. 25, 2021, 8 pages.
Office Action received for Australian Patent Application No. 2020239743, mailed on Sep. 3, 2021, 4 pages.
Office Action received for Australian Patent Application No. 2020239748, mailed on Apr. 21, 2021, 6 pages.
Office Action received for Australian Patent Application No. 2020239748, mailed on Feb. 11, 2022, 9 pages.
Office Action received for Australian Patent Application No. 2020239748, mailed on Sep. 1, 2021, 4 pages.
Office Action received for Australian Patent Application No. 2020239752, mailed on Jun. 4, 2021, 8 pages.
Office Action received for Australian Patent Application No. 2020239752, mailed on Oct. 25, 2021, 5 pages.
Office Action received for Australian Patent Application No. 2020256383, mailed on Jun. 4, 2021, 3 pages.
Office Action received for Australian Patent Application No. 2020268150, mailed on Aug. 24, 2023, 5 pages.
Office Action received for Australian Patent Application No. 2020268150, mailed on Feb. 6, 2023, 5 pages.
Office Action received for Australian Patent Application No. 2020268150, mailed on May 8, 2023, 4 pages.
Office Action received for Australian Patent Application No. 2020268150, mailed on Nov. 3, 2022, 4 pages.
Office Action received for Australian Patent Application No. 2020288139, mailed on Oct. 31, 2022, 3 pages.
Office Action received for Australian Patent Application No. 2021201130, mailed on Jan. 27, 2022, 2 pages.
Office Action received for Australian Patent Application No. 2021203636, mailed on Mar. 23, 2022, 3 pages.
Office Action received for Australian Patent Application No. 2021204422, mailed on May 31, 2022, 2 pages.
Office Action received for Australian Patent Application No. 2021266294, mailed on Nov. 11, 2022, 3 pages.
Office Action received for Australian Patent Application No. 2022201761, mailed on Feb. 28, 2023, 5 pages.
Office Action received for Australian Patent Application No. 2022202977, mailed on Jul. 21, 2023, 3 pages.
Office Action received for Australian Patent Application No. 2022202977, mailed on May 2, 2023, 5 pages.
Office Action received for Australian Patent Application No. 2022209277, mailed on Mar. 10, 2023, 6 pages.
Office Action received for Australian Patent Application No. 2022235614, mailed on May 9, 2023, 2 pages.
Office Action received for Australian Patent Application No. 2023203050, mailed on Sep. 1, 2023, 3 pages.
Office Action received for Chinese Patent Application No. 201380081349.6, mailed on Feb. 26, 2019, 12 pages.
Office Action received for Chinese Patent Application No. 201380081349.6, mailed on Jan. 5, 2021, 16 pages.
Office Action received for Chinese Patent Application No. 201380081349.6, mailed on Jan. 16, 2020, 11 pages.
Office Action received for Chinese Patent Application No. 201380081349.6, mailed on Jul. 15, 2019, 10 pages.
Office Action received for Chinese Patent Application No. 201380081349.6, mailed on Jul. 15, 2020, 9 pages.
Office Action received for Chinese Patent Application No. 201380081349.6, mailed on Jun. 2, 2021, 17 pages.
Office Action received for Chinese Patent Application No. 201580037927.5, mailed on Apr. 22, 2019, 9 pages.
Office Action received for Chinese Patent Application No. 201580037927.5, mailed on Jul. 20, 2018, 21 pages.
Office Action received for Chinese Patent Application No. 201380047983.1, mailed on Feb. 1, 2021, 6 pages.
Office Action received for Chinese Patent Application No. 201680047983.1, mailed on Jul. 1, 2020, 6 pages.
Office Action received for Chinese Patent Application No. 201680047983.1, mailed on Mar. 18, 2019, 18 pages.
Office Action received for Chinese Patent Application No. 201680047983.1, mailed on Nov. 28, 2019, 9 pages.
Office Action received for Chinese Patent Application No. 201710439448.7, mailed on Mar. 27, 2020, 13 pages.
Office Action received for Chinese Patent Application No. 201710439448.7, mailed on Oct. 10, 2020, 19 pages.
Office Action received for Chinese Patent Application No. 201780034203.4, mailed on Jul. 14, 2021, 12 pages.
Office Action received for Chinese Patent Application No. 201780034203.4, mailed on Sep. 24, 2021, 7 pages.
Office Action received for Chinese Patent Application No. 201810105846.X, mailed on Aug. 27, 2019, 12 pages.
Office Action received for Chinese Patent Application No. 201810105846.X, mailed on Feb. 25, 2019, 10 pages.
Office Action received for Chinese Patent Application No. 201810105846.X, mailed on Nov. 28, 2019, 9 pages.
Office Action received for Chinese Patent Application No. 201811303556.2 mailed on May 19, 2023, 6 pages.
Office Action received for Chinese Patent Application No. 201811303556.2, mailed on Nov. 28, 2022, 18 pages.
Office Action received for Chinese Patent Application No. 201880032190.1, mailed on May 31, 2023, 20 pages.
Office Action received for Chinese Patent Application No. 201880032190.1, mailed on Nov. 14, 2022, 23 pages.
Office Action received for Chinese Patent Application No. 201910858933.7, mailed on Aug. 18, 2020, 14 pages.
Office Action received for Chinese Patent Application No. 201910858933.7, mailed on Dec. 30, 2021, 9 pages.
Office Action received for Chinese Patent Application No. 201910858933.7, mailed on Jun. 29, 2021, 8 pages.
Office Action received for Chinese Patent Application No. 201911396643.1, mailed on Apr. 6, 2023, 26 pages.
Office Action received for Chinese Patent Application No. 201911396744.9, mailed on Apr. 6, 2023, 19 pages.
Office Action received for Chinese Patent Application No. 201911396819.3, mailed on Apr. 6, 2023, 21 pages.
Office Action received for Chinese Patent Application No. 201911396876.1, mailed on Apr. 7, 2023, 16 pages.
Office Action received for Chinese Patent Application No. 201911401161.0, mailed on Aug. 9, 2022, 17 pages.
Office Action received for Chinese Patent Application No. 201911401161.0, mailed on Dec. 15, 2022, 14 pages.
Office Action received for Chinese Patent Application No. 201911401161.0, mailed on Jan. 24, 2022, 6 pages.
Office Action received for Chinese Patent Application No. 201911401375.8, mailed on Apr. 7, 2023, 10 pages.
Office Action received for Chinese Patent Application No. 202010606407.4, mailed on Jan. 27, 2021, 16 pages.
Office Action received for Chinese Patent Application No. 202010606407.4, mailed on Jun. 2, 2021, 12 pages.
Office Action received for Chinese Patent Application No. 202010606407.4, mailed on Nov. 18, 2021, 6 pages.
Office Action received for Chinese Patent Application No. 202110363565.6, mailed on May 7, 2022, 12 pages.
Office Action received for Chinese Patent Application No. 202110363565.6, mailed on Nov. 16, 2021, 16 pages.
Office Action received for Chinese Patent Application No. 202110783860.7, mailed on Mar. 10, 2022, 15 pages.
Office Action received for Chinese Patent Application No. 202110783860.7, mailed on Nov. 15, 2022, 8 pages.
Office Action received for Chinese Patent Application No. 202211193170.7, mailed on Jun. 30, 2023, 19 pages.
Office Action received for Danish Patent Application No. PA201570666, mailed on Feb. 2, 2016, 9 pages.
Office Action received for Danish Patent Application No. PA2015706686, mailed on Apr. 8, 2016, 8 pages.

(56) References Cited

OTHER PUBLICATIONS

Office Action received for Danish Patent Application No. PA201670656, mailed on Nov. 3, 2016, 8 pages.
Office Action received for Danish Patent Application No. PA 2020 70612, mailed on Mar. 1, 2022, 2 pages.
Office Action received for Danish Patent Application No. PA201570666, mailed on Jun. 27, 2016, 4 pages.
Office Action received for Danish Patent Application No. PA201570668, mailed on Sep. 9, 2016, 3 pages.
Office Action received for Danish Patent Application No. PA201670656, mailed on Jul. 1, 2020, 4 pages.
Office Action received for Danish Patent Application No. PA201670656, mailed on Jun. 14, 2017, 3 pages.
Office Action received for Danish Patent Application No. PA201670656, mailed on May 2, 2019, 4 pages.
Office Action received for Danish Patent Application No. PA201670656, mailed on May 30, 2018, 5 pages.
Office Action received for Danish Patent Application No. PA201770191, mailed on Jan. 25, 2018, 3 pages.
Office Action received for Danish Patent Application No. PA201770191, mailed on Nov. 21, 2018, 4 pages.
Office Action received for Danish Patent Application No. PA201770191, mailed on Oct. 25, 2019, 4 pages.
Office Action received for Danish Patent Application No. PA201770423, mailed on Jun. 12, 2018, 7 pages.
Office Action received for Danish Patent Application No. PA201770423, mailed on Mar. 29, 2019, 6 pages.
Office Action received for Danish Patent Application No. PA201870378, mailed on Feb. 25, 2019, 3 pages.
Office Action received for Danish Patent Application No. PA201870378, mailed on Jan. 6, 2020, 3 pages.
Office Action received for Danish Patent Application No. PA201870379, mailed on Feb. 28, 2019, 3 pages.
Office Action received for Danish Patent Application No. PA201870380, mailed on Mar. 5, 2020, 2 pages.
Office Action received for Danish Patent Application No. PA201870380, mailed on Mar. 27, 2019, 4 pages.
Office Action received for Danish Patent Application No. PA201870380, mailed on Sep. 11, 2018, 9 pages.
Office Action received for Danish Patent Application No. PA201970532, mailed on May 29, 2020, 3 pages.
Office Action received for Danish Patent Application No. PA202070612, mailed on May 10, 2022, 2 pages.
Office Action received for Danish Patent Application No. PA202070612, mailed on Sep. 12, 2022, 3 pages.
Office Action received for Danish Patent Application No. PA202070613, mailed on May 10, 2022, 2 pages.
Office Action received for Danish Patent Application No. PA202070613, mailed on Oct. 13, 2022, 7 pages.
Office Action received for Danish Patent Application No. PA202070613, mailed on Sep. 30, 2021, 4 pages.
Office Action received for Danish Patent Application No. PA202070614, mailed on Apr. 28, 2022, 4 pages.
Office Action received for Danish Patent Application No. PA202070614, mailed on Sep. 28, 2021, 4 pages.
Office Action received for Danish Patent Application No. PA202070615, mailed on Nov. 16, 2021, 4 pages.
Office Action received for Danish Patent Application No. PA202070616, mailed on Jan. 27, 2022, 2 pages.
Office Action received for Danish Patent Application No. PA202070616, mailed on May 5, 2022, 3 pages.
Office Action received for Danish Patent Application No. PA202070815, mailed on Jun. 14, 2022, 3 pages.
Office Action received for Danish Patent Application No. PA202070815, mailed on Oct. 18, 2021, 2 pages.
Office Action received for Danish Patent Application No. PA202170113, mailed on Apr. 15, 2021, 2 pages.
Office Action received for Danish Patent Application No. PA202170113, mailed on Aug. 18, 2022, 2 pages.
Office Action received for Danish Patent Application No. PA202170113, mailed on May 3, 2022, 2 pages.
Office Action received for European Patent Application No. 13811085.3, mailed on Apr. 20, 2018, 15 pages.
Office Action received for European Patent Application No. 16837432.0, mailed on Jan. 10, 2020, 7 pages.
Office Action received for European Patent Application No. 16837432.0, mailed on Jan. 27, 2021, 7 pages.
Office Action received for European Patent Application No. 17810749.6, mailed on Aug. 20, 2019, 9 pages.
Office Action received for European Patent Application No. 18154145.9, mailed on Apr. 3, 2018, 6 pages.
Office Action received for European Patent Application No. 18727543.3, mailed on Mar. 26, 2021, 7 pages.
Office Action received for European Patent Application No. 19721883.7, mailed on Jan. 10, 2020, 4 pages.
Office Action received for European Patent Application No. 19721883.7, mailed on Jun. 15, 2021, 9 pages.
Office Action received for European Patent Application No. 19721883.7, mailed on May 28, 2020, 11 pages.
Office Action received for European Patent Application No. 20182116.2, mailed on May 25, 2021, 9 pages.
Office Action received for European Patent Application No. 20182116.2, mailed on Nov. 6, 2020, 9 pages.
Office Action received for European Patent Application No. 20203526.7, mailed on Nov. 23, 2021, 9 pages.
Office Action received for European Patent Application No. 20721342.2, mailed on Nov. 4, 2021, 9 pages.
Office Action received for European Patent Application No. 21165295.3, mailed on Jul. 1, 2021, 10 pages.
Office Action received for European Patent Application No. 21168916.1, mailed on Aug. 23, 2021, 8 pages.
Office Action received for European Patent Application No. 15771747.1, mailed on Oct. 31, 2017, 7 pages.
Office Action received for German Patent Application No. 112015002326.7, mailed on Feb. 20, 2019, 7 pages.
Office Action received for German Patent Application No. 112015007285.3, mailed on Mar. 7, 2023, 15 pages.
Office Action received for Indian Patent Application No. 202014041563, mailed on Dec. 30, 2021, 6 pages.
Office Action received for Indian Patent Application No. 202014041571, mailed on Dec. 17, 2021, 5 pages.
Office Action received for Japanese Patent Application No. 2016-535045, mailed on May 12, 2017, 10 pages.
Office Action received for Japanese Patent Application No. 2016-557650, mailed on Apr. 13, 2018, 9 pages.
Office Action received for Japanese Patent Application No. 2016-557650, mailed on Aug. 10, 2017, 10 pages.
Office Action received for Japanese Patent Application No. 2016-557650, mailed on Nov. 9, 2018, 6 pages.
Office Action received for Japanese Patent Application No. 2018-014096, mailed on Aug. 28, 2020, 4 pages.
Office Action received for Japanese Patent Application No. 2018-014096, mailed on Jan. 6, 2020, 17 pages.
Office Action received for Japanese Patent Application No. 2018-014096, mailed on Jun. 29, 2018, 20 pages.
Office Action received for Japanese Patent Application No. 2018-014096, mailed on May 8, 2019, 14 pages.
Office Action received for Japanese Patent Application No. 2018-014096, mailed on Nov. 6, 2018, 15 pages.
Office Action received for Japanese Patent Application No. 2018-014096, mailed on Jan. 8, 2019, 6 pages.
Office Action received for Japanese Patent Application No. 2018-184532, mailed on Mar. 1, 2021, 11 pages.
Office Action received for Japanese Patent Application No. 2019-044107, mailed on Jul. 30, 2021, 9 pages.
Office Action received for Japanese Patent Application No. 2019-044107, mailed on May 29, 2020, 6 pages.
Office Action received for Japanese Patent Application No. 2019-162293, mailed on Jan. 31, 2020, 8 pages.
Office Action received for Japanese Patent Application No. 2019-162293, mailed on Jul. 27, 2020, 9 pages.

(56) References Cited

OTHER PUBLICATIONS

Office Action received for Japanese Patent Application No. 2019-563407, mailed on Feb. 5, 2021, 5 pages.
Office Action received for Japanese Patent Application No. 2020-000492, mailed on Dec. 11, 2020, 6 pages.
Office Action received for Japanese Patent Application No. 2022-104679, mailed on Sep. 18, 2020, 13 pages.
Office Action received for Japanese Patent Application No. 2020-115940, mailed on May 7, 2021, 3 pages.
Office Action received for Japanese Patent Application No. 2020-160052, mailed on Dec. 17, 2021, 10 pages.
Office Action received for Japanese Patent Application No. 2020-160053, mailed on Aug. 1, 2022, 8 pages.
Office Action received for Japanese Patent Application No. 2020-160053, mailed on Jan. 31, 2022, 8 pages.
Office Action received for Japanese Patent Application No. 2020-160054, mailed on Jan. 21, 2022, 8 pages.
Office Action received for Japanese Patent Application No. 2021-131726, mailed on Aug. 22, 2022, 8 pages.
Office Action received for Japanese Patent Application No. 2021-131726, mailed on Dec. 2, 2022, 4 pages.
Office Action received for Japanese Patent Application No. 2021-153558, mailed on Nov. 21, 2022, 8 pages.
Office Action received for Japanese Patent Application No. 2021-565912, mailed on Jan. 12, 2023, 9 pages.
Office Action received for Japanese Patent Application No. 2021-565912, mailed on Jun. 26, 2023, 3 pages.
Office Action received for Japanese Patent Application No. 2021-571468, mailed on Jan. 5, 2023, 14 pages.
Office Action received for Japanese Patent Application No. 2022-022159, mailed on Feb. 20, 2023, 10 pages.
Office Action received for Japanese Patent Application No. 2022-076722, mailed on Mar. 13, 2023, 6 pages.
Office Action received for Korean Patent Application No. 10-2016-7014577, mailed on Dec. 26, 2017, 14 pages.
Office Action received for Korean Patent Application No. 10-2016-7014577, mailed on Oct. 31, 2018, 11 pages.
Office Action received for Korean Patent Application No. 10-2016-7033638, mailed on Jan. 31, 2017, 6 pages.
Office Action received for Korean Patent Application No. 10-2016-7025538, mailed on Aug. 15, 2020, 8 pages.
Office Action received for Korean Patent Application No. 10-2019-7025538, mailed on Feb. 17, 2020, 12 pages.
Office Action received for Korean Patent Application No. 10-20196-7025781, mailed on Nov. 26, 2019, 10 pages.
Office Action received for Korean Patent Application No. 10-2019-7025781, mailed on Oct. 30, 2020, 10 pages.
Office Action received for Korean Patent Application No. 10-2019-7033834, mailed on Jan. 22, 2021, 13 pages.
Office Action received for Korean Patent Application No. 10-2020-0123815, mailed on May 31, 2022, 10 pages.
Office Action received for Korean Patent Application No. 10-2020-0123821, mailed on Sep. 20, 2022, 11 pages.
Office Action received for Korean Patent Application No. 10-2020-0123840, mailed on Nov. 21, 2022, 18 pages.
Office Action received for Korean Patent Application No. 10-2020-7026035, mailed on Feb. 19, 2021, 13 pages.
Office Action received for Korean Patent Application No. 10-2021-7026284, mailed on Aug. 31, 2021, 10 pages.
Office Action received for Korean Patent Application No. 10-2021-7031939, mailed on Oct. 19, 2021, 11 pages.
Office Action received for Korean Patent Application No. 10-2021-7036242, mailed on Sep. 19, 2023, 13 pages.
Office Action received for Korean Patent Application No. 10-2022-0061486, mailed on Aug. 29, 2022, 5 pages.
Office Action received for Korean Patent Application No. 10-2022-7031866, mailed on Nov. 18, 2022, 11 pages.
Office Action received for Korean Patent Application No. 10-2022-7036278, mailed on Jun. 30, 2023, 10 pages.
Office Action received for Taiwanese Patent Application No. 104128685, mailed on Jan. 4, 2017, 40 pages.
Partial Supplementary European Search Report received for European Patent Application No. 17810749.6, mailed on Apr. 25, 2019, 8 pages.
RAZYKDREViEWS, "In Depth Review of Apple Watch Activity: and Workaut App", available at <URL: https://www.youtube.com/watch?v=GkKl3qlK0ow>., Category: X Ciaims: 1-5 Category: L Reason: Internet citation/video, May 11, 2015, 1 page.
Result of Consultation received for European Patent Application No. 17810749.6, mailed on Dec. 15, 2020, 3 pages.
Result of Consultation received for European Patent Application No. 17810749.6, mailed on Jan. 18, 2021, 3 pages.
Result of Consultation received for European Patent Application No. 18154145.9, mailed on Nov. 30, 2020, 17 pages.
Result of Consultation received for European Patent Application No. 18154145.9, mailed on Sep. 4, 2020, 3 pages.
Result of Consultation received for European Patent Application No. 18727543.3, mailed on Mar. 15, 2023, 6 pages.
Result of Consultation received for European Patent Application No. 19721883.7, mailed on Oct. 7, 2020, 3 pages.
Result of Consultation received for European Patent Application No. 20203526.7, mailed on Jan. 13, 2023, 3 pages.
Result of Consultation received for European Patent Application No. 20721342.2, mailed on Oct. 18, 2022, 3 pages.
RiZKNOWS, "Garmin Connect Mobile App—REVIEW #2", https://www.youtube.com/watch?v=7my3wMpeRbe, Category: X Claims: 1-5 Category: L Reason: Internet citation/video, Oct. 22, 2015, 1 page.
RIZKNOWS, "TomTom Multisport Cardio Review", Online available at :—https://www.youtube.com/watch?v=WoVCzLrSN9A, Sep. 4, 2015, 1 page.
Search report and opinion received for Danish Patent Application No. PA201770191, mailed on Jun. 30, 2017, 9 pages.
Search report and Opinion received for Danish Patent Application No. PA201770423, mailed on Oct. 4, 2017, 10 pages.
Search Report and Opinion received for Danish Patent Application No. PA201870378, mailed on Sep. 10, 2018, 9 pages.
Search Report and Opinion received for Danish Patent Application No. PA201870379, mailed on Sep. 14, 2018, 9 pages.
Search Report and Opinion received for Danish Patent Application No. PA201970532, mailed on Nov. 8, 2019, 9 pages.
Search Report and Opinion received for Danish Patent Application No. PA202070612, mailed on Jun. 7, 2021, 9 pages.
Search Report and Opinion received for Danish Patent Application No. PA202070613, mailed on Jan. 22, 2021, 9 pages.
Search Report and Opinion received for Danish Patent Application No. PA202070614, mailed on Jan. 14, 2021, 9 pages.
Search Report and Opinion received for Danish Patent Application No. PA202070615, mailed on Jan. 22, 2021, 9 pages.
Search Report and Opinion received for Danish Patent Application No. PA202070616, mailed on Feb. 3, 2021, 8 pages.
Search Report and Opinion received for Danish Patent Application No. PA202070815, mailed on Mar. 16, 2021, 8 pages.
Search Report and Opinion received for Danish Patent Application No. PA202170113, mailed on Nov. 30, 2021, 9 pages.
Smith, "Garmin Fenix 5 Activity/Smart Watch Review", Online Available at :—https://www.youtube.com/watch?v=6PkQxXqxpoU, Sep. 2, 2017, 1 page.
SPORTSTECHGUIDES, "Garmin Fenix 5: How to Add Power Data Fields", Online Available at :—https://www.youtube.com/watch?v=ZkPptnnXEiQ; Apr. 29, 2017, 2 pages.
SPORTSTECHGUIDES, "Garmin Fenix 5: How to Set Up Run Alerts", Online Availabie at :—https://www.youtube.com/watch?v=gSMwv8vlhB4, May 13, 2017, 2 pages.
Summons to Attend oral proceedings received for European Patent Application No. 13811085.3, mailed on Jan. 26, 2018, 14 pages.
Summons to Attend Oral Proceedings received for European Patent Application No. 13811085.3, mailed on Mar. 3, 2022, 3 pages.
Summons to Attend Oral Proceedings received for European Patent Application No. 17810749.6, mailed on Aug. 12, 2020, 11 pages.
Summons to Attend Oral Proceedings received for European Patent Application No. 18154145.9, mailed on Sep. 17, 2020, 11 pages.

(56) References Cited

OTHER PUBLICATIONS

Summons to Attend Oral Proceedings received for European Patent Application No. 18727543.3, mailed on Oct. 25, 2022, 8 pages.
Summons to Attend Oral Proceedings received for European Patent Application No. 20182116.2, mailed on Dec. 21, 2021, 7 pages.
Summons to Attend Oral Proceedings received for European Patent Application No. 20203526.7, mailed on Jun. 23, 2022, 9 pages.
Summons to Attend Oral Proceedings received for European Patent Application No. 20721342.2, mailed on May 20, 2022, 11 pages.
Summons to Attend Oral Proceedings received for European Patent Application No. 21165295.3, mailed on Jul. 25, 2023, 14 pages.
Summons to Attend Oral Proceedings received for European Patent Application No. 21168916.1, mailed on Jul. 14, 2023, 12 pages.
Summons to Attend Oral Proceedings received for European Patent Application No. 15771747.1, mailed on May 25, 2018, 17 pages.
Summons to Oral Proceedings received for European Patent Application No. 15771747.1, mailed on Apr. 29, 2021, 8 pages.
Supplemental Notice of Allowance received for U.S. Appl. No. 15/616,480, mailed on Mar. 28, 2019, 2 pages.
Supplemental Notice of Allowance received for U.S. Appl. No. 15/627,069, mailed on Jul. 12, 2021, 2 pages.
Supplemental Notice of Allowance received for U.S. Appl. No. 15/925,652, mailed on Feb. 27, 2021, 3 pages.
Supplemental Notice of Allowance received for U.S. Appl. No. 15/925,652, mailed on Jan. 6, 2021, 3 pages.
Supplemental Notice of Allowance received for U.S. Appl. No. 15/925,652, mailed on Jan. 26, 2021, 3 pages.
Supplemental Notice of Allowance received for U.S. Appl. No. 16/144,849, mailed on Mar. 31, 2020, 2 pages.
Supplemental Notice of Allowance received for U.S. Appl. No. 16/556,023, mailed on Feb. 3, 2021, 2 pages.
Supplemental Notice of Allowance received for U.S. Appl. No. 16/588,950, mailed on Apr. 1, 2020, 2 pages.
Supplemental Notice of Allowance received for U.S. Appl. No. 16/588,950, mailed on Jul. 29, 2020, 2 pages.
Supplemental Notice of Allowance received for U.S. Appl. No. 16/588,950, mailed on Jun. 18, 2020, 2 pages.
Supplemental Notice of Allowance received for U.S. Appl. No. 16/894,309, mailed on Apr. 8, 2022, 3 pages.
Supplemental Notice of Allowance received for U.S. Appl. No. 16/894,309, mailed on Dec. 24, 2021, 2 pages.
Supplemental Notice of Allowance received for U.S. Appl. No. 16/894,309, mailed on Jan. 25, 2022, 2 pages.
Supplemental Notice of Allowance received for U.S. Appl. No. 16/994,352, mailed on Jun. 20, 2022, 2 pages.
Supplemental Notice of Allowance received for U.S. Appl. No. 17/030,318, mailed on Apr. 4, 2022, 2 pages.
Supplemental Notice of Allowance received for U.S. Appl. No. 17/030,318, mailed on Feb. 22, 2022, 2 pages.
Supplemental Notice of Allowance received for U.S. Appl. No. 17/030,318, mailed on Mar. 16, 2022, 2 pages.
Supplemental Notice of Allowance received for U.S. Appl. No. 17/030,321, mailed on Apr. 15, 2022, 2 pages.
Supplemental Notice of Allowance received for U.S. Appl. No. 17/030,321, mailed on Jul. 27, 2012, 2 pages.
Supplemental Notice of Allowance received for U.S. Appl. No. 17/030,321, mailed on Jun. 10, 2022, 2 pages.
Supplemental Notice of Allowance received for U.S. Appl. No. 17/030,321, mailed on May 27, 2022, 2 pages.
Supplemental Notice of Allowance received for U.S. Appl. No. 17/030,343, mailed on Jan. 6, 2023, 2 pages.
Supplemental Notice of Allowance received for U.S. Appl. No. 17/030,343, mailed on Nov. 9, 2022, 2 pages.
Supplemental Notice of Allowance received for U.S. Appl. No. 17/030,343, mailed on Oct. 5, 2022, 2 pages.
Supplemental Notice of Allowance received for U.S. Appl. No. 17/192,161, mailed on Jul. 13, 2022, 2 pages.
Supplemental Notice of Allowance received for U.S. Appl. No. 17/192,161, mailed on May 13, 2022, 2 pages.
Supplemental Notice of Allowance received for U.S. Appl. No. 17/381,570, mailed on Aug. 11, 2023, 2 pages.
Supplemental Notice of Allowance received for U.S. Appl. No. 17/381,570, mailed on Sep. 13, 2023, 2 pages.
Supplemental Notice of Allowance received for U.S. Appl. No. 17/666,301, mailed on Jun. 5, 2023, 2 pages.
Supplemental Notice of Allowance received for U.S. Appl. No. 17/666,301, mailed on May 17, 2023, 2 pages.
Supplemental Notice of Allowance received for U.S. Appl. No. 17/852,020, mailed on Aug. 4, 2023, 2 pages.
Supplemental Notice of Allowance received for U.S. Appl. No. 17/951,875, mailed on Aug. 25, 2023, 2 pages.
Supplemental Notice of Allowance received for U.S. Appl. No. 17/952,185, mailed on Oct. 2, 2023, 2 pages.
Supplemental European Search Report received for European Patent Application No. 17810749.6, mailed on Aug. 6, 2019, 6 pages.
SUUNTO, "Suunto Spartan—Heart Rate Zones", Oniine Availabie at :—https://www.y0utube.com/watch?v=aixfoCnS0OU, Mar. 19, 2018, 2 pages.
SUUNTO Spartan Trainer Wrist HR 1.12, Online Available at :—https://web.archive.org/webs/20180127155200/https://ns.suunto.com/Manuals/Spartan_Trainer_WristHR/Userguides/Suunto_Spartan_Trainer_WristHR_UserGuide_EN.pdf, Jan. 17, 2018, 47 pages.
TEUNMO, "Data field: Visual Pace Alarm", Garmin Forum; Available online at: https://forums.garmin.com/forum/developers/connect-iq/connect-iq-showcase/115996-data-field-visual-pace-alarm, Nov. 17, 2015, 10 pages.
TOMTOM, "TomTom Runner & Multi-Sport Reference Guide", Online available at :—https://web.archive.org/web/20150908075934/http://download.tomtom.com/open/manuals/Runner_Multi-Sport/refman-TomTom-Runner-Multi-Sport-RG-en-gb.pdf, Sep. 8, 2015, 44 pages.
Updated Notice of Allowance received for U.S. Appl. No. 17/030,318, mailed on Feb. 23, 2023, 3 pages.
Updated Notice of Allowance received for U.S. Appl. No. 17/030,340, mailed on Dec. 2, 2022, 2 pages.
Updated Notice of Allowance received for U.S. Appl. No. 17/030,340, mailed on Nov. 2, 2022, 2 pages.
Updated Notice of Allowance received for U.S. Appl. No. 17/030,340, mailed on Nov. 10, 2022, 2 pages.
Utilization of Galaxy S4—S Health, ChatOn and Samsung Hub, Available at: http://seeit.kr/1263, Jun. 12, 2013, 25 pages.
VENUSIVENUS, "Nike Training Club", Available online at: https://www.youtube.com/watch?v=_pe6fqJPA04, Mar. 28, 2011, 6 pages.
Vicky's Blog, "How to Log in to PS4 Automatically with Particular User?", Online available on :—https://www.youtube.com/watch?v=kqdlzXAvOkY. May 30, 2018, 3 pages.
Visual Pace Alarm app, Available Online at: https://apps.garmin.com/en-US/apps/3940f3a2-4847-4078-a911-d77422966c82, Oct. 19, 2016, 1 page.
Wesley, "Apple Watch Series 1", online available at:—http://toolbox.info/blog/archives/1737-unknown.html, May 28, 2015, 5 pages.
Youtube, "Apple Watch Series 3", Online available at:—https://www.youtube.com/watch?v=iBPr9gEfkK8, Nov. 21, 2017, 15 pages.
YoyoDavid, "How to Use Multipie Accounts on the Playstation 4", Online available at:—https://www.youtube.com/watch?v=5V21obRMeKE, Jan. 9, 2014, 3 pages.
Yuling et al., "Research on Motion Modeling of Virtual Gear Measuring Center", Tool Technology, vol. 43, No. 2, 2009, pp. 85-87.
Zlelik. "Garmin Fenix 5 Open Water Swimming Activity Demo", Online Available at :—https://www.youtube.com./watch?v=iSVhdvw2dcs, Jun. 9, 2017, 1 page.
Applicant-Initiated Interview Summary received for U.S. Appl. No. 17/735,395, mailed on May 30, 2024, 2 pages.
Applicant-Initiated Interview Summary received for U.S. Appl. No. 17/951,945, mailed on May 30, 2024, 2 pages.
Applicant-Initiated Interview Summary received for U.S Appl. No. 17/952,133, mailed on Apr. 23, 2024, 3 pages.
Applicant-Initiated Interview Summary received for U.S. Appl. No. 17/952,233, mailed on Apr. 2, 2024, 4 pages.
Corrected Notice of Allowance received for U.S. Appl. No. 16/820,383, mailed on Mar. 27, 2024, 2 pages.

(56) References Cited

OTHER PUBLICATIONS

Corrected Notice of Allowance received for U.S. Appl. No. 17/041,438, mailed on Mar. 28, 2024, 2 pages.
Corrected Notice of Allowance received for U.S. Appl. No. 17/735,395, mailed on Jul. 16, 2024, 3 pages.
Corrected Notice of Allowance received for U.S. Appl. No. 17/892,534, mailed on Jun. 5, 2024, 6 pages.
Corrected Notice of Allowance received for U.S. Appl. No. 17/896,791, mailed on Jun. 7, 2024, 2 pages.
Corrected Notice of Allowance received for U.S. Appl. No. 17/951,945, mailed on Jul. 9, 2024, 2 pages.
Corrected Notice of Allowance received for U.S. Appl. No. 17/952,185, mailed on Mar. 27, 2024, 2 pages.
Corrected Notice of Allowance received for U.S. Appl. No. 17/952,233, mailed on May 9, 2024, 2 pages.
Corrected Notice of Allowance received for U.S. Appl. No. 18/135,056, mailed on Jul. 17, 2024, 6 pages.
Corrected Notice of Allowance received for U.S. Appl. No. 18/135,056, mailed on Jul. 22, 2024, 3 pages.
Decision to Grant received for European Patent Application No. 21714460.9, mailed on Jun. 20, 2024, 4 pages.
Decision to Refuse received for European Patent Application No. 21165295.3, mailed on Apr. 29, 2024, 14 pages.
Decision to Refuse received for Japanese Patent Application No. 2022-130087, mailed on Apr. 30, 2024, 6 pages (3 pages of English Translation and 3 pages of Official Copy).
Extended European Search Report received for European Patent Application No. 23217005.0, mailed on Mar. 13, 2024, 12 pages.
Extended European Search Report received for European Patent Application No. 23218255.0, mailed on Mar. 27, 2024, 10 pages.
Extended European Search Report received for European Patent Application No. 24152191.3, mailed on Apr. 15, 2024, 11 pages.
Final Office Action received for U.S. Appl. No. 17/031,854, mailed on May 16, 2024, 21 pages.
Final Office Action received for U.S. Appl. No. 18/135,056, mailed on May 2, 2024, 18 pages.
Intention to Grant received for European Patent Application No. 23153898.4, mailed on Jul. 2, 2024, 11 pages.
Minutes of Oral Proceedings received for European Patent Application No. 21165295.3, mailed on Apr. 26, 2024, 6 pages.
Non-Final Office Action received for U.S. Appl. No. 17/735,395, mailed on Mar. 19, 2024, 32 pages.
Non-Final Office Action received for U.S. Appl. No. 17/951,945, mailed on Mar. 20, 2024, 22 pages.
Notice of Allowance received for Chinese Patent Application No. 202210326960.1, mailed on Jun. 21, 2024, 5 pages (1 page of English Translation and 4 pages of Official Copy).
Notice of Allowance received for Chinese Patent Application No. 202310775734.6, mailed on Apr. 18, 2024, 4 pages (1 page of English Translation and 3 pages of Official Copy).
Notice of Allowance received for Chinese Patent Application No. 202311059240.4, mailed on May 23, 2024, 2 pages (1 page of English Translation and 1 page of Official Copy).
Notice of Allowance received for U.S. Appl. No. 17/735,395, mailed on Jul. 3, 2024, 11 pages.
Notice of Allowance received for U.S. Appl. No. 17/951,945, mailed on Jun. 26, 2024, 10 pages.
Notice of Allowance received for U.S. Appl. No. 17/952,233, mailed on May 1, 2024, 9 pages.
Notice of Allowance received for U.S. Appl. No. 18/135,056, mailed on Jul. 10, 2024, 10 pages.
Notice of Allowance received for U.S. Appl. No. 18/204,217, mailed on Mar. 26, 2024, 7 pages.
Office Action received for Australian Patent Application No. 2023210876, mailed on Jun. 21, 2024, 2 pages.
Office Action received for Australian Patent Application No. 2023214377, mailed on Jun. 5, 2024, 4 pages.
Office Action received for Australian Patent Application No. 2023214377, mailed on Mar. 27, 2024, 3 pages.
Office Action received for Chinese Patent Application No. 202080039364.4, mailed on Apr. 9, 2024, 15 pages (7 pages of English Translation and 8 pages of Official Copy).
Office Action received for Chinese Patent Application No. 202310774963.6, mailed on Apr. 21, 2024, 18 pages (11 pages of English Translation and 7 pages of Official Copy).
Office Action received for Chinese Patent Application No. 202310774963.6, mailed on Feb. 8, 2024, 11 pages (5 pages of English Translation and 6 pages of Official Copy).
Office Action received for Chinese Patent Application No. 202310775734.6, mailed on Mar. 2, 2024, 11 pages (5 pages of English Translation and 6 pages of Official Copy).
Office Action received for Chinese Patent Application No. 202310828052.7, mailed on Mar. 6, 2024, 16 pages (7 pages of English Translation and 9 pages of Official Copy).
Office Action received for Chinese Patent Application No. 202311059240.4, mailed on Mar. 19, 2024, 11 pages (5 pages of English Translation and 6 pages of Official Copy).
Office Action received for European Patent Application No. 22731852.4, mailed on Jun. 26, 2024, 7 pages.
Office Action received for European Patent Application No. 23153899.2, mailed on Jun. 25, 2024, 11 pages.
Office Action received for European Patent Application No. 23153900.8, mailed on Jun. 26, 2024, 11 pages.
Office Action received for Japanese Patent Application No. 2021-565912, mailed on Jun. 18, 2024, 3 pages (1 page of English Translation and 2 pages of Official Copy).
Office Action received for Japanese Patent Application No. 2023-041035, mailed on Jul. 16, 2024, 4 pages (2 pages of English Translation and 2 pages of Official Copy).
Office Action received for Japanese Patent Application No. 2023-065859, mailed on Mar. 11, 2024, 8 pages (4 pages of English Translation and 4 pages of Official Copy).
Office Action received for Japanese Patent Application No. 2023-097896, mailed on Jul. 5, 2024, 10 pages (5 pages of English Translation and 5 pages of Official Copy).
Office Action received for Korean Patent Application No. 10-2021-7036242, mailed on May 31, 2024, 7 pages (2 pages of English Translation and 5 pages of Official Copy).
Office Action received for Korean Patent Application No. 10-2023-0114488, mailed on Apr. 30, 2024, 16 pages (6 pages of English Translation and 10 pages of Official Copy).
Office Action received for Korean Patent Application No. 10-2023-7025320, mailed on Mar. 11, 2024, 9 pages (4 pages of English Translation and 5 pages of Official Copy).
Result of Consultation received for European Patent Application No. 21165295.3, mailed on Apr. 18, 2024, 3 pages.
"Workout and Fitness Tracker for Humans", Available online at: https://gentler.app/, Retrieved on: May 14, 2024, 11 pages.
Applicant-Initiated Interview Summary received for U.S. Appl. No. 17/735,395, mailed on Jan. 31, 2024, 2 pages.
Applicant-Initiated Interview Summary received for U.S. Appl. No. 17/892,534. mailed on Feb. 1, 2024, 4 pages.
Applicant-Initiated Interview Summary received for U.S. Appl. No. 17/951,945, mailed on Jan. 31, 2024, 2 pages.
Final Office Action received for U.S. Appl. No. 17/951,624, mailed on Jan. 25, 2024, 48 pages.
Non-Final Office Action received for U.S. Appl. No. 17/952,233, mailed on Feb. 2, 2024, 18 pages.
Notice of Allowance received for U.S. Appl. No. 17/951,613, mailed on Feb. 2, 2024, 5 pages.
Advisory Action received for U.S. Appl. No. 17/591,184, mailed on Nov. 14, 2023, 5 pages.
Advisory Action received for U.S. Appl. No. 17/744,500, mailed on Nov. 14, 2023, 5 pages.
Advisory Action received for U.S. Appl. No. 17/952,133, mailed on Oct. 20, 2023, 7 pages.
Applicant-Initiated Interview Summary received for U.S. Appl. No. 17/031,854, mailed on Dec. 21, 2023, 5 pages.
Applicant-Initiated Interview Summary received for U.S. Appl. No. 17/591,184, mailed on Oct. 30, 2023, 2 pages.
Applicant-Initiated Interview Summary received for U.S. Appl. No. 17/735,395, mailed on Nov. 15, 2023, 2 pages.

(56) References Cited

OTHER PUBLICATIONS

Applicant-Initiated Interview Summary received for U.S. Appl. No. 17/744,500, mailed on Oct. 17, 2023, 4 pages.
Applicant-Initiated Interview Summary received for U.S. Appl. No. 17/896,791, mailed on Oct. 12, 2023, 2 pages.
Applicant-Initiated Interview Summary received for U.S. Appl. No. 17/951,624, mailed on Nov. 16, 2023, 3 pages.
Applicant-Initiated Interview Summary received for U.S. Appl. No. 17/951,945, mailed on Nov. 15, 2023, 2 pages.
Applicant-Initiated Interview Summary received for U.S. Appl. No. 18/135,056, mailed on Jan. 3, 2024, 2 pages.
Corrected Notice of Allowance received for U.S. Appl. No. 17/041,438, mailed on Dec. 1, 2023, 2 pages.
Corrected Notice of Allowance received for U.S. Appl. No. 17/744,500, mailed on Jan. 12, 2024, 3 pages.
Corrected Notice of Allowance received for U.S. Appl. No. 17/896,791, mailed on Jan. 2, 2024, 2 pages.
Corrected Notice of Allowance received for U.S. Appl. No. 17/951,613, mailed on Jan. 2, 2024, 2 pages.
Corrected Notice of Allowance received for U.S. Appl. No. 17/952,027, mailed on Jan. 22, 2024, 3 pages.
Decision to Grant received for European Patent Application No. 16837432.0, mailed on Dec. 21, 2023, 2 pages.
Extended European Search Report received for European Patent Application No. 23189089.8, mailed Nov. 23, 2023, 11 pages.
Final Office Action received for U.S. Appl. No. 17/031,859, mailed on Nov. 13, 2023, 15 pages.
Final Office Action received for U.S. Appl. No. 17/735,395, mailed on Dec. 7, 2023, 29 pages.
Final Office Action received for U.S. Appl. No. 17/892,534, mailed on Nov. 9, 2023, 17 pages.
Final Office Action received for U.S. Appl. No. 17/951,945, mailed on Dec. 7, 2023, 20 pages.
International Preliminary Report on Patentability received for PCT Patent Application No. PCT/US2022/029297, mailed on Nov. 30, 2023, 10 pages.
International Search Report on and Written Opinion received for PCT Patent Application No. PCT/US2023/024185, mailed on Sep. 18, 2023, 12 pages.
Minutes of the Oral Proceedings received for European Patent Application No. 21168916.1, mailed on Jan. 3, 2024, 5 pages.
Non-Final Office Action received for U.S. Appl. No. 17/031,854, mailed on Oct. 18, 2023, 22 pages.
Non-Final Office Action received for U.S. Appl. No. 17/952,075, mailed on Jan. 16, 2024, 27 pages.
Non-Final Office Action received for U.S. Appl. No. 18/135,056, mailed on Dec. 7, 2023, 16 pages.
Notice of Acceptance received for Australian Patent Application No. 2023203050, mailed on Oct. 24, 2023, 3 pages.
Notice of Acceptance received for Australian Patent Application No. 2023203776, mailed on Dec. 12, 2023, 3 pages.
Notice of Allowance received for Chinese Patent Application No. 201880032190.1, mailed on Oct. 7, 2023, 4 pages (1 page of English Translation and 3 pages of Official Copy).
Notice of Allowance received for Chinese Patent Application No. 201911401375.8, mailed on Nov. 26, 2023, 2 pages (1 page of English Translation and 1 page of Official Copy).
Notice of Allowance received for U.S. Appl. No. 16/820,383, mailed on Dec. 7, 2023, 13 pages.
Notice of Allowance received for U.S. Appl. No. 17/041,438, mailed on Jan. 22, 2024, 10 pages.
Notice of Allowance received for U.S. Appl. No. 17/041,438, mailed on Oct. 19, 2023, 2 pages.
Notice of Allowance received for U.S. Appl. No. 17/591,184, mailed on Dec. 11, 2023, 9 pages.
Notice of Allowance received fur U.S. Appl. No. 17/744,500, mailed on Dec. 22, 2023, 38 pages.
Notice of Allowance received for U.S. Appl. No. 17/896,791, mailed on Dec. 15, 2023, 9 pages.
Notice of Allowance received for U.S. Appl. No. 17/951,613, mailed on Dec. 8, 2023, 13 pages.
Notice of Allowance received for U.S. Appl. No. 17/951,875, mailed on Dec. 26, 2023, 7 pages.
Notice of Allowance received for U.S. Appl. No. 17/951,875, mailed on Oct. 20, 2023, 8 pages.
Notice of Allowance received for U.S. Appl. No. 17/951,976, mailed on Nov. 17, 2023, 9 pages.
Notice of Allowance received for U.S. Appl. No. 17/952,027, mailed on Dec. 29, 2023, 6 pages.
Notice of Allowance received for U.S. Appl. No. 17/952,185, mailed on Dec. 13, 2023, 9 pages.
Office Action received for Australian Patent Application No. 2023203776, mailed on Nov. 7, 2023, 2 pages.
Office Action received for Australian Patent Application No. 2023237090, mailed on Oct. 18, 2023, 3 pages.
Office Action received for Chinese Patent Application No. 201911401375.8, mailed on Sep. 26, 2023, 13 pages (6 pages of English Translation and 7 pages of Official Copy).
Office Action received for European Patent Application No. 20733174.5, mailed on Dec. 18, 2023, 9 pages.
Office Action received for European Patent Application No. 21714460.9, mailed on Oct. 24, 2023, 13 pages.
Office Action received for Japanese Patent Application No. 2022-130087, mailed on Oct. 2, 2023, 12 pages (6 pages of English Translation and 6 pages of Official Copy).
Office Action received for Japanese Patent Application No. 2023-110196, mailed on Nov. 6, 2023, 4 pages (2 pages of English Translation and 2 pages of Official Copy).
Pre-Appeai Review Report received for Japanese Patent Application No. 2021-565912, mailed on Oct. 12, 2023, 5 pages (2 pages of English Translation and 3 pages of Official Copy).
Result of Consultation received for European Patent Application No. 21168916.1, mailed on Dec. 11, 2023, 25 pages.
Supplemental Notice of Allowance received for U.S. Appl. No. 17/952,181, mailed on Dec. 20, 2023, 2 pages.
Supplemental Notice of Allowance received for U.S. Appl. No. 17/952,181, mailed on Oct. 6, 2023, 2 pages.
Supplemental Notice of Allowance received for U.S. Appl. No. 17/952,181, mailed on Oct. 27, 2023, 2 pages.
Supplemental Notice of Allowance received for U.S. Appl. No. 17/952,185, mailed on Nov. 30, 2023, 2 pages.
Intention to Grant received for European Patent Application No. 21714460.9, mailed on Feb. 8, 2024, 12 pages.
Non-Final Office Action received for U.S. Appl. No. 18/204,217, mailed on Feb. 13, 2024, 21 pages.
Notice of Allowance received for Japanese Patent Application No. 2023-110196, mailed on Feb. 13, 2024, 4 pages (1 page of English Translation and 3 pages of Official Copy).
Notice of Allowance received for Korean Patent Application No. 10-2022-7036278, mailed on Jan. 30, 2024, 8 pages (2 pages of English Translation and 6 pages of Official Copy).
Office Action received for Japanese Patent Application No. 2023-041035, mailed on Feb. 9, 2024, 13 pages (6 pages of English Translation and 7 pages of Official Copy).
International Search Report and Written Opinion received for PCT Patent Application No. PCT/US2023/030718, mailed on Jan. 9, 2024, 12 pages.
Notice of Allowance received for U.S. Appl. No. 17/896,791, mailed on Mar. 13, 2024, 8 pages.
Notice of Allowance received for U.S. Appl. No. 17/951,976, mailed on Mar. 12, 2024, 5 pages.
Office Action received for Chinese Patent Application No. 202211193170.7, mailed on Jan. 6, 2024, 13 pages (6 pages of English Translation and 7 pages of Official Copy).
Corrected Notice of Allowance received for U.S. Appl. No. 17/952,181, mailed on Aug. 28, 2024, 2 pages.
Office Action received for German Patent Application No. 112015007313.2, mailed on Aug. 6, 2024, 12 pages (6 pages of English Translation and 6 pages of Official Copy).

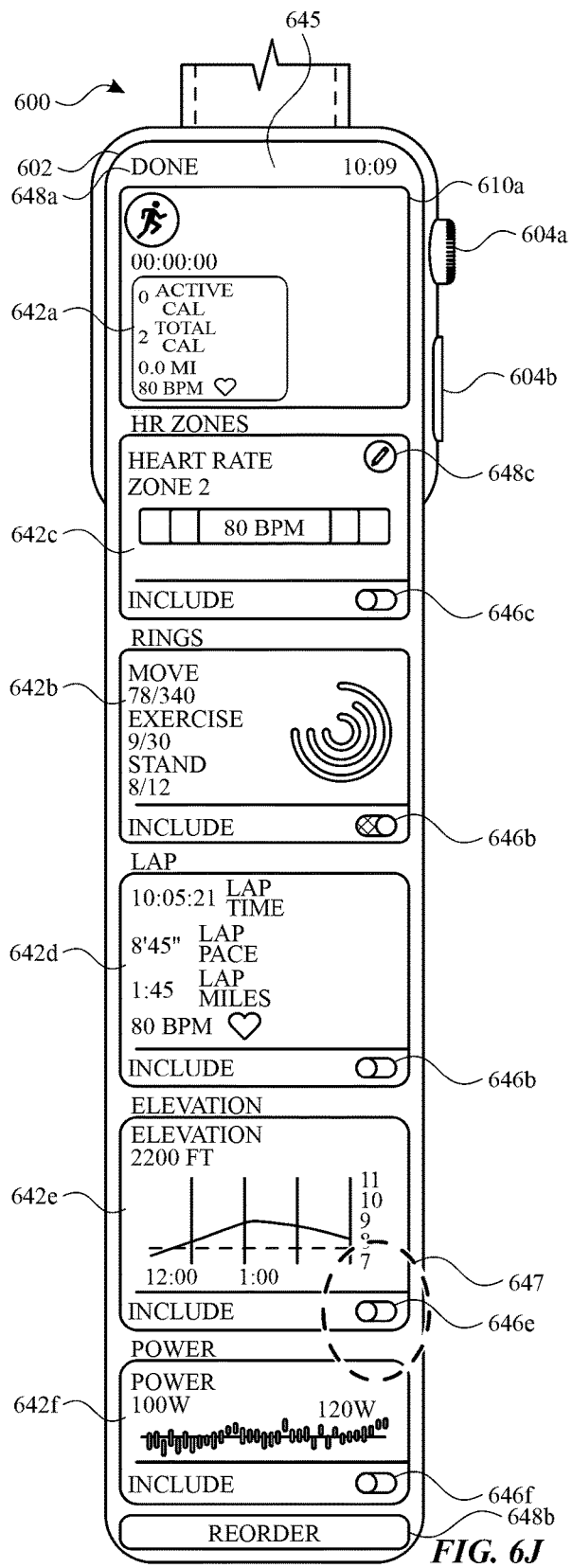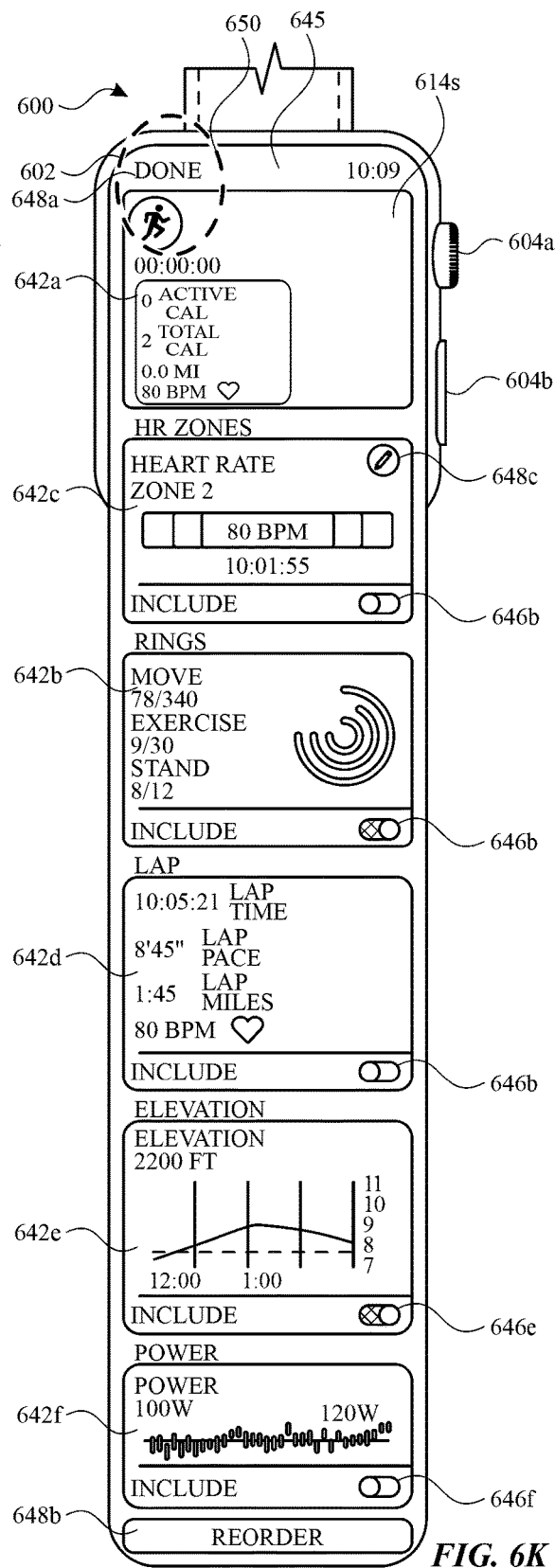

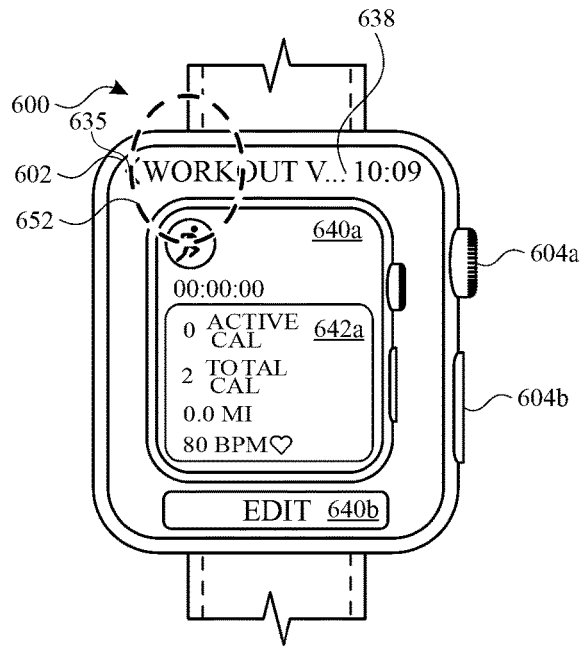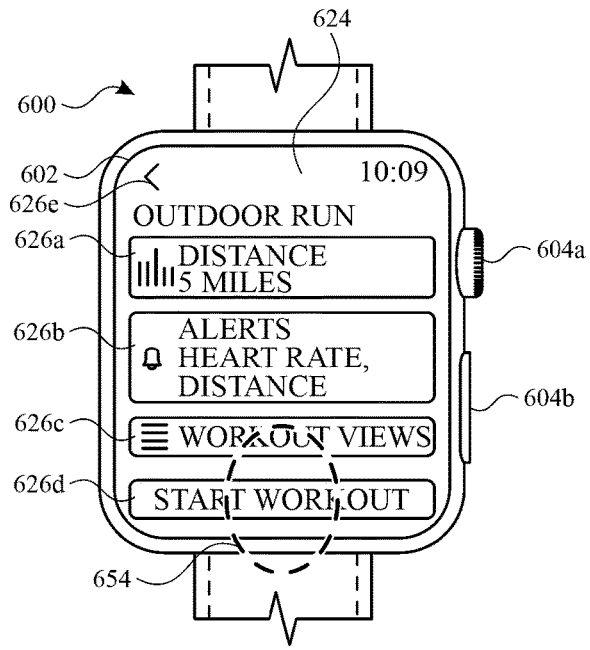
*FIG. 6L*          *FIG. 6M*
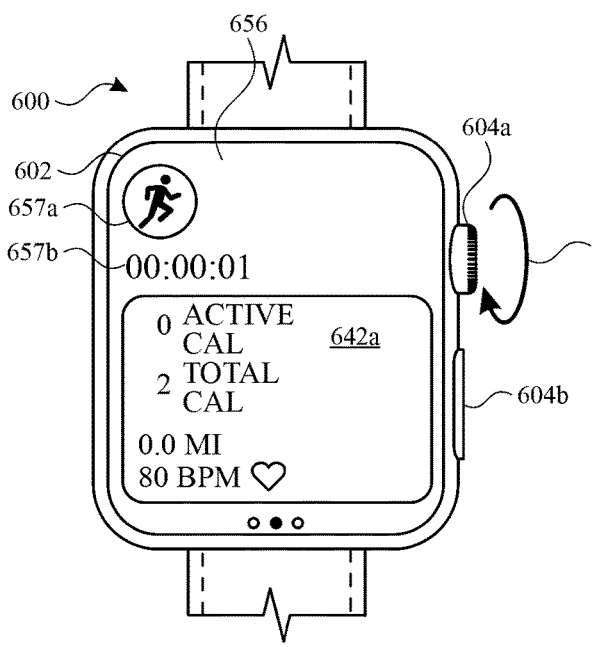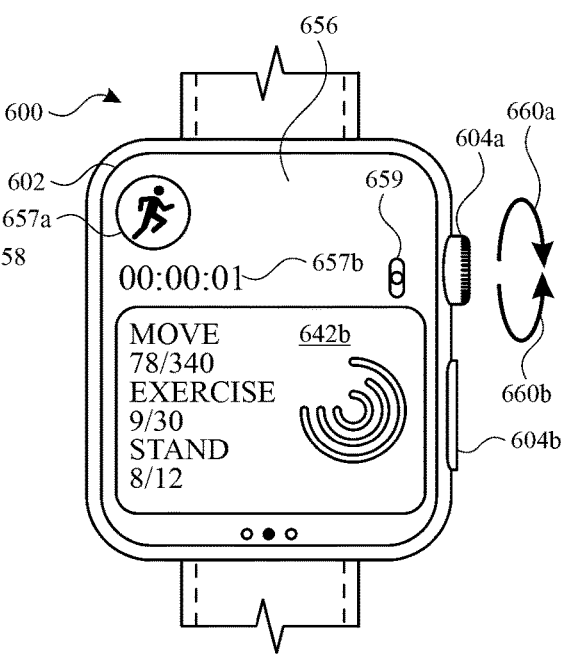
*FIG. 6N*          *FIG. 6O*

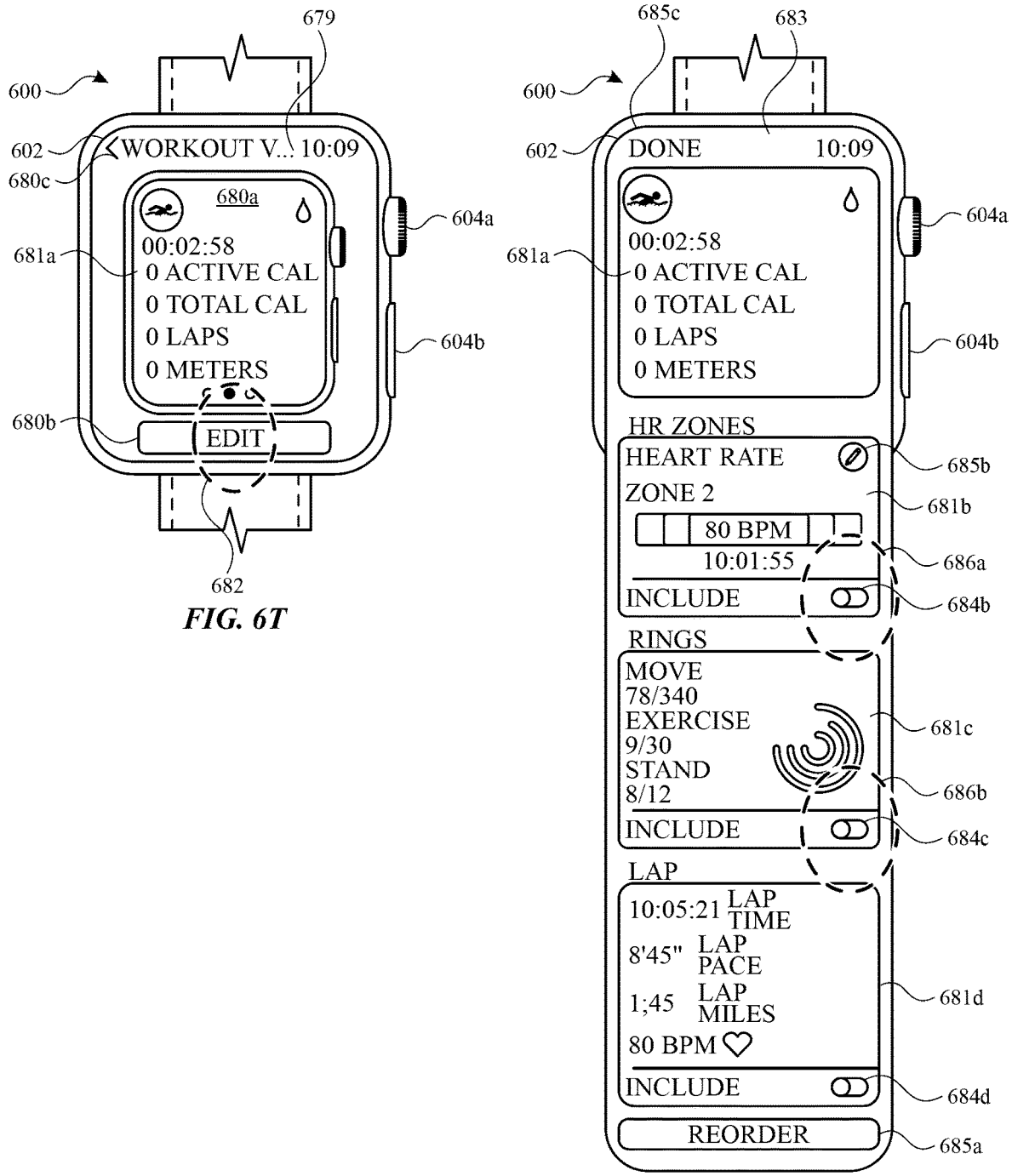

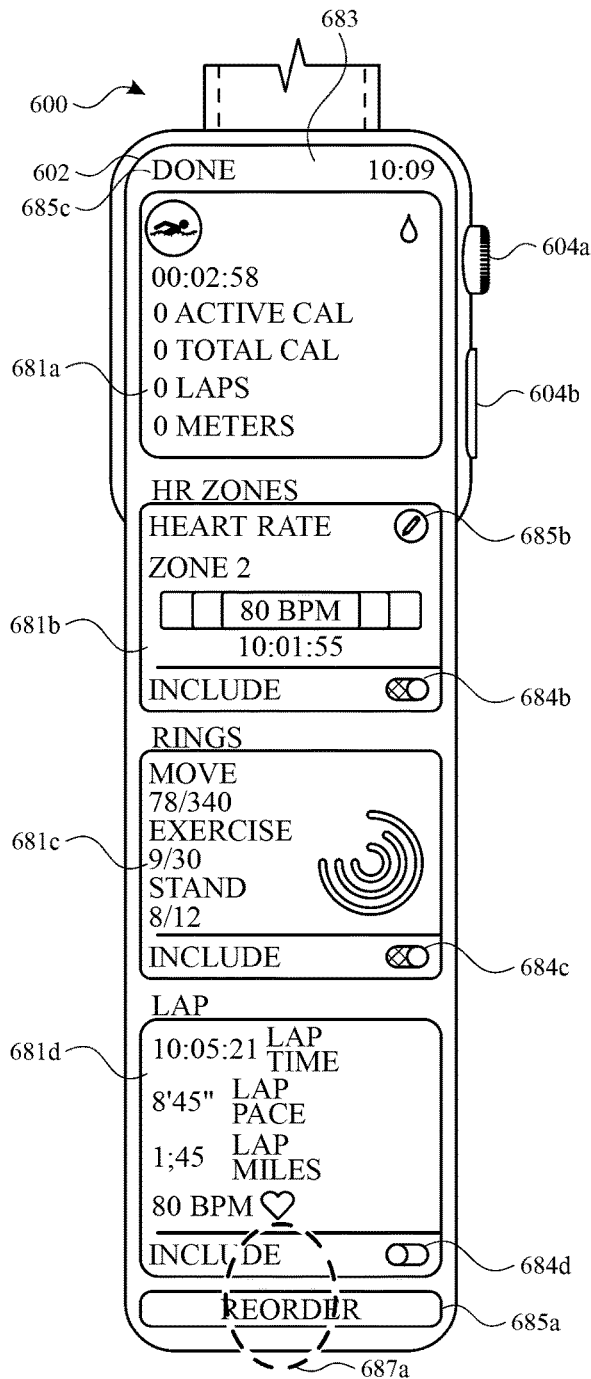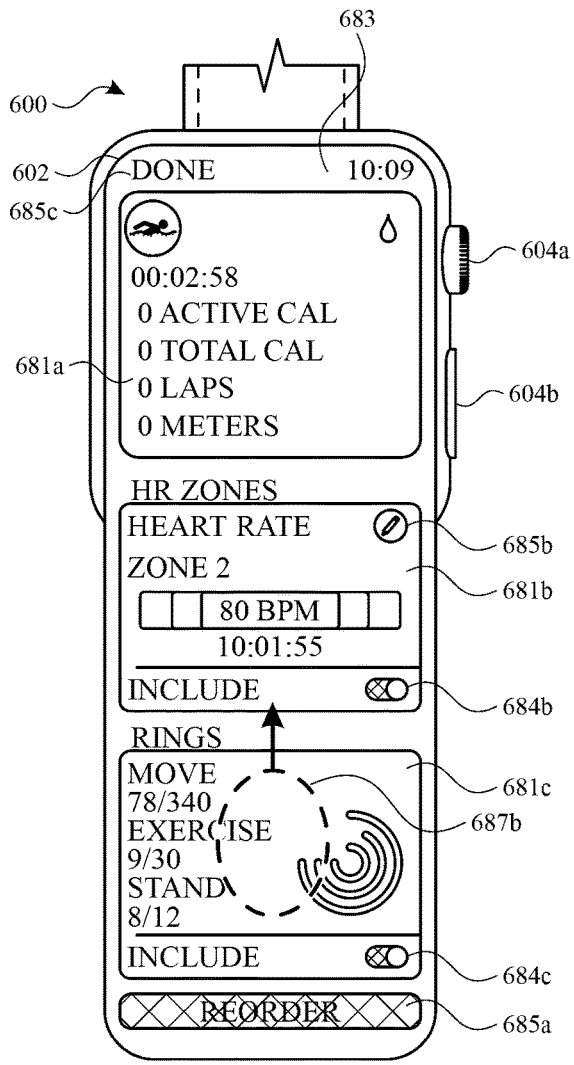
FIG. 6V
FIG. 6W

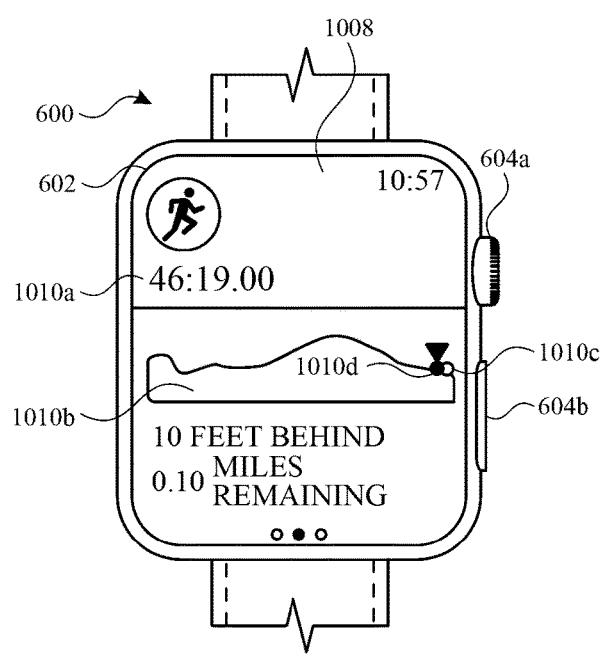 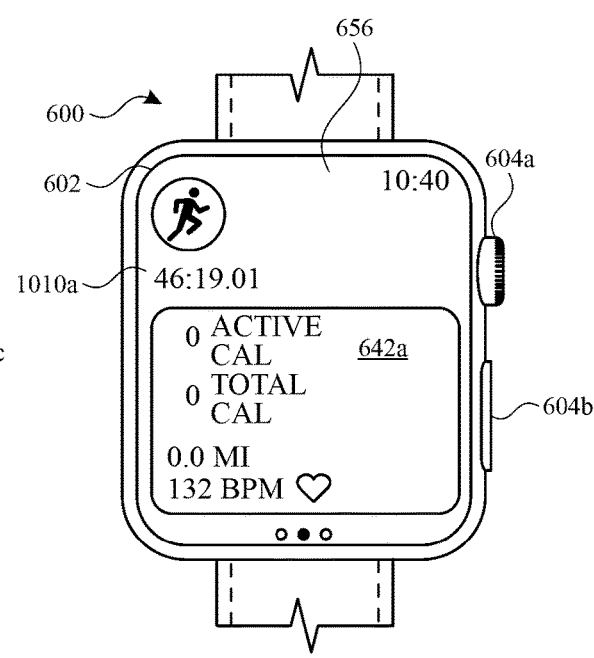
*FIG. 10J*     *FIG. 10K*

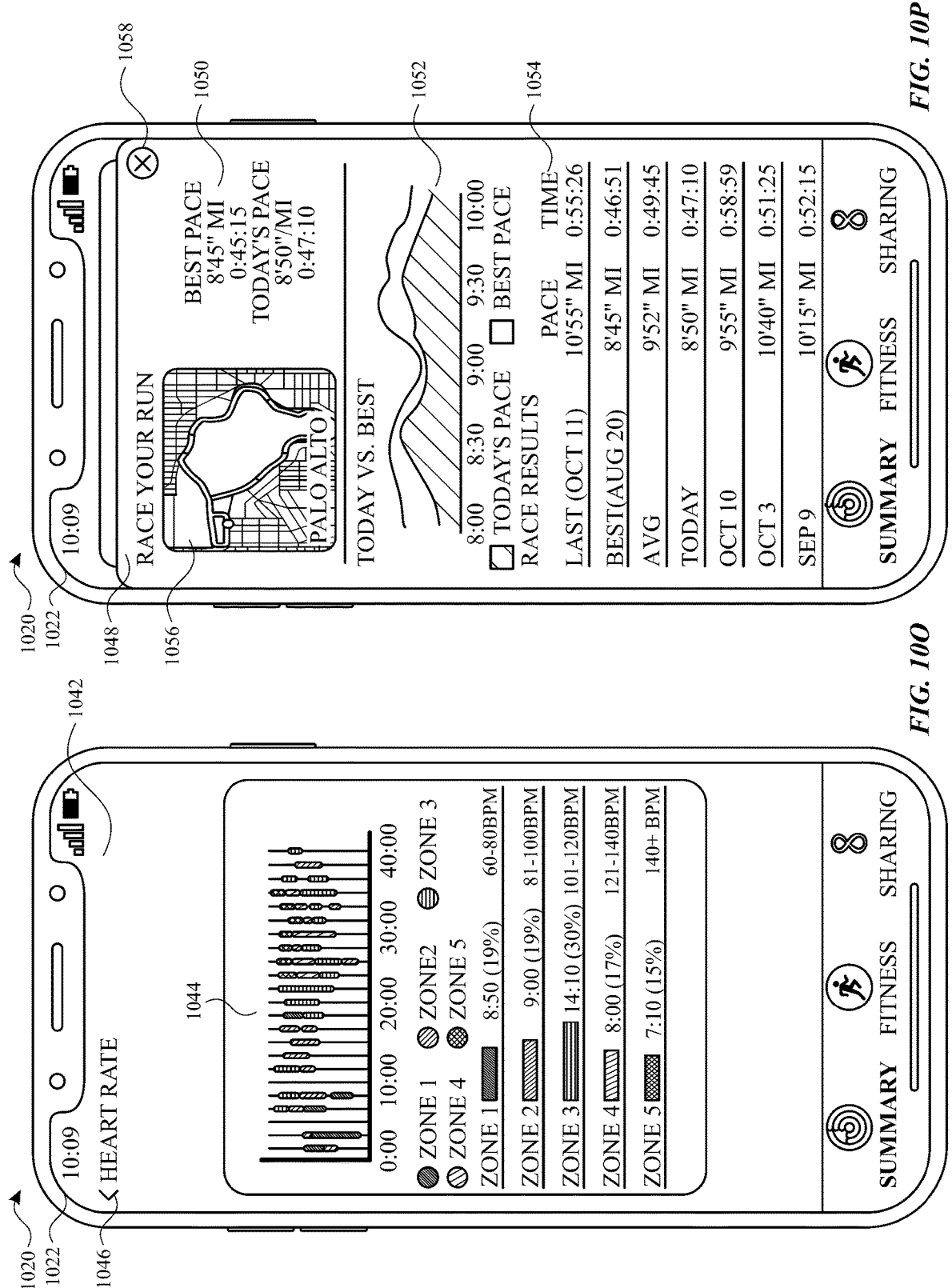

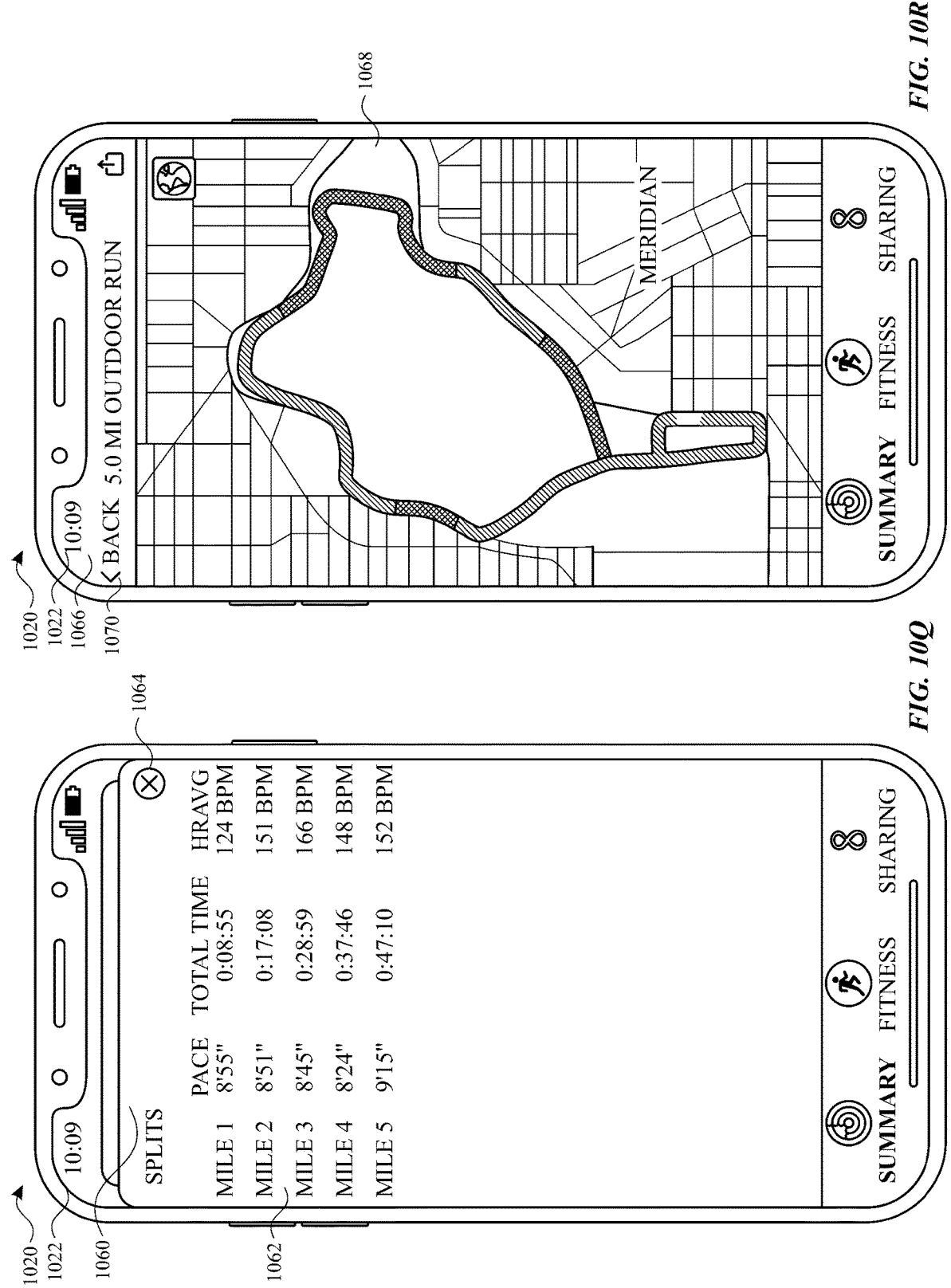

1116
In response to receiving the second user input:

1118
Initiate a workout session.

1120
Display a workout session user interface, including concurrently displaying:

1122
A representation of the previously completed route.

1124
A representation of a current position of a user of the computer system.

1126
A representation of a position of the user during a previously completed workout instance, wherein:

1128
In accordance with a determination that the second user input corresponds to selection of the second user interface object, the representation of the position of the user during the previously completed workout instance is a representation of the position of the user during the first previously completed workout instance.

1130
In accordance with a determination that the second user input corresponds to selection of the third user interface object, the representation of the position of the user during the previously completed workout instance is a representation of the position of the user during the second previously completed workout instance.

*FIG. 11B*

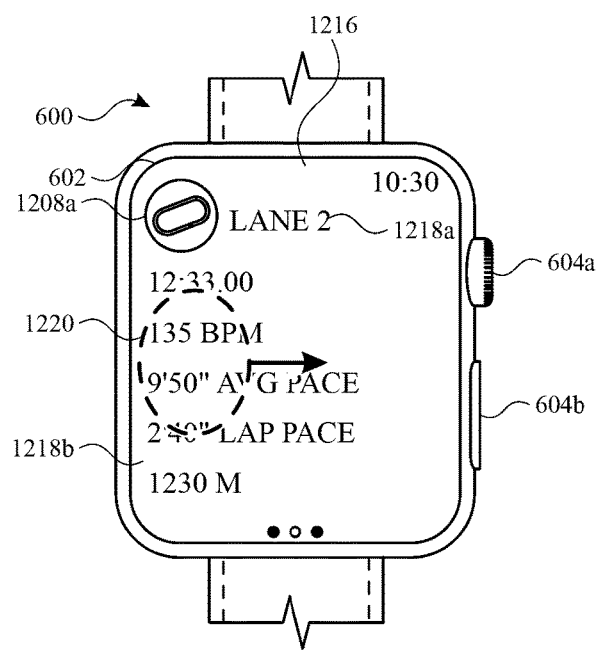
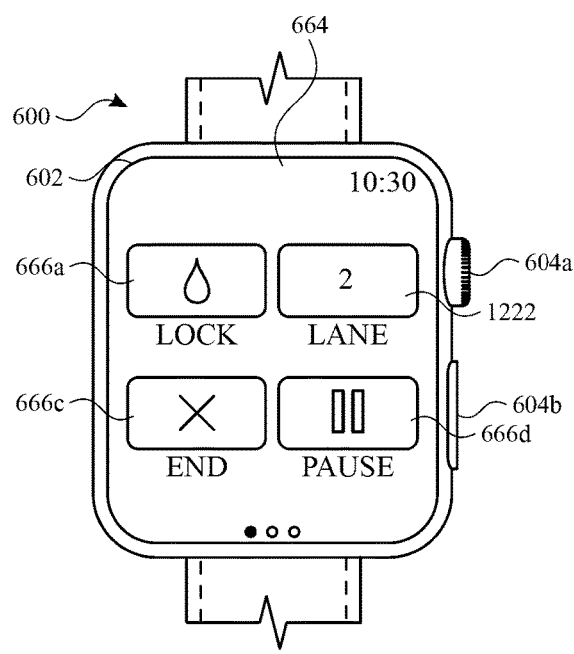
*FIG. 12I*      *FIG. 12J*

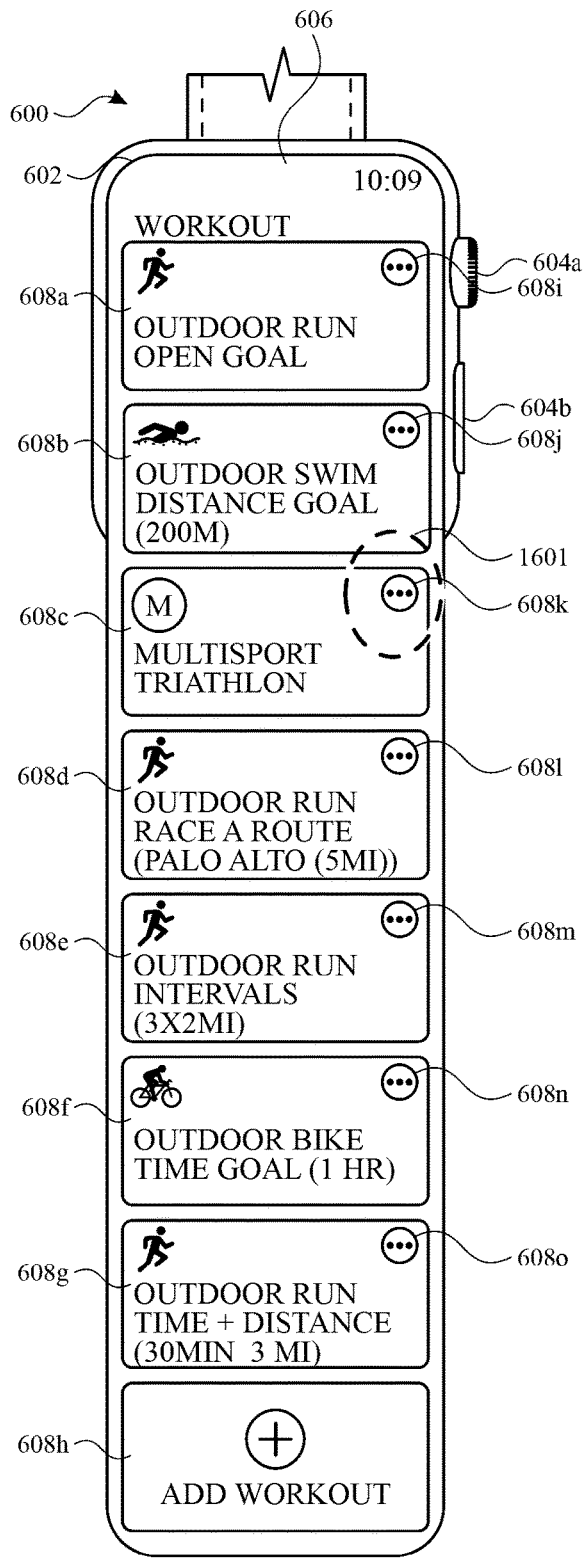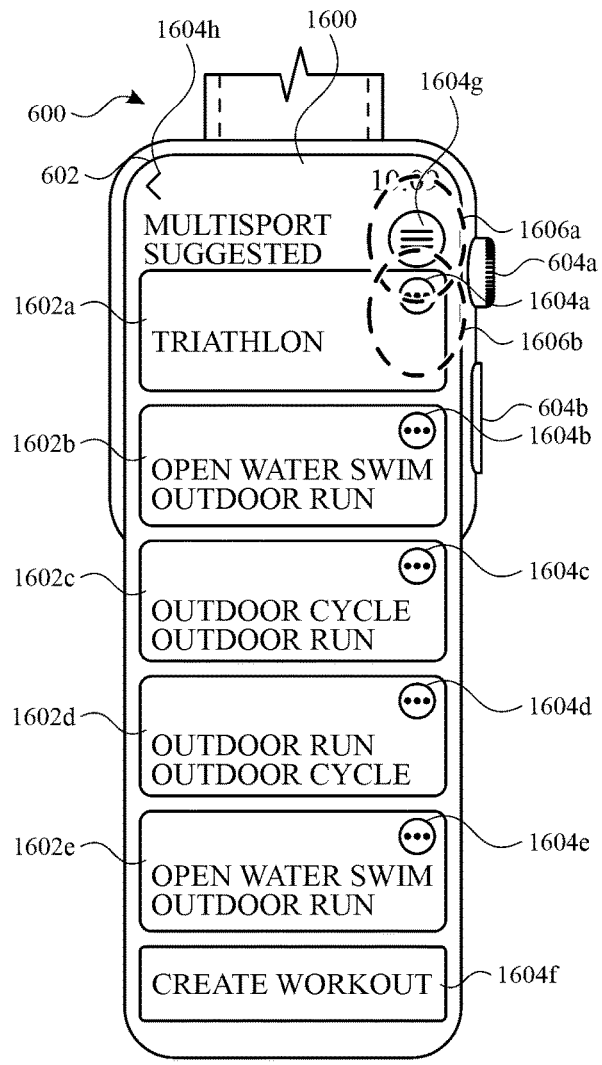
FIG. 16A
FIG. 16B

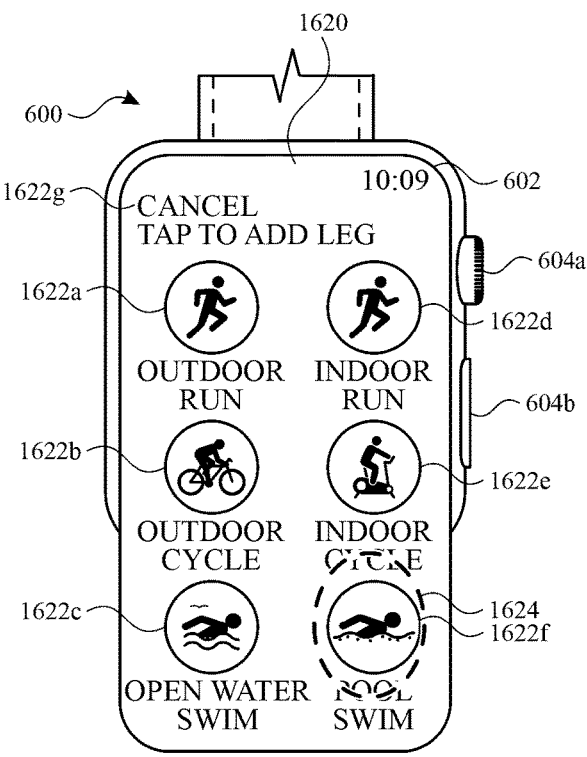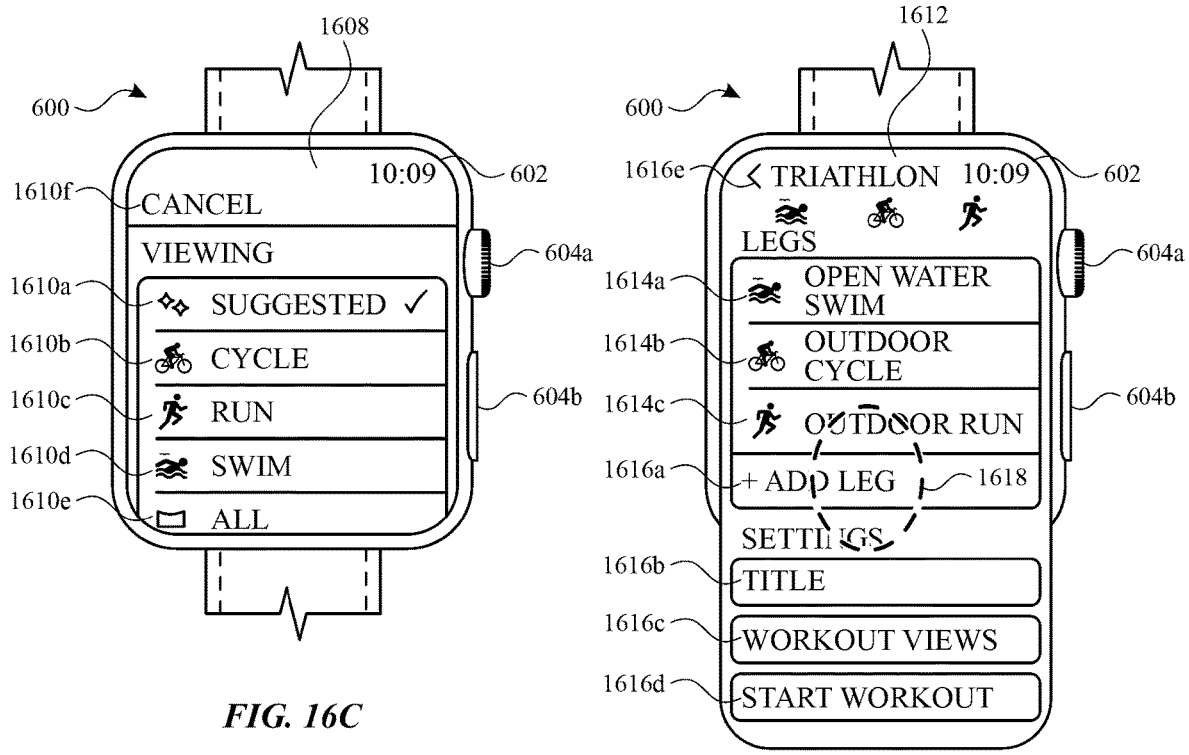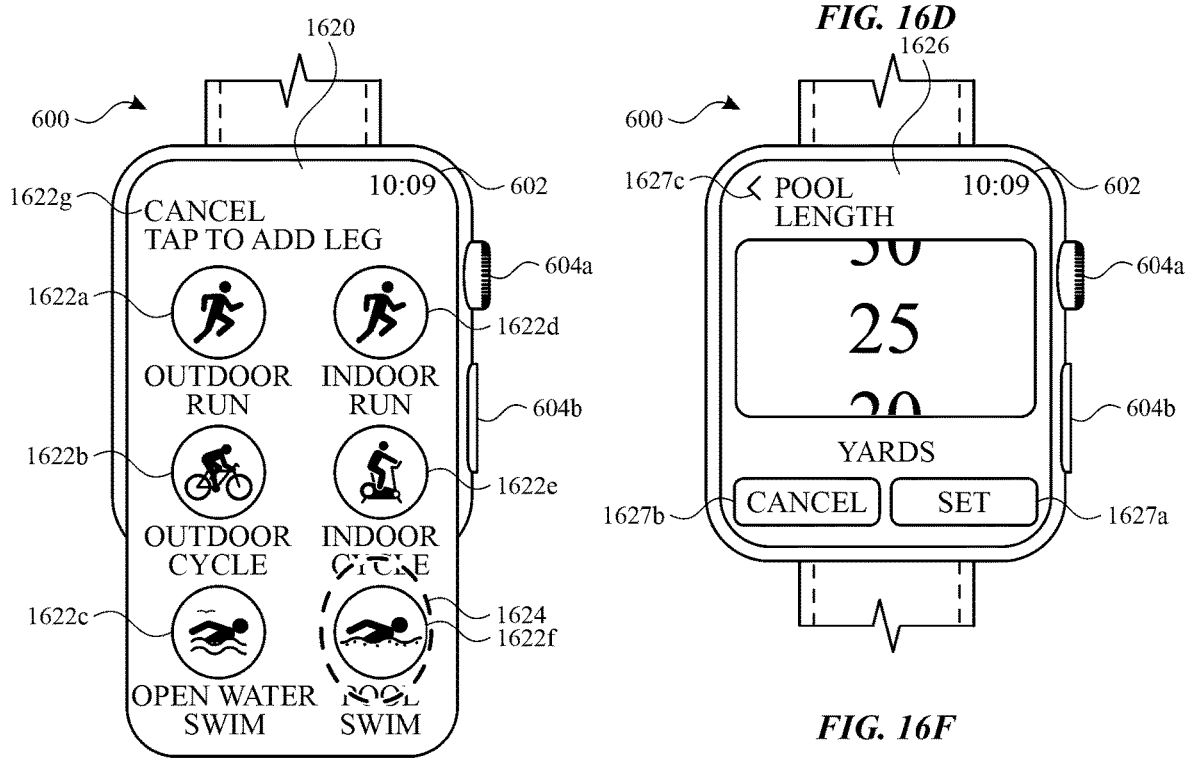

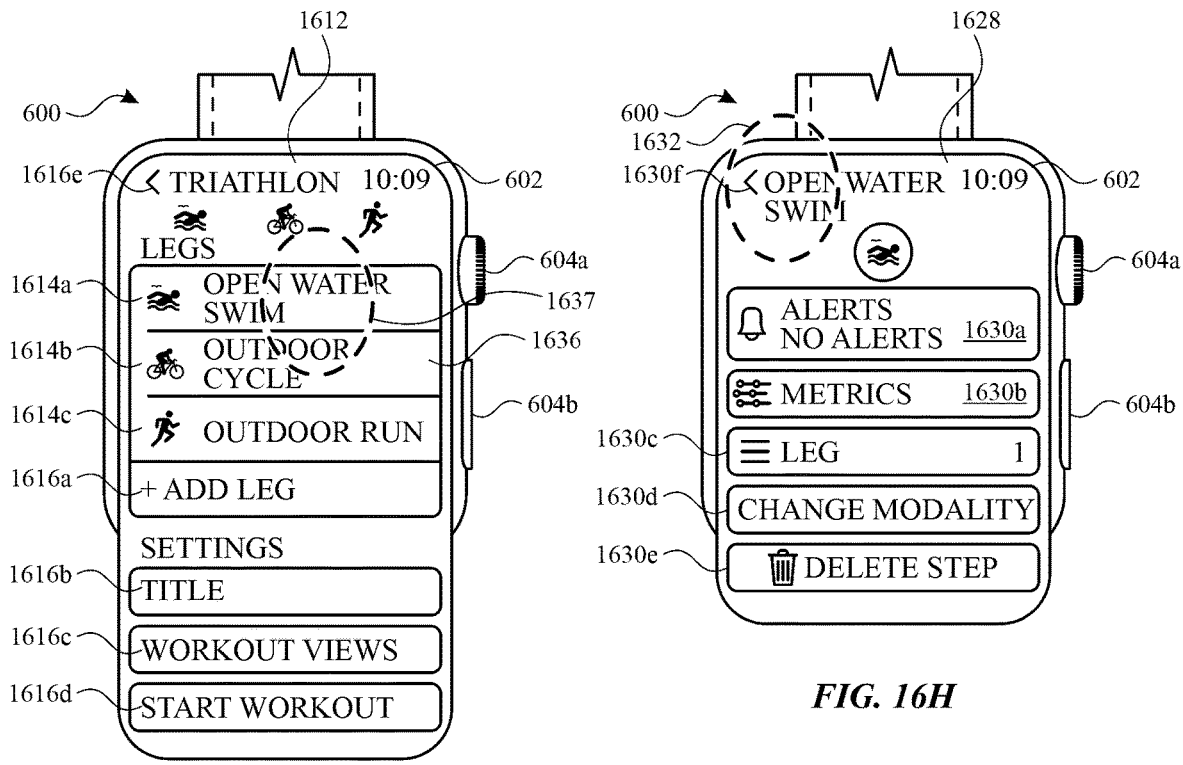
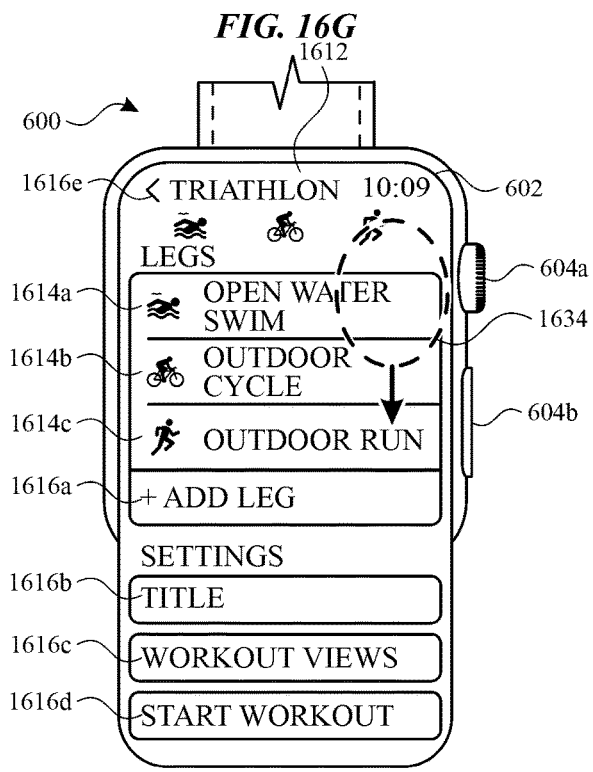
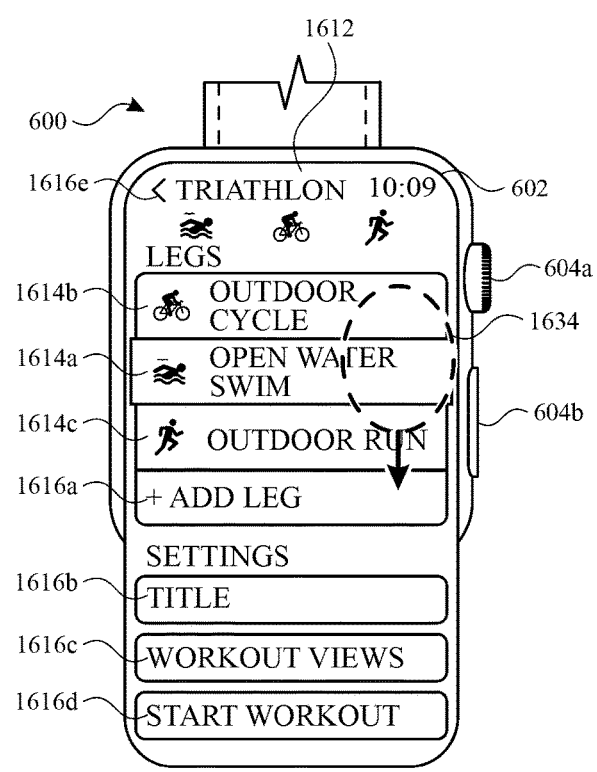

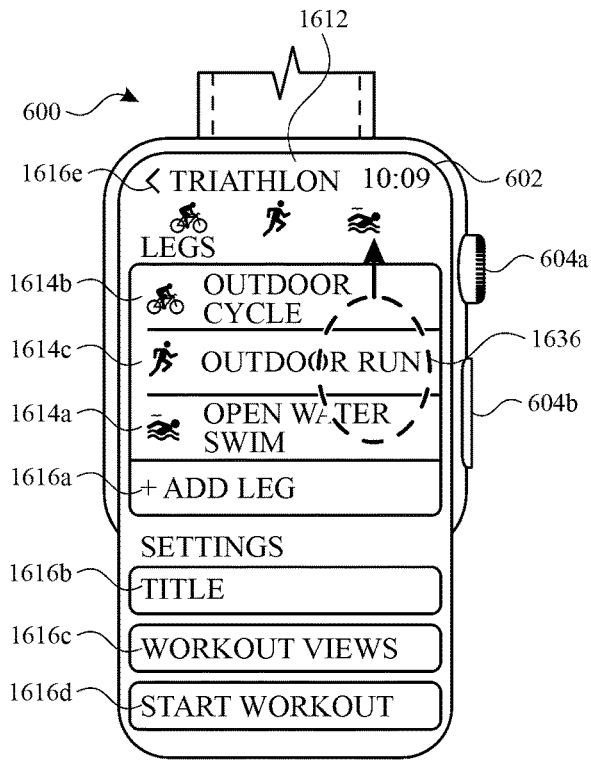
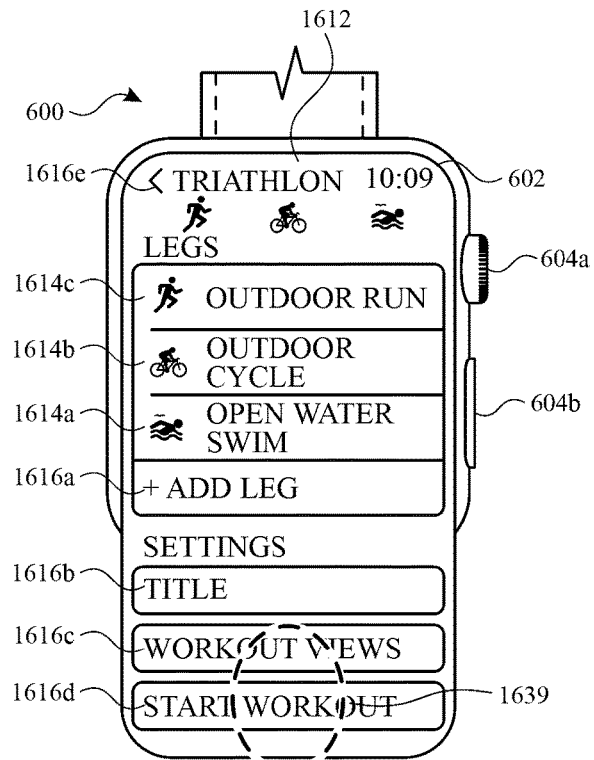
*FIG. 16K*  *FIG. 16K-1*
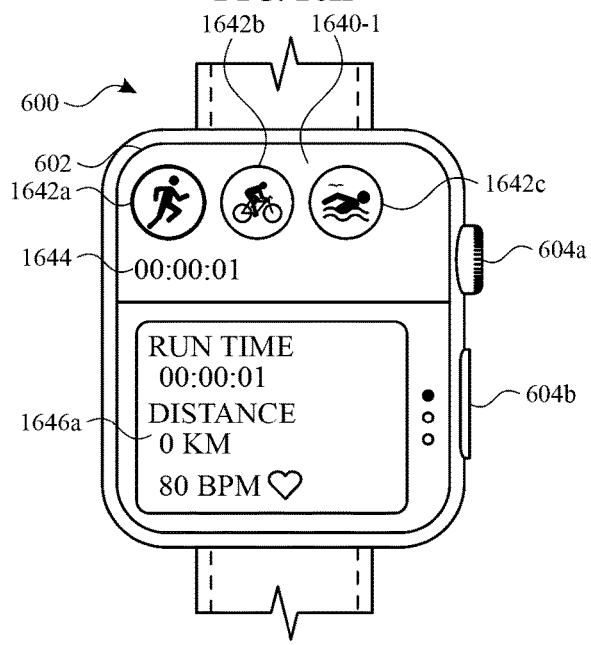
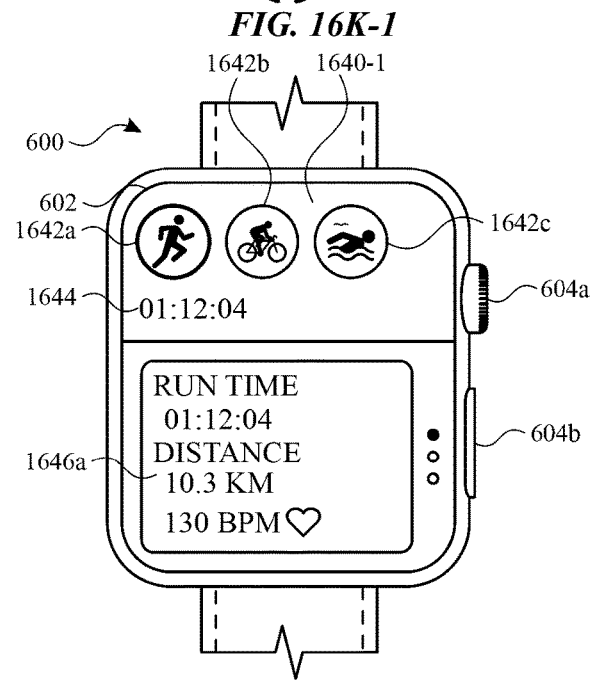
*FIG. 16L*  *FIG. 16M*

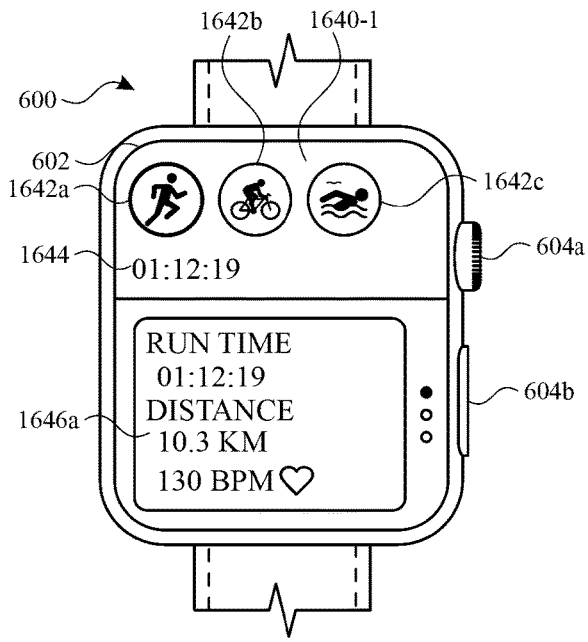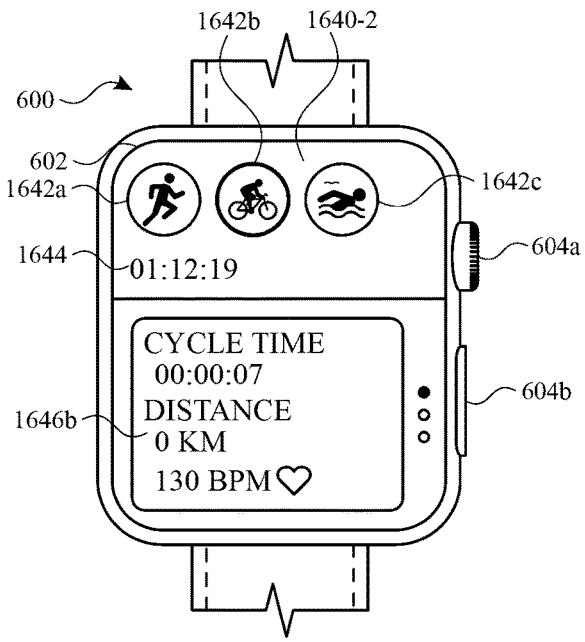
*FIG. 16Q*  *FIG. 16R*
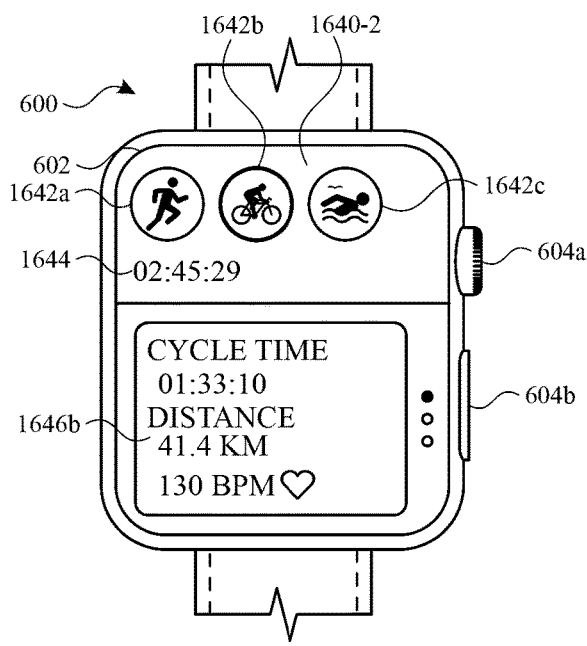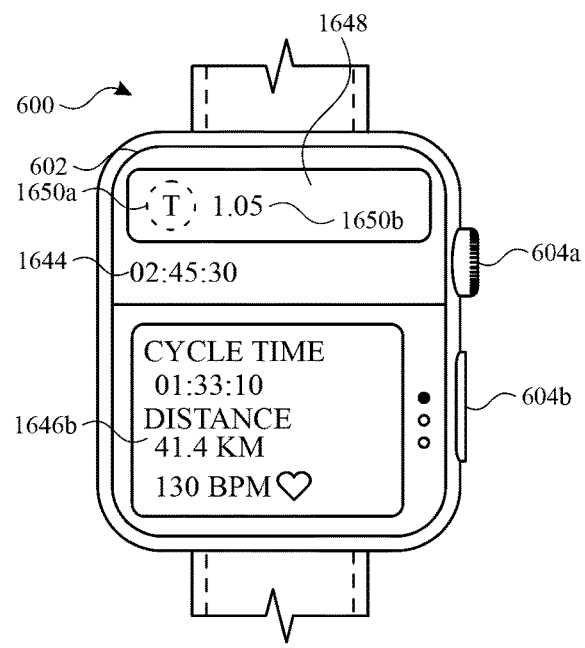
*FIG. 16S*  *FIG. 16T*

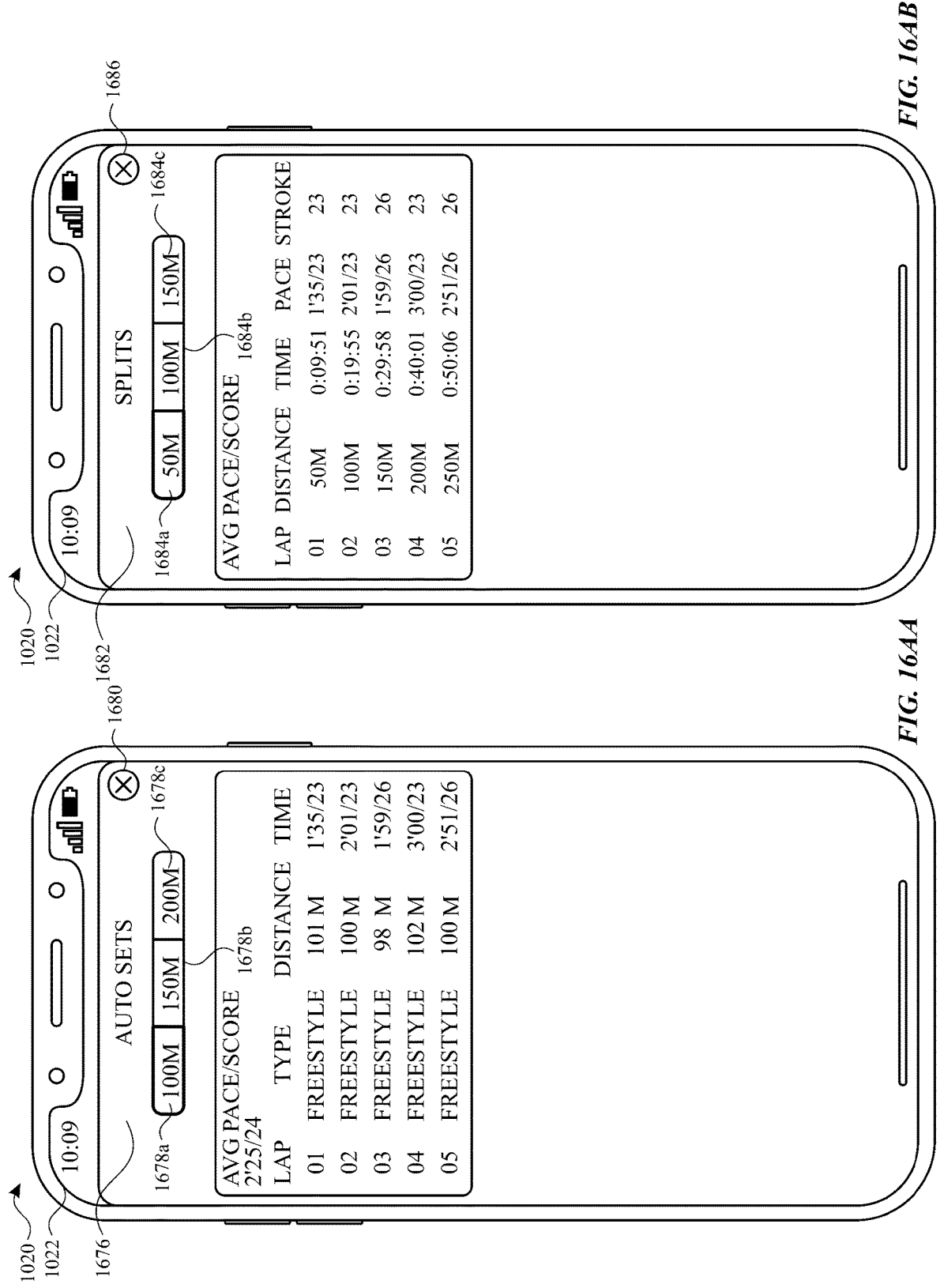

1800 ⟶

1802
Determine that a user has completed a workout session.

1804
In response to determining that the user has completed the workout session, display, via the display generation component, a workout summary user interface, including concurrently displaying:

1806
A first user interface object corresponding to a first set of workout metrics that are grouped into a first category.

1808
A second user interface object corresponding to a second set of workout metrics that are different from the first set of workout metrics and are grouped into a second category different from the first category, wherein:

1810
The first user interface object is selectable to display a first workout category user interface that displays a first set of workout metric information that corresponds to the first set of workout metrics, wherein at least some of the first set of workout metric information is not displayed in the workout summary user interface.

1812
The second user interface object is selectable to display a second workout category user interface that is different from the first workout category user interface and displays a second set of workout metric information that corresponds to the second set of workout metrics, wherein the second set of workout metric information is different from the first set of workout metric information and at least some of the second set of workout metric information is not displayed in the workout summary user interface.

*FIG. 18*

USER INTERFACES FOR PHYSICAL ACTIVITY INFORMATION

CROSS-REFERENCE TO RELATED APPLICATIONS

This application is a continuation of U.S. Nonprovisional patent application Ser. No. 17/952,239, entitled "USER INTERFACES FOR PHYSICAL ACTIVITY INFORMATION," filed on Sep. 24, 2022, which claims priority from U.S. Provisional Patent Application Ser. No. 63/349,119, entitled "USER INTERFACES FOR PHYSICAL ACTIVITY INFORMATION," filed on Jun. 5, 2022, the contents of which are hereby incorporated by reference in their entirety.

FIELD

The present disclosure relates generally to computer user interfaces, and more specifically to techniques for navigating, modifying, and outputting workout content.

BACKGROUND

As electronic devices, such as smartphones have become more widely used, their functions have grown beyond phone calls and text messaging. Providing an efficient method for using and implementing the various functions on these electronic devices can be complex and time-consuming.

BRIEF SUMMARY

Some techniques for navigating, modifying, and outputting workout content using electronic devices, however, are generally cumbersome and inefficient. For example, some existing techniques use a complex and time-consuming user interface, which may include multiple key presses or keystrokes. Existing techniques require more time than necessary, wasting user time and device energy. This latter consideration is particularly important in battery-operated devices.

Accordingly, the present technique provides electronic devices with faster, more efficient methods and interfaces for navigating, modifying, and outputting workout content. Such methods and interfaces optionally complement or replace other methods for navigating, modifying, and outputting workout content. Such methods and interfaces reduce the cognitive burden on a user and produce a more efficient human-machine interface. For battery-operated computing devices, such methods and interfaces conserve power and increase the time between battery charges.

In accordance with some embodiments, a method is described. The method comprises: at a computer system that is in communication with a display generation component and one or more input devices: displaying, via the display generation component, a workout selection user interface, wherein the workout selection user interface includes a first workout platter associated with a first workout type and a second workout platter associated with a second workout type; while displaying the workout selection user interface, receiving, via the one or more input devices, a first user input; in response to receiving the first user input: in accordance with a determination that the first user input corresponds to selection of a first region associated with the first workout platter: initiating a workout session of the first workout type, including initiating recording of one or more physical activity metrics for the workout session of the first workout type; and displaying a first workout session user interface indicative of an active workout session; and in accordance with a determination that the first user input corresponds to selection of a second region associated with the first workout platter different from the first region, displaying, via the display generation component, a first workout customization user interface that includes one or more selectable options that are selectable to initiate one or more processes for customizing one or more aspects of the first workout type.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: displaying, via the display generation component, a workout selection user interface, wherein the workout selection user interface includes a first workout platter associated with a first workout type and a second workout platter associated with a second workout type; while displaying the workout selection user interface, receiving, via the one or more input devices, a first user input; in response to receiving the first user input: in accordance with a determination that the first user input corresponds to selection of a first region associated with the first workout platter: initiating a workout session of the first workout type, including initiating recording of one or more physical activity metrics for the workout session of the first workout type; and displaying a first workout session user interface indicative of an active workout session; and in accordance with a determination that the first user input corresponds to selection of a second region associated with the first workout platter different from the first region, displaying, via the display generation component, a first workout customization user interface that includes one or more selectable options that are selectable to initiate one or more processes for customizing one or more aspects of the first workout type.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: displaying, via the display generation component, a workout selection user interface, wherein the workout selection user interface includes a first workout platter associated with a first workout type and a second workout platter associated with a second workout type; while displaying the workout selection user interface, receiving, via the one or more input devices, a first user input; in response to receiving the first user input: in accordance with a determination that the first user input corresponds to selection of a first region associated with the first workout platter: initiating a workout session of the first workout type, including initiating recording of one or more physical activity metrics for the workout session of the first workout type; and displaying a first workout session user interface indicative of an active workout session; and in accordance with a determination that the first user input corresponds to selection of a second region associated with the first workout platter different from the first region, displaying, via the display generation component, a first workout customization user interface that includes one or more selectable options that are selectable to initiate one or more processes for customizing one or more aspects of the first workout type.

In accordance with some embodiments, a computer system configured to communicate with a display generation component and one or more input devices is described. The computer system comprises: one or more processors; and memory storing one or more programs configured to be executed by the one or more processors, the one or more programs including instructions for: displaying, via the display generation component, a workout selection user interface, wherein the workout selection user interface includes a first workout platter associated with a first workout type and a second workout platter associated with a second workout type; while displaying the workout selection user interface, receiving, via the one or more input devices, a first user input; in response to receiving the first user input: in accordance with a determination that the first user input corresponds to selection of a first region associated with the first workout platter: initiating a workout session of the first workout type, including initiating recording of one or more physical activity metrics for the workout session of the first workout type; and displaying a first workout session user interface indicative of an active workout session; and in accordance with a determination that the first user input corresponds to selection of a second region associated with the first workout platter different from the first region, displaying, via the display generation component, a first workout customization user interface that includes one or more selectable options that are selectable to initiate one or more processes for customizing one or more aspects of the first workout type.

In accordance with some embodiments, a computer system configured to communicate with a display generation component and one or more input devices is described. The computer system comprises: means for displaying, via the display generation component, a workout selection user interface, wherein the workout selection user interface includes a first workout platter associated with a first workout type and a second workout platter associated with a second workout type; means for, while displaying the workout selection user interface, receiving, via the one or more input devices, a first user input; means for, in response to receiving the first user input: in accordance with a determination that the first user input corresponds to selection of a first region associated with the first workout platter: initiating a workout session of the first workout type, including initiating recording of one or more physical activity metrics for the workout session of the first workout type; and displaying a first workout session user interface indicative of an active workout session; and in accordance with a determination that the first user input corresponds to selection of a second region associated with the first workout platter different from the first region, displaying, via the display generation component, a first workout customization user interface that includes one or more selectable options that are selectable to initiate one or more processes for customizing one or more aspects of the first workout type.

In accordance with some embodiments, a computer program product is described. The computer program product comprises one or more programs configured to be executed by one or more processors of a computer system that is in communication with a display generation component and one or more input devices, the one or more programs including instructions for: displaying, via the display generation component, a workout selection user interface, wherein the workout selection user interface includes a first workout platter associated with a first workout type and a second workout platter associated with a second workout type; while displaying the workout selection user interface, receiving, via the one or more input devices, a first user input; in response to receiving the first user input: in accordance with a determination that the first user input corresponds to selection of a first region associated with the first workout platter: initiating a workout session of the first workout type, including initiating recording of one or more physical activity metrics for the workout session of the first workout type; and displaying a first workout session user interface indicative of an active workout session; and in accordance with a determination that the first user input corresponds to selection of a second region associated with the first workout platter different from the first region, displaying, via the display generation component, a first workout customization user interface that includes one or more selectable options that are selectable to initiate one or more processes for customizing one or more aspects of the first workout type.

In accordance with some embodiments, a method is described. The method comprises: at a computer system that is in communication with a display generation component and one or more input devices: receiving, via the one or more input devices, a first user input corresponding to a user request to begin a workout session; in response to receiving the first user input, displaying, via the display generation component, a first workout metrics user interface that includes a first set of workout metrics; while displaying the first workout metrics user interface, receiving, via the one or more input devices, a second user input; and in response to receiving the second user input: in accordance with a determination that a second workout metrics user interface has been enabled, displaying, via the display generation component, a second workout metrics user interface that includes a second set of workout metrics that are different from the first set of workout metrics; and in accordance with a determination that the second workout metrics user interface has not been enabled, displaying, via the display generation component, a third workout metrics user interface that includes a third set of workout metrics that are different from the second set of workout metrics and the first set of workout metrics.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: receiving, via the one or more input devices, a first user input corresponding to a user request to begin a workout session; in response to receiving the first user input, displaying, via the display generation component, a first workout metrics user interface that includes a first set of workout metrics; while displaying the first workout metrics user interface, receiving, via the one or more input devices, a second user input; and in response to receiving the second user input: in accordance with a determination that a second workout metrics user interface has been enabled, displaying, via the display generation component, a second workout metrics user interface that includes a second set of workout metrics that are different from the first set of workout metrics; and in accordance with a determination that the second workout metrics user interface has not been enabled, displaying, via the display generation component, a third workout metrics user interface that includes a third set of workout metrics that are different from the second set of workout metrics and the first set of workout metrics.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: receiving, via the one or more input devices, a first user input corresponding to a user request to begin a workout session; in response to receiving the first user input, displaying, via the display generation component, a first workout metrics user interface that includes a first set of workout metrics; while displaying the first workout metrics user interface, receiving, via the one or more input devices, a second user input; and in response to receiving the second user input: in accordance with a determination that a second workout metrics user interface has been enabled, displaying, via the display generation component, a second workout metrics user interface that includes a second set of workout metrics that are different from the first set of workout metrics; and in accordance with a determination that the second workout metrics user interface has not been enabled, displaying, via the display generation component, a third workout metrics user interface that includes a third set of workout metrics that are different from the second set of workout metrics and the first set of workout metrics.

In accordance with some embodiments, a computer system configured to communicate with a display generation component and one or more input devices is described. The computer system comprises: one or more processors; and memory storing one or more programs configured to be executed by the one or more processors, the one or more programs including instructions for: receiving, via the one or more input devices, a first user input corresponding to a user request to begin a workout session; in response to receiving the first user input, displaying, via the display generation component, a first workout metrics user interface that includes a first set of workout metrics; while displaying the first workout metrics user interface, receiving, via the one or more input devices, a second user input; and in response to receiving the second user input: in accordance with a determination that a second workout metrics user interface has been enabled, displaying, via the display generation component, a second workout metrics user interface that includes a second set of workout metrics that are different from the first set of workout metrics; and in accordance with a determination that the second workout metrics user interface has not been enabled, displaying, via the display generation component, a third workout metrics user interface that includes a third set of workout metrics that are different from the second set of workout metrics and the first set of workout metrics.

In accordance with some embodiments, a computer system configured to communicate with a display generation component and one or more input devices is described. The computer system comprises: means for receiving, via the one or more input devices, a first user input corresponding to a user request to begin a workout session; means for, in response to receiving the first user input, displaying, via the display generation component, a first workout metrics user interface that includes a first set of workout metrics; means for, while displaying the first workout metrics user interface, receiving, via the one or more input devices, a second user input; and means for, in response to receiving the second user input: in accordance with a determination that a second workout metrics user interface has been enabled, displaying, via the display generation component, a second workout metrics user interface that includes a second set of workout metrics that are different from the first set of workout metrics; and in accordance with a determination that the second workout metrics user interface has not been enabled, displaying, via the display generation component, a third workout metrics user interface that includes a third set of workout metrics that are different from the second set of workout metrics and the first set of workout metrics.

In accordance with some embodiments, a computer program product is described. The computer program product comprises one or more programs configured to be executed by one or more processors of a computer system that is in communication with a display generation component and one or more input devices, the one or more programs including instructions for: receiving, via the one or more input devices, a first user input corresponding to a user request to begin a workout session; in response to receiving the first user input, displaying, via the display generation component, a first workout metrics user interface that includes a first set of workout metrics; while displaying the first workout metrics user interface, receiving, via the one or more input devices, a second user input; and in response to receiving the second user input: in accordance with a determination that a second workout metrics user interface has been enabled, displaying, via the display generation component, a second workout metrics user interface that includes a second set of workout metrics that are different from the first set of workout metrics; and in accordance with a determination that the second workout metrics user interface has not been enabled, displaying, via the display generation component, a third workout metrics user interface that includes a third set of workout metrics that are different from the second set of workout metrics and the first set of workout metrics.

In accordance with some embodiments, a method is described. The method comprises: at a computer system that is in communication with a display generation component and one or more input devices: displaying, via the display generation component, a first user interface corresponding to a first workout type, including displaying a first user interface object; while displaying the first user interface, receiving, via the one or more input devices, a first user input corresponding to selection of the first user interface object; in response to receiving the first user input, displaying, via the display generation component, a first workout views user interface, wherein the first workout views user interface includes: a representation of a first workout metrics user interface, wherein the first workout metrics user interface corresponds to a first set of workout metrics; and a representation of a second workout metrics user interface, wherein the second workout metrics user interface corresponds to a second set of workout metrics different from the first set of workout metrics; and while displaying the first workout views user interface, receiving, via the one or more input devices, a second user input corresponding to a user request to transition the second workout metrics user interface from a deactivated state to an activated state, wherein: when the second workout metrics user interface is in the activated state, the second workout metrics user interface, including the second set of workout metrics, is accessible by a user during a workout session of the first workout type; and when the second workout metrics user interface is in the deactivated state, the second workout metrics user interface, including the second set of workout metrics, is not accessible by a user during a workout session of the first workout type.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: displaying, via the display generation component, a first user interface corresponding to a first workout type, including displaying a first user interface object; while displaying the first user interface, receiving, via the one or more input devices, a first user input corresponding to selection of the first user interface object; in response to receiving the first user input, displaying, via the display generation component, a first workout views user interface, wherein the first workout views user interface includes: a representation of a first workout metrics user interface, wherein the first workout metrics user interface corresponds to a first set of workout metrics; and a representation of a second workout metrics user interface, wherein the second workout metrics user interface corresponds to a second set of workout metrics different from the first set of workout metrics; and while displaying the first workout views user interface, receiving, via the one or more input devices, a second user input corresponding to a user request to transition the second workout metrics user interface from a deactivated state to an activated state, wherein: when the second workout metrics user interface is in the activated state, the second workout metrics user interface, including the second set of workout metrics, is accessible by a user during a workout session of the first workout type; and when the second workout metrics user interface is in the deactivated state, the second workout metrics user interface, including the second set of workout metrics, is not accessible by a user during a workout session of the first workout type.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: displaying, via the display generation component, a first user interface corresponding to a first workout type, including displaying a first user interface object; while displaying the first user interface, receiving, via the one or more input devices, a first user input corresponding to selection of the first user interface object; in response to receiving the first user input, displaying, via the display generation component, a first workout views user interface, wherein the first workout views user interface includes: a representation of a first workout metrics user interface, wherein the first workout metrics user interface corresponds to a first set of workout metrics; and a representation of a second workout metrics user interface, wherein the second workout metrics user interface corresponds to a second set of workout metrics different from the first set of workout metrics; and while displaying the first workout views user interface, receiving, via the one or more input devices, a second user input corresponding to a user request to transition the second workout metrics user interface from a deactivated state to an activated state, wherein: when the second workout metrics user interface is in the activated state, the second workout metrics user interface, including the second set of workout metrics, is accessible by a user during a workout session of the first workout type; and when the second workout metrics user interface is in the deactivated state, the second workout metrics user interface, including the second set of workout metrics, is not accessible by a user during a workout session of the first workout type.

In accordance with some embodiments, a computer system configured to communicate with a display generation component and one or more input devices is described. The computer system comprises: one or more processors; and memory storing one or more programs configured to be executed by the one or more processors, the one or more programs including instructions for: displaying, via the display generation component, a first user interface corresponding to a first workout type, including displaying a first user interface object; while displaying the first user interface, receiving, via the one or more input devices, a first user input corresponding to selection of the first user interface object; in response to receiving the first user input, displaying, via the display generation component, a first workout views user interface, wherein the first workout views user interface includes: a representation of a first workout metrics user interface, wherein the first workout metrics user interface corresponds to a first set of workout metrics; and a representation of a second workout metrics user interface, wherein the second workout metrics user interface corresponds to a second set of workout metrics different from the first set of workout metrics; and while displaying the first workout views user interface, receiving, via the one or more input devices, a second user input corresponding to a user request to transition the second workout metrics user interface from a deactivated state to an activated state, wherein: when the second workout metrics user interface is in the activated state, the second workout metrics user interface, including the second set of workout metrics, is accessible by a user during a workout session of the first workout type; and when the second workout metrics user interface is in the deactivated state, the second workout metrics user interface, including the second set of workout metrics, is not accessible by a user during a workout session of the first workout type.

In accordance with some embodiments, a computer system configured to communicate with a display generation component and one or more input devices is described. The computer system comprises: means for displaying, via the display generation component, a first user interface corresponding to a first workout type, including displaying a first user interface object; means for, while displaying the first user interface, receiving, via the one or more input devices, a first user input corresponding to selection of the first user interface object; means for, in response to receiving the first user input, displaying, via the display generation component, a first workout views user interface, wherein the first workout views user interface includes: a representation of a first workout metrics user interface, wherein the first workout metrics user interface corresponds to a first set of workout metrics; and a representation of a second workout metrics user interface, wherein the second workout metrics user interface corresponds to a second set of workout metrics different from the first set of workout metrics; and means for, while displaying the first workout views user interface, receiving, via the one or more input devices, a second user input corresponding to a user request to transition the second workout metrics user interface from a deactivated state to an activated state, wherein: when the second workout metrics user interface is in the activated state, the second workout metrics user interface, including the second set of workout metrics, is accessible by a user during a workout session of the first workout type; and when the second workout metrics user interface is in the deactivated state, the second workout metrics user interface, including the second set of workout metrics, is not accessible by a user during a workout session of the first workout type.

In accordance with some embodiments, a computer program product is described. The computer program product comprises one or more programs configured to be executed by one or more processors of a computer system that is in communication with a display generation component and one or more input devices, the one or more programs including instructions for: displaying, via the display generation component, a first user interface corresponding to a first workout type, including displaying a first user interface object; while displaying the first user interface, receiving, via the one or more input devices, a first user input corresponding to selection of the first user interface object; in response to receiving the first user input, displaying, via the display generation component, a first workout views user interface, wherein the first workout views user interface includes: a representation of a first workout metrics user interface, wherein the first workout metrics user interface corresponds to a first set of workout metrics; and a representation of a second workout metrics user interface, wherein the second workout metrics user interface corresponds to a second set of workout metrics different from the first set of workout metrics; and while displaying the first workout views user interface, receiving, via the one or more input devices, a second user input corresponding to a user request to transition the second workout metrics user interface from a deactivated state to an activated state, wherein: when the second workout metrics user interface is in the activated state, the second workout metrics user interface, including the second set of workout metrics, is accessible by a user during a workout session of the first workout type; and when the second workout metrics user interface is in the deactivated state, the second workout metrics user interface, including the second set of workout metrics, is not accessible by a user during a workout session of the first workout type.

In accordance with some embodiments, a method is described. The method comprises: at a computer system that is in communication with a display generation component and one or more input devices: determining that the computer system satisfies one or more proximity criteria with respect to a previously completed route, wherein the previously completed route corresponds to one or more previously completed workout instances; in response to determining that the computer system satisfies one or more proximity criteria with respect to the previously completed route, displaying, via the display generation component, a first user interface object corresponding to the previously completed route; while displaying the first user interface object, receiving, via the one or more input devices, a first user input corresponding to selection of the first user interface object; and in response to receiving the first user input, concurrently displaying: a second user interface object corresponding to a first previously completed workout instance of the one or more previously completed workout instances corresponding to the previously completed route; and a third user interface object corresponding to a second previously completed workout instance of the one or more previously completed workout instances corresponding to the previously completed route, wherein the second previously completed workout instance is different from the first previously completed workout instance; while concurrently displaying the second user interface object and the third user interface object, receiving, via the one or more input devices, a second user input; and in response to receiving the second user input: initiating a workout session; and displaying a workout session user interface, including concurrently displaying: a representation of the previously completed route; a representation of a current position of a user of the computer system; and a representation of a position of the user during a previously completed workout instance, wherein: in accordance with a determination that the second user input corresponds to selection of the second user interface object, the representation of the position of the user during the previously completed workout instance is a representation of the position of the user during the first previously completed workout instance; and in accordance with a determination that the second user input corresponds to selection of the third user interface object, the representation of the position of the user during the previously completed workout instance is a representation of the position of the user during the second previously completed workout instance.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: determining that the computer system satisfies one or more proximity criteria with respect to a previously completed route, wherein the previously completed route corresponds to one or more previously completed workout instances; in response to determining that the computer system satisfies one or more proximity criteria with respect to the previously completed route, displaying, via the display generation component, a first user interface object corresponding to the previously completed route; while displaying the first user interface object, receiving, via the one or more input devices, a first user input corresponding to selection of the first user interface object; and in response to receiving the first user input, concurrently displaying: a second user interface object corresponding to a first previously completed workout instance of the one or more previously completed workout instances corresponding to the previously completed route; and a third user interface object corresponding to a second previously completed workout instance of the one or more previously completed workout instances corresponding to the previously completed route, wherein the second previously completed workout instance is different from the first previously completed workout instance; while concurrently displaying the second user interface object and the third user interface object, receiving, via the one or more input devices, a second user input; and in response to receiving the second user input: initiating a workout session; and displaying a workout session user interface, including concurrently displaying: a representation of the previously completed route; a representation of a current position of a user of the computer system; and a representation of a position of the user during a previously completed workout instance, wherein: in accordance with a determination that the second user input corresponds to selection of the second user interface object, the representation of the position of the user during the previously completed workout instance is a representation of the position of the user during the first previously completed workout instance; and in accordance with a determination that the second user input corresponds to selection of the third user interface object, the representation of the position of the user during the previously completed workout instance is a representation of the position of the user during the second previously completed workout instance.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: determining that the computer system satisfies one or more proximity criteria with respect to a previously completed route, wherein the previously completed route corresponds to one or more previously completed workout instances; in response to determining that the computer system satisfies one or more proximity criteria with respect to the previously completed route, displaying, via the display generation component, a first user interface object corresponding to the previously completed route; while displaying the first user interface object, receiving, via the one or more input devices, a first user input corresponding to selection of the first user interface object; and in response to receiving the first user input, concurrently displaying: a second user interface object corresponding to a first previously completed workout instance of the one or more previously completed workout instances corresponding to the previously completed route; and a third user interface object corresponding to a second previously completed workout instance of the one or more previously completed workout instances corresponding to the previously completed route, wherein the second previously completed workout instance is different from the first previously completed workout instance; while concurrently displaying the second user interface object and the third user interface object, receiving, via the one or more input devices, a second user input; and in response to receiving the second user input: initiating a workout session; and displaying a workout session user interface, including concurrently displaying: a representation of the previously completed route; a representation of a current position of a user of the computer system; and a representation of a position of the user during a previously completed workout instance, wherein: in accordance with a determination that the second user input corresponds to selection of the second user interface object, the representation of the position of the user during the previously completed workout instance is a representation of the position of the user during the first previously completed workout instance; and in accordance with a determination that the second user input corresponds to selection of the third user interface object, the representation of the position of the user during the previously completed workout instance is a representation of the position of the user during the second previously completed workout instance.

In accordance with some embodiments, a computer system configured to communicate with a display generation component and one or more input devices is described. The computer system comprises: one or more processors; and memory storing one or more programs configured to be executed by the one or more processors, the one or more programs including instructions for: determining that the computer system satisfies one or more proximity criteria with respect to a previously completed route, wherein the previously completed route corresponds to one or more previously completed workout instances; in response to determining that the computer system satisfies one or more proximity criteria with respect to the previously completed route, displaying, via the display generation component, a first user interface object corresponding to the previously completed route; while displaying the first user interface object, receiving, via the one or more input devices, a first user input corresponding to selection of the first user interface object; and in response to receiving the first user input, concurrently displaying: a second user interface object corresponding to a first previously completed workout instance of the one or more previously completed workout instances corresponding to the previously completed route; and a third user interface object corresponding to a second previously completed workout instance of the one or more previously completed workout instances corresponding to the previously completed route, wherein the second previously completed workout instance is different from the first previously completed workout instance; while concurrently displaying the second user interface object and the third user interface object, receiving, via the one or more input devices, a second user input; and in response to receiving the second user input: initiating a workout session; and displaying a workout session user interface, including concurrently displaying: a representation of the previously completed route; a representation of a current position of a user of the computer system; and a representation of a position of the user during a previously completed workout instance, wherein: in accordance with a determination that the second user input corresponds to selection of the second user interface object, the representation of the position of the user during the previously completed workout instance is a representation of the position of the user during the first previously completed workout instance; and in accordance with a determination that the second user input corresponds to selection of the third user interface object, the representation of the position of the user during the previously completed workout instance is a representation of the position of the user during the second previously completed workout instance.

In accordance with some embodiments, a computer system configured to communicate with a display generation component and one or more input devices is described. The computer system comprises: means for determining that the computer system satisfies one or more proximity criteria with respect to a previously completed route, wherein the previously completed route corresponds to one or more previously completed workout instances; means for, in response to determining that the computer system satisfies one or more proximity criteria with respect to the previously completed route, displaying, via the display generation component, a first user interface object corresponding to the previously completed route; means for, while displaying the first user interface object, receiving, via the one or more input devices, a first user input corresponding to selection of the first user interface object; and means for, in response to receiving the first user input, concurrently displaying: a second user interface object corresponding to a first previously completed workout instance of the one or more previously completed workout instances corresponding to the previously completed route; and a third user interface object corresponding to a second previously completed workout instance of the one or more previously completed workout instances corresponding to the previously completed route, wherein the second previously completed workout instance is different from the first previously completed workout instance; means for, while concurrently displaying the second user interface object and the third user interface object, receiving, via the one or more input devices, a second user input; and means for, in response to receiving the second user input: initiating a workout session; and displaying a workout session user interface, including concurrently displaying: a representation of the previously completed route; a representation of a current position of a user of the computer system; and a representation of a position of the user during a previously completed workout instance, wherein: in accordance with a determination that the second user input corresponds to selection of the second user interface object, the representation of the position of the user during the previously completed workout instance is a representation of the position of the user during the first previously completed workout instance; and in accordance with a determination that the second user input corresponds to selection of the third user interface object, the representation of the position of the user during the previously completed workout instance is a representation of the position of the user during the second previously completed workout instance.

In accordance with some embodiments, a computer program product is described. The computer program product comprises one or more programs configured to be executed by one or more processors of a computer system that is in communication with a display generation component and one or more input devices, the one or more programs including instructions for: determining that the computer system satisfies one or more proximity criteria with respect to a previously completed route, wherein the previously completed route corresponds to one or more previously completed workout instances; in response to determining that the computer system satisfies one or more proximity criteria with respect to the previously completed route, displaying, via the display generation component, a first user interface object corresponding to the previously completed route; while displaying the first user interface object, receiving, via the one or more input devices, a first user input corresponding to selection of the first user interface object; and in response to receiving the first user input, concurrently displaying: a second user interface object corresponding to a first previously completed workout instance of the one or more previously completed workout instances corresponding to the previously completed route; and a third user interface object corresponding to a second previously completed workout instance of the one or more previously completed workout instances corresponding to the previously completed route, wherein the second previously completed workout instance is different from the first previously completed workout instance; while concurrently displaying the second user interface object and the third user interface object, receiving, via the one or more input devices, a second user input; and in response to receiving the second user input: initiating a workout session; and displaying a workout session user interface, including concurrently displaying: a representation of the previously completed route; a representation of a current position of a user of the computer system; and a representation of a position of the user during a previously completed workout instance, wherein: in accordance with a determination that the second user input corresponds to selection of the second user interface object, the representation of the position of the user during the previously completed workout instance is a representation of the position of the user during the first previously completed workout instance; and in accordance with a determination that the second user input corresponds to selection of the third user interface object, the representation of the position of the user during the previously completed workout instance is a representation of the position of the user during the second previously completed workout instance.

In accordance with some embodiments, a method is described. The method comprises: at a computer system that is in communication with a display generation component and one or more input devices: displaying, via the display generation component, a first user interface object corresponding to a first workout type; while displaying the first user interface object, receiving, via the one or more input devices, a first user input corresponding to selection of the first user interface object; and in response to receiving the first user input: in accordance with a determination that the computer system satisfies one or more proximity criteria with respect to a workout track, displaying, via the display generation component, a first user interface; and in accordance with a determination that the computer system does not satisfy the one or more proximity criteria with respect to a workout track, displaying, via the display generation component, a second user interface different from the first user interface.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: displaying, via the display generation component, a first user interface object corresponding to a first workout type; while displaying the first user interface object, receiving, via the one or more input devices, a first user input corresponding to selection of the first user interface object; and in response to receiving the first user input: in accordance with a determination that the computer system satisfies one or more proximity criteria with respect to a workout track, displaying, via the display generation component, a first user interface; and in accordance with a determination that the computer system does not satisfy the one or more proximity criteria with respect to a workout track, displaying, via the display generation component, a second user interface different from the first user interface.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: displaying, via the display generation component, a first user interface object corresponding to a first workout type; while displaying the first user interface object, receiving, via the one or more input devices, a first user input corresponding to selection of the first user interface object; and in response to receiving the first user input: in accordance with a determination that the computer system satisfies one or more proximity criteria with respect to a workout track, displaying, via the display generation component, a first user interface; and in accordance with a determination that the computer system does not satisfy the one or more proximity criteria with respect to a workout track, displaying, via the display generation component, a second user interface different from the first user interface.

In accordance with some embodiments, a computer system configured to communicate with a display generation component and one or more input devices is described. The computer system comprises: one or more processors; and memory storing one or more programs configured to be executed by the one or more processors, the one or more programs including instructions for: displaying, via the display generation component, a first user interface object corresponding to a first workout type; while displaying the first user interface object, receiving, via the one or more input devices, a first user input corresponding to selection of the first user interface object; and in response to receiving the first user input: in accordance with a determination that the computer system satisfies one or more proximity criteria with respect to a workout track, displaying, via the display generation component, a first user interface; and in accordance with a determination that the computer system does not satisfy the one or more proximity criteria with respect to a workout track, displaying, via the display generation component, a second user interface different from the first user interface.

In accordance with some embodiments, a computer system configured to communicate with a display generation component and one or more input devices is described. The computer system comprises: means for displaying, via the display generation component, a first user interface object corresponding to a first workout type; means for, while displaying the first user interface object, receiving, via the one or more input devices, a first user input corresponding to selection of the first user interface object; and means for, in response to receiving the first user input: in accordance with a determination that the computer system satisfies one or more proximity criteria with respect to a workout track, displaying, via the display generation component, a first user interface; and in accordance with a determination that the computer system does not satisfy the one or more proximity criteria with respect to a workout track, displaying, via the display generation component, a second user interface different from the first user interface.

In accordance with some embodiments, a computer program product is described. The computer program product comprises one or more programs configured to be executed by one or more processors of a computer system that is in communication with a display generation component and one or more input devices, the one or more programs including instructions for: displaying, via the display generation component, a first user interface object corresponding to a first workout type; while displaying the first user interface object, receiving, via the one or more input devices, a first user input corresponding to selection of the first user interface object; and in response to receiving the first user input: in accordance with a determination that the computer system satisfies one or more proximity criteria with respect to a workout track, displaying, via the display generation component, a first user interface; and in accordance with a determination that the computer system does not satisfy the one or more proximity criteria with respect to a workout track, displaying, via the display generation component, a second user interface different from the first user interface.

In accordance with some embodiments, a method is described. The method comprises: at a computer system that is in communication with a display generation component and one or more input devices: displaying, via the display generation component, a workout creation user interface that includes: a first selectable object that is selectable to initiate a process for adding one or more segments to a workout; and a second selectable object that is selectable to initiate the workout; while displaying the workout creation user interface that includes the first selectable object and the second selectable object, receiving, via the one or more input devices, a first user input corresponding to selection of the first user interface object; and in response to receiving the first user input: in accordance with a determination that the workout includes one or more repeatable segments, displaying, via the display generation component, a first interval creation user interface, including concurrently displaying: a third selectable object that is selectable to initiate a process for adding a new segment to the workout; and a fourth selectable object that is selectable to initiate a process for adding repetitions of at least some of the one or more repeatable segments; and in accordance with a determination that the workout does not include repeatable segments, displaying, via the display generation component, a second interval creation user interface, including displaying the third selectable object without displaying the fourth selectable object.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: displaying, via the display generation component, a workout creation user interface that includes: a first selectable object that is selectable to initiate a process for adding one or more segments to a workout; and a second selectable object that is selectable to initiate the workout; while displaying the workout creation user interface that includes the first selectable object and the second selectable object, receiving, via the one or more input devices, a first user input corresponding to selection of the first user interface object; and in response to receiving the first user input: in accordance with a determination that the workout includes one or more repeatable segments, displaying, via the display generation component, a first interval creation user interface, including concurrently displaying: a third selectable object that is selectable to initiate a process for adding a new segment to the workout; and a fourth selectable object that is selectable to initiate a process for adding repetitions of at least some of the one or more repeatable segments; and in accordance with a determination that the workout does not include repeatable segments, displaying, via the display generation component, a second interval creation user interface, including displaying the third selectable object without displaying the fourth selectable object.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: displaying, via the display generation component, a workout creation user interface that includes: a first selectable object that is selectable to initiate a process for adding one or more segments to a workout; and a second selectable object that is selectable to initiate the workout; while displaying the workout creation user interface that includes the first selectable object and the second selectable object, receiving, via the one or more input devices, a first user input corresponding to selection of the first user interface object; and in response to receiving the first user input: in accordance with a determination that the workout includes one or more repeatable segments, displaying, via the display generation component, a first interval creation user interface, including concurrently displaying: a third selectable object that is selectable to initiate a process for adding a new segment to the workout; and a fourth selectable object that is selectable to initiate a process for adding repetitions of at least some of the one or more repeatable segments; and in accordance with a determination that the workout does not include repeatable segments, displaying, via the display generation component, a second interval creation user interface, including displaying the third selectable object without displaying the fourth selectable object.

In accordance with some embodiments, a computer system configured to communicate with a display generation component and one or more input devices is described. The computer system comprises: one or more processors; and memory storing one or more programs configured to be executed by the one or more processors, the one or more programs including instructions for: displaying, via the display generation component, a workout creation user interface that includes: a first selectable object that is selectable to initiate a process for adding one or more segments to a workout; and a second selectable object that is selectable to initiate the workout; while displaying the workout creation user interface that includes the first selectable object and the second selectable object, receiving, via the one or more input devices, a first user input corresponding to selection of the first user interface object; and in response to receiving the first user input: in accordance with a determination that the workout includes one or more repeatable segments, displaying, via the display generation component, a first interval creation user interface, including concurrently displaying: a third selectable object that is selectable to initiate a process for adding a new segment to the workout; and a fourth selectable object that is selectable to initiate a process for adding repetitions of at least some of the one or more repeatable segments; and in accordance with a determination that the workout does not include repeatable segments, displaying, via the display generation component, a second interval creation user interface, including displaying the third selectable object without displaying the fourth selectable object.

In accordance with some embodiments, a computer system configured to communicate with a display generation component and one or more input devices is described. The computer system comprises: means for displaying, via the display generation component, a workout creation user interface that includes: a first selectable object that is selectable to initiate a process for adding one or more segments to a workout; and a second selectable object that is selectable to initiate the workout; means for, while displaying the workout creation user interface that includes the first selectable object and the second selectable object, receiving, via the one or more input devices, a first user input corresponding to selection of the first user interface object; and means for, in response to receiving the first user input: in accordance with a determination that the workout includes one or more repeatable segments, displaying, via the display generation component, a first interval creation user interface, including concurrently displaying: a third selectable object that is selectable to initiate a process for adding a new segment to the workout; and a fourth selectable object that is selectable to initiate a process for adding repetitions of at least some of the one or more repeatable segments; and in accordance with a determination that the workout does not include repeatable segments, displaying, via the display generation component, a second interval creation user interface, including displaying the third selectable object without displaying the fourth selectable object.

In accordance with some embodiments, a computer program product is described. The computer program product comprises one or more programs configured to be executed by one or more processors of a computer system that is in communication with a display generation component and one or more input devices, the one or more programs including instructions for: displaying, via the display generation component, a workout creation user interface that includes: a first selectable object that is selectable to initiate a process for adding one or more segments to a workout; and a second selectable object that is selectable to initiate the workout; while displaying the workout creation user interface that includes the first selectable object and the second selectable object, receiving, via the one or more input devices, a first user input corresponding to selection of the first user interface object; and in response to receiving the first user input: in accordance with a determination that the workout includes one or more repeatable segments, displaying, via the display generation component, a first interval creation user interface, including concurrently displaying: a third selectable object that is selectable to initiate a process for adding a new segment to the workout; and a fourth selectable object that is selectable to initiate a process for adding repetitions of at least some of the one or more repeatable segments; and in accordance with a determination that the workout does not include repeatable segments, displaying, via the display generation component, a second interval creation user interface, including displaying the third selectable object without displaying the fourth selectable object.

In accordance with some embodiments, a method is described. The method comprises: at a computer system that is in communication with a display generation component and one or more input devices: displaying, via the display generation component, a first user interface corresponding to a first workout modality, wherein the first workout modality is part of a multi-modality workout that includes a plurality of workout modalities arranged in an ordered sequence; while displaying the first user interface, automatically detecting that the user may be transitioning from the first workout modality to a second workout modality; in response to detecting that the user may be transitioning from the first workout modality to the second workout modality, displaying, via the display generation component, a second user interface different from the first user interface, wherein the second user interface is indicative of detecting a possible transition from the first workout modality to the second workout modality; while displaying the second user interface, detecting, via the one or more input devices, movement by the user; and in response to detecting the movement by the user: in accordance with a determination that the movement by the user indicates that the user has transitioned from the first workout modality to the second workout modality, displaying, via the display generation component, a third user interface corresponding to the second workout modality, wherein the third user interface is different from the first user interface and the second user interface; and in accordance with a determination that the movement by the user indicates that the user has not transitioned from the first workout modality to the second workout modality, re-displaying the first user interface.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: displaying, via the display generation component, a first user interface corresponding to a first workout modality, wherein the first workout modality is part of a multi-modality workout that includes a plurality of workout modalities arranged in an ordered sequence; while displaying the first user interface, automatically detecting that the user may be transitioning from the first workout modality to a second workout modality; in response to detecting that the user may be transitioning from the first workout modality to the second workout modality, displaying, via the display generation component, a second user interface different from the first user interface, wherein the second user interface is indicative of detecting a possible transition from the first workout modality to the second workout modality; while displaying the second user interface, detecting, via the one or more input devices, movement by the user; and in response to detecting the movement by the user: in accordance with a determination that the movement by the user indicates that the user has transitioned from the first workout modality to the second workout modality, displaying, via the display generation component, a third user interface corresponding to the second workout modality, wherein the third user interface is different from the first user interface and the second user interface; and in accordance with a determination that the movement by the user indicates that the user has not transitioned from the first workout modality to the second workout modality, re-displaying the first user interface.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: displaying, via the display generation component, a first user interface corresponding to a first workout modality, wherein the first workout modality is part of a multi-modality workout that includes a plurality of workout modalities arranged in an ordered sequence; while displaying the first user interface, automatically detecting that the user may be transitioning from the first workout modality to a second workout modality; in response to detecting that the user may be transitioning from the first workout modality to the second workout modality, displaying, via the display generation component, a second user interface different from the first user interface, wherein the second user interface is indicative of detecting a possible transition from the first workout modality to the second workout modality; while displaying the second user interface, detecting, via the one or more input devices, movement by the user; and in response to detecting the movement by the user: in accordance with a determination that the movement by the user indicates that the user has transitioned from the first workout modality to the second workout modality, displaying, via the display generation component, a third user interface corresponding to the second workout modality, wherein the third user interface is different from the first user interface and the second user interface; and in accordance with a determination that the movement by the user indicates that the user has not transitioned from the first workout modality to the second workout modality, re-displaying the first user interface.

In accordance with some embodiments, a computer system configured to communicate with a display generation component and one or more input devices is described. The computer system comprises: one or more processors; and memory storing one or more programs configured to be executed by the one or more processors, the one or more programs including instructions for: displaying, via the display generation component, a first user interface corresponding to a first workout modality, wherein the first workout modality is part of a multi-modality workout that includes a plurality of workout modalities arranged in an ordered sequence; while displaying the first user interface, automatically detecting that the user may be transitioning from the first workout modality to a second workout modality; in response to detecting that the user may be transitioning from the first workout modality to the second workout modality, displaying, via the display generation component, a second user interface different from the first user interface, wherein the second user interface is indicative of detecting a possible transition from the first workout modality to the second workout modality; while displaying the second user interface, detecting, via the one or more input devices, movement by the user; and in response to detecting the movement by the user: in accordance with a determination that the movement by the user indicates that the user has transitioned from the first workout modality to the second workout modality, displaying, via the display generation component, a third user interface corresponding to the second workout modality, wherein the third user interface is different from the first user interface and the second user interface; and in accordance with a determination that the movement by the user indicates that the user has not transitioned from the first workout modality to the second workout modality, re-displaying the first user interface.

In accordance with some embodiments, a computer system configured to communicate with a display generation component and one or more input devices is described. The computer system comprises: means for displaying, via the display generation component, a first user interface corresponding to a first workout modality, wherein the first workout modality is part of a multi-modality workout that includes a plurality of workout modalities arranged in an ordered sequence; means for, while displaying the first user interface, automatically detecting that the user may be transitioning from the first workout modality to a second workout modality; means for, in response to detecting that the user may be transitioning from the first workout modality to the second workout modality, displaying, via the display generation component, a second user interface different from the first user interface, wherein the second user interface is indicative of detecting a possible transition from the first workout modality to the second workout modality; means for, while displaying the second user interface, detecting, via the one or more input devices, movement by the user; and means for, in response to detecting the movement by the user: in accordance with a determination that the movement by the user indicates that the user has transitioned from the first workout modality to the second workout modality, displaying, via the display generation component, a third user interface corresponding to the second workout modality, wherein the third user interface is different from the first user interface and the second user interface; and in accordance with a determination that the movement by the user indicates that the user has not transitioned from the first workout modality to the second workout modality, re-displaying the first user interface.

In accordance with some embodiments, a computer program product is described. The computer program product comprises one or more programs configured to be executed by one or more processors of a computer system that is in communication with a display generation component and one or more input devices, the one or more programs including instructions for: displaying, via the display generation component, a first user interface corresponding to a first workout modality, wherein the first workout modality is part of a multi-modality workout that includes a plurality of workout modalities arranged in an ordered sequence; while displaying the first user interface, automatically detecting that the user may be transitioning from the first workout modality to a second workout modality; in response to detecting that the user may be transitioning from the first workout modality to the second workout modality, displaying, via the display generation component, a second user interface different from the first user interface, wherein the second user interface is indicative of detecting a possible transition from the first workout modality to the second workout modality; while displaying the second user interface, detecting, via the one or more input devices, movement by the user; and in response to detecting the movement by the user: in accordance with a determination that the movement by the user indicates that the user has transitioned from the first workout modality to the second workout modality, displaying, via the display generation component, a third user interface corresponding to the second workout modality, wherein the third user interface is different from the first user interface and the second user interface; and in accordance with a determination that the movement by the user indicates that the user has not transitioned from the first workout modality to the second workout modality, re-displaying the first user interface.

In accordance with some embodiments, a method is described. The method comprises: at a computer system that is in communication with a display generation component and one or more input devices: determining that a user has completed a workout session; and in response to determining that the user has completed the workout session, displaying, via the display generation component, a workout summary user interface, including concurrently displaying: a first user interface object corresponding to a first set of workout metrics that are grouped into a first category; and a second user interface object corresponding to a second set of workout metrics that are different from the first set of workout metrics and are grouped into a second category different from the first category, wherein: the first user interface object is selectable to display a first workout category user interface that displays a first set of workout metric information that corresponds to the first set of workout metrics, wherein at least some of the first set of workout metric information is not displayed in the workout summary user interface; and the second user interface object is selectable to display a second workout category user interface that is different from the first workout category user interface and displays a second set of workout metric information that corresponds to the second set of workout metrics, wherein the second set of workout metric information is different from the first set of workout metric information and at least some of the second set of workout metric information is not displayed in the workout summary user interface.

In accordance with some embodiments, a non-transitory computer-readable storage medium is described. The non-transitory computer-readable storage medium stores one or more programs configured to be executed by one or more processors of a computer system that is in communication with a display generation component and one or more input devices, the one or more programs including instructions for: determining that a user has completed a workout session; and in response to determining that the user has completed the workout session, displaying, via the display generation component, a workout summary user interface, including concurrently displaying: a first user interface object corresponding to a first set of workout metrics that are grouped into a first category; and a second user interface object corresponding to a second set of workout metrics that are different from the first set of workout metrics and are grouped into a second category different from the first category, wherein: the first user interface object is selectable to display a first workout category user interface that displays a first set of workout metric information that corresponds to the first set of workout metrics, wherein at least some of the first set of workout metric information is not displayed in the workout summary user interface; and the second user interface object is selectable to display a second workout category user interface that is different from the first workout category user interface and displays a second set of workout metric information that corresponds to the second set of workout metrics, wherein the second set of workout metric information is different from the first set of workout metric information and at least some of the second set of workout metric information is not displayed in the workout summary user interface.

In accordance with some embodiments, a transitory computer-readable storage medium is described. The transitory computer-readable storage medium stores one or more programs configured to be executed by one or more processors of a computer system that is in communication with a display generation component and one or more input devices, the one or more programs including instructions for: determining that a user has completed a workout session; and in response to determining that the user has completed the workout session, displaying, via the display generation component, a workout summary user interface, including concurrently displaying: a first user interface object corresponding to a first set of workout metrics that are grouped into a first category; and a second user interface object corresponding to a second set of workout metrics that are different from the first set of workout metrics and are grouped into a second category different from the first category, wherein: the first user interface object is selectable to display a first workout category user interface that displays a first set of workout metric information that corresponds to the first set of workout metrics, wherein at least some of the first set of workout metric information is not displayed in the workout summary user interface; and the second user interface object is selectable to display a second workout category user interface that is different from the first workout category user interface and displays a second set of workout metric information that corresponds to the second set of workout metrics, wherein the second set of workout metric information is different from the first set of workout metric information and at least some of the second set of workout metric information is not displayed in the workout summary user interface.

In accordance with some embodiments, a computer system configured to communicate with a display generation component and one or more input devices is described. The computer system comprises: one or more processors; and memory storing one or more programs configured to be executed by the one or more processors, the one or more programs including instructions for: determining that a user has completed a workout session; and in response to determining that the user has completed the workout session, displaying, via the display generation component, a workout summary user interface, including concurrently displaying: a first user interface object corresponding to a first set of workout metrics that are grouped into a first category; and a second user interface object corresponding to a second set of workout metrics that are different from the first set of workout metrics and are grouped into a second category different from the first category, wherein: the first user interface object is selectable to display a first workout category user interface that displays a first set of workout metric information that corresponds to the first set of workout metrics, wherein at least some of the first set of workout metric information is not displayed in the workout summary user interface; and the second user interface object is selectable to display a second workout category user interface that is different from the first workout category user interface and displays a second set of workout metric information that corresponds to the second set of workout metrics, wherein the second set of workout metric information is different from the first set of workout metric information and at least some of the second set of workout metric information is not displayed in the workout summary user interface.

In accordance with some embodiments, a computer system configured to communicate with a display generation component and one or more input devices is described. The computer system comprises: means for determining that a user has completed a workout session; and means for, in response to determining that the user has completed the workout session, displaying, via the display generation component, a workout summary user interface, including concurrently displaying: a first user interface object corresponding to a first set of workout metrics that are grouped into a first category; and a second user interface object corresponding to a second set of workout metrics that are different from the first set of workout metrics and are grouped into a second category different from the first category, wherein: the first user interface object is selectable to display a first workout category user interface that displays a first set of workout metric information that corresponds to the first set of workout metrics, wherein at least some of the first set of workout metric information is not displayed in the workout summary user interface; and the second user interface object is selectable to display a second workout category user interface that is different from the first workout category user interface and displays a second set of workout metric information that corresponds to the second set of workout metrics, wherein the second set of workout metric information is different from the first set of workout metric information and at least some of the second set of workout metric information is not displayed in the workout summary user interface.

In accordance with some embodiments, a computer program product is described. The computer program product comprises one or more programs configured to be executed by one or more processors of a computer system that is in communication with a display generation component and one or more input devices, the one or more programs including instructions for: determining that a user has completed a workout session; and in response to determining that the user has completed the workout session, displaying, via the display generation component, a workout summary user interface, including concurrently displaying: a first user interface object corresponding to a first set of workout metrics that are grouped into a first category; and a second user interface object corresponding to a second set of workout metrics that are different from the first set of workout metrics and are grouped into a second category different from the first category, wherein: the first user interface object is selectable to display a first workout category user interface that displays a first set of workout metric information that corresponds to the first set of workout metrics, wherein at least some of the first set of workout metric information is not displayed in the workout summary user interface; and the second user interface object is selectable to display a second workout category user interface that is different from the first workout category user interface and displays a second set of workout metric information that corresponds to the second set of workout metrics, wherein the second set of workout metric information is different from the first set of workout metric information and at least some of the second set of workout metric information is not displayed in the workout summary user interface. Executable instructions for performing these functions are, optionally, included in a non-transitory computer-readable storage medium or other computer program product configured for execution by one or more processors. Executable instructions for performing these functions are, optionally, included in a transitory computer-readable storage medium or other computer program product configured for execution by one or more processors.

Thus, devices are provided with faster, more efficient methods and interfaces for navigating, modifying, and outputting workout content, thereby increasing the effectiveness, efficiency, and user satisfaction with such devices. Such methods and interfaces may complement or replace other methods for navigating, modifying, and outputting workout content.

DESCRIPTION OF THE FIGURES

For a better understanding of the various described embodiments, reference should be made to the Description of Embodiments below, in conjunction with the following drawings in which like reference numerals refer to corresponding parts throughout the figures.

FIGS. 11A-11B illustrate a flow diagram depicting a method for outputting workout content, in accordance with some embodiments.

FIGS. 12A-12J illustrate exemplary user interfaces for outputting track workout content, in accordance with some embodiments.

FIG. 18 illustrates a flow diagram depicting a method for navigating and outputting workout content, in accordance with some embodiments.

DESCRIPTION OF EMBODIMENTS

The following description sets forth exemplary methods, parameters, and the like. It should be recognized, however, that such description is not intended as a limitation on the scope of the present disclosure but is instead provided as a description of exemplary embodiments.

There is a need for electronic devices that provide efficient methods and interfaces for navigating, modifying, and outputting workout content. For example, a user would benefit from improved user interfaces that allow users to navigate, modify, and/or output workout content, particularly for electronic devices that have smaller form factors, such as smartwatches. Such techniques can reduce the cognitive burden on a user who navigates, modifies, and/or accesses workout content, thereby enhancing productivity. Further, such techniques can reduce processor and battery power otherwise wasted on redundant user inputs.

Figure 6A:
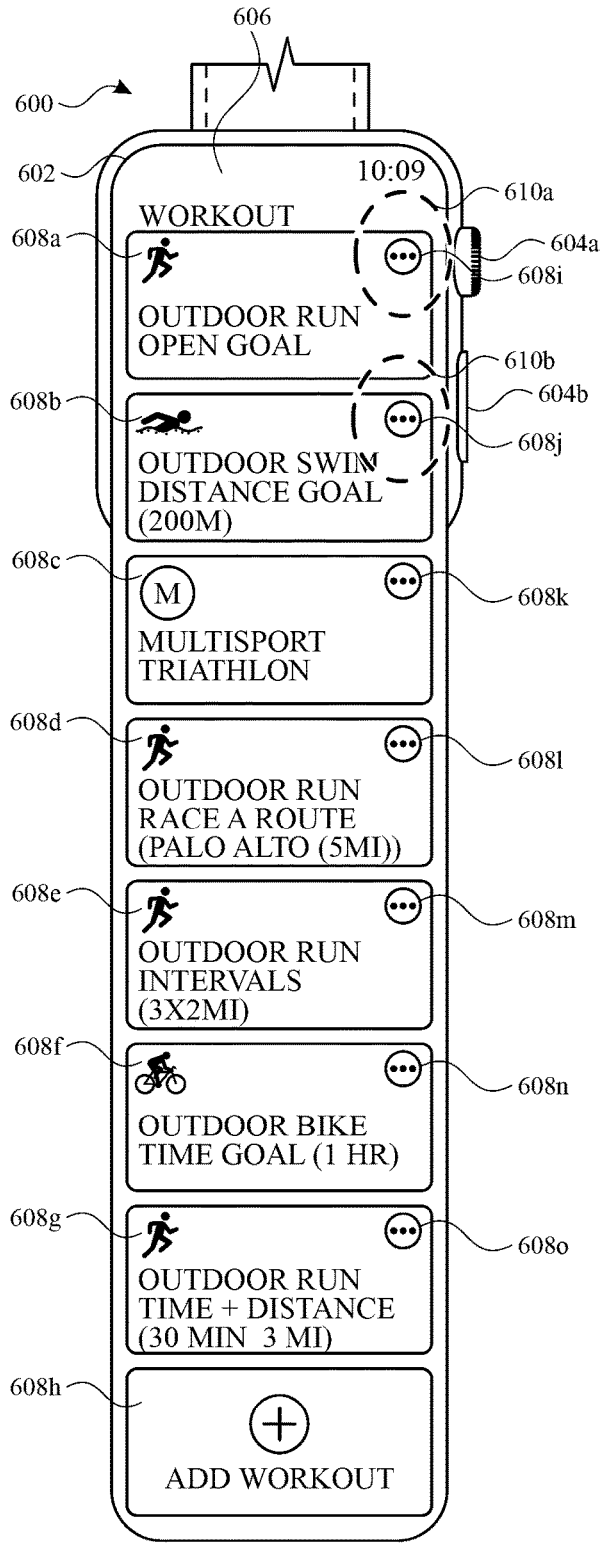
FIGS. 6A-6AE illustrate exemplary user interfaces for navigating, modifying, and outputting workout content, in accordance with some embodiments.
Figure 7:
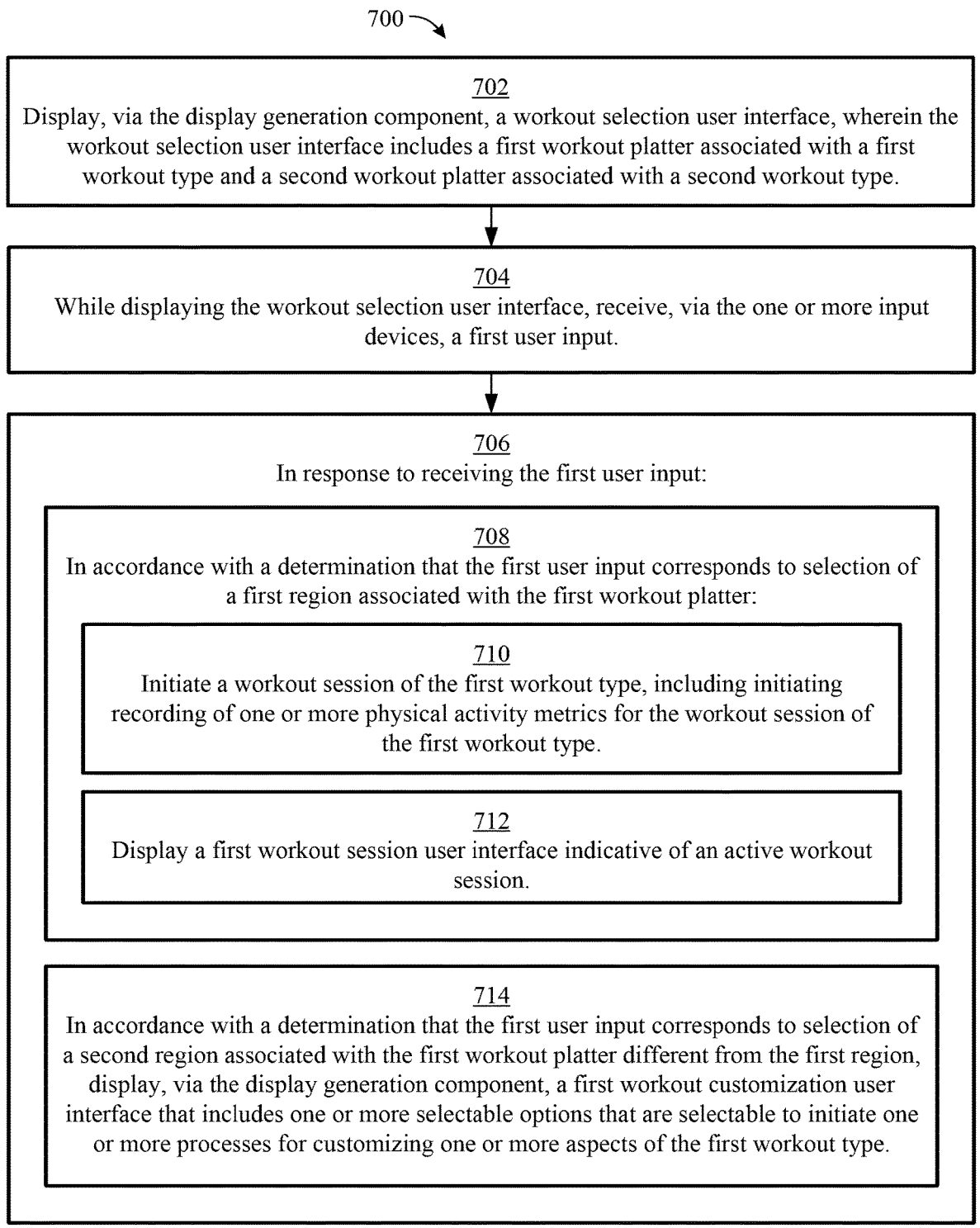
FIG. 7 illustrates a flow diagram depicting a method for navigating, modifying, and outputting workout content, in accordance with some embodiments.
Figure 8:
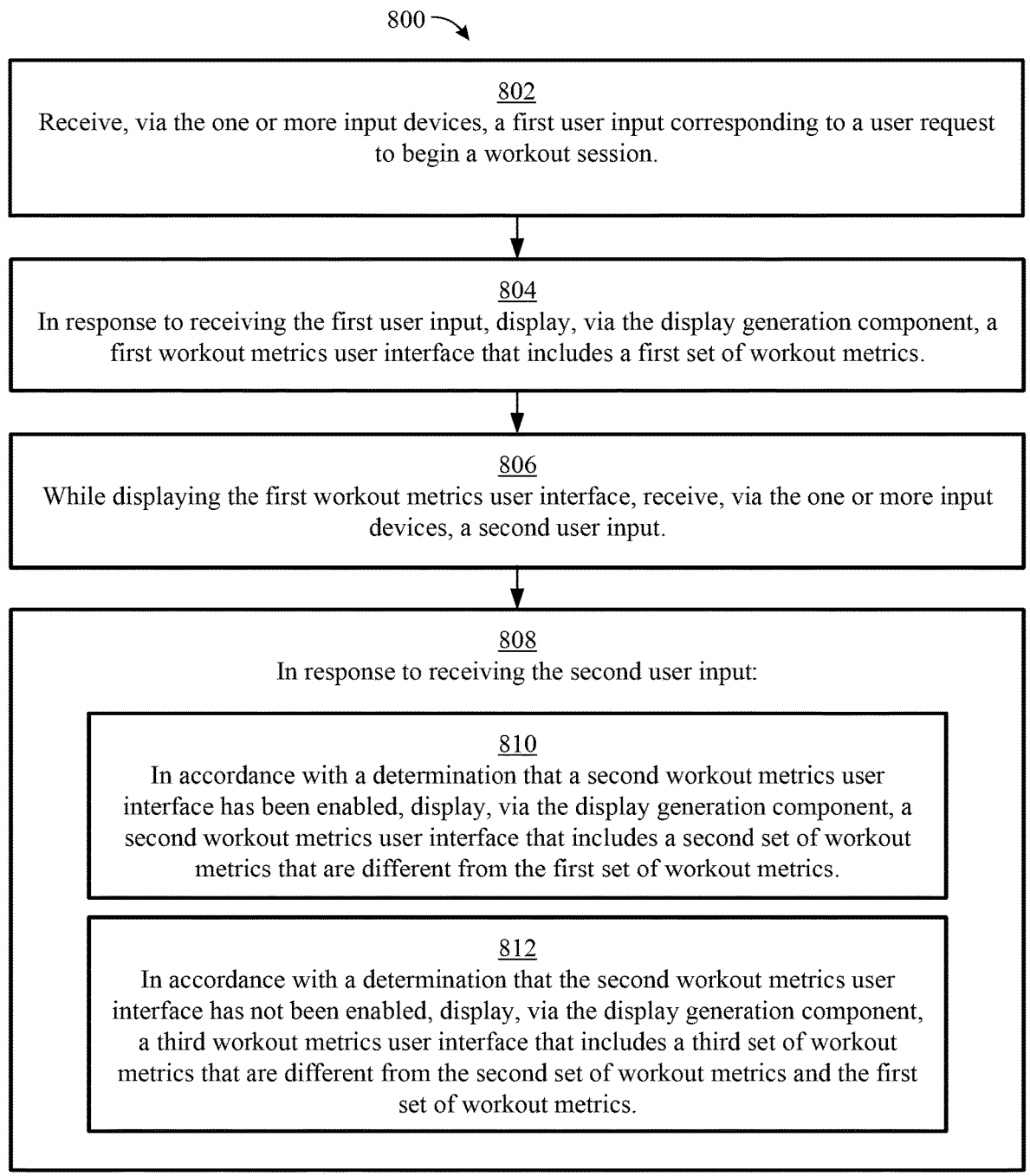
FIG. 8 illustrates a flow diagram depicting a method for navigating, modifying, and outputting workout content, in accordance with some embodiments.
Figure 9:
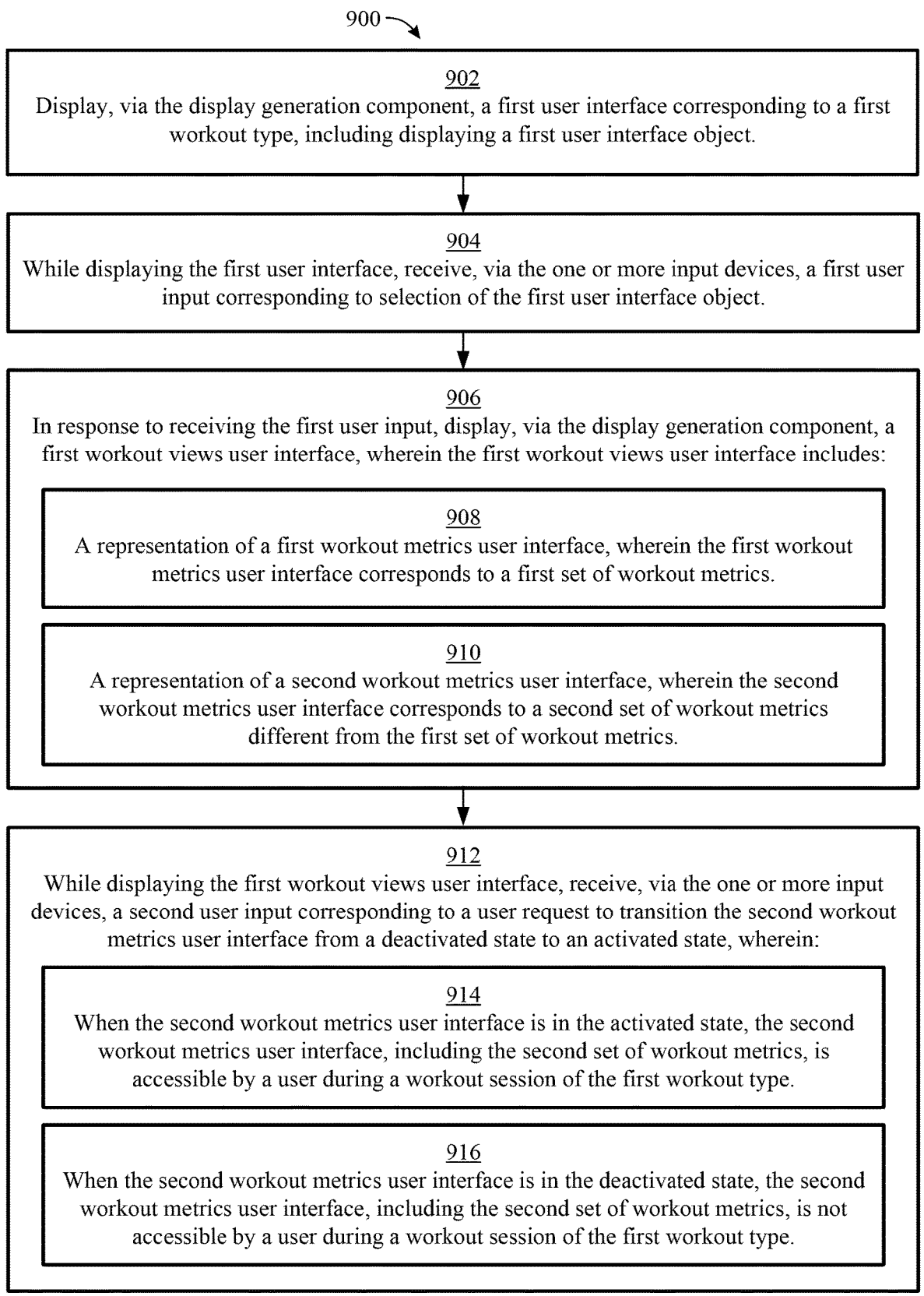
FIG. 9 illustrates a flow diagram depicting a method for navigating, modifying, and outputting workout content, in accordance with some embodiments.
Figure 10A:
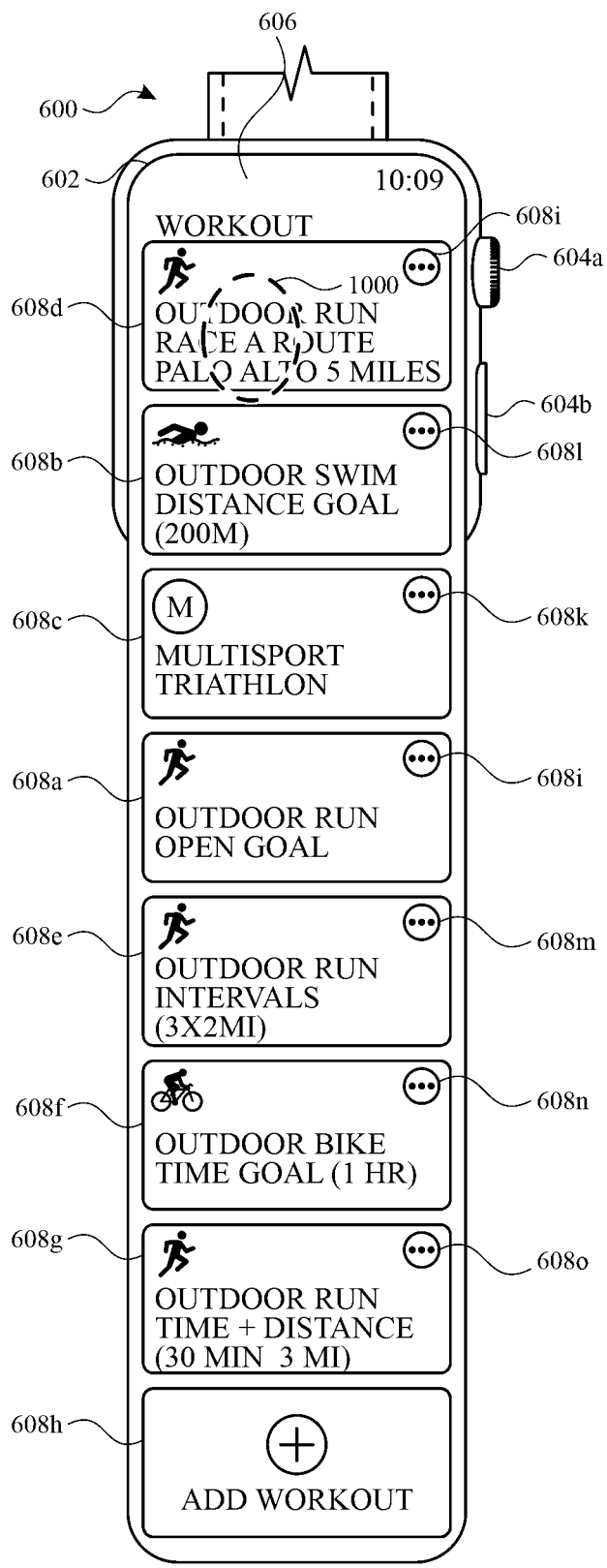
FIGS. 10A-10S illustrate exemplary user interfaces for outputting workout content, in accordance with some embodiments.
Figure 10S:
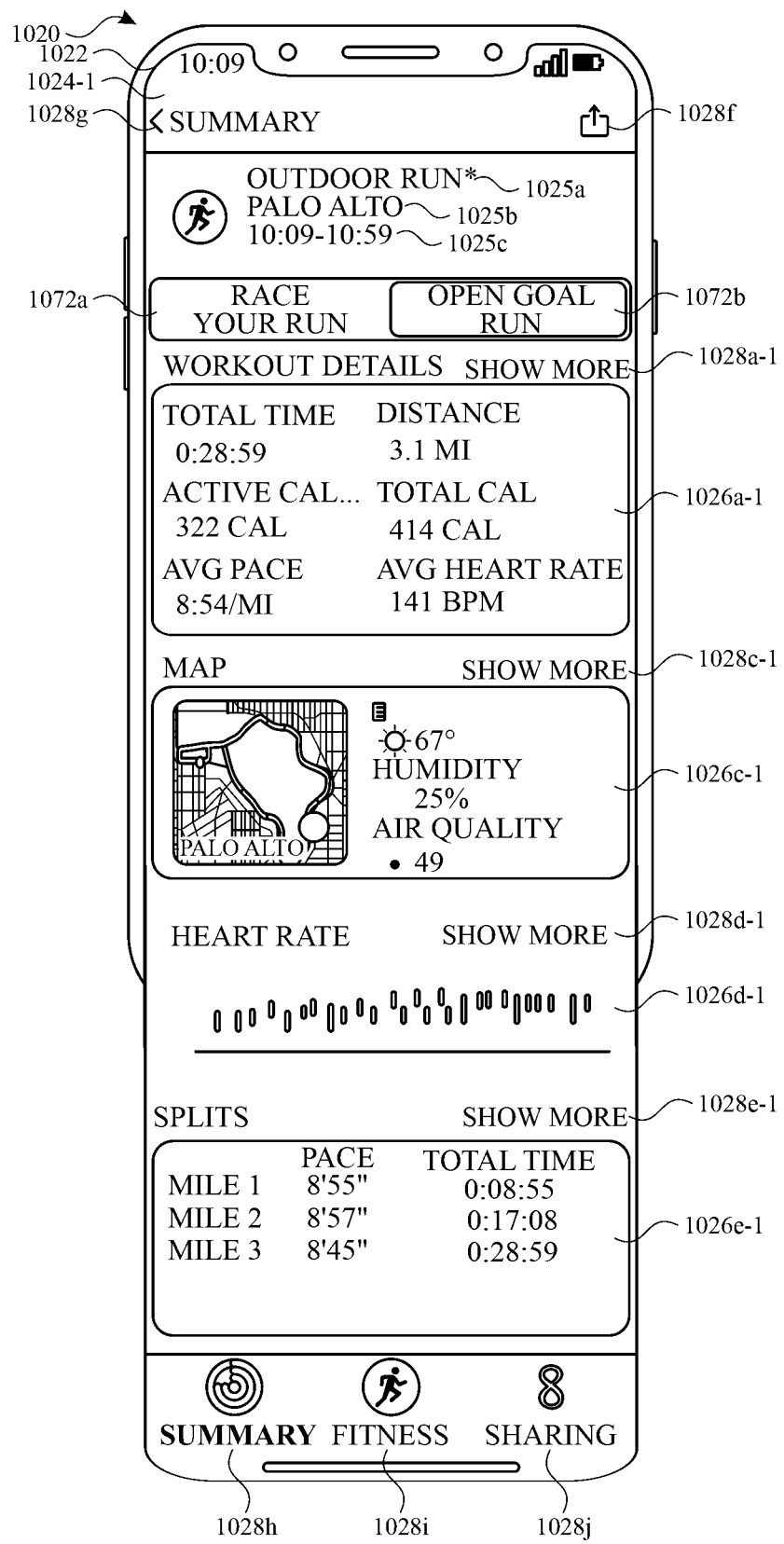
Figure 11A:
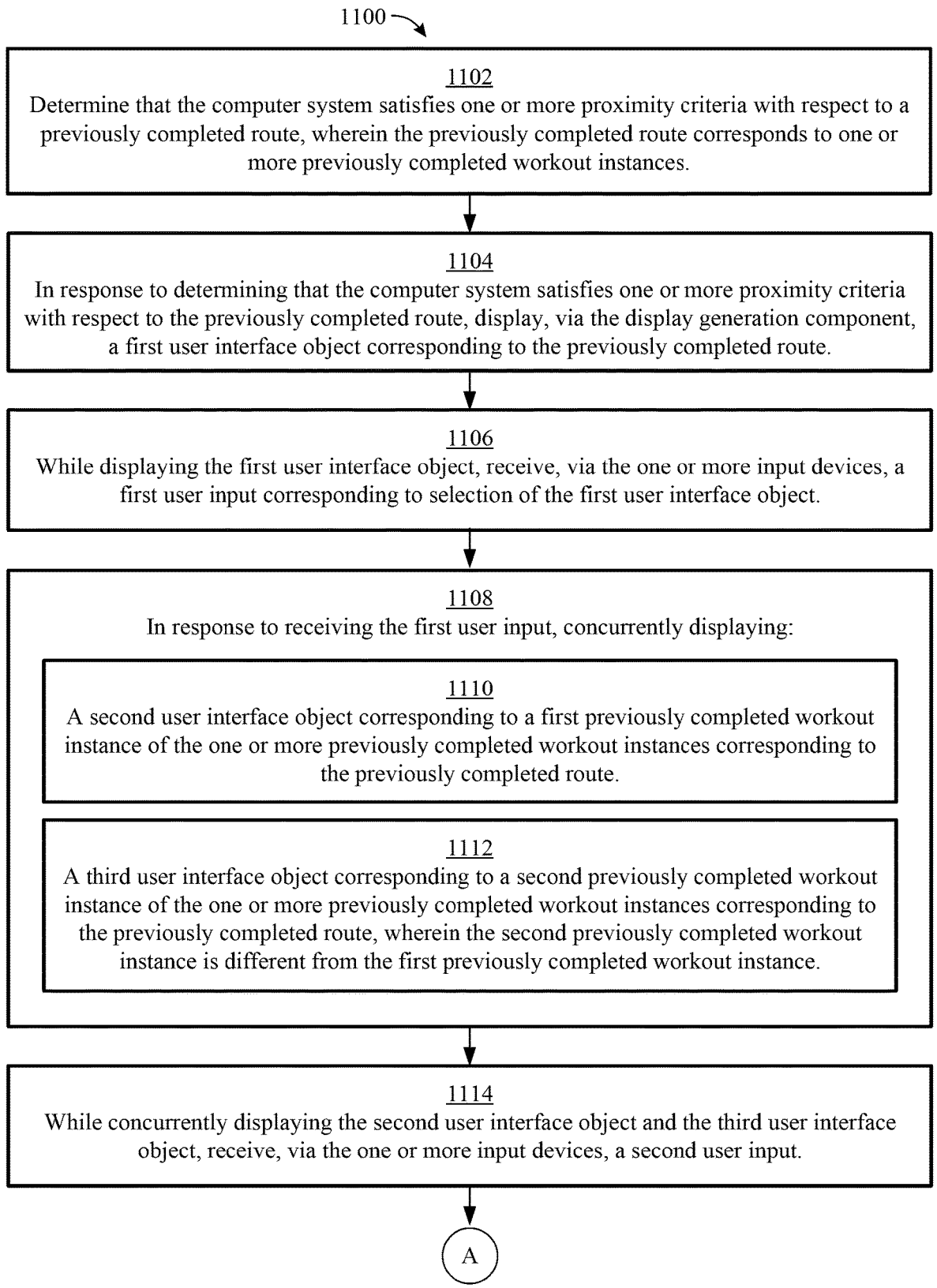
Figure 13:
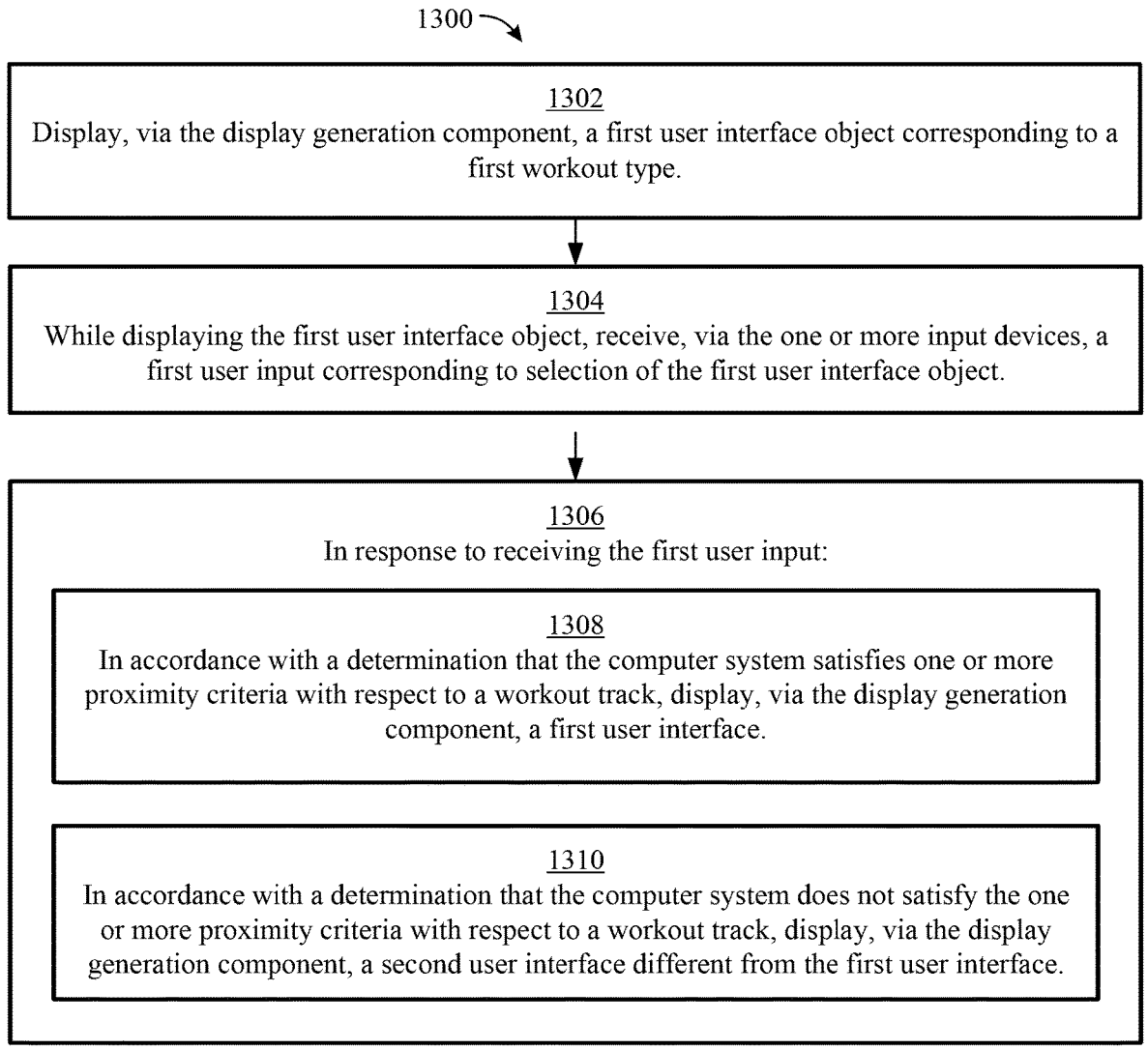
FIG. 13 illustrates a flow diagram depicting a method for outputting track workout content, in accordance with some embodiments.
Figure 14A:
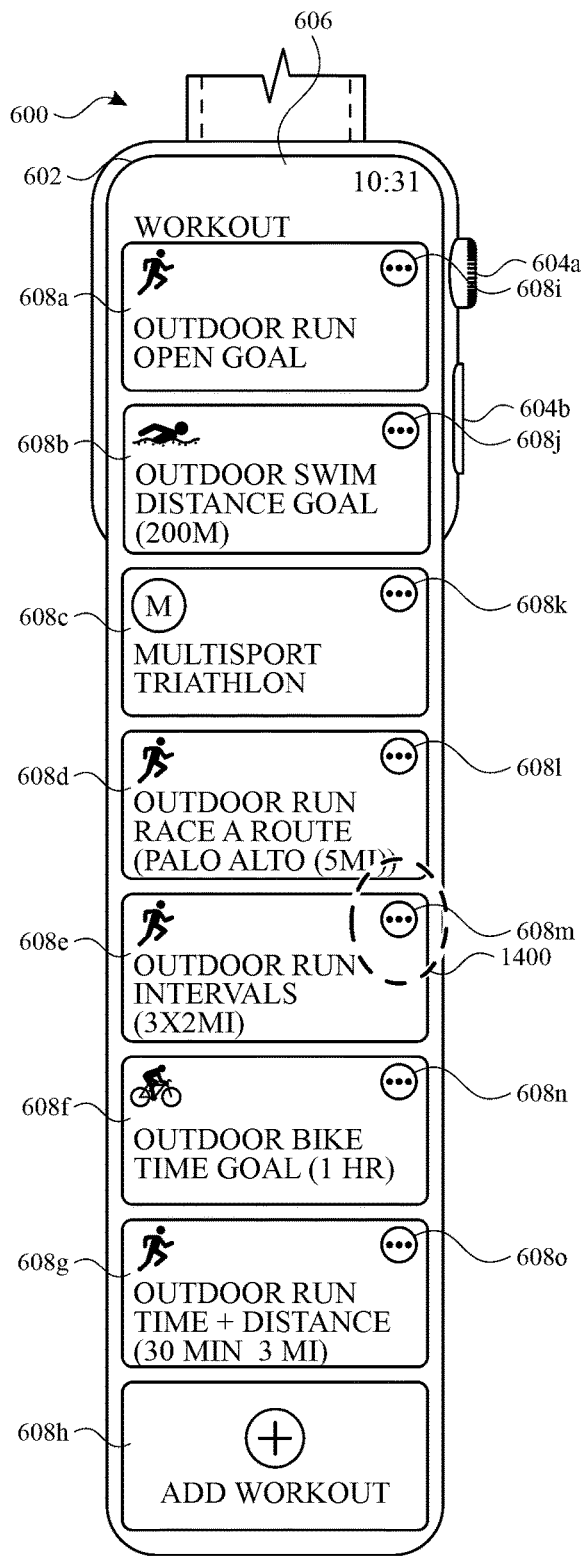
FIGS. 14A-14Y illustrate exemplary user interfaces for navigating, modifying, and outputting interval workout content, in accordance with some embodiments.
Figure 14Y:
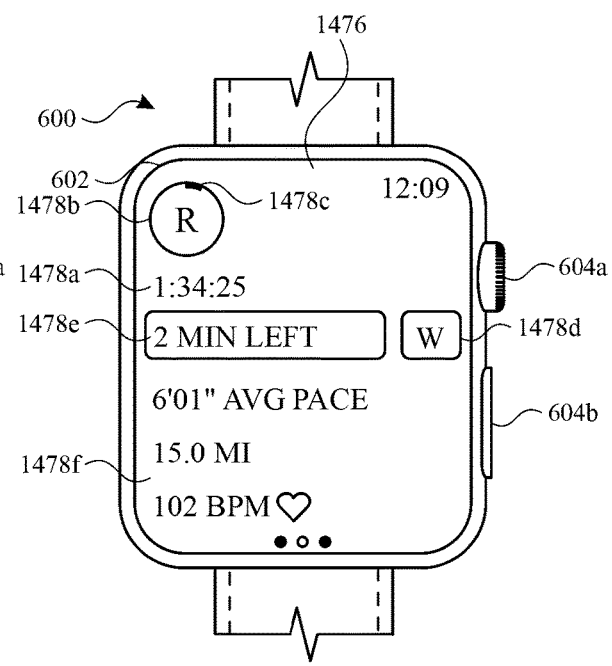
Figure 15:
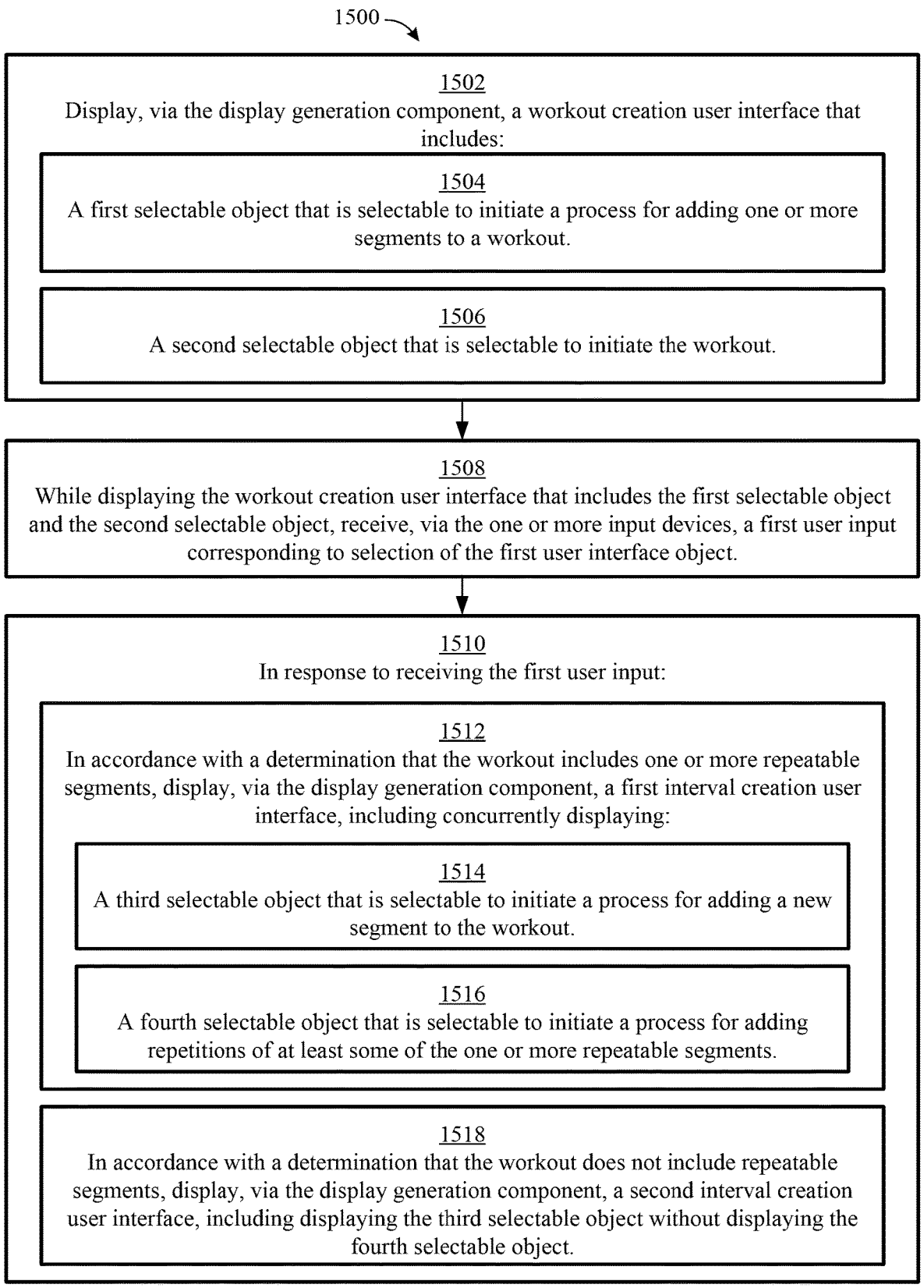
FIG. 15 illustrates a flow diagram depicting a method for navigating, modifying, and outputting interval workout content, in accordance with some embodiments.

Below, FIGS. 1A-1B, 2, 3, 4A-4B, and 5A-5B provide a description of exemplary devices for performing the techniques for managing event notifications. FIGS. 6A-6AE illustrate exemplary user interfaces for navigating, modifying, and outputting workout content. FIG. 7 is a flow diagram illustrating methods of modifying, navigating, and outputting workout content in accordance with some embodiments. FIG. 8 is a flow diagram illustrating methods of modifying, navigating, and outputting workout content in accordance with some embodiments. FIG. 9 is a flow diagram illustrating methods of modifying, navigating, and outputting workout content in accordance with some embodiments. The user interfaces in FIGS. 6A-6AE are used to illustrate the processes described below, including the processes in FIGS. 7, 8, and 9. FIGS. 10A-10S illustrate exemplary user interfaces for outputting workout content. FIGS. 11A-11B are a flow diagram illustrating methods of outputting workout content in accordance with some embodiments. The user interfaces in FIGS. 10A-10S are used to illustrate the processes described below, including the processes in FIGS. 11A-11B and FIG. 18. FIGS. 12A-12J illustrate exemplary user interfaces for outputting track workout content. FIG. 13 is a flow diagram illustrating methods of outputting track workout content in accordance with some embodiments. The user interfaces in FIGS. 12A-12J are used to illustrate the processes described below, including the processes in FIG. 13. FIGS. 14A-14Y illustrate exemplary user interfaces for navigating, modifying, and outputting interval workout content. FIG. 15 is a flow diagram illustrating methods of navigating, modifying, and outputting interval workout content in accordance with some embodiments. The user interfaces in FIGS. 14A-14Y are used to illustrate the processes described below, including the processes in FIG. 15. FIGS. 16A-16AB illustrate exemplary user interfaces for navigating, modifying, and outputting multisport workout content. FIG. 17 is a flow diagram illustrating methods of navigating, modifying, and outputting multisport workout content in accordance with some embodiments. FIG. 18 is a flow diagram depicting a method for navigating and outputting workout content, in accordance with some embodiments. The user interfaces in FIGS. 16A-16AB are used to illustrate the processes described below, including the processes in FIGS. 17 and 18.

The processes described below enhance the operability of the devices and make the user-device interfaces more efficient (e.g., by helping the user to provide proper inputs and reducing user mistakes when operating/interacting with the device) through various techniques, including by providing improved visual feedback to the user, reducing the number of inputs needed to perform an operation, providing additional control options without cluttering the user interface with additional displayed controls, performing an operation when a set of conditions has been met without requiring further user input, and/or additional techniques. These techniques also reduce power usage and improve battery life of the device by enabling the user to use the device more quickly and efficiently.

In addition, in methods described herein where one or more steps are contingent upon one or more conditions having been met, it should be understood that the described method can be repeated in multiple repetitions so that over the course of the repetitions all of the conditions upon which steps in the method are contingent have been met in different repetitions of the method. For example, if a method requires performing a first step if a condition is satisfied, and a second step if the condition is not satisfied, then a person of ordinary skill would appreciate that the claimed steps are repeated until the condition has been both satisfied and not satisfied, in no particular order. Thus, a method described with one or more steps that are contingent upon one or more conditions having been met could be rewritten as a method that is repeated until each of the conditions described in the method has been met. This, however, is not required of system or computer readable medium claims where the system or computer readable medium contains instructions for performing the contingent operations based on the satisfaction of the corresponding one or more conditions and thus is capable of determining whether the contingency has or has not been satisfied without explicitly repeating steps of a method until all of the conditions upon which steps in the method are contingent have been met. A person having ordinary skill in the art would also understand that, similar to a method with contingent steps, a system or computer readable storage medium can repeat the steps of a method as many times as are needed to ensure that all of the contingent steps have been performed.

Although the following description uses terms "first," "second," etc. to describe various elements, these elements should not be limited by the terms. In some embodiments, these terms are used to distinguish one element from another. For example, a first touch could be termed a second touch, and, similarly, a second touch could be termed a first touch, without departing from the scope of the various described embodiments. In some embodiments, the first touch and the second touch are two separate references to the same touch. In some embodiments, the first touch and the second touch are both touches, but they are not the same touch.

The terminology used in the description of the various described embodiments herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

Embodiments of electronic devices, user interfaces for such devices, and associated processes for using such devices are described. In some embodiments, the device is a portable communications device, such as a mobile telephone, that also contains other functions, such as PDA and/or music player functions. Exemplary embodiments of portable multifunction devices include, without limitation, the iPhone®, iPod Touch®, and iPad® devices from Apple Inc. of Cupertino, California. Other portable electronic devices, such as laptops or tablet computers with touch-sensitive surfaces (e.g., touch screen displays and/or touchpads), are, optionally, used. It should also be understood that, in some embodiments, the device is not a portable communications device, but is a desktop computer with a touch-sensitive surface (e.g., a touch screen display and/or a touchpad). In some embodiments, the electronic device is a computer system that is in communication (e.g., via wireless communication, via wired communication) with a display generation component. The display generation component is configured to provide visual output, such as display via a CRT display, display via an LED display, or display via image projection. In some embodiments, the display generation component is integrated with the computer system. In some embodiments, the display generation component is separate from the computer system. As used herein, "displaying" content includes causing to display the content (e.g., video data rendered or decoded by display controller 156) by transmitting, via a wired or wireless connection, data (e.g., image data or video data) to an integrated or external display generation component to visually produce the content.

In the discussion that follows, an electronic device that includes a display and a touch-sensitive surface is described. It should be understood, however, that the electronic device optionally includes one or more other physical user-interface devices, such as a physical keyboard, a mouse, and/or a joystick.

The device typically supports a variety of applications, such as one or more of the following: a drawing application, a presentation application, a word processing application, a website creation application, a disk authoring application, a spreadsheet application, a gaming application, a telephone application, a video conferencing application, an e-mail application, an instant messaging application, a workout support application, a photo management application, a digital camera application, a digital video camera application, a web browsing application, a digital music player application, and/or a digital video player application.

The various applications that are executed on the device optionally use at least one common physical user-interface device, such as the touch-sensitive surface. One or more functions of the touch-sensitive surface as well as corresponding information displayed on the device are, optionally, adjusted and/or varied from one application to the next and/or within a respective application. In this way, a common physical architecture (such as the touch-sensitive surface) of the device optionally supports the variety of applications with user interfaces that are intuitive and transparent to the user.

Figure 1A:
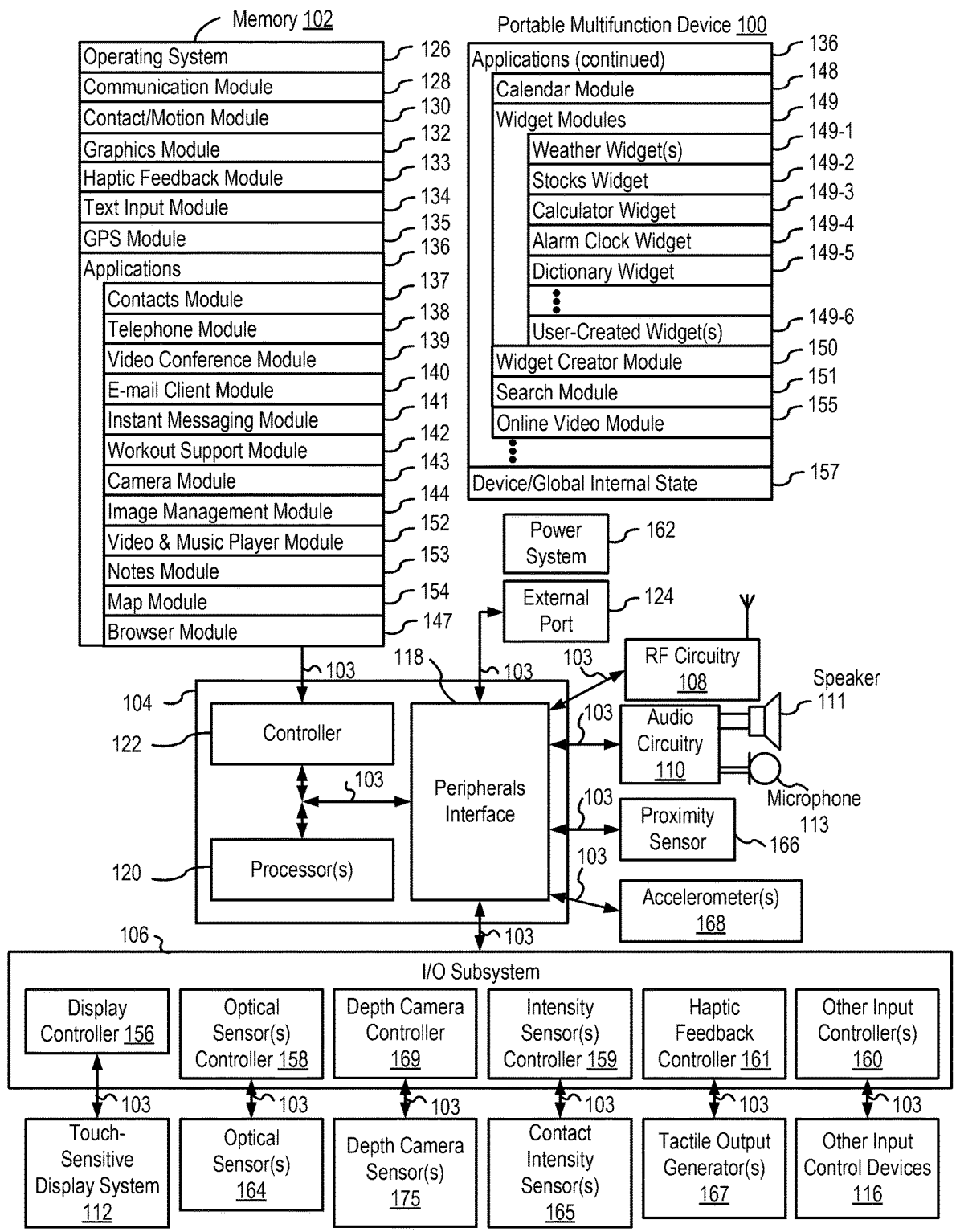
FIG. 1A is a block diagram illustrating a portable multifunction device with a touch-sensitive display in accordance with some embodiments.

Attention is now directed toward embodiments of portable devices with touch-sensitive displays. FIG. 1A is a block diagram illustrating portable multifunction device 100 with touch-sensitive display system 112 in accordance with some embodiments. Touch-sensitive display 112 is sometimes called a "touch screen" for convenience and is sometimes known as or called a "touch-sensitive display system." Device 100 includes memory 102 (which optionally includes one or more computer-readable storage mediums), memory controller 122, one or more processing units (CPUs) 120, peripherals interface 118, RF circuitry 108, audio circuitry 110, speaker 111, microphone 113, input/output (I/O) subsystem 106, other input control devices 116, and external port 124. Device 100 optionally includes one or more optical sensors 164. Device 100 optionally includes one or more contact intensity sensors 165 for detecting intensity of contacts on device 100 (e.g., a touch-sensitive surface such as touch-sensitive display system 112 of device 100). Device 100 optionally includes one or more tactile output generators 167 for generating tactile outputs on device 100 (e.g., generating tactile outputs on a touch-sensitive surface such as touch-sensitive display system 112 of device 100 or touchpad 355 of device 300). These components optionally communicate over one or more communication buses or signal lines 103.

As used in the specification and claims, the term "intensity" of a contact on a touch-sensitive surface refers to the force or pressure (force per unit area) of a contact (e.g., a finger contact) on the touch-sensitive surface, or to a substitute (proxy) for the force or pressure of a contact on the touch-sensitive surface. The intensity of a contact has a range of values that includes at least four distinct values and more typically includes hundreds of distinct values (e.g., at least 256). Intensity of a contact is, optionally, determined (or measured) using various approaches and various sensors or combinations of sensors. For example, one or more force sensors underneath or adjacent to the touch-sensitive surface are, optionally, used to measure force at various points on the touch-sensitive surface. In some implementations, force measurements from multiple force sensors are combined (e.g., a weighted average) to determine an estimated force of a contact. Similarly, a pressure-sensitive tip of a stylus is, optionally, used to determine a pressure of the stylus on the touch-sensitive surface. Alternatively, the size of the contact area detected on the touch-sensitive surface and/or changes thereto, the capacitance of the touch-sensitive surface proximate to the contact and/or changes thereto, and/or the resistance of the touch-sensitive surface proximate to the contact and/or changes thereto are, optionally, used as a substitute for the force or pressure of the contact on the touch-sensitive surface. In some implementations, the substitute measurements for contact force or pressure are used directly to determine whether an intensity threshold has been exceeded (e.g., the intensity threshold is described in units corresponding to the substitute measurements). In some implementations, the substitute measurements for contact force or pressure are converted to an estimated force or pressure, and the estimated force or pressure is used to determine whether an intensity threshold has been exceeded (e.g., the intensity threshold is a pressure threshold measured in units of pressure). Using the intensity of a contact as an attribute of a user input allows for user access to additional device functionality that may otherwise not be accessible by the user on a reduced-size device with limited real estate for displaying affordances (e.g., on a touch-sensitive display) and/or receiving user input (e.g., via a touch-sensitive display, a touch-sensitive surface, or a physical/mechanical control such as a knob or a button).

As used in the specification and claims, the term "tactile output" refers to physical displacement of a device relative to a previous position of the device, physical displacement of a component (e.g., a touch-sensitive surface) of a device relative to another component (e.g., housing) of the device, or displacement of the component relative to a center of mass of the device that will be detected by a user with the user's sense of touch. For example, in situations where the device or the component of the device is in contact with a surface of a user that is sensitive to touch (e.g., a finger, palm, or other part of a user's hand), the tactile output generated by the physical displacement will be interpreted by the user as a tactile sensation corresponding to a perceived change in physical characteristics of the device or the component of the device. For example, movement of a touch-sensitive surface (e.g., a touch-sensitive display or trackpad) is, optionally, interpreted by the user as a "down click" or "up click" of a physical actuator button. In some cases, a user will feel a tactile sensation such as an "down click" or "up click" even when there is no movement of a physical actuator button associated with the touch-sensitive surface that is physically pressed (e.g., displaced) by the user's movements. As another example, movement of the touch-sensitive surface is, optionally, interpreted or sensed by the user as "roughness" of the touch-sensitive surface, even when there is no change in smoothness of the touch-sensitive surface. While such interpretations of touch by a user will be subject to the individualized sensory perceptions of the user, there are many sensory perceptions of touch that are common to a large majority of users. Thus, when a tactile output is described as corresponding to a particular sensory perception of a user (e.g., an "up click," a "down click," "roughness"), unless otherwise stated, the generated tactile output corresponds to physical displacement of the device or a component thereof that will generate the described sensory perception for a typical (or average) user.

It should be appreciated that device 100 is only one example of a portable multifunction device, and that device 100 optionally has more or fewer components than shown, optionally combines two or more components, or optionally has a different configuration or arrangement of the components. The various components shown in FIG. 1A are implemented in hardware, software, or a combination of both hardware and software, including one or more signal processing and/or application-specific integrated circuits.

Memory 102 optionally includes high-speed random access memory and optionally also includes non-volatile memory, such as one or more magnetic disk storage devices, flash memory devices, or other non-volatile solid-state memory devices. Memory controller 122 optionally controls access to memory 102 by other components of device 100.

Peripherals interface 118 can be used to couple input and output peripherals of the device to CPU 120 and memory 102. The one or more processors 120 run or execute various software programs (such as computer programs (e.g., including instructions)) and/or sets of instructions stored in memory 102 to perform various functions for device 100 and to process data. In some embodiments, peripherals interface 118, CPU 120, and memory controller 122 are, optionally, implemented on a single chip, such as chip 104. In some other embodiments, they are, optionally, implemented on separate chips.

RF (radio frequency) circuitry 108 receives and sends RF signals, also called electromagnetic signals. RF circuitry 108 converts electrical signals to/from electromagnetic signals and communicates with communications networks and other communications devices via the electromagnetic signals. RF circuitry 108 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 108 optionally communicates with networks, such as the Internet, also referred to as the World Wide Web (WWW), an intranet and/or a wireless network, such as a cellular telephone network, a wireless local area network (LAN) and/or a metropolitan area network (MAN), and other devices by wireless communication. The RF circuitry 108 optionally includes well-known circuitry for detecting near field communication (NFC) fields, such as by a short-range communication radio. The wireless communication optionally uses any of a plurality of communications standards, protocols, and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Bluetooth Low Energy (BTLE), Wireless Fidelity (Wi-Fi) (e.g., IEEE 802.11a, IEEE 802.11b, IEEE 802.11g, IEEE 802.11n, and/or IEEE 802.11ac), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of this document.

Audio circuitry 110, speaker 111, and microphone 113 provide an audio interface between a user and device 100. Audio circuitry 110 receives audio data from peripherals interface 118, converts the audio data to an electrical signal, and transmits the electrical signal to speaker 111. Speaker 111 converts the electrical signal to human-audible sound waves. Audio circuitry 110 also receives electrical signals converted by microphone 113 from sound waves. Audio circuitry 110 converts the electrical signal to audio data and transmits the audio data to peripherals interface 118 for processing. Audio data is, optionally, retrieved from and/or transmitted to memory 102 and/or RF circuitry 108 by peripherals interface 118. In some embodiments, audio circuitry 110 also includes a headset jack (e.g., 212, FIG. 2). The headset jack provides an interface between audio circuitry 110 and removable audio input/output peripherals, such as output-only headphones or a headset with both output (e.g., a headphone for one or both ears) and input (e.g., a microphone).

I/O subsystem 106 couples input/output peripherals on device 100, such as touch screen 112 and other input control devices 116, to peripherals interface 118. I/O subsystem 106 optionally includes display controller 156, optical sensor controller 158, depth camera controller 169, intensity sensor controller 159, haptic feedback controller 161, and one or more input controllers 160 for other input or control devices. The one or more input controllers 160 receive/send electrical signals from/to other input control devices 116. The other input control devices 116 optionally include physical buttons (e.g., push buttons, rocker buttons, etc.), dials, slider switches, joysticks, click wheels, and so forth. In some embodiments, input controller(s) 160 are, optionally, coupled to any (or none) of the following: a keyboard, an infrared port, a USB port, and a pointer device such as a mouse. The one or more buttons (e.g., 208, FIG. 2) optionally include an up/down button for volume control of speaker 111 and/or microphone 113. The one or more buttons optionally include a push button (e.g., 206, FIG. 2). In some embodiments, the electronic device is a computer system that is in communication (e.g., via wireless communication, via wired communication) with one or more input devices. In some embodiments, the one or more input devices include a touch-sensitive surface (e.g., a trackpad, as part of a touch-sensitive display). In some embodiments, the one or more input devices include one or more camera sensors (e.g., one or more optical sensors 164 and/or one or more depth camera sensors 175), such as for tracking a user's gestures (e.g., hand gestures and/or air gestures) as input. In some embodiments, the one or more input devices are integrated with the computer system. In some embodiments, the one or more input devices are separate from the computer system. In some embodiments, an air gesture is a gesture that is detected without the user touching an input element that is part of the device (or independently of an input element that is a part of the device) and is based on detected motion of a portion of the user's body through the air including motion of the user's body relative to an absolute reference (e.g., an angle of the user's arm relative to the ground or a distance of the user's hand relative to the ground), relative to another portion of the user's body (e.g., movement of a hand of the user relative to a shoulder of the user, movement of one hand of the user relative to another hand of the user, and/or movement of a finger of the user relative to another finger or portion of a hand of the user), and/or absolute motion of a portion of the user's body (e.g., a tap gesture that includes movement of a hand in a predetermined pose by a predetermined amount and/or speed, or a shake gesture that includes a predetermined speed or amount of rotation of a portion of the user's body).

A quick press of the push button optionally disengages a lock of touch screen 112 or optionally begins a process that uses gestures on the touch screen to unlock the device, as described in U.S. patent application Ser. No. 11/322,549, "Unlocking a Device by Performing Gestures on an Unlock Image," filed Dec. 23, 2005, U.S. Pat. No. 7,657,849, which is hereby incorporated by reference in its entirety. A longer press of the push button (e.g., 206) optionally turns power to device 100 on or off. The functionality of one or more of the buttons are, optionally, user-customizable. Touch screen 112 is used to implement virtual or soft buttons and one or more soft keyboards.

Touch-sensitive display 112 provides an input interface and an output interface between the device and a user. Display controller 156 receives and/or sends electrical signals from/to touch screen 112. Touch screen 112 displays visual output to the user. The visual output optionally includes graphics, text, icons, video, and any combination thereof (collectively termed "graphics"). In some embodiments, some or all of the visual output optionally corresponds to user-interface objects.

Touch screen 112 has a touch-sensitive surface, sensor, or set of sensors that accepts input from the user based on haptic and/or tactile contact. Touch screen 112 and display controller 156 (along with any associated modules and/or sets of instructions in memory 102) detect contact (and any movement or breaking of the contact) on touch screen 112 and convert the detected contact into interaction with user-interface objects (e.g., one or more soft keys, icons, web pages, or images) that are displayed on touch screen 112. In an exemplary embodiment, a point of contact between touch screen 112 and the user corresponds to a finger of the user.

Touch screen 112 optionally uses LCD (liquid crystal display) technology, LPD (light emitting polymer display) technology, or LED (light emitting diode) technology, although other display technologies are used in other embodiments. Touch screen 112 and display controller 156 optionally detect contact and any movement or breaking thereof using any of a plurality of touch sensing technologies now known or later developed, including but not limited to capacitive, resistive, infrared, and surface acoustic wave technologies, as well as other proximity sensor arrays or other elements for determining one or more points of contact with touch screen 112. In an exemplary embodiment, projected mutual capacitance sensing technology is used, such as that found in the iPhone® and iPod Touch® from Apple Inc. of Cupertino, California.

A touch-sensitive display in some embodiments of touch screen 112 is, optionally, analogous to the multi-touch sensitive touchpads described in the following U.S. Pat. No. 6,323,846 (Westerman et al.), U.S. Pat. No. 6,570,557 (Westerman et al.), and/or U.S. Pat. No. 6,677,932 (Westerman), and/or U.S. Patent Publication 2002/0015024A1, each of which is hereby incorporated by reference in its entirety. However, touch screen 112 displays visual output from device 100, whereas touch-sensitive touchpads do not provide visual output.

A touch-sensitive display in some embodiments of touch screen 112 is described in the following applications: (1) U.S. patent application Ser. No. 11/381,313, "Multipoint Touch Surface Controller," filed May 2, 2006; (2) U.S. patent application Ser. No. 10/840,862, "Multipoint Touchscreen," filed May 6, 2004; (3) U.S. patent application Ser. No. 10/903,964, "Gestures For Touch Sensitive Input Devices," filed Jul. 30, 2004; (4) U.S. patent application Ser. No. 11/048,264, "Gestures For Touch Sensitive Input Devices," filed Jan. 31, 2005; (5) U.S. patent application Ser. No. 11/038,590, "Mode-Based Graphical User Interfaces For Touch Sensitive Input Devices," filed Jan. 18, 2005; (6)

U.S. patent application Ser. No. 11/228,758, "Virtual Input Device Placement On A Touch Screen User Interface," filed Sep. 16, 2005; (7) U.S. patent application Ser. No. 11/228,700, "Operation Of A Computer With A Touch Screen Interface," filed Sep. 16, 2005; (8) U.S. patent application Ser. No. 11/228,737, "Activating Virtual Keys Of A Touch-Screen Virtual Keyboard," filed Sep. 16, 2005; and (9) U.S. patent application Ser. No. 11/367,749, "Multi-Functional Hand-Held Device," filed Mar. 3, 2006. All of these applications are incorporated by reference herein in their entirety.

Touch screen 112 optionally has a video resolution in excess of 100 dpi. In some embodiments, the touch screen has a video resolution of approximately 160 dpi. The user optionally makes contact with touch screen 112 using any suitable object or appendage, such as a stylus, a finger, and so forth. In some embodiments, the user interface is designed to work primarily with finger-based contacts and gestures, which can be less precise than stylus-based input due to the larger area of contact of a finger on the touch screen. In some embodiments, the device translates the rough finger-based input into a precise pointer/cursor position or command for performing the actions desired by the user.

In some embodiments, in addition to the touch screen, device 100 optionally includes a touchpad for activating or deactivating particular functions. In some embodiments, the touchpad is a touch-sensitive area of the device that, unlike the touch screen, does not display visual output. The touchpad is, optionally, a touch-sensitive surface that is separate from touch screen 112 or an extension of the touch-sensitive surface formed by the touch screen.

Device 100 also includes power system 162 for powering the various components. Power system 162 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

Device 100 optionally also includes one or more optical sensors 164. FIG. 1A shows an optical sensor coupled to optical sensor controller 158 in I/O subsystem 106. Optical sensor 164 optionally includes charge-coupled device (CCD) or complementary metal-oxide semiconductor (CMOS) phototransistors. Optical sensor 164 receives light from the environment, projected through one or more lenses, and converts the light to data representing an image. In conjunction with imaging module 143 (also called a camera module), optical sensor 164 optionally captures still images or video. In some embodiments, an optical sensor is located on the back of device 100, opposite touch screen display 112 on the front of the device so that the touch screen display is enabled for use as a viewfinder for still and/or video image acquisition. In some embodiments, an optical sensor is located on the front of the device so that the user's image is, optionally, obtained for video conferencing while the user views the other video conference participants on the touch screen display. In some embodiments, the position of optical sensor 164 can be changed by the user (e.g., by rotating the lens and the sensor in the device housing) so that a single optical sensor 164 is used along with the touch screen display for both video conferencing and still and/or video image acquisition.

Device 100 optionally also includes one or more depth camera sensors 175. FIG. 1A shows a depth camera sensor coupled to depth camera controller 169 in I/O subsystem 106. Depth camera sensor 175 receives data from the environment to create a three dimensional model of an object (e.g., a face) within a scene from a viewpoint (e.g., a depth camera sensor). In some embodiments, in conjunction with imaging module 143 (also called a camera module), depth camera sensor 175 is optionally used to determine a depth map of different portions of an image captured by the imaging module 143. In some embodiments, a depth camera sensor is located on the front of device 100 so that the user's image with depth information is, optionally, obtained for video conferencing while the user views the other video conference participants on the touch screen display and to capture selfies with depth map data. In some embodiments, the depth camera sensor 175 is located on the back of device, or on the back and the front of the device 100. In some embodiments, the position of depth camera sensor 175 can be changed by the user (e.g., by rotating the lens and the sensor in the device housing) so that a depth camera sensor 175 is used along with the touch screen display for both video conferencing and still and/or video image acquisition.

Device 100 optionally also includes one or more contact intensity sensors 165. FIG. 1A shows a contact intensity sensor coupled to intensity sensor controller 159 in I/O subsystem 106. Contact intensity sensor 165 optionally includes one or more piezoresistive strain gauges, capacitive force sensors, electric force sensors, piezoelectric force sensors, optical force sensors, capacitive touch-sensitive surfaces, or other intensity sensors (e.g., sensors used to measure the force (or pressure) of a contact on a touch-sensitive surface). Contact intensity sensor 165 receives contact intensity information (e.g., pressure information or a proxy for pressure information) from the environment. In some embodiments, at least one contact intensity sensor is collocated with, or proximate to, a touch-sensitive surface (e.g., touch-sensitive display system 112). In some embodiments, at least one contact intensity sensor is located on the back of device 100, opposite touch screen display 112, which is located on the front of device 100.

Device 100 optionally also includes one or more proximity sensors 166. FIG. 1A shows proximity sensor 166 coupled to peripherals interface 118. Alternately, proximity sensor 166 is, optionally, coupled to input controller 160 in I/O subsystem 106. Proximity sensor 166 optionally performs as described in U.S. patent application Ser. No. 11/241,839, "Proximity Detector In Handheld Device"; Ser. No. 11/240,788, "Proximity Detector In Handheld Device"; Ser. No. 11/620,702, "Using Ambient Light Sensor To Augment Proximity Sensor Output"; Ser. No. 11/586,862, "Automated Response To And Sensing Of User Activity In Portable Devices"; and Ser. No. 11/638,251, "Methods And Systems For Automatic Configuration Of Peripherals," which are hereby incorporated by reference in their entirety. In some embodiments, the proximity sensor turns off and disables touch screen 112 when the multifunction device is placed near the user's ear (e.g., when the user is making a phone call).

Device 100 optionally also includes one or more tactile output generators 167. FIG. 1A shows a tactile output generator coupled to haptic feedback controller 161 in I/O subsystem 106. Tactile output generator 167 optionally includes one or more electroacoustic devices such as speakers or other audio components and/or electromechanical devices that convert energy into linear motion such as a motor, solenoid, electroactive polymer, piezoelectric actuator, electrostatic actuator, or other tactile output generating component (e.g., a component that converts electrical signals into tactile outputs on the device). Contact intensity sensor 165 receives tactile feedback generation instructions from haptic feedback module 133 and generates tactile outputs on device 100 that are capable of being sensed by a user of device 100. In some embodiments, at least one tactile output generator is collocated with, or proximate to, a touch-sensitive surface (e.g., touch-sensitive display system 112) and, optionally, generates a tactile output by moving the touch-sensitive surface vertically (e.g., in/out of a surface of device 100) or laterally (e.g., back and forth in the same plane as a surface of device 100). In some embodiments, at least one tactile output generator sensor is located on the back of device 100, opposite touch screen display 112, which is located on the front of device 100.

Device 100 optionally also includes one or more accelerometers 168. FIG. 1A shows accelerometer 168 coupled to peripherals interface 118. Alternately, accelerometer 168 is, optionally, coupled to an input controller 160 in I/O subsystem 106. Accelerometer 168 optionally performs as described in U.S. Patent Publication No. 20050190059, "Acceleration-based Theft Detection System for Portable Electronic Devices," and U.S. Patent Publication No. 20060017692, "Methods And Apparatuses For Operating A Portable Device Based On An Accelerometer," both of which are incorporated by reference herein in their entirety. In some embodiments, information is displayed on the touch screen display in a portrait view or a landscape view based on an analysis of data received from the one or more accelerometers. Device 100 optionally includes, in addition to accelerometer(s) 168, a magnetometer and a GPS (or GLONASS or other global navigation system) receiver for obtaining information concerning the location and orientation (e.g., portrait or landscape) of device 100.

Figure 3:
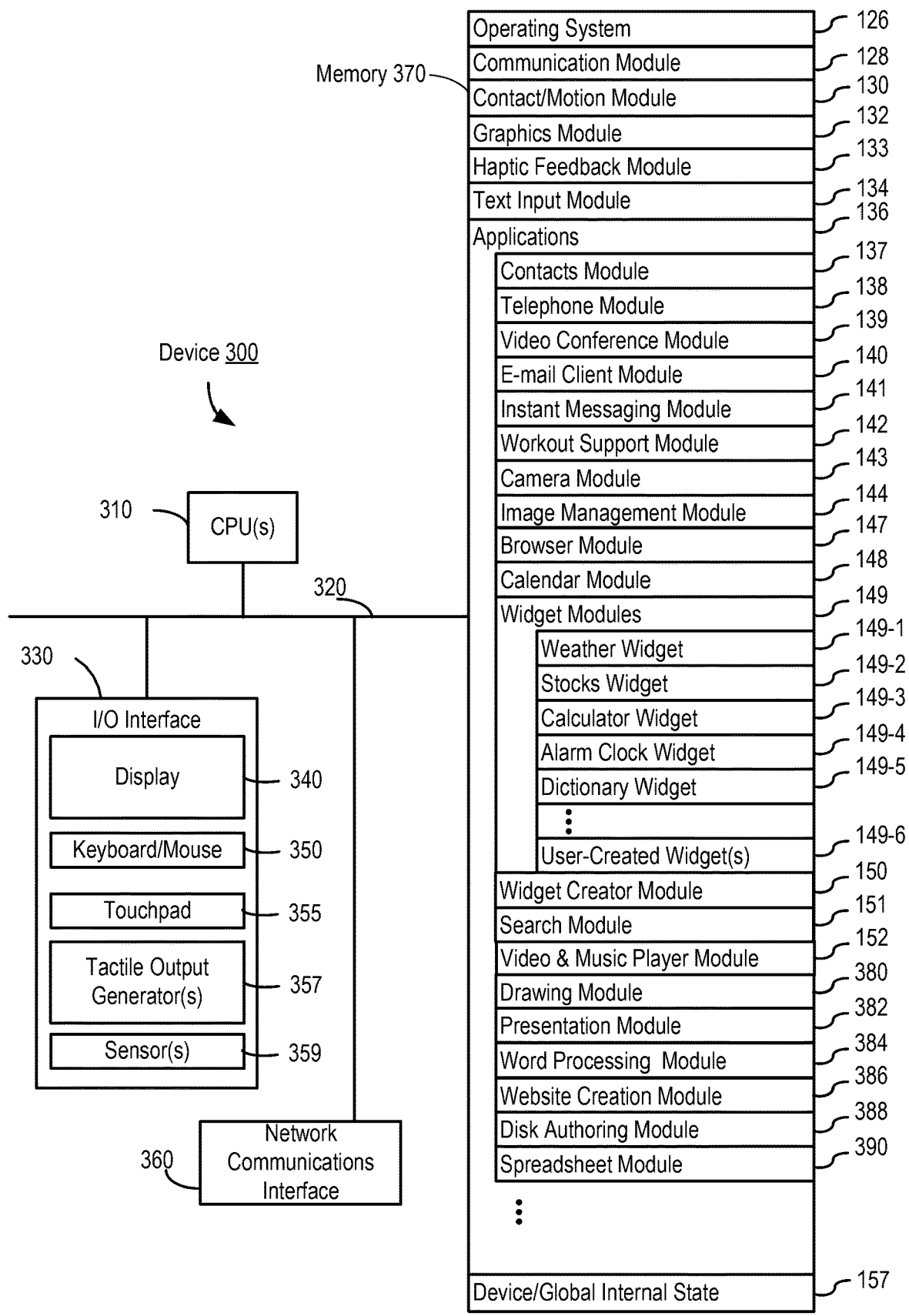
FIG. 3 is a block diagram of an exemplary multifunction device with a display and a touch-sensitive surface in accordance with some embodiments.

In some embodiments, the software components stored in memory 102 include operating system 126, communication module (or set of instructions) 128, contact/motion module (or set of instructions) 130, graphics module (or set of instructions) 132, text input module (or set of instructions) 134, Global Positioning System (GPS) module (or set of instructions) 135, and applications (or sets of instructions) 136. Furthermore, in some embodiments, memory 102 (FIG. 1A) or 370 (FIG. 3) stores device/global internal state 157, as shown in FIGS. 1A and 3. Device/global internal state 157 includes one or more of: active application state, indicating which applications, if any, are currently active; display state, indicating what applications, views or other information occupy various regions of touch screen display 112; sensor state, including information obtained from the device's various sensors and input control devices 116; and location information concerning the device's location and/or attitude.

Operating system 126 (e.g., Darwin, RTXC, LINUX, UNIX, OS X, iOS, WINDOWS, or an embedded operating system such as VxWorks) includes various software components and/or drivers for controlling and managing general system tasks (e.g., memory management, storage device control, power management, etc.) and facilitates communication between various hardware and software components.

Communication module 128 facilitates communication with other devices over one or more external ports 124 and also includes various software components for handling data received by RF circuitry 108 and/or external port 124. External port 124 (e.g., Universal Serial Bus (USB), FIREWIRE, etc.) is adapted for coupling directly to other devices or indirectly over a network (e.g., the Internet, wireless LAN, etc.). In some embodiments, the external port is a multi-pin (e.g., 30-pin) connector that is the same as, or similar to and/or compatible with, the 30-pin connector used on iPod® (trademark of Apple Inc.) devices.

Contact/motion module 130 optionally detects contact with touch screen 112 (in conjunction with display controller 156) and other touch-sensitive devices (e.g., a touchpad or physical click wheel). Contact/motion module 130 includes various software components for performing various operations related to detection of contact, such as determining if contact has occurred (e.g., detecting a finger-down event), determining an intensity of the contact (e.g., the force or pressure of the contact or a substitute for the force or pressure of the contact), determining if there is movement of the contact and tracking the movement across the touch-sensitive surface (e.g., detecting one or more finger-dragging events), and determining if the contact has ceased (e.g., detecting a finger-up event or a break in contact). Contact/motion module 130 receives contact data from the touch-sensitive surface. Determining movement of the point of contact, which is represented by a series of contact data, optionally includes determining speed (magnitude), velocity (magnitude and direction), and/or an acceleration (a change in magnitude and/or direction) of the point of contact. These operations are, optionally, applied to single contacts (e.g., one finger contacts) or to multiple simultaneous contacts (e.g., "multitouch"/multiple finger contacts). In some embodiments, contact/motion module 130 and display controller 156 detect contact on a touchpad.

In some embodiments, contact/motion module 130 uses a set of one or more intensity thresholds to determine whether an operation has been performed by a user (e.g., to determine whether a user has "clicked" on an icon). In some embodiments, at least a subset of the intensity thresholds are determined in accordance with software parameters (e.g., the intensity thresholds are not determined by the activation thresholds of particular physical actuators and can be adjusted without changing the physical hardware of device 100). For example, a mouse "click" threshold of a trackpad or touch screen display can be set to any of a large range of predefined threshold values without changing the trackpad or touch screen display hardware. Additionally, in some implementations, a user of the device is provided with software settings for adjusting one or more of the set of intensity thresholds (e.g., by adjusting individual intensity thresholds and/or by adjusting a plurality of intensity thresholds at once with a system-level click "intensity" parameter).

Contact/motion module 130 optionally detects a gesture input by a user. Different gestures on the touch-sensitive surface have different contact patterns (e.g., different motions, timings, and/or intensities of detected contacts). Thus, a gesture is, optionally, detected by detecting a particular contact pattern. For example, detecting a finger tap gesture includes detecting a finger-down event followed by detecting a finger-up (liftoff) event at the same position (or substantially the same position) as the finger-down event (e.g., at the position of an icon). As another example, detecting a finger swipe gesture on the touch-sensitive surface includes detecting a finger-down event followed by detecting one or more finger-dragging events, and subsequently followed by detecting a finger-up (liftoff) event.

Graphics module 132 includes various known software components for rendering and displaying graphics on touch screen 112 or other display, including components for changing the visual impact (e.g., brightness, transparency, saturation, contrast, or other visual property) of graphics that are displayed. As used herein, the term "graphics" includes any object that can be displayed to a user, including, without limitation, text, web pages, icons (such as user-interface objects including soft keys), digital images, videos, animations, and the like.

In some embodiments, graphics module 132 stores data representing graphics to be used. Each graphic is, optionally, assigned a corresponding code. Graphics module 132 receives, from applications etc., one or more codes specifying graphics to be displayed along with, if necessary, coordinate data and other graphic property data, and then generates screen image data to output to display controller 156.

Haptic feedback module 133 includes various software components for generating instructions used by tactile output generator(s) 167 to produce tactile outputs at one or more locations on device 100 in response to user interactions with device 100.

Text input module 134, which is, optionally, a component of graphics module 132, provides soft keyboards for entering text in various applications (e.g., contacts module 137, e-mail client module 140, IM module 141, browser module 147, and any other application that needs text input).

GPS module 135 determines the location of the device and provides this information for use in various applications (e.g., to telephone module 138 for use in location-based dialing; to camera module 143 as picture/video metadata; and to applications that provide location-based services such as weather widgets, local yellow page widgets, and map/navigation widgets).

Applications 136 optionally include the following modules (or sets of instructions), or a subset or superset thereof:
- Contacts module 137 (sometimes called an address book or contact list);
- Telephone module 138;
- Video conference module 139;
- E-mail client module 140;
- Instant messaging (IM) module 141;
- Workout support module 142;
- Camera module 143 for still and/or video images;
- Image management module 144;
- Video player module;
- Music player module;
- Browser module 147;
- Calendar module 148;
- Widget modules 149, which optionally include one or more of: weather widget 149-1, stocks widget 149-2, calculator widget 149-3, alarm clock widget 149-4, dictionary widget 149-5, and other widgets obtained by the user, as well as user-created widgets 149-6;
- Widget creator module 150 for making user-created widgets 149-6;
- Search module 151;
- Video and music player module 152, which merges video player module and music player module;
- Notes module 153;
- Map module 154; and/or
- Online video module 155.

Examples of other applications 136 that are, optionally, stored in memory 102 include other word processing applications, other image editing applications, drawing applications, presentation applications, JAVA-enabled applications, encryption, digital rights management, voice recognition, and voice replication.

In conjunction with touch screen 112, display controller 156, contact/motion module 130, graphics module 132, and text input module 134, contacts module 137 are, optionally, used to manage an address book or contact list (e.g., stored in application internal state 192 of contacts module 137 in memory 102 or memory 370), including: adding name(s) to the address book; deleting name(s) from the address book; associating telephone number(s), e-mail address(es), physical address(es) or other information with a name; associating an image with a name; categorizing and sorting names; providing telephone numbers or e-mail addresses to initiate and/or facilitate communications by telephone module 138, video conference module 139, e-mail client module 140, or IM module 141; and so forth.

In conjunction with RF circuitry 108, audio circuitry 110, speaker 111, microphone 113, touch screen 112, display controller 156, contact/motion module 130, graphics module 132, and text input module 134, telephone module 138 are optionally, used to enter a sequence of characters corresponding to a telephone number, access one or more telephone numbers in contacts module 137, modify a telephone number that has been entered, dial a respective telephone number, conduct a conversation, and disconnect or hang up when the conversation is completed. As noted above, the wireless communication optionally uses any of a plurality of communications standards, protocols, and technologies.

In conjunction with RF circuitry 108, audio circuitry 110, speaker 111, microphone 113, touch screen 112, display controller 156, optical sensor 164, optical sensor controller 158, contact/motion module 130, graphics module 132, text input module 134, contacts module 137, and telephone module 138, video conference module 139 includes executable instructions to initiate, conduct, and terminate a video conference between a user and one or more other participants in accordance with user instructions.

In conjunction with RF circuitry 108, touch screen 112, display controller 156, contact/motion module 130, graphics module 132, and text input module 134, e-mail client module 140 includes executable instructions to create, send, receive, and manage e-mail in response to user instructions. In conjunction with image management module 144, e-mail client module 140 makes it very easy to create and send e-mails with still or video images taken with camera module 143.

In conjunction with RF circuitry 108, touch screen 112, display controller 156, contact/motion module 130, graphics module 132, and text input module 134, the instant messaging module 141 includes executable instructions to enter a sequence of characters corresponding to an instant message, to modify previously entered characters, to transmit a respective instant message (for example, using a Short Message Service (SMS) or Multimedia Message Service (MMS) protocol for telephony-based instant messages or using XMPP, SIMPLE, or IMPS for Internet-based instant messages), to receive instant messages, and to view received instant messages. In some embodiments, transmitted and/or received instant messages optionally include graphics, photos, audio files, video files and/or other attachments as are supported in an MMS and/or an Enhanced Messaging Service (EMS). As used herein, "instant messaging" refers to both telephony-based messages (e.g., messages sent using SMS or MMS) and Internet-based messages (e.g., messages sent using XMPP, SIMPLE, or IMPS).

In conjunction with RF circuitry 108, touch screen 112, display controller 156, contact/motion module 130, graphics module 132, text input module 134, GPS module 135, map module 154, and music player module, workout support module 142 includes executable instructions to create workouts (e.g., with time, distance, and/or calorie burning goals); communicate with workout sensors (sports devices); receive workout sensor data; calibrate sensors used to monitor a workout; select and play music for a workout; and display, store, and transmit workout data.

In conjunction with touch screen 112, display controller 156, optical sensor(s) 164, optical sensor controller 158, contact/motion module 130, graphics module 132, and image management module 144, camera module 143 includes executable instructions to capture still images or video (including a video stream) and store them into memory 102, modify characteristics of a still image or video, or delete a still image or video from memory 102.

In conjunction with touch screen 112, display controller 156, contact/motion module 130, graphics module 132, text input module 134, and camera module 143, image management module 144 includes executable instructions to arrange, modify (e.g., edit), or otherwise manipulate, label, delete, present (e.g., in a digital slide show or album), and store still and/or video images.

In conjunction with RF circuitry 108, touch screen 112, display controller 156, contact/motion module 130, graphics module 132, and text input module 134, browser module 147 includes executable instructions to browse the Internet in accordance with user instructions, including searching, linking to, receiving, and displaying web pages or portions thereof, as well as attachments and other files linked to web pages.

In conjunction with RF circuitry 108, touch screen 112, display controller 156, contact/motion module 130, graphics module 132, text input module 134, e-mail client module 140, and browser module 147, calendar module 148 includes executable instructions to create, display, modify, and store calendars and data associated with calendars (e.g., calendar entries, to-do lists, etc.) in accordance with user instructions.

In conjunction with RF circuitry 108, touch screen 112, display controller 156, contact/motion module 130, graphics module 132, text input module 134, and browser module 147, widget modules 149 are mini-applications that are, optionally, downloaded and used by a user (e.g., weather widget 149-1, stocks widget 149-2, calculator widget 149-3, alarm clock widget 149-4, and dictionary widget 149-5) or created by the user (e.g., user-created widget 149-6). In some embodiments, a widget includes an HTML (Hypertext Markup Language) file, a CSS (Cascading Style Sheets) file, and a JavaScript file. In some embodiments, a widget includes an XML (Extensible Markup Language) file and a JavaScript file (e.g., Yahoo! Widgets).

In conjunction with RF circuitry 108, touch screen 112, display controller 156, contact/motion module 130, graphics module 132, text input module 134, and browser module 147, the widget creator module 150 are, optionally, used by a user to create widgets (e.g., turning a user-specified portion of a web page into a widget).

In conjunction with touch screen 112, display controller 156, contact/motion module 130, graphics module 132, and text input module 134, search module 151 includes executable instructions to search for text, music, sound, image, video, and/or other files in memory 102 that match one or more search criteria (e.g., one or more user-specified search terms) in accordance with user instructions.

In conjunction with touch screen 112, display controller 156, contact/motion module 130, graphics module 132, audio circuitry 110, speaker 111, RF circuitry 108, and browser module 147, video and music player module 152 includes executable instructions that allow the user to download and play back recorded music and other sound files stored in one or more file formats, such as MP3 or AAC files, and executable instructions to display, present, or otherwise play back videos (e.g., on touch screen 112 or on an external, connected display via external port 124). In some embodiments, device 100 optionally includes the functionality of an MP3 player, such as an iPod (trademark of Apple Inc.).

In conjunction with touch screen 112, display controller 156, contact/motion module 130, graphics module 132, and text input module 134, notes module 153 includes executable instructions to create and manage notes, to-do lists, and the like in accordance with user instructions.

In conjunction with RF circuitry 108, touch screen 112, display controller 156, contact/motion module 130, graphics module 132, text input module 134, GPS module 135, and browser module 147, map module 154 are, optionally, used to receive, display, modify, and store maps and data associated with maps (e.g., driving directions, data on stores and other points of interest at or near a particular location, and other location-based data) in accordance with user instructions.

In conjunction with touch screen 112, display controller 156, contact/motion module 130, graphics module 132, audio circuitry 110, speaker 111, RF circuitry 108, text input module 134, e-mail client module 140, and browser module 147, online video module 155 includes instructions that allow the user to access, browse, receive (e.g., by streaming and/or download), play back (e.g., on the touch screen or on an external, connected display via external port 124), send an e-mail with a link to a particular online video, and otherwise manage online videos in one or more file formats, such as H.264. In some embodiments, instant messaging module 141, rather than e-mail client module 140, is used to send a link to a particular online video. Additional description of the online video application can be found in U.S. Provisional Patent Application No. 60/936,562, "Portable Multifunction Device, Method, and Graphical User Interface for Playing Online Videos," filed Jun. 20, 2007, and U.S. patent application Ser. No. 11/968,067, "Portable Multifunction Device, Method, and Graphical User Interface for Playing Online Videos," filed Dec. 31, 2007, the contents of which are hereby incorporated by reference in their entirety.

Each of the above-identified modules and applications corresponds to a set of executable instructions for performing one or more functions described above and the methods described in this application (e.g., the computer-implemented methods and other information processing methods described herein). These modules (e.g., sets of instructions) need not be implemented as separate software programs (such as computer programs (e.g., including instructions)), procedures, or modules, and thus various subsets of these modules are, optionally, combined or otherwise rearranged in various embodiments. For example, video player module is, optionally, combined with music player module into a single module (e.g., video and music player module 152, FIG. 1A). In some embodiments, memory 102 optionally stores a subset of the modules and data structures identified above. Furthermore, memory 102 optionally stores additional modules and data structures not described above.

In some embodiments, device 100 is a device where operation of a predefined set of functions on the device is performed exclusively through a touch screen and/or a touchpad. By using a touch screen and/or a touchpad as the primary input control device for operation of device 100, the number of physical input control devices (such as push buttons, dials, and the like) on device 100 is, optionally, reduced.

The predefined set of functions that are performed exclusively through a touch screen and/or a touchpad optionally include navigation between user interfaces. In some embodiments, the touchpad, when touched by the user, navigates device 100 to a main, home, or root menu from any user interface that is displayed on device 100. In such embodiments, a "menu button" is implemented using a touchpad. In some other embodiments, the menu button is a physical push button or other physical input control device instead of a touchpad.

Figure 1B:
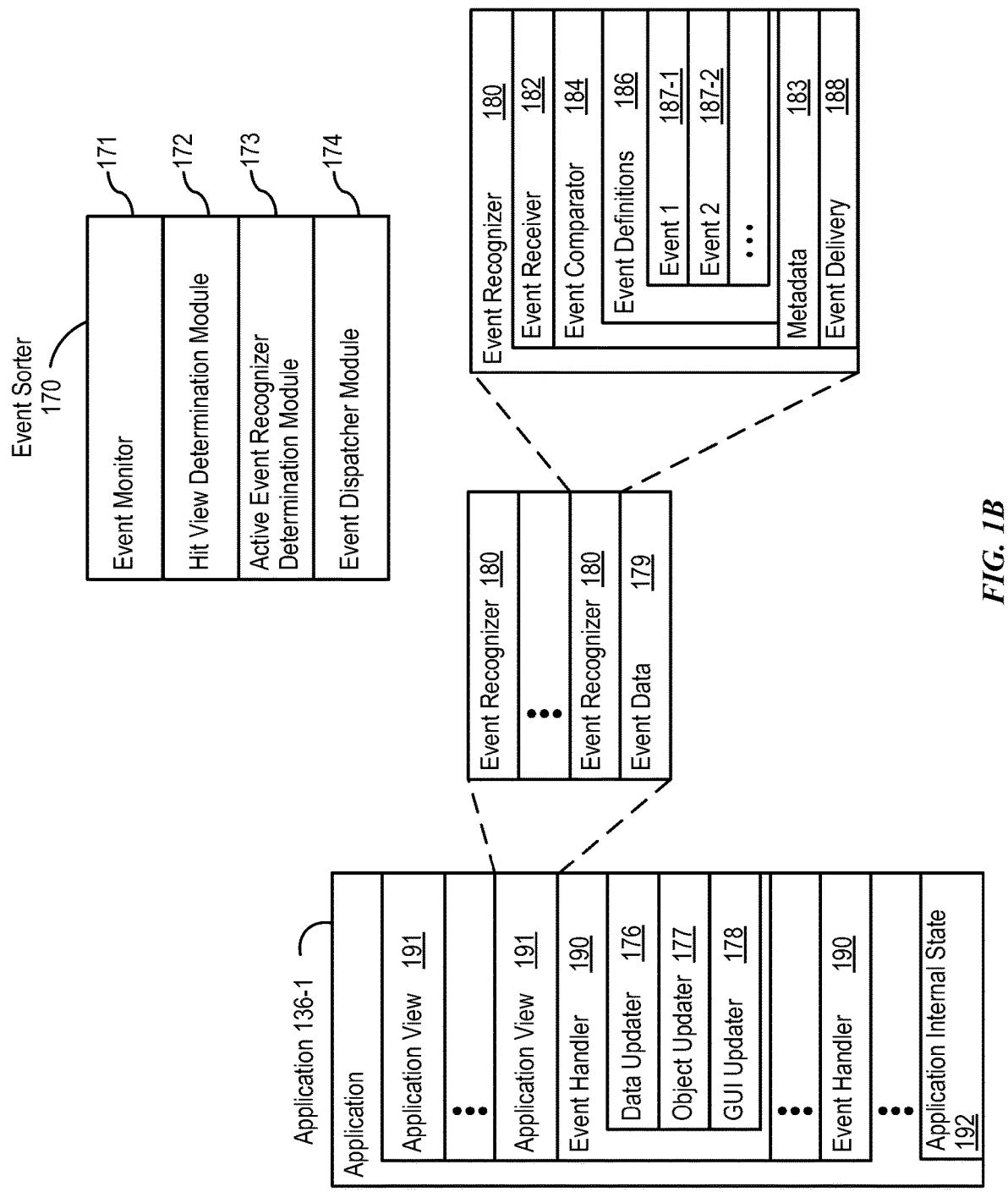
FIG. 1B is a block diagram illustrating exemplary components for event handling in accordance with some embodiments.

FIG. 1B is a block diagram illustrating exemplary components for event handling in accordance with some embodiments. In some embodiments, memory 102 (FIG. 1A) or 370 (FIG. 3) includes event sorter 170 (e.g., in operating system 126) and a respective application 136-1 (e.g., any of the aforementioned applications 137-151, 155, 380-390).

Event sorter 170 receives event information and determines the application 136-1 and application view 191 of application 136-1 to which to deliver the event information. Event sorter 170 includes event monitor 171 and event dispatcher module 174. In some embodiments, application 136-1 includes application internal state 192, which indicates the current application view(s) displayed on touch-sensitive display 112 when the application is active or executing. In some embodiments, device/global internal state 157 is used by event sorter 170 to determine which application(s) is (are) currently active, and application internal state 192 is used by event sorter 170 to determine application views 191 to which to deliver event information.

In some embodiments, application internal state 192 includes additional information, such as one or more of: resume information to be used when application 136-1 resumes execution, user interface state information that indicates information being displayed or that is ready for display by application 136-1, a state queue for enabling the user to go back to a prior state or view of application 136-1, and a redo/undo queue of previous actions taken by the user.

Event monitor 171 receives event information from peripherals interface 118. Event information includes information about a sub-event (e.g., a user touch on touch-sensitive display 112, as part of a multi-touch gesture). Peripherals interface 118 transmits information it receives from I/O subsystem 106 or a sensor, such as proximity sensor 166, accelerometer(s) 168, and/or microphone 113 (through audio circuitry 110). Information that peripherals interface 118 receives from I/O subsystem 106 includes information from touch-sensitive display 112 or a touch-sensitive surface.

In some embodiments, event monitor 171 sends requests to the peripherals interface 118 at predetermined intervals. In response, peripherals interface 118 transmits event information. In other embodiments, peripherals interface 118 transmits event information only when there is a significant event (e.g., receiving an input above a predetermined noise threshold and/or for more than a predetermined duration).

In some embodiments, event sorter 170 also includes a hit view determination module 172 and/or an active event recognizer determination module 173.

Hit view determination module 172 provides software procedures for determining where a sub-event has taken place within one or more views when touch-sensitive display 112 displays more than one view. Views are made up of controls and other elements that a user can see on the display.

Another aspect of the user interface associated with an application is a set of views, sometimes herein called application views or user interface windows, in which information is displayed and touch-based gestures occur. The application views (of a respective application) in which a touch is detected optionally correspond to programmatic levels within a programmatic or view hierarchy of the application. For example, the lowest level view in which a touch is detected is, optionally, called the hit view, and the set of events that are recognized as proper inputs are, optionally, determined based, at least in part, on the hit view of the initial touch that begins a touch-based gesture.

Hit view determination module 172 receives information related to sub-events of a touch-based gesture. When an application has multiple views organized in a hierarchy, hit view determination module 172 identifies a hit view as the lowest view in the hierarchy which should handle the sub-event. In most circumstances, the hit view is the lowest level view in which an initiating sub-event occurs (e.g., the first sub-event in the sequence of sub-events that form an event or potential event). Once the hit view is identified by the hit view determination module 172, the hit view typically receives all sub-events related to the same touch or input source for which it was identified as the hit view.

Active event recognizer determination module 173 determines which view or views within a view hierarchy should receive a particular sequence of sub-events. In some embodiments, active event recognizer determination module 173 determines that only the hit view should receive a particular sequence of sub-events. In other embodiments, active event recognizer determination module 173 determines that all views that include the physical location of a sub-event are actively involved views, and therefore determines that all actively involved views should receive a particular sequence of sub-events. In other embodiments, even if touch sub-events were entirely confined to the area associated with one particular view, views higher in the hierarchy would still remain as actively involved views.

Event dispatcher module 174 dispatches the event information to an event recognizer (e.g., event recognizer 180). In embodiments including active event recognizer determination module 173, event dispatcher module 174 delivers the event information to an event recognizer determined by active event recognizer determination module 173. In some embodiments, event dispatcher module 174 stores in an event queue the event information, which is retrieved by a respective event receiver 182.

In some embodiments, operating system 126 includes event sorter 170. Alternatively, application 136-1 includes event sorter 170. In yet other embodiments, event sorter 170 is a stand-alone module, or a part of another module stored in memory 102, such as contact/motion module 130.

In some embodiments, application 136-1 includes a plurality of event handlers 190 and one or more application views 191, each of which includes instructions for handling touch events that occur within a respective view of the application's user interface. Each application view 191 of the application 136-1 includes one or more event recognizers 180. Typically, a respective application view 191 includes a plurality of event recognizers 180. In other embodiments, one or more of event recognizers 180 are part of a separate module, such as a user interface kit or a higher level object from which application 136-1 inherits methods and other properties. In some embodiments, a respective event handler 190 includes one or more of: data updater 176, object updater 177, GUI updater 178, and/or event data 179 received from event sorter 170. Event handler 190 optionally utilizes or calls data updater 176, object updater 177, or GUI updater 178 to update the application internal state 192. Alternatively, one or more of the application views 191 include one or more respective event handlers 190. Also, in some embodiments, one or more of data updater 176, object updater 177, and GUI updater 178 are included in a respective application view 191.

A respective event recognizer 180 receives event information (e.g., event data 179) from event sorter 170 and identifies an event from the event information. Event recognizer 180 includes event receiver 182 and event comparator 184. In some embodiments, event recognizer 180 also includes at least a subset of: metadata 183, and event delivery instructions 188 (which optionally include sub-event delivery instructions).

Event receiver 182 receives event information from event sorter 170. The event information includes information about a sub-event, for example, a touch or a touch movement. Depending on the sub-event, the event information also includes additional information, such as location of the sub-event. When the sub-event concerns motion of a touch, the event information optionally also includes speed and direction of the sub-event. In some embodiments, events include rotation of the device from one orientation to another (e.g., from a portrait orientation to a landscape orientation, or vice versa), and the event information includes corresponding information about the current orientation (also called device attitude) of the device.

Event comparator 184 compares the event information to predefined event or sub-event definitions and, based on the comparison, determines an event or sub-event, or determines or updates the state of an event or sub-event. In some embodiments, event comparator 184 includes event definitions 186. Event definitions 186 contain definitions of events (e.g., predefined sequences of sub-events), for example, event 1 (187-1), event 2 (187-2), and others. In some embodiments, sub-events in an event (e.g., 187-1 and/or 187-2) include, for example, touch begin, touch end, touch movement, touch cancellation, and multiple touching. In one example, the definition for event 1 (187-1) is a double tap on a displayed object. The double tap, for example, comprises a first touch (touch begin) on the displayed object for a predetermined phase, a first liftoff (touch end) for a predetermined phase, a second touch (touch begin) on the displayed object for a predetermined phase, and a second liftoff (touch end) for a predetermined phase. In another example, the definition for event 2 (187-2) is a dragging on a displayed object. The dragging, for example, comprises a touch (or contact) on the displayed object for a predetermined phase, a movement of the touch across touch-sensitive display 112, and liftoff of the touch (touch end). In some embodiments, the event also includes information for one or more associated event handlers 190.

In some embodiments, event definitions 186 include a definition of an event for a respective user-interface object. In some embodiments, event comparator 184 performs a hit test to determine which user-interface object is associated with a sub-event. For example, in an application view in which three user-interface objects are displayed on touch-sensitive display 112, when a touch is detected on touch-sensitive display 112, event comparator 184 performs a hit test to determine which of the three user-interface objects is associated with the touch (sub-event). If each displayed object is associated with a respective event handler 190, the event comparator uses the result of the hit test to determine which event handler 190 should be activated. For example, event comparator 184 selects an event handler associated with the sub-event and the object triggering the hit test.

In some embodiments, the definition for a respective event (187) also includes delayed actions that delay delivery of the event information until after it has been determined whether the sequence of sub-events does or does not correspond to the event recognizer's event type.

When a respective event recognizer 180 determines that the series of sub-events do not match any of the events in event definitions 186, the respective event recognizer 180 enters an event impossible, event failed, or event ended state, after which it disregards subsequent sub-events of the touch-based gesture. In this situation, other event recognizers, if any, that remain active for the hit view continue to track and process sub-events of an ongoing touch-based gesture.

In some embodiments, a respective event recognizer 180 includes metadata 183 with configurable properties, flags, and/or lists that indicate how the event delivery system should perform sub-event delivery to actively involved event recognizers. In some embodiments, metadata 183 includes configurable properties, flags, and/or lists that indicate how event recognizers interact, or are enabled to interact, with one another. In some embodiments, metadata 183 includes configurable properties, flags, and/or lists that indicate whether sub-events are delivered to varying levels in the view or programmatic hierarchy.

In some embodiments, a respective event recognizer 180 activates event handler 190 associated with an event when one or more particular sub-events of an event are recognized. In some embodiments, a respective event recognizer 180 delivers event information associated with the event to event handler 190. Activating an event handler 190 is distinct from sending (and deferred sending) sub-events to a respective hit view. In some embodiments, event recognizer 180 throws a flag associated with the recognized event, and event handler 190 associated with the flag catches the flag and performs a predefined process.

In some embodiments, event delivery instructions 188 include sub-event delivery instructions that deliver event information about a sub-event without activating an event handler. Instead, the sub-event delivery instructions deliver event information to event handlers associated with the series of sub-events or to actively involved views. Event handlers associated with the series of sub-events or with actively involved views receive the event information and perform a predetermined process.

In some embodiments, data updater 176 creates and updates data used in application 136-1. For example, data updater 176 updates the telephone number used in contacts module 137, or stores a video file used in video player module. In some embodiments, object updater 177 creates and updates objects used in application 136-1. For example, object updater 177 creates a new user-interface object or updates the position of a user-interface object. GUI updater 178 updates the GUI. For example, GUI updater 178 prepares display information and sends it to graphics module 132 for display on a touch-sensitive display.

In some embodiments, event handler(s) 190 includes or has access to data updater 176, object updater 177, and GUI updater 178. In some embodiments, data updater 176, object updater 177, and GUI updater 178 are included in a single module of a respective application 136-1 or application view 191. In other embodiments, they are included in two or more software modules.

It shall be understood that the foregoing discussion regarding event handling of user touches on touch-sensitive displays also applies to other forms of user inputs to operate multifunction devices 100 with input devices, not all of which are initiated on touch screens. For example, mouse movement and mouse button presses, optionally coordinated with single or multiple keyboard presses or holds; contact movements such as taps, drags, scrolls, etc. on touchpads; pen stylus inputs; movement of the device; oral instructions; detected eye movements; biometric inputs; and/or any combination thereof are optionally utilized as inputs corresponding to sub-events which define an event to be recognized.

Figure 2:
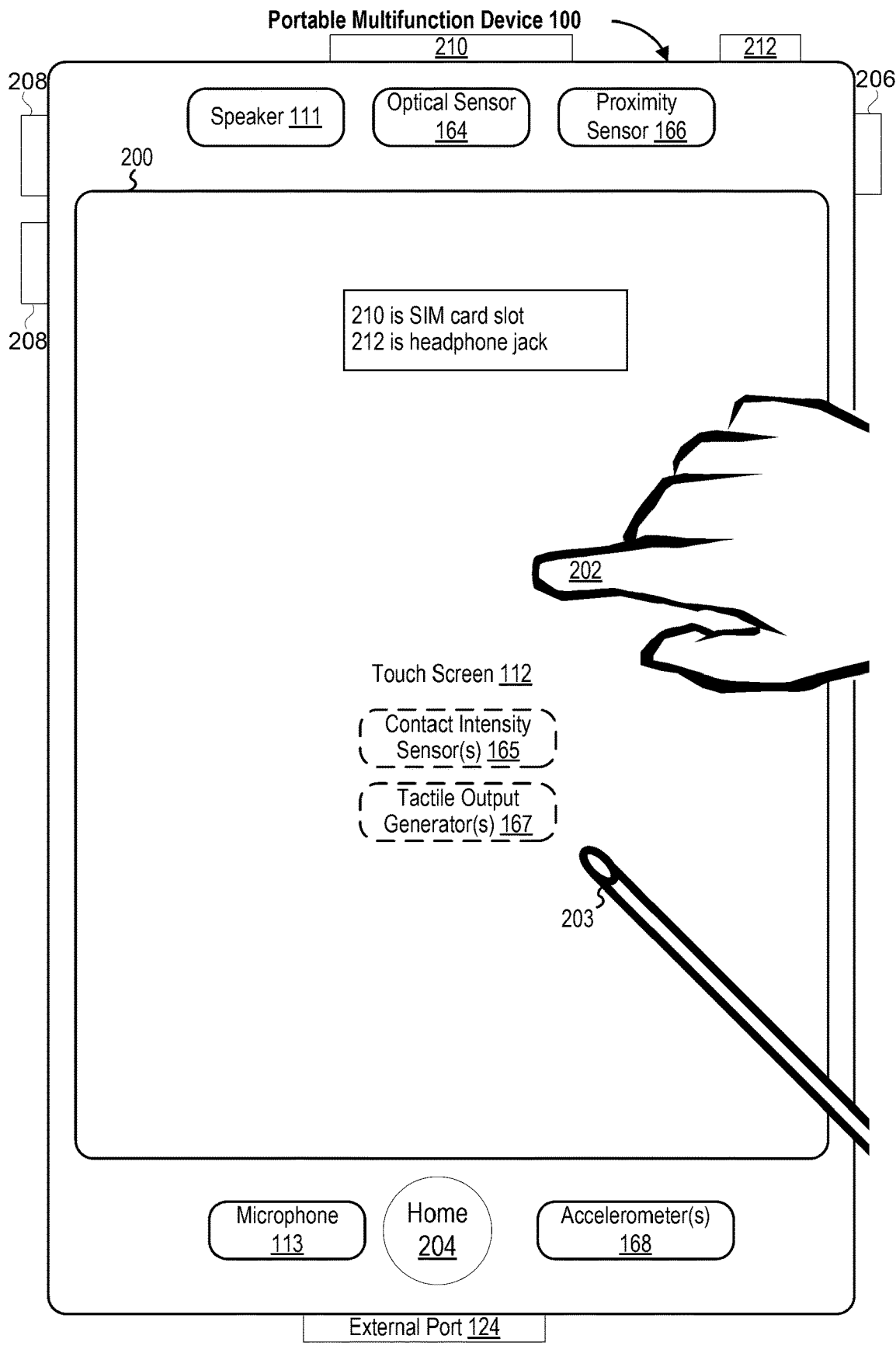
FIG. 2 illustrates a portable multifunction device having a touch screen in accordance with some embodiments.

FIG. 2 illustrates a portable multifunction device 100 having a touch screen 112 in accordance with some embodiments. The touch screen optionally displays one or more graphics within user interface (UI) 200. In this embodiment, as well as others described below, a user is enabled to select one or more of the graphics by making a gesture on the graphics, for example, with one or more fingers 202 (not drawn to scale in the figure) or one or more styluses 203 (not drawn to scale in the figure). In some embodiments, selection of one or more graphics occurs when the user breaks contact with the one or more graphics. In some embodiments, the gesture optionally includes one or more taps, one or more swipes (from left to right, right to left, upward and/or downward), and/or a rolling of a finger (from right to left, left to right, upward and/or downward) that has made contact with device 100. In some implementations or circumstances, inadvertent contact with a graphic does not select the graphic. For example, a swipe gesture that sweeps over an application icon optionally does not select the corresponding application when the gesture corresponding to selection is a tap.

Device 100 optionally also include one or more physical buttons, such as "home" or menu button 204. As described previously, menu button 204 is, optionally, used to navigate to any application 136 in a set of applications that are, optionally, executed on device 100. Alternatively, in some embodiments, the menu button is implemented as a soft key in a GUI displayed on touch screen 112.

In some embodiments, device 100 includes touch screen 112, menu button 204, push button 206 for powering the device on/off and locking the device, volume adjustment button(s) 208, subscriber identity module (SIM) card slot 210, headset jack 212, and docking/charging external port 124. Push button 206 is, optionally, used to turn the power on/off on the device by depressing the button and holding the button in the depressed state for a predefined time interval; to lock the device by depressing the button and releasing the button before the predefined time interval has elapsed; and/or to unlock the device or initiate an unlock process. In an alternative embodiment, device 100 also accepts verbal input for activation or deactivation of some functions through microphone 113. Device 100 also, optionally, includes one or more contact intensity sensors 165 for detecting intensity of contacts on touch screen 112 and/or one or more tactile output generators 167 for generating tactile outputs for a user of device 100.

FIG. 3 is a block diagram of an exemplary multifunction device with a display and a touch-sensitive surface in accordance with some embodiments. Device 300 need not be portable. In some embodiments, device 300 is a laptop computer, a desktop computer, a tablet computer, a multimedia player device, a navigation device, an educational device (such as a child's learning toy), a gaming system, or a control device (e.g., a home or industrial controller). Device 300 typically includes one or more processing units (CPUs) 310, one or more network or other communications interfaces 360, memory 370, and one or more communication buses 320 for interconnecting these components. Communication buses 320 optionally include circuitry (sometimes called a chipset) that interconnects and controls communications between system components. Device 300 includes input/output (I/O) interface 330 comprising display 340, which is typically a touch screen display. I/O interface 330 also optionally includes a keyboard and/or mouse (or other pointing device) 350 and touchpad 355, tactile output generator 357 for generating tactile outputs on device 300 (e.g., similar to tactile output generator(s) 167 described above with reference to FIG. 1A), sensors 359 (e.g., optical, acceleration, proximity, touch-sensitive, and/or contact intensity sensors similar to contact intensity sensor(s) 165 described above with reference to FIG. 1A). Memory 370 includes high-speed random access memory, such as DRAM, SRAM, DDR RAM, or other random access solid state memory devices; and optionally includes non-volatile memory, such as one or more magnetic disk storage devices, optical disk storage devices, flash memory devices, or other non-volatile solid state storage devices. Memory 370 optionally includes one or more storage devices remotely located from CPU(s) 310. In some embodiments, memory 370 stores programs, modules, and data structures analogous to the programs, modules, and data structures stored in memory 102 of portable multifunction device 100 (FIG. 1A), or a subset thereof. Furthermore, memory 370 optionally stores additional programs, modules, and data structures not present in memory 102 of portable multifunction device 100. For example, memory 370 of device 300 optionally stores drawing module 380, presentation module 382, word processing module 384, website creation module 386, disk authoring module 388, and/or spreadsheet module 390, while memory 102 of portable multifunction device 100 (FIG. 1A) optionally does not store these modules.

Each of the above-identified elements in FIG. 3 is, optionally, stored in one or more of the previously mentioned memory devices. Each of the above-identified modules corresponds to a set of instructions for performing a function described above. The above-identified modules or computer programs (e.g., sets of instructions or including instructions) need not be implemented as separate software programs (such as computer programs (e.g., including instructions)), procedures, or modules, and thus various subsets of these modules are, optionally, combined or otherwise rearranged in various embodiments. In some embodiments, memory 370 optionally stores a subset of the modules and data structures identified above. Furthermore, memory 370 optionally stores additional modules and data structures not described above.

Attention is now directed towards embodiments of user interfaces that are, optionally, implemented on, for example, portable multifunction device 100.

Figure 4A:
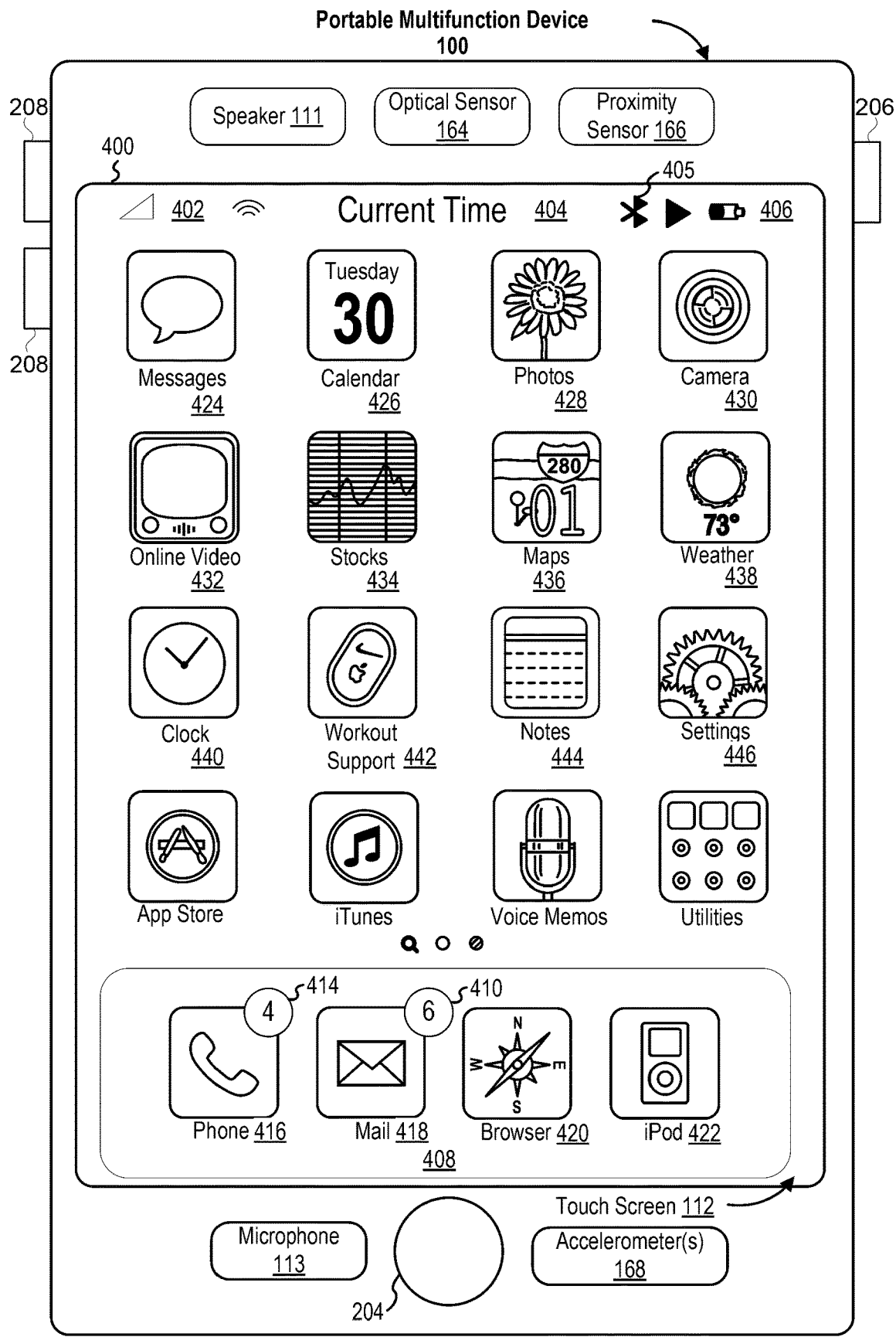
FIG. 4A illustrates an exemplary user interface for a menu of applications on a portable multifunction device in accordance with some embodiments.

FIG. 4A illustrates an exemplary user interface for a menu of applications on portable multifunction device 100 in accordance with some embodiments. Similar user interfaces are, optionally, implemented on device 300. In some embodiments, user interface 400 includes the following elements, or a subset or superset thereof:

Signal strength indicator(s) 402 for wireless communication(s), such as cellular and Wi-Fi signals;

Time 404;

Bluetooth indicator 405;

Battery status indicator 406;

Tray 408 with icons for frequently used applications, such as:

Icon 416 for telephone module 138, labeled "Phone," which optionally includes an indicator 414 of the number of missed calls or voicemail messages;

Icon 418 for e-mail client module 140, labeled "Mail," which optionally includes an indicator 410 of the number of unread e-mails;

Icon 420 for browser module 147, labeled "Browser;" and

Icon 422 for video and music player module 152, also referred to as iPod (trademark of Apple Inc.) module 152, labeled "iPod;" and Icons for other applications, such as:
- Icon 424 for IM module 141, labeled "Messages;"
- Icon 426 for calendar module 148, labeled "Calendar;"
- Icon 428 for image management module 144, labeled "Photos;"
- Icon 430 for camera module 143, labeled "Camera;"
- Icon 432 for online video module 155, labeled "Online Video;"
- Icon 434 for stocks widget 149-2, labeled "Stocks;"
- Icon 436 for map module 154, labeled "Maps;"
- Icon 438 for weather widget 149-1, labeled "Weather;"
- Icon 440 for alarm clock widget 149-4, labeled "Clock;"
- Icon 442 for workout support module 142, labeled "Workout Support;"
- Icon 444 for notes module 153, labeled "Notes;" and
- Icon 446 for a settings application or module, labeled "Settings," which provides access to settings for device 100 and its various applications 136.

It should be noted that the icon labels illustrated in FIG. 4A are merely exemplary. For example, icon 422 for video and music player module 152 is labeled "Music" or "Music Player." Other labels are, optionally, used for various application icons. In some embodiments, a label for a respective application icon includes a name of an application corresponding to the respective application icon. In some embodiments, a label for a particular application icon is distinct from a name of an application corresponding to the particular application icon.

Figure 4B:
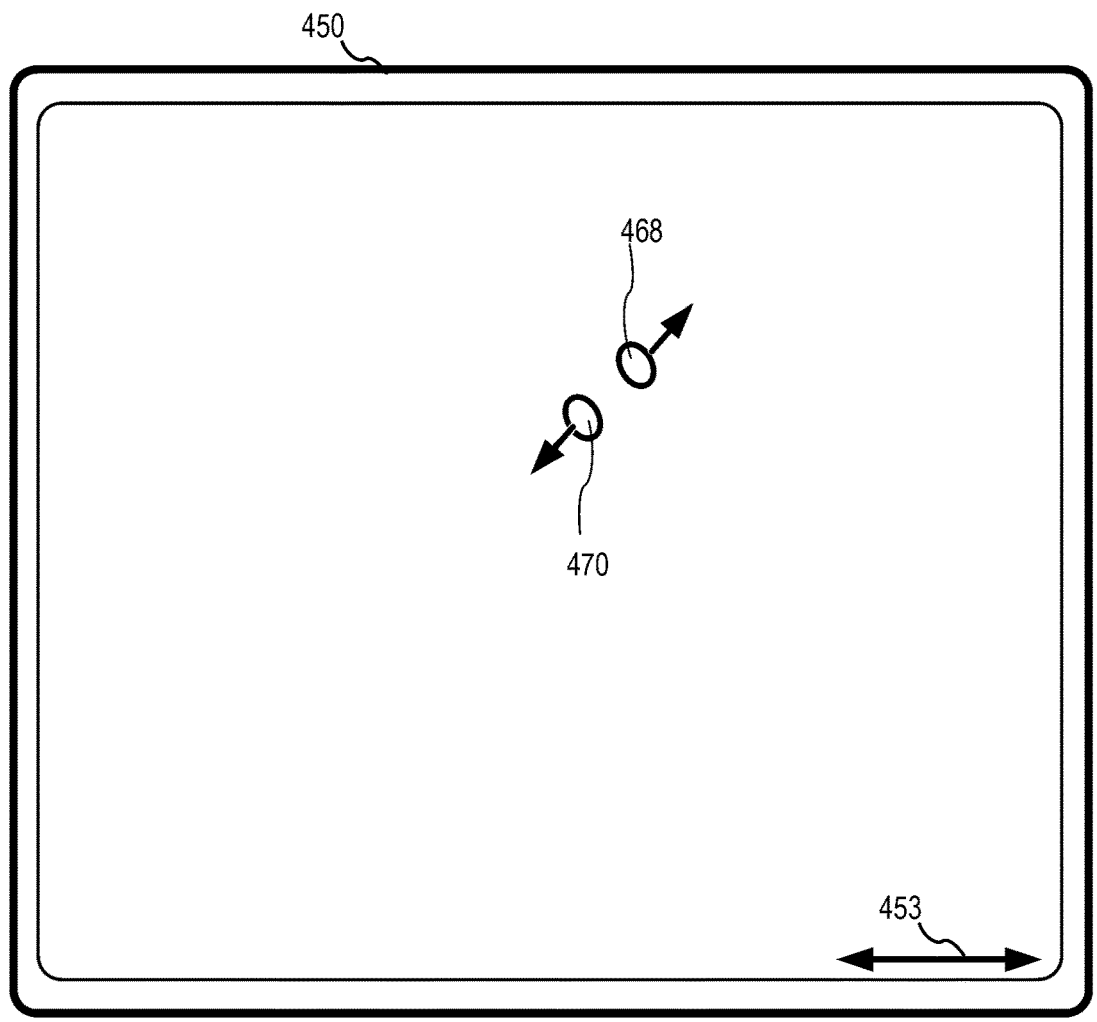
FIG. 4B illustrates an exemplary user interface for a multifunction device with a touch-sensitive surface that is separate from the display in accordance with some embodiments.
Figure 4B:
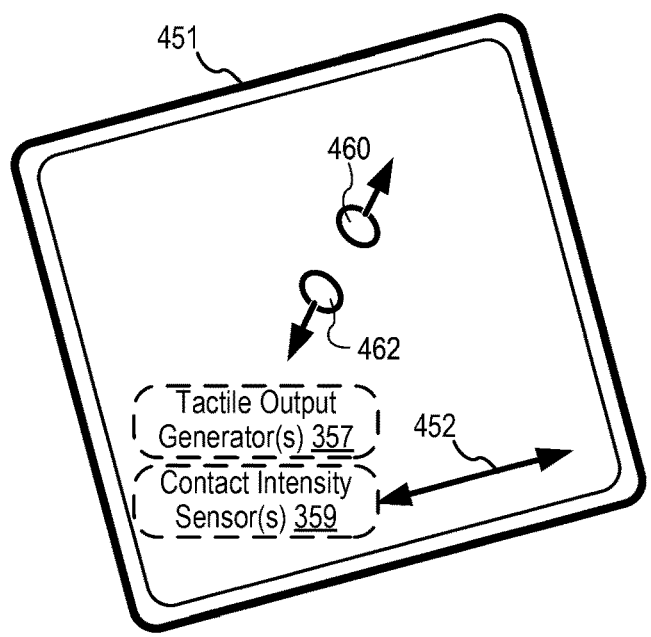

FIG. 4B illustrates an exemplary user interface on a device (e.g., device 300, FIG. 3) with a touch-sensitive surface 451 (e.g., a tablet or touchpad 355, FIG. 3) that is separate from the display 450 (e.g., touch screen display 112). Device 300 also, optionally, includes one or more contact intensity sensors (e.g., one or more of sensors 359) for detecting intensity of contacts on touch-sensitive surface 451 and/or one or more tactile output generators 357 for generating tactile outputs for a user of device 300.

Although some of the examples that follow will be given with reference to inputs on touch screen display 112 (where the touch-sensitive surface and the display are combined), in some embodiments, the device detects inputs on a touch-sensitive surface that is separate from the display, as shown in FIG. 4B. In some embodiments, the touch-sensitive surface (e.g., 451 in FIG. 4B) has a primary axis (e.g., 452 in FIG. 4B) that corresponds to a primary axis (e.g., 453 in FIG. 4B) on the display (e.g., 450). In accordance with these embodiments, the device detects contacts (e.g., 460 and 462 in FIG. 4B) with the touch-sensitive surface 451 at locations that correspond to respective locations on the display (e.g., in FIG. 4B, 460 corresponds to 468 and 462 corresponds to 470). In this way, user inputs (e.g., contacts 460 and 462, and movements thereof) detected by the device on the touch-sensitive surface (e.g., 451 in FIG. 4B) are used by the device to manipulate the user interface on the display (e.g., 450 in FIG. 4B) of the multifunction device when the touch-sensitive surface is separate from the display. It should be understood that similar methods are, optionally, used for other user interfaces described herein.

Additionally, while the following examples are given primarily with reference to finger inputs (e.g., finger contacts, finger tap gestures, finger swipe gestures), it should be understood that, in some embodiments, one or more of the finger inputs are replaced with input from another input device (e.g., a mouse-based input or stylus input). For example, a swipe gesture is, optionally, replaced with a mouse click (e.g., instead of a contact) followed by movement of the cursor along the path of the swipe (e.g., instead of movement of the contact). As another example, a tap gesture is, optionally, replaced with a mouse click while the cursor is located over the location of the tap gesture (e.g., instead of detection of the contact followed by ceasing to detect the contact). Similarly, when multiple user inputs are simultaneously detected, it should be understood that multiple computer mice are, optionally, used simultaneously, or a mouse and finger contacts are, optionally, used simultaneously.

Figure 5A:
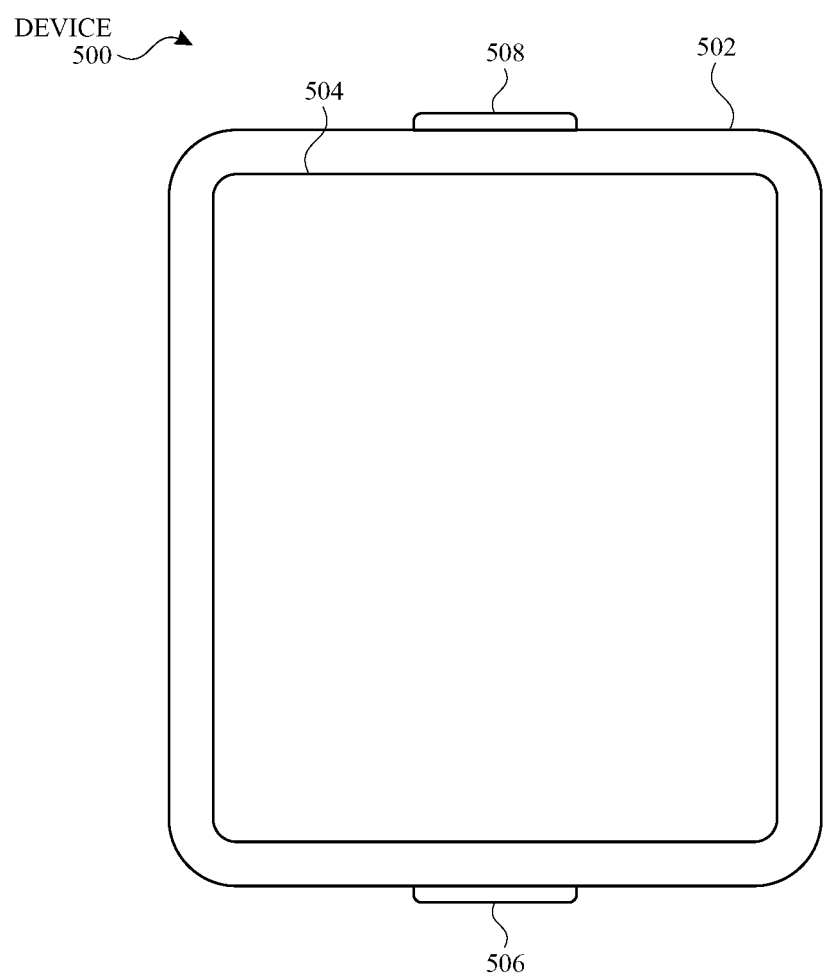
FIG. 5A illustrates a personal electronic device in accordance with some embodiments.

FIG. 5A illustrates exemplary personal electronic device 500. Device 500 includes body 502. In some embodiments, device 500 can include some or all of the features described with respect to devices 100 and 300 (e.g., FIGS. 1A-4B). In some embodiments, device 500 has touch-sensitive display screen 504, hereafter touch screen 504. Alternatively, or in addition to touch screen 504, device 500 has a display and a touch-sensitive surface. As with devices 100 and 300, in some embodiments, touch screen 504 (or the touch-sensitive surface) optionally includes one or more intensity sensors for detecting intensity of contacts (e.g., touches) being applied. The one or more intensity sensors of touch screen 504 (or the touch-sensitive surface) can provide output data that represents the intensity of touches. The user interface of device 500 can respond to touches based on their intensity, meaning that touches of different intensities can invoke different user interface operations on device 500.

Exemplary techniques for detecting and processing touch intensity are found, for example, in related applications: International Patent Application Serial No. PCT/US2013/040061, titled "Device, Method, and Graphical User Interface for Displaying User Interface Objects Corresponding to an Application," filed May 8, 2013, published as WIPO Publication No. WO/2013/169849, and International Patent Application Serial No. PCT/US2013/069483, titled "Device, Method, and Graphical User Interface for Transitioning Between Touch Input to Display Output Relationships," filed Nov. 11, 2013, published as WIPO Publication No. WO/2014/105276, each of which is hereby incorporated by reference in their entirety.

In some embodiments, device 500 has one or more input mechanisms 506 and 508. Input mechanisms 506 and 508, if included, can be physical. Examples of physical input mechanisms include push buttons and rotatable mechanisms. In some embodiments, device 500 has one or more attachment mechanisms. Such attachment mechanisms, if included, can permit attachment of device 500 with, for example, hats, eyewear, earrings, necklaces, shirts, jackets, bracelets, watch straps, chains, trousers, belts, shoes, purses, backpacks, and so forth. These attachment mechanisms permit device 500 to be worn by a user.

Figure 5B:
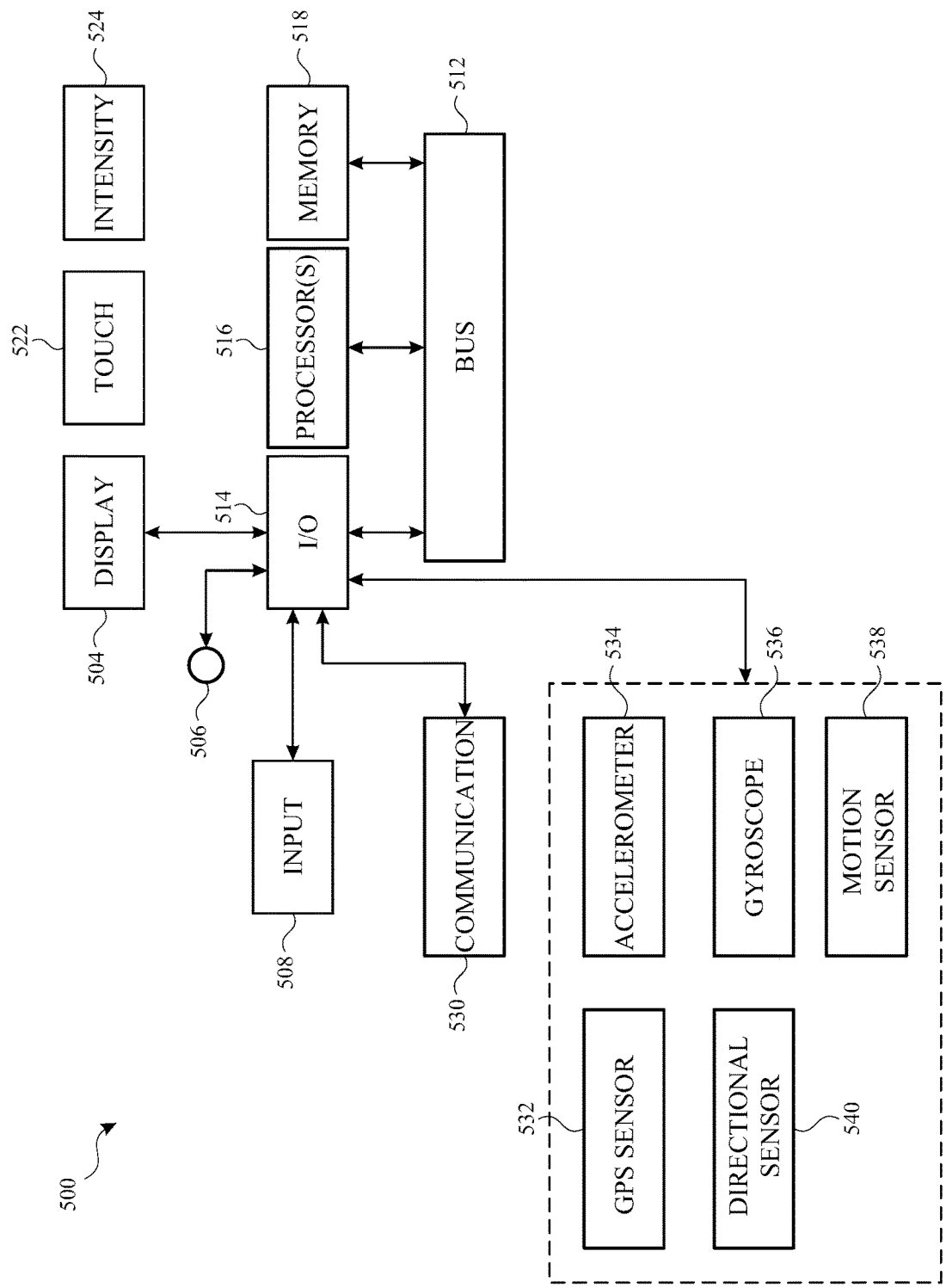
FIG. 5B is a block diagram illustrating a personal electronic device in accordance with some embodiments.

FIG. 5B depicts exemplary personal electronic device 500. In some embodiments, device 500 can include some or all of the components described with respect to FIGS. 1A, 1B, and 3. Device 500 has bus 512 that operatively couples I/O section 514 with one or more computer processors 516 and memory 518. I/O section 514 can be connected to display 504, which can have touch-sensitive component 522 and, optionally, intensity sensor 524 (e.g., contact intensity sensor). In addition, I/O section 514 can be connected with communication unit 530 for receiving application and operating system data, using Wi-Fi, Bluetooth, near field communication (NFC), cellular, and/or other wireless communication techniques. Device 500 can include input mechanisms 506 and/or 508. Input mechanism 506 is, optionally, a rotatable input device or a depressible and rotatable input device, for example. Input mechanism 508 is, optionally, a button, in some examples.

Input mechanism 508 is, optionally, a microphone, in some examples. Personal electronic device 500 optionally includes various sensors, such as GPS sensor 532, accelerometer 534, directional sensor 540 (e.g., compass), gyroscope 536, motion sensor 538, and/or a combination thereof, all of which can be operatively connected to I/O section 514.

Memory 518 of personal electronic device 500 can include one or more non-transitory computer-readable storage mediums, for storing computer-executable instructions, which, when executed by one or more computer processors 516, for example, can cause the computer processors to perform the techniques described below, including processes 700, 800, 900, 1100, 1300, 1500, 1700, and 1800 (FIGS. 7, 8, 9, 11, 13, 15, 17, and 18). A computer-readable storage medium can be any medium that can tangibly contain or store computer-executable instructions for use by or in connection with the instruction execution system, apparatus, or device. In some examples, the storage medium is a transitory computer-readable storage medium. In some examples, the storage medium is a non-transitory computer-readable storage medium. The non-transitory computer-readable storage medium can include, but is not limited to, magnetic, optical, and/or semiconductor storages. Examples of such storage include magnetic disks, optical discs based on CD, DVD, or Blu-ray technologies, as well as persistent solid-state memory such as flash, solid-state drives, and the like. Personal electronic device 500 is not limited to the components and configuration of FIG. 5B, but can include other or additional components in multiple configurations.

As used here, the term "affordance" refers to a user-interactive graphical user interface object that is, optionally, displayed on the display screen of devices 100, 300, and/or 500 (FIGS. 1A, 3, and 5A-5B). For example, an image (e.g., icon), a button, and text (e.g., hyperlink) each optionally constitute an affordance.

As used herein, the term "focus selector" refers to an input element that indicates a current part of a user interface with which a user is interacting. In some implementations that include a cursor or other location marker, the cursor acts as a "focus selector" so that when an input (e.g., a press input) is detected on a touch-sensitive surface (e.g., touchpad 355 in FIG. 3 or touch-sensitive surface 451 in FIG. 4B) while the cursor is over a particular user interface element (e.g., a button, window, slider, or other user interface element), the particular user interface element is adjusted in accordance with the detected input. In some implementations that include a touch screen display (e.g., touch-sensitive display system 112 in FIG. 1A or touch screen 112 in FIG. 4A) that enables direct interaction with user interface elements on the touch screen display, a detected contact on the touch screen acts as a "focus selector" so that when an input (e.g., a press input by the contact) is detected on the touch screen display at a location of a particular user interface element (e.g., a button, window, slider, or other user interface element), the particular user interface element is adjusted in accordance with the detected input. In some implementations, focus is moved from one region of a user interface to another region of the user interface without corresponding movement of a cursor or movement of a contact on a touch screen display (e.g., by using a tab key or arrow keys to move focus from one button to another button); in these implementations, the focus selector moves in accordance with movement of focus between different regions of the user interface. Without regard to the specific form taken by the focus selector, the focus selector is generally the user interface element (or contact on a touch screen display) that is controlled by the user so as to communicate the user's intended interaction with the user interface (e.g., by indicating, to the device, the element of the user interface with which the user is intending to interact). For example, the location of a focus selector (e.g., a cursor, a contact, or a selection box) over a respective button while a press input is detected on the touch-sensitive surface (e.g., a touchpad or touch screen) will indicate that the user is intending to activate the respective button (as opposed to other user interface elements shown on a display of the device).

As used in the specification and claims, the term "characteristic intensity" of a contact refers to a characteristic of the contact based on one or more intensities of the contact. In some embodiments, the characteristic intensity is based on multiple intensity samples. The characteristic intensity is, optionally, based on a predefined number of intensity samples, or a set of intensity samples collected during a predetermined time period (e.g., 0.05, 0.1, 0.2, 0.5, 1, 2, 5, 10 seconds) relative to a predefined event (e.g., after detecting the contact, prior to detecting liftoff of the contact, before or after detecting a start of movement of the contact, prior to detecting an end of the contact, before or after detecting an increase in intensity of the contact, and/or before or after detecting a decrease in intensity of the contact). A characteristic intensity of a contact is, optionally, based on one or more of: a maximum value of the intensities of the contact, a mean value of the intensities of the contact, an average value of the intensities of the contact, a top 10 percentile value of the intensities of the contact, a value at the half maximum of the intensities of the contact, a value at the 90 percent maximum of the intensities of the contact, or the like. In some embodiments, the duration of the contact is used in determining the characteristic intensity (e.g., when the characteristic intensity is an average of the intensity of the contact over time). In some embodiments, the characteristic intensity is compared to a set of one or more intensity thresholds to determine whether an operation has been performed by a user. For example, the set of one or more intensity thresholds optionally includes a first intensity threshold and a second intensity threshold. In this example, a contact with a characteristic intensity that does not exceed the first threshold results in a first operation, a contact with a characteristic intensity that exceeds the first intensity threshold and does not exceed the second intensity threshold results in a second operation, and a contact with a characteristic intensity that exceeds the second threshold results in a third operation. In some embodiments, a comparison between the characteristic intensity and one or more thresholds is used to determine whether or not to perform one or more operations (e.g., whether to perform a respective operation or forgo performing the respective operation), rather than being used to determine whether to perform a first operation or a second operation.

As used herein, the term "closed application" refers to software applications without retained state information (e.g., state information for closed applications is not stored in a memory of the device). Accordingly, closing an application includes stopping and/or removing application processes for the application and removing state information for the application from the memory of the device. Generally, opening a second application while in a first application does not close the first application. When the second application is displayed and the first application ceases to be displayed, the first application becomes a background application.

In some embodiments, the computer system is in a locked state or an unlocked state. In the locked state, the computer system is powered on and operational but is prevented from performing a predefined set of operations in response to user input. The predefined set of operations optionally includes navigation between user interfaces, activation or deactivation of a predefined set of functions, and activation or deactivation of certain applications. The locked state can be used to prevent unintentional or unauthorized use of some functionality of the computer system or activation or deactivation of some functions on the computer system. In some embodiments, in the unlocked state, the computer system is power on and operational and is not prevented from performing at least a portion of the predefined set of operations that cannot be performed while in the locked state. When the computer system is in the locked state, the computer system is said to be locked. When the computer system is in the unlocked state, the computer is said to be unlocked. In some embodiments, the computer system in the locked state optionally responds to a limited set of user inputs, including input that corresponds to an attempt to transition the computer system to the unlocked state or input that corresponds to powering the computer system off.

Attention is now directed towards embodiments of user interfaces ("UP") and associated processes that are implemented on an electronic device, such as portable multifunction device 100, device 300, or device 500.

FIGS. 6A-6AE illustrate exemplary user interfaces for navigating, modifying, and outputting workout content, in accordance with some embodiments. The user interfaces in these figures are used to illustrate the processes described below, including the processes in FIGS. 7, 8, and 9.

FIG. 6A illustrates electronic device 600, which is a smartwatch with touch-sensitive display 602, rotatable and depressible input mechanism 604a, and button 604b. In FIG. 6A, electronic device 600 displays, on display 602, workout selection user interface 606. Workout selection user interface 606 includes various workout options 608a-608g, with each workout option 608a-608g corresponding to a particular workout (e.g., a preconfigured workout). Workout selection user interface 606 also includes option 608h that is selectable to initiate a process for creating and/or defining a new workout. In some embodiments, creating a new workout includes selecting a modality type for the workout, selecting a goal type for the workout and, if needed, defining a goal value for the selected goal type, as will be described in greater detail below.

In some embodiments, a workout includes (e.g., is defined by and/or is defined partially by) a modality type and a goal type. Furthermore, for certain goal types, a workout includes a goal value. For example, workout option 608a has outdoor run as its modality type, and open goal as its goal type. In some embodiments, an open goal workout does not have any defined duration or goal, so there is no goal value associated with an open goal workout. Workout option 608b has outdoor swim as its modality type, and distance goal as its goal type, and a goal value of 200 meters. Workout option 608c has multisport as its modality type. In some embodiments, workouts with multisport as their modality type do not have a goal type, but rather are defined by an ordered sequence of a plurality of workout segments, with each workout segment having its own modality type. For example, in FIG. 6A, workout option 608c is a preconfigured "triathlon" multisport workout that has three segments: an outdoor swim segment, an outdoor cycle segment, and an outdoor run segment. Option 608d is a workout that has outdoor run as its modality type, and race a route as its goal type, which is a workout in which a user races against a previous instance in which the user ran a particular route, and the goal value corresponds to the route the user completed previously (identified in FIG. 6A as "Palo Alto (5 MI)"). Option 608e corresponds to a workout with outdoor run as its modality type, and intervals as its goal type, and 3 by 2 miles as its goal value. Option 608f corresponds to a workout with outdoor bike as its modality type, time goal as its goal type, and 1 hour as its goal value. Option 608g corresponds to a workout with outdoor run as its modality type, time and distance as its goal type, and 30 minutes and 3 miles as its goal values.

In some embodiments, workout options 608a-608g are sorted and/or ordered based on one or more factors. In various embodiments, the one or more factors include one or more of: how recently the workout was completed by the user (e.g., workouts performed more recently by the user are given preference (e.g., a higher score and/or a higher ranking)), how recently the workout was created (e.g., workouts created more recently are given preference), how many times the user has completed the workout (e.g., workouts performed more often by the user are given preference), and/or other situational information (e.g., if the user is nearby a route that the user previously completed in a workout, a race a route workout option corresponding to the previously completed route is given preference). Furthermore, in some embodiments, electronic device 600 has more preconfigured workouts than what is shown in workout selection user interface 606, but a subset of those preconfigured workouts are presented in and/or included in workout selection user interface 606 based on the sorting and/or ranking of preconfigured workouts (e.g., the top x workouts are selected for display in workout selection user interface 606).

Figure 6B:
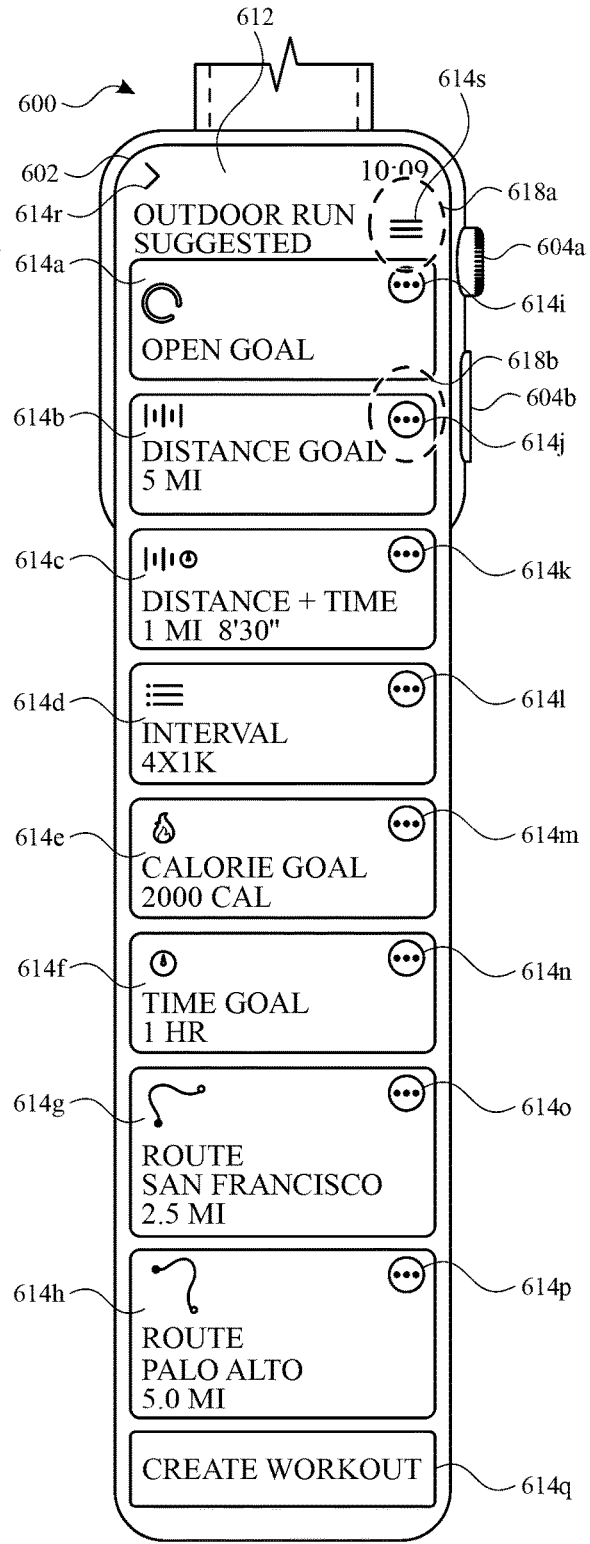
Figure 6C:
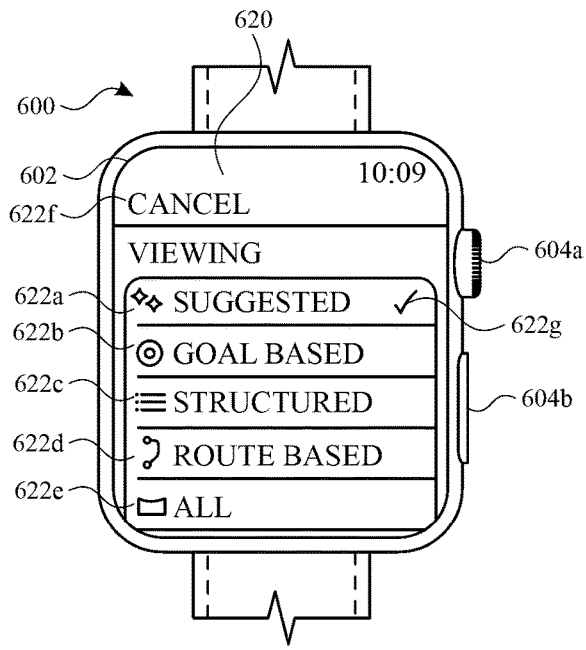
Figure 6D:
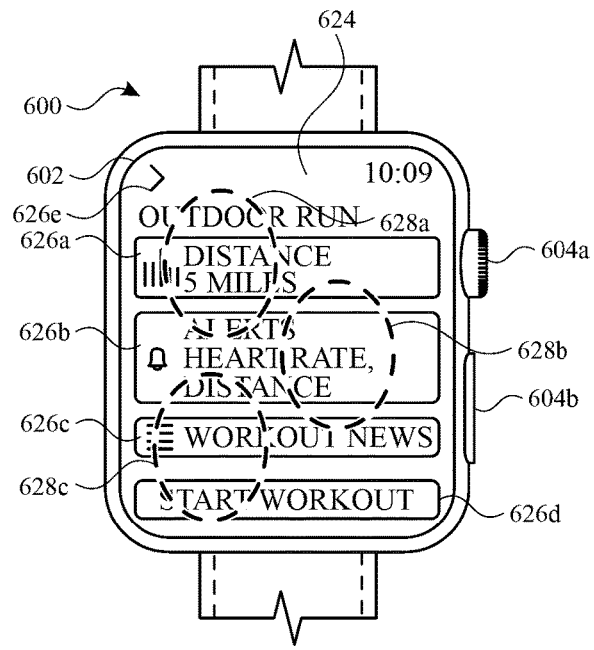

In the depicted embodiment, each workout option 608a-608g is selectable to initiate a corresponding workout session (e.g., a workout session corresponding to the workout represented by the workout option). Furthermore, each workout option 608a-608g has a corresponding option 608i-608o that is selectable to view additional options corresponding to the selected workout. For example, for workout option 608a, a user is able to select workout option 608a to initiate an open goal outdoor run workout session (and display a corresponding in-workout user interface), or select option 608i to display additional options corresponding to the outdoor run open goal workout. At FIG. 6A, electronic device 600 detects user input 610a, (e.g., a tap input) corresponding to selection of option 608i, and user input 610b corresponding to selection of option 608j. FIGS. 6B-6R will describe a first example scenario in which electronic device 600 detects user input 610a corresponding to selection of option 608i, and FIGS. 6S-6AE will describe a second example scenario in which electronic device 600 detects user input 610b corresponding to selection of option 608j.

At FIG. 6B, in response to user input 610a from FIG. 6A, electronic device 600 displays outdoor run room user interface 612. In the depicted embodiment, because the user selected option 608i, which corresponds to an outdoor run modality type, electronic device 600 displays outdoor run room user interface 612. If the user had selected option 608l or 608m, which also have the same modality types as option 608a (e.g., outdoor run) but different goal types (e.g., race a route, and intervals, respectively), electronic device 600 would still display outdoor run room user interface 612. However, if the user had selected an option corresponding to a different modality type, the user would be taken to a user interface corresponding to the selected modality type. For example, if the user had selected option 608j, electronic device 600 would display an outdoor swim room user interface (as will be shown in FIGS. 6S-6AE), or if the user had selected option 608k, electronic device 600 would display a multisport room user interface.

In FIG. 6B, outdoor run room user interface 612 includes options 614a-614h corresponding to a plurality of preconfigured workouts of the outdoor run modality type. Each option 614a-614h is selectable to initiate a workout session (and, in some embodiments, display a corresponding in-workout user interface) for the selected workout. Furthermore, each option 614a-614h includes a corresponding option 614i-614p that is selectable to display one or more options for modifying one or more aspects of the selected workout, as will be described in greater detail below.

Outdoor run room user interface 612 also includes option 614q that is selectable to create a new outdoor run workout, option 614r that is selectable to return to workout selection user interface 606, and option 614s that is selectable to filter the workout options that are presented in outdoor run room 612. In FIG. 6B, electronic device detects user input 614s (e.g., a tap input) corresponding to selection of option 614s. In FIG. 6C, in response to user input 614s, electronic device 600 displays user interface 620. User interface 620 includes options 622a-622e that are selectable to display different sets of outdoor run workouts in outdoor run room user interface 612 (e.g., sets of outdoor run workouts that satisfy and/or meet selected filtering criteria). Option 622a is selectable to display a set of suggested workout options within outdoor run room user interface 612. Option 622b is selectable to display (e.g., only display) workout options corresponding to a first set of goal types (e.g., distance goal, time goal, calorie goal, and/or distance+time goal types) in outdoor run room user interface 612. Option 622c is selectable to display (e.g., only display) workouts of the interval goal type within outdoor run room user interface 612. Option 622d is selectable to display (e.g., only display) workout of the race a route goal type within outdoor run room user interface 612. Option 622e is selectable to display all preconfigured outdoor run workouts in outdoor run room user interface 612. User interface 620 also includes option 622f that is selectable to return to outdoor run room user interface 612.

Returning to FIG. 6B, electronic device 600 detects user input 618b (e.g., a tap input) corresponding to selection of option 614j. At FIG. 6D, in response to user input 618b, electronic device 600 displays workout modification user interface 624. Workout modification user interface 624 displays one or more options 626a-c for modifying one or more aspects of the selected workout (e.g., which, in FIG. 6D, is an outdoor run distance goal workout of 5 miles corresponding to options 614b and 614j in FIG. 6B). Option 626a is selectable to modify a goal type and a goal value for the workout. Option 626a displays a currently selected goal type ("Distance") and a currently selected goal value ("5 Miles"). Option 626b is selectable to modify alerts that are configured to be output during the workout. Option 626b displays currently enabled alert types (e.g., heart rate alert and distance alert). Option 626c is selectable to modify workout metrics that are configured to be displayed and/or that are accessible during the workout. User interface 624 also includes option 626d that is selectable to initiate the workout (e.g., initiate a workout session corresponding to the workout and, in some embodiments, display a corresponding in-workout user interface), and option 626e that is selectable to return to outdoor run room user interface 612.

In FIG. 6D, electronic device 600 detects user input 628a (e.g., a tap input) corresponding to selection of option 626a, user input 628b (e.g., a tap input) corresponding to selection of option 626b, and user input 628c (e.g., a tap input) corresponding to selection of option 626c. Each of these user inputs will be discussed in turn below.

Figure 6E:
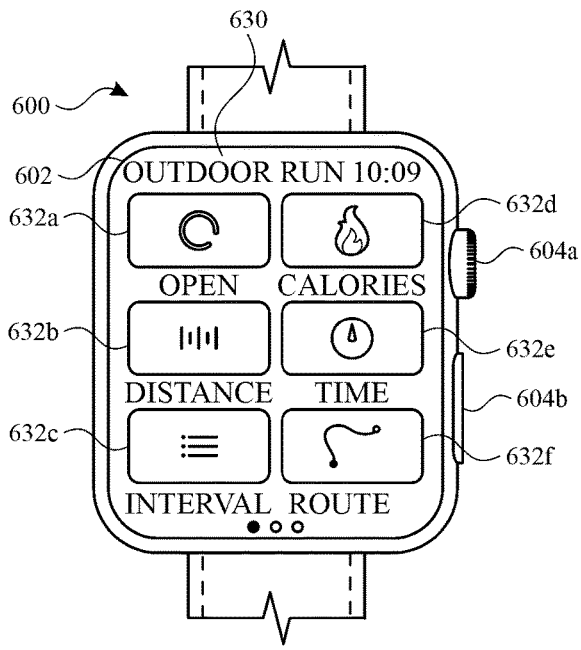

At FIG. 6E, in response to user input 628a, electronic device 600 displays user interface 630, which includes various options 632a-632f corresponding to various goal types. Selection of a particular goal type, in some embodiments, causes electronic device 600 to display a goal value setting user interface in which the user can define a goal value for the selected goal type in order to define a new goal type and new goal value for the workout.

Figure 6F:
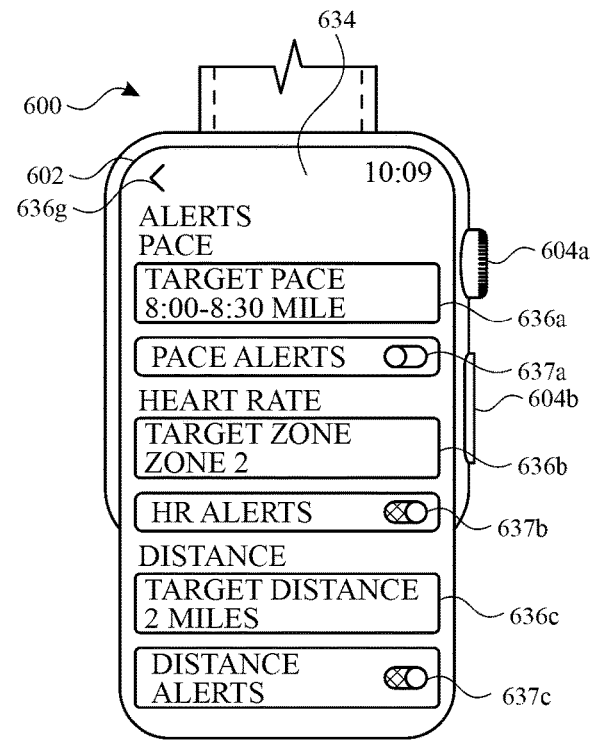

At FIG. 6F, in response to user input 628b (from FIG. 6D), electronic device 600 displays alert setting user interface 634. Alert setting user interface 634 includes representations 636a, 636b, 636c that represent different alert types. In some embodiments, an alert is defined by an alert condition. When the alert condition is met during a workout session, electronic device 600 outputs (e.g., displays, and/or outputs an audible alert, and/or outputs a haptic alert) an alert indicating that the alert condition has been met. In some embodiments, an alert condition includes a first value, such that when an activity metric falls above or below the value, an alert is triggered. In some embodiments, an alert condition includes a range of values (e.g., a minimum and a maximum value) such that when an activity metric falls inside of the range or falls outside of the range, an alert is triggered.

In FIG. 6F, representation 636a represents a pace alert type (e.g., an alert that is triggered when the user's pace falls below a target value, goes above a target value, enters into a range of target values, and/or exits a range of target values). Representation 636a is selectable to define a target pace value and/or a target pace range. Representation 636b represents a heart rate alert type (e.g., an alert that is triggered when the user's heart rate falls below a target value, goes above a target value, enters into a range of target values, and/or exits a range of target values). Representation 636b is selectable to define a target heart rate, a target heart rate range, and/or a target heart rate zone (which, in some embodiments, is a range of heart rate values). Representation 636c represents a distance alert type (e.g., an alert that is triggered when the user traverses a target distance during a workout). Representation 636c is selectable to define a target distance value. Alert setting user interface 634 also includes option 637a that is selectable to toggle pace alerts on or off, option 637b that is selectable to toggle heart rate alerts on or off, and option 637c that is selectable to toggle distance alerts on or off. In FIG. 6F, option 637b and option 637c are in an enabled state, indicating that heart rate and distance alerts are enabled and corresponding alerts will be output during a workout session, while option 637a is in a disabled state, indicating that pace alerts are disabled and will not be output during a workout session. In some embodiments, alert setting user interface 634 corresponds to the outdoor run modality type, such that alerts defined and enabled in alert setting user interface 634 will be enabled for all outdoor run workouts (e.g., regardless of goal type). In some embodiments, different modality types have their own alert setting user interfaces for defining alerts that are to be provided during workout sessions of those different modality types.

Figure 6G:
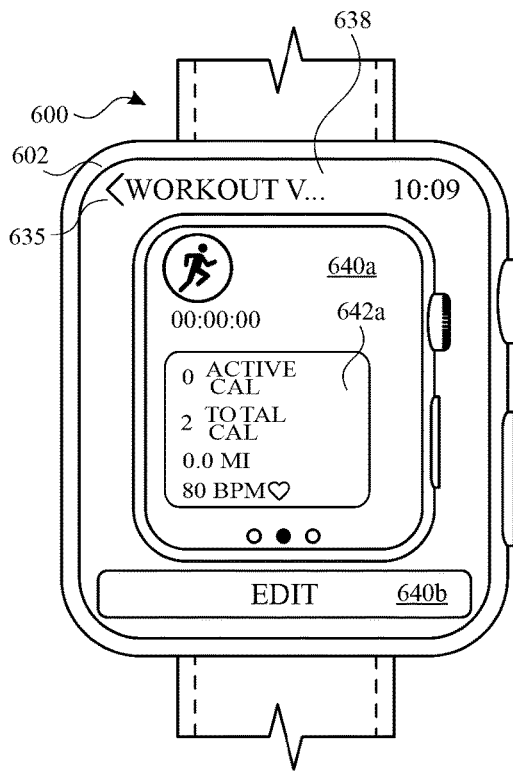

At FIG. 6G, in response to user input 628c (from FIG. 6D), electronic device 600 displays metrics preview user interface 638. In some embodiments, during a workout session, electronic device 600 displays an in-workout user interface that includes one or more workout metrics (e.g., physical activity metrics) indicative of the user's physical activity level during the workout. In some embodiments, users are able to modify workout metrics that are accessible (e.g., that the user can view) during their workouts. In FIG. 6G, metrics preview user interface 638 displays preview 640a which provides the user with an animation that displays for the user one or more metrics user interfaces that are currently set to be displayed (e.g., currently enabled and/or currently accessible) during an outdoor run workout.

Figure 6H:
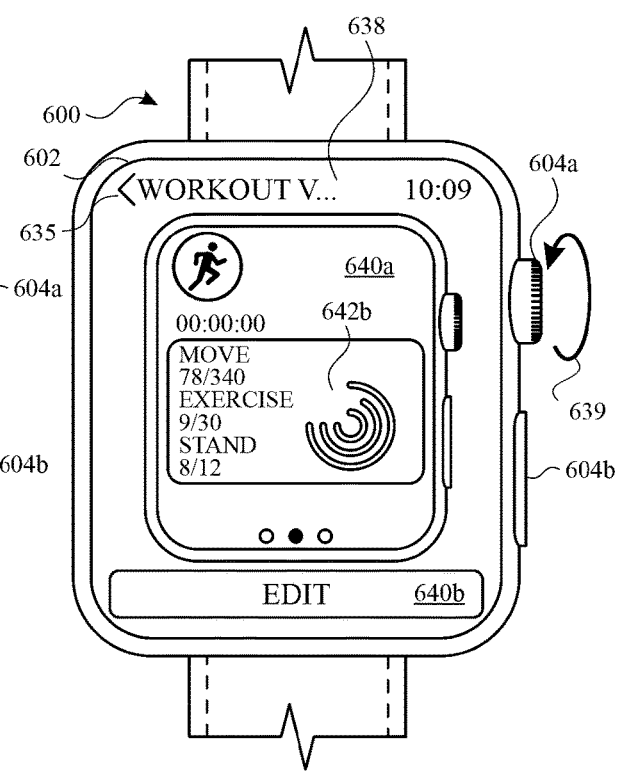
Figure 6I:
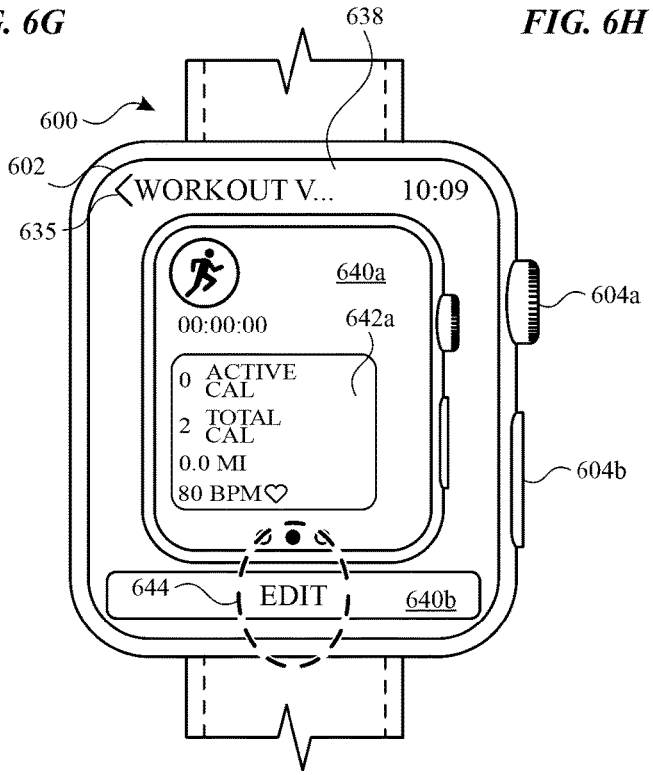

In FIG. 6G, preview 640a displays first workout metrics user interface 642a, which presents a first set of workout metrics. In FIG. 6H, the animation of preview 640a progresses (e.g., without user input) to show second workout metrics user interface 642b, which presents a second set of workout metrics. By displaying the animation of preview 640a, a user is able to see which workout metrics are currently enabled for outdoor run workouts, and can then decide if he or she would like to modify those metrics. In the depicted embodiment, preview 640a is also scrollable by a user so that the user can manually view the workout metrics user interfaces that are currently enabled. In FIG. 6H, electronic device 600 detects user input 639, which is a counter-clockwise rotation of rotatable input mechanism 604a. At FIG. 6I, in response to user input 639, electronic device 600 ceases display of workout metrics user interface 642b and displays workout metrics user interface 642a.

Metrics preview user interface 638 also includes option 640b that is selectable to modify workout metrics that are accessible during a workout session. At FIG. 6I, electronic device 600 detects user input 644 (e.g., a tap input) corresponding to selection of option 640b.

At FIG. 6J, electronic device 600 displays metrics setting user interface 645. Metrics setting user interface 645 corresponds to the outdoor run modality type, and displays a set of workout metrics user interfaces 642a-642f that are available for display during an outdoor run workout. Each workout metrics user interface displays a different set of workout metrics. For example, workout metrics user interface 642a displays active calorie information, total calorie information, distance traversed during the workout, and heartrate information. Workout metrics user interface 642c displays heart rate zone information indication the user's current heart rate zone during a workout session. Workout metrics user interface 642d displays lap information. Workout metrics user interface 642e displays elevation information. Workout metrics user interface 642f displays run power information. Workout metrics user interface 642b displays a move goal representation (e.g., the outmost ring of the three concentric rings), which is an indication of the user's progress towards a daily calories goal for a current calendar day, and includes physical activity information for the user that precedes the workout session. Workout metrics user interface 642b also displays an exercise goal representation (e.g., a middle ring of the three concentric rings), which is an indication of the user's progress towards a daily exercise minutes goal for the current calendar day (e.g., a target number of minutes of exercise for each calendar day), and includes physical activity information for the user that precedes the workout session. Workout metrics user interface 642b also displays a stand goal representation (e.g., an innermost ring of the three concentric rings), which is an indication of the user's progress towards a daily stand goal for the current calendar day (e.g., a target number of hours each day during which the user stood for a threshold number of minutes), which also includes physical activity information for the user that precedes the workout session.

Workout metrics user interfaces 642b-642f include corresponding toggles 646b-646f that are selectable to selectively enable or disable the corresponding workout metrics user interface. If a workout metrics user interface is enabled, a user is able to view the workout metrics user interface during an outdoor run workout session, and if a workout metrics user interface is disabled, a user is not able to view the workout metrics user interface during an outdoor run workout session. In FIG. 6J, workout metrics user interface 642a does not have a corresponding toggle. This is because, in the depicted embodiment, workout metrics user interface 642a represents a default workout metrics user interface for the outdoor run modality type and is therefore displayed by default and cannot be disabled. In the depicted embodiment, metrics setting user interface 645 corresponds to the outdoor run modality type, and displays workout metrics user interfaces that are available for the outdoor run modality type. Different modality types will, in various embodiments, have different metrics setting user interfaces that display at least some different workout metrics user interfaces from what is presented in metrics setting user interface 645, as will be demonstrated below, for example, with reference to FIG. 6U.

In FIG. 6J, workout metrics user interface 642c is displayed with edit option 648c, indicating that workout metrics user interface 642c can be edited by a user. For example, workout metrics user interface 642c indicates to the user the heart rate zone the user is in during a workout session. In some embodiments, the user can select edit option 648c to define and/or customize different heart rate zones (e.g., define a first range of heart rate values for a first zone, define a second range of heart rate values for a second zone, and so forth). Other workout metrics user interfaces 642a, 642b, 642d, 642e, 642f are not shown with edit options, indicating that those workout metrics user interfaces do not have features that can be edited or customized by a user.

In FIG. 6J, workout metrics user interfaces 642a and 642b are currently enabled. At FIG. 6J, electronic device 600 detects user input 647 (e.g., a tap input) corresponding to selection of toggle 646e. At FIG. 6K, in response to user input 647, electronic device displays toggle 646e in the enabled state, indicating that workout metrics user interface 642e is now enabled and is accessible during an outdoor run workout session. The three enabled workout metrics user interfaces 642a, 642b, 642e will be presented in the order they are shown in metrics setting user interface 645 (e.g., with workout metrics user interface 642a as a first and/or topmost interface, workout metrics user interface 642b as a second and/or middle interface, and workout metrics user interface 642e as a third and/or last interface). Metrics setting user interface 645 includes option 648b that is selectable to reorder the enabled metrics setting user interfaces. In some embodiments, metrics setting user interface 645 does not include option 648b and is configured to be reordered in response to drag and drop user inputs. In some embodiments, workout metrics user interface 642a, as a default user interface for the outdoor run modality type, is always displayed at the first and/or topmost interface, and cannot be reordered. At FIG. 6K, electronic device 600 detects user input 650 (e.g., a tap input), corresponding to selection of option 648a.

At FIG. 6L, in response to user input 650, electronic device 600 displays metrics preview user interface 638. At FIG. 6L, electronic device 600 detects user input 652 corresponding to selection of option 635. At FIG. 6M, in response to user input 652, electronic device 600 displays workout modification user interface 624. At FIG. 6M, electronic device 600 detects user input 654 (e.g., a tap input) corresponding to selection of option 626d.

At FIG. 6N, in response to user input 654, electronic device 600 initiates an outdoor run workout (e.g., an outdoor run workout with a distance goal type and 5 mile goal value) and displays in-workout user interface 656. In-workout user interface 656 indicates that a workout session (e.g., a workout) is in progress. In-workout user interface 656 includes workout modality indication 657a, which indicates that the current workout session is an outdoor running workout session. In-workout user interface 656 also includes elapsed time indication 657b which indicates the elapsed time for the current workout. In FIG. 6N, in-workout user interface 656 includes workout metrics user interface 642a which, as discussed above, represents a default workout metrics user interface for the outdoor running workout modality. In the depicted embodiment, a user is able to transition and/or switch between enabled workout metrics user interfaces by rotating rotatable input mechanism 604a. At FIG. 6N, electronic device 600 detects user input 658, which is a rotation of rotatable input mechanism 604a in a first direction (e.g., clockwise).

At FIG. 6O, in response to user input 658, electronic device 600 ceases display of workout metrics user interface 642a and displays workout metrics user interface 642b, which was also enabled in metrics setting user interface 645. In FIG. 6O, in response to user input 658, electronic device 600 also displays scroll indication 659, which provides the user with an indication of whether there are any additional workout metrics user interfaces available above and/or below the currently displayed workout metrics user interface. At FIG. 6O, electronic device 600 detects user input 660a, which is rotation of rotatable input mechanism 604a in the first direction (e.g., clockwise), and user input 660b, which is rotation of rotatable input mechanism 604a in a second direction opposite the first direction (e.g., counterclockwise). In FIG. 6O, user input 660b (e.g., rotation in the counterclockwise direction) would cause electronic device 600 to cease display of workout metrics user interface 642b and re-display workout metrics user interface 642a.

Figure 6P:
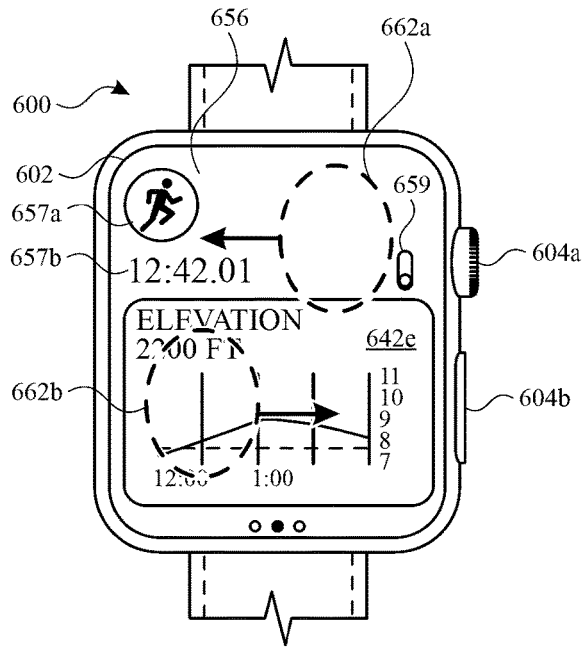

At FIG. 6P, in response to user input 660a, electronic device 600 ceases display of workout metrics user interface 642b, and displays workout metrics user interface 642e, which was enabled in metrics setting user interface 645. In FIG. 6P, in response to user input 660a, electronic device 600 also displays scroll indication 659, which shows that workout metrics user interface 642e is the bottom-most and/or last workout metrics user interface (e.g., there are no further workout metrics user interfaces to be displayed if the user continues turning rotatable input mechanism 604a in the clockwise direction). In FIG. 6P, the user is able to rotate rotatable input mechanism 604a in a counterclockwise direction to view workout metrics user interface 642b.

Figure 6Q:
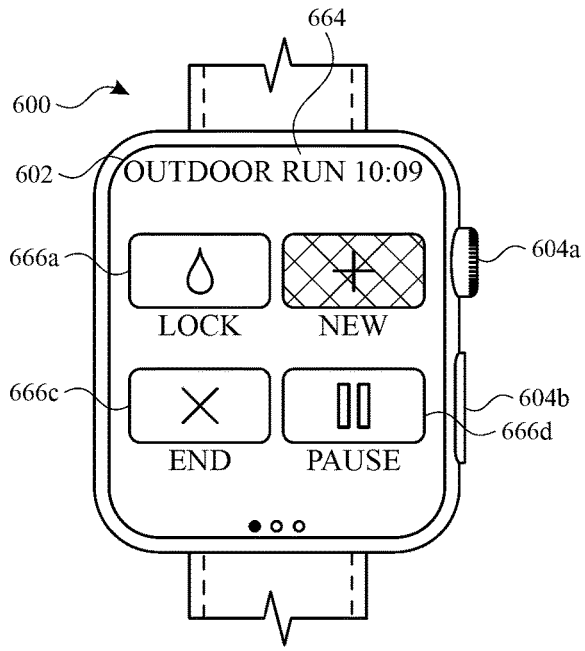
Figure 6R:
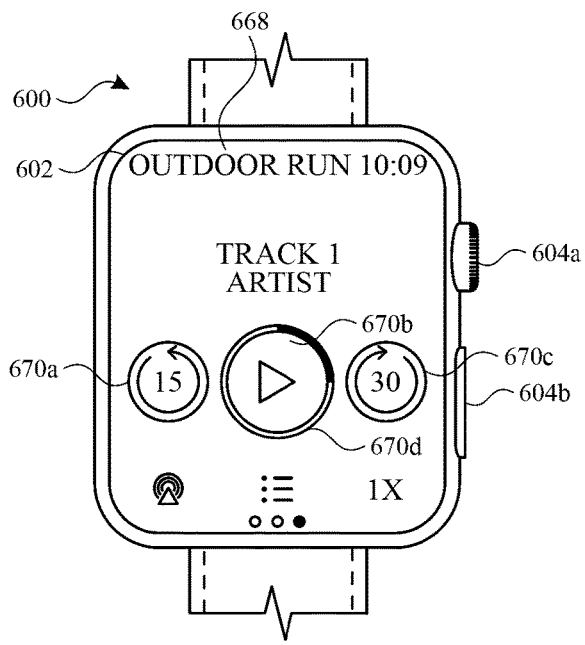

At FIG. 6P, electronic device 600 detects user input 662a (e.g., a swipe left touch input), and user input 662b (e.g., a swipe right touch input). At FIG. 6Q, in response to user input 662b, electronic device 600 displays control center user interface 664, that includes option 666a that is selectable to engage a water lock function of electronic device 600, option 666c that is selectable to end the current workout session, and option 666d that is selectable to pause the current workout session. From control center user interface 664, a user is able to return to in-workout user interface 656 and a previously displayed workout metrics user interface (e.g., workout metrics user interface 642e) by providing a swipe left input. At FIG. 6R, in response to user input 662a, electronic device 600 displays audio playback user interface 668, which displays one or more controls for controlling output of audio content (e.g., music or other audio content) during the workout session. Audio playback user interface 668 includes option 670a that is selectable to rewind audio content by 15 seconds, option 670b that is selectable to play audio content, and option 670c that is selectable to fast forward audio content by 30 seconds. From audio playback user interface 668, a user is able to return to in-workout user interface 656 the previously displayed workout metrics user interface (e.g., workout metrics user interface 642e) with a swipe left input. In some embodiments, a user is able to access control center user interface 664 and/or audio playback user interface 668 with a swipe right input or swipe left input from in-workout user interface 656 regardless of what workout metrics user interface (e.g., 642a, 642b, 642e) is displayed.

Figure 6S:
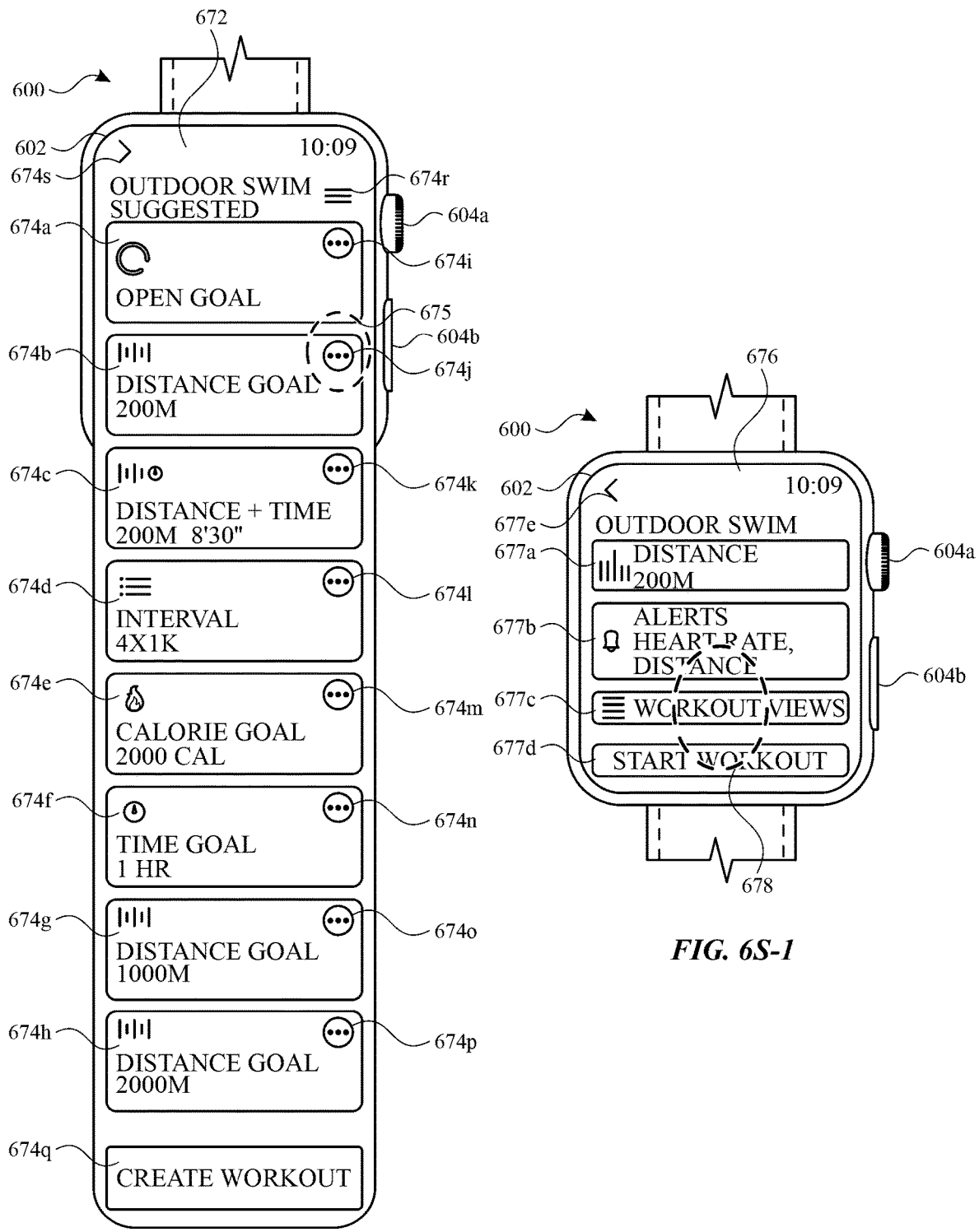

At FIG. 6S, in response to user input 610b from FIG. 6B, electronic device 600 displays outdoor swim room user interface 672, which corresponds to the outdoor swim modality type. Outdoor swim room user interface includes a plurality of workout options 674a-674h corresponding to different preconfigured workouts of the outdoor swim modality type. Each workout option 674a-674h is selectable to initiate an outdoor swim workout session of the corresponding goal type. Each workout option 674a-674 also has a corresponding option 674j-674p that is selectable to display one or more options for customizing and/or modifying one or more aspects of the workout. Outdoor swim room user interface 672 also includes option 674q that is selectable to initiate a process for creating a new outdoor swim workout, option 674r that is selectable to filter the workout options that are presented in outdoor swim room user interface 672, and option 674s that is selectable to return to workout selection user interface 606. At FIG. 6S, electronic device 600 detects user input 675 (e.g., a tap input) corresponding to selection of option 674j.

At FIG. 6S-1, in response to user input 675, electronic device 600 displays workout modification user interface 676. Workout modification user interface 676 includes option 677e that is selectable to return to outdoor swim room user interface 672, and option 677d that is selectable to initiate an outdoor swim workout (and, in some embodiments, display a corresponding in-workout user interface). Workout modification user interface 676 also includes option 677a that is selectable to modify a goal type and goal value for the outdoor swim workout (similar to option 626a of FIG. 6D), option 677b that is selectable to modify alerts for the outdoor swim workout (similar to option 626b of FIG. 6D) (and, in some embodiments, is selectable to modify alerts for all workouts of the outdoor swim modality type (e.g., regardless of goal type)), and option 677c that is selectable to modify workout metrics that are accessible during the outdoor swim workout (and, in some embodiments, that are accessible for all workouts of the outdoor swim modality type (e.g., regardless of goal type)). At FIG. 6S-1, electronic device 600 detects user input 678 (e.g., a tap input) corresponding to selection of option 677c.

At FIG. 6T, in response to user input 678, electronic device 600 displays metrics preview user interface 679, which is functionally identical to metrics preview user interface 638 described above. Metrics preview user interface 679 displays animated preview 680a, which previews for the user one or more workout metrics user interface that are enabled for outdoor swim workouts. In FIG. 6T, only one workout metrics user interface is enabled for outdoor swim workout (workout metrics user interface 680a). Metrics preview user interface 679 also includes option 680b that is selectable to modify workout metrics that are accessible during the outdoor swim workout. At FIG. 6T, electronic device 600 detects user input 682 (e.g., a tap input) corresponding to selection of option 680*b*.

At FIG. 6U, in response to user input 682, electronic device 600 displays metrics setting user interface 683. Metrics setting user interface 683 is very similar to metrics setting user interface 645 discussed above. However, metrics setting user interface 683 corresponds to the outdoor swim modality type, whereas metrics setting user interface 645 corresponds to the outdoor run modality type. As such, metrics setting user interface 683 displays a different set of workout metrics user interfaces 681*a*-681*d* that are available for the outdoor swim modality type. Furthermore, metrics setting user interface 683 displays workout metrics user interface 681*a* as a default workout metrics user interface, and it is presented without the option to disable workout metrics user interface 681*a*, because it is the default workout metrics user interface for the outdoor swim modality type. Workout metrics user interfaces 681*b*-681*d* are displayed with corresponding toggles 684*b*-684*d* (to selectively enable and/or disable these workout metrics user interfaces). Workout metrics user interface is shown with an edit option 685*b*, indicating that this workout metrics user interface can be edited by a user, whereas the other workout metrics user interfaces 681*a*, 681*c*, 681*d* are not. Workout metrics user interfaces 681*b*, 681*c*, and 681*d* are identical to workout metrics user interfaces 642*c*, 642*b*, and 642*d*, respectively, from metrics setting user interface 645, but metrics setting user interface 645 included additional workout metrics user interfaces that are not included in metrics setting user interface 683. At FIG. 6U, electronic device 600 detects user input 686*a* (e.g., a tap input) corresponding to selection of option 684*b* and user input 686*b* (e.g., a tap input) corresponding to selection of option 684*c*.

Figure 6X:
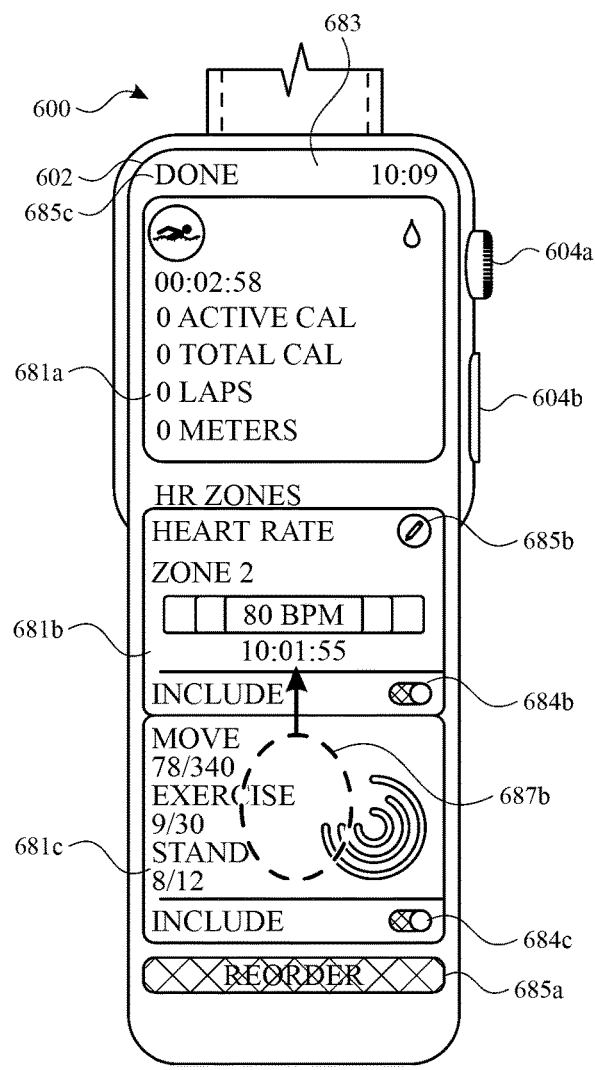
Figure 6Y:
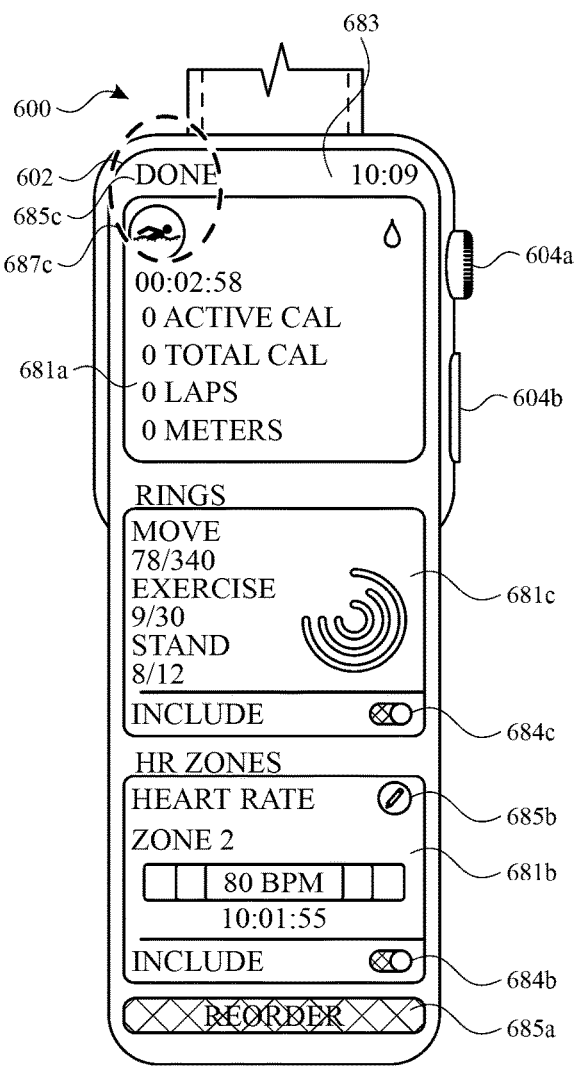

At FIG. 6V, in response to user inputs 686*a* and 686*b*, electronic device 600 displays metrics setting user interface 683 with options 684*b* and 686*c* in the enabled state. At FIG. 6V, electronic device 600 detects user input 687*a* corresponding to selection of reorder option 685*a*. At FIG. 6W, in response to user input 687*a*, electronic device 600 ceases display of disabled metrics user interface 681*d* and grays out option 685*a*, indicating that metrics setting user interface 683 is in a reordering mode. At FIG. 6W, while metrics setting user interface 683 is in the reordering mode, electronic device 600 detects user input 687*b* (e.g., a drag user input). At FIG. 6X, in response to user input 687*b*, electronic device 600 displays workout metrics user interface 681*c* moving upwards, and in FIG. 6Y, in response to continued detection of user input 687*b*, electronic device displays workout metrics user interface 681*c* moved above workout metrics user interface 681*b*, indicating that workout metrics user interface 681*c* will now be displayed before and/or above workout metrics user interface 681*b* during an outdoor swim workout session. At FIG. 6Y, electronic device 600 detects user input 687*c* (e.g., a tap input) corresponding to selection of done option 685*c*. At FIG. 6Z, in response to user input 687*c*, electronic device exits out of the reordering mode and re-displays disabled workout metrics user interface 681*d*. Although the depicted embodiment shows a reorder option 685*a* that is selectable to engage a reordering mode to reorder workout metrics user interfaces, in some embodiments, a user is able to reorder workout metrics user interfaces with a drag and drop input without the need to engage a reordering mode. Accordingly, in some embodiments, metrics setting user interface 683 does not include reorder option 685*a*.

Figure 6Z:
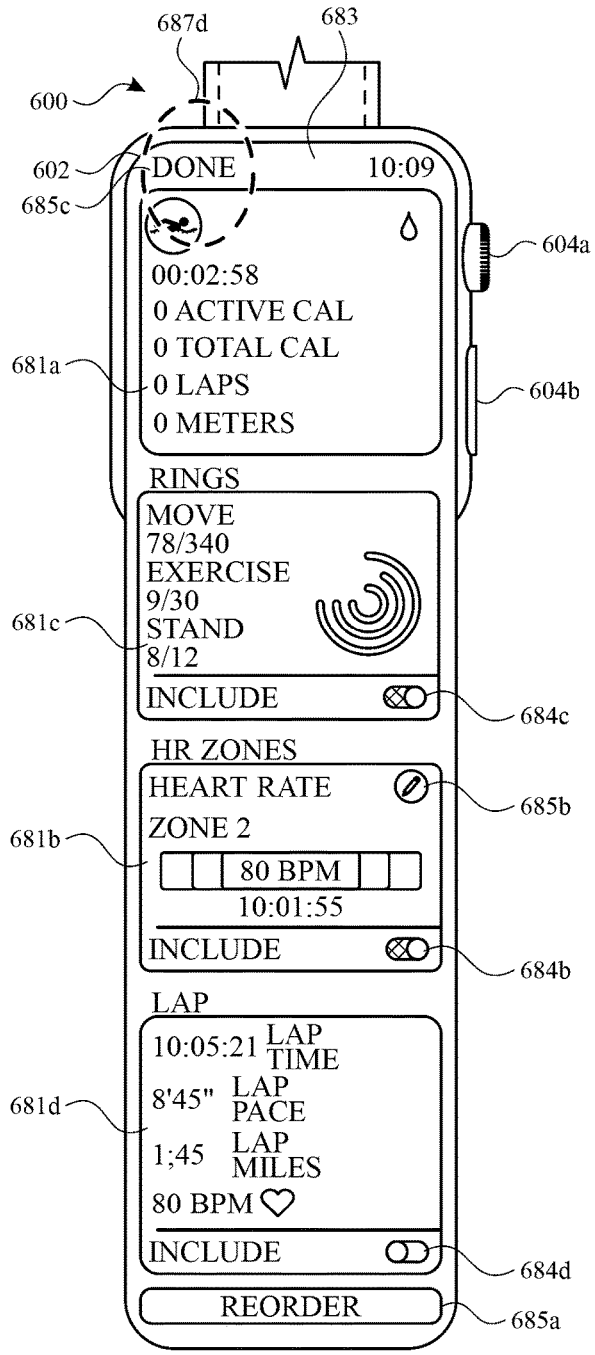
Figure 6A:
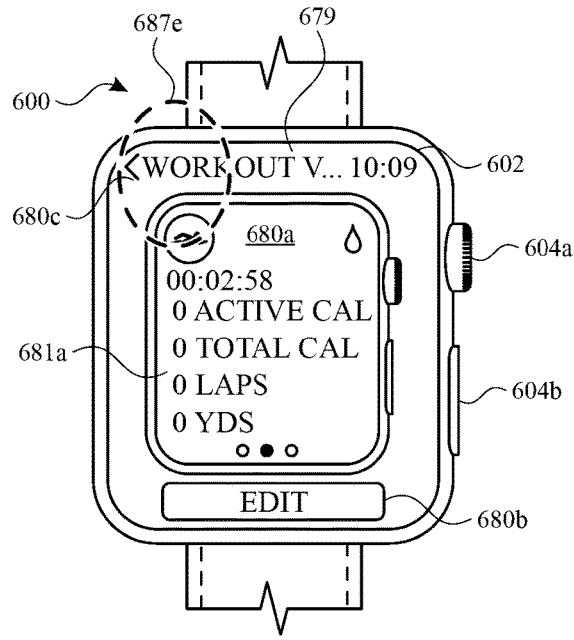
Figure 6A:
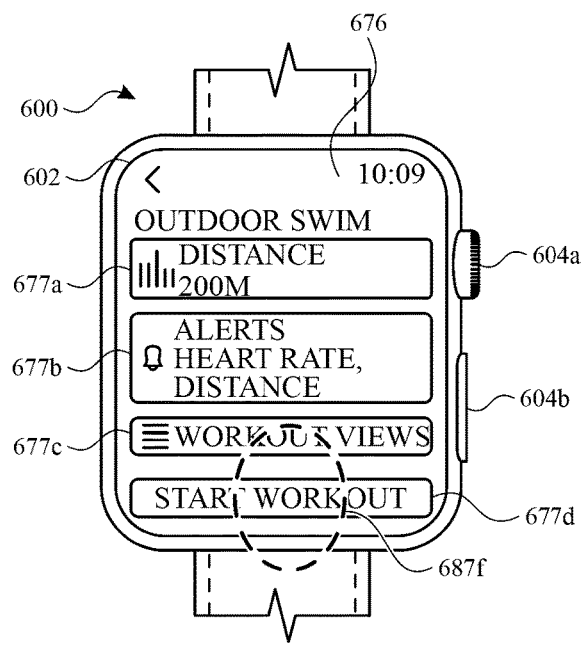
Figure 6A:
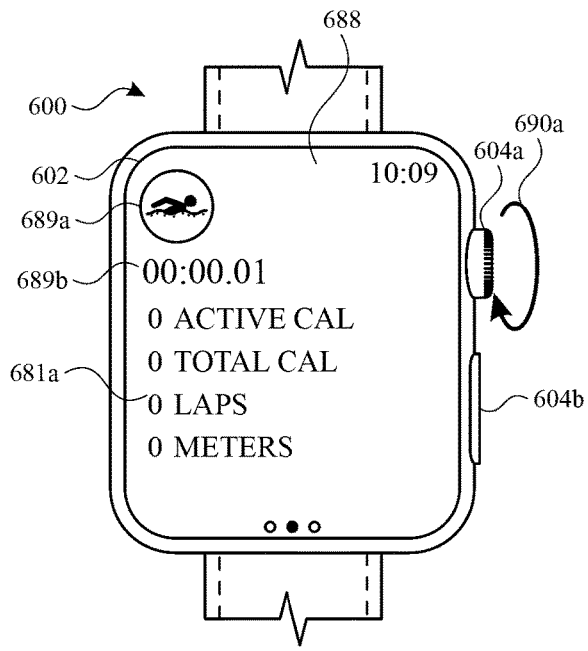
Figure 6A:
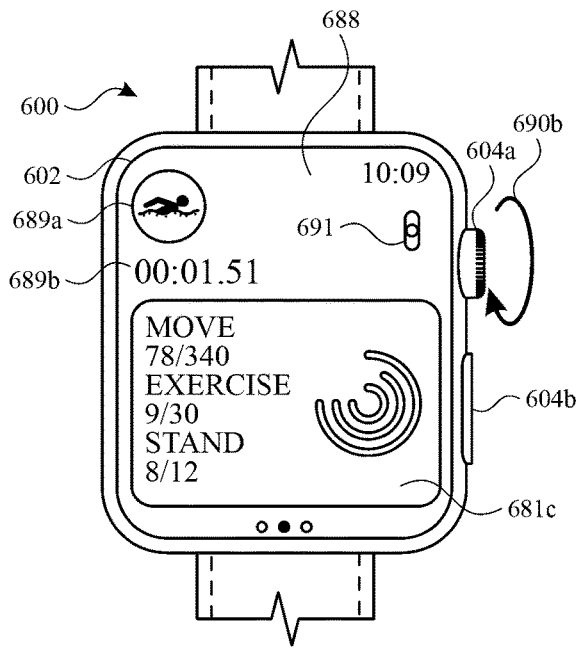
Figure 6A:
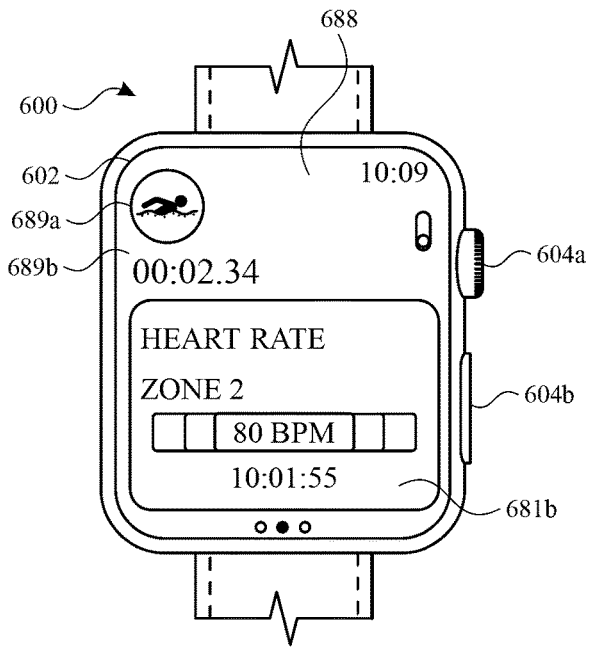

At FIG. 6Z, electronic device 600 detects user input 687*d* (e.g., a tap input) corresponding to selection of option 685*c*.

At FIG. 6AA, in response to user input 687*d*, electronic device 600 displays metrics preview user interface 679. At FIG. 6AA, electronic device 600 detects user input 687*e* (e.g., a tap input) corresponding to selection of option 680*c*. At FIG. 6AB, in response to user input 687*e*, electronic device 600 displays workout modification user interface 676. At FIG. 6AB, electronic device 600 detects user input 687*f* (e.g., a tap input) corresponding to selection of option 677*d*.

At FIG. 6AC, in response to user input 687*f*, electronic device 600 displays in-workout user interface 688 corresponding to the outdoor swim modality type. In-workout user interface 688 includes modality indication 689*a* (displaying an image that corresponds to the outdoor swim modality type), elapsed time indication 689*b*, and workout metrics user interface 681*a*. At FIG. 6AC, electronic device detects user input 690*a*, which is a clockwise rotation of rotatable input mechanism 604*a*. At FIG. 6AD, in response to user input 690*a*, electronic device 600 replaces display of workout metrics user interface 681*a* with workout metrics user interface 681*c*. At FIG. 6AD, electronic device 600 detects user input 690*b*, which is a clockwise rotation of rotatable input mechanism 604*a*. At FIG. 6AE, in response to user input 690*b*, electronic device 600 replaces display of workout metrics user interface 681*c* with workout metrics user interface 681*b*. As discussed above with reference to FIGS. 6P-6R, while displaying in-workout user interface 688 (regardless of which workout metrics user interface is displayed in in-workout user interface 688), a user is able to access control center user interface 664 with a swipe right gesture, and audio playback user interface 668 with a swipe left gesture.

FIG. 7 is a flow diagram illustrating a method for navigating, modifying, and outputting workout content using a computer system in accordance with some embodiments. Method 700 is performed at a computer system (e.g., 100, 300, 500) (e.g., a wearable device, a smart watch, a smart phone, a tablet, and/or a computer system controlling an external display) that is in communication with a display generation component (e.g., a display controller, a touch-sensitive display system; and/or a display (e.g., integrated and/or connected)) and one or more input devices (e.g., a touch-sensitive surface (e.g., a touch-sensitive display); an accelerometer; a rotatable input mechanism; a depressible input mechanism; and/or a rotatable and depressible input mechanism). Some operations in method 700 are, optionally, combined, the orders of some operations are, optionally, changed, and some operations are, optionally, omitted.

As described below, method 700 provides an intuitive way for navigating, modifying, and outputting workout content. The method reduces the cognitive burden on a user for navigating, modifying, and accessing workout content, thereby creating a more efficient human-machine interface. For battery-operated computing devices, enabling a user to navigate, modify, and access workout content faster and more efficiently conserves power and increases the time between battery charges.

The computer system (e.g., 600) displays (702), via the display generation component (e.g., 602), a workout selection user interface (e.g., 606, 612), wherein the workout selection user interface includes a first workout platter (e.g., 608*a*-608*g*, 614*a*-614*h*) (e.g., user interface object and/or affordance) associated with a first workout type (e.g., a first workout modality and/or a first workout goal type) and a second workout platter (e.g., 608*a*-608*g*, 614*a*-614*h*, 674*a*-674*h*) (e.g., user interface object and/or affordance) associated with a second workout type (e.g., a second workout modality and/or a second workout goal type) (in some embodiments, a second workout platter distinct from and/or separate from the first workout platter). In some embodiments, the first workout type is a first workout modality and the second workout type is a second workout modality different from the first workout modality. In some embodiments, the first workout type and the second workout type share the same workout modality, but are different workout goal types (e.g., the first workout type is a first workout goal type and the second workout type is a second workout goal type different from the first workout goal type. In some embodiments, the first workout type is a first workout modality and goal type combination, and the second workout type is a second workout modality and goal type combination.

In some embodiments, while displaying the workout selection user interface (e.g., 606, 612), the computer system receives (704), via the one or more input devices, a first user input (e.g., 610a, 610b, a user input selecting one of workout platters 608a-608g, 618a, 618b, a user input selecting one of workout platters 614a-614h, 675 and/or a user input selecting one of workout platters 674a-674h) (e.g., one or more user inputs) (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures).

In some embodiments, in response to receiving the first user input (706): in accordance with a determination that the first user input corresponds to selection of a first region associated with the first workout platter (708) (e.g., 608a-608g, 614a-614h, and/or 674a-674h) (e.g., a first displayed portion and/or displayed region of the workout selection user interface associated with the first workout platter) (in some embodiments, a first region of the first workout platter)): the computer system initiates (710) a workout session of the first workout type (e.g., a workout session of a first modality and/or a workout session of a first goal type), including initiating recording (e.g., tracking and/or measuring) of one or more physical activity metrics for the workout session of the first workout type (e.g., one or more physical activity metrics indicative of a physical activity level of the user during the workout session (e.g., heart rate, calories burned, steps taken, and/or distance traversed)); and the computer system displays (712) a first workout session user interface (e.g., 656, 688) indicative of an active workout session (e.g., indicative of a currently active and/or in-progress workout session). In some embodiments, the first workout session user interface displays one or more workout performance metrics that are indicative of a physical activity level of the user during the current workout session. In some embodiments, a first workout session user interface indicative of an active workout session of the first workout type (e.g., that is indicative of the current workout session being of the first workout type).

In some embodiments, in response to receiving the first user input (706): in accordance with a determination that the first user input corresponds to selection of a second region associated with the first workout platter (e.g., 608i-608o, 614i-614p, and/or 674i-674p) (e.g., a second displayed portion and/or displayed region of the workout selection user interface associated with the first workout platter) (in some embodiments, a second region of the first workout platter) different from the first region, the computer system displays (714), via the display generation component (e.g., 602), a first workout customization user interface (e.g., 624, 676) (in some embodiments, without displaying the workout session user interface and/or without initiating a workout session of the first workout type) that includes one or more selectable options that are selectable to initiate one or more processes for customizing one or more aspects of the first workout type (e.g., an option to customize alerts for the first workout type and/or an option to customize workout performance metrics for the first workout type) (in some embodiments, the one or more selectable options are selectable to initiate one or more processes for customizing one or more aspects of the first workout type and the second workout type).

In some embodiments, the computer system further performs: in response to receiving the first user input: in accordance with a determination that the first user input corresponds to selection of a third region associated with the second workout platter (e.g., a third displayed portion and/or displayed region of the workout selection user interface associated with the second workout platter) (in some embodiments, a third portion of the second workout platter) (e.g., a third region different from the first and second regions), initiating a workout session of the second workout type, including initiating recording (e.g., tracking and/or measuring) of one or more physical activity metrics for the workout session of the second workout type (e.g., one or more physical activity metrics indicative of a physical activity level of the user during the workout session (e.g., heart rate, calories burned, steps taken, and/or distance traversed)); and displaying a second workout session user interface indicative of an active workout session (e.g., a workout session user interface indicative of an active workout session of the second workout type) (in some embodiments, a second workout session user interface different from the workout session user interface) (e.g., indicative of a currently active and/or in-progress workout session) (in some embodiments, the workout session user interface displays one or more workout performance metrics that are indicative of a physical activity level of the user during the current workout session); and in accordance with a determination that the first user input corresponds to selection of a fourth region associated with the second workout platter (e.g., a fourth displayed portion and/or displayed region of the workout selection user interface associated with the second workout platter) (in some embodiments, a fourth region of the second workout platter) different from the first region, the second region, and the third region, displaying, via the display generation component, a second workout customization user interface (in some embodiments, without displaying the second workout session user interface and/or without initiating a workout session of the second workout type) that includes one or more selectable options that are selectable to initiate one or more processes for customizing one or more aspects of the second workout type (e.g., an option to customize alerts for the second workout type and/or an option to customize workout performance metrics for the second workout type).

In some embodiments, initiating a workout session includes initiating recording (e.g., tracking, logging, collecting) of physical activity metrics corresponding to the workout session (e.g., physical activity metrics indicative of a physical activity level of the user during the workout session). In some embodiments, the physical activity metrics are recorded (e.g., captured) using one or more sensors (e.g., GPS, accelerometer, gyroscope, heart rate) of the computer system or an external device that is in communication with the computer system. In some embodiments, the physical activity metrics were not being recorded or were being recorded at a lower frequency and/or lower degree of precision prior to initiating (e.g., immediately prior to initiating) the workout session. In some embodiments, initiating the workout session includes causing one or more sensors to be enabled and/or activated to improve accurate measurements of user physical activity metrics during the workout session. Providing a user with a first workout platter wherein selection of a first region of the workout platter initiates a workout, and selection of a second region of the workout platter allows the user to customize one or more aspects of the workout reduces the number of inputs needed to perform either of these functions. Doing so also enables these functions to be performed without displaying additional controls.

In some embodiments, in response to receiving the first user input: in accordance with a determination that the first user input corresponds to selection of a third region different from the first region and the second region and associated with the second workout platter (e.g., 608a-608g, 614a-614h, and/or 674a-674) (e.g., a third displayed portion and/or displayed region of the workout selection user interface associated with the second workout platter) (in some embodiments, a third portion of the second workout platter) (e.g., a third region different from the first and second regions): the computer system initiates a workout session of the second workout type (e.g., a workout session of a second modality and/or a workout session of a second goal type), including initiating recording (e.g., tracking and/or measuring) of one or more physical activity metrics for the workout session of the second workout type (e.g., one or more physical activity metrics indicative of a physical activity level of the user during the workout session (e.g., heart rate, calories burned, steps taken, and/or distance traversed)); and the computer system displays a second workout session user interface (e.g., 656, 688) indicative of an active workout session (e.g., a workout session user interface indicative of an active workout session of the second workout type) (in some embodiments, a second workout session user interface different from the first workout session user interface) (e.g., indicative of a currently active and/or in-progress workout session). In some embodiments, the second workout session user interface displays one or more workout performance metrics that are indicative of a physical activity level of the user during the current workout session.

In some embodiments, in response to receiving the first user input: in accordance with a determination that the first user input corresponds to selection of a fourth region (e.g., 608i-608o, 614i-614p, and/or 674i-674p) associated with the second workout platter (e.g., a fourth displayed portion and/or displayed region of the workout selection user interface associated with the second workout platter) (in some embodiments, a fourth region of the second workout platter) and different from the first region, the second region, and the third region, the computer system displays, via the display generation component, a second workout customization user interface (e.g., 624, 676) (in some embodiments, without displaying the second workout session user interface and/or without initiating a workout session of the second workout type) that includes one or more selectable options that are selectable to initiate one or more processes for customizing one or more aspects of the second workout type (e.g., an option to customize alerts for the second workout type and/or an option to customize workout performance metrics for the second workout type). Providing a user with a second workout platter wherein selection of a third region of the workout platter initiates a workout, and selection of a fourth region of the workout platter allows the user to customize one or more aspects of the workout reduces the number of inputs needed to perform either of these functions. Doing so also enables these functions to be performed without displaying additional controls.

In some embodiments, the one or more selectable options in the first workout customization user interface includes a first selectable option (e.g., 626c, 677c) that is selectable to initiate a process for modifying one or more workout metrics (e.g., physical activity metrics and/or metrics that are indicative of the physical activity level of the user) that are accessible during a workout session of the first workout type (e.g., that are able to be displayed during a workout session of the first workout type (e.g., that are automatically displayed during a workout session of the first workout type and/or that a user is able to display during a workout session of the first workout type with one or more user inputs)). In some embodiments, modifying one or more workout metrics includes selecting one or more workout metrics for display and/or one or more workout metrics to be accessible during a workout session of the first workout type and excluding one or more workout metrics from being displayed and/or being accessible during a workout session of the first workout type. Providing a user with a selectable option that is selectable to initiate a process for modifying one or more workout metrics that are accessible during a workout session of the first workout type reduces the number of inputs needed to perform this function. Doing so also enables this function to be performed without displaying additional controls.

In some embodiments, while displaying the first workout customization user interface (e.g., 624), the computer system receives, via the one or more input devices, a user input (e.g., 628c) (e.g., one or more user inputs) (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures) corresponding to selection of the first selectable option (e.g., 626c). In some embodiments, in response to receiving the user input corresponding to selection of the first selectable option, the computer system displays, via the display generation component, a preview user interface (e.g., 638) that includes: a first workout metric (e.g., a workout metric shown in 642a) that is accessible (e.g., enabled and/or selected to be accessible) (e.g., at the time of receiving the user input corresponding to selection of the first selectable option) during a workout session of the first workout type; and a second workout metric (e.g., a workout metric shown in 642b) that is accessible (e.g., enabled and/or selected to be accessible) (e.g., at the time of receiving the user input corresponding to selection of the first selectable option) during a workout session of the first workout type and is different from the first workout metric. In some embodiments, while displaying, via the display generation component and within the preview user interface, the first workout metric without displaying the second workout metric, the computer system receives, via the one or more inputs devices, a user input (e.g., rotation of input mechanism 604a in FIG. 6H) corresponding to a request to scroll the preview user interface. In some embodiments, in response to receiving the user input (e.g., one or more user inputs) (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures) corresponding to a request to scroll the preview user interface: the computer system ceases display of the first workout metric (e.g., 642*a*); and the computer system displays, via the display generation component and within the preview user interface, the second workout metric (e.g., 642*b*). In some embodiments, the preview user interface excludes (e.g., does not display and/or does not include) a third workout metric that is not selected to be accessible during a workout session of the first workout type. Displaying a scrollable preview user interface that includes a preview of one or more workout metrics that are selected to be accessible during a workout session of the first workout type provides the user with feedback about the state of the device (e.g., that a certain set of workout metrics are currently selected to be accessible during a workout session of the first workout type).

In some embodiments, the user input corresponding to the request to scroll the preview user interface includes rotation of a rotatable input mechanism (e.g., 604*a*) (e.g., FIG. 6H). In some embodiments, rotation of the rotatable input mechanism in a first rotation direction causes the preview user interface to be scrolled in a first direction, and rotation of the rotatable input mechanism in a second rotation direction different from the first rotation direction causes the preview user interface to be scrolled in a second direction different from the first direction. Allowing a user to scroll the preview user interface by rotating a rotatable input mechanism reduces the number of inputs needed to perform this function. Doing so also enables this function to be performed without displaying additional controls.

In some embodiments, while displaying, within the preview user interface (e.g., 638), the first workout metric (e.g., 642*a*): the computer system displays, via the display generation component, an edit option (e.g., 640*b*) that is selectable to indicate a user request to modify one or more workout metrics that are selected to be accessible during a workout session of the first workout type. In some embodiments, the edit option is selectable to display an edit metrics user interface that includes a first option that is selectable to enable a first workout metric to be accessed during a workout session of the first workout type, and a second option that is selectable to enable a second workout metric to be accessed during a workout session of the first workout type. Displaying an edit option that is selectable to indicate a user request to modify one or more workout metrics that are selected to be accessible during a workout session of the first workout type reduces the number of inputs needed to perform this function.

In some embodiments, in response to receiving the user input corresponding to selection of the first selectable option, the computer system displays, via the display generation component (and, optionally, in some embodiments, within the preview user interface), an automated preview animation (e.g., 640*a*) (e.g., an automated preview animation that scrolls through one or more workout metrics that are selected to be accessible during a workout session of the first workout type (e.g., without displaying one or more workout metrics that are not selected to be accessible during a workout session of the first workout type)) including: displaying, at a first time of the automated preview animation (e.g., 640*a*), the first workout metric (e.g., 642*a*) without displaying the second workout metric (e.g., 642*b*) (e.g., FIG. 6G); displaying, at a second time of the automated preview animation subsequent to the first time, scrolling of the first workout metric; and displaying, at a third time of the automated preview animation subsequent to the second time, the second workout metric without displaying the first workout metric (e.g., FIG. 6H).

In some embodiments, after displaying the automated preview animation (e.g., 640*a*) (e.g., after completion of the automated preview animation and/or after the automated preview animation has begun playing), the computer system displays, via the display generation component, an edit option (e.g., 640*b*) that is selectable to indicate a user request to modify one or more workout metrics that are selected to be accessible during a workout session of the first workout type. In some embodiments, the edit option is selectable to display an edit metrics user interface that includes a first option that is selectable to enable a first workout metric to be accessed during a workout session of the first workout type, and a second option that is selectable to enable a second workout metric to be accessed during a workout session of the first workout type. Displaying the automated preview animation provides the user with feedback about the state of the device (e.g., that a certain set of workout metrics are currently selected to be accessible during a workout session of the first workout type). Doing so also reduces the number of inputs required for a user to see which workout metrics are currently selected to be accessible during a workout session of the first workout type. Displaying an edit option that is selectable to indicate a user request to modify one or more workout metrics that are selected to be accessible during a workout session of the first workout type reduces the number of inputs needed to perform this function.

In some embodiments, the one or more selectable options in the first workout customization user interface (e.g., 624) includes a second selectable option (e.g., 626*b*) that is selectable to initiate a process for modifying one or more alerts (e.g., one or more displayed alerts and/or one or more audio alerts) that are enabled during a workout session of the first workout type. In some embodiments, modifying the one or more alerts that are enabled to be displayed during a workout session of the first workout type includes enabling a first alert type to be displayed during a workout session of the first workout type, and disabling a second alert type from being displayed during a workout session of the first workout type (e.g., based on one or more user inputs). In some embodiments, an alert includes a set of alert criteria and, if the alert criteria met during a workout session of the first workout type, the computer system and/or an external device displays an alert user interface and/or notification corresponding to the alert. In some embodiments, the one or more alerts includes a distance alert that includes a first condition that is met if the user travels and/or achieves a target distance during a workout session of the first workout type. In some embodiments, the one or more alerts includes a time alert that includes a second condition that is met if a threshold time duration elapses during a workout session of the first workout type. In some embodiments, the one or more alerts includes a calories alert that includes a third condition that is met if the user achieves a threshold number of calories (e.g., calories burned and/or active calories burned) during a workout session of the first workout type. In some embodiments, the one or more includes a heart rate alert that includes a fourth condition that is met if the user achieves a target heart rate (e.g., goes above the target heart rate and/or falls below the target heart rate) during a workout session of the first workout type. Providing a user with a selectable option that is selectable to initiate a process for modifying one or more alerts that are enabled to be presented during a workout session of the first workout type reduces the number of inputs needed to perform this function. Doing so also enables this function to be performed without displaying additional controls.

In some embodiments, while displaying, via the display generation component, the first workout customization user interface (e.g., 624) that includes the one or more selectable options that are selectable to initiate one or more processes for customizing one or more aspects of the first workout type: the computer system displays, via the display generation component, a start workout option (e.g., 626d) that is selectable to initiate a workout session of the first workout type and display the first workout session user interface. In some embodiments, while concurrently displaying the one or more selectable options that are selectable to initiate one or more processes for customizing one or more aspects of the first workout type and the start workout option, the computer system receives a user input corresponding to selection of the start workout option; and in response to receiving the user input corresponding to selection of the start workout option, the computer system: initiates a workout session of the first workout type including initiate recording of one or more physical activity metrics for the workout session of the first workout type; and displays the first workout session user interface. Providing a user with a selectable option that is selectable to initiate a workout session of the first workout type reduces the number of inputs needed to perform this function. Doing so also enables this function to be performed without displaying additional controls.

In some embodiments, the first workout platter (e.g., 608a-608g, 614a-614h, and/or 674a-674h) is associated with a first workout modality (e.g., running, biking, swimming, multisport, outdoor running, indoor running, outdoor biking, indoor biking, outdoor swimming, and/or indoor swimming), and the first workout type is a first workout type of the first workout modality (e.g., a first workout goal type (e.g., open goal, distance goal, calorie goal, route goal, distance+time goal, and/or time goal) of the first workout modality and/or a first pre-configured workout of the first workout modality). In some embodiments, the second workout platter is associated with the first workout modality, and the second workout type is a second workout type of the first workout modality (e.g., a second workout goal type (e.g., open goal, distance goal, calorie goal, route goal, distance+time goal, and/or time goal) of the first workout modality and/or a second pre-configured workout of the first workout modality). Providing a user with a first workout platter wherein selection of a first region of the workout platter initiates a workout, and selection of a second region of the workout platter allows the user to customize one or more aspects of the workout reduces the number of inputs needed to perform either of these functions. Doing so also enables these functions to be performed without displaying additional controls.

In some embodiments, the workout selection user interface (e.g., 606) further comprises a new workout option (e.g., 608h) that is selectable to initiate a process for creating (e.g., defining and/or generating) a new workout of the first workout modality. In some embodiments, after creation of a new workout of the first workout modality, the computer system displays, via the display generation component, the workout selection user interface, wherein the workout selection user interface includes the first workout platter, the second workout platter, and a third workout platter corresponding to the new workout of the first workout modality. Providing a user with a new workout option that is selectable to initiate a process for creating a new workout of the first workout modality reduces the number of inputs needed to perform this function. Doing so also enables this function to be performed without displaying additional controls.

In some embodiments, the first workout type includes a plurality of segments (e.g., multisport workout 608c) (e.g., a plurality of legs and/or a plurality of portions) arranged in an order, including a first segment (e.g., a first segment associated with a first workout modality and/or a first segment associated with a first set of actions) (e.g., a first leg and/or first portion) and a second segment (e.g., a second segment associated with a second workout modality and/or a second segment associated with a second set of actions) (e.g., a second leg and/or a second portion) (in some embodiments, a workout session of the first workout type includes the user performing the first segment before performing the second segment). In some embodiments, the one or more selectable options that are selectable to initiate one or more processes for customizing one or more aspects of the first workout type include: a third selectable option (e.g., 1614a-1614c) that is associated with the first segment (e.g., exclusively associated with the first segment; and/or without corresponding to and/or being associated with the second segment) (e.g., a third selectable option that is selectable to initiate one or more processes for customizing one or more aspects of the first segment of the first workout type (e.g., without customizing one or more aspects of the second segment of the first workout type)); and a fourth selectable option (e.g., 1614a-1614c) that is associated with the second segment (e.g., exclusively associated with the second segment; and/or without corresponding to and/or being associated with the first segment) (e.g., a fourth selectable option that is selectable to initiate one or more processes for customizing one or more aspects of the second segment of the first workout type (e.g., without customizing one or more aspects of the first segment of the first workout type)). Providing a user with a first workout platter wherein selection of a first region of the workout platter initiates a workout, and selection of a second region of the workout platter allows the user to customize one or more aspects of the workout reduces the number of inputs needed to perform either of these functions. Doing so also enables these functions to be performed without displaying additional controls.

In some embodiments, while displaying the first workout customization user interface (e.g., 1612), including displaying the third selectable option (e.g., 1614a-1614c) and the fourth selectable option (e.g., 1614a-1614c), the computer system receives, via the one or more input devices, a second user input (e.g., 1637) (e.g., one or more user inputs) (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures). In some embodiments, in response to receiving the second user input: in accordance with a determination that the second user input corresponds to selection of the third selectable option, the computer system displays, via the display generation component, a first segment customization user interface (e.g., 1628) that includes one or more selectable options (e.g., 1630a-1630e) that are selectable to initiate one or more processes for customizing one or more aspects of the first segment of the first workout type (e.g., an option to customize alerts for the first segment of the first workout type and/or an option to customize workout performance metrics for the first segment of the first workout type), including: a fifth selectable option (e.g., 1630a) that is selectable to initiate a process for modifying one or more alerts that are enabled to be displayed during the first segment of the first workout type (e.g., without modifying one or more alerts that are enabled to be displayed during the second segment of the first workout type).

In some embodiments, modifying the one or more alerts that are enabled to be displayed during the first segment of a workout session of the first workout type includes enabling a first alert type to be displayed during the first segment of a workout session of the first workout type, and disabling a second alert type from being displayed during the first segment of a workout session of the first workout type (e.g., based on one or more user inputs). In some embodiments, an alert includes a set of alert criteria and, if the alert criteria met during a workout session of the first workout type, the computer system and/or an external device displays an alert user interface and/or notification corresponding to the alert. In some embodiments, the one or more alerts includes a distance alert that includes a first condition that is met if the user travels and/or achieves a target distance during the first segment of a workout session of the first workout type. In some embodiments, the one or more alerts includes a time alert that includes a second condition that is met if a threshold time duration elapses during the first segment of a workout session of the first workout type. In some embodiments, the one or more alerts includes a calories alert that includes a third condition that is met if the user achieves a threshold number of calories (e.g., calories burned and/or active calories burned) during the first segment of a workout session of the first workout type. In some embodiments, the one or more includes a heart rate alert that includes a fourth condition that is met if the user achieves a target heart rate (e.g., goes above the target heart rate and/or falls below the target heart rate) during the first segment of a workout session of the first workout type.

In some embodiments, in response to receiving the second user input, in accordance with a determination that the second user input corresponds to selection of the fourth selectable option, the computer system displays, via the display generation component, a second segment customization user interface (e.g., different from the first segment customization user interface) that includes one or more selectable options that are selectable to initiate one or more processes for customizing one or more aspects of the second segment of the first workout type (e.g., an option to customize alerts for the second segment of the first workout type and/or an option to customize workout performance metrics for the second segment of the first workout type), including a sixth selectable option that is selectable to initiate a process for modifying one or more alerts that are enabled to be displayed during the second segment of the first workout type (e.g., without modifying one or more alerts that are enabled to be displayed during the first segment of the first workout type).

Providing a user with a selectable option that is selectable to initiate a process for modifying one or more alerts that are enabled to be presented during a first segment of the first workout type reduces the number of inputs needed to perform this function. Doing so also enables this function to be performed without displaying additional controls.

In some embodiments, while displaying the first workout customization user interface (e.g., 1612), including displaying the third selectable option (e.g., 1614a-1614c) and the fourth selectable option (e.g., 1614a-1614c), the computer system receives, via the one or more input devices, a third user input (e.g., 1637) (e.g., one or more user inputs) (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures).

In some embodiments, in response to receiving the third user input: in accordance with a determination that the third user input corresponds to selection of the third selectable option (e.g., 1614a-1614c), the computer system displays, via the display generation component, a second segment customization user interface (e.g., 1628) that includes one or more selectable options (e.g., 1630a-1630e) that are selectable to initiate one or more processes for customizing one or more aspects of the first segment of the first workout type (e.g., an option to customize alerts for the first segment of the first workout type and/or an option to customize workout performance metrics for the first segment of the first workout type), including: a sixth selectable option (e.g., 1630b) that is selectable to initiate a process for modifying one or more workout metrics (e.g., physical activity metrics and/or metrics that are indicative of the physical activity level of the user) that are accessible during the first segment of the first workout type (e.g., that are able to be displayed during a first segment of a workout session of the first workout type (e.g., that are automatically displayed during the first segment of a workout session of the first workout type and/or that a user is able to display during the first segment of a workout session of the first workout type with one or more user inputs)) (e.g., without modifying one or more workout metrics that are accessible during the second segment of the first workout type).

In some embodiments, modifying one or more workout metrics includes selecting one or more workout metrics for display and/or one or more workout metrics to be accessible during the first segment of a workout session of the first workout type and excluding one or more workout metrics from being displayed and/or being accessible during the first segment of a workout session of the first workout type. In some embodiments, in response to receiving the third user input, in accordance with a determination that the third user input corresponds to selection of the fourth selectable option, the computer system displays, via the display generation component, a third segment customization user interface (e.g., different from the second segment customization user interface) that includes one or more selectable options that are selectable to initiate one or more processes for customizing one or more aspects of the second segment of the first workout type (e.g., an option to customize alerts for the second segment of the first workout type and/or an option to customize workout performance metrics for the second segment of the first workout type), including a seventh selectable option that is selectable to initiate a process for modifying one or more workout metrics (e.g., physical activity metrics and/or metrics that are indicative of the physical activity level of the user) that are accessible during the second segment of the first workout type (e.g., that are able to be displayed during a second segment of a workout session of the first workout type (e.g., that are automatically displayed during the second segment of a workout session of the first workout type and/or that a user is able to display during the second segment of a workout session of the first workout type with one or more user inputs)) (e.g., without modifying one or more workout metrics that are accessible during the first segment of the first workout type). Providing a user with a selectable option that is selectable to initiate a process for modifying one or more workout metrics that are accessible and/or enabled to be presented during a first segment of the first workout type reduces the number of inputs needed to perform this function. Doing so also enables this function to be performed without displaying additional controls.

In some embodiments, the one or more selectable options (e.g., 1614a-1614c, 1616a-1616d) that are selectable to initiate one or more processes for customizing one or more aspects of the first workout type include a seventh selectable option (e.g., 1616a) that is selectable to initiate a process for adding a new segment to the first workout type (e.g., a third segment different from the first segment and the second segment) (e.g., a new leg and/or new portion to the first workout type). Providing a user with a selectable option that is selectable to initiate a process for adding a new segment to the first workout type reduces the number of inputs needed to perform this function. Doing so also enables this function to be performed without displaying additional controls.

In some embodiments, the one or more selectable options (e.g., 1614a-1614c, 1616a-1616d) that are selectable to initiate one or more processes for customizing one or more aspects of the first workout type include an eighth selectable option (e.g., 1630c, 1406f) that is selectable to initiate a process for reordering the plurality of segments of the first workout type (e.g., rearranging and/or changing the order of the plurality of segments). Providing a user with a selectable option that is selectable to initiate a process for reordering the plurality of segments of the first workout type reduces the number of inputs needed to perform this function. Doing so also enables this function to be performed without displaying additional controls.

In some embodiments, the workout selection user interface (e.g., 606) displays a plurality of workout platters (e.g., 608a-608g) corresponding to a plurality of workout types, including the first workout platter and the second workout platter, in a predefined order. In some embodiments, at a first time, the first workout platter is displayed before the second workout platter based on a first set of considerations, wherein the first set of considerations includes: the number of times a workout of the first workout type was completed by a user of the computer system (e.g., during a predefined duration of time (e.g., the last week, the last month, and/or the last year) or at any time); the number of times a workout of the second workout type was completed by a user of the computer system (e.g., during a predefined duration of time (e.g., the last week, the last month, and/or the last year) or at any time); how recently the first workout type was created (e.g., by a user of the computer system and/or by the computer system); and how recently the second workout type was created (e.g., by a user of the computer system and/or by the computer system). Ordering and/or re-ordering the plurality of workout platters based on the first set of considerations causes the computer system to automatically perform ordering the plurality of workout platters. Ordering the plurality of workout platters based on the first set of considerations reduces the number of inputs required to access a workout by making it easier for the user to access workouts that are more frequently used by the user.

In some embodiments, the first set of considerations further includes: how recently a workout of the first workout type was completed by a user of the computer system; and how recently a workout of the second workout type was completed by a user of the computer system. Ordering and/or re-ordering the plurality of workout platters based on the first set of considerations causes the computer system to automatically perform ordering the plurality of workout platters. Ordering the plurality of workout platters based on the first set of considerations reduces the number of inputs required to access a workout by making it easier for the user to access workouts that are more frequently used by the user and/or that have been more recently used by the user.

Note that details of the processes described above with respect to method 700 (e.g., FIG. 7) are also applicable in an analogous manner to the methods described below. For example, methods 800, 900, 1100, 1300, 1500, 1700, and/or 1800 optionally include one or more of the characteristics of the various methods described above with reference to method 700. For example, in some embodiments, the workout session in method 700 is the workout session recited in methods 800, 900, 1100, and/or 1800, and/or the workout session recited in method 700 corresponds to the workouts recited in methods 1300, 1500, and/or 1700. For brevity, these details are not repeated below.

FIG. 8 is a flow diagram illustrating a method for navigating, modifying, and outputting workout content using a computer system in accordance with some embodiments. Method 800 is performed at a computer system (e.g., 100, 300, 500) (e.g., a wearable device, a smart watch, a smart phone, a tablet, and/or a computer system controlling an external display) that is in communication with a display generation component (e.g., a display controller, a touch-sensitive display system; and/or a display (e.g., integrated and/or connected)) and one or more input devices (e.g., a touch-sensitive surface (e.g., a touch-sensitive display); an accelerometer; a rotatable input mechanism; a depressible input mechanism; and/or a rotatable and depressible input mechanism). Some operations in method 800 are, optionally, combined, the orders of some operations are, optionally, changed, and some operations are, optionally, omitted.

As described below, method 800 provides an intuitive way for navigating, modifying, and outputting workout content. The method reduces the cognitive burden on a user for navigating, modifying, and accessing workout content, thereby creating a more efficient human-machine interface. For battery-operated computing devices, enabling a user to navigate, modify, and access workout content faster and more efficiently conserves power and increases the time between battery charges.

The computer system (e.g., 600) receives (802), via the one or more input devices, a first user input (e.g., one or more user inputs) (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures) corresponding to a user request to begin a workout session (e.g., user input selecting workout platter 608a-608g, 614a-614h, and/or 674a-674h; 654; and/or 687f) (e.g., a workout session corresponding to a first workout type and/or a first workout modality) (e.g., one or more user inputs selecting an user interface object (e.g., affordance) corresponding to a user request to begin a workout session). In some embodiments, in response to receiving the first user input, the computer system displays (804), via the display generation component (e.g., 602), a first workout metrics user interface (e.g., 656, 642a) that includes a first set of workout metrics (e.g., one or more workout metrics) (e.g., a first workout metrics user interface and/or a first set of workout metrics that correspond to a workout type of the workout session) (e.g., one or more workout metrics that are indicative of the level of physical activity of the user (e.g., during the workout session)).

In some embodiments, while displaying the first workout metrics user interface, the computer system receives (806), via the one or more input devices, a second user input (e.g., 658, 660a, 660b, 690a, 690b) (e.g., one or more inputs) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures). In some embodiments, in response to receiving the second user input (808): in accordance with a determination that a second workout metrics user interface (e.g., 642a-642f, 681a-681d) has been enabled (e.g., enabled by a user) (in some embodiments, in accordance with a determination that a user setting corresponding to the second workout metrics user interface has been enabled (e.g., is in an enabled and/or activated state and not in a disabled and/or de-activated state)), the computer system displays (810), via the display generation component, the second workout metrics user interface (e.g., 642a-642f, 681a-681d) that includes a second set of workout metrics that are different from the first set of workout metrics (e.g., one or more workout metrics) (e.g., one or more workout metrics that are indicative of the level of physical activity of the user (e.g., during the workout session)) (in some embodiments, replacing display of the first workout metrics user interface with display of the second workout metrics user interface). In some embodiments, in response to receiving the second user input: in accordance with a determination that the second workout metrics user interface has not been enabled (e.g., has not been enabled by a user) (in some embodiments, in accordance with a determination that a user setting corresponding to the second workout metrics user interface has not been enabled (e.g., is in a disabled and/or de-activated state and not in an enabled and/or activated state)), the computer system displays (812), via the display generation component, a third workout metrics user interface (e.g., 642a-642f, 681a-681d) that includes a third set of workout metrics (e.g., one or more workout metrics) (e.g., one or more workout metrics that are indicative of the level of physical activity of the user (e.g., during the workout session)) that are different from the second set of workout metrics and the first set of workout metrics (in some embodiments, replacing display of the first workout metrics user interface with display of the third workout metrics user interface). In some embodiments, the third workout metrics user interface is displayed in accordance with a determination that a user setting corresponding to the third workout metrics user interface has been enabled (e.g., by a user) (e.g., is in an enabled and/or activated state and not in a disabled and/or de-activated state)). In some embodiments, in response to receiving the first user input, the computer system causes recording (e.g., tracking, logging, collecting) of physical activity metrics corresponding to the workout session (e.g., physical activity metrics indicative of a physical activity level of the user during the workout session). In some embodiments, the physical activity metrics are recorded (e.g., captured) using one or more sensors (e.g., GPS, accelerometer, gyroscope, heart rate) of the computer system or an external device that is in communication with the computer system. In some embodiments, the physical activity metrics were not being recorded or were being recorded at a lower frequency and/or lower degree of precision prior to detecting (e.g., immediately prior to detecting) the first user input corresponding to a user request to begin the workout session. In some embodiments, in response to detecting the first user input, the computer system causes one or more sensors to be enabled and/or activated to improve accurate measurements of user physical activity metrics during the workout session. Switching between workout metrics user interfaces based on user input enables this operation to be performed without displaying additional controls. Displaying the second workout metrics user interface in accordance with a determination that the second workout metrics user interface has been disabled and/or displaying the third workout metrics user interface in accordance with a determination that the second workout metrics user interface has not been enabled causes the device to automatically perform these functions without additional user input.

In some embodiments, the first user input (e.g., user input selecting workout platter 608a-608g, 614a-614h, and/or 674a-674h; 654; and/or 687f) corresponds to a user request to begin a workout session of a first workout modality (e.g., running, biking, swimming, multisport, outdoor running, indoor running, outdoor biking, indoor biking, outdoor swimming, and/or indoor swimming). In some embodiments, the first workout metrics user interface (e.g., 656, 642a) is a default workout metrics user interface for the first workout modality. In some embodiments, the computer system displays, via the display generation component, a first workout metrics configuration user interface (e.g., 645, 683) corresponding to the first workout modality, including concurrently displaying: a first selectable option (e.g., 646b-f, 684b-d) that is selectable to selectively disable (e.g., and/or selectively enable) the second workout metrics user interface for the first workout modality (e.g., for workout sessions of the first workout modality); and a second selectable option (e.g., 646b-f, 684b-d) that is selectable to selectively disable (e.g., and/or selectively enable) the third workout metrics user interface for the first workout modality (e.g., for workout sessions of the first workout modality), without displaying a selectable option to selectively disable (e.g., and/or selectively enable) the first workout metrics user interface for the first workout modality (e.g., in FIG. 6J, there is no option to selectively disable metrics user interface 642a). In some embodiments, the first workout metrics user interface does not include a selectable option to selectively disable the first workout metrics user interface for the first workout modality. In some embodiments, the first workout metrics user interface, as the default workout metrics user interface for the first workout modality, is always enabled for workout sessions of the first workout modality. In some embodiments, the second workout metrics user interface and the third workout metrics user interface are configured to be selectively enabled and/or disabled by a user for workouts of the first workout modality. Displaying the first and second selectable options corresponding to the second and third workout metrics user interface without displaying a corresponding selectable option for the first workout metrics user interface provides the user with feedback about the state of the device (e.g., that the first workout metrics user interface cannot be selectively disabled). Displaying the first and second selectable options also allows the user to selectively enable and/or disable the second and/or third workout metrics user interfaces with fewer user inputs.

In some embodiments, the computer system receives, via the one or more input devices, a third user input (e.g., user input selecting workout platter 608a-608g, 614a-614h, and/or 674a-674h; 654; and/or 687f) (e.g., one or more user inputs) (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures) corresponding to a user request to begin a second workout session (e.g., a workout session corresponding to a first workout type and/or a first workout modality) (e.g., one or more user inputs selecting an user interface object (e.g., affordance) corresponding to a user request to begin a workout session). In some embodiments, in response to receiving the third user input: in accordance with a determination that the third user input corresponds to a user request to begin a workout session of a first workout modality (e.g., user input selecting workout platter 614a-614h and/or user input 654 correspond to a user request to begin a workout session of an outdoor running modality), the computer system displays, via the display generation component, the first workout metrics user interface (e.g., 642a) that includes the first set of workout metrics; and in accordance with a determination that the third user input corresponds to a user request to begin a workout session of a second workout modality (e.g., user input selecting workout platter 674a-674h and/or user input 687f correspond to a user request to begin a workout session of an outdoor swim modality) different from the first workout modality, the computer system displays, via the display generation component, a fourth workout metrics user interface (e.g., 681a) different from the first workout metrics user interface, that includes a fourth set of workout metrics different from the first set of workout metrics. In some embodiments, the first workout metrics user interface is a default metrics user interface for the first workout modality, and the fourth workout metrics user interface is a default metrics user interface for the second workout modality. In some embodiments, different workout modalities have different default metrics user interfaces. In some embodiments, in response to a user input corresponding to a request to initiate a workout session corresponding to a respective workout modality, the computer system displays a respective default metrics user interface corresponding to the respective workout modality. Displaying the first workout metrics user interface in accordance with a determination that the third user input corresponds to a request to begin a workout session of the first workout modality, and displaying the fourth workout metrics user interface in accordance with a determination that the third user input corresponds to a request to begin a workout session of the second workout modality, causes the device to automatically perform these operations without further user input. Furthermore, displaying the fourth workout metrics user interface instead of the first workout metrics user interface when the user input corresponds to a request to initiate a workout session of the second workout modality prevents the user interface from displaying information that is not relevant to the particular user.

In some embodiments, the one or more input devices includes a rotatable input mechanism (e.g., 604a); and the second user input includes rotation of the rotatable input mechanism (e.g., 658, 660a, 660b, 690b). In some embodiments, while displaying the second workout metrics user interface: the computer system receives a user input that includes rotation of the rotatable input mechanism; and in response to the user input that includes rotation of the rotatable input mechanism: in accordance with a determination that the rotation of the rotatable input mechanism is a rotation in a first direction, the computer system displays the first workout metrics user interface; and in accordance with a determination that the rotation of the rotatable input mechanism is a rotation in a second direction different from the first direction, the computer system displays a fifth workout metrics user interface different from the first and second workout metrics user interfaces. Switching between workout metrics user interfaces based on rotation of a rotatable input mechanism enables this operation to be performed without displaying additional controls.

In some embodiments, while displaying the first workout metrics user interface (e.g., 642a), the computer system receives, via the one or more input devices, a fourth user input (e.g., 660a, 660b, 662a, 662b)) (e.g., one or more inputs) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures). In some embodiments, in response to receiving the fourth user input: in accordance with a determination that the fourth user input includes rotation of a rotatable input mechanism (e.g., 604a) in a first direction (e.g., 660a) (e.g., in an upward direction or downward direction) (and, optionally, in some embodiments, in accordance with a determination that the second workout metrics user interface has been enabled), the computer system displays, via the display generation component, the second workout metrics user interface (e.g., 642a, 642b); and in accordance with a determination that the fourth user input includes a touch input that includes movement in a second direction (e.g., 662a, 662b) (e.g., a swipe left or a swipe right) different from the first direction, the computer system displays, via the display generation component, an in-workout user interface (e.g., 664, 668) different from the first workout metrics user interface, the second workout metrics user interface, and the third workout metrics user interface. In some embodiments, while displaying the second workout metrics user interface, the computer system receives a fifth user input; and in response to receiving the fifth user input: in accordance with a determination that the fifth user input includes rotation of the rotatable input mechanism in the first direction (e.g., up or down), the computer system displays, via the display generation component, a fourth workout metrics user interface (e.g., different from the first, second, and/or third workout metrics user interfaces); in accordance with a determination that the fifth user input includes rotation of the rotatable input mechanism in a third direction different from the first and second directions (e.g., opposite the first direction) (e.g., down or up), the computer system displays, via the display generation component, the first workout metrics user interface; in accordance with a determination that the fifth user input includes a touch input that includes movement in the second direction, the computer system displays, via the display generation component, the in-workout user interface; and in accordance with a determination that the fifth user input includes a touch input that includes movement in a fourth direction different from the first, second, and third directions, the computer system displays, via the display generation component, a second in-workout user interface different from the first and second workout metrics user interfaces and the in-workout user interface. In some embodiments, the second direction is perpendicular to the first direction. Switching between workout metrics user interfaces based on rotation of a rotatable input mechanism, and switching between user interfaces in response to touch inputs (e.g., swipe inputs) enables these operations to be performed without displaying additional controls.

In some embodiments, the user request to begin a workout session comprises a user request to begin a workout session of a first workout type (e.g., a first workout modality and/or a first workout goal type). In some embodiments, displaying the first workout metrics user interface (e.g., 642a) includes concurrently displaying: the first set of workout metrics (e.g., 642a) (e.g., without displaying the second set of workout metrics and/or the third set of workout metrics); an icon associated with the first workout type (e.g., 657a) (e.g., an icon indicative of the first workout type (e.g., an icon indicative of the first workout modality and/or the first workout goal type)); and an elapsed workout time (e.g., 657*b*) for the workout session (e.g., the duration of time for which the workout session has been active). In some embodiments, displaying the second workout metrics user interface (e.g., 642*b*) includes concurrently displaying: the second set of workout metrics (e.g., 642*b*) (e.g., without displaying the first set of workout metrics and/or the third set of workout metrics); the icon associated with the first workout type (e.g., 657*a*); and the elapsed workout time (e.g., 657*b*) for the workout session. In some embodiments, displaying the third workout metrics user interface (e.g., 642*e*) includes concurrently displaying: the third set of workout metrics (e.g., 642*e*) (e.g., without displaying the first set of workout metrics and/or the second set of workout metrics); the icon associated with the first workout type (e.g., 657*a*); and the elapsed workout time (e.g., 657*b*) for the workout session. Displaying the icon associated with the first workout type and the elapsed workout time for the workout session provides the user with feedback about the state of the device (e.g., that the device has detected a currently active workout session of the first workout type and/or that the device has measured the elapsed workout time for the workout session). Switching between workout metrics user interfaces based on user input enables this operation to be performed without displaying additional controls. Displaying the second workout metrics user interface in accordance with a determination that the second workout metrics user interface has been disabled and/or displaying the third workout metrics user interface in accordance with a determination that the second workout metrics user interface has not been enabled causes the device to automatically perform these functions without additional user input.

In some embodiments, the computer system receives, via the one or more input devices, a sixth user input (e.g., 647) corresponding to a request to enable the second workout metrics user interface (e.g., 642*e*) for a second workout modality (e.g., running, biking, swimming, multisport, outdoor running, indoor running, outdoor biking, indoor biking, outdoor swimming, and/or indoor swimming). In some embodiments, in response to receiving the sixth user input, the computer system enables the second workout metrics user interface for the second workout modality, including enabling the second workout metrics user interface for: a first workout type corresponding to the second workout modality (e.g., in FIG. 6B, each workout platter corresponds to the outdoor run workout modality, but each is of a different type) (e.g., a first workout goal type (e.g., open goal, distance goal, calorie goal, time goal, time and distance goal, and/or route goal) of the first workout modality and/or a first preconfigured workout of the first workout modality) and a second workout type corresponding to the second workout modality (e.g., in FIG. 6B, each workout platter corresponds to the outdoor run workout modality, but each is of a different type) (e.g., a second workout goal type of the first workout modality and/or a second preconfigured workout of the first workout modality) different from the first workout type. In some embodiments, in response to receiving the sixth user input, the computer system enables the second workout metrics user interface for the second workout modality, including enabling the second workout metrics user interface for: a first workout type corresponding to the second workout modality; a second workout type corresponding to the second workout modality; and a third workout type corresponding to the second workout modality. In some embodiments, in response to receiving the sixth user input, the computer system forgoes enabling the second workout metrics user interface for a fourth workout type corresponding to a third workout modality different from the second workout modality. Enabling a workout metrics user interface for a plurality of workout types associated with a particular workout modality in response to a single user input corresponding to a request to enable the second workout metrics user interface for the particular workout modality reduces the number of inputs required to perform these operations.

In some embodiments, the second workout metrics user interface (e.g., 642*b*) includes (in some embodiments, concurrently displays): a representation of a first physical activity metric (e.g., outermost ring (e.g., move ring)), and a representation of a second physical activity metric (e.g., innermost ring (e.g., stand ring) and/or center ring (e.g., exercise ring)), wherein: the representation of the first physical activity metric and the representation of the second physical activity metric correspond to a predetermined amount of time (e.g., the current calendar day and/or the current 24 hour period) that includes a period of time preceding a current workout session (e.g., preceding the first user input and/or preceding displaying the first workout metrics user interface) (e.g., includes measurement of the first physical activity metric and/or the second physical activity metric during the predetermined amount of time (e.g., during the current calendar day and/or during the current 24 hour period) even while the user was not engaged in an active workout session). In some embodiments, the representation of the first physical activity metric is indicative of progress towards a first goal value for the first physical activity metric during the predetermined amount of time (e.g., a target number of hours during the current calendar day during which the user has stood for a predetermined amount of time; a target number of minutes of activity above a threshold activity level (e.g., above a target heart rate and/or within a workout session) during the current calendar day; a target number of total calories burned during the current calendar day; a target number of active calories burned during the current calendar day; a target distance traveled during the current calendar day; and/or a target number of stairs climbed during the current calendar day); and the representation of the second physical activity metric is indicative of progress towards a second goal value for the second physical activity metric during the predetermined amount of time. Displaying the representation of the first physical activity metric and/or the representation of the second physical activity metric provides the user with feedback about the state of the device (e.g., that the device has detected a certain amount of progress towards the goal value for the first physical activity metric and/or towards the goal value for the second physical activity metric).

Note that details of the processes described above with respect to method 800 (e.g., FIG. 8) are also applicable in an analogous manner to the methods described below and/or above. For example, methods 700, 900, 1100, 1300, 1500, 1700, and/or 1800 optionally include one or more of the characteristics of the various methods described above with reference to method 800. For example, in some embodiments, the workout session in method 800 is the workout session recited in methods 700, 900, 1100, and/or 1800, and/or the workout session recited in method 800 corresponds to the workouts recited in methods 1300, 1500, and/or 1700. For brevity, these details are not repeated below.

FIG. 9 is a flow diagram illustrating a method for navigating, modifying, and outputting workout content using a computer system in accordance with some embodiments.

Method 900 is performed at a computer system (e.g., 100, 300, 500) (e.g., a wearable device, a smart watch, a smart phone, a tablet, and/or a computer system controlling an external display) that is in communication with a display generation component (e.g., a display controller, a touch-sensitive display system; and/or a display (e.g., integrated and/or connected)) and one or more input devices (e.g., a touch-sensitive surface (e.g., a touch-sensitive display); an accelerometer; a rotatable input mechanism; a depressible input mechanism; and/or a rotatable and depressible input mechanism). Some operations in method 900 are, optionally, combined, the orders of some operations are, optionally, changed, and some operations are, optionally, omitted.

As described below, method 900 provides an intuitive way for navigating, modifying, and outputting workout content. The method reduces the cognitive burden on a user for navigating, modifying, and accessing workout content, thereby creating a more efficient human-machine interface. For battery-operated computing devices, enabling a user to navigate, modify, and access workout content faster and more efficiently conserves power and increases the time between battery charges.

The computer system (e.g., 600) displays (902), via the display generation component (e.g., 602), a first user interface (e.g., 638) corresponding to a first workout type (e.g., a first workout modality), including displaying a first user interface object (e.g., 640*b*). In some embodiments, displaying the first user interface includes concurrently displaying a plurality of user interface objects including the first user interface object. In some embodiments, the first user interface includes a second user interface object that is selectable to initiate a workout session of the first workout type. In some embodiments, the first user interface includes a second user interface object that includes a preview animation of currently enabled and/or activated workout metrics user interfaces for workouts of the first workout type. In some embodiments, while displaying the first user interface (e.g., 638), the computer system receives (904), via the one or more input devices, a first user input (e.g., 644) (e.g., one or more user inputs) (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures) corresponding to selection of the first user interface object (e.g., 640*b*).

In some embodiments, in response to receiving the first user input (e.g., 644), the computer system displays (906), via the display generation component, a first workout views user interface (e.g., 645) (in some embodiments, replacing display of the first user interface with display of the first workout views user interface), wherein the first workout views user interface includes: a representation of a first workout metrics user interface (e.g., 642*a*-642*f*) (908), wherein the first workout metrics user interface corresponds to a first set of workout metrics (e.g., one or more workout metrics) (e.g., one or more workout metrics that are indicative of the level of physical activity by the user (e.g., during a workout session and/or during a period of time that includes the workout session as well as time outside of the workout session)); and a representation of a second workout metrics user interface (e.g., 642*a*-642*f*) (910), wherein the second workout metrics user interface corresponds to a second set of workout metrics (e.g., one or more workout metrics) (e.g., one or more workout metrics that are indicative of the level of physical activity by the user (e.g., during a workout session)) different from the first set of workout metrics.

In some embodiments, while displaying the first workout views user interface (e.g., 645), the computer system receives (912), via the one or more input devices, a second user input (e.g., 647) (e.g., one or more user inputs) (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures) corresponding to a user request to transition the second workout metrics user interface (e.g., 642*e*) from a deactivated state to an activated state (e.g., without transitioning the first workout metrics user interface from a deactivated state to an activated state), wherein: when the second workout metrics user interface is in the activated state (914), the second workout metrics user interface, including the second set of workout metrics, is accessible by a user (e.g., can be viewed by a user) during a workout session of the first workout type (e.g., a workout session corresponding to the first workout type); and when the second workout metrics user interface is in the deactivated state (916), the second workout metrics user interface, including the second set of workout metrics, is not accessible by a user (e.g., cannot be viewed by a user) during a workout session of the first workout type (e.g., a workout session corresponding to the first workout).

In some embodiments, while displaying the first workout views user interface, the computer system receives a third user input corresponding to a user request to transition the first workout metrics user interface from a deactivated state to an activated state (e.g., without transitioning the second workout metrics user interface from a deactivated state to an activated state), wherein when the first workout metrics user interface is in the activated state, the first workout metrics user interface is accessible by a user (e.g., can be viewed by a user) during a workout session of the first workout type; and when the first workout metrics user interface is in the deactivated state, the first workout metrics user interface is not accessible by a user (e.g., cannot be viewed by a user) during a workout session of the first workout type.

In some embodiments, the first workout views user interface (e.g., 645) includes a first selectable option (e.g., 646*b*-646*f*) that is selectable to transition the second workout metrics user interface between a deactivated state and an activated state (e.g., a first selectable option that is selectable to cause the second workout metrics user interface to be transitioned from the deactivated state to the activated state and/or to be transitioned from the activated state to the deactivated state; and/or a first selectable option that is selectable to initiate a process for transitioning the second workout metrics user interface from the deactivated state to the activated state and/or from the activated state to the deactivated state). In some embodiments, the first workout views user interface does not include a selectable option that is selectable to transition the first workout metrics user interface between a deactivated state and an activated state (e.g., workout views user interface 645 does not include an option to deactivate workout metrics user interface 642*a*) (e.g., does not include an option that is selectable and/or allows a user to transition the first workout metrics user interface to a deactivated state). In some embodiments, the first workout metrics user interface represents a default workout metrics user interface for the first workout type. Displaying the first selectable option corresponding to the second workout metrics user interface without displaying a corresponding selectable option for the first workout metrics user interface provides the user with feedback about the state of the device (e.g., that the first workout metrics user interface cannot be selectively disabled). Displaying the first selectable option also allows the user to selectively enable and/or disable the second workout metrics user interface with fewer user inputs.

In some embodiments, the first workout views user interface (e.g., 645) corresponds to the first workout type. In some embodiments, the computer system (e.g., 600) displays, via the display generation component (e.g., 602), a second workout views user interface (e.g., 683) corresponding to a second workout type different from the first workout type, wherein the second workout views user interface includes: a representation of a third workout metrics user interface (e.g., 681*a*) different from the first workout metrics user interface and the second workout metrics user interface (e.g., 681*c* in FIG. 6U is the same as 642*b* in FIG. 6J), wherein the third workout metrics user interface corresponds to a third set of workout metrics (e.g., one or more workout metrics) (e.g., one or more workout metrics that are indicative of the level of physical activity by the user (e.g., during a workout session and/or during a period of time that includes the workout session as well as time outside of the workout session)) different from the first set of workout metrics and the second set of workout metrics; a representation of a fourth workout metrics user interface (e.g., 681*d*) different from the third workout metrics user interface, wherein the fourth workout metrics user interface corresponds to a fourth set of workout metrics (e.g., one or more workout metrics) (e.g., one or more workout metrics that are indicative of the level of physical activity by the user (e.g., during a workout session and/or during a period of time that includes the workout session as well as time outside of the workout session)) different from the third set of workout metrics; and a second selectable option (e.g., 684*d*) that is selectable to transition the fourth workout metrics user interface (e.g., 681*d*) between a deactivated state and an activated state (e.g., a second selectable option that is selectable to cause the fourth workout metrics user interface to be transitioned from the deactivated state to the activated state and/or to be transitioned from the activated state to the deactivated state; and/or a second selectable option that is selectable to initiate a process for transitioning the fourth workout metrics user interface from the deactivated state to the activated state and/or from the activated state to the deactivated state) without including a selectable option that is selectable to transition the third workout metrics user interface between a deactivated state and an activated state. In some embodiments, the third workout metrics user interface represents a default workout metrics user interface for the second workout type. In some embodiments, when the fourth workout metrics user interface is in the activated state, the fourth workout metrics user interface, including the fourth set of workout metrics, is accessible by a user (e.g., can be viewed by a user) during a workout session of the second workout type (e.g., a workout session corresponding to the second workout type); and when the fourth workout metrics user interface is in the deactivated state, the fourth workout metrics user interface, including the fourth set of workout metrics, is not accessible by a user (e.g., cannot be viewed by a user) during a workout session of the second workout type (e.g., a workout session corresponding to the second workout type). Displaying the second selectable option corresponding to the fourth workout metrics user interface without displaying a corresponding selectable option for the third workout metrics user interface provides the user with feedback about the state of the device (e.g., that the third workout metrics user interface cannot be selectively disabled). Displaying the second selectable option also allows the user to selectively enable and/or disable the fourth workout metrics user interface with fewer user inputs.

In some embodiments, the first workout views user interface (e.g., 645) corresponds to the first workout type (e.g., a first workout modality). In some embodiments, the computer system (e.g., 600) displays, via the display generation component (e.g., 602), a third workout views user interface (e.g., 683) corresponding to a third workout type (e.g., a third workout modality) different from the first workout type. In some embodiments, the third workout views user interface includes a representation of a fifth workout metrics user interface (e.g., 681*a*-681*d*) different from the first workout metrics user interface and the second workout metrics user interface (e.g., 681*c* in FIG. 6U is the same as 642*b* in FIG. 6J) and the fifth workout metrics user interface corresponds to a fifth set of workout metrics (e.g., one or more workout metrics) (e.g., one or more workout metrics that are indicative of the level of physical activity by the user (e.g., during a workout session and/or during a period of time that includes the workout session as well as time outside of the workout session)) different from the first set of workout metrics and the second set of workout metrics. In some embodiments, the third workout views user interface (e.g., 683) does not include the representation of the first workout metrics user interface (e.g., 642*a*). In some embodiments, the first workout views user interface does not include the representation of the fifth workout metrics user interface. In some embodiments, the third workout views user interface does not include the representation of the second workout metrics user interface. In some embodiments, the third workout views user interface includes the representation of the second workout metrics user interface. Displaying the third workout views user interface that includes the representation of the fifth workout metrics user interface without including the representation of the first workout metrics user interface provides the user with feedback about the state of the device (e.g., that the first workout metrics user interface is not available for the third workout type while the fifth workout metrics user interface is available for the third workout type). Furthermore, doing so also avoids cluttering the display with user interface elements that are not relevant to the particular user and/or the particular workout type.

In some embodiments, the third workout views user interface (e.g., 683) includes the representation of the second workout metrics user interface (e.g., 681*c* in FIG. 6U is the same as 642*b* in FIG. 6J). Displaying the third workout views user interface that includes the representation of the second and fifth workout metrics user interfaces without including the representation of the first workout metrics user interface provides the user with feedback about the state of the device (e.g., that the first workout metrics user interface is not available for the third workout type while the second and fifth workout metrics user interfaces are available for the third workout type).

In some embodiments, the first workout views user interface (e.g., 645) further comprises: a representation of a sixth workout metrics user interface (e.g., 642*b*-642*f*) different from the representation of the first without metrics user interface and the second workout metrics user interface, wherein the sixth workout metrics user interface corresponds to a sixth set of workout metrics different from the first set of workout metrics and the second set of workout metrics; an activation option (e.g., 646*b*-646*f*) corresponding to the second workout metrics user interface that is selectable to transition the second workout metrics user interface between a deactivated state and an activated state; an activation option (e.g., 646b-646f) corresponding to the sixth workout metrics user interface that is selectable to transition the sixth workout metrics user interface between a deactivated state and an activated state; and an edit option (e.g., 648c) corresponding to the second workout metrics user interface that is selectable to initiate a process for editing the second set of workout metrics corresponding to the second workout metrics user interface. In some embodiments, the first workout views user interface does not include: an activation option corresponding to the first workout metrics user interface (e.g., 642a does not have a corresponding activation option) that is selectable to transition the first workout metrics user interface between a deactivated state and an activated state; and an edit option corresponding to the third workout metrics user interface (e.g., in FIG. 6J only platter 642c has a corresponding edit option 648c—platters 642a, 642b, 642d-642f does not have a corresponding edit option) that is selectable to initiate a process for editing the sixth set of workout metrics corresponding to the sixth workout metrics user interface. In some embodiments, when the sixth workout metrics user interface is in the activated state, the sixth workout metrics user interface, including the sixth set of workout metrics, is accessible by a user (e.g., can be viewed by a user) during a workout session of the first workout type (e.g., a workout session corresponding to the first workout type); and when the sixth workout metrics user interface is in the deactivated state, the sixth workout metrics user interface, including the sixth set of workout metrics, is not accessible by a user (e.g., cannot be viewed by a user) during a workout session of the first workout type (e.g., a workout session corresponding to the first workout type). Displaying the first workout views user interface that includes activation options for the second and sixth workout metrics user interfaces but does not include a corresponding activation option for the first workout metrics user interface provides the user with feedback about the state of the device (e.g., that the first workout metrics user interface cannot be deactivated for the first workout type). Displaying the first workout views user interface that includes an edit option for the second workout metrics user interface but does not include a corresponding edit option for the sixth workout metrics user interface provides the user with feedback about the state of the device (e.g., that the sixth workout metrics user interface cannot be edited). Furthermore, doing so also avoids cluttering the display with user interface elements that are not relevant to the particular user and/or the particular workout type.

In some embodiments, in response to receiving the second user input (e.g., 647) corresponding to the user request to transition the second workout metrics user interface from the deactivated state to the activated state: the computer system activates the second workout metrics user interface for the first workout type (e.g., enabling the second workout metrics user interface to be accessed and/or viewed during workout sessions of the first workout type) (e.g., without activating the second workout metrics user interface for a second workout type), including activating the second workout metrics user interface for: a first workout subtype (e.g., a workout goal type and/or a pre-configured workout) corresponding to the first workout type (e.g., activating the second workout metrics user interface for all the different workouts in FIG. 6B, which each correspond to the outdoor run workout type) (e.g., a first workout goal type and/or a first pre-configured workout for a first workout modality); and a second workout subtype (e.g., a workout goal type and/or a pre-configured workout) corresponding to the first workout type (e.g., activating the second workout metrics user interface for all the different workouts in FIG. 6B, which each correspond to the outdoor run workout type) (e.g., a second workout goal type and/or a second pre-configured workout for a first workout modality) and different from the first workout subtype. Activating a workout metrics user interface for a plurality of workout subtypes associated with a particular workout type in response to a single user input corresponding to a request to activate the second workout metrics user interface for the particular workout type reduces the number of inputs required to perform these operations.

In some embodiments, displaying the first user interface (e.g., 638) corresponding to the first workout type includes: displaying, via the display generation component (and, optionally, in some embodiments, within the first user interface), an automated preview animation (e.g., 640a) (e.g., an automated preview animation that scrolls through one or more workout metrics user interfaces that are activated, enabled, and/or selected to be accessible during a workout session of the first workout type (e.g., without displaying one or more workout metrics user interface that are not activated, enabled, and/or selected to be accessible during a workout session of the first workout type)) including: displaying, at a first time of the automated preview animation (e.g., 640a), the first workout metrics user interface (e.g., 642a) without displaying the second workout metrics user interface; displaying, at a second time of the automated preview animation (e.g., 640a) subsequent to the first time, scrolling of the first workout metric; and displaying, at a third time of the automated preview animation (e.g., 640a) subsequent to the second time, the second workout metrics user interface (e.g., 642b) without displaying the first workout metrics user interface. In some embodiments, after displaying the automated preview animation (e.g., after completion of the automated preview animation and/or after the automated preview animation has begun playing), the computer system displays, via the display generation component, the first user interface object. Displaying the automated preview animation provides the user with feedback about the state of the device (e.g., that a certain set of workout metrics user interfaces are currently activated, enabled, and/or selected to be accessible during a workout session of the first workout type). Doing so also reduces the number of inputs required for a user to see which workout metrics are currently activated, enabled, and/or selected to be accessible during a workout session of the first workout type.

Note that details of the processes described above with respect to method 900 (e.g., FIG. 9) are also applicable in an analogous manner to the methods described below and/or above. For example, methods 700, 800, 1100, 1300, 1500, 1700, and/or 1800 optionally include one or more of the characteristics of the various methods described above with reference to method 900. For example, in some embodiments, the workout session in method 900 is the workout session recited in methods 700, 800, 1100, and/or 1800, and/or the workout session recited in method 900 corresponds to the workouts recited in methods 1300, 1500, and/or 1700. For brevity, these details are not repeated below.

FIGS. 10A-10S illustrate exemplary user interfaces for outputting workout content, in accordance with some embodiments. The user interfaces in these figures are used to illustrate the processes described below, including the processes in FIGS. 11A-11B and 18.

FIG. 10A illustrates electronic device 600, which is a smart watch with touch-sensitive display 602, rotatable input mechanism 604a, and button 604b. At FIG. 10A, electronic device 600 displays workout selection user interface 606, which was discussed above with reference to FIG. 6A. However, whereas in FIG. 6A, workout option 608d was displayed as a fourth workout, workout option 608d is displayed as the first and/or top workout in FIG. 10A. Workout option 608d is a workout with the outdoor run modality type and the race a route goal type, in which the user races against previous instances in which the user completed the same route during a workout. In FIG. 10A, workout option 608d is displayed at the top of workout selection user interface 606 in response to a determination that electronic device 600 is nearby (e.g., satisfies proximity criteria relative to) a route that the user previously completed during a workout (e.g., a 5-mile route in Palo Alto). In some embodiments, during and/or after a run (e.g., an outdoor run of one or more goal types), the user is provided with an option to either save the route from the run as an option for future race a route workouts, or forget the route so that the route is not surfaced and/or saved as a race a route option in the future. At FIG. 10A, electronic device 600 detects user input 1000 (e.g., a tap input) corresponding to selection of workout option 608d.

Figure 10B:
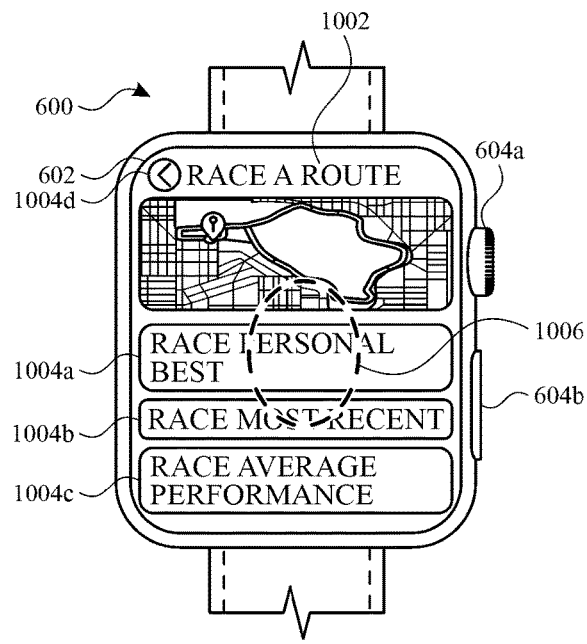

At FIG. 10B, in response to user input 1000, electronic device 600 displays user interface 1002. User interface 1002 includes a map representation of the previously completed 5-mile Palo Alto route, and options 1004a-1004c corresponding to different instances in which the user completed the 5-mile Palo Alto route. Option 1004a is selectable for the user to race against a first previous instance in which the user completed the 5-mile Palo Alto route in the fastest time. Option 1004b is selectable for the user to race against a most recent instance in which the user completed the 5-mile Palo Alto route. Option 1004c is selectable for the user to race against an average performance of the user on the 5-mile Palo Alto route, which takes one or more previous instances (e.g., all previous instances and/or a set of previous instances) in which the user completed the 5-mile Palo alto route and generates an average performance based on the one or more previous instances. Although FIG. 10B depicts only three options in user interface 1002, in various embodiments, additional options are presented. For example, in some embodiments, the user is able to select any previous instance in which he or she completed the route to race against that instance. In some embodiments, rather than choosing to race a particular previous workout instance, the user is able to define a target completion time for the previously completed route, and is able to race against a representation of the target completion time. In some embodiments, the user is able to define a target route and define a target completion time without previously completing the route. At FIG. 10B, electronic device 600 detects user input 1006 (e.g., a tap input) corresponding to option 1004a.

Figure 10C:
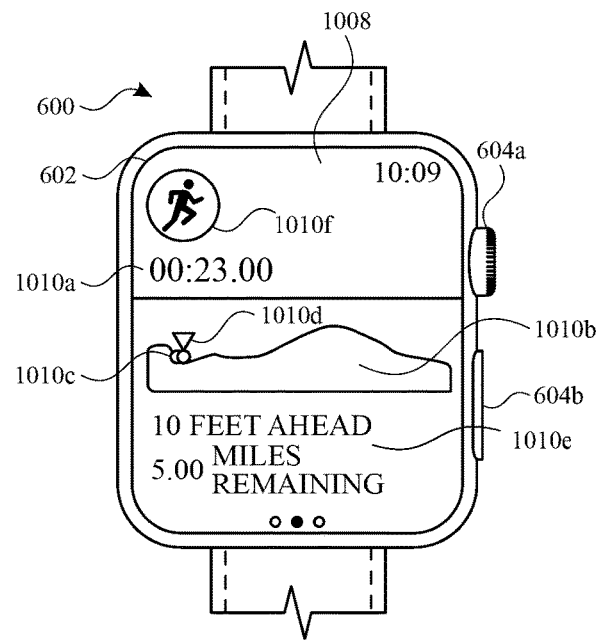

At FIG. 10C, in response to user input 1006, electronic device 600 displays in-workout user interface 1008 corresponding to the outdoor run modality type, the race a route goal type, and the 5-mile Palo Alto route. In-workout user interface 1008 includes modality indication 1010f (indicative of the outdoor run modality type) and elapsed time indication 1010a (indicative of the time that has elapsed in the workout). In-workout user interface 1008 also includes route representation 1010b, which in FIG. 10C is an elevation profile representation of the 5 mile Palo Alto route, user position indication 1010d, which is indicative of the user's current position on the route, and target (e.g., previous) instance representation 1010c, which is indicative of the target completion time (e.g., the user's position on the route at the same time (e.g., the same elapsed time) during the previous workout instance (e.g., the previous workout instance the user chose to race) and/or a target pace associated with a target completion time defined by the user). The user can see whether he or she is ahead of or behind the target completion time, e.g., his or her previous performance, by looking at representations 1010c and 1010d. In-workout user interface also includes position information 1010e, which indicates whether the user is ahead of or behind their previous performance, and by how much. In FIG. 10C, at the 23 second mark of the run, the user is 10 feet ahead of where the user was during their previous best performance. In some embodiments, one or more elements of in-workout user interface 1008 are displayed differently based on whether the user is ahead of or behind their previous performance. For example, in some embodiments, user position representation 1010d is displayed in a visually distinct way, e.g., using a first color, if the user is beating their previous performance, and displayed in a second visually distinct way, e.g., using a second color, if the user is behind their previous performance.

Figure 10D:
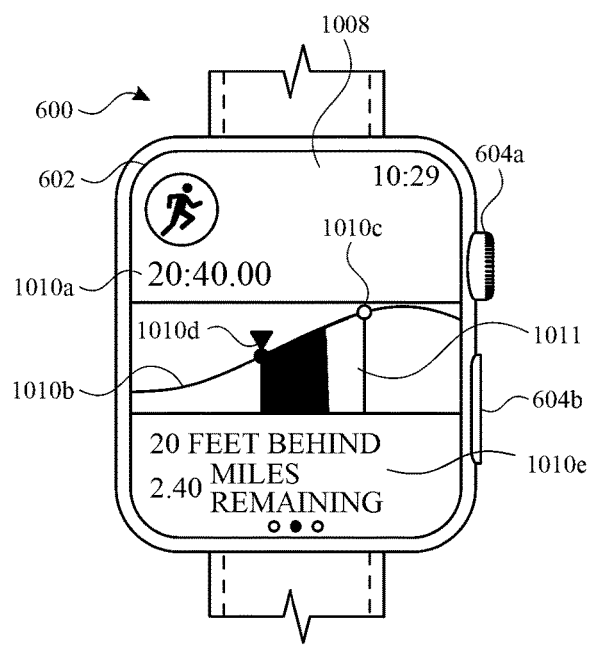

At FIG. 10D, the user is 20 minutes and 40 seconds into their run, and are now 20 feet behind the target time, e.g., their previous workout instance. In FIG. 10D, electronic device 600 is displaying a zoomed-in version of in-workout user interface 1008, whereas FIG. 10C depicted a zoomed-out version. In the depicted embodiment, the zoomed-out version of in-workout user interface 1008 displays a representation of the entirety of the route in route representation 1010b, and in the zoomed-in version of in-workout user interface 1008, only a small portion of the route is displayed. In the zoomed-out version, the user is able to get a better sense of how much of the route is still remaining, whereas in the zoomed-in version, the user is able to see more clearly how far the user is from his or her previous performance (either behind or ahead). In some embodiments, in the zoomed-in version of in-workout user interface 1008, a color gradient 1011 is displayed between user position indication 1010d and target instance representation 1010c. In some embodiments, color gradient 1011 is displayed in a first color if the user is ahead of his or her previous workout instance, and displayed in a different color if the user is behind. In some embodiments, the color gradient is not displayed in the zoomed-out version of in-workout user interface 1008. In some embodiments, electronic device 600 automatically and/or periodically transitions between the zoomed-in and zoomed-out versions of in-workout user interface 1008. In some embodiments, electronic device 600 transitions between the two versions based on user input.

Figure 10E:
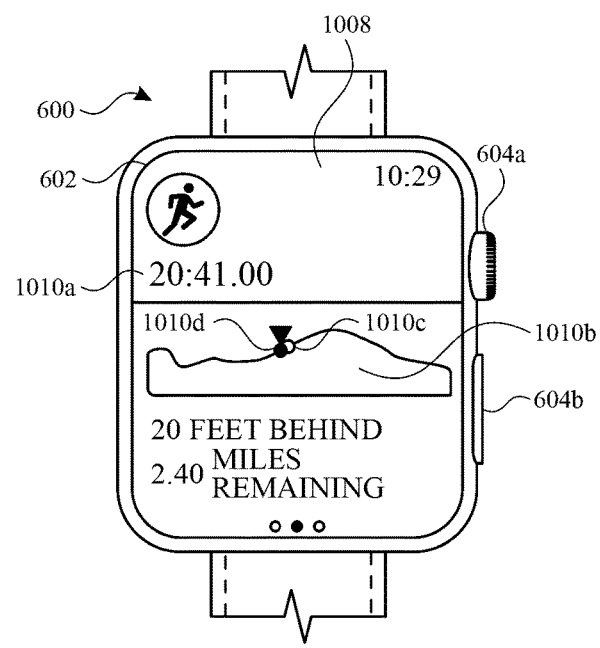

At FIG. 10E, electronic device 600 transitions back to displaying the zoomed-out version of in-workout user interface 1008. In FIGS. 10D and 10E, user position indication 1010d is displayed in a different color from FIG. 10C, because the user has fallen behind the previous workout instance.

Figure 10F:
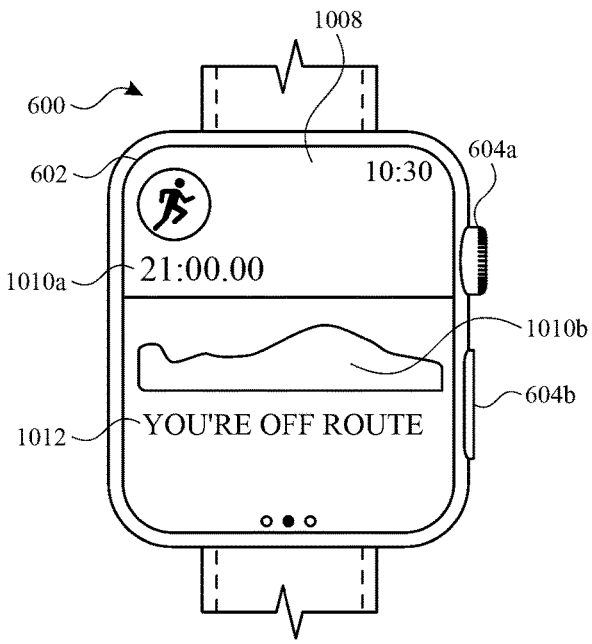

At FIG. 10F, electronic device 600 detects that the user is no longer on the route (e.g., is a threshold distance away from the route). In response, electronic device 600 ceases display of user position indication 1010d and target instance representation 1010c, and displays indication 1012.

Figure 10G:
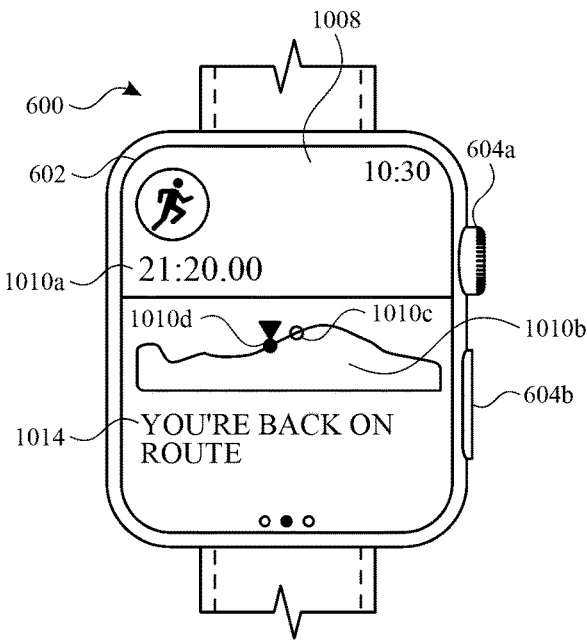

FIG. 10G depicts a first example scenario in which, after FIG. 10F, electronic device 600 detects (e.g., within a threshold period of time) that the user is back on the route and, in response, re-displays user position indication 1010*d* and target instance representation 1010*c*, and displays indication 1014.

Figure 10H:
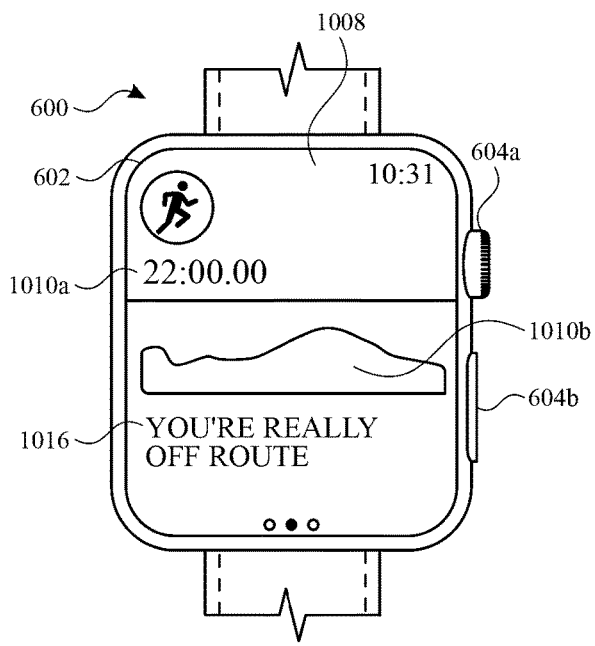
Figure 10I:
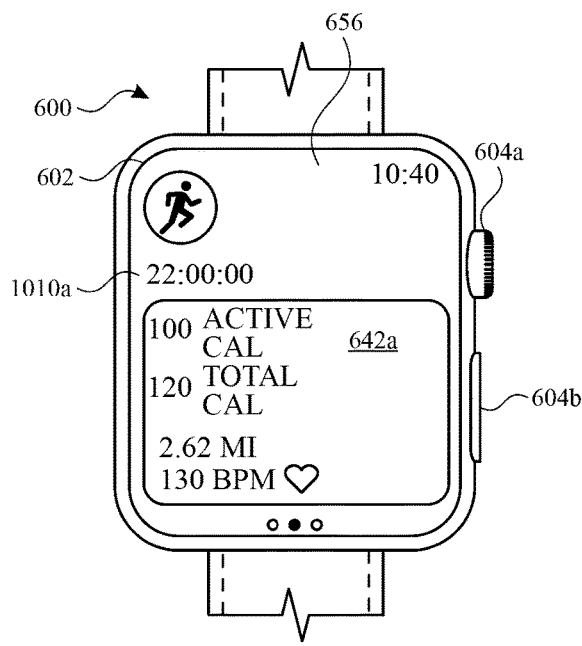

FIG. 10H depicts a second example scenario in which, after FIG. 10F, electronic device 600 detects that the user is further away from the route and, in response displays indication 1016. In FIG. 10I, electronic device 600 detects that the user is greater than a second threshold distance away from the route and, in response, replaces display of in-workout user interface 1008 (which corresponds to the race a route goal type of the outdoor run modality type) with display of in-workout user interface 656, which corresponds to an open goal type of the outdoor run modality type. In FIG. 10I, the user is no longer racing against his or her previous workout instance, and is shown a user interface for an open goal run. In FIG. 10I, in-workout user interface 656 displays workout metrics 642*a* for the entirety of the run, even prior to transitioning from user interface 1008 to user interface 656.

FIG. 10J depicts an example scenario in which the user stayed on the route and is nearing completion of the route. In FIG. 10K, the user has completed the route, but has continued to run. In FIG. 10K, in response to the user completing the route and continuing to run, electronic device 600 replaces display of in-workout user interface 1008 (corresponding to the race a route goal type) with display of in-workout user interface 656 (corresponding to an open goal type of the outdoor run modality type). In FIG. 10K, in-workout user interface 656 maintains display of elapsed time indication 1010*a*, but displays new and/or reset workout metrics 604*b* for just the open goal portion of the user's run.

Figure 10L:
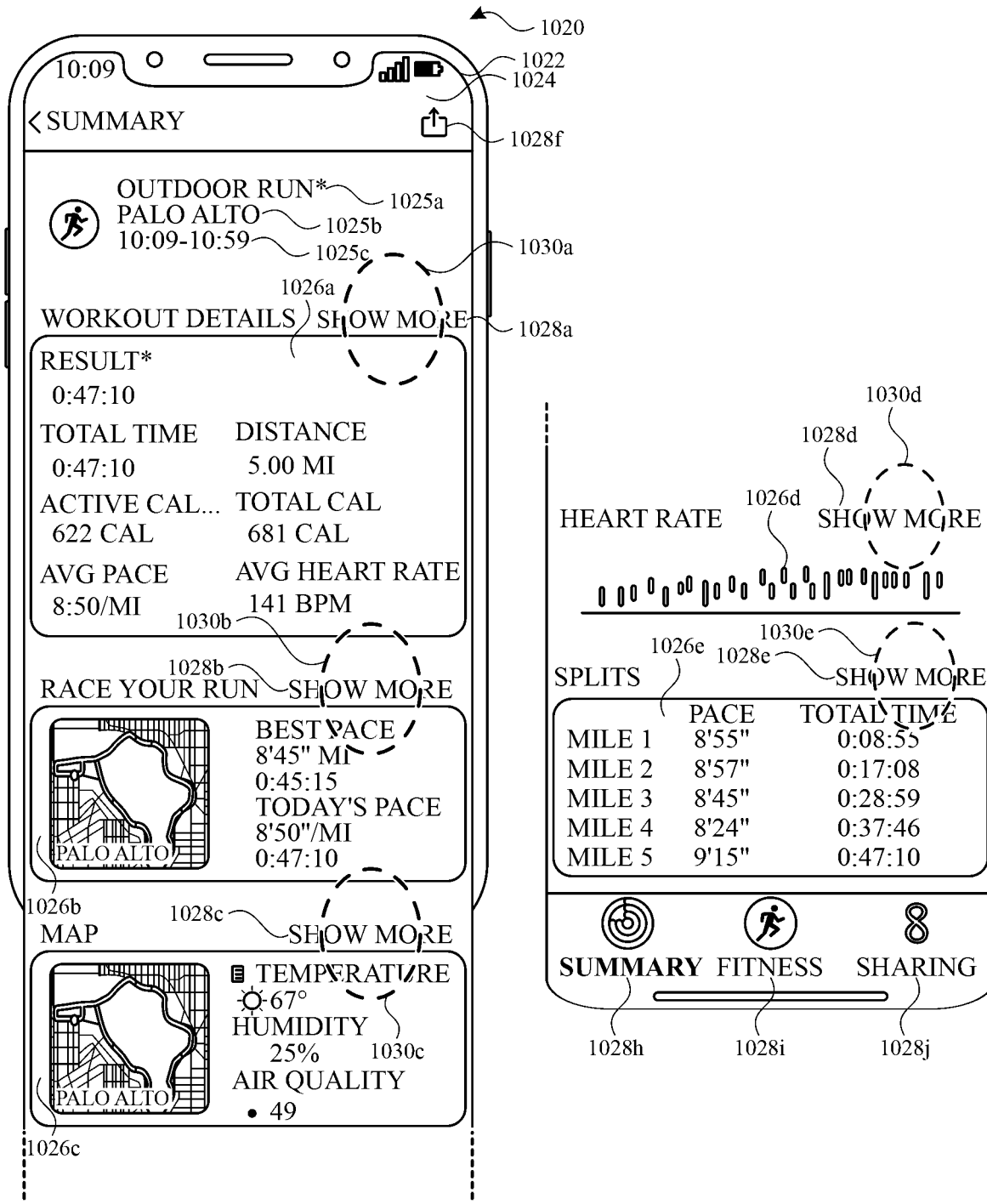

FIG. 10L depicts electronic device 1020, which is a smartphone with touch-sensitive display 1022. In FIG. 10L, after completion of a race a route workout, electronic device 1020 displays workout summary user interface 1024. While the example embodiment in FIG. 10L shows workout summary user interface 1024 being displayed on electronic device 1020, in some embodiments, workout summary user interface 1024 is displayed on electronic device 600.

In FIG. 10L, workout summary user interface 1024 includes modality indication 1025*a*, location information 1025*b*, and date/time information 1025*c* corresponding to the completed workout. Workout summary user interface 1024 also includes share option 1028*f* that is selectable to initiate a process for sharing workout summary information with one or more other users and/or devices.

Workout summary user interface 1024 displays various categories of workout information 1026*a*-1026*e*, and also displays options 1028*a*-1028*e* that are selectable to display additional workout information in each category. Workout summary user interface 1024 includes workout details section 1026*a*, race your run section 1026*b*, map section 1026*c*, heart rate section 1026*d*, and splits section 1028*e*. Workout details section 1026*a* includes total time, distance, active calories, total calories, average pace, and average heart rate for the workout. Race your run section 1026*b* includes a map representation of the route, metrics for the previous workout instance (e.g., pace during the previous workout instance and completion time for the previous workout instance) as well as metrics for the current workout (e.g., pace and completion time for the current workout). Map section 1026*c* includes a map representation of the route, temperature information, humidity information, and air quality information for the current workout. Heart rate section 1026*d* displays an x-axis timeline of the workout, and a chart of the user's heartrate at various times throughout the workout. Splits section 1026*e* displays workout metrics for different segments of the workout (e.g., for each mile of the 5 mile workout).

At FIG. 10L, electronic device 600 detects user input 1030*a* (e.g., a tap input) corresponding to selection of option 1028*a*, user input 1030*b* (e.g., a tap input) corresponding to selection of option 1028*b*, user input 1030*c* (e.g., a tap input) corresponding to selection of option 1028*c*, user input 1030*d* (e.g., a tap input) corresponding to selection of option 1028*d*, and user input 1030*e* (e.g., a tap input) corresponding to selection of option 1028*e*, each of which will be discussed in turn below.

Figure 10M:
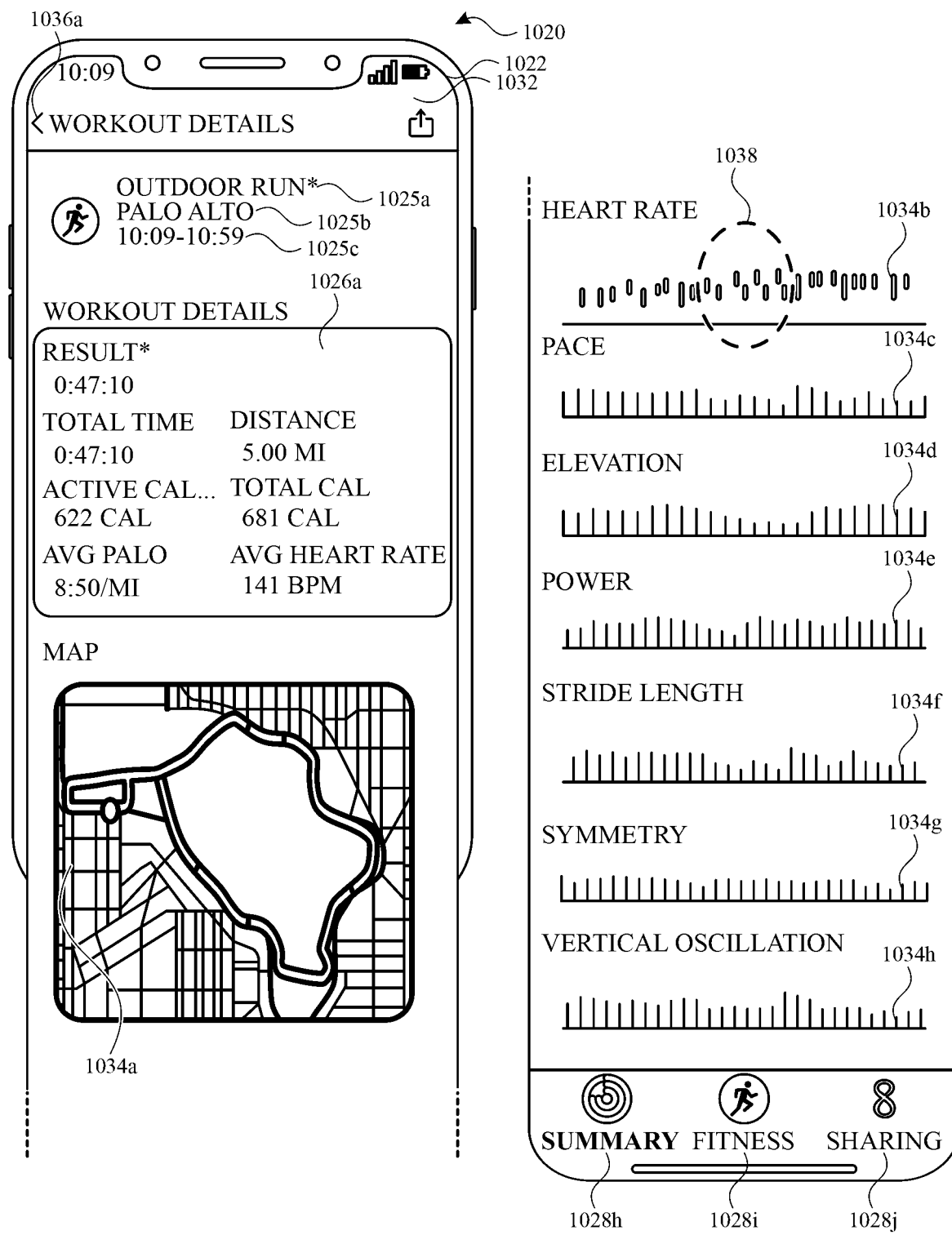

At FIG. 10M, in response to user input 1030*a*, electronic device 600 displays workout details user interface 1032. Workout details user interface 1032 includes the same information 1025*a*-1025*c* and 1026*a* that was presented in workout summary user interface 1024, but also displays additional workout information that was not displayed in workout summary user interface 1024. Workout details user interface 1032 includes map representation 1034*a* of the completed route. Workout details user interface 1032 also includes charts 1034*a*-1034*h* in which various workout metrics are charted along a timeline representative of the workout. For example, chart 1034*b* charts the user's heartrate at various times from the beginning of the workout (leftmost point on the timeline) to the end of the workout (rightmost point on the timeline); chart 1034*c* charts the user's pace at various times from the beginning of the workout to the end of the workout; chart 1034*d* charts the user's elevation at various times from the beginning of the workout to the end of the workout, and so forth. In some embodiments, the user is able to tap on any of the charts 1034*b* to view workout metrics for the time position that corresponds to the user's input. At FIG. 10M, electronic device 600 detects user input 1038 (e.g., a tap input), which corresponds to a position on chart 1034*b* that is approximately at a middle point of the workout.

Figure 10N:
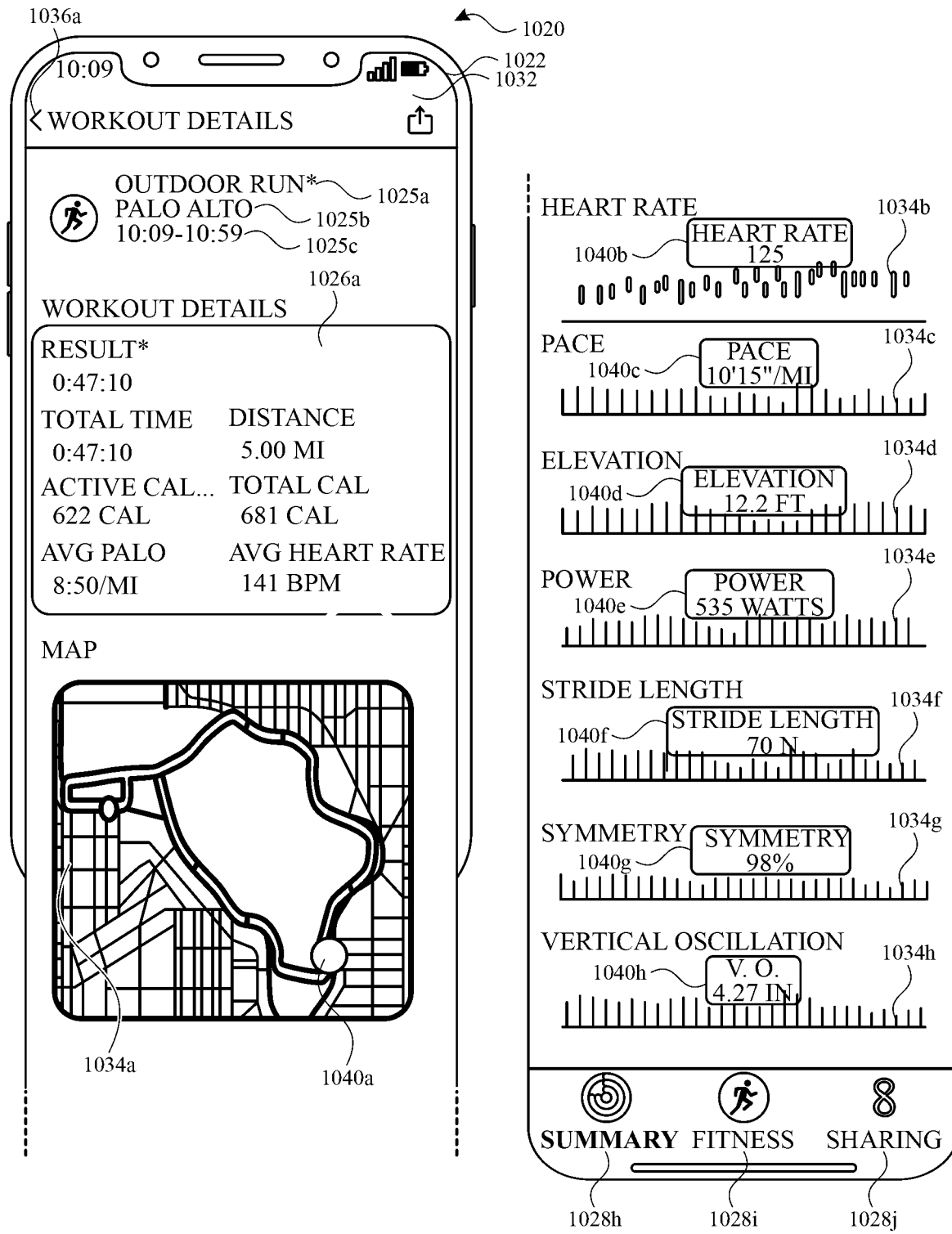

At FIG. 10N, in response to user input 1038, electronic device 600 displays information objects 1040*b*-1040*h* for each of the workout metrics represented by charts 1034*b*-1034*h*. Information objects 1040*b*-1040*h* display a workout metric value for each workout metric corresponding to the time position selected by the user. For example, in FIG. 10M, user input 1038 corresponded to an elapsed time of 25 minutes and 0 seconds. Accordingly, information object 1040*b* displays the user's heartrate at 25 minutes and 0 seconds into the workout, information object 1040*c* displays the user's pace at 25 minutes and 0 seconds into the workout, information object 1040*d* displays the user's elevation at 25 minutes and 0 seconds into the workout, information object 1040*e* displays the user's run power at 25 minutes and 0 seconds into the workout, and so forth. Furthermore, in response to user input 1038, map representation 1034*a* displays position indication 1040*a* indicative of the user's geographic position on the route at the 25 minutes and 0 seconds mark of the workout. The user is able to provide another user input corresponding to a second, different time position along any of charts 1034*b*-1034*h* to display workout metrics for the second time position. Workout details user interface 1032 includes option 1036*a* that is selectable to return to workout summary user interface 1024.

At FIG. 10O, in response to user input 1030*d* (from FIG. 10L), electronic device 600 displays heart rate details user interface 1042. Heart rate details user interface 1042 includes a chart 1044 similar to chart 1026*d* of workout summary user interface 1024, but also includes additional heart rate information. In some embodiments, chart 1044 shows more information than chart 1026*d*. For example, chart 1044 displays colors and/or other indications indicating, for various time segments through the workout, what heart rate zone the user was in for that time segment of the workout. Heart rate details user interface 1042 also includes information indicating how much time the user spent in each heart rate zone during the workout (e.g., 8:50 in Zone 1, 9:00 in Zone 2, 14:10 in Zone 3, 8:00 in Zone 4, and 7:10 in Zone 5), as well as the heart rate ranges for each zone. Heart rate details user interface 1042 also includes option 1046 that is selectable to return to workout summary user interface 1024.

At FIG. 10P, in response to user input 1030*b* (from FIG. 10L), electronic device 600 displays race a route details user interface 1048. Race a route details user interface 1048 includes map representation 1056 and information 1050 that was displayed in workout summary user interface 1024, as well as additional information. Race a route details user interface 1048 includes chart 1052 which charts the user's pace over time during today's workout against the user's pace over time during the previous workout instance. Race a route details user interface 1048 also includes list 1054 which displays workout metrics (e.g., pace and time) for today's workout, and for the previous workout instance the user raced today (e.g., "BEST"), as well as additional previous instances. In some embodiments, list 1054 displays all previous workout instances in which the user completed the route. In some embodiments, list 1054 is ranked (e.g., by pace and/or completion time or a different metric) so that the user can see how his or her performance today ranks among all of their instances completing the same route. Race a route details user interface 1048 includes option 1058 that is selectable to return to workout summary user interface 1024.

At FIG. 10Q, in response to user input 1030*e* (from FIG. 10L), electronic device 600 displays splits details user interface 1060, which provides additional workout metrics (e.g., HR AVG in FIG. 10Q) for each of the splits shown in workout summary user interface 1024. In some embodiments, splits details user interface 1060 includes one or more options that are selectable to change how the workout is split (e.g., to change the splits distance from 1 mile to half mile, or to 2.5 miles, etc.), and allows the user to see splits information for different types of splits. Splits details user interface 1060 includes option 1064 that is selectable to return to workout summary user interface 1024.

At FIG. 10R, in response to user input 1030*c* (from FIG. 10L), electronic device 600 displays map details user interface 1066. Map details user interface 1066 displays a larger map representation 1068 than what was presented in workout summary user interface 1024. Map details user interface 1066 also depicts additional information. For example, map details user interface 1066 displays map representation 1068 with two or more colors to indicate which portions of the route the user was ahead of the previous workout instance, and which portions of the route the user was behind of the previous workout instance. Accordingly, the user is also able to see locations on the map where the user overtook (e.g., caught up to) the previous workout instance (e.g., where the maps changes from the first color to the second color) or where the user fell behind the previous workout instance (e.g., where the map changes from the second color to the first color). In some embodiments, in map details user interface 1066, the user is also able to zoom in on the map or zoom out of the map (e.g., via a pinch or spread gesture), whereas the user is not able to zoom on map representation 1026*c* in workout summary user interface 1024. Map details user interface 1066 includes option 1070 that is selectable to return to workout summary user interface 1024.

FIG. 10S depicts a continuation of the example scenario shown in FIG. 10K, where the user completed the previously run route, but continued to run, and electronic device 600 transitioned from a race a route workout to an additional open goal workout. In FIG. 10S, electronic device 600 displays workout summary user interface 1024-1, which is similar to workout summary user interface 1024, but now includes selectable objects 1072*a* and 1072*b*. Object 1072*a* corresponds to a race a rate portion of the user's workout, and option 1072*b* corresponds to an open goal portion of the user's workout. Object 1072*a* is selectable to view the same information that was shown in workout summary user interface 1024, while option 1072*b* is selectable to view workout metrics for the open goal portion of the user workout (e.g., that occurred after the user completed the 5 mile Palo Alto route). In FIG. 10S, option 1072*b* is selected, and workout summary user interface 1024-1 displays workout metrics for the open goal portion of the user's run, which was 28 minutes and 59 seconds long and covered 3.1 additional miles. Map region 1026*c*-1, heart rate region 1026*d*-1, and splits region 1026*e*-1 show workout metrics for only the open goal portion of the user's workout, and does not show workout metrics for the race a route portion of the user's workout. Similarly, options 1028*c*-1, 1028*d*-1, and 1028*e*-1 are selectable to display additional workout information and workout metrics for the open goal portion of the user's workout.

FIGS. 11A-11B are a flow diagram illustrating a method for outputting workout content using a computer system in accordance with some embodiments. Method 1100 is performed at a computer system (e.g., 100, 300, 500) (e.g., a wearable device, a smart watch, a smart phone, a tablet, and/or a computer system controlling an external display) that is in communication with a display generation component (e.g., a display controller, a touch-sensitive display system; and/or a display (e.g., integrated and/or connected)) and one or more input devices (e.g., a touch-sensitive surface (e.g., a touch-sensitive display); an accelerometer; a rotatable input mechanism; a depressible input mechanism; and/or a rotatable and depressible input mechanism). Some operations in method 1100 are, optionally, combined, the orders of some operations are, optionally, changed, and some operations are, optionally, omitted.

As described below, method 1100 provides an intuitive way for outputting workout content. The method reduces the cognitive burden on a user for accessing workout content, thereby creating a more efficient human-machine interface. For battery-operated computing devices, enabling a user to access workout content faster and more efficiently conserves power and increases the time between battery charges.

The computer system (e.g., 600) determines (1102) that the computer system satisfies one or more proximity criteria with respect to a previously completed route (e.g., determining that the computer system is within a threshold distance of the previously completed route (in some embodiments, within a threshold distance of a starting point of the previously completed route and/or within a threshold distance of any point along the previously completed route)), wherein the previously completed route corresponds to one or more previously completed workout instances (in some embodiments, the one or more previously completed workout instances include traversal of the previously completed route and/or traversal of at least a threshold portion of the previously completed route). In some embodiments, in response to determining that the computer system satisfies one or more proximity criteria with respect to the previously completed route, the computer system displays (1104), via the display generation component (e.g., 602), a first user interface object (e.g., 608*d*) (e.g., affordance) corresponding to the previously completed route (e.g., "PALO ALTO 5 MILES") (e.g., option 608*d* is displayed within workout selection user interface 606 in response to determining that the computer system satisfies one or more proximity criteria and/or option 608*d* is moved to the top of workout selection user interface 606 in response to determining that the computer system satisfies one or more proximity criteria). In some embodiments, the user interface object corresponding to the previously completed route is displayed within a user interface that also includes one or more additional user interface objects that correspond to different workout types (e.g., 608*a*-608*g*) (e.g., different workout modalities). In some embodiments, displaying the first user interface object in response to determining that the computer system satisfies one or more proximity criteria with respect to the previously completed route includes causing the first user interface object to be included in a workout selection user interface (e.g., 606). In some embodiments, displaying the first user interface object in response to determining that the computer system satisfies one or more proximity criteria with respect to the previously completed route includes causing the first user interface object to be moved to a position within a workout selection user interface that is displayed (e.g., moved to the top of workout selection user interface 606).

In some embodiments, while displaying the first user interface object (e.g., 608*d*), the computer system receives (1106), via the one or more input devices, a first user input (e.g., 1000) (e.g., one or more inputs) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to selection of the first user interface object. In some embodiments, in response to receiving the first user input, the computer system concurrently displays (1108): a second user interface object (e.g., 1004*a*-1004*c*) (1110) (e.g., affordance) corresponding to a first previously completed workout instance of the one or more previously completed workout instances corresponding to the previously completed route (e.g., a personal best performance of the previously completed route, an aggregated average performance of the previously completed route, and/or a most recent completion of the previously completed route); and a third user interface object (e.g., 1004*a*-1004*c*) (1112) (e.g., affordance) corresponding to a second previously completed workout instance of the one or more previously completed workout instances corresponding to the previously completed route (e.g., a personal best performance of the previously completed route, an aggregated average performance of the previously completed route, and/or a most recent completion of the previously completed route), wherein the second previously completed workout instance is different from the first previously completed workout instance. In some embodiments, the second user interface object is selectable to race and/or compete against the first previously completed workout instance. In some embodiments, the third user interface object is selectable to race and/or compete against the second previously completed workout instance.

In some embodiments, while concurrently displaying the second user interface object (e.g., 1004*a*-1004*c*) and the third user interface object (e.g., 1004*a*-1004*c*), the computer system receives (1114), via the one or more input devices, a second user input (e.g., 1006) (e.g., one or more inputs) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures). In some embodiments, in response to receiving the second user input (1116): the computer system initiates (1118) a workout session (e.g., initiating a timer corresponding to the workout session and/or initiating capture of one or more physical activity metrics corresponding to the workout session); and the computer system displays (1120) a workout session user interface (e.g., 1008) (e.g., a workout session user interface indicative of an active and/or in-progress workout session), including concurrently displaying: a representation of the previously completed route (e.g., 1010*b*) (1122) (e.g., a geographic map, an elevation map, and/or a straight-line representation); a representation of a current position (1124) (e.g., current geographic position and/or current progress position) of a user (e.g., 1010*d*) of the computer system (e.g., current position of the computer system) (in some embodiments, the representation of the current position of the user is displayed along the representation of the previously completed route); and a representation of a position of the user during a previously completed workout instance (e.g., 1010*c*) (1126). In some embodiments, the representation of the position of the user during the previously completed workout instance is displayed along the representation of the previously completed route (e.g., is displayed, over time, moving along the representation of the previously completed route according to the performance of the user during the previously completed workout instance).

In some embodiments, in accordance with a determination that the second user input corresponds to selection of the second user interface object (e.g., 1004*a*-1004*c*), the representation of the position of the user during the previously completed workout instance is a representation of the position of the user during the first previously completed workout instance (1128) (in some embodiments, without displaying a representation of the position of the user during the second previously completed workout instance). In some embodiments, the representation of the position of the user during the first previously completed workout instance is displayed along the representation of the previously completed route (e.g., is displayed, over time, moving along the representation of the previously completed route according to the performance of the user during the first previously completed workout instance). In some embodiments, in accordance with a determination that the second user input corresponds to selection of the third user interface object (e.g., 1004*a*-1004*c*), the representation of the position of the user during the previously completed workout instance is a representation of the position of the user during the second previously completed workout instance (1130) (in some embodiments, without displaying a representation of the position of the user during the first previously completed workout instance). In some embodiments, the representation of the position of the user during the second previously completed workout instance is displayed along the representation of the previously completed route (e.g., is displayed, over time, moving along the representation of the previously completed route according to the performance of the user during the second previously completed workout instance).

In some embodiments, the representation of the position of the user during the first previously completed workout instance (e.g., 1010*c*) is displayed moving along the representation of the completed route (e.g., 1010*b*) over time to indicate the position and/or progress of the user during the first previously completed workout instance over time. In some embodiments, the representation of the position of the user during the second previously completed workout instance (e.g., 1010*c*) is displayed moving along the representation of the completed route (e.g., 1010*b*) over time to indicate the position and/or progress of the user during the second previously completed workout instance over time. In some embodiments, initiating a workout session includes initiating recording (e.g., tracking, logging, collecting) of physical activity metrics corresponding to the workout session (e.g., physical activity metrics indicative of a physical activity level of the user during the workout session). In some embodiments, the physical activity metrics are recorded (e.g., captured) using one or more sensors (e.g., GPS, accelerometer, gyroscope, heart rate) of the computer system or an external device that is in communication with the computer system. In some embodiments, the physical activity metrics were not being recorded or were being recorded at a lower frequency and/or lower degree of precision prior to initiating (e.g., immediately prior to initiating) the workout session. In some embodiments, initiating the workout session includes causing one or more sensors to be enabled and/or activated so as to improve accurate measurements of user physical activity metrics during the workout session. Displaying the first user interface object corresponding to the previously completed route in response to determining that the computer system satisfies one or more proximity criteria with respect to the previously completed route provides the user with feedback about the state of the device (e.g., that the computer system has determined that the computer system satisfies one or more proximity criteria with respect to the previously completed route). Doing so also allows the user to initiate a workout session corresponding to the previously completed route with fewer user inputs.

In some embodiments, the computer system (e.g., 600) displays, at a first time, via the display generation component (e.g., 602), the first user interface object (e.g., 608*d*) corresponding to the previously completed route at a first position within an ordered set of workout options (e.g., 606, 608*a*-608*g*) (e.g., a plurality of workout options corresponding to one or more workout types (e.g., one or more workout modalities and/or one or more workout types)). In some embodiments, the computer system determines, at a second time subsequent to the first time, that the computer system satisfies the one or more proximity criteria with respect to the previously completed route. In some embodiments, in response to determining that the computer system satisfies the one or more proximity criteria with respect to the previously completed route, the computer system displays, via the display generation component, the first user interface object (e.g., 608*d*) at a second position within the ordered set of workout options different from the first position (e.g., 606, 608*a*-608*g*) (e.g., a second position that is higher in the order and/or at a position in the order that is accessible with fewer user inputs (e.g., with less scrolling of the user interface)). In some embodiments, the ordered set of workout options are displayed in a workout selection user interface. In some embodiments, the set of workout options includes a first workout option corresponding to a first workout type that is selectable to initiate a workout session of the first workout type and a second workout option corresponding to a second workout type that is selectable to initiate a workout session of the second workout type. Changing the display position of the first user interface object in response to determining that the computer system satisfies one or more proximity criteria with respect to the previously completed route provides the user with feedback about the state of the device (e.g., that the computer system has determined that the computer system satisfies one or more proximity criteria with respect to the previously completed route). Doing so also allows the user to initiate a workout session corresponding to the previously completed route with fewer user inputs.

In some embodiments, displaying the workout session user interface (e.g., 1008) comprises: in accordance with a determination that a current position of the user of the computer system is ahead of a corresponding position of the user during the previously completed workout instance (e.g., FIG. 10C) (e.g., the user is progressing at a better pace than the user did during the previously completed workout instance and/or at a current elapsed time in the workout session, the user has covered a greater distance than the user did at a corresponding elapsed time in the previously completed workout instance), displaying, via the display generation component, one or more elements of the workout session user interface in a first manner (e.g., 1010*d* is displayed in a first color) (e.g., with a first set of visual characteristics, with a first color, with a first line thickness, with a first shape, and/or with a first brightness). In some embodiments, displaying the workout session user interface comprises: in accordance with a determination that a current position of the user of the computer system is behind a corresponding position of the user during the previously completed workout instance (e.g., FIG. 10D) (e.g., the user is progressing at a worse pace than the user did during the previously completed workout instance and/or at a current elapsed time in the workout session, the user has covered a smaller distance than the user did at a corresponding elapsed time in the previously completed workout instance), displaying, via the display generation component, the one or more elements of the workout session user interface in a second manner (e.g., 1010*d* is displayed in a second color) (e.g., with a second set of visual characteristics, with a second color, with a second line thickness, with a second shape, and/or with a second brightness) different from the first manner. Displaying the workout session user interface differently based on whether the user is ahead of or behind the previously completed workout instance provides the user with feedback about the state of the device (e.g., that the computer system has determined that the user is either ahead of or behind the previously completed workout instance). Doing so also performs these operations automatically without further user input.

In some embodiments, the representation of the previously completed route (e.g., 1010*b*) includes a geographic map (e.g., a map of a geographic region within which the previously completed route is location and/or a visual indication of the previously completed route within a map of a geographic region). Displaying the representation of the previously completed route provides the user with feedback about the current state of the device (e.g., that the computer system has identified that the user is near a previously completed route). Displaying a geographic map representation of the previously completed route also allows a user to see geographic map information without providing further inputs.

In some embodiments, the representation of the previously completed route (e.g., 1010*b*) includes an elevation profile (e.g., FIG. 10C) (e.g., a visual representation of the elevation (e.g., geographic elevation) at a plurality of points along the previously completed route). Displaying the representation of the previously completed route provides the user with feedback about the current state of the device (e.g., that the computer system has identified that the user is near a previously completed route). Displaying an elevation map representation of the previously completed route also allows a user to see elevation information without providing further inputs.

In some embodiments, the representation of the previously completed route (e.g., 1010*b*) includes a line representation of the previously completed route (e.g., a visual representation of previously completed route as a straight line, with various positions along the straight line corresponding to various positions along the previously completed route). Displaying the representation of the previously completed route provides the user with feedback about the current state of the device (e.g., that the computer system has identified that the user is near a previously completed route).

In some embodiments, the first previously completed workout instance corresponds to a shortest completion time (e.g., a fastest and/or best completion time) of the previously completed route (e.g., 1004*a*) (e.g., a shortest, fastest, and/or best completion time of the one or more previously completed workout instances corresponding to the previously completed route). In some embodiments, in accordance with a determination that the second user input corresponds to selection of the second user interface object, the representation of the position of the user during the previously completed workout instance (e.g., 1010*c*) is a representation of the position of the user during the first previously completed workout instance in which the user achieved the shortest completion time of the previously completed route. Displaying the representation of the position of the user during the previously completed workout instance provides the user with feedback about the current state of the device. Doing so also allows the user to view their current position relative to their position in the previously completed workout instance without further user input and without displaying additional controls.

In some embodiments, the first previously completed workout instance corresponds to a most recent workout instance (e.g., 1004*b*) in which the user completed the previously completed route (e.g., the most recent workout instance in which the user completed the previously completed route). In some embodiments, in accordance with a determination that the second user input corresponds to selection of the second user interface object, the representation of the position of the user during the previously completed workout instance (e.g., 1010*c*) is a representation of the position of the user during the most recent workout instance in which the user completed the previously completed route. Displaying the representation of the position of the user during the previously completed workout instance provides the user with feedback about the current state of the device. Doing so also allows the user to view their current position relative to their position in the previously completed workout instance without further user input and without displaying additional controls.

In some embodiments, in response to receiving the first user input, the computer system concurrently displays, with the second user interface object (e.g., 1004*a*, 1004*b*) and the third user interface object (e.g., 1004*a*, 1004*b*), a fourth user interface object (e.g., 1004*c*) corresponding to a plurality of previously completed workout instances of the one or more previously completed workout instances corresponding to the previously completed route (e.g., a fourth user interface object corresponding to an average of the plurality of previously completed workout instances and/or a combination of the previously completed workout instances corresponding to the previously completed route). In some embodiments, displaying the workout session user interface (e.g., 1008) further comprises, in accordance with a determination that the second user input corresponds to selection of the fourth user interface object, the representation of the position of the user during the previously completed workout instance (e.g., 1010*c*) is a representation of a computed position of the user based on a combination of the plurality of previously completed workout instances (e.g., an average position of the user during the plurality of previously completed workout instances). Displaying the representation of the position of the user during the previously completed workout instance provides the user with feedback about the current state of the device. Doing so also allows the user to view their current position relative to their position in the previously completed workout instance without further user input and without displaying additional controls.

In some embodiments, while displaying the workout session user interface (e.g., 1008), the computer system detects that the user is greater than a first threshold distance away from the previously completed route (e.g., FIG. 10F) (e.g., detecting that the computer system and/or an external device is greater than the first threshold distance away from the previously completed route). In some embodiments, in response to detecting that the user is greater than the first threshold distance away from the previously completed route, the computer system displays, via the display generation component, an indication (e.g., 1012, and/or ceasing display of 1010*c* and 1010*d* in FIG. 10F) (e.g., a textual indication, a symbol, and/or other visual indication) that the user is not on the previously completed route. Displaying the indication that the user is not on the previously completed route in response to determining that that user is not on the previously completed route provides the user with feedback about the current state of the device. Doing so also performs these operations automatically without further user input.

In some embodiments, while displaying the workout session user interface (e.g., 1008), the computer system detects that the user is greater than a second threshold distance away from the previously completed route (e.g., FIGS. 10H-10I) (e.g., detecting that the computer system and/or an external device is greater than the second threshold distance away from the previously completed route and/or is at a geographic position that is greater than the second threshold distance away from the previously completed route). In some embodiments, in response to detecting that the user is greater than the second threshold distance away from the previously completed route: the computer system (e.g., 600) ceases display of the workout session user interface (e.g., 1008); and the computer system displays, via the display generation component, a second workout session user interface (e.g., 656) different from the workout session user interface (e.g., a second workout session user interface that corresponds to a different workout type and/or a different workout goal type than the workout session user interface). In some embodiments, the second workout session user interface is indicative of an active workout session corresponding to a second workout type. In some embodiments, while displaying the workout session user interface, the computer system detects that the user is greater than the threshold distance away from the previously completed route for a threshold duration of time and in response to detecting that the user is greater than the threshold distance away from the previously completed route for the threshold duration of time, the computer system ceases display of the workout session user interface and displays the second workout session user interface. Replacing display of the workout session user interface with display of the second workout session user interface in response to determining that that user is greater than a threshold distance away from the previously completed route provides the user with feedback about the current state of the device. Doing so also performs these operations automatically without further user input.

In some embodiments, displaying the workout session user interface (e.g., 1008) further comprises displaying, concurrently with the representation of the previously completed route (e.g., 1010*b*), the representation of the current position of the user of the computer system (e.g., 1010*d*), and the representation of the position of the user during the previously completed workout instance (e.g., 1010*c*), one or more physical activity metrics of the user during the workout session (e.g., 1010*a*) (e.g., elapsed time, heartrate, and/or calories burned). In some embodiments, displaying the second workout session user interface (e.g., 656) comprises maintaining display of the one or more physical activity metrics (e.g., 1010*a* in FIG. 10I) of the user during the workout session without maintaining display of the representation of the previously completed route, the representation of the current position of the user of the computer system, and the representation of the position of the user during the previously completed workout instance. Replacing display of the workout session user interface with display of the second workout session user interface in response to determining that that user is greater than a threshold distance away from the previously completed route provides the user with feedback about the current state of the device. Doing so also performs these operations automatically without further user input.

In some embodiments, after completion of the workout session, the computer system displays, via the display generation component, a first workout summary user interface that includes a ranked list that includes: a representation of the workout session (e.g., physical activity metrics corresponding to the workout session (e.g., pace, completion time, heartrate, and/or calories burned)), and representations of at least a subset of the one or more previously completed workout instances corresponding to the previously completed route (e.g., physical activity metrics corresponding to the at least the subset of the one or more previously completed workout instances corresponding to the previously completed route). In some embodiments, the ranked list ranks workout instances based on completion time (e.g., time to complete the previously completed route). Displaying the first workout summary user interface that includes the ranked list reduces the number of inputs required for the user to see how their current workout session compares to one or more previous workout instances.

In some embodiments, after completion of the workout session, the computer system displays, via the display generation component, a second workout summary user interface (e.g., 1024, 1066) that includes a map representation of the previously completed route (e.g., 1026*b*, 1026*c*, 1068), wherein the map representation of the previously completed route includes an indication of a first instance during the workout session in which the user went from being behind the representation of the position of the user during the previously completed workout instance to being ahead of the representation of the position of the user during the previously completed workout instance. In some embodiments, the map representation of the previously completed route and/or the indication of the first instance identify a first geographic location corresponding to the first instance. In some embodiments, the map representation of the previously completed route includes an indication of a second instance during the workout session in which the user went from being behind the representation of the user during the previously completed workout instance to being ahead of the representation of the position of the user during the previously completed workout instance. In some embodiments, the map representation of the previously completed route and/or the indication of the second instance identify a geographic location corresponding to the second instance. In some embodiments, the indication of the first instance and the indication of the second instance are concurrently displayed. Displaying the second workout summary user interface that includes the indication of the first instance provides the user with feedback about the state of the device (e.g., that the computer system detected during the workout session that the user passed the previously completed workout instance). Doing so also reduces the number of inputs required for the user to see when they moved ahead of the previously completed workout instance.

In some embodiments, after completion of the workout session, the computer system displays, via the display generation component, a third workout summary user interface (e.g., 1048) that includes: a first visual object (e.g., "today's pace" in 1052) that indicates a pace of the user over time during the workout session (e.g., a chart that displays elapsed time on a first axis, and user pace during the workout session on a second axis); and a second visual object (e.g., "best pace" in 1052) that indicates a pace of the user over time during the previously completed workout instance (e.g., a chart that displays elapsed time on a first axis, and user pace during the previously completed workout instance on a second axis). In some embodiments, the first visual object and the second visual object are displayed (e.g., concurrently displayed) on a single chart. Displaying the third workout summary user interface reduces the number of inputs required for the user to compare the user's pace over time during the workout session with the user's pace over time during the previously completed workout instance.

In some embodiments, while displaying the workout session user interface (e.g., 1008), the computer system detects (e.g., automatically and/or without user input), via the one or more input devices, that the user has completed the previously completed route. In some embodiments, in response to detecting that the user has completed the previously completed route: the computer system ceases display of the workout session user interface (e.g., 1008); and the computer system displays, via the display generation component, a third workout session user interface (e.g., 656 in FIG. 10K) different from the workout session user interface, wherein the workout session user interface and the third workout session user interface are indicative of an active workout session. In some embodiments, the workout session user interface corresponds to a first workout type (e.g., a route goal workout type (e.g., a workout in which the user is completing a previously completed route)) and the third workout session user interface corresponds to a second workout type different from the first workout type (e.g., an open goal workout type (e.g., a workout in which there is not a defined beginning or ending condition and/or a workout that continues indefinitely until ended by the user)). Replacing display of the workout session user interface with display of the third workout session user interface in response to determining that that user has completed the previously completed route provides the user with feedback about the current state of the device (e.g., that the computer system has detected that the user has completed the previously completed route). Doing so also performs these operations automatically without further user input.

In some embodiments, after displaying the third workout session user interface (e.g., 656), the computer system displays, via the display generation component, a fourth workout summary user interface (e.g., 1024-1) that includes: a first section (e.g., 1072a) comprising a first set of physical activity metrics (e.g., one or more physical activity metrics measured while the workout session user interface was displayed) corresponding to a first portion of the workout session (e.g., a portion of the workout session during which the user was traversing the previously completed route) during which the workout session user interface was displayed; and a second section (e.g., 1072b) different from the first section and comprising a second set of physical activity metrics (e.g., one or more physical activity metrics measured while the third workout session user interface was displayed) corresponding to a second portion of the workout session (e.g., a portion of the workout session during which the user was not traversing the previously completed route and/or a portion of the workout session that occurred after the user completed the previously completed route) during which the third workout session user interface was displayed. In some embodiments, the first portion of the workout session and the second portion of the workout session are non-overlapping. Displaying the third workout summary user interface provides the user with feedback about the state of the device (e.g., that the device measured the first set of physical activity metrics during the first portion of the workout session and measured the second set of physical activity metrics during the second portion of the workout session). Doing so also reduces the number of inputs required for the user to view physical activity metrics corresponding to the first portion and/or the second portion of the workout session.

In some embodiments, the computer system displays, via the display generation component, a zoomed in workout session user interface (e.g., 1008 in FIG. 10D) that includes concurrently displaying: the representation of current position of the user of the computer system (e.g., 1010d); the representation of the position of the user during the previously completed workout instance (e.g., 1010c); a color gradient (e.g., 1011) that gradually transitions from a first color to a second color, wherein at least a portion of the color gradient is displayed between the representation of the current position of the user of the computer system and the representation of the position of the user during the previously completed workout instance; and the representation of the previously completed route, wherein in the zoomed in workout session user interface, the representation of the previously completed route is a representation of a first portion of the previously completed route.

In some embodiments, the computer system displays, via the display generation component, a zoomed out workout session user interface (e.g., 1008 in FIG. 10C) that includes concurrently displaying: the representation of the current position of the user of the computer system (e.g., 1010d); the representation of the position of the user during the previously completed workout instance (e.g., 1010c); and the representation of the previously completed route (e.g., 1010b) without displaying the color gradient, wherein in the zoomed out workout session user interface, the representation of the previously completed route is a representation of a second portion (e.g., the entire route and/or less than the entire route) of the previously completed route that is larger than the first portion of the previously completed route (e.g., the second portion represents a larger portion and/or percentage of the previously completed route than the first portion). In some embodiments, the second portion includes the first portion. In some embodiments, the second portion includes the entirety of the previously completed route. In some embodiments, the first color of the color gradient is determined based on whether the representation of the current position of the user is ahead of or behind the representation of the position of the user during the previously completed workout instance. Displaying the zoomed in workout session user interface with the color gradient and displaying the zoomed out workout session user interface without the color gradient provides the user with feedback about the state of the device (e.g., whether the device is displayed the zoomed in workout session user interface or the zoomed out workout session user interface).

Note that details of the processes described above with respect to method 1100 (e.g., FIGS. 11A-11B) are also applicable in an analogous manner to the methods described below and/or above. For example, methods 700, 800, 900, 1300, 1500, 1700, and/or 1800 optionally include one or more of the characteristics of the various methods described above with reference to method 1100. For example, in some embodiments, the workout session in method 1100 is the workout session recited in methods 700, 800, 900, and/or 1800, and/or the workout session recited in method 800 corresponds to the workouts recited in methods 1300, 1500, and/or 1700. For brevity, these details are not repeated below.

FIGS. 12A-12J illustrate exemplary user interfaces for outputting track workout content, in accordance with some embodiments. The user interfaces in these figures are used to illustrate the processes described below, including the processes in FIG. 13.

Figure 12A:
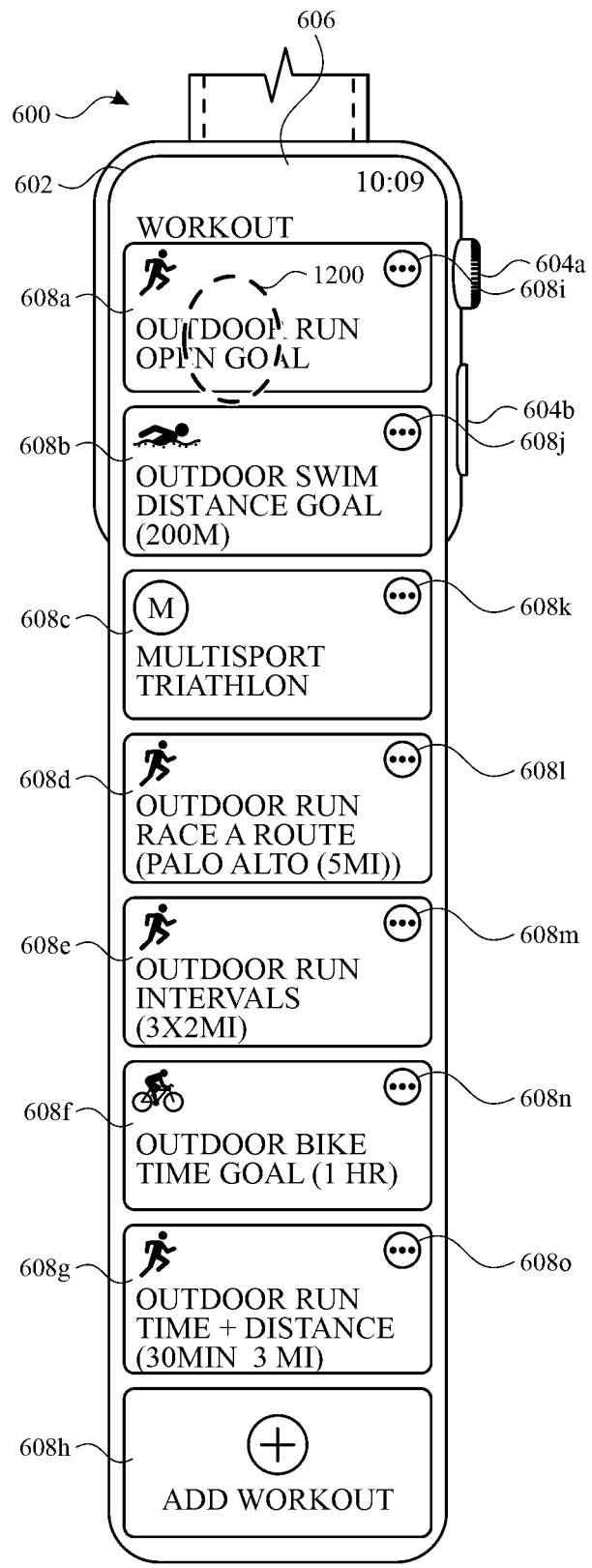

FIG. 12A illustrates electronic device 600, which is a smartwatch with touch-sensitive display 602, rotatable and depressible input mechanism 604a, and button 604b. At FIG. 12A, electronic device 600 detects user input 1200 (e.g., a tap input) corresponding to selection of workout option 608a. Workout option 608a corresponds to an open goal outdoor run workout (e.g., a workout that has outdoor run as its modality type and open goal as its goal type).

FIGS. 12B-12I illustrate various example scenarios of various embodiments in which different user interfaces are displayed based on whether electronic device 600 satisfies proximity criteria relative to a workout track (e.g., whether electronic device 600 is within a threshold distance of a workout track) (e.g., a workout track facility, a running track, and/or a running track facility).

Figure 12B:
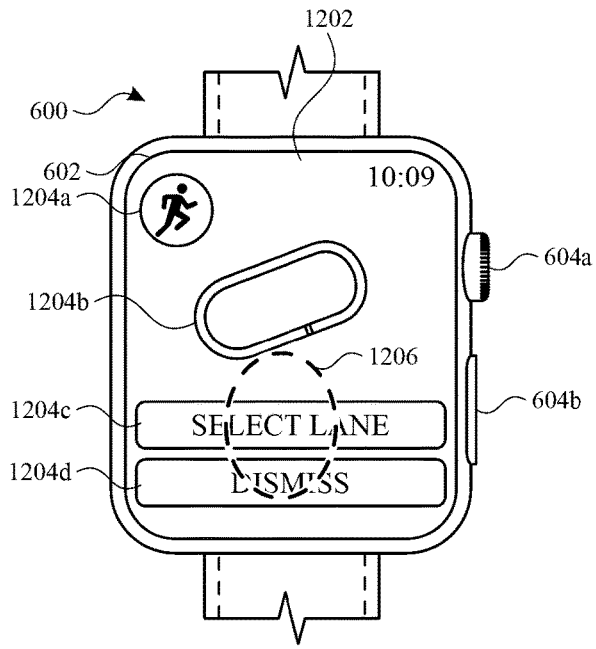

At FIG. 12B, in response to user input 1200, and in accordance with a determination that electronic device 600 satisfies proximity criteria relative to a workout track (e.g., in accordance with a determination that electronic device 600 is within a threshold distance of a workout track), electronic device 600 displays user interface 1202. User interface 1202 includes modality indication 1204a (indicating that the workout is an outdoor run workout), and indication 1204b indicating that device 600 has detected that it is near a workout track. User interface 1202 includes option 1204c that is selectable for a user to indicate a lane number the user is in, and option 1204d that is selectable to dismiss user interface 1202 (e.g., and display an in-workout user interface corresponding to an open goal outdoor run (e.g., in-workout user interface 656)). At FIG. 12B, electronic device 600 detects user input 1206 (e.g., a tap input) corresponding to selection of option 1204c.

Figure 12C:
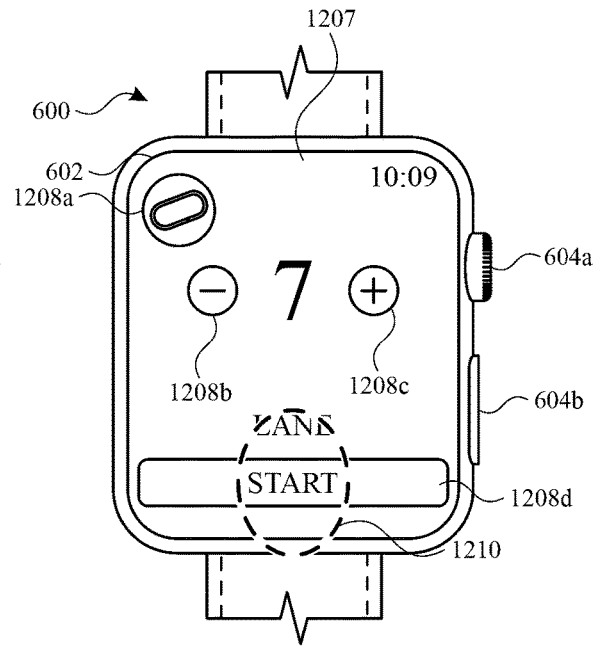

At FIG. 12C, in response to user input 1202, electronic device 600 displays user interface 1207, which prompts the user to identify a track lane number the user is running in. User interface 1202 includes modality indication 1208a, which now indicates that the user has confirmed (e.g., via user input 1206) that the user is at a track, options 1208b and 1208c to set a lane number, and option 1208d that is selectable to confirm the lane number. At FIG. 12C, electronic device 600 detects user input 1210 (e.g., a tap input) corresponding to selection of option 1208d.

Figure 12D:
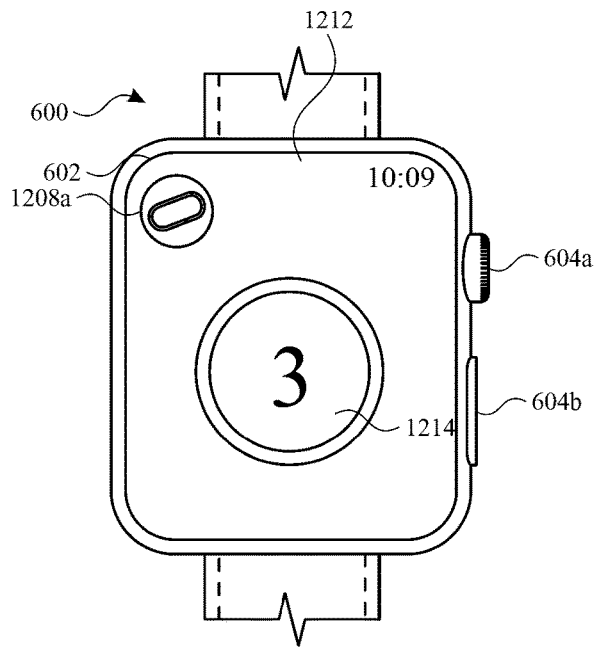
Figure 12E:
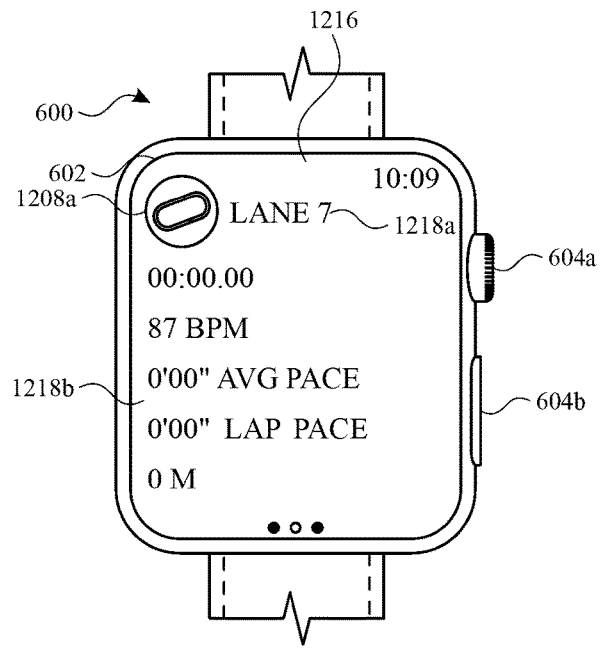

At FIG. 12D, in response to user input 1210, electronic device displays countdown user interface 1212 which displays a 3-second countdown 1214 until the workout begins. At FIG. 12E, after the 3-second countdown has completed, electronic device 600 displays track running in-workout user interface 1216. Track running in-workout user interface 1216 includes modality indication 1208a (indicative of a track running workout), lane indication 1218a indicating the lane number the user is in, and workout metrics 1218b. In some embodiments, workout metrics 1218b represent a default workout metrics user interface for a track running workout. In some embodiments, in response to user input 1200 in FIG. 12A, in accordance with a determination that computer system 600 satisfies proximity criteria relative to a workout track, electronic device 600 displays track running in-workout user interface 1216 (without displaying the user interfaces in FIGS. 12B-12D).

Figure 12F:
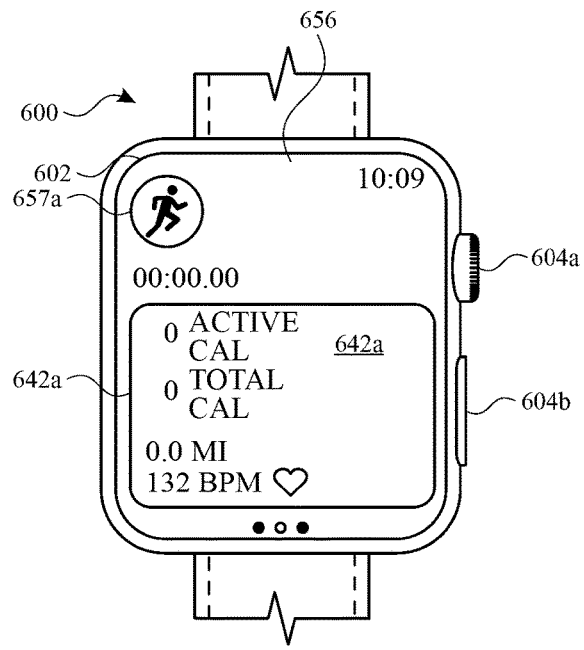

FIG. 12F depicts a different example scenario in which, in response to user input 1200 of FIG. 12A, and in accordance with a determination that computer system 600 does not satisfy proximity criteria with respect to a workout track (e.g., computer system 600 is not close to a workout track), electronic device 600 displays in-workout user interface 656, which was discussed above with reference to FIG. 6N, and corresponds to a non-track outdoor run workout. Accordingly, in response to user input 1200 in FIG. 12A, electronic device 600 displays different user interfaces based on whether or not electronic device 600 satisfies proximity criteria with respect to a workout track (e.g., based on whether or not electronic device 600 is near a workout track).

Figure 12G:
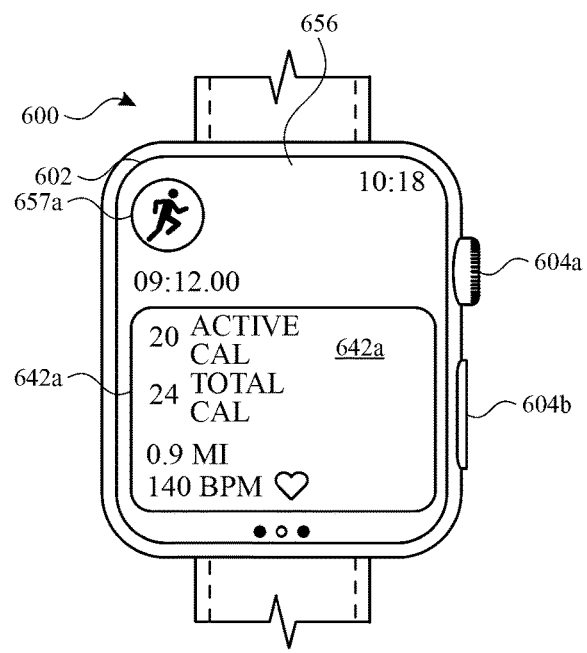
Figure 12H:
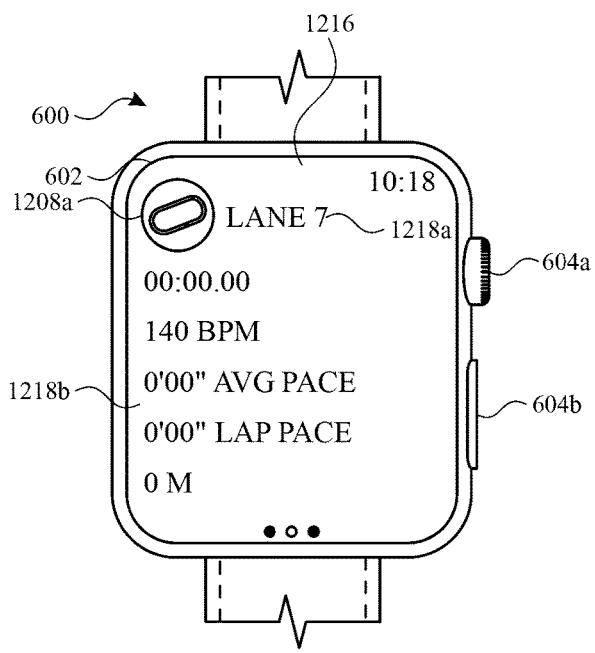

At FIG. 12G, the user has continued their workout from FIG. 12F, and has run for nine minutes and 12 seconds and for 0.9 miles. At FIG. 12G, electronic device 600 determines that electronic device 600 satisfies the proximity criteria with respect to a workout track. At FIG. 12H, in response to determining that electronic device 600 satisfies the proximity criteria with respect to a workout track, electronic device 600 ceases display of in-workout user interface 656 and displays track running in-workout user interface 1216. In FIG. 12H, track running in-workout user interface 1216 resets workout metrics 1218b. However, in some embodiments, track running in-workout user interface 1216 carries over workout metrics from the first portion of the user's workout (e.g., before they arrived at the track).

At FIG. 12I, electronic device 600 detects that the user has switched track lanes. In some embodiments, electronic device 600 detects that the user has switched track lanes automatically (e.g., without user input) (e.g., based on user location information, signal strength information and/or user movement information (e.g., based on the shape and/or distance of the user's loops around the track)). In some embodiments, electronic device 600 detects that the user has switched track lanes based on one or more user inputs (e.g., one or more button presses and/or touch-screen inputs). In response to detecting that the user has switched track lanes, electronic device 600 updates lane indication 1218a in track running in-workout user interface 1216 to indicate that the user has moved from Lane 7 to Lane 2.

At FIG. 12I, electronic device 600 detects user input 1220 (e.g., a swipe right user input). At FIG. 12J, in response to user input 1220, electronic device 600 displays control center user interface 664. In FIG. 12J, control center user interface 664 includes option 1222 that is selectable to manually enter the lane number the user is in (e.g., selectable to display user interface 1207).

FIG. 13 is a flow diagram illustrating a method for outputting track workout content using a computer system in accordance with some embodiments. Method 1300 is performed at a computer system (e.g., 100, 300, 500) (e.g., a wearable device, a smart watch, a smart phone, a tablet, and/or a computer system controlling an external display) that is in communication with a display generation component (e.g., a display controller, a touch-sensitive display system; and/or a display (e.g., integrated and/or connected)) and one or more input devices (e.g., a touch-sensitive surface (e.g., a touch-sensitive display); an accelerometer; a rotatable input mechanism; a depressible input mechanism; and/or a rotatable and depressible input mechanism). Some operations in method 1300 are, optionally, combined, the orders of some operations are, optionally, changed, and some operations are, optionally, omitted.

As described below, method 1300 provides an intuitive way for outputting track workout content. The method reduces the cognitive burden on a user for accessing track workout content thereby creating a more efficient human-machine interface. For battery-operated computing devices, enabling a user to access track workout content faster and more efficiently conserves power and increases the time between battery charges.

The computer system (e.g., 600) displays (1302), via the display generation component (e.g., 602), a first user interface object (e.g., 608a) (e.g., affordance) corresponding to a first workout type (e.g., a running workout, an outdoor running workout, an indoor running workout, a cycling workout, an outdoor cycling workout, an indoor cycling workout, a swimming workout, an outdoor swimming workout, an indoor swimming workout, a walking workout, an outdoor walking workout, and/or an indoor walking workout). In some embodiments, the first user interface object (e.g., 608a) is displayed within a user interface (e.g., 6060) that also includes a second user interface object (e.g., 608b-608g) corresponding to a second workout type different from the first workout type. In some embodiments, the second user interface object is selectable to initiate a workout session corresponding to the second workout type, and the first user interface object is selectable to initiate a workout session corresponding to the first workout type.

In some embodiments, while displaying the first user interface object (e.g., 608a), the computer system receives (1304), via the one or more input devices, a first user input (e.g., 1200) (e.g., one or more inputs) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to selection of the first user interface object. In some embodiments, in response to receiving the first user input (1306): in accordance with a determination that the computer system satisfies one or more proximity criteria (e.g., detecting that the computer system is within a threshold distance of a workout track and/or workout track facility; and/or detecting that the computer system is inside of a workout track facility) with respect to a workout track (e.g., a running track, a cycling track, and/or a walking track) (e.g., determining that the computer system is within a threshold distance of a running track and/or cycling track) (e.g., determining that the computer system satisfies one or more proximity criteria with respect to a running track and/or cycling track at the time the first user input is received) (and/or, in some embodiments, in accordance with a determination that a user is traversing a predetermined shape (e.g., a track shape and/or an oval shape)), the computer system displays (1308), via the display generation component, a first user interface (e.g., 1202 and/or 1216) (e.g., a track running user interface and/or track cycling user interface); and in accordance with a determination that the computer system does not satisfy the one or more proximity criteria with respect to a workout track (e.g., determining that the computer system is not within a threshold distance of a running track), the computer system displays (1310), via the display generation component, a second user interface (e.g., 656) different from the first user interface (e.g., a non-track running workout session user interface and/or non-track biking workout session user interface). In some embodiments, the first user interface includes information that is not included in the second user interface (e.g., track information and/or lane information). Displaying the first user interface when the user is at a track and displaying the second user interface when the user is not at a track provides the user with feedback about the state of the device (e.g., that the computer system has detected whether or not the user is at a track). Doing so also enables these operations to be performed without user input, and without cluttering the display with additional controls.

In some embodiments, the computer system displays, via the display generation component, the second user interface (e.g., 656) (e.g., a non-track running workout session user interface and/or non-track biking workout session user interface). In some embodiments, while displaying the second user interface (e.g., 656), the computer system detects that the computer system satisfies the one or more proximity criteria (e.g., detecting that the computer system is within a threshold distance of a workout track and/or workout track facility; and/or detecting that the computer system is inside of a workout track facility) with respect to a first workout track (e.g., a running track, a cycling track, and/or a walking track) (e.g., determining that the computer system is within a threshold distance of a running track and/or cycling track) (e.g., determining that the computer system satisfies one or more proximity criteria with respect to a running track and/or cycling track at the time the first user input is received). In some embodiments, in response to detecting that the computer system satisfies the one or more proximity criteria with respect to the first workout track: the computer system displays the first user interface (e.g., 1216) (e.g., a track running user interface and/or track cycling user interface) (and, optionally, in some embodiments, ceasing display of the second user interface). Displaying the second user interface when the user is not at a track and displaying the first user interface when the user is at a track provides the user with feedback about the state of the device (e.g., that the computer system has detected whether or not the user is at a track). Doing so also enables these operations to be performed without user input, and without cluttering the display with additional controls.

In some embodiments, the first user interface (e.g., 1216) includes lane information (e.g., 1218*a*) identifying a lane in which the user is positioned (e.g., a lane number or other identifier). In some embodiments, the second user interface does not include the lane indication. Displaying the first user interface with the lane information provides the user with feedback about the state of the device (e.g., that the computer system has detected that the user is in a particular lane of the workout track).

In some embodiments, the first user interface includes distance information (e.g., "1230M" in FIG. 12I) that indicates a distance traversed (e.g., distance run, walked, and/or cycled) by the user during a current workout session, wherein the distance information is determined based on the lane in which the user is positioned (e.g., the distance the user traversed is determined based on the lane the user is positioned in). Displaying the first user interface with the distance information provides the user with feedback about the state of the device (e.g., that the computer system has detected that the user has traversed a particular distance during the workout session). Furthermore, calculating the distance traversed based on the lane the user is positioned in allows for these operations to be performed without user input.

In some embodiments, the lane information (e.g., 1218*a*) is automatically determined without user input (e.g., based on GPS information, signal strength information, and/or other position information corresponding to the user and/or the computer system). Displaying the first user interface with the lane information provides the user with feedback about the state of the device (e.g., that the computer system has detected that the user is in a particular lane of the workout track). Furthermore, automatically detecting the lane the user is in without user input allows for these operations to be performed without user input.

In some embodiments, the lane information (e.g., 1218*a*) is input by a user (e.g., via one or more user inputs (e.g., one or more touch inputs, one or more non-touch inputs, and/or one or more gestures). Displaying the first user interface with the lane information provides the user with feedback about the state of the device (e.g., that the computer system has received information (e.g., for the user) indicating that the user is in a particular lane).

In some embodiments, the computer system displays, via the display generation component, the first user interface (e.g., 1216) with first lane information (e.g., 1218*a*) indicative of the user being positioned in a first lane of a workout track. In some embodiments, while displaying the first user interface with the first lane information, the computer system detects (e.g., automatically without user input and/or based on one or more user inputs), via the one or more input devices, that the user has moved from the first lane of the workout track to a second lane of the workout track different from the first lane. In some embodiments, in response to detecting that the user has moved from the first lane to the second lane, the computer system displays, via the display generation component, the first user interface (e.g., 1216) with second lane information (e.g., 1218*a* changes from a first lane number to a second lane number in FIGS. 12H-12I) indicative of the user being positioned in the second lane of the workout track. Displaying the first user interface with the first lane information and then with the second lane information in response to detecting that the user has moved from the first lane to the second lane provides the user with feedback about the state of the device (e.g., that the computer system has detected that the user has moved from the first lane to the second lane). Doing so also enables these operations to be performed automatically without user input.

In some embodiments, detecting that the user has moved from the first lane of the workout track to the second lane of the workout track is performed without user input (e.g., based on GPS information, signal strength information, and/or other position information corresponding to the user and/or the computer system). Displaying the first user interface with the first lane information and then with the second lane information in response to detecting that the user has moved from the first lane to the second lane provides the user with feedback about the state of the device (e.g., that the computer system has detected that the user has moved from the first lane to the second lane). Doing so also enables these operations to be performed automatically without user input.

In some embodiments, detecting that the user has moved from the first lane of the workout track to the second lane of the workout track comprises: receiving, via the one or more input devices, one or more user inputs (e.g., option 1222 to modify lane information) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) indicative of the user having moved from the first lane of the workout track to the second lane of the workout track. Displaying the first user interface with the first lane information and then with the second lane information in response to detecting that the user has moved from the first lane to the second lane provides the user with feedback about the state of the device (e.g., that the computer system has detected that the user has moved from the first lane to the second lane).

Note that details of the processes described above with respect to method 1300 (e.g., FIG. 13) are also applicable in an analogous manner to the methods described below and/or above. For example, methods 700, 800, 900, 1100, 1500, 1700, and/or 1800 optionally include one or more of the characteristics of the various methods described above with reference to method 1300. For example, in some embodiments, user interfaces recited in method 1300 are displayed as part of a workout session recited in methods 700, 800, 900, and/or 1800. For brevity, these details are not repeated below.

FIGS. 14A-14Y illustrate exemplary user interfaces for navigating, modifying, and outputting interval workout content, in accordance with some embodiments. The user interfaces in these figures are used to illustrate the processes described below, including the processes in FIG. 15.

FIG. 14A illustrates electronic device 600, which is a smartwatch with touch-sensitive display 602, rotatable and depressible input mechanism 604a, and button 604b. At FIG. 14A, electronic device 600 displays workout selection user interface 606, which was discussed above with reference to FIG. 6A. At FIG. 14A, electronic device 600 detects user input 1400 (e.g., a tap input) corresponding to selection of option 608m.

Figure 14B:
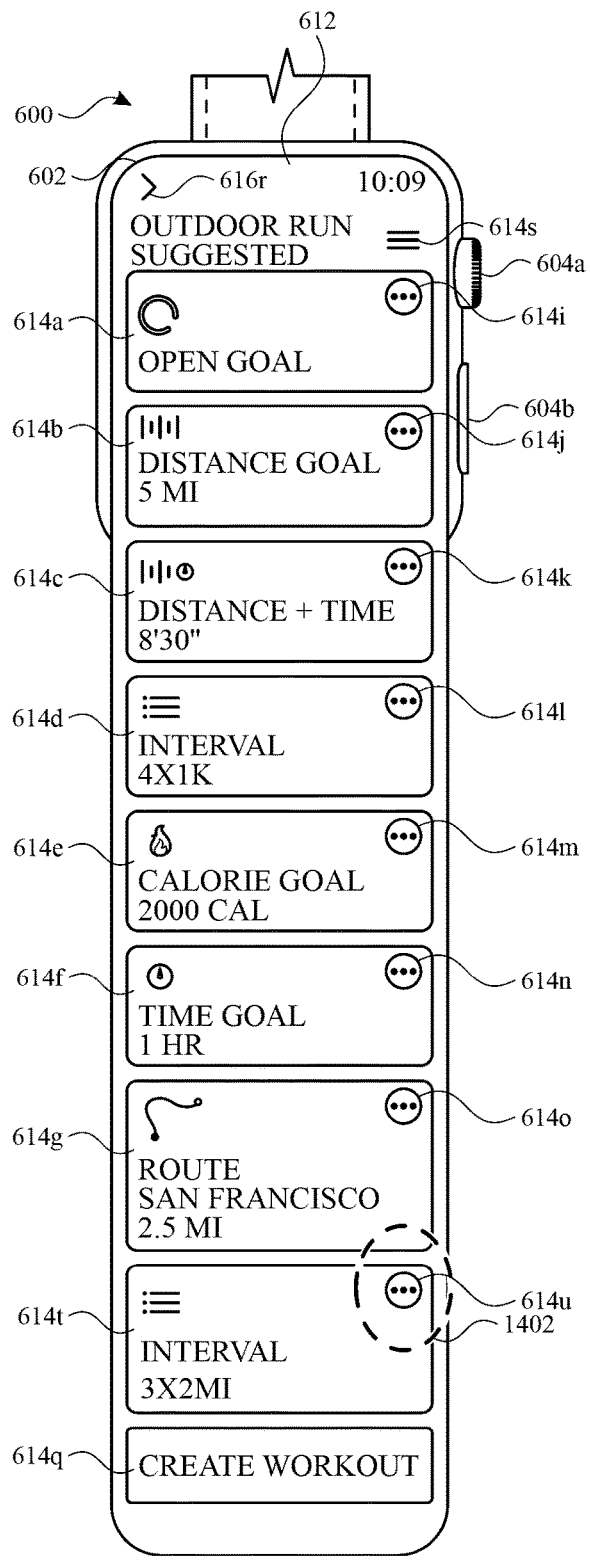

At FIG. 14B, in response to user input 1400, electronic device displays outdoor run room user interface 612 (e.g., based on the fact that option 608m corresponds to a preconfigured workout that has outdoor run as its modality type), which was discussed above with reference to FIG. 6B. At FIG. 14B, electronic device 600 detects user input 1402 corresponding to selection of option 614u. Option 614u is associated with a preconfigured outdoor run interval workout.

Figure 14C:
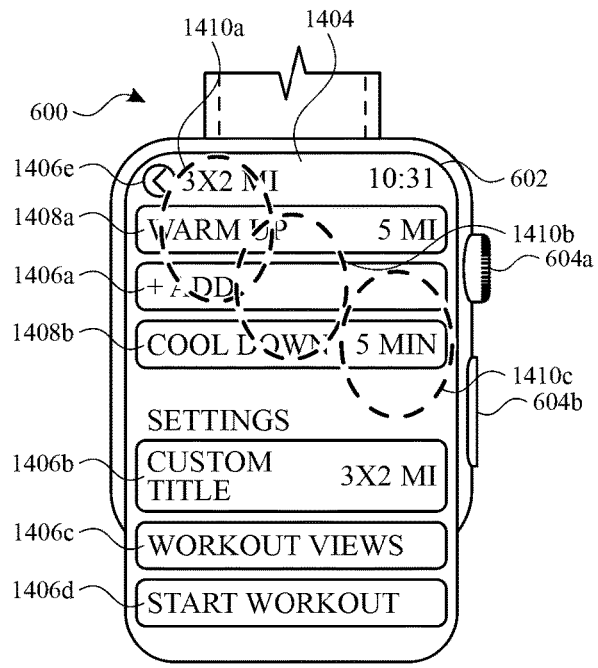

At FIG. 14C, in response to user input 1402, electronic device 600 displays interval workout creation user interface 1404. Interval workout creation user interface 1404 includes segment representation 1408a corresponding to a warm up segment of the interval workout and segment representation 1408b corresponding to a cool down segment of the interval workout. In some embodiments, in response to user input 1402, interval workout creation user interface 1404 includes additional segment representations corresponding to workout segments in the preconfigured 3 by 2 mile workout (e.g., three segments of two miles each). However, in the depicted embodiment, and for ease and/or clarity of explanation, interval workout creation user interface 1404 is shown with only a warmup segment and a cooldown segment pre-populated.

In FIG. 14C, interval workout creation user interface 1404 also includes selectable options 1406a-1406e. Option 1406a is selectable to initiate a process for adding a segment to the interval workout. Option 1406b is selectable to modify a title of the interval workout. Option 1406b displays the current title, "3X2 MI." Option 1406c is selectable to modify one or more workout metrics and/or workout metrics user interfaces that are accessible during the interval workout (e.g., as described above with reference to FIGS. 6A-6AE). Option 1406d is selectable to initiate a workout session for the interval workout as it is currently configured (in FIG. 14C, it is configured with only a 5 mile warm up and a 5 minute cool down). Option 1406e is selectable to return to outdoor run room user interface 612.

At FIG. 14C, electronic device 600 detects user input 1410a (e.g., a tap input) corresponding to selection of segment representation 1408a, user input 1410b (e.g., a tap input) corresponding to selection of option 1406a, and user input 1410c (e.g., a tap input) corresponding to selection of segment representation 1408b. Each of these user inputs will be discussed below.

Figure 14D:
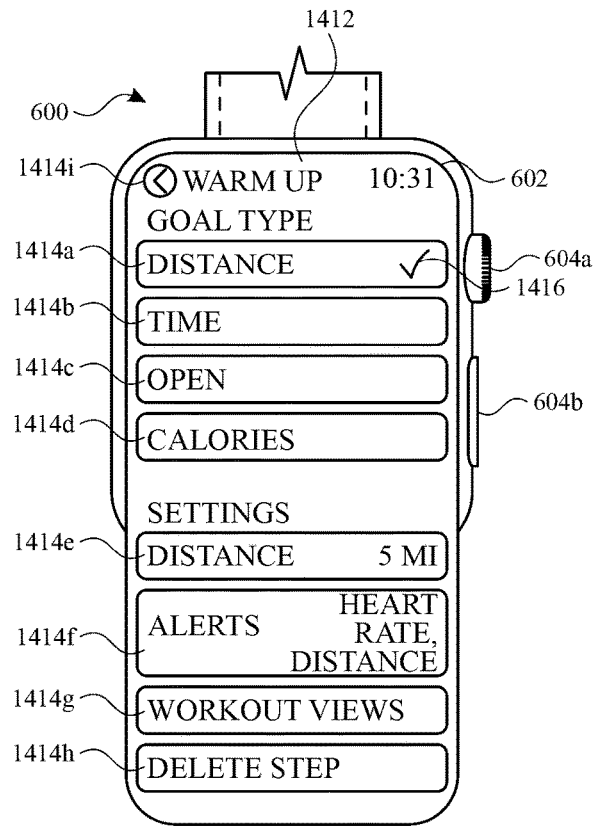

At FIG. 14D, in response to user input 1410a, electronic device 600 displays warm up segment configuration user interface 1412. Warm up segment configuration user interface 1412 includes options 141a-141d that are selectable to set a goal type for the warm up segment. Indication 1416 indicates that distance goal is the currently selected goal type for the warm up segment. In some embodiments, in an interval workout, each segment of the workout is associated with a goal type and a goal value, and the segment of the workout automatically ends once the goal value is achieved. For example, in FIG. 14D, the warm up segment has distance goal as its goal type, and goal value of 5 miles, such that once the user has run 5 miles (e.g., as determined by electronic device 600), electronic device 600 automatically ends the warm up segment and transitions to a next segment of the workout. Warm up segment configuration user interface 1412 also includes selectable options 1414e-1414i. Option 1414e is selectable to define a goal value for the workout segment. Option 1414f is selectable to modify one or more alerts that are to be output during the segment (e.g., in a manner similar to what was described above with reference to FIGS. 6A-6AE). Option 1414g is selectable to modify one or more workout metrics and/or workout metrics user interfaces that are accessible during the workout segment (e.g., in a manner similar to what was described above with reference to FIGS. 6A-6AE). In some embodiments, the user can define alerts and/or workout metrics for each individual segment of the interval workout. Option 1414h is selectable to delete the workout segment from the interval workout. Option 1414i is selectable to return to interval workout creation user interface 1404.

Figure 14E:
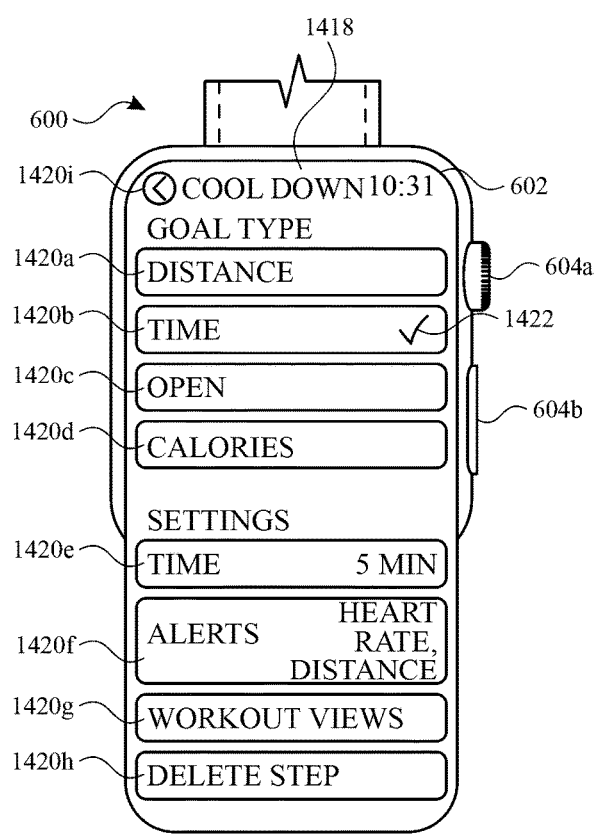

At FIG. 14E, in response to user input 1410c (in FIG. 14C), electronic device 600 displays cool down segment configuration user interface 1418, which is substantially similar to warm up segment configuration user interface 1412. Options 1420a-1420d are selectable to choose a goal type for the cool down segment, and option 1420e is selectable to define a goal value for the cool down segment.

Currently, the cool down segment is configured as a time goal segment with a time goal value of 5 minutes. Option 1420*f* is selectable to modify alerts to be output during the cool down segment, option 1420*g* is selectable to modify workout metrics that are accessible during the cool down segment, option 1420*h* is selectable to remove the cool down segment from the interval workout, and option 1420*i* is selectable to return to interval workout creation user interface 1404.

Figure 14F:
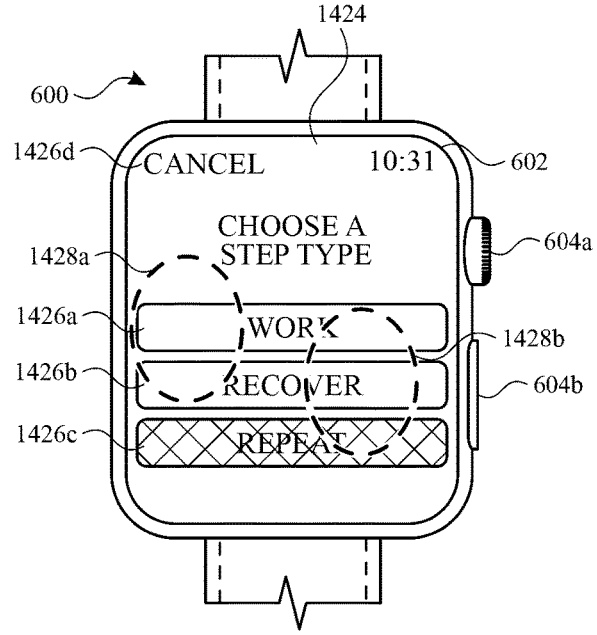

At FIG. 14F, in response to user input 1410*b* (in FIG. 14C), electronic device 600 displays segment type user interface 1424, which includes options 1426*a*-1426*d*. Option 1426*a* is selectable to add a work step to the interval workout and option 1426*b* is selectable to add a recovery step to the interval workout. In some embodiments, segment type user interface 1424 includes options to add other segment types, such as a warm up segment, a cool down segment, or other segments. In FIG. 14F, step type user interface includes option 1426*c*, which is made to be not selectable in FIG. 14F because the interval workout does not have any repeatable segments (e.g., the warm up segment and the cool down segment are the only segments current in the interval workout, and, in the depicted embodiment, they are non-repeatable segments). Accordingly, repeat option 1426*c* is not selectable in FIG. 14F. Option 1426*d* is selectable to return to interval workout creation user interface 1404.

At FIG. 14F, electronic device 600 detects user input 1428*a* (e.g., a tap input) corresponding to selection of option 1426*a*, and user input 1428*b* (e.g., a tap input) corresponding to selection of option 1426*b*.

Figure 14G:
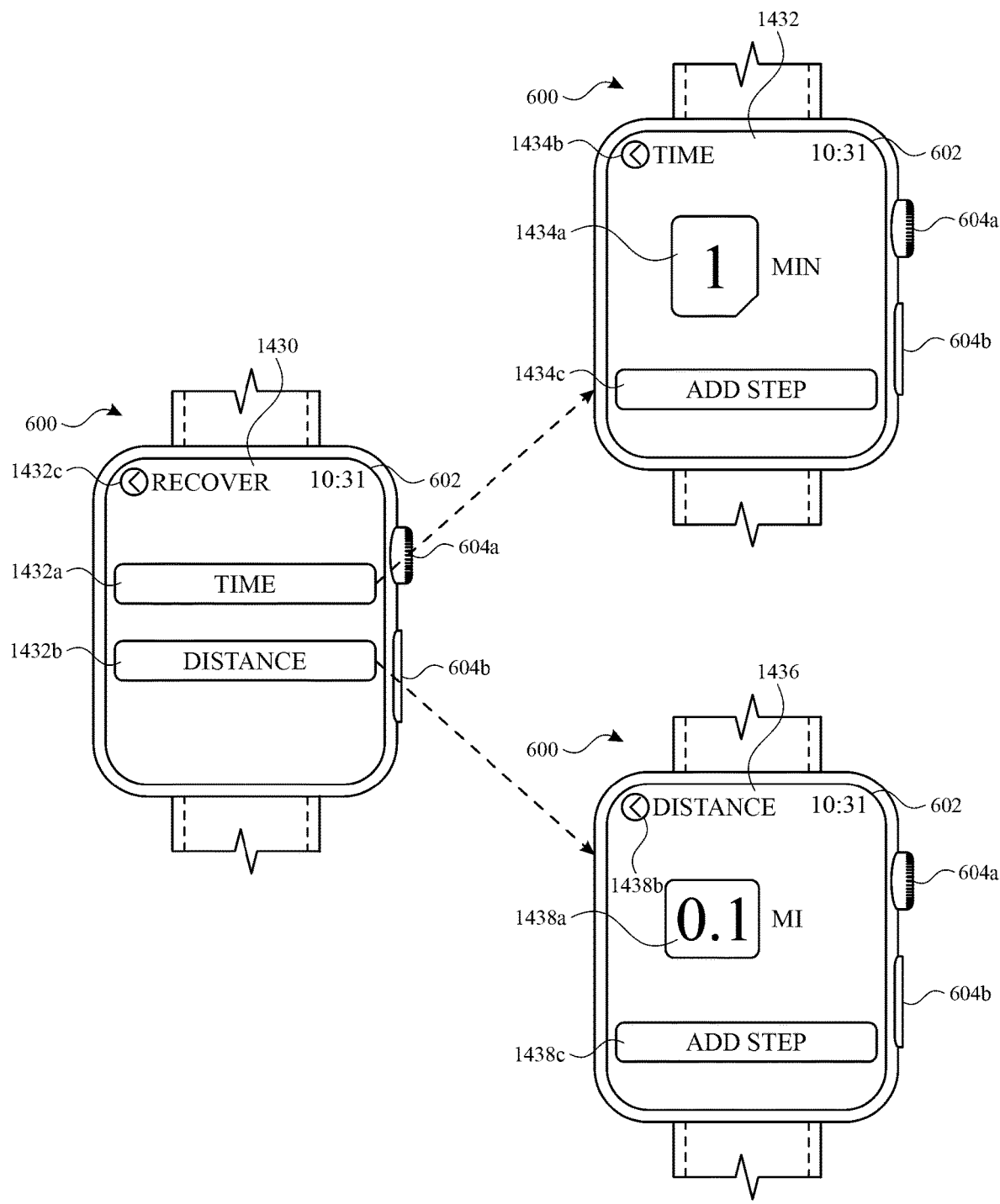

At FIG. 14G, in response to user input 1426*b*, electronic device 600 displays user interface 1430, which allows the user to select a goal type for the recovery segment the user would like to add to the interval workout. Option 1432*a* is selectable to add a recovery step with a time goal as its goal type, and option 1432*b* is selectable to add a recovery step with a distance goal as its goal type. Selecting option 1432*a* causes electronic device 600 to display user interface 1432 to define a goal value for the time goal, and selecting option 1432*b* causes electronic device 600 to display user interface 1436 to define a goal value for the distance goal. Selection of option 1434*c* results in a time-based recovery step being added to the interval workout, and selection of option 1438*c* results in a distance-based recovery step being added to the interval workout.

Figure 14H:
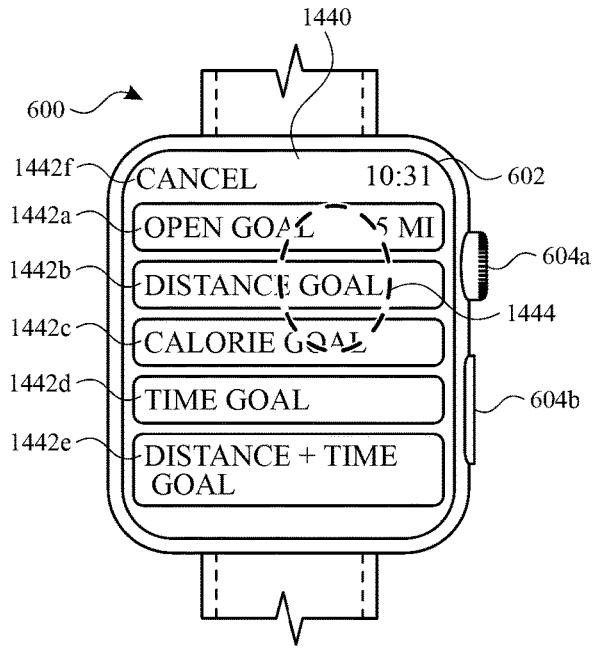

At FIG. 14H, in response to user input 1426*a* (in FIG. 14F), electronic device 600 displays user interface 1440 which allows a user to select a goal type for the work step the user would like to add to the interval workout. Option 1442*a* corresponds to an open goal type, option 1442*b* corresponds to a distance goal type, option 1442*c* corresponds to a calorie goal type, option 1442*d* corresponds to a time goal type, and option 1442*e* corresponds to a distance+time goal type. Option 1442*f* is selectable to return to interval workout creation user interface 1404. At FIG. 14H, electronic device 600 detects user input 1444 (e.g., a tap input) corresponding to selection of option 1442*b*.

Figure 14I:
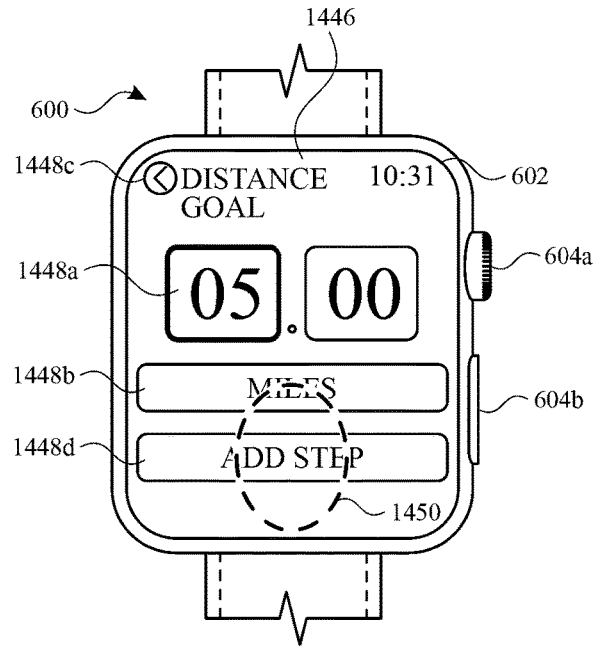

At FIG. 14I, in response to user input 1444, electronic device 600 displays user interface 1446 which prompts the user to set a distance goal value. Had the user chosen a different goal type in FIG. 14H, electronic device 600 would display a different user interface prompting the user to define a goal value for the selected goal type. In some embodiments, the user can adjust the goal value up or down by, for example, rotating rotatable input mechanism 604*a*. In FIG. 14I, electronic device 600 detects user input 1450 (e.g., a tap input) corresponding to selection of option 1448*d*.

Figure 14J:
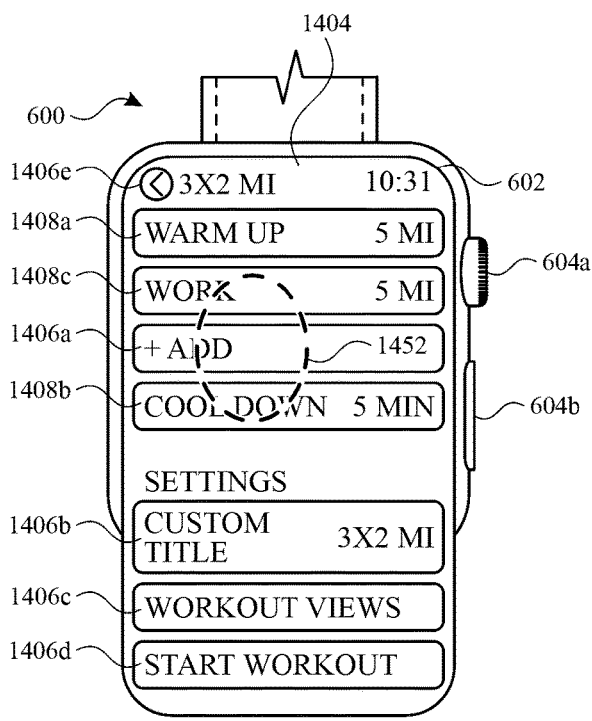

At FIG. 14J, in response to user input 1450, electronic device 600 displays interval workout creation user interface 1404 with a new segment representation 1408*c* representing the 5-mile work segment that was added in response to user input 1450. At FIG. 14J, electronic device 600 detects user input 1452 (e.g., a tap input) corresponding to selection of option 1406*a*.

Figure 14K:
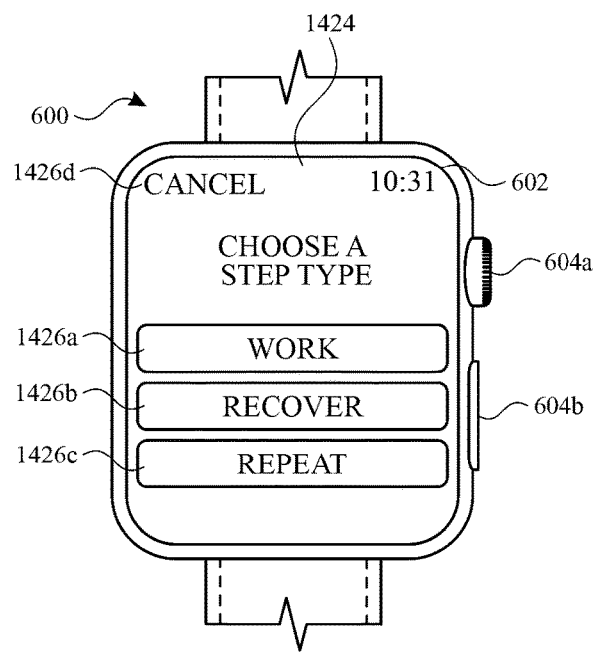

At FIG. 14K, in response to user input 1452, electronic device 600 displays segment type user interface 1424. However, now that a repeatable segment has been added to the interval workout (e.g., the 5-mil work step represented by representation 1408*c*), segment type user interface 1424 now includes selectable option 1426*c*. Details of selectable option 1426*c* will be explored in the next few figures.

Figure 14L:
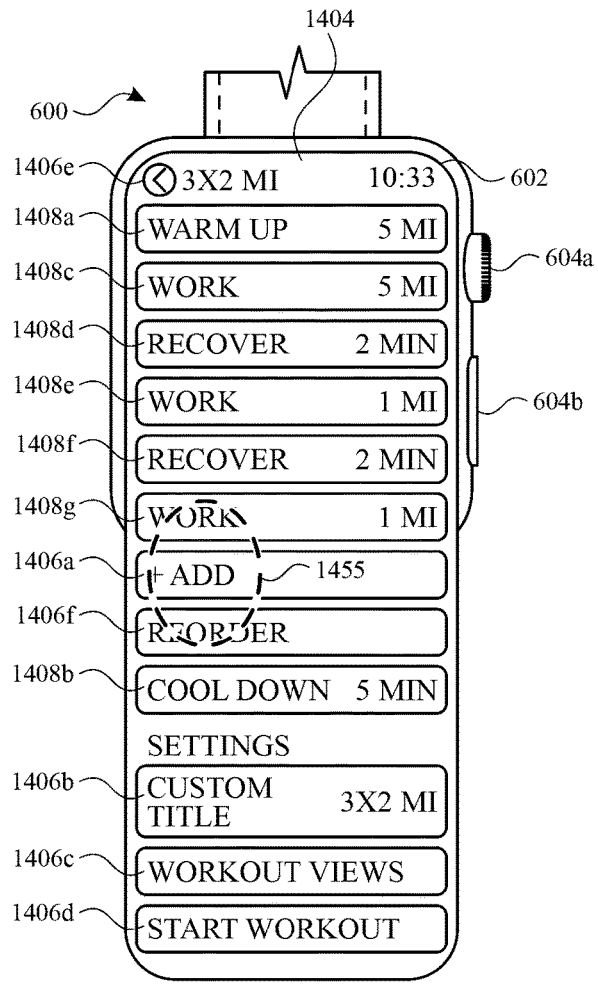

At FIG. 14L, the user has added four additional segments represented by segment representations 1408*d*-1408*g* (e.g., using the steps described above with reference to FIGS. 14C-14J). At FIG. 14L, electronic device 600 detects user input 1455 (e.g., a tap input) corresponding to selection of option 1406*a*.

Figure 14M:
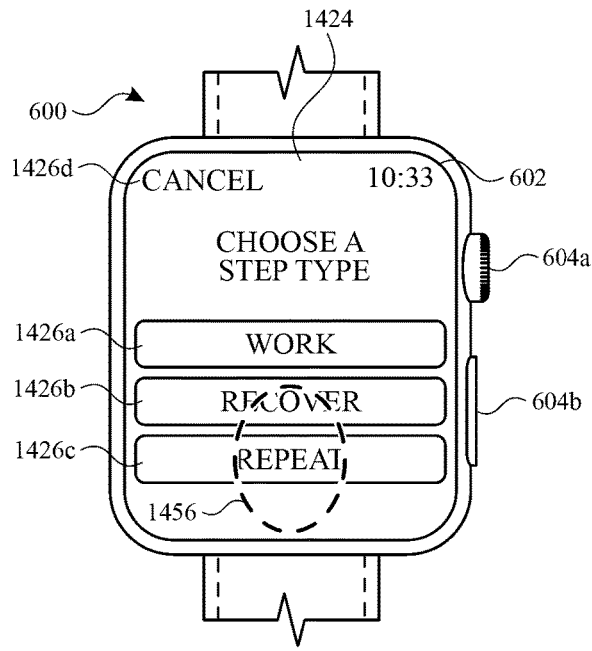

At FIG. 14M, in response to user input 1455, electronic device 600 displays segment type user interface 1424 which, in accordance with a determination that the interval workout includes one or more repeatable segments, including selectable option 1426*c*. At FIG. 14M, electronic device 600 detects user input 1456 (e.g., a tap input) corresponding to selection of option 1426*c*.

Figure 14N:
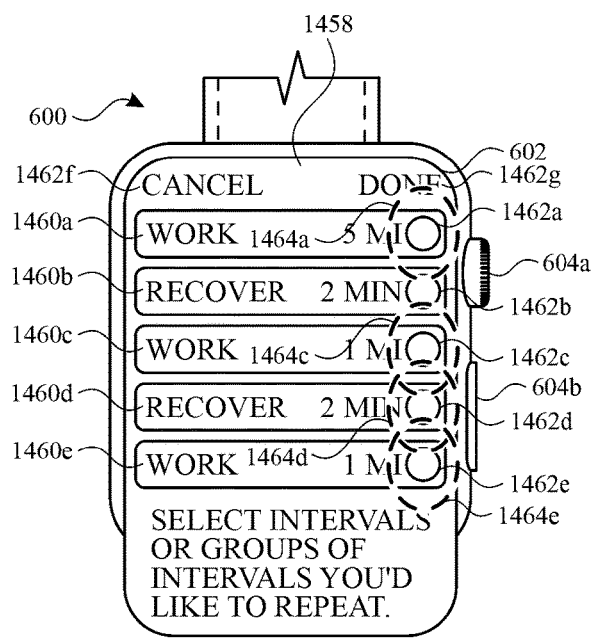

At FIG. 14N, in response to user input 1456, electronic device displays user interface 1458, which displays options 1462*a*-1462*e* corresponding to each repeatable segment in the interval workout. By interacting with user interface 1458, the user is able to identify which repeatable segment the user would like to repeat in the interval workout. At FIG. 14N, electronic device 600 detects user input 1464*a* (e.g., a tap input) corresponding to selection of option 1462*a*, user input 1464*c* (e.g., a tap input) corresponding to selection of option 1462*c*, user input 1464*d* (e.g., a tap input) corresponding to selection of option 1462*d*, and user input 1464*e* (e.g., a tap input) corresponding to selection of option 1462*e*.

Figure 14O:
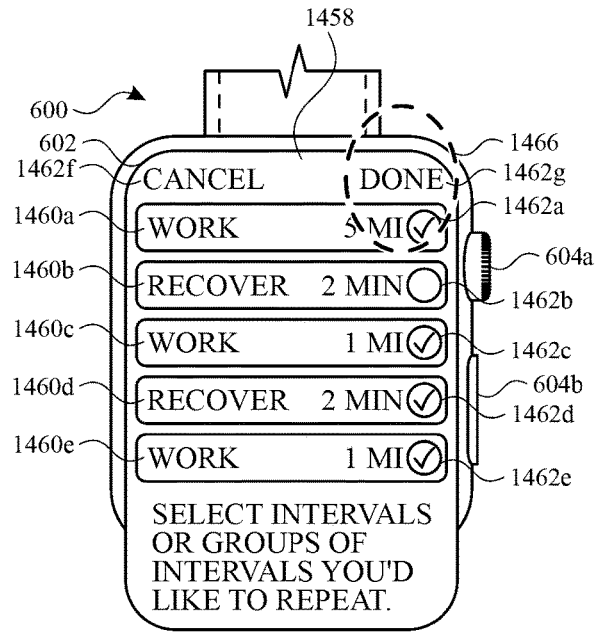

At FIG. 14O, in response to user inputs 1464*a*, 1464*c*, 1464*d*, and 1464*e*, electronic device 600 displays user interface 1458 with options 1462*a*, 1462*c*, 1462*d*, and 1462*e* displayed in a manner indicating that their corresponding segments have been selected for repetition. At FIG. 14O, electronic device 600 detects user input 1466 corresponding to selection of done option 1462*g*.

Figure 14P:
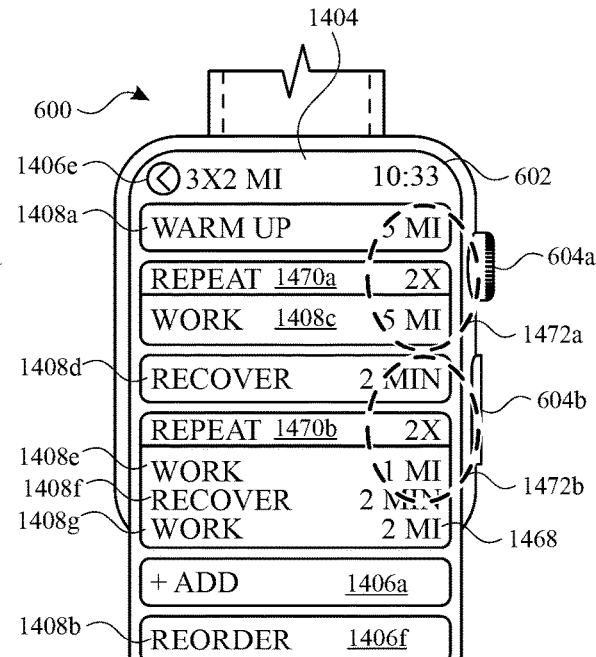

At FIG. 14P, in response to user input 1466, electronic device 600 displays interval workout creation user interface 1404 with various modifications. Segment representation 1408*c* is now display with indication 1470*a* indicating that the workout segment corresponding to segment representation 1408*c* is to be repeated two times. Additionally, in accordance with a determination that segment representations 1408*e*, 1408*f*, and 1408*g* were selected for repetition and are adjacent to one another, segment representations 1408*e*, 1408*f*, 1408*g*, are grouped into a single grouping 1468, and grouping 1468 is displayed with indication 1470*b* indicating that the entire grouping 1468 is to be repeated two times during the interval workout.

Figure 14Q:
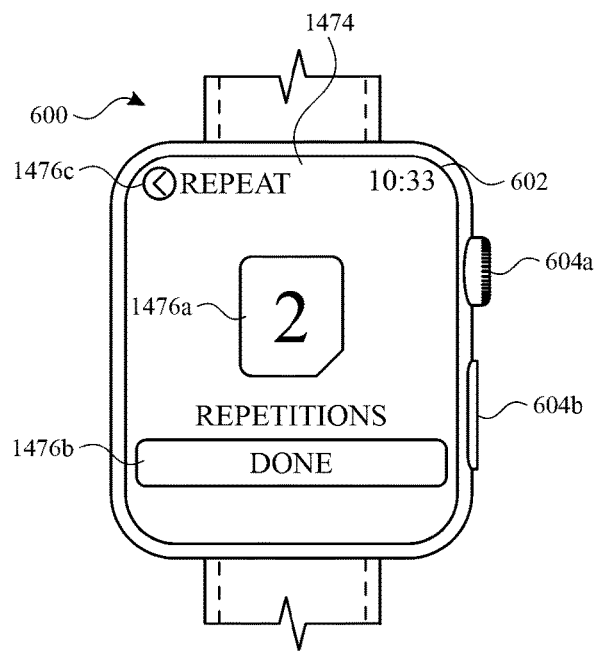

At FIG. 14P, electronic device 600 detects user input 1472*a* (e.g., a tap input) corresponding to selection of indication 1470*a*, and user input 1472*b* (e.g., a tap input) corresponding to selection of indication 1470*b*. At FIG. 14Q, in response to user input 1472*a* and/or in response to user input 1472b, electronic device 600 displays user interface 1474, that allows the user to define how many times the segment and/or the group of segments should be repeated. In some embodiments, a user defines the number of repetitions by, for example, rotating rotatable input mechanism 604a to adjust repetition indication 1476a, and selecting done option 1476b.

Returning to FIG. 14P, electronic device 600 detects user input 1472c (e.g., a tap input) corresponding to selection of option 1406d.

Figure 14R:
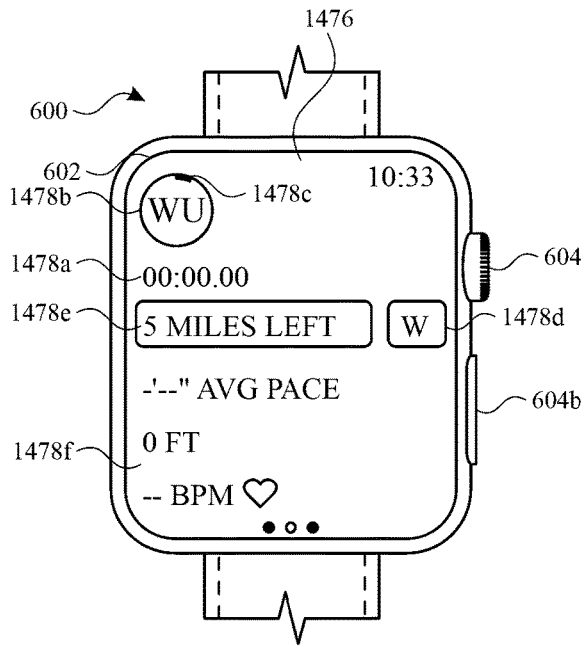

At FIG. 14R, electronic device 600 displays interval workout in-workout user interface 1476. Interval workout in-workout user interface includes a set of workout metrics 1478f. In some embodiments, the user can display different workout metrics by, for example, rotating rotatable input mechanism 604a (e.g., in a similar manner as was discussed above with reference to FIGS. 6A-6AE). Interval workout in-workout user interface 1476 also includes segment type indication 1478b, which identifies the type of segment that is currently taking place (e.g., WU in FIG. 14R indicates that the current segment is a warm up segment). Segment type indication 1478b is surrounded by segment progress indication 1478c, which is indicative of the progress the user has made in completing the current workout segment. Interval workout in-workout user interface 1476 also includes indication 1478e, which indicates how close the user is to completing the current workout segment (e.g., based on the goal value of the current workout segment). For example, in FIG. 14R, indication 1478e indicates that there are 5 miles left until the next workout segment. If the warm up segment had been a time-based warm up segment, indication 1478e could indicate that there are 5 minutes left until the next workout segment. Interval workout in-workout user interface 1476 also includes next interval indication 1478d, which indicates the segment type for the next upcoming workout segment (e.g., W in FIG. 14R indicates that the next upcoming workout segment is a work type workout segment), as well as elapsed time indication 1478a which indicates how much time has elapsed in the workout.

Figure 14S:
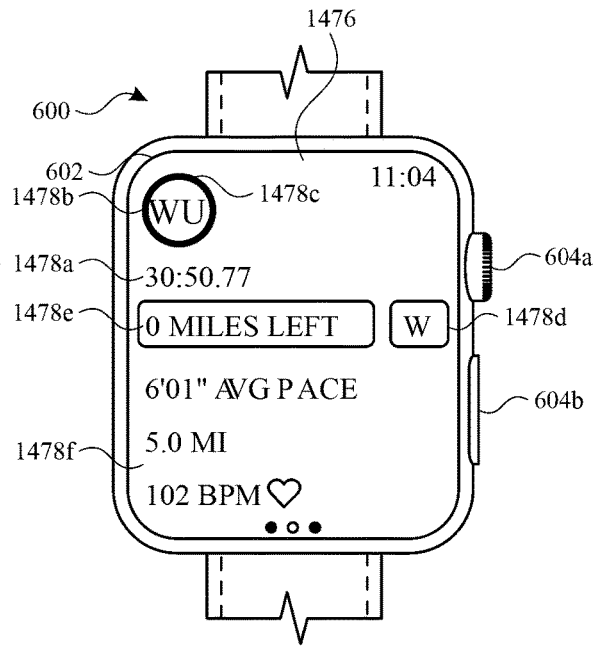
Figure 14T:
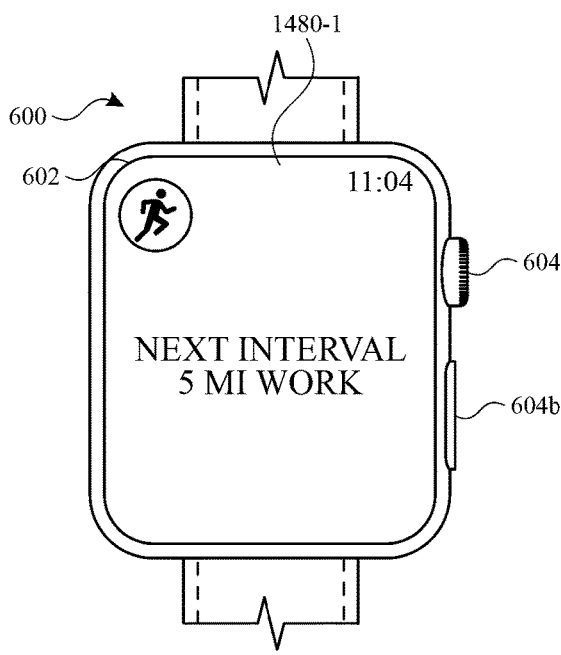

At FIG. 14S, the user has been working out for 30 minutes and 50.77 seconds, and has traversed five miles. The warm up segment is a 5-mile warm up segment, so progress indication 1478c indicates that the user has essentially completed the warm up segment, and indication 1478c indicates that there are 0 miles left to the next workout segment. At FIG. 14T, in response to a determination that the user has completed the first workout segment, electronic device 600 displays indication 1480-1 indicating that the next workout segment is a 5 mile work segment.

Figure 14U:
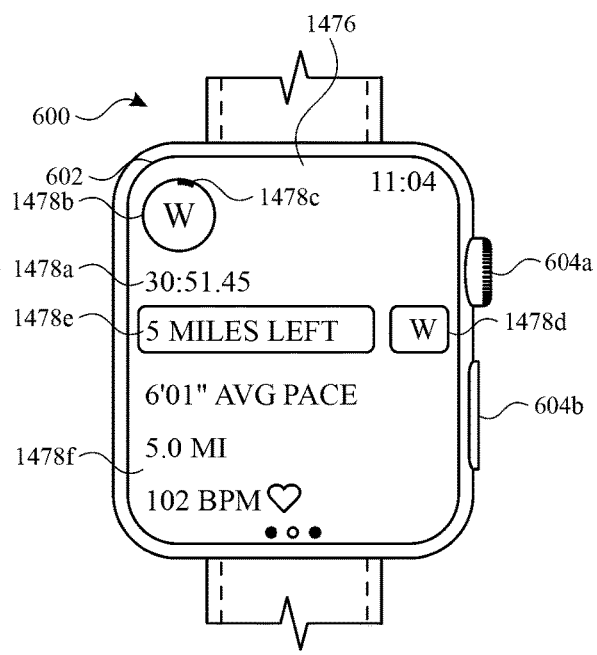

At FIG. 14U, after displaying indication 1480-1 (e.g., after display indication 1480-1 for a predefined duration of time), electronic device 600 re-displays interval workout in-workout user interface 1476. In some embodiments, electronic device 600 does not display indication 1480-1, and goes straight from the state depicted in FIG. 14S to the state depicted in FIG. 14U. Indication 1478b now indicates that the current workout segment is a work segment, and progress indication 1478c indicates that the user has just started the workout segment, and indication 1478e indicates that there are 5 miles left until the next workout segment. Indication 1478d also indicates that the next workout segment is another work segment.

Figure 14V:
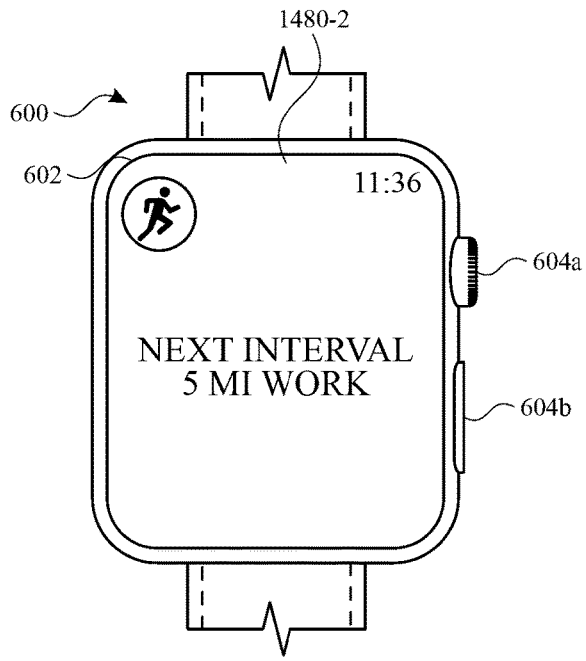
Figure 14W:
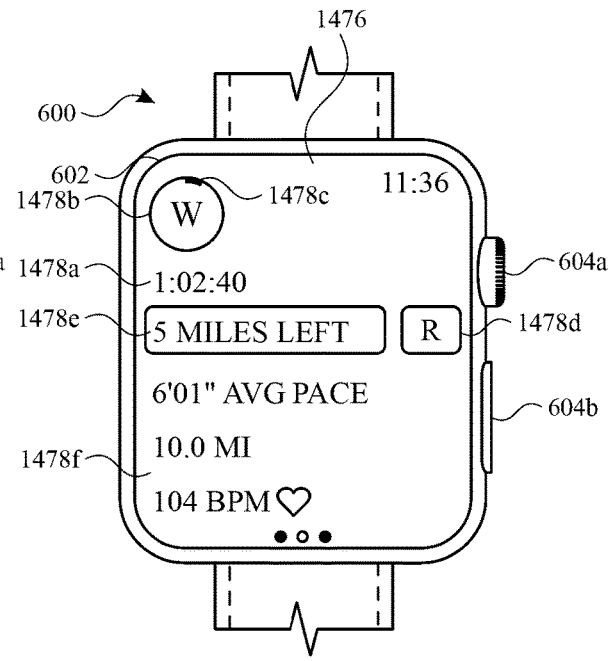

At FIG. 14V, the user has completed the first 5-mile work segment, and electronic device 600 displays indication 1480-2 indicating that the next workout segment is another 5-mile work segment. At FIG. 14W, the user has started the second 5-mile work segment, and indications 1478e and 1478d indicate that there are 5 miles remaining until the next workout segment, which is a recovery segment.

Figure 14X:
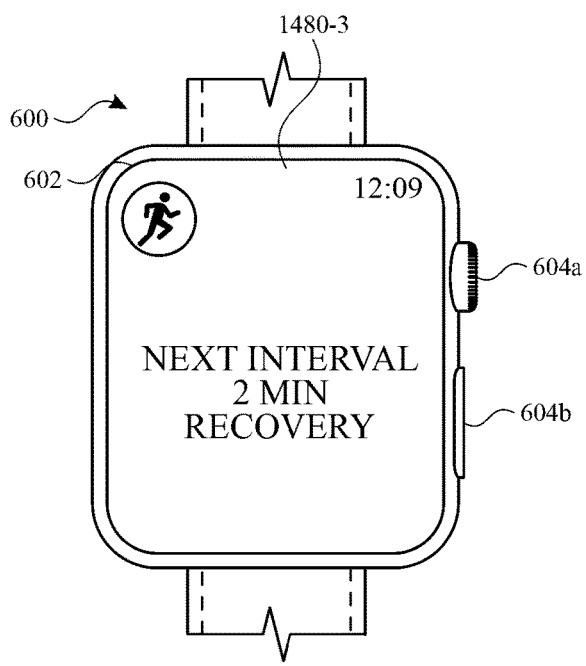

At FIG. 14X, the user has completed the second 5-mile work segment, and electronic device 600 displays indication 1480-3 indicating that the next workout segment is a 2 minute recovery segment. At FIG. 14Y, indication 1478b indicates that the current workout segment is a recovery segment, and indications 1478e and 1478d indicate that there are two minutes remaining in this recovery segment, until the next workout segment, which is a work segment.

FIG. 15 is a flow diagram illustrating a method for navigating, modifying, and outputting interval workout content using a computer system in accordance with some embodiments. Method 1500 is performed at a computer system (e.g., 100, 300, 500) (e.g., a wearable device, a smart watch, a smart phone, a tablet, and/or a computer system controlling an external display) that is in communication with a display generation component (e.g., a display controller, a touch-sensitive display system; and/or a display (e.g., integrated and/or connected)) and one or more input devices (e.g., a touch-sensitive surface (e.g., a touch-sensitive display); an accelerometer; a rotatable input mechanism; a depressible input mechanism; and/or a rotatable and depressible input mechanism). Some operations in method 1500 are, optionally, combined, the orders of some operations are, optionally, changed, and some operations are, optionally, omitted.

As described below, method 1500 provides an intuitive way for navigating, modifying, and outputting interval workout content. The method reduces the cognitive burden on a user for navigating, modifying, and accessing interval workout content, thereby creating a more efficient human-machine interface. For battery-operated computing devices, enabling a user to navigate, modify, and access interval workout content faster and more efficiently conserves power and increases the time between battery charges.

The computer system (e.g., 600) displays (1502), via the display generation component (e.g., 602), a workout creation user interface (e.g., 1404) (e.g., a user interface that includes one or more options for defining and/or creating a workout) that includes: a first selectable object (e.g., 1406a) (1504) (e.g., affordance) that is selectable to initiate a process for adding one or more segments to a workout (e.g., an interval workout, a workout that comprises a plurality of segments, and/or a user-defined workout); and a second selectable object (e.g., 1406d) (1506) (e.g., affordance) that is selectable to initiate the workout. In some embodiments, selection of the second selectable object (e.g., 1406d) also causes and/or initiates a process for creating a user interface object (e.g., within a workout user interface (e.g., 606) that includes a plurality of user interface objects corresponding to a plurality of different workouts) that is selectable to initiate the workout. In some embodiments, the first selectable object and the second selectable object are concurrently displayed. In some embodiments, the first selectable object and the second selectable object are part of the same user interface but are not concurrently displayed (e.g., the second selectable object can be made visible by scrolling from the first selectable object without changing the displayed user interface, and/or the first selectable object can be made visible by scrolling from the second selectable object without changing the displayed user interface.

In some embodiments, while displaying the workout creation user interface (e.g., 1404) that includes the first selectable object (e.g., 1408b) and the second selectable object (e.g., 1406d), the computer system receives (1508), via the one or more input devices, a first user input (e.g.,

1410b)(e.g., one or more inputs) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to selection of the first user interface object (e.g., 1406a).

In some embodiments, in response to receiving the first user input (e.g., 1410b) (1510): in accordance with a determination that the workout includes one or more repeatable segments (e.g., 1408c-1408g) (e.g., when the first user input is received) (e.g., one or more repeatable segments were previously added to the workout prior to the first user input (e.g., previously added to the workout by the user)), the computer system displays (1512), via the display generation component, a first interval creation user interface (e.g., 1424 in FIG. 14M) (in some embodiments, replacing display of the workout creation user interface with display of the first interval creation user interface), including concurrently displaying: a third selectable object (e.g., 1426a, 1426b) (1514) (e.g., affordance) that is selectable to initiate a process for adding a new segment (in some embodiments, a segment of a first type (e.g., a work segment and/or a recover segment)) to the workout; and a fourth selectable object (e.g., 1426c) (1516) (e.g., affordance) that is selectable to initiate a process for adding repetitions of at least some of the one or more repeatable segments (e.g., segments that were previously added to the workout) (in some embodiments, selection of the fourth selectable object causes display of representations of the one or more repeatable segments for selection by a user).

In some embodiments, in response to receiving the first user input (e.g., 1410b): in accordance with a determination that the workout does not include repeatable segments (e.g., FIG. 14C) (e.g., when the first user input is received) (e.g., repeatable segments were not previously added to the workout prior to the first user input (e.g., were not previously added to the workout by the user)), the computer system displays (1518), via the display generation component, a second interval creation user interface (e.g., 1424 in FIG. 14F) (e.g., a second interval creation user interface different from the first interval creation user interface)) (in some embodiments, replacing display of the workout creation user interface with display of the second interval creation user interface), including displaying the third selectable object (e.g., 1426a, 1426b) without displaying the fourth selectable object (e.g., 1426c in FIG. 14F is not selectable, so computer system 600 does not display a selectable object (e.g., it displays a non-selectable representation of the selectable object)). In some embodiments, the second interval creation user interface includes a non-selectable representation of the fourth selectable object.

In some embodiments, the computer system (e.g., 600) displays, via the display generation component (e.g., 602), a workout creation user interface (e.g., 1404) that includes: a first selectable object (e.g., 1406a) that is selectable to initiate a process for adding one or more segments to a workout; and a second selectable object (e.g., 1406d) that is selectable to initiate the workout; while displaying the workout creation user interface that includes the first selectable object and the second selectable object, the computer system receives, via the one or more input devices, a first user input (e.g., 1410b) corresponding to selection of the first user interface object; and in response to receiving the first user input: the computer system displays a third selectable object (e.g., 1426a, 1426b) that is selectable to initiate a process for adding a new segment to the workout; and: in accordance with a determination that the workout includes one or more repeatable segments, the computer system displays a fourth selectable object (e.g., 1426c) that is selectable to initiate a process for adding repetitions of at least some of the one or more repeatable segments; and in accordance with a determination that the workout does not include repeatable segments, the computer system forgoes displaying the fourth selectable object (e.g., 1426c in FIG. 14F is not selectable, so computer system 600 does not display a selectable object (e.g., it displays a non-selectable representation of the selectable object)).

Displaying the first interval creation user interface if the workout includes one or more repeatable segments, and displaying the second interval creation user interface if the workout does not include repeatable segments, provides the user with feedback about the state of the device (e.g., whether or not the device has detected that the workout includes repeatable segments). Doing so also enables these operations to be performed automatically without user input. Furthermore, displaying the second interval creation user interface instead of the first interval creation user interface when a workout does not have repeatable segments prevents the user interface from display information and/or elements that are not relevant to the particular user.

In some embodiments, while displaying the third selectable object (e.g., 1425a, 1426b) (e.g., while displaying the first interval creation user interface or while displaying the second interval creation user interface), the computer system receives, via the one or more input devices, a user input corresponding to selection of the third selectable object (e.g., 1428a, 1428b). In some embodiments, in response to detecting the user input corresponding to selection of the third selectable object, the computer system displays, via the display generation component, a plurality of segment duration options (e.g., 1432a-1432b and/or 1442a-1442e), including concurrently displaying: a first segment duration option (e.g., 1432a-1432b and/or 1442a-1442e) corresponding to a first duration type (e.g., a first duration unit and/or a first set of duration units) (e.g., time-based duration; distance-based duration, and/or calorie-based duration); and a second segment duration option (e.g., 1432a-1432b and/or 1442a-1442e) corresponding to a second duration type different from the first duration type (e.g., a second duration unit and/or a second set of duration units) (e.g., time-based duration; distance-based duration, and/or calorie-based duration). In some embodiments, selection of the first segment duration option corresponding to the first duration type initiates a process for defining a workout segment duration based on the first duration type. For example, in some embodiments, the first duration type is a time-based duration, and selection of the first segment duration option initiates a process for defining a time-based duration (e.g., x seconds, minutes, and/or hours) for the new workout segment. In some embodiments, the first duration type is a distance-based duration, and selection of the first segment duration option initiates a process for defining a distance-based duration (e.g., x feet, meters, kilometers, and/or miles) for the new workout segment. In some embodiments, the first duration type is a calorie-based duration, and selection of the first segment duration option initiates a process for defining a calorie-based duration (e.g., x calories). Displaying the first and second segment duration options in response to detecting the user input corresponding to selection of the third selectable object provides the user with feedback about the state of the device (e.g., that the device detected the user input corresponding to selection of the third selectable object). Doing so also enables the user to define segment duration types with fewer user inputs.

In some embodiments, the first segment duration option corresponds to a time-based duration (e.g., 1432*a* and/or 1442*d*) (e.g., defining duration of a workout segment based on a time limit and/or a threshold time (e.g., a workout segment that lasts for and/or ends after x seconds, minutes, or hours)). In some embodiments, while displaying the first segment duration option and the second segment duration option, the computer system receives, via the one or more input devices, a user input corresponding to selection of the first segment duration option; and in response to detecting the user input corresponding to selection of the first segment duration option, the computer system displays, via the display generation component, a time duration user interface that prompts the user to define a time-based duration for the workout segment (e.g., prompts the user to define after how many seconds, minutes, and/or hours the workout segment will end). Displaying the first segment duration option that corresponds to a time-based duration allows a user to define a time-based duration for a workout segment with fewer inputs.

In some embodiments, the first segment duration option corresponds to a distance-based duration (e.g., 1432*b* and/or 1442*b*) (e.g., defining duration of a workout segment based on a distance limit and/or a threshold distance (e.g., a workout segment that lasts for and/or ends after x miles, feet, meters, or kilometers)). In some embodiments, while displaying the first segment duration option and the second segment duration option, the computer system receives, via the one or more input devices, a user input corresponding to selection of the first segment duration option; and in response to detecting the user input corresponding to selection of the first segment duration option, the computer system displays, via the display generation component, a distance duration user interface that prompts the user to define a distance-based duration for the workout segment (e.g., prompts the user to define after how many feet, meters, kilometers, and/or miles the workout segment will end). Displaying the first segment duration option that corresponds to a distance-based duration allows a user to define a distance-based duration for a workout segment with fewer inputs.

In some embodiments, the first segment duration option corresponds to a calorie-based duration (e.g., 1442*c*) (e.g., defining duration of a workout segment based on a calorie limit and/or a threshold number of calories (e.g., a workout segment that lasts for and/or ends after x calories burned)). In some embodiments, while displaying the first segment duration option and the second segment duration option, the computer system receives, via the one or more input devices, a user input corresponding to selection of the first segment duration option; and in response to detecting the user input corresponding to selection of the first segment duration option, the computer system displays, via the display generation component, a calorie duration user interface that prompts the user to define a calorie-based duration for the workout segment (e.g., prompts the user to define after how many calories the workout segment will end). Displaying the first segment duration option that corresponds to a calorie-based duration allows a user to define a calorie-based duration for a workout segment with fewer inputs.

In some embodiments, the computer system (e.g., 600) displays, via the display generation component (e.g., 602), the workout creation user interface (e.g., 1404), wherein the workout creation user interface includes: the first selectable object (e.g., 1406*a*) (e.g., an add option); and the second selectable object (e.g., 1406*d*) (e.g., a start workout option). In some embodiments, the computer system receives, via the one or more input devices, one or more user inputs corresponding to a request to add a new segment to the workout (e.g., user inputs 1410*b*, 1444, 1450), wherein the one or more user inputs include a first set of user inputs (e.g., 1410*b*) (e.g., one or more user inputs) corresponding to selection of the third selectable object.

In some embodiments, in response to receiving the one or more user inputs corresponding to a request to add a new segment to the workout, the computer system displays, via the display generation component, the workout creation user interface (e.g., 1404 in FIG. 14J after user inputs 1410*b*, 1444, 1450). In some embodiments, the workout creation user interface (e.g., 1404 in FIG. 14J) includes: the first selectable object (e.g., 1406*a*); the second selectable object (e.g., 1460*d*); and a representation of a first workout segment in the workout (e.g., 1408*c*), wherein the representation of the first workout segment is added to the workout creation user interface in response to receiving the one or more user inputs corresponding to a request to add a new segment to the workout (e.g., was not displayed in and/or included in the workout creation user interface prior to receiving the one or more user inputs corresponding to the a request to add a new segment to the workout). Displaying the representation of the first workout segment in the workout creation user interface in response to receiving the one or more user inputs corresponding to the request to add a new segment to the workout provides the user with feedback about the state of the device (e.g., that the device has added the new workout segment to the workout).

In some embodiments, while displaying the workout creation user interface (e.g., 1404) including the first selectable object (e.g., 1406*a*), the second selectable object (e.g., 1406*d*), and the representation of the first workout segment in the workout (e.g., 1408*c*), the computer system receives, via the one or more input devices, a second user input (e.g., 1452) (e.g., one or more inputs) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to selection of the first user interface object (e.g., 1406*a*). In some embodiments, in response to receiving the second user input, in accordance with a determination that the workout includes one or more repeatable segments, displaying, via the display generation component, the first interval creation user interface (e.g., 1424), including concurrently displaying: the third selectable object (e.g., 1426*a*, 1426*b*) (e.g., an add segment option); and the fourth selectable object (e.g., 1426*c*) (e.g., a repeat segment(s) option). Displaying the first interval creation user interface in response to receiving the second user input and in accordance with a determination that the workout includes one or more repeatable segments provides the user with feedback about the state of the device (e.g., that the device has detected the second user input and/or that the device has detected that the workout includes one or more repeatable segments). Doing so also allows a user to add a new segment to the workout and/or repeat one or more existing segments with fewer user inputs.

In some embodiments, while displaying the first interval creation user interface (e.g., 1424), including concurrently displaying the third selectable object (e.g., 1426*a*, 1426*b*) and the fourth selectable object (e.g., 1426*c*), the computer system receives, via the one or more input devices, one or more user inputs (e.g., 1456) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to selection of the fourth selectable object. In some embodiments, in response to receiving the one or more user inputs corresponding to selection of the fourth selectable object, the computer system displays, via the display generation component, a repetition user interface (e.g., 1458), wherein the repetition user interface includes: a representation of a second workout segment in the workout (e.g., 1460a-1460e); and a representation of a third workout segment in the workout (e.g., 1460a-1460e) different from the second workout segment. In some embodiments, the repetition user interface includes a representation of a fourth workout segment in the workout different from the second and third workout segments. In some embodiments, the workout includes a plurality of repeatable workout segments, and the repetition user interface includes representations of each repeatable workout segment in the workout. Displaying the repetition user interface that includes the representation of the second workout segment and the representation of the third workout segment provides the user with feedback about the state of the device (e.g., that second and third workout segments are able to be repeated). Doing so also allows a user to repeat one or more existing segments in the workout with fewer user inputs.

In some embodiments, while displaying the repetition user interface (e.g., 1458) including the representation of the second workout segment (e.g., 1460a-1460e) and the representation of the third workout segment (e.g., 1460a-1460e), the computer system receives, via the one or more input devices, one or more user inputs (e.g., 1464a, 1464c, 1464d, 1464e, 1466) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to selection of the second workout segment for repetition (e.g., without receiving one or more user inputs corresponding to selection of the third workout segment for repetition). In some embodiments, in response to receiving the one or more user inputs corresponding to selection of the second workout segment for repetition, the computer system displays, via the display generation component, the workout creation user interface (e.g., 1404), wherein the workout creation user interface includes: the first selectable object (e.g., 1406a); the second selectable object (e.g., 1406d); a second representation of the second workout segment (e.g., 1408c); and a second representation of the third workout segment (e.g., 1408f), wherein: in accordance with a determination that the second workout segment has been selected for repetition (and, in some embodiments, in accordance with a determination that the third workout segment has not been selected for repetition), the second representation of the second workout segment is displayed in a first manner (e.g., with indication 1470a) (e.g., with a first visual indication and/or with a first visual style) indicative of the second workout segment being repeated during the workout, and the second representation of the third workout segment is not displayed in the first manner (e.g., without repetition indication 1470a) (e.g., without the first visual indication and/or without the first visual style; and/or displayed in a second manner different from the first manner indicative of the third workout segment not being repeated during the workout). In some embodiments, the representation of the second workout segment is displayed with a first visual indication that indicates the number of times the second workout segment is to be repeated during the workout. Displaying the second representation of the second workout segment in the first manner provides the user with feedback about the state of the device (e.g., that the second workout segment is to be repeated during the workout). Displaying the repetition user interface that includes the representation of the second workout segment and the representation of the third workout segment also allows a user to repeat one or more segments of the workout with fewer user inputs.

In some embodiments, displaying the second representation of the second workout segment (e.g., 1408c) in the first manner (e.g., with indication 1470a) includes displaying the second representation of the second workout segment with a first visual indication (e.g., 1470a) indicating the number of times the second workout segment is to be repeated during the workout. In some embodiments, while displaying the second representation of the second workout segment with the first visual indication, the computer system receives, via the one or more input devices, one or more user inputs (e.g., 1472a) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to selection of the first visual indication. In some embodiments, in response to receiving the one or more user inputs corresponding to selection of the first visual indication, the computer system displays, via the display generation, a user interface (e.g., 1474) that prompts the user to define the number of times the second workout segment is to be repeated during the workout (e.g., a user interface that includes one or more user interface elements that are selectable by a user to enter a number, and/or a user interface that displays a number that is modifiable via one or more user inputs (e.g., one or more touch screen inputs, one or more button presses, and/or one or more rotations of a rotatable input mechanism)). Displaying the first visual indication provides the user with feedback about the state of the device (e.g., that the second workout segment is to be repeated a certain number of times during the workout). Displaying the user interface that prompts the user to define the number of times the second workout segment is to be repeated allows a user to define the number of times the second workout segment is to be repeated with fewer user inputs.

In some embodiments, the second workout segment (e.g., 1408e) and the third workout segment (e.g., 1408f) are consecutive workout segments (e.g., workout segments that immediately precede and/or succeed one another) (in some embodiments, the representation of the second workout segment and the representation of the third workout segment are displayed immediately adjacent to one another (e.g., without any representations of workout segments between them)). In some embodiments, while displaying the repetition user interface (e.g., 1458) including the representation of the second workout segment (e.g., 1460c) and the representation of the third workout segment (e.g., 1460d), the computer system receives, via the one or more input devices, one or more user inputs (e.g., 1462c, 1462d, 1466) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to selection of the second workout segment and the third workout segment for repetition.

In some embodiments, in response to receiving the one or more user inputs (e.g., 1462c, 1462d, 1466) corresponding to selection of the second workout segment and the third workout segment for repetition, the computer system displays, via the display generation component, the workout creation user interface (e.g., 1404). In some embodiments, the workout creation user interface includes: the first selectable object (e.g., 1406a); the second selectable object (e.g., 1406d); a second representation of the second workout segment (e.g., "WORK 1 MI" in 1468); and a second representation of the third workout segment (e.g., "RECOVER 2 MIN" in 1468). In some embodiments, in accordance with a determination that the second workout segment and the third workout segment have been selected for repetition, and in accordance with a determination that the second workout segment and the third workout segment are consecutive workout segments: the workout creation user interface (e.g., 1404) includes a first grouping indicator (e.g., 1468 and/or a box around 1468) (e.g., a box and/or a line and/or a shape that encloses the second representation of the second workout segment and the second representation of the third workout segment) indicative of the second workout segment and the third workout segment being part of a first group; and the first grouping indicator is displayed with a second visual indication (e.g., 1470b) indicating that workout segments in the first group are to be repeated during the workout. In some embodiments, the second visual indication indicates the number of times workout segments in the first group are to be repeated during the workout. Displaying the first group indicator and the second visual indication provides the user with feedback about the state of the device (e.g., that the second workout segment and the third workout segment are grouped into a group, and that the group is to be repeated during the workout). Displaying the repetition user interface that includes the representation of the second workout segment and the representation of the third workout segment also allows a user to repeat one or more segments of the workout with fewer user inputs.

In some embodiments, the second workout segment (e.g., 1408c) and the third workout segment (e.g., 1408e) are non-consecutive workout segments (e.g., workout segments that do not immediately precede and/or succeed one another). In some embodiments, the representation of the second workout segment and the representation of the third workout segment are displayed in a non-adjacent manner (e.g., with representations of one or more workout segments between the representation of the second workout segment and the representation of the third workout segment). In some embodiments, while displaying the repetition user interface (e.g., 1458) including the representation of the second workout segment (e.g., 1460a) and the representation of the third workout segment (e.g., 1460c), the computer system receives, via the one or more input devices, one or more user inputs (e.g., 1464a, 1464c, 1466) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to selection of the second workout segment and the third workout segment for repetition.

In some embodiments, in response to receiving the one or more user inputs (e.g., 1464a, 1464c, 1466) corresponding to selection of the second workout segment and the third workout segment for repetition, the computer system displays, via the display generation component, the workout creation user interface (e.g., 1404). In some embodiments, the workout creation user interface includes: the first selectable object (e.g., 1406a); the second selectable object (e.g., 1406d); a second representation of the second workout segment (e.g., 1408c); and a second representation of the third workout segment (e.g., "WORK 1 MI" in 1468). In some embodiments, in accordance with a determination that the second workout segment and the third workout segment have been selected for repetition, and in accordance with a determination that the second workout segment and the third workout segment are non-consecutive workout segments: the second representation of the second workout segment is displayed in a second manner (e.g., with indication 1470a) (e.g., with a second visual indication and/or with a second visual style) indicative of the second workout segment being repeated during the workout; and the second representation of the third workout segment is displayed in the second manner (e.g., with indication 1470b). In some embodiments, the second representation of the second workout segment is displayed with a third visual indication indicating the number of times the second workout segment is to be repeated during the workout. In some embodiments, the second representation of the third workout segment is displayed with a fourth visual indication separate from the third visual indication indicating the number of times the third workout segment is to be repeated during the workout. Displaying the second representation of the second and third workout segments in the second manner provides the user with feedback about the state of the device (e.g., that the second and third workout segments are to be repeated during the workout). Displaying the repetition user interface that includes the representation of the second workout segment and the representation of the third workout segment also allows a user to repeat one or more segments of the workout with fewer user inputs.

In some embodiments, displaying the first interval creation user interface (e.g., 1424) comprises concurrently displaying: the third selectable object (e.g., 1426a, 1426b), wherein the third selectable object is selectable to initiate a process for adding a new segment of a first type (e.g., a warm up segment, a cool down segment, a work segment and/or a recover segment) to the workout; the fourth selectable object (e.g., 1426c) that is selectable to initiate a process for adding repetitions of one or more segments that were previously added to the workout; and a fifth selectable object (e.g., 1426a, 1426b) that is selectable to initiate a process for adding a new segment of a second type (e.g., a warm up segment, a cool down segment, a work segment and/or a recover segment) different from the first type to the workout. In some embodiments, displaying the second interval creation user interface comprises concurrently displaying the third selectable object and the fifth selectable object without displaying the fourth selectable object. Displaying the first interval creation user interface with the third selectable object and the fifth selectable object allows a user to add new segments of different types to the workout with fewer user inputs. Displaying the second interval creation user interface instead of the first interval creation user interface when a workout does not have repeatable segments prevents the user interface from display information and/or elements that are not relevant to the particular user.

In some embodiments, the workout creation user interface (e.g., 1404) further includes a workout views object (e.g., 1406c) that is selectable to initiate a process for modifying one or more workout metrics (e.g., physical activity metrics and/or metrics that are indicative of the physical activity level of the user) that are accessible during the workout (e.g., during a workout session corresponding to the workout) (e.g., one or more workout metrics that are able to be displayed during the workout (e.g., that are automatically displayed during a workout session corresponding to the workout and/or that a user is able to display during a workout session corresponding to the workout with one or more user inputs)). In some embodiments, modifying one or more workout metrics includes selecting one or more workout metrics for display and/or one or more workout metrics to be accessible during a workout session corresponding to the workout and excluding one or more workout metrics from being displayed and/or being accessible during a workout session corresponding to the workout. Providing a user with a selectable option that is selectable to initiate a process for modifying one or more workout metrics that are accessible during a workout session reduces the number of inputs needed to perform this function. Doing so also enables this function to be performed without displaying additional controls.

In some embodiments, the computer system displays, at a first time, via the display generation component, the workout creation user interface (e.g., 1404). In some embodiments, the workout creation user interface includes: the first selectable object (e.g., 1406a); the second selectable object (e.g., 1406d); a representation of a fourth workout segment in the workout (e.g., 1408c-1408g); and a representation of a fifth workout segment in the workout (e.g., 1408c-1408g) different from the fourth workout segment, wherein at the first time, the representation of the fourth workout segment and the representation of the fifth workout segment are presented within the workout creation user interface in a first order indicative of the fourth workout segment preceding the fifth workout segment in the workout. In some embodiments, while displaying the workout creation user interface including the representation of the fourth workout segment and the representation of the fifth workout segment presented in the first order, the computer system receives, via the one or more input devices, one or more user inputs (e.g., user input that includes selection of option 1406f) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to a request to re-order the fourth workout segment within the workout. In some embodiments, in response to receiving the one or more user inputs corresponding to a request to re-order the fourth workout segment within the workout: the computer system displays, via the display generation component, movement of the representation of the fourth workout segment from a first display position to a second display position within the workout creation user interface, wherein after movement of the representation of the fourth workout segment to the second display position within the workout creation user interface, the representation of the fourth workout segment and the representation of the fifth workout segment are presented in a second order different from the first order and indicative of the fifth workout segment preceding the fourth workout segment in the workout. Re-ordering the fourth workout segment in response to one or more user inputs allows for this operation to be performed without displaying additional controls.

In some embodiments, the one or more user inputs corresponding to the request to re-order the fourth workout segment includes a drag and drop user input (e.g., a user input in which a user contacts (e.g., touches) a first position on a touch-sensitive surface (e.g., a touch-sensitive display) corresponding to the representation of the fourth workout segment and, while maintaining contact with the touch-sensitive surface, moves the contact point on the touch-sensitive surface to a second position on the touch-sensitive surface, and then terminates contact with the touch-sensitive surface). Re-ordering the fourth workout segment in response to a drag and drop input allows for this operation to be performed without displaying additional controls.

In some embodiments, the workout creation user interface (e.g., 1404) further comprises a rename option (e.g., 1406b) that is selectable to initiate a process for renaming the workout. Providing a user with a selectable option that is selectable to initiate a process for renaming a workout reduces the number of inputs needed to perform this function.

In some embodiments, while displaying the workout creation user interface (e.g., 1404), the computer system receives, via the one or more input devices, one or more user inputs (e.g., 1472c)(e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to selection of the second selectable object (e.g., 1406d). In some embodiments, in response to receiving the one or more user inputs corresponding to selection of the second selectable object: the computer system initiates a workout session corresponding to the workout, wherein the workout comprises a plurality of workout segments including a sixth workout segment (e.g., 1408c, 1408f, segments in 1468, 1408c-1408g) and a seventh workout segment (e.g., 1408c, 1408f, segments in 1468, 1408c-1408g) different from the sixth workout segment; and the computer system displays, via the display generation component, a workout session user interface (e.g., 1476) indicative of an active workout session, wherein the workout session user interface includes a segment progress indicator (e.g., 1478c) indicative of a user's progress in completing a current workout segment of the plurality of workout segments.

In some embodiments, each workout segment has a duration defined by a duration value, and the segment progress indicator is indicative of the user's progress in achieving the duration value for the current workout segment. For example, in some embodiments, the current workout segment has a time duration defined by a time duration value (e.g., x minutes), and the segment progress indicator is indicative of how much time is left for the user to achieve the time duration value and complete the current workout segment (e.g., y minutes remaining). In some embodiments, the current workout segment has a distance duration defined by a distance duration value (e.g., x miles, x kilometers, x meters, and/or x feet), and the segment progress indicator is indicative of how much distance remains for the user to achieve the distance duration value and complete the current workout segment (e.g., y miles remaining, y kilometers remaining, y meters remaining, and/or y feet remaining).

In some embodiments, initiating a workout session includes initiating recording (e.g., tracking, logging, collecting) of physical activity metrics corresponding to the workout session (e.g., physical activity metrics indicative of a physical activity level of the user during the workout session). In some embodiments, the physical activity metrics are recorded (e.g., captured) using one or more sensors (e.g., GPS, accelerometer, gyroscope, heart rate) of the computer system or an external device that is in communication with the computer system. In some embodiments, the physical activity metrics were not being recorded or were being recorded at a lower frequency and/or lower degree of precision prior to initiating (e.g., immediately prior to initiating) the workout session. In some embodiments, initiating the workout session includes causing one or more sensors to be enabled and/or activated to improve accurate measurements of user physical activity metrics during the workout session.

Providing a user with the second selectable object that is selectable to initiate a workout session reduces the number of inputs needed to perform either of these functions. Displaying the segment progress indicator provides the user with feedback about the state of the device. Doing so also allows the user to view his or her progress in the current workout segment without providing additional user inputs.

In some embodiments, the workout session user interface (e.g., 1476) further comprises an upcoming segment indicator (e.g., 1478d) that indicates a segment type (e.g., warm up, cool down, recover, and/or work) of a next upcoming workout segment. Displaying the upcoming segment indicator provides the user with feedback about the state of the device (e.g., that the device has determined that a next upcoming segment has a particular segment type). Doing so also allows the user to view the next upcoming workout segment without providing additional user inputs.

Note that details of the processes described above with respect to method 1500 (e.g., FIG. 15) are also applicable in an analogous manner to the methods described below and/or above. For example, methods 700, 800, 900, 1100, 1300, 1700, and/or 1800 optionally include one or more of the characteristics of the various methods described above with reference to method 1500. For example, in some embodiments, the workout recited in method 1500 corresponds to the workout session recited in methods 700, 800, 900, and/or 1800. For brevity, these details are not repeated below.

FIGS. 16A-16AB illustrate exemplary user interfaces for navigating, modifying, and outputting multisport workout content, in accordance with some embodiments. The user interfaces in these figures are used to illustrate the processes described below, including the processes in FIGS. 17 and 18.

FIG. 16A illustrates electronic device 600, which is a smartwatch with touch-sensitive display 602, rotatable and depressible input mechanism 604a, and button 604b. At FIG. 16A, electronic device 600 displays workout selection user interface 606, which was discussed above with reference to FIG. 6A. At FIG. 16A, electronic device 600 detects user input 1601 (e.g., a tap input) corresponding to selection of option 608k. Option 608k corresponds to a pre-configured multisport workout. As discussed above, in some embodiments, a multisport workout is a workout that has a multisport modality type, and is defined by a plurality of workout segments in an ordered sequence, wherein each workout segment corresponds to a particular modality type and the plurality of workout segments include two or more modality types.

At FIG. 16B, in response to user input 608k, and in accordance with a determination that option 608k corresponds to a workout that is of the multisport modality type, electronic device 600 displays multisport room user interface 1600, which is similar to outdoor run room user interface 612 and outdoor swim room user interface 672 discussed above with reference to FIGS. 6A-6AE. Multisport room user interface 1600 includes workout options 1602a-1602e corresponding to various preconfigured multisport workouts. Option 1602a corresponds to a preconfigured workout that includes an open water swim segment followed by an outdoor cycle segment follow by an outdoor run segment. Option 1602b corresponds to a preconfigured workout that includes an open water swim segment followed by an outdoor run segment. Option 1602c corresponds to a preconfigured workout that includes an outdoor cycle segment followed by an outdoor run segment. Option 1602d corresponds to a preconfigured workout that includes an outdoor run segment followed by an outdoor cycle segment. Option 1602e corresponds to a preconfigured workout that includes an open water swim segment followed by an outdoor run segment. Each of options 1602a-1602e are selectable to initiate a workout session corresponding to the selected preconfigured workout. Each workout option 1602a-1602e also includes a corresponding selection options 1604a-1604e that is selectable to modify one or more characteristics of the preconfigured workout.

Multi sport room user interface 1600 also includes option 1604h that is selectable to return to workout selection user interface 606, option 1604f that is selectable to create a new multisport workout, and option 1604g that is selectable to modify and/or filter the preconfigured workouts that are presented in multisport room user interface 1600. At FIG. 16B, electronic device 600 detects user input 1606a (e.g., a tap input) corresponding to selection of option 1604g, and user input 1606b (e.g., a tap input) corresponding to selection of option 1604a. Each of these user inputs will be discussed below.

At FIG. 16C, in response to user input 1606a, electronic device 600 displays filtering user interface 1608. Filtering user interface 1608 is substantially similar to user interface 620 discussed above with reference to FIG. 6C. Filtering user interface 1608 includes selectable options 1610a-1610f that are selectable to display different sets of multisport workouts in multisport room user interface 1600 (e.g., sets of multisport workouts that satisfy and/or meet selected filtering criteria). Option 1610a is selectable to display a set of suggested workout options within multisport room user interface 1600. Option 1610b is selectable to display (e.g., only display) workout options that include a cycling segment in multisport room user interface 1600. Option 1610c is selectable to display (e.g., only display) workouts that include a run segment within multisport room user interface 1600. Option 1610d is selectable to display (e.g., only display) preconfigured multisport workouts that include a swim segment within multisport room user interface 1600. Option 1610e is selectable to display all preconfigured multisport workouts in multisport room user interface 1600. Option 1610f is selectable to return to multisport room user interface 1600.

At FIG. 16D, in response to user input 1606b (in FIG. 16B), electronic device 600 displays multisport workout modification user interface 1612. Multisport workout modification user interface 1612 includes segment representations 1614a-1614c. Segment representations 1614a-1614c are pre-populated into multisport workout modification user interface 1612 based on the user selecting 1604a in FIG. 16B, which corresponds to a triathlon preconfigured multisport workout, which includes an open water swim segment followed by an outdoor cycle segment follow by an outdoor run segment. Multisport workout modification user interface 1612 also includes selectable options 1616a-1616e. Option 1616a is selectable to add a new segment to the multisport workout. Option 1616b is selectable to modify a title of the multisport workout (currently titled "Triathlon" in FIG. 16D). Option 1616c is selectable to modify one or more workout metrics and/or workout metrics user interfaces that are accessible during the multisport workout. Option 1616d is selectable to start a workout session of the multisport workout as it is currently configured (e.g., at the time of selecting option 1616d). Option 1616e is selectable to return to multisport room user interface 1600. At FIG. 16D, electronic device 600 detects user input 1618 (e.g., a tap input) corresponding to selection of option 1616a.

At FIG. 16E, in response to user input 1618, electronic device 600 displays user interface 1620. User interface 1620 includes options 1622a corresponding to various modality types. In some embodiments, selection of one of options 1622a-1622c results in display of multisport workout modification user interface 1612 with an additional segment representation added corresponding to the selected modality type. In some embodiments, selection of option 1622f (e.g., as shown via user input 1624) results in electronic device 600 displaying user interface 1626, which prompts the user to define a pool length for the indoor swim segment. Then, selection of option 1627 results in display of multisport workout modification user interface 1612 with an additional indoor swim segment representation added to the workout.

At FIG. 16G, electronic device 600 displays multisport workout modification user interface 1612. At FIG. 16G, electronic device 600 detects user input 1637 (e.g., a tap input) corresponding to selection of segment representation 1614a.

At FIG. 16H, in response to user input 1637, electronic device 600 displays segment modification user interface 1628. Segment modification user interface 1628 includes selectable options 1630a-1630e that are selectable to modify one or more characteristics of the selected workout segment (e.g., the open water swim segment). Option 1630a is selectable to modify one or more alerts that are configured to be output during the open water swim segment, and option 1630b is selectable to modify one or more workout metrics and/or workout metrics user interfaces that are accessible during the open water swim segment (e.g., in a manner similar to what was described above with reference to FIGS. 6A-6AE). Using these options, a user is able to customize what alerts and/or workout metrics are enabled for each individual segment of the multisport workout. Option 1630c is selectable to modify the order position of the selected segment (for example, to move the segment from being performed first in the multisport workout to being performed second or third). Option 1630d is selectable to change the modality type of the workout segment (e.g., from open water swim to a different modality type). Option 1630e is selectable to delete the workout segment from the multisport workout. At FIG. 16H, electronic device 600 detects user input 1632 (e.g., a tap input) corresponding to selection of back arrow 1630f.

At FIG. 16I, in response to user input 1632, electronic device 600 displays multisport workout modification user interface 1612. At FIG. 16I, electronic device 600 detects user input 1634 (e.g., a drag and/or swipe down user input). At FIG. 16J, in response to user input 1634, electronic device 600 displays segment representation 1614a moving down such that segment representation 1614b is now displayed above segment representation 1614a. At FIG. 16J, electronic device 600 detects continued downward movement of user input 1634. At FIG. 16K, in response to continued detection of user input 1634, electronic device 600 displays movement of segment representation 1614a below segment representation 1614c. At FIG. 16K, electronic device 600 detects termination of user input 1634. After user input 1634, the multisport workout has been modified such that the outdoor cycle leg (representation 1614b) is now performed first, the outdoor run leg (representation 1614c) is now performed second, and the open water swim leg (representation 1614a) is now performed last.

At FIG. 16K, electronic device 600 detects user input 1636 (e.g., a drag and/or swipe up). At FIG. 16K-1, in response to user input 1636, electronic device 600 displays movement of segment representation 1614c above segment representation 1614b. At FIG. 16K-1, electronic device 600 detects termination of user input 1636. After user input 1636, the multisport workout has once again been modified such that the outdoor run leg is now performed before the outdoor cycle leg. At FIG. 16K-1, electronic device 600 detects user input 1639 (e.g., a tap input) corresponding to selection of start workout option 1616d.

At FIG. 16L, in response to user input 1639, electronic device 600 displays in-workout user interface 1640-1. In-workout user interface 1640-1 includes elapsed time representation 1644, which displays elapsed time for the entire workout, as well as workout metrics 1646a, which displays workout metrics (including run time and distance) corresponding to the first segment of the multisport workout (e.g., the outdoor run segment). In-workout user interface also includes modality representations 1642a-1642c, which indicate the order in which various modalities will be performed in the multisport workout. Modality representation 1642a, corresponding to the first segment of the workout (e.g., an outdoor run segment), is displayed in bold, indicating that that is the current segment of the workout.

Figure 16N:
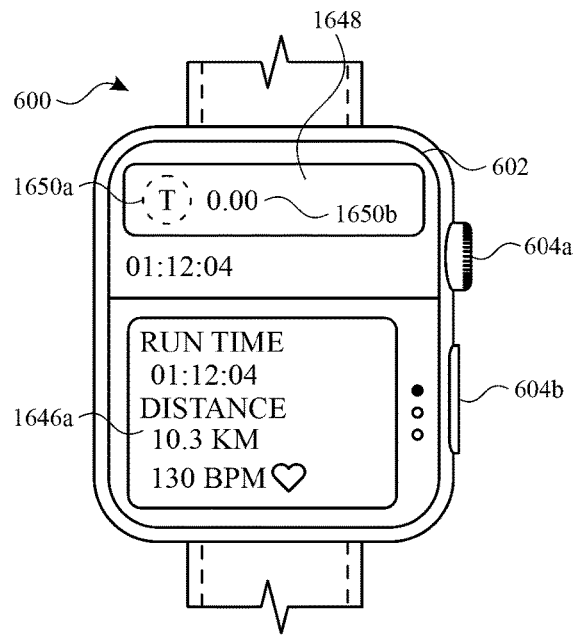
FIGS. 16A-16AB illustrate exemplary user interfaces for navigating, modifying, and outputting multisport workout content, in accordance with some embodiments.
Figure 17:
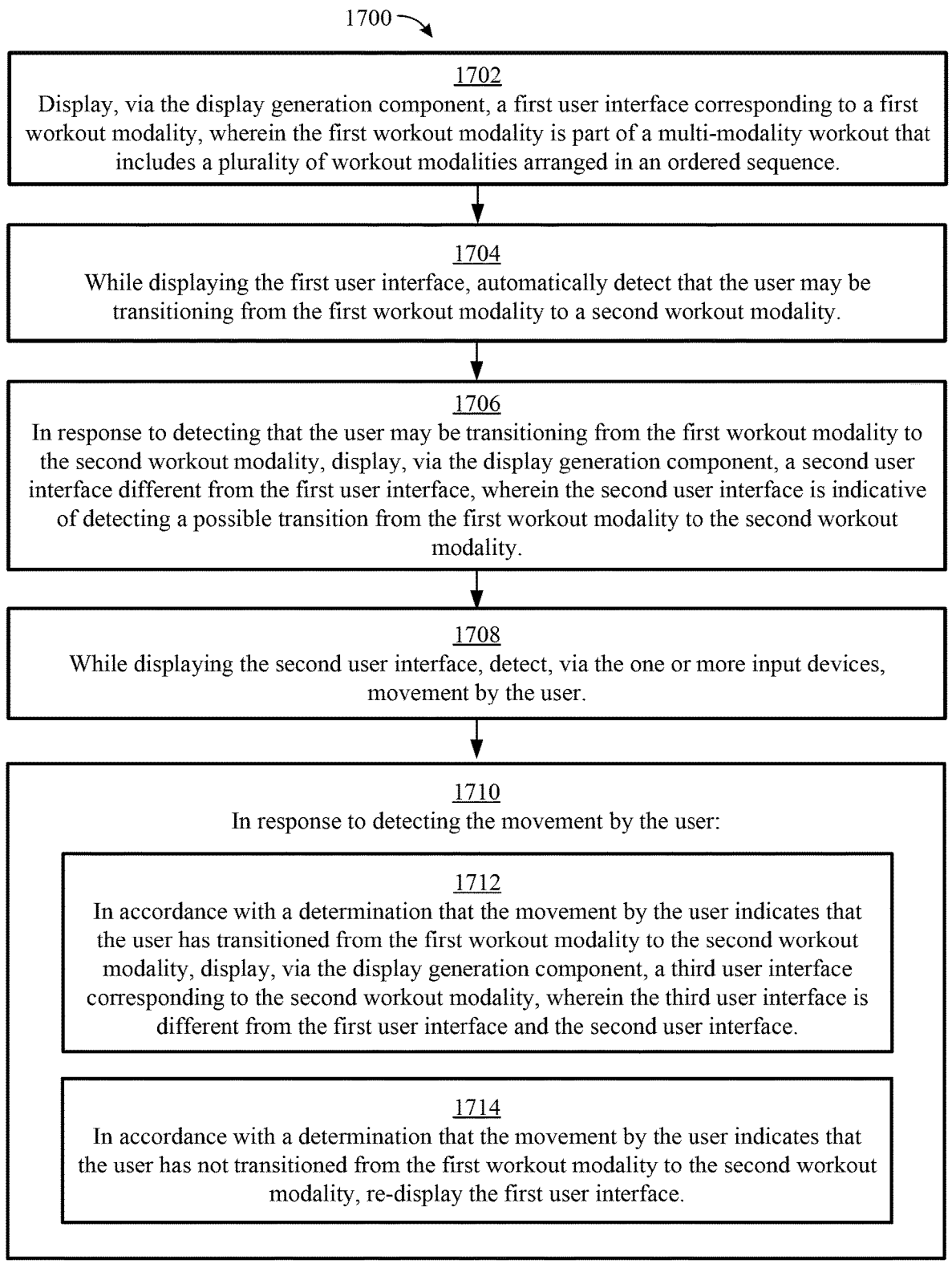
FIG. 17 illustrates a flow diagram depicting a method for navigating, modifying, and outputting multisport workout content, in accordance with some embodiments.

At FIG. 16M, the user has run for an hour and twelve minutes and four seconds, and has run 10.3 km. At FIG. 16N, electronic device 600 detects (e.g., based on movement patterns of the user), that the user may be transitioning from the first workout modality (e.g., outdoor run) to the second workout modality (e.g., outdoor cycle). In response to this, electronic device 600 displays transition user interface 1648, which includes transition indication 1650a and is indicative of a potential transition being automatically detected by electronic device 600. Transition user interface 1648 includes transition timer 1650b, which indicates the duration of time of the potential transition (e.g., the duration of time that transition user interface 1648 has been displayed).

Figure 16O:
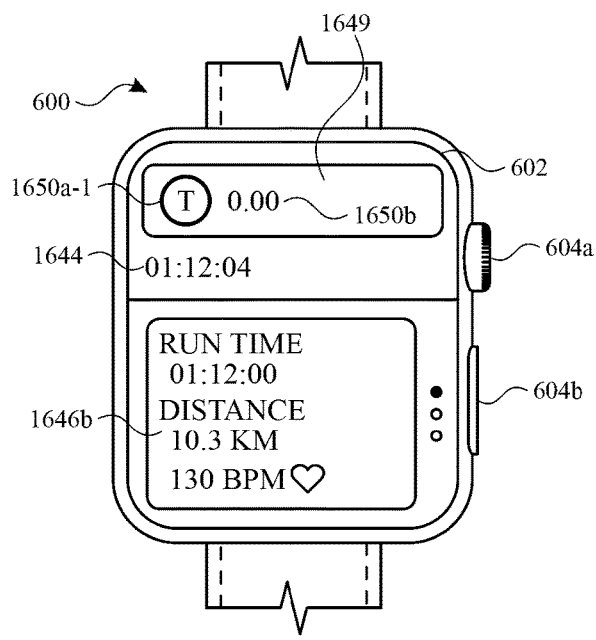

In some embodiments, electronic device 600 detects potential transitions from one workout modality to the next automatically (e.g., based on movement patterns of the user or sensors of the user's devices or equipment). In some embodiments, the user provides a user input (e.g., button press of button 604b and/or depression of rotatable and depressible input mechanism 604a) to manually indicate that the user is transitioning from the first workout modality to the second workout modality. In some embodiments, the user is provided with a user setting in which the user can indicate whether they want to enable automatic transition detection or whether they want to indicate transitions manually. In some embodiments, if the user indicates that the user wants to indicate transitions manually, the user is provided with a further option as to whether a user input indicating a transition should result in display of a transition user interface (e.g., 1648, 1649), or should result in immediate display of a user interface corresponding to the second workout modality (e.g., 1640-2, FIG. 16R) (e.g., without measuring and/or tracking any transition time). In some embodiments, if the user opts to provide manual user input to indicate a transition, and also opts to display the transition user interface, a first user input (e.g., a first button press) results in display of the transition user interface, and a second user input after the first user input (e.g., a second button press)

results in display of a second in-workout user interface corresponding to the second workout modality (e.g., FIG. 16R). In some embodiments, the transition user interface is visually different based on whether the transition user interface is caused by an automatic transition detection or caused by a manual transition input. For example, FIG. 16O depicts an example manual transition user interface 1649, in which indication 1650a-1 is displayed different from indication 1650a in user interface 1648, to indicate that the transition was signaled manually by a user input.

Figure 16P:
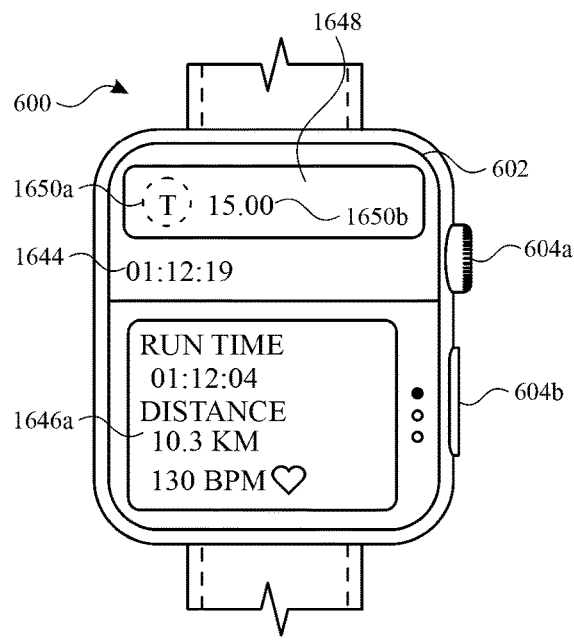

At FIG. 16P, transition user interface 1648 has been displayed for 15 seconds. It can be seen in FIG. 16P that while transition user interface 1648 is displayed (e.g., while electronic device 600 continues to detect a potential transition), transition timer 1650b and elapsed time indication 1644 continue to progress, but the run time timer in segment workout metrics 1646a has been paused.

FIG. 16Q depicts an example scenario in which electronic device 600 has determined that the potential transition was a false transition (e.g., has determined, based on movement patterns of the user, that the user has not transitioned to the second workout modality and continues to perform the first workout modality). In response to this determination, electronic device 600 re-displays in-workout user interface 1640-1 corresponding to the first workout modality, and adds the time from transition timer 1650b to the segment timer corresponding to the first workout modality (e.g., "RUN TIME" in 1646a).

FIG. 16R depicts a second example scenario in which electronic device 600 has determined that the potential transition is a real and/or confirmed transition (e.g., has determined, based on movement patterns of the user, that the user has transitioned into the second workout modality). In response to this determination, electronic device 600 displays in-workout user interface 1640-2, which now shows modality representation 1642b bold and modality representation 1642 not bold, and segment workout metrics 1646a replaced with segment workout metrics 1646b corresponding to the second segment and/or the second workout modality. Furthermore, in the depicted embodiment, a portion of the time measured in transition timer 1650b is attributed to the second workout modality, as indicated by the "CYCLE TIME" timer in segment workout metrics 1646b being advanced to seven seconds.

In FIG. 16S, the user has now been cycling for one hour, thirty-three minutes, and ten seconds, and has cycled 41.4 km. Elapsed time indication 1644 shows that the user has been working out for a title of two hours, forty-five minutes, and twenty nine seconds (a combination of their time for the first segment, the first transition, and the second segment). At FIG. 16T, electronic device 600 detects a potential transition (e.g., based on movement patterns of the user) from the second workout modality to the third workout modality and, in response, displays transition user interface 1648.

Figure 16U:
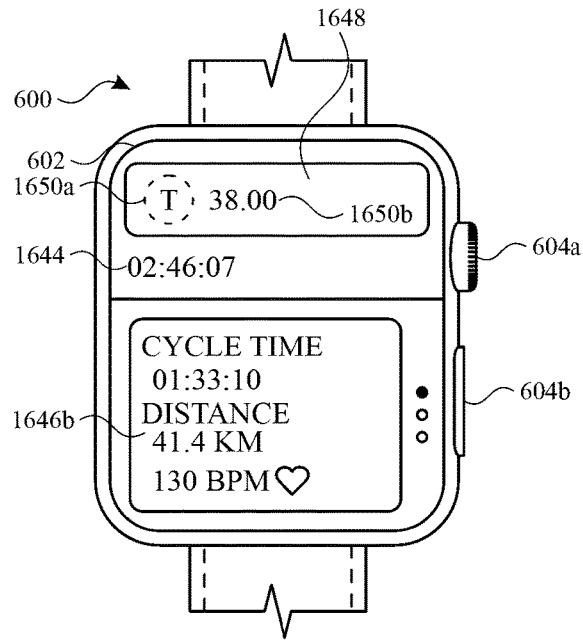

At FIG. 16U, electronic device 600 has detected a potential transition for 38 seconds. Again, as discussed above, elapsed time indication 1644 continues to progress while transition user interface 1648 is displayed (e.g., while the potential transition is detected), but segment elapsed time (e.g., "CYCLE TIME") corresponding to the second workout modality and/or the second segment of the workout is paused at one hour, thirty-three minutes, and ten seconds.

Figure 16V:
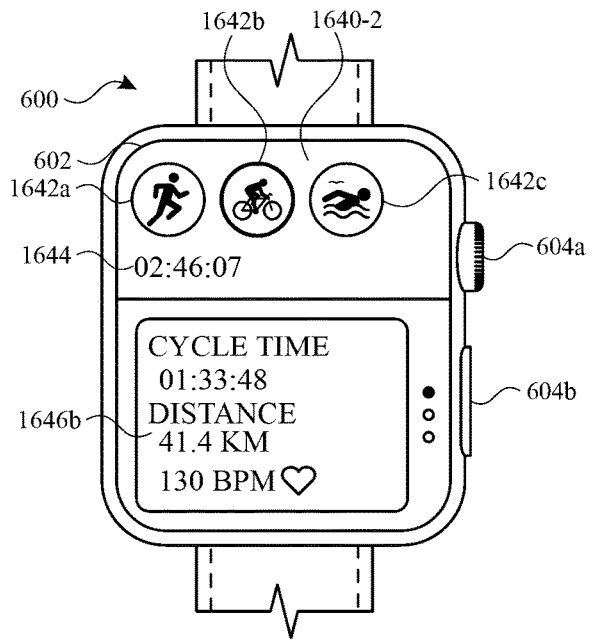

FIG. 16V depicts a first example scenario in which electronic device 600 determines that the potential transition was a false transition. In response to this determination, electronic device 600 re-displays in-workout user interface 1640-2, and adds the time from transition timer 1650b to the second workout segment's elapsed time (e.g., "CYCLE TIME" in segment workout metrics 1646b).

Figure 16W:
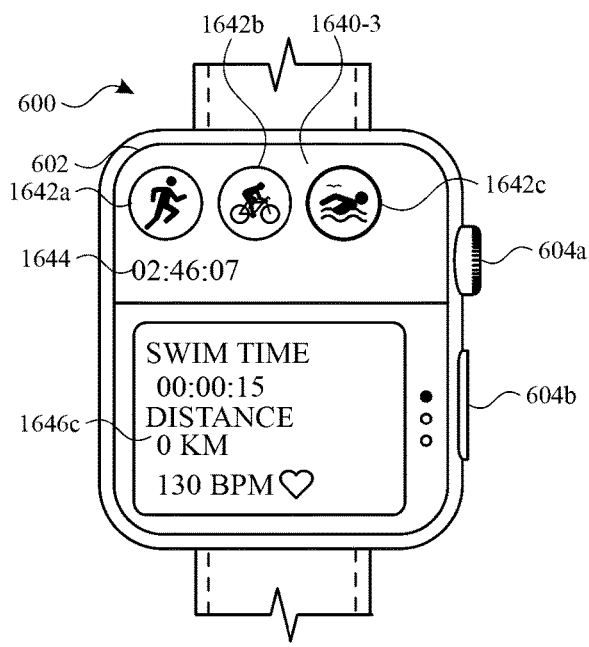
Figure 16X:
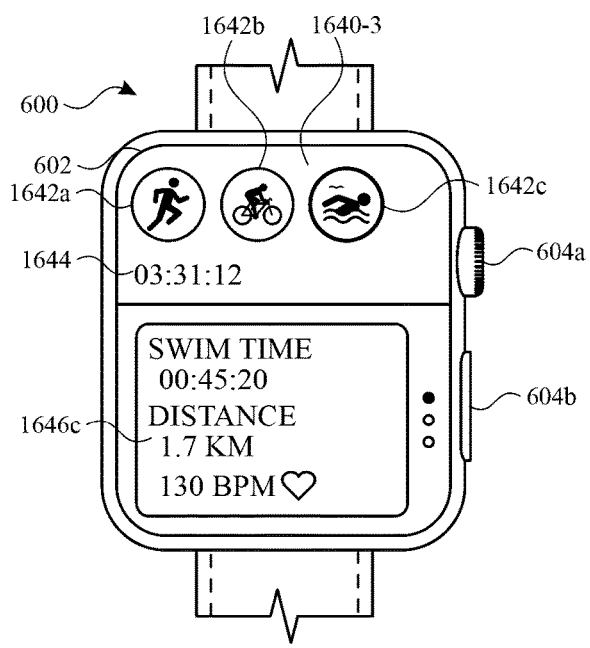

FIG. 16W indicates a second example scenario in which electronic device 600 determines that the potential transition is confirmed. In response to this determination, electronic device 600 displays in-workout user interface 1640-3 corresponding to the third workout segment and/or the third workout modality, in which modality representation 1642c is bolded and/or visually emphasized, and segment workout metrics 1646b are replaced with segment workout metrics 1646c corresponding to the third workout segment and/or the third workout modality. At FIG. 16X, the user has been swimming for forty-five minutes and twenty seconds and has traversed 1.7 km.

Figure 16Y:
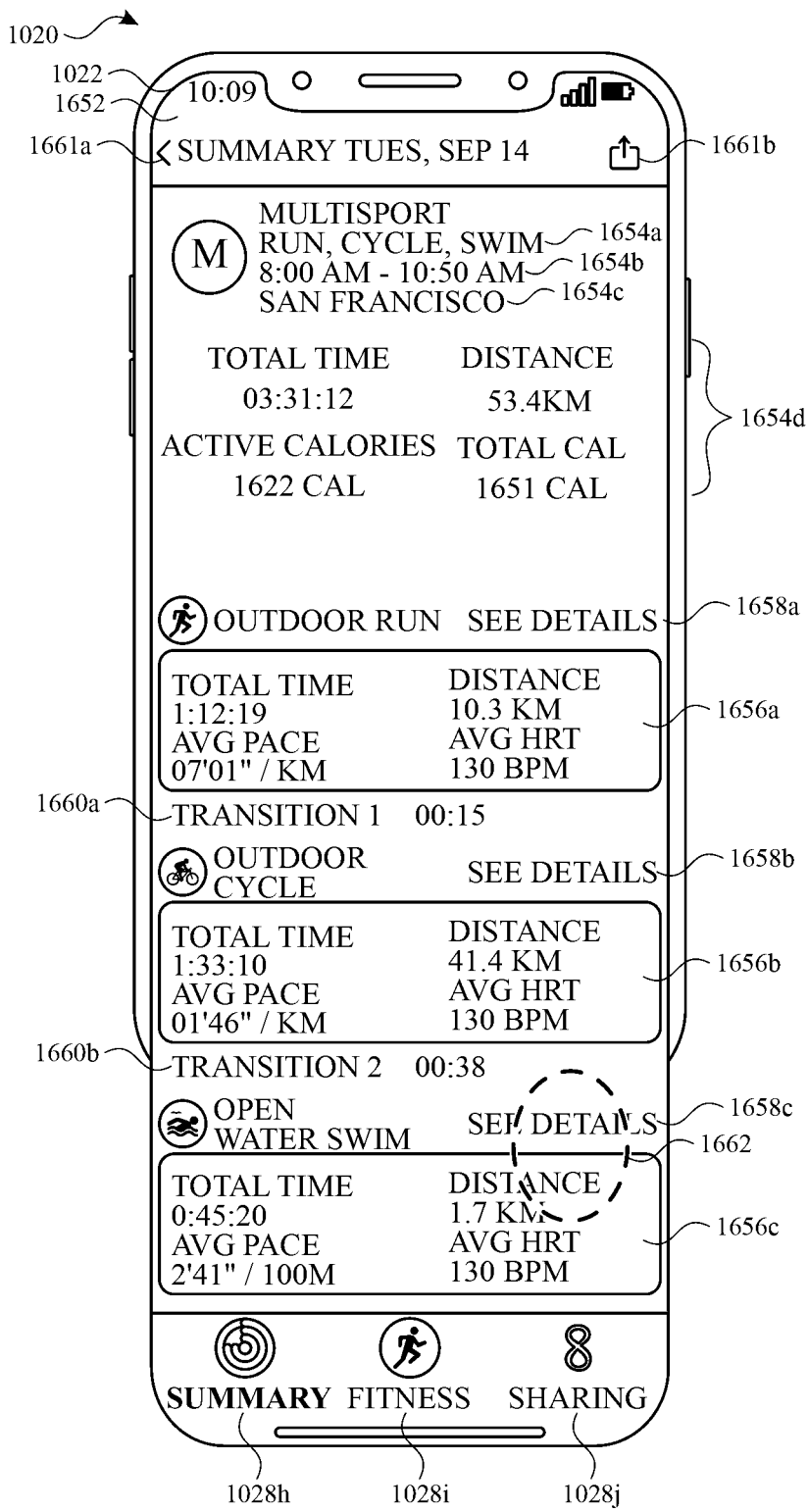

FIG. 16Y depicts electronic device 1020, which is a smartphone with touch-sensitive display 1022. Electronic device 1020 displays workout summary user interface 1652 corresponding to the multisport workout described above with reference to FIGS. 16L-16X. Although the depicted embodiment shows workout summary user interface 1652 displayed on electronic device 1020, in some embodiments, workout summary user interface 1652 is displayed on electronic device 600.

In FIG. 16Y, workout summary user interface 1652 includes modality information 1654a indicating the workout modality types that are performed in the workout and the order in which they were performed, time information 1654b, and location information 1654c. Workout summary user interface 1652 also includes total workout metrics 1654d that displays workout metrics for the entirety of the multisport workout (e.g., total elapsed time, total distance, total calories and total active calories). Workout summary user interface 1652 also includes outdoor run section 1656a that displays workout metrics from the outdoor run segment of the workout, outdoor cycle section 1656b that displays workout metrics from the outdoor cycle segment of the workout, and open water swim section 1656c that displays workout metrics from the open water swim segment of the workout. Sections 1656a-1656c are displayed in the order in which the corresponding workout modalities were performed in the workout. Furthermore, between outdoor run section 1656a and outdoor cycle section 1656b, there is transition information 1660a indicating the length of the transition from the first workout modality to the second workout modality. Similarly, between outdoor cycle section 1656b and open water swim section 1656c, there is transition information 1660b which indicates the length of the transition from the second workout modality to the third workout modality.

Workout summary user interface 1652 also includes selectable options 1658a-1658c that correspond to the three workout modalities and/or workout segments. Each option is selectable to display a workout summary user interface that is specific to the corresponding workout modality. In some embodiments, selection of option 1658a causes display of an outdoor run workout summary user interface that is identical or substantially identical to a workout summary user interface that would have been presented to the user had the user performed an open goal outdoor run workout (e.g., workout summary user interface 1024 described above with reference to FIGS. 10L-10S without the segments that are specific to the race a route goal type) (with metrics from the first segment of the multisport workout). Similarly, selection of option 1658b causes display of an outdoor cycling workout summary user interface that is identical or substantially identical to a workout summary user interface that would have been presented to the user had the user performed an open goal outdoor cycling workout (with metrics from the second segment of the multisport workout). Finally, selection of option 1658c causes display of an open water swim workout summary user interface that is identical or substantially identical to a workout summary user interface that would have been presented to the user had the user performed an open goal open water swim workout.

Figure 16Z:
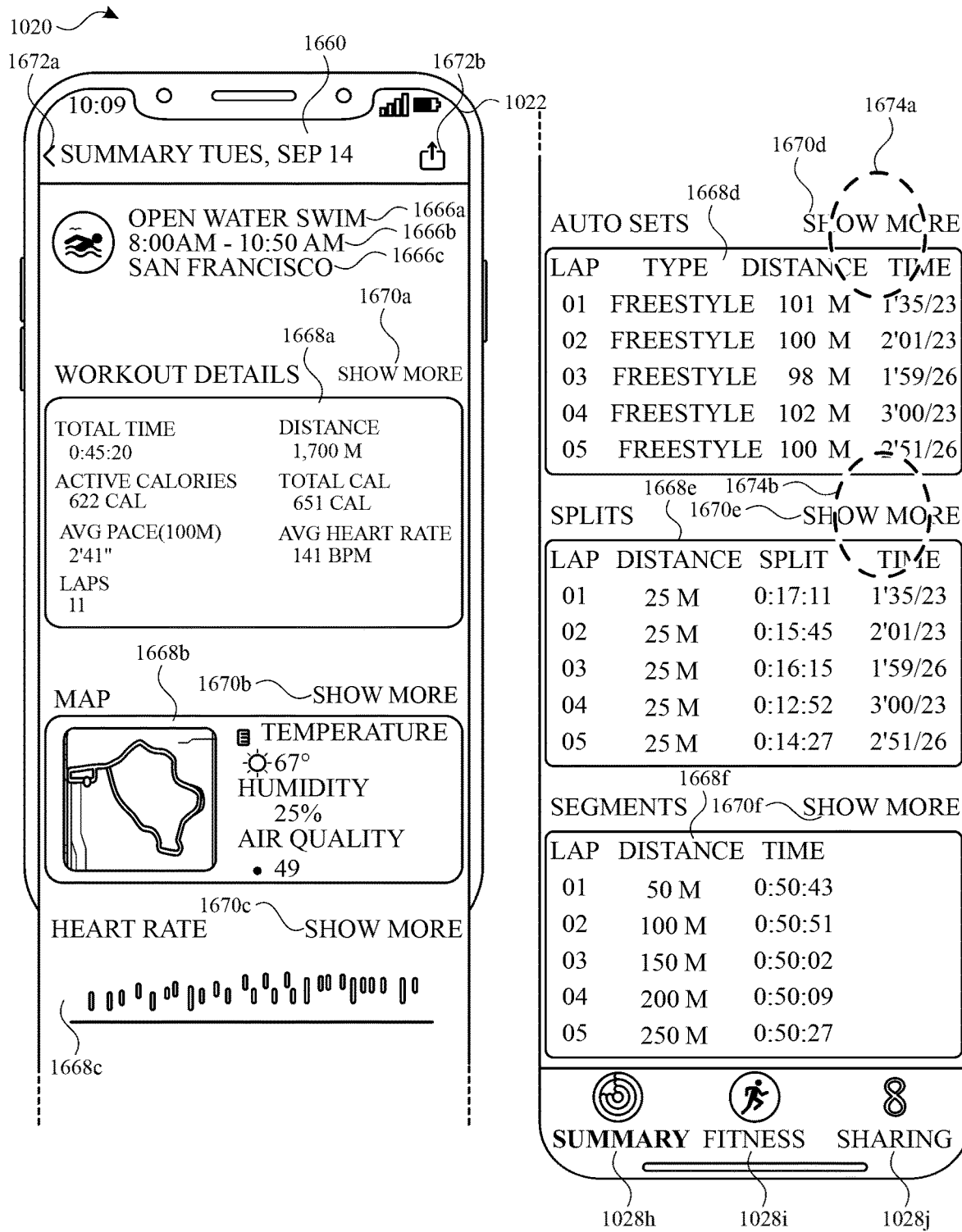

At FIG. 16Y, electronic device 600 detects user input 1662 corresponding to selection of option 1658c. At FIG. 16Z, in response to user input 1662, electronic device 600 displays open water swim workout summary user interface 1660. Open water swim workout summary user interface 1660 displays workout metrics for the third segment of the multisport workout (e.g., without displaying metrics for the first or second segments of the multisport workout), and includes workout details section 1668a, corresponding option 1670a, map section 1668b, corresponding option 1670b, heart rate section 1668c, and corresponding option 1670b that are substantially identical to corresponding sections and options in workout summary user interface 1024 of FIG. 10L.

Open water swim workout summary user interface 1660 also includes auto sets section 1668d, which displays information for one or more automatically generated sets; splits section 1668e, which displays information for one or more splits (e.g., portions) of the open water swim segment of the workout; and segments information 1668f for one or more segments of the open water swim segment of the workout. Option 1670d is selectable to display additional auto sets information, option 1070e is selectable to display additional splits information, and option 1070f is selectable to display additional segments information. At FIG. 16Z, electronic device 600 detects user input 1674a (e.g., a tap input) corresponding to selection of option 1670d, and user input 1674b (e.g., a tap input) corresponding to selection of option 1670e.

At FIG. 16AA, in response to user input 1674a, electronic device 600 displays auto sets user interface 1676 that displays auto sets information that is not included in open water swim workout summary user interface 1660. This includes, for example, selectable options 1678a, 1678b, 1678c that are selectable to change the distance of each automatically generated set, and to display workout metrics for the new sets of the changed distance.

At FIG. 16AB, in response to user input 1674b, electronic device 600 displays splits user interface 1672, which displays splits information that is not included in open water swim workout summary user interface 1660. This includes, for example, stroke information for each split, as well as options 1684a-1684c that are selectable to change the distance of each split, and to display workout metrics for the new set of splits based on the changed split distance.

FIG. 17 is a flow diagram illustrating a method for navigating, modifying, and outputting multisport workout content using a computer system in accordance with some embodiments. Method 1700 is performed at a computer system (e.g., 100, 300, 500) (e.g., a wearable device, a smart watch, a smart phone, a tablet, and/or a computer system controlling an external display) that is in communication with a display generation component (e.g., a display controller, a touch-sensitive display system; and/or a display (e.g., integrated and/or connected)) and one or more input devices (e.g., a touch-sensitive surface (e.g., a touch-sensitive display); an accelerometer; a rotatable input mechanism; a depressible input mechanism; and/or a rotatable and depressible input mechanism). Some operations in method 1700 are, optionally, combined, the orders of some operations are, optionally, changed, and some operations are, optionally, omitted.

As described below, method 1700 provides an intuitive way for navigating, modifying, and outputting multisport workout content. The method reduces the cognitive burden on a user for navigating, modifying, and accessing multisport workout content, thereby creating a more efficient human-machine interface. For battery-operated computing devices, enabling a user to navigate, modify, and access multisport workout content faster and more efficiently conserves power and increases the time between battery charges.

The computer system (e.g., 600) displays (1702), via the display generation component (e.g., 602), a first user interface (e.g., 1640-1, 1640-2) corresponding to a first workout modality (e.g., running, cycling, and/or swimming), wherein the first workout modality is part of a multi-modality workout that includes a plurality of workout modalities arranged in an ordered sequence. In some embodiments, while displaying the first user interface, the computer system automatically detects (1704) that the user may be transitioning from the first workout modality to a second workout modality. In some embodiments, automatically detecting that the user may be transitioning from the first workout modality to the second workout modality is performed without intentional user input (e.g., without user input interacting with a user interface, without user input interacting with a touch-sensitive surface and/or a touch-sensitive display, without user input interacting with one or more buttons, and/or without user input interacting with one or more rotatable and/or depressible input mechanisms) (e.g., in which the user is not required to provide any explicit or intentional input indicating a transition from one workout modality to the next) (e.g., without additional input from a user other than natural movements that are taken by the user in transitioning from the first workout modality to the second workout modality). In some embodiments, detecting that the user may be transitioning from the first workout modality to the second workout modality comprises detecting one or more movements by a user, and determining that the one or more movements by the user satisfy one or more transition criteria indicative of a transition from the first workout modality to a second workout modality. In some embodiments, determining that the one or more movements by the user satisfy one or more transition criteria includes detecting slowing or stopping of one or more motions by the user and/or detecting a change in motion by the user.

In some embodiments, in response to detecting that the user may be transitioning from the first workout modality to the second workout modality, the computer system displays (1706), via the display generation component, a second user interface (e.g., 1648) different from the first user interface (in some embodiments, replacing display of the first user interface with display of the second user interface), wherein the second user interface is indicative of detecting a possible transition from the first workout modality to the second workout modality. In some embodiments, while displaying the second user interface (e.g., 1648), the computer system detects (1708), via the one or more input devices, movement by the user (e.g., based on one or more sensors within the computer system and/or in communication with the computer system (e.g., one or more gyroscopes, and/or one or more accelerometers). In some embodiments, the movement by the user does not include intentional interaction with a user interface, intentional interaction with a touch-sensitive surface and/or a touch-sensitive display, intentional interaction with one or more buttons, and/or intentional interaction with one or more rotatable and/or depressible input mechanisms.

In some embodiments, in response to detecting the movement by the user (1710): in accordance with a determination that the movement by the user indicates that the user has transitioned from the first workout modality to the second workout modality (in some embodiments, in accordance with a determination that the movement by the user satisfies a first set of movement criteria (e.g., movement criteria indicative of the user performing actions consistent with the second workout modality)), the computer system displays (1712), via the display generation component, a third user interface (e.g., 1640-2, 1640-3) corresponding to the second workout modality (in some embodiments, replacing display of the second user interface with the third user interface), wherein the third user interface is different from the first user interface and the second user interface; and in accordance with a determination that the movement by the user indicates that the user has not transitioned from the first workout modality to the second workout modality (e.g., in accordance with a determination that the movement by the user indicates that the user has resumed the first workout modality) (in some embodiments, in accordance with a determination that the movement by the user satisfies a second set of movement criteria different from the first set of movement criteria (e.g., movement criteria indicative of the user performing actions consistent with the first workout modality)), the computer system re-displays (1714) the first user interface (e.g., 1640-1, 1640-2) (in some embodiments, replacing display of the second user interface with the first user interface). Displaying the second user interface in response to detecting that the user may be transitioning from the first workout modality to the second workout modality provides the user with feedback about the state of the device (e.g., that the device has detected a possible transition from the first workout modality to the second workout modality). Doing so also enables these operations to be performed without user input. Furthermore, transitioning from the second user interface to the third user interface in accordance with a determination that movement by the user indicates that the user has transitioned from the first workout modality to the second workout modality enables these operations to be performed without user input and without displaying additional controls.

In some embodiments, the second user interface (e.g., 1648) includes a transition duration timer (e.g., 1650*b*) that indicates how long the second user interface has been displayed (e.g., a transition duration timer that is indicative of how much time has elapsed after the computer system detects that the user may be transitioning from the first workout modality to the second workout modality (and, in some embodiments, until and/or before the determination that the movement by the user indicates that the user has transitioned from the first workout modality to the second workout modality and/or the determination that the movement by the user indicates that the user has not transitioned from the first workout modality to the second workout modality)). Displaying the second user interface in response to detecting that the user may be transitioning from the first workout modality to the second workout modality provides the user with feedback about the state of the device (e.g., that the second user interface has been displayed and/or the computer system has been in the transition state for a particular duration of time). Furthermore, displaying the second user interface in response to detecting that the user may be transitioning from the first workout modality to the second workout modality allows for these operations to be performed without user input.

In some embodiments, the first user interface includes a first workout metric (e.g., "run time" in 1646*a*, "swim time" in 1646*b*, "cycle time" in 1646*c*) (e.g., a physical activity metric and/or a metric indicative of a physical activity level of the user during the multi-modality workout). In some embodiments, the third user interface includes a second workout metric (e.g., "run time" in 1646*a*, "swim time" in 1646*b*, "cycle time" in 1646*c*) different from the first workout metric without including the first workout metric. In some embodiments, the first user interface does not include the second workout metric. In some embodiments, the second user interface does include the second workout metric. Transitioning from the second user interface to the third user interface in accordance with a determination that movement by the user indicates that the user has transitioned from the first workout modality to the second workout modality enables these operations to be performed without user input and without displaying additional controls. Furthermore, displaying the third user interface that includes the second workout metric without including the first workout metric prevents the user interface from displaying information that is not relevant to the particular user and/or situation.

In some embodiments, the first user interface includes a third workout metric (e.g., heart rate in 1646*a*, 1646*b*, 1646*c*) different from the first workout metric and the second workout metric. In some embodiments, the third user interface includes the third workout metric (e.g., heart rate in 1646*a*, 1646*b*, 1646*c*). Transitioning from the second user interface to the third user interface in accordance with a determination that movement by the user indicates that the user has transitioned from the first workout modality to the second workout modality enables these operations to be performed without user input and without displaying additional controls.

In some embodiments, the first user interface includes a first set of user interface objects (e.g., 1642*a*-1642*c*) (e.g., one or more user interface objects) that are representative of the plurality of workout modalities in the multi-modality workout and the ordered sequence of the plurality of workout modalities (for example, in some embodiments, the first set of user interface objects are displayed in an order representative of the ordered sequence of the plurality of workout modalities), wherein the first set of user interface objects includes a representation of the first workout modality (e.g., 1642*a*-1642*c*) and a representation of the second workout modality (e.g., 1642*a*-1642*c*). In some embodiments, displaying the first user interface includes: displaying the representation of the first workout modality in a first manner (e.g., 1642*a* bolded and/or visually emphasized in FIG. 16Q) (e.g., with a first set of visual characteristics (e.g., with a first color, a first line thickness, and/or at a first size)) (e.g., a first manner indicative of the first workout modality being a current workout modality), and displaying the representation of the second workout modality in a second manner (e.g., 1642*b* not visually emphasized and/or not bolded in FIG. 16Q) (e.g., with a second set of visual characteristics (e.g., with a second color, a second line thickness, and/or at a second size)) (e.g., a second manner indicative of the second workout modality not being a current workout modality) different from the first manner.

In some embodiments, the third user interface (e.g., 1640-2) includes the first set of user interface objects (e.g., 1642*a*-1642*c*). In some embodiments, displaying the third user interface includes: displaying the representation of the first workout modality in the second manner (e.g., 1642*a* not bolded and/or not visually emphasized in FIG. 16R) and displaying the representation of the second workout modality in the first manner (e.g., 1642b bolded and/or visually emphasized in FIG. 16R). Displaying the first user interface with the representation of the first workout modality displayed in the first manner, and displaying the third user interface with the representation of the first workout modality displayed in the second manner, provides the user with feedback about the current state of the device (e.g., feedback about a current workout modality). Doing so also enables these operations to be performed without further user input.

In some embodiments, the first user interface (e.g., 1640-1) includes a total workout timer (e.g., 1644) indicative of an elapsed time of the multi-modality workout (e.g., the elapsed time during which the user has been in an active workout session corresponding to the multi-modality workout, and/or that the user has been performing any workout modality of the plurality of workout modalities in the multi-modality workout). In some embodiments, the first user interface includes a first modality timer (e.g., "RUN TIME" in 1640-1) indicative of an elapsed time corresponding to the first workout modality of the plurality of workout modalities (e.g., the elapsed time during which the user has been performing the first workout modality).

In some embodiments, displaying the first user interface (e.g., 1640-1) includes displaying progression of the total workout timer (e.g., advancement of the total workout timer as time elapses). In some embodiments, displaying the first user interface (e.g., 1640-1) includes displaying progression of the first modality timer (e.g., advancement of the first modality timer as time elapses). In some embodiments, the second user interface (e.g., 1648) includes the total workout timer (e.g., 1644) and the first modality timer (e.g., "RUN TIME" in FIG. 16P). In some embodiments, displaying the second user interface (e.g., 1648) includes: displaying progression of the total workout timer (e.g., 1644); and maintaining display of the first modality timer at a first time (e.g., a first time at which the computer system ceased displaying the first user interface and/or began displaying the second user interface) without progressing the first modality timer (e.g., "RUN TIME" in FIGS. 16N-16P). Displaying the first user interface with the total workout timer and the first modality timer progressing, and displaying the second user interface with the total workout timer progressing and the first modality timer being maintained at a first time, provides the user with feedback about the current state of the device (e.g., that the device is in a transition state and/or that the device is keeping track of total workout time but is not attributing the additional time to the first workout modality). Doing so also enables these operations to be performed without further user input.

In some embodiments, displaying the first user interface (e.g., 1640-1 in FIG. 16Q) in accordance with the determination that the movement of the user indicates that the user has not transitioned from the first workout modality to the second workout modality comprises, in accordance with the determination that the movement by the user indicates that the user has not transitioned from the first workout modality to the second workout modality, advancing the first modality timer (e.g., "RUN TIME" in 1640-1) from the first time to a second time (e.g., progressing "RUN TIME" from 1:12:04 in FIG. 16P to 1:12:19 in FIG. 16Q) (e.g., adding additional time to the first modality timer). In some embodiments, the additional time that is added to the first modality timer is determined based on how long the second user interface was displayed and/or based on the duration of time between detecting that the user may be transitioning from the first workout modality to the second workout modality and the determination that the movement by the user indicates that the user has not transitioned from the first workout modality to the second workout modality. In some embodiments, displaying the first user interface in accordance with the determination that the movement of the user indicates that the user has not transitioned from the first workout modality to the second workout modality comprises, in accordance with the determination that the movement by the user indicates that the user has not transitioned from the first workout modality to the second workout modality, displaying, within the first user interface, progression of the first modality timer from the second time (e.g., progressing "RUN TIME" from 1:12:04 in FIG. 16P to 1:12:19 in FIG. 16Q). Displaying the first user interface with the first modality timer advanced to the second time and continuing to progress provides the user with feedback about the current state of the device (e.g., that the device has resumed attributing the elapsed time to the first workout modality). Doing so also enables these operations to be performed without further user input.

In some embodiments, the second user interface (e.g., 1648) includes a first transition timer (e.g., 1650b) indicative of an elapsed transition time during which the second user interface has been displayed. In some embodiments, the third user interface (e.g., 1640-2) includes a second modality timer (e.g., "CYCLE TIME" in 1640-2) indicative of an elapsed time corresponding to the second workout modality. In some embodiments, displaying the third user interface comprises initiating progression of the second modality timer from a third time (e.g., in FIG. 16R, starting the "CYCLE TIME" timer at 00:00:07 instead of 00:00:00), wherein the third time is determined based on the elapsed transition time (e.g., based on 1650b in FIG. 16P) (e.g., the third time represents a predetermined portion and/or fraction of the elapsed transition time). Displaying the third user interface with progression of the second modality timer starting from a third time provides the user with feedback about the current state of the device (e.g., that the device has detected a transition to the second workout modality and/or that the device is attributing a portion of the elapsed transition time to the second workout modality). Doing so also enables these operations to be performed without further user input.

In some embodiments, the computer system (e.g., 600) displays, via the display generation component (e.g., 602), a workout selection user interface (e.g., 606) comprising a plurality of workout options (e.g., representations of a plurality of workouts corresponding to a plurality of workout types (e.g., workout modality and/or workout goal types)), wherein the plurality of workout options includes a representation (e.g., 608c, 608k) of the multi-modality workout. In some embodiments, while displaying the workout selection user interface, the computer system receives, via the one or more input devices, one or more user inputs (e.g., 1601) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures) corresponding to the representation of the multi-modality workout (e.g., corresponding to selection of the representation of the multi-modality workout, corresponding to selection of a first region of the representation of the multi-modality workout, and/or corresponding to selection of an object associated with the representation of the multi-modality workout).

In some embodiments, in response to receiving the one or more user inputs corresponding to the representation of the multi-modality workout, the computer system displays, via the display generation component, a multi-modality workout room user interface (e.g., 1600), wherein the multi-modality workout room user interface includes: a representation (e.g., 1602a-1602e) of a first pre-configured multi-modality workout (e.g., a pre-configured workout that includes two or more workout modalities (e.g., two or more workout modalities arranged in a defined order)); a representation (e.g., 1602a-1602e) of a second pre-configured multi-modality workout different from the first pre-configured multi-modality workout; and a new workout option (e.g., 1604f) that is selectable to initiate a process for creating a new multi-modality workout. In some embodiments, the representation of the first pre-configured multi-modality workout is selectable to initiate a workout session corresponding to the first pre-configured multi-modality workout. In some embodiments, the representation of the second pre-configured multi-modality workout is selectable to initiate a workout session corresponding to the second pre-configured multi-modality workout. In some embodiments, a first portion of the representation of the first pre-configured multi-modality workout is selectable to initiate a workout session corresponding to the first pre-configured multi-modality workout and a second portion of the representation of the first pre-configured multi-modality workout is selectable to initiate a process to modify the first pre-configured multi-modality workout. In some embodiments, a first portion of the representation of the second pre-configured multi-modality workout is selectable to initiate a workout session corresponding to the second pre-configured multi-modality workout and a second portion of the representation of the second pre-configured multi-modality workout is selectable to initiate a process to modify the second pre-configured multi-modality workout. Displaying the multi-modality workout room user interface including the new workout option enables a user to initiate a process for creating a new multi-modality workout with fewer user inputs.

In some embodiments, the new workout option (e.g., 1604f) is selectable to initiate a process for selecting two or more workout modalities for inclusion in the new multi-modality workout and defining an order for the two or more workout modalities in the new multi-modality workout. Displaying the multi-modality workout room user interface including the new workout option enables a user to initiate a process for creating a new multi-modality workout with fewer user inputs.

In some embodiments, while displaying the multi-modality workout room user interface (e.g., 1600), the computer system receives, via the one or more input devices, a first set of user inputs (e.g., 1606a, 1606b) (e.g., one or more user inputs) (e.g., one or more touch inputs (e.g., via a touch-sensitive display and/or a touch-sensitive surface); one or more non-touch inputs; one or more button presses; activation of a depressible input mechanism; rotation of a rotatable input mechanism; and/or one or more gestures). In some embodiments, in response to receiving the first set of user inputs, in accordance with a determination that the first set of user inputs corresponds to selection of a first region of the representation of the first pre-configured multi-modality workout (e.g., selection of one of workout platters 1602a-1602e): the computer system initiates a workout session corresponding to the first pre-configured multi-modality workout; and the computer system displays, via the display generation component, a fourth user interface (e.g., 1640-1, 1640-2, 1640-3) indicative of an active workout session and corresponding to a first workout modality of the first pre-configured multi-modality workout. In some embodiments, in response to receiving the first set of user inputs, in accordance with a determination that the first set of user inputs corresponds to selection of a second region (e.g., 1604a-1604e) (e.g., a second region different from the first region) of the representation of the first pre-configured multi-modality workout: the computer system displays, via the display generation component, a first workout modification user interface (e.g., 1612) comprising one or more options that are selectable to initiate one or more processes for modifying one or more aspects of the first pre-configured multi-modality workout. In some embodiments, initiating a workout session includes initiating recording (e.g., tracking, logging, collecting) of physical activity metrics corresponding to the workout session (e.g., physical activity metrics indicative of a physical activity level of the user during the workout session). In some embodiments, the physical activity metrics are recorded (e.g., captured) using one or more sensors (e.g., GPS, accelerometer, gyroscope, heart rate) of the computer system or an external device that is in communication with the computer system. In some embodiments, the physical activity metrics were not being recorded or were being recorded at a lower frequency and/or lower degree of precision prior to initiating (e.g., immediately prior to initiating) the workout session. In some embodiments, initiating the workout session includes causing one or more sensors to be enabled and/or activated to improve accurate measurements of user physical activity metrics during the workout session. Displaying the fourth user interface in accordance with a determination that the first set of user inputs corresponds to selection of the first region of the representation of the first pre-configured multi-modality workout, and displaying the first workout modification user interface in accordance with a determination that the first set of user inputs corresponds to selection of the second region of the representation of the first pre-configured multi-modality workout enables these operations to be performed without further user input.

In some embodiments, the first workout modification user interface (e.g., 1612) includes a first option (e.g., 1616a) that is selectable to initiate a process for adding a new segment to the first pre-configured multi-modality workout. Displaying the first option that is selectable to initiate a process for adding a new segment to the first pre-configured multi-modality workout enables a user to perform this operation with fewer user inputs.

In some embodiments, the first workout modification user interface (e.g., 1612) includes a second option (e.g., in FIGS. 16D-16H, a user can initiate a process for removing a segment from the workout by selecting one of segment representations 1614a-1614c) that is selectable to initiate a process for removing a segment (e.g., removing a workout modality) from the first pre-configured multi-modality workout. In some embodiments, the first pre-configured multi-modality workout comprises a second set of workout modalities, including a third workout modality and a fourth workout modality, and the first workout modification user interface includes a representation of the third workout modality and a representation of the fourth workout modality (e.g., 1614a-1614c). In some embodiments, the representation of the third workout modality (e.g., 1614a-1614c) is selectable to display one or more options (e.g., 1630a-1630e) for modifying one or more aspects of the third workout modality, including a third option (e.g., 1630e) that is selectable to remove the third workout modality from the first pre-configured multi-modality workout. In some embodiments, the first pre-configured multi-modality workout comprises a set of workout segments corresponding to a plurality of workout modalities, including a first workout segment (e.g., 1614a-1614c) corresponding to a third workout modality and a second workout segment (e.g., 1614a-1614c) corresponding to a fourth workout modality, and the first workout modification user interface (e.g., 1612) includes a representation of the first workout segment and a representation of the second workout segment (e.g., 1614a-1614c). In some embodiments, the representation of the first workout segment is selectable to display one or more options (e.g., 1630a-1630e) for modifying one or more aspects of the first workout segment, including a third option (e.g., 1630e) that is selectable to remove the first workout segment from the first pre-configured multi-modality workout. Displaying the second option that is selectable to initiate a process for removing a segment from the first pre-configured multi-modality workout enables a user to perform this operation with fewer user inputs.

In some embodiments, the first pre-configured multi-modality workout comprises a set of workout segments (in some embodiments, a set of workout segments arranged in an order) corresponding to a plurality of workout modalities, including a first workout segment corresponding to a third workout modality and a second workout segment corresponding to a fourth workout modality. In some embodiments, the first workout modification user interface (e.g., 1612) includes a representation (e.g., 1614a-1614c) of the first workout segment and a representation (e.g., 1614a-1614c) of the second workout segment. In some embodiments, the computer system displays, at a first time, via the display generation component, the first workout modification user interface (e.g., 1612), wherein, at the first time, the representation of the first workout segment and the representation of the second workout segment are presented within the first workout modification user interface in a first order indicative of the first workout segment preceding the second workout segment in the first pre-configured multi-modality workout (e.g., FIG. 16I)

In some embodiments, while displaying the first workout modification user interface, the computer system receives, via the one or more input devices, one or more user inputs (e.g., 1634) (e.g., a drag and drop user input) corresponding to a request to move the representation of the first workout segment (e.g., 1614a). In some embodiments, in response to receiving the one or more user inputs corresponding to the request to move the representation of the first workout segment, the computer system displays, via the display generation component, movement of the representation of the first workout segment from a first display position to a second display position within the first workout modification user interface (e.g., FIGS. 16I-16K), wherein after movement of the representation of the first workout segment (e.g., 1614a) to the second display position within the first workout modification user interface, the representation of the first workout segment (e.g., 1614a) and the representation of the second workout segment (e.g., 1614b) are presented in a second order different from the first order and indicative of the second workout segment preceding the first workout segment in the first pre-configured multi-modality workout (e.g., FIG. 16K). Re-ordering the first workout segment in response to one or more user inputs allows for this operation to be performed without displaying additional controls.

In some embodiments, the first pre-configured multi-modality workout comprises a set of workout segments (in some embodiments, a set of workout segments arranged in an order) corresponding to a plurality of workout modalities, including a third workout segment corresponding to a fifth workout modality and a fourth workout segment corresponding to a sixth workout modality. In some embodiments, the first workout modification user interface (e.g., 1612) includes a representation of the third workout segment (e.g., 1614a-1614c) and a representation of the fourth workout segment (e.g., 1614a-1614c). In some embodiments, while displaying the first workout modification user interface (e.g., 1612), the computer system receives, via the one or more input devices, one or more user inputs (e.g., 1637) corresponding to selection of the representation of the third workout segment. In some embodiments, in response to receiving the one or more user inputs corresponding to selection of the representation of the third workout segment, the computer system displays, via the display generation component, a workout segment modification user interface (e.g., 1628) including one or more options (e.g., 1630a-1630e) that are selectable to initiate one or more processes for modifying one or more aspects of the third workout segment, wherein the one or more options includes a change modality option (e.g., 1630d) that is selectable to initiate a process for changing a workout modality associated with the third workout segment. Displaying the change modality option that is selectable to initiate a process for changing a workout modality of the third workout segment enables a user to perform this operation with fewer user inputs.

In some embodiments, the first pre-configured multi-modality workout comprises a set of workout segments (in some embodiments, a set of workout segments arranged in an order) corresponding to a plurality of workout modalities, including a fifth workout segment corresponding to a seventh workout modality and a sixth workout segment corresponding to an eighth workout modality. In some embodiments, the first workout modification user interface (e.g., 1612) includes a representation of the fifth workout segment (e.g., 1614a-1614c) and a representation of the sixth workout segment (e.g., 1614a-1614c). In some embodiments, while displaying the first workout modification user interface, the computer system receives, via the one or more input devices, one or more user inputs (e.g., 1637) corresponding to selection of the representation of the fifth workout segment. In some embodiments, in response to receiving the one or more user inputs corresponding to selection of the representation of the fifth workout segment, the computer system displays, via the display generation component, a second workout segment modification user interface (e.g., 1628) including one or more options (e.g., 1630a-1630e) that are selectable to initiate one or more processes for modifying one or more aspects of the fifth workout segment, wherein the one or more options includes an alerts option (e.g., 1630a) that is selectable to initiate a process for modifying one or more alerts (e.g., one or more displayed alerts and/or one or more audio alerts) that are enabled during the fifth workout segment of the first pre-configured multi-modality workout (and, in some embodiments, without modifying one or more alerts that are enabled during the sixth workout segment of the first pre-configured multi-modality workout).

In some embodiments, modifying the one or more alerts that are enabled to be displayed includes enabling a first alert type to be displayed during a particular segment of a workout, and disabling a second alert type from being displayed during the particular segment of the workout (e.g., based on one or more user inputs). In some embodiments, an alert includes a set of alert criteria and, if the alert criteria met during a workout session of the first workout type, the computer system and/or an external device displays an alert user interface and/or notification corresponding to the alert. In some embodiments, the one or more alerts includes a distance alert that includes a first condition that is met if the user travels and/or achieves a target distance during a workout session and/or a segment of a workout session (e.g., a workout session corresponding to the first pre-configured multi-modality workout). In some embodiments, the one or more alerts includes a time alert that includes a second condition that is met if a threshold time duration elapses during a workout session and/or a segment of a workout session (e.g., a workout session corresponding to the first pre-configured multi-modality workout). In some embodiments, the one or more alerts includes a calories alert that includes a third condition that is met if the user achieves a threshold number of calories (e.g., calories burned and/or active calories burned) during a workout session and/or a segment of a workout session (e.g., a workout session corresponding to the first pre-configured multi-modality workout). In some embodiments, the one or more includes a heart rate alert that includes a fourth condition that is met if the user achieves a target heart rate (e.g., goes above the target heart rate and/or falls below the target heart rate) during a workout session and/or a segment of a workout session (e.g., a workout session corresponding to the first pre-configured multi-modality workout). Providing a user with a selectable option that is selectable to initiate a process for modifying one or more alerts that are enabled to be presented during a particular segment of a workout session reduces the number of inputs needed to perform this function.

In some embodiments, the first pre-configured multi-modality workout comprises a set of workout segments (in some embodiments, a set of workout segments arranged in an order) corresponding to a plurality of workout modalities, including a seventh workout segment corresponding to a ninth workout modality and an eighth workout segment corresponding to a tenth workout modality. In some embodiments, the first workout modification user interface (e.g., 1612) includes a representation of the seventh workout segment (e.g., 1614a-1614c) and a representation of the eighth workout segment (e.g., 1614a-1614c). In some embodiments, while displaying the first workout modification user interface, the computer system receives, via the one or more input devices, one or more user inputs (e.g., 1637) corresponding to selection of the representation of the seventh workout segment. In some embodiments, in response to receiving the one or more user inputs corresponding to selection of the representation of the seventh workout segment, the computer system displays, via the display generation component, a third workout segment modification user interface (e.g., 1628) including one or more options (e.g., 1630a-1630e) that are selectable to initiate one or more processes for modifying one or more aspects of the seventh workout segment, wherein the one or more options includes a metrics option (e.g., 1630b) that is selectable to initiate a process for modifying one or more workout metrics (e.g., physical activity metrics and/or metrics that are indicative of the physical activity level of the user) that are accessible during the seventh workout segment of the first pre-configured multi-modality workout (e.g., that are able to be displayed during the seventh workout segment of the first pre-configured multi-modality workout (e.g., that are automatically displayed during the seventh workout segment of the first pre-configured multi-modality workout and/or that a user is able to display during the seventh workout segment of the first pre-configured multi-modality workout with one or more user inputs)). In some embodiments, modifying one or more workout metrics includes selecting one or more workout metrics for display and/or one or more workout metrics to be accessible during the seventh workout segment of the first pre-configured multi-modality workout and excluding one or more workout metrics from being displayed and/or being accessible during the seventh workout segment of the first pre-configured multi-modality workout. Providing a user with a selectable option that is selectable to initiate a process for modifying one or more workout metrics that are enabled to be presented during a particular segment of a workout session reduces the number of inputs needed to perform this function.

In some embodiments, after completion of the multi-modality workout (in some embodiments, in response to completion of the multi-modality workout), the computer system displays, via the display generation component, a first workout summary user interface (e.g., 1652) that includes: a first region (e.g., 1656a-1656c) corresponding to the first workout modality and including a first set of workout metrics corresponding to the first workout modality (e.g., one or more workout metrics that were measured while the user was performing the first workout modality and/or during a first segment of the multi-modality workout corresponding to the first workout modality); a second region (e.g., 1656a-1656c) different from the first region and corresponding to the second workout modality, and including a second set of workout metrics corresponding to the second workout modality (e.g., one or more workout metrics that were measured while the user was performing the second workout modality and/or during a second segment of the multi-modality workout corresponding to the second workout modality); a first object (e.g., 1658a-1658c) corresponding to the first workout modality (and, in some embodiments, associated with and/or corresponding to the first region) that is selectable to cause display of one or more additional workout metrics corresponding to the first workout modality that are not displayed in the first region of the first workout summary user interface (and, in some embodiments, without causing display of additional workout metrics corresponding to the second workout modality that are not displayed in the first workout summary user interface); and a second object (e.g., 1658a-1658c) corresponding to the second workout modality (and, in some embodiments, associated with and/or corresponding to the second region) that is selectable to cause display of one or more additional workout metrics corresponding to the second workout modality that are not displayed in the second region of the first workout summary user interface (and, in some embodiments, without causing display of additional workout metrics corresponding to the first workout modality that are not displayed in the first workout summary user interface). Displaying the first object that is selectable by a user to view additional workout metrics corresponding to the first workout modality allows a user to perform these functions with fewer user inputs. Doing so also prevents the user interface from displaying information that is not relevant and/or interesting to the particular user.

In some embodiments, the computer system receives, via the one or more input devices, a user input to transition an automatic transition setting from an enabled state to a disabled state, wherein, when the automatic transition setting is in the enabled state, the computer system automatically (e.g., without user inputs and/or user interaction with one or more input devices and/or user interfaces) detects possible transitions between workout modalities during multi-modality workouts. In some embodiments, the computer system receives, via the one or more input devices, a user input to transition an automatic transition setting from an enabled state to a disabled state, wherein, when the automatic transition setting is in the disabled state, the computer system does not automatically detect transitions between workout modalities during multi-modality workouts, and the computer system detects transitions between workout modalities during multi-modality workouts based on one or more user inputs (e.g., one or more button presses, one or more touch inputs, one or more user inputs interact with a user interface, and/or one or more rotations of a rotatable input mechanism). Providing an option that transitions the automatic transition setting from the enabled state to the disabled state allows a user to perform these functions with fewer user inputs.

In some embodiments, in accordance with a determination that the automatic transition setting is in the disabled state, the computer system provides access to (in some embodiments, displaying; and in some embodiments, making selectable and/or making accessible) a selectable object that is selectable to transition a transition period setting between an enabled state and a disabled state. In some embodiments, while the automatic transition setting is in the disabled state, the computer system displays, via the display generation component, the first user interface corresponding to the first workout modality of the multi-modality workout. In some embodiments, while displaying the first user interface, the computer system receives, via the one or more input devices, one or more user inputs indicating that the user has completed the first workout modality (e.g., that the user has completed a first segment of the multi-modality workout corresponding to the first workout modality). In some embodiments, in response to receiving the one or more user inputs indicating that the user has completed the first workout modality, in accordance with a determination that the transition period setting is in the disabled state, the computer system displays, via the display generation component, the third user interface corresponding to the second workout modality of the multi-modality workout. In some embodiments, in response to receiving the one or more user inputs indicating that the user has completed the first workout modality, in accordance with a determination that the transition period setting is in the enabled state, the computer system displays, via the display generation component, a transition user interface different from the first user interface and the third user interface and indicative of a transition between the first workout modality and the second workout modality. In some embodiments, the transition user interface is different from the second user interface. In some embodiments, while displaying the transition user interface, the computer system receives one or more user inputs indicating that the user has transitioned to the second workout modality; and in response to receiving the one or more user inputs indicating that the user has transitioned to the second workout modality, the computer system displays the third user interface. In some embodiments, the one or more user inputs indicating that the user has completed the first workout modality includes one or more pushes of a first button; and the one or more user inputs indicating that the user has transitioned to the second workout modality includes one or more pushes of the first button. Providing an option that transitions the transition period setting from the enabled state to the disabled state allows a user to perform these functions with fewer user inputs.

Note that details of the processes described above with respect to method 1700 (e.g., FIG. 17) are also applicable in an analogous manner to the methods described below and/or above. For example, methods 700, 800, 900, 1100, 1300, 1500, and/or 1800 optionally include one or more of the characteristics of the various methods described above with reference to method 1700. For example, in some embodiments, the workout recited in method 1700 corresponds to the workout session recited in methods 700, 800, 900, and/or 1800. For brevity, these details are not repeated below.

FIG. 18 is a flow diagram illustrating a method for navigating and outputting workout content using a computer system in accordance with some embodiments. Method 1800 is performed at a computer system (e.g., 100, 300, 500) (e.g., a wearable device, a smart watch, a smart phone, a tablet, and/or a computer system controlling an external display) that is in communication with a display generation component (e.g., a display controller, a touch-sensitive display system; and/or a display (e.g., integrated and/or connected)) and one or more input devices (e.g., a touch-sensitive surface (e.g., a touch-sensitive display); an accelerometer; a rotatable input mechanism; a depressible input mechanism; and/or a rotatable and depressible input mechanism). Some operations in method 1800 are, optionally, combined, the orders of some operations are, optionally, changed, and some operations are, optionally, omitted.

As described below, method 1800 provides an intuitive way for navigating and outputting workout content. The method reduces the cognitive burden on a user for navigating and accessing workout content, thereby creating a more efficient human-machine interface. For battery-operated computing devices, enabling a user to navigate and access workout content faster and more efficiently conserves power and increases the time between battery charges.

The computer system (e.g., 600, 1020) determines (1802) that a user has completed a workout session (e.g., based on one or more user inputs and/or based on a predetermined duration of the workout session expiring). In some embodiments, in response to determining that the user has completed the workout session, the computer system displays (1804), via the display generation component (e.g., 602, 1022), a workout summary user interface (e.g., 1652, 1660, 1024) (in some embodiments, replacing display of a workout session user interface indicative of an active and/or in-progress workout session with the workout summary user interface), including concurrently displaying: a first user interface object (e.g., 1026a-1026e, 1028a-1028e, 1656a-1656c, 1658a-1658c, 1668a-1668f) (1806) corresponding to a first set of workout metrics (e.g., one or more workout metrics) that are grouped into a first category (in some embodiments, the first set of workout metrics includes one or more workout metrics that are collected and/or recorded during the workout session) (in some embodiments, the first set of workout metrics are indicative of physical activity by the user during the workout session); and a second user interface object (e.g., 1026a-1026e, 1028a-1028e, 1656a-1656c, 1658a-1658c, 1668a-1668f) (1808) corresponding to a second set of workout metrics (e.g., one or more workout metrics) that are different from the first set of workout metrics and are grouped into a second category different from the first category (in some embodiments, the second set of workout metrics includes one or more workout metrics that are collected and/or recorded during the workout session). In some embodiments, the second set of workout metrics are indicative of physical activity by the user during the workout session.

In some embodiments, the first user interface object (e.g., 1026a-1026e, 1028a-1028e, 1656a-1656c, 1658a-1658c, 1668a-1668f) (1806) is selectable to display a first workout category user interface (e.g., 1032, 1042, 1048, 1060, 1066,

1660, 1676, 1682) (in some embodiments, selectable to replace display of the workout summary user interface with display of the first workout category user interface) that displays a first set of workout metric information that corresponds to the first set of workout metrics, wherein at least some of the first set of workout metric information is not displayed in the workout summary user interface (1810). In some embodiments, the second user interface object (e.g., 1026a-1026e, 1028a-1028e, 1656a-1656c, 1658a-1658c, 1668a-1668f) is selectable to display a second workout category user interface (e.g., 1032, 1042, 1048, 1060, 1066, 1660, 1676, 1682) (in some embodiments, selectable to replace display of the workout summary user interface with display of the second workout category user interface) that is different from the first workout category user interface and displays a second set of workout metric information that corresponds to the second set of workout metrics, wherein the second set of workout metric information is different from the first set of workout metric information and at least some of the second set of workout metric information is not displayed in the workout summary user interface (1812). Displaying the workout summary user interface in response to determining that the user has completed the workout session enables these functions to be performed without user input. Displaying the first user interface object that is selectable to display the first workout category user interface enables a user to access additional workout metrics with fewer user inputs while preventing the workout summary user interface from presenting information that is not relevant to and/or interesting to the particular user.

In some embodiments, the first workout category user interface (e.g., 1032) comprises: a representation of a first workout metric displayed along a first timeline (e.g., 1034b-1034h); and a representation of a second workout metric (e.g., a second workout metric different from the first workout metric) displayed along a second timeline (e.g., 1034b-1034h) (e.g., different and/or separate from the first timeline). In some embodiments, while displaying the first workout category user interface, including concurrently displaying the representation of the first workout metric displayed along the first timeline and the representation of the second workout metric displayed along the second timeline, the computer system receives, via the one or more input devices, one or more user inputs (e.g., 1038) (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures) corresponding to a first position along the first timeline, wherein the first position along the first timeline corresponds to a first time in the workout session (e.g., a first timestamp and/or a first elapsed time in the workout session). In some embodiments, in response to receiving the one or more user inputs corresponding to the first position along the first timeline, the computer system concurrently displays, via the display generation component: a value for the first workout metric corresponding to the first time in the workout session (e.g., 1040b-1040h) (e.g., a value for the first workout metric that was measured at the first time in the workout session); and a value for the second workout metric corresponding to the first time in the workout session (e.g., 1040b-1040h) (e.g., a value for the second workout metric that was measured at the first time in the workout session). In some embodiments, the representation of the first workout metric displayed along the first timeline and the representation of the second workout metric displayed along the second timeline are not included in the workout summary user interface. In some embodiments, while displaying the first workout category user interface, the computer system receives one or more user inputs corresponding to a second position along the second timeline, wherein the second position corresponds to a second time in the workout session; and in response to receiving the one or more user inputs, the computer system concurrently displays a value for the first workout metric corresponding to the second time in the workout session and a value for the second workout metric corresponding to the second time in the workout session. Displaying values for the first workout metric and the second workout metric corresponding to the first time in the workout session in response to the user input corresponding to the first position along the first timeline enables a user to access workout metrics with fewer user inputs.

In some embodiments, while concurrently displaying the value for the first workout metric (e.g., 1040b-1040h) corresponding to the first time in the workout session and the value for the second workout metric (e.g., 1040b-1040h) corresponding to the first time in the workout session, the computer system receives, via the one or more input devices, one or more user inputs corresponding to a second position along the second timeline (e.g., 1034b-1034h), wherein the second position along the second timeline corresponds to a second time in the workout session different from the first time. In some embodiments, in response to receiving the one or more user inputs corresponding to the second position along the second timeline, the computer system concurrently displays, via the display generation component: a value for the first workout metric corresponding to the second time in the workout session (e.g., a different value for 1040b-1040h) (e.g., a value for the first workout metric that was measured at the second time in the workout session) (e.g., different from the value for the first workout metric corresponding to the first time in the workout session); and a value for the second workout metric corresponding to the second time in the workout session (e.g., a different value for 1040b-1040h) (e.g., a value for the second workout metric that was measured at the second time in the workout session) (e.g., different from the value for the second workout metric corresponding to the first time in the workout session) (and, optionally, in some embodiments, ceasing display of the value for the first workout metric corresponding to the first time in the workout session and the value for the second workout metric corresponding to the second time in the workout session). Displaying values for the first workout metric and the second workout metric corresponding to the second time in the workout session in response to the user input corresponding to the second position along the second timeline enables a user to access workout metrics with fewer user inputs.

In some embodiments, while concurrently displaying the value for the first workout metric (e.g., a different value for 1040b-1040h) corresponding to the first time in the workout session and the value for the second workout metric (e.g., a different value for 1040b-1040h) corresponding to the first time in the workout session, the computer system receives, via the one or more input devices, a first user input that includes movement from the first position along the first timeline to a third position along the first timeline (e.g., a swipe input and/or a drag input), wherein the third position along the first timeline corresponds to a third time in the workout session different from the first time. In some embodiments, in response to receiving the first user input, as the first user input moves from the first position along the first timeline to the third position along the first timeline, the computer system displays, via the display generation component, sequentially over time, a plurality of values for the first workout metric and a plurality of values for the second workout metric, including, at a first time during the first user input, concurrently displaying, via the display generation component: a value for the first workout metric corresponding to a fourth time in the workout between the first time and the third time; and a value for the second workout metric corresponding to the fourth time in the workout. In some embodiments, in response to receiving the first user input, as the first user input moves from the first position along the first timeline to the third position along the first timeline, the computer system displays, via the display generation component, sequentially over time, a plurality of values for the first workout metric and a plurality of values for the second workout metric, including, at a second time during the first user input subsequent to the first time, concurrently displaying, via the display generation component: a value for the first workout metric corresponding to the third time in the workout session (e.g., without displaying the value for the first workout metric corresponding to the first time and/or the fourth time in the workout); and a value for the second workout metric corresponding to the third time in the workout session (e.g., with displaying the value for the second workout metric corresponding to the first time and/or fourth time in the workout). In some embodiments, displaying, sequentially over time, the plurality of values for the first workout metric and the plurality of values for second workout metric further includes: at a third time during the first user input subsequent to the first time and prior to the second time, concurrently displaying, via the display generation component: a value for the first workout metric corresponding to a fifth time in the workout between the fourth time and the third time; and a value for the second workout metric corresponding to the fifth time in the workout. Enabling a user to scrub along a timeline to view corresponding values for a plurality of workout metrics at various times in a workout enables a user to access workout metrics with fewer user inputs, and enables the user to do so without displaying additional controls.

In some embodiments, the first workout metric (e.g., 1034b-1034h) is selected from a group consisting of: heart rate, pace, elevation, run power, stride length, symmetry, and vertical oscillation. In some embodiments, the second workout metric (e.g., 1034b-1034h) is selected from a group consisting of: heart rate, pace, elevation, run power, stride length, symmetry, and vertical oscillation. In some embodiments, the first workout metric is different from the second workout metric. Displaying values for the first workout metric and the second workout metric corresponding to the first time in the workout session in response to the user input corresponding to the first position along the first timeline enables a user to access workout metrics with fewer user inputs.

In some embodiments, the first workout category user interface (e.g., 1032) comprises a geographic map (e.g., 1040a) corresponding to the workout session (e.g., a geographic map displaying a route traversed by the user during the workout session). In some embodiments, in response to receiving the one or more user inputs (e.g., 1037) corresponding to the first position along the first timeline, the computer system displays, via the display generation component, and concurrently with the value for the first workout metric (e.g., 1034b-1034h) corresponding to the first time in the workout session and the value for the second workout metric (e.g., 1034b-1034h) corresponding to the first time in the workout session, a first position indicator (e.g., 1040a) on the geographic map (e.g., 1034a) indicating a geographic position of the user at the first time in the workout session. Displaying values for the first workout metric and the second workout metric corresponding to the first time in the workout session and the first position indicator in response to the user input corresponding to the first position along the first timeline enables a user to access workout metrics with fewer user inputs.

In some embodiments, the workout session corresponds to a previously completed route that is associated with one or more previously completed workout instances (e.g., FIGS. 10A-10S). In some embodiments, the one or more previously completed workout instances include traversal of the previously completed route and/or traversal of at least a threshold portion of the previously completed route. In some embodiments, in accordance with a determination that the workout session corresponds to a first workout type (e.g., a previously completed route workout type), the workout summary user interface (e.g., 1024) further includes a third user interface object (e.g., 1026b, 1028b) corresponding to a third set of workout metrics that are associated with the first workout type and are grouped into a third category different from the first category and the second category. In some embodiments, the workout summary user interface concurrently displays, within a region of the workout summary user interface that corresponds to the third user interface object: a value for a third workout metric corresponding to the workout session (e.g., "TODAY'S PACE" in 1026b) (e.g., a value for the third workout metric measured during the workout session); and a value for the third workout metric corresponding to a first previously completed workout instance of the one or more previously completed workout instances corresponding to the previously completed route (e.g., "BEST PACE" in 1026b) (e.g., a value for the third workout metric that was measured during the first previously completed workout instance). In some embodiments, in accordance with a determination that the workout session does not correspond to the first workout type (e.g., corresponds to a second workout type different from the first workout type), the workout summary user interface does not include the third user interface object corresponding to the third set of workout metrics and does not display the value for the third workout metric corresponding to the first previously completed workout instance. Displaying the third user interface object in accordance with a determination that the workout session corresponds to a first workout type enables these functions to be performed without user input and prevents the user interface from displaying information that is not relevant to the particular user.

In some embodiments, while displaying the workout summary user interface (e.g., 1024) including the third user interface object (e.g., 1026b, 1028b), the computer system receives, via the one or more input devices, one or more user inputs (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures) corresponding to selection of the third user interface object (e.g., 1030b). In some embodiments, in response to receiving the one or more user inputs corresponding to selection of the third user interface object, the computer system displays, via the display generation component, a third workout category user interface (e.g., 1048) different from the first workout category user interface and the second workout category user interface. In some embodiments, the third workout category user interface includes a ranked list (e.g., in some embodiments, 1054 is ranked based on time and/or pace) that includes: a representation of the workout session (e.g., "TODAY" in 1054) (e.g., one or more physical activity metrics corresponding to the workout session (e.g., pace, completion time, heartrate, and/or calories burned)), and representations of at least a subset of the one or more previously completed workout instances corresponding to the previously completed route (e.g., "LAST," "BEST," "AVG" in 1054) (e.g., physical activity metrics corresponding to the at least the subset of the one or more previously completed workout instances corresponding to the previously completed route). In some embodiments, the ranked list ranks workout instances based on completion time (e.g., time to complete the previously completed route). Displaying the third workout category user interface that includes the ranked list reduces the number of inputs required for the user to see how their current workout session compares to one or more previous workout instances.

In some embodiments, while displaying the workout summary user interface (e.g., 1024) including the third user interface object (e.g., 1026b, 1028b), the computer system receives, via the one or more input devices, one or more user inputs (e.g., 1030b) (e.g., one or more touch inputs (e.g., via a touch-sensitive display and/or a touch-sensitive surface); one or more non-touch inputs; one or more button presses; one or more activations of a depressible input mechanism; one or more rotations of a rotatable input mechanism; and/or one or more gestures) corresponding to selection of the third user interface object. In some embodiments, in response to receiving the one or more user inputs corresponding to selection of the third user interface object, the computer system displays, via the display generation component, a third workout category user interface (e.g., 1048) different from the first workout category user interface and the second workout category user interface. In some embodiments, the third workout category user interface includes: a first visual object (e.g., "TODAY'S PACE" in 1052) that indicates a first workout metric of the user over time during the workout session (e.g., a chart that displays elapsed time on a first axis, and values for the first workout metric during the workout session on a second axis); and a second visual object (e.g., "BEST PACE" in 1052) that indicates the first workout metric of the user over time during a second previously completed workout instance (e.g., a chart that displays elapsed time on a first axis, and values for the first workout metric during the second previously completed workout instance on a second axis). In some embodiments, the first visual object and the second visual object are displayed (e.g., concurrently displayed) on a single chart. Displaying the third workout category user interface that includes the first visual object and the second visual object reduces the number of inputs required for the user to see how their current workout session compares to one or more previous workout instances.

In some embodiments, while displaying the workout summary user interface (e.g., 1024) including the first user interface object (e.g., 1026a-1026e) and the second user interface object (e.g., 1026a-1026e), the computer system receives, via the one or more input devices, one or more user inputs (e.g., 1030d) corresponding to selection of the first user interface object (e.g., 1026d, 1028d). In some embodiments, in response to receiving the one or more user inputs corresponding to selection of the first user interface object, the computer system displays, via the display generation component, the first workout category user interface (e.g., 1042), including: a representation of a first heart rate zone (e.g., "ZONE 1" in FIG. 10O) (e.g., a first range of heart rate values); and a representation of a second heart rate zone (e.g., "ZONE 2" in FIG. 10O) different from the first heart rate zone (e.g., a second range of heart rate value). In some embodiments, the representation of the first heart rate zone is indicative of an amount of time that the user was in the first heart rate zone during the workout session (e.g., a percentage of the total workout session duration that the user was in the first heart rate zone (e.g., that the user had a heart rate that was within the first range of heart rate values)). In some embodiments, the representation of the second heart rate zone is indicative of an amount of time that the user was in the second heart rate zone during the workout session (e.g., a percentage of the total workout session duration that the user was in the second heart rate zone (e.g., that the user had a heart rate that was within the second range of heart rate values)). In some embodiments, the first workout category user interface further includes a representation of a third heart rate zone (e.g., a third range of heart rate values) different from the first and second heart rate zones, wherein the representation of the third heart rate zone is indicative of an amount of time that the user was in the third heart rate zone during the workout session (e.g., a percentage of the total workout session duration that the user was in the third heart rate zone (e.g., that the user had a heart rate that was within the third range of heart rate values)). In some embodiments, the workout summary user interface includes a first set of heart rate information corresponding to the workout session, but does not include the representation of the first heart rate zone and/or the representation of the second heart rate zone. Displaying the first workout category user interface including the representation of the first heart rate zone and the representation of the second heart rate zone reduces the number of inputs required for a user to see heart rate zone information.

In some embodiments, in accordance with a determination that the workout session includes a plurality of workout segments (e.g., a plurality of splits, a plurality of laps, and/or a plurality of legs), the workout summary user interface (e.g., 1024) further includes a fourth user interface object (e.g., 1026e, 1028e) corresponding to a fourth set of workout metrics that are different from the first set of workouts metrics and the second set of workout metrics and are grouped into a fourth category different from the first category and the second category. In some embodiments, the workout summary user interface (e.g., 1024) concurrently displays, within a region of the workout summary user interface corresponding to the fourth user interface object (e.g., 1026e, 1028e): values for a first set of workout metrics corresponding to a first segment of the plurality of workout segments (e.g., "PACE" and "TOTAL TIME" for "MILE 1" in 1026e) (e.g., values for the first set of workout metrics measured during the first segment of the workout session); values for the first set of workout metrics corresponding to a second segment of the plurality of workout segments (e.g., "PACE" and "TOTAL TIME" for "MILE 2" in 1026e) different from the first set (e.g., values for the first set of workout metrics measured during the second segment of the workout session); and values for the first set of workout metrics corresponding to a third segment of the plurality of workout segments (e.g., "PACE" and "TOTAL TIME" for "MILE 3" in 1026e) different from the first set and the second set (e.g., values for the first set of workout metrics measured during the third segment of the workout session). In some embodiments, in accordance with a determination that the workout session does not include a plurality of workout segments, the workout summary user interface does not include the fourth user interface object and/or the values for the first set of workout metrics corresponding to the first, second, and third segments of the plurality of workout segments. Displaying the third user interface object in accordance with a determination that the workout session includes a plurality of workout segments enables these functions to be performed without user input and prevents the user interface from displaying information that is not relevant to the particular user.

In some embodiments, while displaying the fourth user interface object (e.g., 1656a-1656c, 1658a-1658c), the computer system receives, via the one or more input devices, one or more user inputs (e.g., 1030e) corresponding to selection of the fourth user interface object. In some embodiments, in response to receiving the one or more user inputs corresponding to selection of the fourth user interface object, the computer system displays, via the display generation component, a fourth workout category user interface (e.g., 1060). In some embodiments, the fourth workout category user interface includes: values for a second set of workout metrics corresponding to the first segment of the plurality of workout segments (e.g., "HR AVG" for "MILE 1" in 1060) (e.g., values for the second set of workout metrics measured during the first segment of the workout session), wherein the second set of workout metrics is different from the first set of workout metrics and includes one or more workout metrics that are not included in the first set of workout metrics; values for the second set of workout metrics corresponding to the second segment of the plurality of workout segments (e.g., "HR AVG" for "MILE 2" in 1060) (e.g., values for the second set of workout metrics measured during the second segment of the workout session); and values for the second set of workout metrics corresponding to the third segment of the plurality of workout segments (e.g., "HR AVG" for "MILE 3" in 1060) (e.g., values for the second set of workout metrics measured during the third segment of the workout session). Displaying the fourth workout category user interface reduces the number of inputs required for a user to see workout segment and/or workout splits information.

In some embodiments, in accordance with a determination that the workout session includes a plurality of workout modalities (e.g., multi-modality workout in FIG. 16Y) (e.g., running, swimming, biking, outdoor running, indoor running, outdoor swimming, indoor swimming, outdoor biking, and/or indoor biking), the workout summary user interface (e.g., 1652) displays (e.g., concurrently with the first user interface object and/or the second user interface object), within a first region (e.g., 1656a-1656c) of the workout summary user interface, a third set of workout metrics corresponding to a first workout modality of the plurality of workout modalities (e.g., values for a third set of workout metrics measured while the user was performing the first workout modality). In some embodiments, in accordance with a determination that the workout session includes a plurality of workout modalities (e.g., running, swimming, biking, outdoor running, indoor running, outdoor swimming, indoor swimming, outdoor biking, and/or indoor biking), the workout summary user interface (e.g., 1652) displays (e.g., concurrently with the first user interface object and/or the second user interface object), within a second region (e.g., 1656a-1656c) of the workout summary user interface different from the first region, a fourth set of workout metrics corresponding to a second workout modality of the plurality of workout modalities (e.g., values for a fourth set of workout metrics while the user was performing the second workout modality). Displaying the third set of workout metrics and the fourth set of workout metrics in accordance with a determination that the workout session includes a plurality of workout modalities enables these functions to be performed without user input and prevents the user interface from displaying information that is not relevant to the particular user.

In some embodiments, the first user interface object (e.g., 1658a-1658c) corresponds to the first workout modality. In some embodiments, while displaying the workout summary user interface, the computer system receives, via the one or more input devices, one or more user inputs (e.g., 1662c) corresponding to selection of the first user interface object. In some embodiments, in response to receiving the one or more user inputs corresponding to selection of the first user interface object, the computer system displays, via the display generation component, the first workout category user interface (e.g., 1660). In some embodiments, the first workout category user interface (e.g., 1660) includes the first set of workout metric information that corresponds to the first set of workout metrics, the first set of workout metrics correspond to (e.g., correspond exclusively to) the first workout modality; and the first set of workout metrics includes one or more workout metrics that are not included in the third set of workout metrics (in some embodiments, the first set of workout metrics includes all workout metrics in the third set of workout metrics and includes one or more workout metrics that are not included in the third set of workout metrics). In some embodiments, the first workout category user interface does not display workout metrics corresponding to the second workout modality (e.g., measured while the user was performing the second workout modality). Displaying the first workout category user interface reduces the number of inputs required for a user to see workout metrics for the first workout modality.

Note that details of the processes described above with respect to method 1800 (e.g., FIG. 18) are also applicable in an analogous manner to the methods described above. For example, methods 700, 800, 900, 1100, 1300, 1500, and/or 1700 optionally include one or more of the characteristics of the various methods described above with reference to method 1800. For example, in some embodiments, the workout session in method 1800 is the workout session recited in methods 700, 800, 900, and/or 1100, and/or the workout session recited in method 1800 corresponds to the workouts recited in methods 1300, 1500, and/or 1700. For brevity, these details are not repeated below.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

As described above, one aspect of the present technology is the gathering and use of data available from various sources to improve the delivery to users of workout content or any other content that may be of interest to them. The present disclosure contemplates that in some instances, this gathered data may include personal information data that uniquely identifies or can be used to contact or locate a specific person. Such personal information data can include demographic data, location-based data, telephone numbers, email addresses, social network IDs, home addresses, data or records relating to a user's health or level of fitness (e.g., vital signs measurements, medication information, exercise information), date of birth, or any other identifying or personal information.

The present disclosure recognizes that the use of such personal information data, in the present technology, can be used to the benefit of users. For example, the personal information data can be used to deliver targeted content that is of greater interest to the user. Accordingly, use of such personal information data enables users to have calculated control of the delivered content. Further, other uses for personal information data that benefit the user are also contemplated by the present disclosure. For instance, health and fitness data may be used to provide insights into a user's general wellness, or may be used as positive feedback to individuals using technology to pursue wellness goals.

The present disclosure contemplates that the entities responsible for the collection, analysis, disclosure, transfer, storage, or other use of such personal information data will comply with well-established privacy policies and/or privacy practices. In particular, such entities should implement and consistently use privacy policies and practices that are generally recognized as meeting or exceeding industry or governmental requirements for maintaining personal information data private and secure. Such policies should be easily accessible by users, and should be updated as the collection and/or use of data changes. Personal information from users should be collected for legitimate and reasonable uses of the entity and not shared or sold outside of those legitimate uses. Further, such collection/sharing should occur after receiving the informed consent of the users. Additionally, such entities should consider taking any needed steps for safeguarding and securing access to such personal information data and ensuring that others with access to the personal information data adhere to their privacy policies and procedures. Further, such entities can subject themselves to evaluation by third parties to certify their adherence to widely accepted privacy policies and practices. In addition, policies and practices should be adapted for the particular types of personal information data being collected and/or accessed and adapted to applicable laws and standards, including jurisdiction-specific considerations. For instance, in the US, collection of or access to certain health data may be governed by federal and/or state laws, such as the Health Insurance Portability and Accountability Act (HIPAA); whereas health data in other countries may be subject to other regulations and policies and should be handled accordingly. Hence different privacy practices should be maintained for different personal data types in each country.

Despite the foregoing, the present disclosure also contemplates embodiments in which users selectively block the use of, or access to, personal information data. That is, the present disclosure contemplates that hardware and/or software elements can be provided to prevent or block access to such personal information data. For example, in the case of workout content delivery services, the present technology can be configured to allow users to select to "opt in" or "opt out" of participation in the collection of personal information data during registration for services or anytime thereafter. In another example, users can select not to provide personal information for targeted workout content delivery services. In yet another example, users can select to limit the length of personal information is maintained or entirely prohibit the provision of personal information. In addition to providing "opt in" and "opt out" options, the present disclosure contemplates providing notifications relating to the access or use of personal information. For instance, a user may be notified upon downloading an app that their personal information data will be accessed and then reminded again just before personal information data is accessed by the app.

Moreover, it is the intent of the present disclosure that personal information data should be managed and handled in a way to minimize risks of unintentional or unauthorized access or use. Risk can be minimized by limiting the collection of data and deleting data once it is no longer needed. In addition, and when applicable, including in certain health related applications, data de-identification can be used to protect a user's privacy. De-identification may be facilitated, when appropriate, by removing specific identifiers (e.g., date of birth, etc.), controlling the amount or specificity of data stored (e.g., collecting location data a city level rather than at an address level), controlling how data is stored (e.g., aggregating data across users), and/or other methods.

Therefore, although the present disclosure broadly covers use of personal information data to implement one or more various disclosed embodiments, the present disclosure also contemplates that the various embodiments can also be implemented without the need for accessing such personal information data. That is, the various embodiments of the present technology are not rendered inoperable due to the lack of all or a portion of such personal information data. For example, workout content can be selected and delivered to users by inferring preferences based on non-personal information data or a bare minimum amount of personal information, such as the content being requested by the device associated with a user, other non-personal information available to the workout content delivery services, or publicly available information.

What is claimed is:

1. A computer system configured to communicate with a display generation component and one or more input devices, comprising:
   one or more processors; and
   memory storing one or more programs configured to be executed by the one or more processors, the one or more programs including instructions for:
      displaying, via the display generation component, a first user interface corresponding to a first workout modality, wherein the first workout modality is part of a multi-modality workout that includes a plurality of workout modalities arranged in an ordered sequence;
      while displaying the first user interface, automatically detecting that the user may be transitioning from the first workout modality to a second workout modality;
      in response to detecting that the user may be transitioning from the first workout modality to the second workout modality, displaying, via the display generation component, a second user interface different from the first user interface, wherein the second user interface is indicative of detecting a possible transition from the first workout modality to the second workout modality;

while displaying the second user interface, detecting, via the one or more input devices, movement by the user; and
in response to detecting the movement by the user:
in accordance with a determination that the movement by the user indicates that the user has transitioned from the first workout modality to the second workout modality, displaying, via the display generation component, a third user interface corresponding to the second workout modality, wherein the third user interface is different from the first user interface and the second user interface; and
in accordance with a determination that the movement by the user indicates that the user has not transitioned from the first workout modality to the second workout modality, re-displaying the first user interface.

2. The computer system of claim 1, wherein the second user interface includes a transition duration timer that indicates how long the second user interface has been displayed.

3. The computer system of claim 1, wherein:
the first user interface includes a first workout metric; and
the third user interface includes a second workout metric different from the first workout metric without including the first workout metric.

4. The computer system of claim 3, wherein:
the first user interface includes a third workout metric different from the first workout metric and the second workout metric; and
the third user interface includes the third workout metric.

5. The computer system of claim 1, wherein:
the first user interface includes a first set of user interface objects that are representative of the plurality of workout modalities in the multi-modality workout and the ordered sequence of the plurality of workout modalities, wherein the first set of user interface objects includes a representation of the first workout modality and a representation of the second workout modality;
displaying the first user interface includes:
displaying the representation of the first workout modality in a first manner; and
displaying the representation of the second workout modality in a second manner different from the first manner;
the third user interface includes the first set of user interface objects; and
displaying the third user interface includes:
displaying the representation of the first workout modality in the second manner; and
displaying the representation of the second workout modality in the first manner.

6. The computer system of claim 1, wherein:
the first user interface includes:
a total workout timer indicative of an elapsed time of the multi-modality workout; and
a first modality timer indicative of an elapsed time corresponding to the first workout modality of the plurality of workout modalities;
displaying the first user interface includes:
displaying progression of the total workout time; and
displaying progression of the first modality timer;
the second user interface includes the total workout timer and the first modality timer; and
displaying the second user interface includes:
displaying progression of the total workout timer; and
maintaining display of the first modality timer at a first time without progressing the first modality timer.

7. The computer system of claim 6, wherein:
displaying the first user interface in accordance with the determination that the movement of the user indicates that the user has not transitioned from the first workout modality to the second workout modality comprises:
in accordance with the determination that the movement by the user indicates that the user has not transitioned from the first workout modality to the second workout modality:
advancing the first modality timer from the first time to a second time; and
displaying, within the first user interface, progression of the first modality timer from the second time.

8. The computer system of claim 6, wherein:
the second user interface includes a first transition timer indicative of an elapsed transition time during which the second user interface has been displayed;
the third user interface includes a second modality timer indicative of an elapsed time corresponding to the second workout modality; and
displaying the third user interface comprises initiating progression of the second modality timer from a third time, wherein the third time is determined based on the elapsed transition time.

9. The computer system of claim 1, the one or more programs further including instructions for:
displaying, via the display generation component, a workout selection user interface comprising a plurality of workout options, wherein the plurality of workout options includes a representation of the multi-modality workout;
while displaying the workout selection user interface, receiving, via the one or more input devices, one or more user inputs corresponding to the representation of the multi-modality workout; and
in response to receiving the one or more user inputs corresponding to the representation of the multi-modality workout:
displaying, via the display generation component, a multi-modality workout room user interface, wherein the multi-modality workout room user interface includes:
a representation of a first pre-configured multi-modality workout;
a representation of a second pre-configured multi-modality workout different from the first pre-configured multi-modality workout; and
a new workout option that is selectable to initiate a process for creating a new multi-modality workout.

10. The computer system of claim 9, wherein the new workout option is selectable to initiate a process for selecting two or more workout modalities for inclusion in the new multi-modality workout and defining an order for the two or more workout modalities in the new multi-modality workout.

11. The computer system of claim 9, the one or more programs further including instructions for:
while displaying the multi-modality workout room user interface, receiving, via the one or more input devices, a first set of user inputs; and in response to receiving the first set of user inputs:
   in accordance with a determination that the first set of user inputs corresponds to selection of a first region of the representation of the first pre-configured multi-modality workout:
      initiating a workout session corresponding to the first pre-configured multi-modality workout; and
      displaying, via the display generation component, a fourth user interface indicative of an active workout session and corresponding to a first workout modality of the first pre-configured multi-modality workout; and
   in accordance with a determination that the first set of user inputs corresponds to selection of a second region of the representation of the first pre-configured multi-modality workout:
      displaying, via the display generation component, a first workout modification user interface comprising one or more options that are selectable to initiate one or more processes for modifying one or more aspects of the first pre-configured multi-modality workout.

12. The computer system of claim 11, wherein:
the first workout modification user interface includes a first option that is selectable to initiate a process for adding a new segment to the first pre-configured multi-modality workout.

13. The computer system of claim 11, wherein:
the first workout modification user interface includes a second option that is selectable to initiate a process for removing a segment from the first pre-configured multi-modality workout.

14. The computer system of claim 11, wherein:
the first pre-configured multi-modality workout comprises a set of workout segments corresponding to a plurality of workout modalities, including a first workout segment corresponding to a third workout modality and a second workout segment corresponding to a fourth workout modality;
the first workout modification user interface includes a representation of the first workout segment and a representation of the second workout segment; and
the one or more programs further include instructions for:
   displaying, at a first time, via the display generation component, the first workout modification user interface, wherein, at the first time, the representation of the first workout segment and the representation of the second workout segment are presented within the first workout modification user interface in a first order indicative of the first workout segment preceding the second workout segment in the first pre-configured multi-modality workout;
   while displaying the first workout modification user interface, receiving, via the one or more input devices, one or more user inputs corresponding to a request to move the representation of the first workout segment; and
   in response to receiving the one or more user inputs corresponding to the request to move the representation of the first workout segment, displaying, via the display generation component, movement of the representation of the first workout segment from a first display position to a second display position within the first workout modification user interface, wherein after movement of the representation of the first workout segment to the second display position within the first workout modification user interface, the representation of the first workout segment and the representation of the second workout segment are presented in a second order different from the first order and indicative of the second workout segment preceding the first workout segment in the first pre-configured multi-modality workout.

15. The computer system of claim 11, wherein:
the first pre-configured multi-modality workout comprises a set of workout segments corresponding to a plurality of workout modalities, including a third workout segment corresponding to a fifth workout modality and a fourth workout segment corresponding to a sixth workout modality;
the first workout modification user interface includes a representation of the third workout segment and a representation of the fourth workout segment; and
the one or more programs further include instructions for:
   while displaying the first workout modification user interface, receiving, via the one or more input devices, one or more user inputs corresponding to selection of the representation of the third workout segment; and
   in response to receiving the one or more user inputs corresponding to selection of the representation of the third workout segment, displaying, via the display generation component, a workout segment modification user interface including one or more options that are selectable to initiate one or more processes for modifying one or more aspects of the third workout segment, wherein the one or more options includes a change modality option that is selectable to initiate a process for changing a workout modality associated with the third workout segment.

16. The computer system of claim 11, wherein:
the first pre-configured multi-modality workout comprises a set of workout segments corresponding to a plurality of workout modalities, including a fifth workout segment corresponding to a seventh workout modality and a sixth workout segment corresponding to an eighth workout modality;
the first workout modification user interface includes a representation of the fifth workout segment and a representation of the sixth workout segment; and
the one or more programs further include instructions for:
   while displaying the first workout modification user interface, receiving, via the one or more input devices, one or more user inputs corresponding to selection of the representation of the fifth workout segment; and
   in response to receiving the one or more user inputs corresponding to selection of the representation of the fifth workout segment, displaying, via the display generation component, a second workout segment modification user interface including one or more options that are selectable to initiate one or more processes for modifying one or more aspects of the fifth workout segment, wherein the one or more options includes an alerts option that is selectable to initiate a process for modifying one or more alerts that are enabled during the fifth workout segment of the first pre-configured multi-modality workout.

17. The computer system of claim 11, wherein:
the first pre-configured multi-modality workout comprises a set of workout segments corresponding to a plurality of workout modalities, including a seventh workout segment corresponding to a ninth workout modality and an eighth workout segment corresponding to a tenth workout modality;
the first workout modification user interface includes a representation of the seventh workout segment and a representation of the eighth workout segment; and
the one or more programs further include instructions for:
while displaying the first workout modification user interface, receiving, via the one or more input devices, one or more user inputs corresponding to selection of the representation of the seventh workout segment; and
in response to receiving the one or more user inputs corresponding to selection of the representation of the seventh workout segment, displaying, via the display generation component, a third workout segment modification user interface including one or more options that are selectable to initiate one or more processes for modifying one or more aspects of the seventh workout segment, wherein the one or more options includes a metrics option that is selectable to initiate a process for modifying one or more workout metrics that are accessible during the seventh workout segment of the first pre-configured multi-modality workout.

18. The computer system of claim 1, the one or more programs further including instructions for:
after completion of the multi-modality workout, displaying, via the display generation component, a first workout summary user interface that includes:
a first region corresponding to the first workout modality and including a first set of workout metrics corresponding to the first workout modality;
a second region different from the first region and corresponding to the second workout modality, and including a second set of workout metrics corresponding to the second workout modality;
a first object corresponding to the first workout modality that is selectable to cause display of one or more additional workout metrics corresponding to the first workout modality that are not displayed in the first region of the first workout summary user interface; and
a second object corresponding to the second workout modality that is selectable to cause display of one or more additional workout metrics corresponding to the second workout modality that are not displayed in the second region of the first workout summary user interface.

19. The computer system of claim 1, the one or more programs further including instructions for:
receiving, via the one or more input devices, a user input to transition an automatic transition setting from an enabled state to a disabled state, wherein:
when the automatic transition setting is in the enabled state, the computer system automatically detects possible transitions between workout modalities during multi-modality workouts; and
when the automatic transition setting is in the disabled state, the computer system does not automatically detect transitions between workout modalities during multi-modality workouts, and the computer system detects transitions between workout modalities during multi-modality workouts based on one or more user inputs.

20. The computer system of claim 19, the one or more programs further including instructions for:
in accordance with a determination that the automatic transition setting is in the disabled state, providing access to a selectable object that is selectable to transition a transition period setting between the enabled state and the disabled state;
while the automatic transition setting is in the disabled state, displaying, via the display generation component, the first user interface corresponding to the first workout modality of the multi-modality workout;
while displaying the first user interface, receiving, via the one or more input devices, one or more user inputs indicating that the user has completed the first workout modality; and
in response to receiving the one or more user inputs indicating that the user has completed the first workout modality:
in accordance with a determination that the transition period setting is in the disabled state, displaying, via the display generation component, the third user interface corresponding to the second workout modality of the multi-modality workout; and
in accordance with a determination that the transition period setting is in the enabled state, displaying, via the display generation component, a transition user interface different from the first user interface and the third user interface and indicative of a transition between the first workout modality and the second workout modality.

21. A non-transitory computer-readable storage medium storing one or more programs configured to be executed by one or more processors of a computer system that is in communication with a display generation component and one or more input devices, the one or more programs including instructions for:
displaying, via the display generation component, a first user interface corresponding to a first workout modality, wherein the first workout modality is part of a multi-modality workout that includes a plurality of workout modalities arranged in an ordered sequence;
while displaying the first user interface, automatically detecting that the user may be transitioning from the first workout modality to a second workout modality;
in response to detecting that the user may be transitioning from the first workout modality to the second workout modality, displaying, via the display generation component, a second user interface different from the first user interface, wherein the second user interface is indicative of detecting a possible transition from the first workout modality to the second workout modality;
while displaying the second user interface, detecting, via the one or more input devices, movement by the user; and
in response to detecting the movement by the user:
in accordance with a determination that the movement by the user indicates that the user has transitioned from the first workout modality to the second workout modality, displaying, via the display generation component, a third user interface corresponding to the second workout modality, wherein the third user interface is different from the first user interface and the second user interface; and
in accordance with a determination that the movement by the user indicates that the user has not transitioned from the first workout modality to the second workout modality, re-displaying the first user interface.

22. A method, comprising:
at a computer system that is in communication with a display generation component and one or more input devices:
displaying, via the display generation component, a first user interface corresponding to a first workout modality, wherein the first workout modality is part of a multi-modality workout that includes a plurality of workout modalities arranged in an ordered sequence;
while displaying the first user interface, automatically detecting that the user may be transitioning from the first workout modality to a second workout modality;
in response to detecting that the user may be transitioning from the first workout modality to the second workout modality, displaying, via the display generation component, a second user interface different from the first user interface, wherein the second user interface is indicative of detecting a possible transition from the first workout modality to the second workout modality;
while displaying the second user interface, detecting, via the one or more input devices, movement by the user; and
in response to detecting the movement by the user:
in accordance with a determination that the movement by the user indicates that the user has transitioned from the first workout modality to the second workout modality, displaying, via the display generation component, a third user interface corresponding to the second workout modality, wherein the third user interface is different from the first user interface and the second user interface; and
in accordance with a determination that the movement by the user indicates that the user has not transitioned from the first workout modality to the second workout modality, re-displaying the first user interface.

23. The non-transitory computer-readable storage medium of claim 21, wherein the second user interface includes a transition duration timer that indicates how long the second user interface has been displayed.

24. The non-transitory computer-readable storage medium of claim 21, wherein:
the first user interface includes a first workout metric; and
the third user interface includes a second workout metric different from the first workout metric without including the first workout metric.

25. The non-transitory computer-readable storage medium of claim 24, wherein:
the first user interface includes a third workout metric different from the first workout metric and the second workout metric; and
the third user interface includes the third workout metric.

26. The non-transitory computer-readable storage medium of claim 21, wherein:
the first user interface includes a first set of user interface objects that are representative of the plurality of workout modalities in the multi-modality workout and the ordered sequence of the plurality of workout modalities, wherein the first set of user interface objects includes a representation of the first workout modality and a representation of the second workout modality;
displaying the first user interface includes:
displaying the representation of the first workout modality in a first manner; and
displaying the representation of the second workout modality in a second manner different from the first manner;
the third user interface includes the first set of user interface objects; and
displaying the third user interface includes:
displaying the representation of the first workout modality in the second manner; and
displaying the representation of the second workout modality in the first manner.

27. The non-transitory computer-readable storage medium of claim 21, wherein:
the first user interface includes:
a total workout timer indicative of an elapsed time of the multi-modality workout; and
a first modality timer indicative of an elapsed time corresponding to the first workout modality of the plurality of workout modalities;
displaying the first user interface includes:
displaying progression of the total workout timer; and
displaying progression of the first modality timer;
the second user interface includes the total workout timer and the first modality timer; and
displaying the second user interface includes:
displaying progression of the total workout timer; and
maintaining display of the first modality timer at a first time without progressing the first modality timer.

28. The non-transitory computer-readable storage medium of claim 27, wherein:
displaying the first user interface in accordance with the determination that the movement of the user indicates that the user has not transitioned from the first workout modality to the second workout modality comprises:
in accordance with the determination that the movement by the user indicates that the user has not transitioned from the first workout modality to the second workout modality:
advancing the first modality timer from the first time to a second time; and
displaying, within the first user interface, progression of the first modality timer from the second time.

29. The non-transitory computer-readable storage medium of claim 27, wherein:
the second user interface includes a first transition timer indicative of an elapsed transition time during which the second user interface has been displayed;
the third user interface includes a second modality timer indicative of an elapsed time corresponding to the second workout modality; and
displaying the third user interface comprises initiating progression of the second modality timer from a third time, wherein the third time is determined based on the elapsed transition time.

30. The non-transitory computer-readable storage medium of claim 21, the one or more programs further including instructions for:
displaying, via the display generation component, a workout selection user interface comprising a plurality of workout options, wherein the plurality of workout options includes a representation of the multi-modality workout;
while displaying the workout selection user interface, receiving, via the one or more input devices, one or more user inputs corresponding to the representation of the multi-modality workout; and in response to receiving the one or more user inputs corresponding to the representation of the multi-modality workout:
displaying, via the display generation component, a multi-modality workout room user interface, wherein the multi-modality workout room user interface includes:
a representation of a first pre-configured multi-modality workout;
a representation of a second pre-configured multi-modality workout different from the first pre-configured multi-modality workout; and
a new workout option that is selectable to initiate a process for creating a new multi-modality workout.

31. The non-transitory computer-readable storage medium of claim 30, wherein the new workout option is selectable to initiate a process for selecting two or more workout modalities for inclusion in the new multi-modality workout and defining an order for the two or more workout modalities in the new multi-modality workout.

32. The non-transitory computer-readable storage medium of claim 30, the one or more programs further including instructions for:
while displaying the multi-modality workout room user interface, receiving, via the one or more input devices, a first set of user inputs; and
in response to receiving the first set of user inputs:
in accordance with a determination that the first set of user inputs corresponds to selection of a first region of the representation of the first pre-configured multi-modality workout:
initiating a workout session corresponding to the first pre-configured multi-modality workout; and
displaying, via the display generation component, a fourth user interface indicative of an active workout session and corresponding to a first workout modality of the first pre-configured multi-modality workout; and
in accordance with a determination that the first set of user inputs corresponds to selection of a second region of the representation of the first pre-configured multi-modality workout:
displaying, via the display generation component, a first workout modification user interface comprising one or more options that are selectable to initiate one or more processes for modifying one or more aspects of the first pre-configured multi-modality workout.

33. The non-transitory computer-readable storage medium of claim 32, wherein:
the first workout modification user interface includes a first option that is selectable to initiate a process for adding a new segment to the first pre-configured multi-modality workout.

34. The non-transitory computer-readable storage medium of claim 32, wherein:
the first workout modification user interface includes a second option that is selectable to initiate a process for removing a segment from the first pre-configured multi-modality workout.

35. The non-transitory computer-readable storage medium of claim 32, wherein:
the first pre-configured multi-modality workout comprises a set of workout segments corresponding to a plurality of workout modalities, including a first workout segment corresponding to a third workout modality and a second workout segment corresponding to a fourth workout modality;
the first workout modification user interface includes a representation of the first workout segment and a representation of the second workout segment; and
the one or more programs further include instructions for:
displaying, at a first time, via the display generation component, the first workout modification user interface, wherein, at the first time, the representation of the first workout segment and the representation of the second workout segment are presented within the first workout modification user interface in a first order indicative of the first workout segment preceding the second workout segment in the first pre-configured multi-modality workout;
while displaying the first workout modification user interface, receiving, via the one or more input devices, one or more user inputs corresponding to a request to move the representation of the first workout segment; and
in response to receiving the one or more user inputs corresponding to the request to move the representation of the first workout segment, displaying, via the display generation component, movement of the representation of the first workout segment from a first display position to a second display position within the first workout modification user interface, wherein after movement of the representation of the first workout segment to the second display position within the first workout modification user interface, the representation of the first workout segment and the representation of the second workout segment are presented in a second order different from the first order and indicative of the second workout segment preceding the first workout segment in the first pre-configured multi-modality workout.

36. The non-transitory computer-readable storage medium of claim 32, wherein:
the first pre-configured multi-modality workout comprises a set of workout segments corresponding to a plurality of workout modalities, including a third workout segment corresponding to a fifth workout modality and a fourth workout segment corresponding to a sixth workout modality;
the first workout modification user interface includes a representation of the third workout segment and a representation of the fourth workout segment; and
the one or more programs further include instructions for:
while displaying the first workout modification user interface, receiving, via the one or more input devices, one or more user inputs corresponding to selection of the representation of the third workout segment; and
in response to receiving the one or more user inputs corresponding to selection of the representation of the third workout segment, displaying, via the display generation component, a workout segment modification user interface including one or more options that are selectable to initiate one or more processes for modifying one or more aspects of the third workout segment, wherein the one or more options includes a change modality option that is selectable to initiate a process for changing a workout modality associated with the third workout segment.

37. The non-transitory computer-readable storage medium of claim 32, wherein:
- the first pre-configured multi-modality workout comprises a set of workout segments corresponding to a plurality of workout modalities, including a fifth workout segment corresponding to a seventh workout modality and a sixth workout segment corresponding to an eighth workout modality;
- the first workout modification user interface includes a representation of the fifth workout segment and a representation of the sixth workout segment; and
- the one or more programs further include instructions for:
  - while displaying the first workout modification user interface, receiving, via the one or more input devices, one or more user inputs corresponding to selection of the representation of the fifth workout segment; and
  - in response to receiving the one or more user inputs corresponding to selection of the representation of the fifth workout segment, displaying, via the display generation component, a second workout segment modification user interface including one or more options that are selectable to initiate one or more processes for modifying one or more aspects of the fifth workout segment, wherein the one or more options includes an alerts option that is selectable to initiate a process for modifying one or more alerts that are enabled during the fifth workout segment of the first pre-configured multi-modality workout.

38. The non-transitory computer-readable storage medium of claim 32, wherein:
- the first pre-configured multi-modality workout comprises a set of workout segments corresponding to a plurality of workout modalities, including a seventh workout segment corresponding to a ninth workout modality and an eighth workout segment corresponding to a tenth workout modality;
- the first workout modification user interface includes a representation of the seventh workout segment and a representation of the eighth workout segment; and
- the one or more programs further include instructions for:
  - while displaying the first workout modification user interface, receiving, via the one or more input devices, one or more user inputs corresponding to selection of the representation of the seventh workout segment; and
  - in response to receiving the one or more user inputs corresponding to selection of the representation of the seventh workout segment, displaying, via the display generation component, a third workout segment modification user interface including one or more options that are selectable to initiate one or more processes for modifying one or more aspects of the seventh workout segment, wherein the one or more options includes a metrics option that is selectable to initiate a process for modifying one or more workout metrics that are accessible during the seventh workout segment of the first pre-configured multi-modality workout.

39. The non-transitory computer-readable storage medium of claim 21, the one or more programs further including instructions for:
- after completion of the multi-modality workout, displaying, via the display generation component, a first workout summary user interface that includes:
  - a first region corresponding to the first workout modality and including a first set of workout metrics corresponding to the first workout modality;
  - a second region different from the first region and corresponding to the second workout modality, and including a second set of workout metrics corresponding to the second workout modality;
  - a first object corresponding to the first workout modality that is selectable to cause display of one or more additional workout metrics corresponding to the first workout modality that are not displayed in the first region of the first workout summary user interface; and
  - a second object corresponding to the second workout modality that is selectable to cause display of one or more additional workout metrics corresponding to the second workout modality that are not displayed in the second region of the first workout summary user interface.

40. The non-transitory computer-readable storage medium of claim 21, the one or more programs further including instructions for:
- receiving, via the one or more input devices, a user input to transition an automatic transition setting from an enabled state to a disabled state, wherein:
  - when the automatic transition setting is in the enabled state, the computer system automatically detects possible transitions between workout modalities during multi-modality workouts; and
  - when the automatic transition setting is in the disabled state, the computer system does not automatically detect transitions between workout modalities during multi-modality workouts, and the computer system detects transitions between workout modalities during multi-modality workouts based on one or more user inputs.

41. The non-transitory computer-readable storage medium of claim 40, the one or more programs further including instructions for:
- in accordance with a determination that the automatic transition setting is in the disabled state, providing access to a selectable object that is selectable to transition a transition period setting between the enabled state and the disabled state;
- while the automatic transition setting is in the disabled state, displaying, via the display generation component, the first user interface corresponding to the first workout modality of the multi-modality workout;
- while displaying the first user interface, receiving, via the one or more input devices, one or more user inputs indicating that the user has completed the first workout modality; and
- in response to receiving the one or more user inputs indicating that the user has completed the first workout modality:
  - in accordance with a determination that the transition period setting is in the disabled state, displaying, via the display generation component, the third user interface corresponding to the second workout modality of the multi-modality workout; and
  - in accordance with a determination that the transition period setting is in the enabled state, displaying, via the display generation component, a transition user interface different from the first user interface and the third user interface and indicative of a transition between the first workout modality and the second workout modality.

42. The method of claim 22, wherein the second user interface includes a transition duration timer that indicates how long the second user interface has been displayed.

43. The method of claim 22, wherein:
the first user interface includes a first workout metric; and
the third user interface includes a second workout metric different from the first workout metric without including the first workout metric.

44. The method of claim 43, wherein:
the first user interface includes a third workout metric different from the first workout metric and the second workout metric; and
the third user interface includes the third workout metric.

45. The method of claim 22, wherein:
the first user interface includes a first set of user interface objects that are representative of the plurality of workout modalities in the multi-modality workout and the ordered sequence of the plurality of workout modalities, wherein the first set of user interface objects includes a representation of the first workout modality and a representation of the second workout modality;
displaying the first user interface includes:
displaying the representation of the first workout modality in a first manner; and
displaying the representation of the second workout modality in a second manner different from the first manner;
the third user interface includes the first set of user interface objects; and
displaying the third user interface includes:
displaying the representation of the first workout modality in the second manner; and
displaying the representation of the second workout modality in the first manner.

46. The method of claim 22, wherein:
the first user interface includes:
a total workout timer indicative of an elapsed time of the multi-modality workout; and
a first modality timer indicative of an elapsed time corresponding to the first workout modality of the plurality of workout modalities;
displaying the first user interface includes:
displaying progression of the total workout timer; and
displaying progression of the first modality timer;
the second user interface includes the total workout timer and the first modality timer; and
displaying the second user interface includes:
displaying progression of the total workout timer; and
maintaining display of the first modality timer at a first time without progressing the first modality timer.

47. The method of claim 46, wherein:
displaying the first user interface in accordance with the determination that the movement of the user indicates that the user has not transitioned from the first workout modality to the second workout modality comprises:
in accordance with the determination that the movement by the user indicates that the user has not transitioned from the first workout modality to the second workout modality:
advancing the first modality timer from the first time to a second time; and
displaying, within the first user interface, progression of the first modality timer from the second time.

48. The method of claim 46, wherein:
the second user interface includes a first transition timer indicative of an elapsed transition time during which the second user interface has been displayed;
the third user interface includes a second modality timer indicative of an elapsed time corresponding to the second workout modality; and
displaying the third user interface comprises initiating progression of the second modality timer from a third time, wherein the third time is determined based on the elapsed transition time.

49. The method of claim 22, further comprising:
displaying, via the display generation component, a workout selection user interface comprising a plurality of workout options, wherein the plurality of workout options includes a representation of the multi-modality workout;
while displaying the workout selection user interface, receiving, via the one or more input devices, one or more user inputs corresponding to the representation of the multi-modality workout; and
in response to receiving the one or more user inputs corresponding to the representation of the multi-modality workout:
displaying, via the display generation component, a multi-modality workout room user interface, wherein the multi-modality workout room user interface includes:
a representation of a first pre-configured multi-modality workout;
a representation of a second pre-configured multi-modality workout different from the first pre-configured multi-modality workout; and
a new workout option that is selectable to initiate a process for creating a new multi-modality workout.

50. The method of claim 49, wherein the new workout option is selectable to initiate a process for selecting two or more workout modalities for inclusion in the new multi-modality workout and defining an order for the two or more workout modalities in the new multi-modality workout.

51. The method of claim 49, further comprising:
while displaying the multi-modality workout room user interface, receiving, via the one or more input devices, a first set of user inputs; and
in response to receiving the first set of user inputs:
in accordance with a determination that the first set of user inputs corresponds to selection of a first region of the representation of the first pre-configured multi-modality workout:
initiating a workout session corresponding to the first pre-configured multi-modality workout; and
displaying, via the display generation component, a fourth user interface indicative of an active workout session and corresponding to a first workout modality of the first pre-configured multi-modality workout; and
in accordance with a determination that the first set of user inputs corresponds to selection of a second region of the representation of the first pre-configured multi-modality workout:
displaying, via the display generation component, a first workout modification user interface comprising one or more options that are selectable to initiate one or more processes for modifying one or more aspects of the first pre-configured multi-modality workout.

52. The method of claim 51, wherein:

the first workout modification user interface includes a first option that is selectable to initiate a process for adding a new segment to the first pre-configured multi-modality workout.

53. The method of claim 51, wherein:

the first workout modification user interface includes a second option that is selectable to initiate a process for removing a segment from the first pre-configured multi-modality workout.

54. The method of claim 51, wherein:

the first pre-configured multi-modality workout comprises a set of workout segments corresponding to a plurality of workout modalities, including a first workout segment corresponding to a third workout modality and a second workout segment corresponding to a fourth workout modality;

the first workout modification user interface includes a representation of the first workout segment and a representation of the second workout segment; and the method further comprising:
- displaying, at a first time, via the display generation component, the first workout modification user interface, wherein, at the first time, the representation of the first workout segment and the representation of the second workout segment are presented within the first workout modification user interface in a first order indicative of the first workout segment preceding the second workout segment in the first pre-configured multi-modality workout;
- while displaying the first workout modification user interface, receiving, via the one or more input devices, one or more user inputs corresponding to a request to move the representation of the first workout segment; and
- in response to receiving the one or more user inputs corresponding to the request to move the representation of the first workout segment, displaying, via the display generation component, movement of the representation of the first workout segment from a first display position to a second display position within the first workout modification user interface, wherein after movement of the representation of the first workout segment to the second display position within the first workout modification user interface, the representation of the first workout segment and the representation of the second workout segment are presented in a second order different from the first order and indicative of the second workout segment preceding the first workout segment in the first pre-configured multi-modality workout.

55. The method of claim 51, wherein:

the first pre-configured multi-modality workout comprises a set of workout segments corresponding to a plurality of workout modalities, including a third workout segment corresponding to a fifth workout modality and a fourth workout segment corresponding to a sixth workout modality;

the first workout modification user interface includes a representation of the third workout segment and a representation of the fourth workout segment; and the method further comprising:
- while displaying the first workout modification user interface, receiving, via the one or more input devices, one or more user inputs corresponding to selection of the representation of the third workout segment; and
- in response to receiving the one or more user inputs corresponding to selection of the representation of the third workout segment, displaying, via the display generation component, a workout segment modification user interface including one or more options that are selectable to initiate one or more processes for modifying one or more aspects of the third workout segment, wherein the one or more options includes a change modality option that is selectable to initiate a process for changing a workout modality associated with the third workout segment.

56. The method of claim 51, wherein:

the first pre-configured multi-modality workout comprises a set of workout segments corresponding to a plurality of workout modalities, including a fifth workout segment corresponding to a seventh workout modality and a sixth workout segment corresponding to an eighth workout modality;

the first workout modification user interface includes a representation of the fifth workout segment and a representation of the sixth workout segment; and the method further comprising:
- while displaying the first workout modification user interface, receiving, via the one or more input devices, one or more user inputs corresponding to selection of the representation of the fifth workout segment; and
- in response to receiving the one or more user inputs corresponding to selection of the representation of the fifth workout segment, displaying, via the display generation component, a second workout segment modification user interface including one or more options that are selectable to initiate one or more processes for modifying one or more aspects of the fifth workout segment, wherein the one or more options includes an alerts option that is selectable to initiate a process for modifying one or more alerts that are enabled during the fifth workout segment of the first pre-configured multi-modality workout.

57. The method of claim 51, wherein:

the first pre-configured multi-modality workout comprises a set of workout segments corresponding to a plurality of workout modalities, including a seventh workout segment corresponding to a ninth workout modality and an eighth workout segment corresponding to a tenth workout modality;

the first workout modification user interface includes a representation of the seventh workout segment and a representation of the eighth workout segment; and the method further comprising:
- while displaying the first workout modification user interface, receiving, via the one or more input devices, one or more user inputs corresponding to selection of the representation of the seventh workout segment; and
- in response to receiving the one or more user inputs corresponding to selection of the representation of the seventh workout segment, displaying, via the display generation component, a third workout segment modification user interface including one or more options that are selectable to initiate one or more processes for modifying one or more aspects of the seventh workout segment, wherein the one or more options includes a metrics option that is selectable to initiate a process for modifying one or more workout metrics that are accessible during the seventh workout segment of the first pre-configured multi-modality workout.

58. The method of claim 22, further comprising:

after completion of the multi-modality workout, displaying, via the display generation component, a first workout summary user interface that includes:
- a first region corresponding to the first workout modality and including a first set of workout metrics corresponding to the first workout modality;
- a second region different from the first region and corresponding to the second workout modality, and including a second set of workout metrics corresponding to the second workout modality;
- a first object corresponding to the first workout modality that is selectable to cause display of one or more additional workout metrics corresponding to the first workout modality that are not displayed in the first region of the first workout summary user interface; and
- a second object corresponding to the second workout modality that is selectable to cause display of one or more additional workout metrics corresponding to the second workout modality that are not displayed in the second region of the first workout summary user interface.

59. The method of claim 22, further comprising:

receiving, via the one or more input devices, a user input to transition an automatic transition setting from an enabled state to a disabled state, wherein:
- when the automatic transition setting is in the enabled state, the computer system automatically detects possible transitions between workout modalities during multi-modality workouts; and
- when the automatic transition setting is in the disabled state, the computer system does not automatically detect transitions between workout modalities during multi-modality workouts, and the computer system detects transitions between workout modalities during multi-modality workouts based on one or more user inputs.

60. The method of claim 59, further comprising:

in accordance with a determination that the automatic transition setting is in the disabled state, providing access to a selectable object that is selectable to transition a transition period setting between the enabled state and the disabled state;

while the automatic transition setting is in the disabled state, displaying, via the display generation component, the first user interface corresponding to the first workout modality of the multi-modality workout;

while displaying the first user interface, receiving, via the one or more input devices, one or more user inputs indicating that the user has completed the first workout modality; and in response to receiving the one or more user inputs indicating that the user has completed the first workout modality:
- in accordance with a determination that the transition period setting is in the disabled state, displaying, via the display generation component, the third user interface corresponding to the second workout modality of the multi-modality workout; and
- in accordance with a determination that the transition period setting is in the enabled state, displaying, via the display generation component, a transition user interface different from the first user interface and the third user interface and indicative of a transition between the first workout modality and the second workout modality.

* * * * *